US012415868B1

(12) United States Patent
Bamdad et al.

(10) Patent No.: US 12,415,868 B1
(45) Date of Patent: *Sep. 16, 2025

(54) ANTI-NME ANTIBODY AND METHOD OF TREATING CANCER OR CANCER METASTASIS

(71) Applicant: MINERVA BIOTECHNOLOGIES CORPORATION, Waltham, MA (US)

(72) Inventors: Cynthia Bamdad, Boston, MA (US); Benoit Smagghe, Honolulu, HI (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/892,093

(22) Filed: Sep. 20, 2024

Related U.S. Application Data

(60) Division of application No. 18/002,832, filed as application No. PCT/US2021/039291 on Jun. 27, 2021, which is a continuation of application No. PCT/US2021/036500, filed on Jun. 8, 2021.

(60) Provisional application No. 63/044,670, filed on Jun. 26, 2020, provisional application No. 63/046,852, filed on Jul. 1, 2020.

(51) Int. Cl.
*C07K 16/46* (2006.01)
*A61P 35/00* (2006.01)
*C07K 16/40* (2006.01)

(52) U.S. Cl.
CPC .......... *C07K 16/40* (2013.01); *C07K 2317/31* (2013.01); *C07K 2317/33* (2013.01); *C07K 2317/565* (2013.01); *C07K 2317/622* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,631,271 A | 5/1997 | Serfontein | |
| 6,331,415 B1 | 12/2001 | Cabilly et al. | |
| 6,818,749 B1 | 11/2004 | Kashmiri et al. | |
| 8,535,944 B2 | 9/2013 | Bamdad | |
| 8,859,495 B2 | 10/2014 | Bamdad | |
| 9,814,782 B2 | 11/2017 | Park et al. | |
| 9,932,407 B2 | 4/2018 | Bamdad | |
| 10,421,819 B2 | 9/2019 | Bamdad et al. | |
| 10,703,821 B2 | 7/2020 | Bamdad | |
| 10,724,027 B2 | 7/2020 | Bamdad | |
| 11,202,775 B2 | 12/2021 | Bamdad | |
| 11,560,435 B2 | 1/2023 | Bamdad et al. | |
| 11,591,565 B2 | 2/2023 | Bamdad et al. | |
| 11,702,483 B2 | 7/2023 | Bamdad et al. | |
| 11,746,159 B2 | 9/2023 | Bamdad et al. | |
| 11,897,967 B2 | 2/2024 | Bamdad et al. | |
| 11,898,160 B2 | 2/2024 | Bamdad et al. | |
| 11,931,347 B2 | 3/2024 | Bamdad et al. | |
| 11,976,132 B2 | 5/2024 | Bamdad | |
| 11,976,295 B2 | 5/2024 | Bamdad et al. | |
| 12,006,371 B2 | 6/2024 | Bamdad et al. | |
| 12,037,413 B2 * | 7/2024 | Bamdad | A61P 35/00 |
| 12,049,514 B2 * | 7/2024 | Bamdad | A61P 35/04 |
| 12,049,618 B2 | 7/2024 | Bamdad | |
| 12,104,170 B2 | 10/2024 | Bamdad et al. | |
| 12,115,192 B2 | 10/2024 | Bamdad et al. | |
| 2002/0164611 A1 | 11/2002 | Bamdad et al. | |
| 2003/0022306 A1 | 1/2003 | Bandman et al. | |
| 2003/0109690 A1 | 6/2003 | Ruben et al. | |
| 2004/0057952 A1 | 3/2004 | Payne et al. | |
| 2005/0053964 A1 | 3/2005 | Bamdad et al. | |
| 2005/0163784 A1 | 7/2005 | Valentijn et al. | |
| 2009/0075926 A1 | 3/2009 | Bamdad | |
| 2010/0316688 A1 | 12/2010 | Bamdad | |
| 2012/0156246 A1 | 6/2012 | Bamdad | |
| 2013/0287748 A1 | 10/2013 | June et al. | |
| 2014/0010861 A1 | 1/2014 | Bancel et al. | |
| 2014/0044696 A1 | 2/2014 | Bamdad | |
| 2014/0065113 A1 | 3/2014 | Bamdad et al. | |
| 2015/0037371 A1 | 2/2015 | Landry | |
| 2015/0089677 A1 | 3/2015 | Bamdad | |
| 2015/0203823 A1 | 7/2015 | Bamdad | |
| 2015/0252430 A1 | 9/2015 | Bryant et al. | |
| 2015/0320840 A1 | 11/2015 | Bamdad | |
| 2016/0326263 A1 | 11/2016 | Bamdad et al. | |
| 2017/0106046 A1 | 4/2017 | Bamdad et al. | |
| 2017/0119903 A1 | 5/2017 | Park et al. | |
| 2017/0121406 A1 | 5/2017 | Bamdad | |
| 2017/0204191 A1 | 7/2017 | Bamdad et al. | |
| 2017/0204196 A1 | 7/2017 | Bamdad et al. | |

(Continued)

FOREIGN PATENT DOCUMENTS

CN 101918844 A 12/2010
CN 104220458 A 12/2014

(Continued)

OTHER PUBLICATIONS

Apantaku. Breast cancer diagnosis and screening,. An Fam Physician 62(3):596-606 (2000).
Bendig. Humanization of rodent monoclonal antibodies by CDR grafting. Methods: A Companion to Methods in Enzymology 8:83-93 (1995).
Bonsignori et al. Maturation Pathway from Germline to Broad HIV-1 Neutralizer of a CD4-Mimic Antibody. Cell 165(2):449-463 (2016).
Co-pending U.S. Appl. No. 18/644,795, inventors Bamdad; Cynthia et al., filed Apr. 24, 2024.
Co-pending U.S. Appl. No. 18/807,461, inventors Bamdad; Cynthia et al., filed Aug. 16, 2024.
Co-pending U.S. Appl. No. 18/830,957, inventor Bamdad; Cynthia, filed Sep. 11, 2024.

(Continued)

*Primary Examiner* — Sharon X Wen

(74) *Attorney, Agent, or Firm* — WILSON SONSINI GOODRICH & ROSATI

(57) ABSTRACT

The present application discloses anti-NMR antibodies and their use in treating or preventing diseases.

9 Claims, 59 Drawing Sheets

Specification includes a Sequence Listing.

(56) References Cited

U.S. PATENT DOCUMENTS

| | | |
|---|---|---|
| 2018/0230225 A1 | 8/2018 | Fan et al. |
| 2018/0235193 A1 | 8/2018 | Bamdad et al. |
| 2018/0258186 A1 | 9/2018 | Bamdad et al. |
| 2019/0031778 A1 | 1/2019 | Bamdad et al. |
| 2019/0290692 A1 | 9/2019 | Bamdad et al. |
| 2019/0389956 A1 | 12/2019 | Zhang et al. |
| 2020/0062812 A1 | 2/2020 | Bamdad et al. |
| 2020/0165354 A1 | 5/2020 | Liu et al. |
| 2020/0385485 A1 | 12/2020 | Bamdad |
| 2020/0390870 A1 | 12/2020 | Bamdad |
| 2020/0405832 A1 | 12/2020 | Bamdad et al. |
| 2021/0087143 A1 | 3/2021 | Bamdad et al. |
| 2021/0299109 A1 | 9/2021 | Bamdad et al. |
| 2021/0308213 A1 | 10/2021 | Bamdad et al. |
| 2022/0089779 A1 | 3/2022 | Bamdad et al. |
| 2022/0184120 A1 | 6/2022 | Bamdad et al. |
| 2022/0193270 A1 | 6/2022 | Bamdad |
| 2022/0202786 A1 | 6/2022 | Bamdad |
| 2022/0218846 A1 | 7/2022 | Bamdad et al. |
| 2022/0242823 A1 | 8/2022 | Bamdad et al. |
| 2022/0252604 A1 | 8/2022 | Bamdad |
| 2022/0259324 A1* | 8/2022 | Bamdad ............. C07K 16/28 |
| 2022/0289865 A1 | 9/2022 | Bamdad et al. |
| 2023/0049461 A1 | 2/2023 | Bamdad |
| 2023/0242678 A1* | 8/2023 | Bamdad ............. A61P 35/00 424/136.1 |
| 2023/0242874 A1 | 8/2023 | Bamdad et al. |
| 2023/0279141 A1 | 9/2023 | Bamdad et al. |
| 2023/0295340 A1 | 9/2023 | Bamdad et al. |
| 2024/0247229 A1 | 7/2024 | Bamdad et al. |
| 2024/0261331 A1 | 8/2024 | Bamdad et al. |
| 2024/0261406 A1 | 8/2024 | Bamdad et al. |
| 2024/0277803 A1 | 8/2024 | Bamdad et al. |
| 2024/0294590 A1 | 9/2024 | Bamdad et al. |
| 2024/0299507 A1 | 9/2024 | Bamdad |
| 2024/0307359 A1 | 9/2024 | Bamdad et al. |
| 2024/0352149 A1 | 10/2024 | Bamdad |
| 2024/0368578 A1 | 11/2024 | Bamdad |
| 2024/0392038 A1 | 11/2024 | Bamdad et al. |
| 2024/0409515 A1 | 12/2024 | Bamdad et al. |

FOREIGN PATENT DOCUMENTS

| | | | | |
|---|---|---|---|---|
| CN | 113727602 A | * | 11/2021 | ..... A61K 39/001162 |
| CN | 116075318 A | * | 5/2023 | ......... A61K 39/0011 |
| CN | 116367857 A | * | 6/2023 | ......... A01K 67/0275 |
| CN | 113727602 B | * | 10/2023 | ..... A61K 39/001162 |
| CN | 117264064 A | * | 12/2023 | ..... A61K 39/001162 |
| WO | WO-0043783 A2 | | 7/2000 | |
| WO | WO-0043791 A2 | | 7/2000 | |
| WO | WO-0192277 A1 | | 12/2001 | |
| WO | WO-0201228 A2 | | 1/2002 | |
| WO | WO-0201230 A2 | | 1/2002 | |
| WO | WO-0222164 A1 | | 3/2002 | |
| WO | WO-0228507 A2 | | 4/2002 | |
| WO | WO-0229411 A2 | | 4/2002 | |
| WO | WO-0237109 A2 | | 5/2002 | |
| WO | WO-02056022 A2 | | 7/2002 | |
| WO | WO-02061129 A2 | | 8/2002 | |
| WO | WO-03018846 A1 | | 3/2003 | |
| WO | WO-03020279 A2 | | 3/2003 | |
| WO | WO-03020280 A2 | | 3/2003 | |
| WO | WO-2004050860 A2 | | 6/2004 | |
| WO | WO-2004059347 A2 | | 7/2004 | |
| WO | WO-2005019269 A2 | | 3/2005 | |
| WO | WO-2006105448 A2 | | 10/2006 | |
| WO | WO-2007053135 A1 | | 5/2007 | |
| WO | WO-2007072221 A2 | | 6/2007 | |
| WO | WO-2008070171 A2 | | 6/2008 | |
| WO | WO-2008157490 A1 | | 12/2008 | |
| WO | WO-2009042814 A1 | | 4/2009 | |
| WO | WO-2009042815 A1 | | 4/2009 | |
| WO | WO-2010031749 A1 | | 3/2010 | |
| WO | WO-2010042562 A2 | | 4/2010 | |
| WO | WO-2010042891 A2 | | 4/2010 | |
| WO | WO-2010056737 A2 | | 5/2010 | |
| WO | WO-2010144887 A1 | | 12/2010 | |
| WO | WO-2011159960 A2 | | 12/2011 | |
| WO | WO-2012126013 A2 | | 9/2012 | |
| WO | WO-2012154759 A2 | | 11/2012 | |
| WO | WO-2013059373 A2 | | 4/2013 | |
| WO | WO-2013123084 A1 | | 8/2013 | |
| WO | WO-2014012115 A2 | | 1/2014 | |
| WO | WO-2014018679 A2 | | 1/2014 | |
| WO | WO-2014028668 A2 | | 2/2014 | |
| WO | WO-2014052693 A2 | | 4/2014 | |
| WO | WO-2014130741 A2 | | 8/2014 | |
| WO | WO-2015023694 A2 | | 2/2015 | |
| WO | WO-2015157322 A2 | | 10/2015 | |
| WO | WO-2016130726 A1 | | 8/2016 | |
| WO | WO-2017004601 A1 | | 1/2017 | |
| WO | WO-2017053886 A2 | | 3/2017 | |
| WO | WO-2018071583 A2 | | 4/2018 | |
| WO | WO-2018183654 A1 | | 10/2018 | |
| WO | WO-2019104306 A1 | | 5/2019 | |
| WO | WO-2019126357 A1 | | 6/2019 | |
| WO | WO-2019165421 A1 | | 8/2019 | |
| WO | WO-2019173815 A2 | | 9/2019 | |
| WO | WO-2020146902 A2 | | 7/2020 | |
| WO | WO-2020163325 A1 | | 8/2020 | |
| WO | WO-2021252551 A2 | | 12/2021 | |
| WO | WO-2021263227 A2 | | 12/2021 | |
| WO | WO-2021263241 A1 | | 12/2021 | |
| WO | WO-2022027039 A1 | | 2/2022 | |
| WO | WO-2023201234 A2 | | 10/2023 | |
| WO | WO-2023220560 A1 | | 11/2023 | |

OTHER PUBLICATIONS

Cuzick, J. et al. Overview of the Main Outcomes in Breast-cancer Prevention Trials. Lancet 361(9354):296-300 (2003).

Desvignes, Thomas. et al. Nme protein family evolutionary history, a vertebrate perspective. BMC Ecology and Evolution 9:256, 1-25 (2009).

Evans, T R J. et al. Vaccine Therapy for Cancer—Fact or Fiction?. QJM: An International Journal of Medicine 92(6):299-307 (1999).

Expression of NME7 in cancer—Summary—The Human Protein Atlas, printed Mar. 2018.

Hernandez-Ledesma, Blanca. et al. Lunasin, a Novel Seed Peptide for Cancer Prevention. Peptides 30(2):426-430 (2009). Published Online Nov. 13, 2008.

Human Protein Atlas (2 pp.) printed Oct. 2, 2020.

Komenaka, Ian. et al. Immunotherapy for Melanoma. Clinics in Dermatology 22(3):251-265 (2004).

Martin et al. Genetic and hormonal risk factors in breast cancer. J Natl Cancer Inst 92(14):1126-1135 (2000).

Nm23-H7 (C-15): sc-82256 datasheet by Santa Cruz Biotechnology https://datasheets.scbt.com/sc-82256.pdf (ret. 2014).

Panka et al. Variable region framework differences result in decreased or increased affinity of variant anti-digoxin antibodies. PNAS USA 85:3080-3084 (1988).

Paul. Fundamental Immunology, 3rd Edition, Chapter 9, pp. 292-295 (1993).

PCT/US2015/024764 International Search Report and Written Opinion dated Oct. 28, 2015.

PCT/US2020/016570 International Search Report and Written Opinion dated May 21, 2020.

PCT/US2021/036500 International Search Report and Written Opinion dated Aug. 3, 2022.

PCT/US2021/039291 International Invitation to Pay Additional Fees dated Oct. 18, 2021.

PCT/US2021/039291 International Search Report and Written Opinion dated Dec. 30, 2021.

Rudikoff, Stuart. et al. Single amino acid substitution altering antigen-binding specificity. PNAS USA 79(6):1979-1983 (1982).

Schiffman, Mark. et al. The Promise of Global Cervical-cancer Prevention. The New England Journal of Medicine 353(20):2101-2104 (2005).

U.S. Appl. No. 17/392,981 Office Action dated Nov. 16, 2023.

(56) References Cited

OTHER PUBLICATIONS

U.S. Appl. No. 17/719,302 Office Action dated Aug. 5, 2024.
U.S. Appl. No. 17/719,302 Office Action dated Jan. 30, 2024.
U.S. Appl. No. 17/719,302 Office Action dated Jun. 2, 2023.
U.S. Appl. No. 17/719,302 Office Action dated Sep. 14, 2023.
U.S. Appl. No. 18/000,249 Office Action dated Sep. 12, 2023.
U.S. Appl. No. 18/002,832 Office Action dated Jul. 22, 2024.
U.S. Appl. No. 18/002,832 Office Action dated Mar. 21, 2024.
U.S. Appl. No. 18/002,832 Office Action dated Nov. 6, 2023.
Queen, Cary. et al. A Humanized Antibody That Binds to the Interleukin 2 Receptor. Proceedings of the National Academy of Sciences 86(24):10029-10033 (1989).
Riechmann, Lutz et al. Reshaping Human Antibodies for Therapy. Nature 332(6162):323-327 (1988).
U.S. Appl. No. 18/002,832 Office Action dated Jan. 6, 2025.

* cited by examiner

ELISA shows NME7 Dimerizes MUC1*

MUC1* extra cellular domain peptide immobilized on plate was bound by NME7 to saturation; a second MUC1* peptide with a C-terminal His-tag or Biotin tag was added and visualized by HRP labeled antibody to either His-tag or HRP labeled streptavidin

Figure 5
Sequence alignment of human NME1 to human NME7-A and –B domains

```
NME1        MANCERTFIAIKPDGVQRGLVGEIIKRFEQKGFRLVGLKFMQASEDLLKEHYVDLKDRPF  60
NME7A       -----EKTLALIKPDAISK--AGEIIEIINRAGFTITKLRMMMLSRKEALDFHVQHQSRPF  54
             *:*: ****.:.: .****: ::: ** :. **:*  *..    :.:** :.***

NME1        FAGLVKYMHSGPVVAMVWEGLNVVKTGRVMLGETNP---ADSKPGTIRGDFCIQVGRNII  117
NME7A       FNELIQFITTGPIIAMEILRDDAICEWKRLLGPANSGVARTDASESIRALFGTDGIRNAA  114
             *  *:::: :**::**       :.:  :  :** :*.       . :.:**. *  :   **

NME1        HGSDSVESAEKEIGLWFHPEELVDYTSCAQNWIYE  152
NME7A       HGPDSFASAAREMELFP------------------ 131
            **.**. ** :*: *;*

NME1        MANCERTFIAIKPDGVQRGLVGEIIKRFEQKGFRLVGLKFMQASEDLLKEHYVDLK-DRP  59
NME7B       ----NCTCCIVKPHAVSEGLLGKILMAIRDAGFEISAMQMFNMDRVNVEEFYEVYKGVVT  56
                : *    :**..*.:**:*:*:  :.: **.: .::::: ..  ::*.*   *   .

NME1        FPAGLVKYMHSGPVVAMVWEGLNVVKTGRVMLGETNPADS----KPGTIRGDFCIQVGRNI  116
NME7B       EYHDMVTEMYSGPCVAMEIQQNNATKTFREFCGPADPEIARHLRPGTLRAIPGKTKIQNA  116
             :.:*. *:*** *** :  *.,.** * : * ::*  :   :***:*. *    :*

NME1        IHGSDSVESAEKEIGLWFHPEELVDYTSCAQNWIYE  152
NME7B       VHCTDLPEDGLLEVQYFFKILDN------------- 139
            :* :*  *.. *:  :*: :
```

Figure 6

NME7 specific peptides for generating antibodies to inhibit NME7 for the treatment or prevention of cancers.

The following peptide sequences are identified as being immunogenic peptides giving rise to antibodies that target human NME7 but not human NME1. The sequences were chosen for their lack of sequence homology to human NME1.

1. LALIKPDA
2. MMMLSRKEALDFHVDHQS
3. ALDFHVDHQS
4. EILRDDAICEWKRL
5. FNELIQFITTGP
6. RDDAICEW
7. SGVARTDASESIRALFGTDGIRNAA
8. ELFFPSSGG
9. KFTNCTCCIVKPHAVSEGLLGKILMA
10. LMAIRDAGFEISAMQMFNMDRVNVEEFYEVYKGVVT
11. EFYEVYKGVVTEYHD
12. EIQQNNATKTFREFCGPADPEIARHLRPGTLRAIFGKTKIQNA
13. YSGPCVAM
14. FREFCGP
15. VHCTDLPEDGLLEVQYFFKILDN
16. IQNAVHCTD
17. TDLPEDGLLEVQYFFKILDN
18. PEDGLLEVQYFFK
19. EIINKAGFTITK
20. MLSRKEALDFHVDHQS
21. NELIQFITT
22. EILRDDAICEWKRL
23. SGVARTDASESIRALFGTDGI
24. SGVARTDASES

Figure 6 (Continued)

25. ALFGTDGI
26. NCTCCIVKPHAVSE
27. LGKILMAIRDA
28. EISAMQMFNMDRVNVE
29. EVYKGVVT
30. EYHDMVTE
31. EFCGPADPEIARHLR

Figure 7

NME7 specific peptides for generating antibodies to inhibit NME7 for the treatment or prevention of cancers.

The following are preferred as they are likely areas that are important for structural integrity or for binding to the MUC1* peptide. Bivalent antibodies wherein each variable region would bind to each one of a pair are preferred.

35. ICEWKRL
36. LGKILMAIRDA

37. HAVSEGLLGK
38. VTEMYSGP

39. NATKTFREF
40. AIRDAGFEI

41. AICEWKRLLGPAN
42. DHQSRPFF

43. AICEWKRLLGPAN
44. VDHQSRPF
45. PDSFAS
46. KAGEIIEIINKAGFTITK

Figure 8

The following peptide sequences are from human NME1 and were selected for their high homology to human NME7 as well as for their homology to other bacterial NME proteins that are able to mimic its function.

47. MANCERTFIAIKPDGVQRGLVGEIIKRFE
48. VDLKDRPF
49. HGSDSVESAEKEIGLWF

Especially preferred for their high homology to human NME7-A or -B and also to HSP 593 are:

50. ERTFIAIKPDGVQRGLVGEIIKRFE
51. VDLKDRPFFAGLVKYMHSGPVVAMVWEGLN
52. NIIHGSDSVESAEKEIGLWFHPEELV
53. KPDGVQRGLVGEII

Figure 9

NME7-AB specific peptides preferred for generating antibodies for the treatment or prevention of cancer.

NME7A peptide 1
MLSRKEALDFHVDHQS

NME7A peptide 2
SGVARTDASES

NME7B peptide 1
DAGFEISAMQMFNMDRVNVE

NME7B peptide 2 EVYKGVVTEYHDMVTE

NME7B peptide 3
AIFGKTKIQNAVHCTDLPEDGLLEVQYFF

NME7B peptide 3 Cys to Ser mutation
AIFGKTKIQNAVHSTDLPEDGLLEVQYFF

Fig. 14A

Treating cancer cells with anti-NME7 antibodies inhibits transition to "floater" cells, which PCR shows have greatly increased expression of metastatic markers such as CXCR4; xenograft experiments show that the floater cells form a tumor at extremely low copy number – 50 – and thus fulfill the requirement for being classified cancer stem cells or metastatic cancer cells.

| Antibodies | Floater observation |
|---|---|
| Control IgG | 100% |
| 53,55,57 (A1,A2,B1) | 70% |
| 53,57 (A1,B1) | 50% |
| 61 (B3) | 5% |

JR observations

Fig. 14B

| Antibodies | Floater observation |
|---|---|
| Control IgG | 100% |
| 53,55,57 (A1,A2,B1) | 65% |
| 53,57 (A1,B1) | 40% |
| 61 (B3) | 5% |

VH observations

The number of "Floater" cells, which are the ones that have higher expression of metastatic markers and that form tumors in animals at extremely low copy number is typically 20% of the amount of plated cells by Day 7. Here, we define 100% as the number of floater cells that results when a control antibody is added. Other percentages of floater cells is relative to the control in which a control IgG antibody was added.

Figures 14A-14B

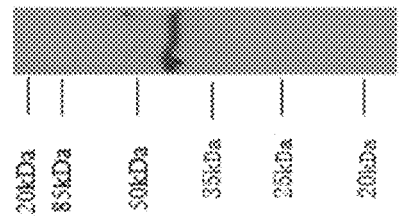
Fig. 19E
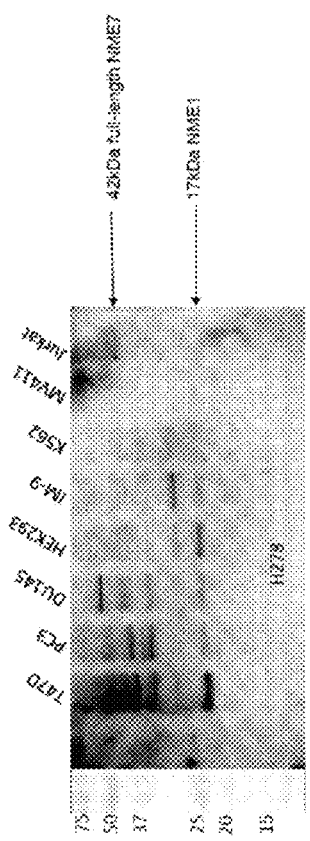
Fig. 19D
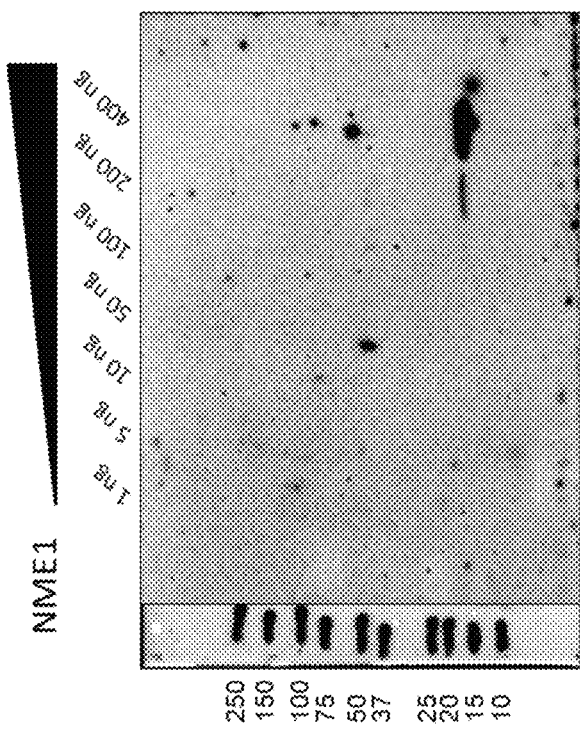
Fig. 19F
Figures 19D-19F

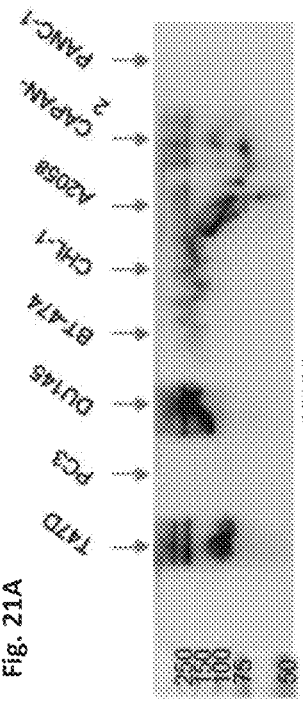
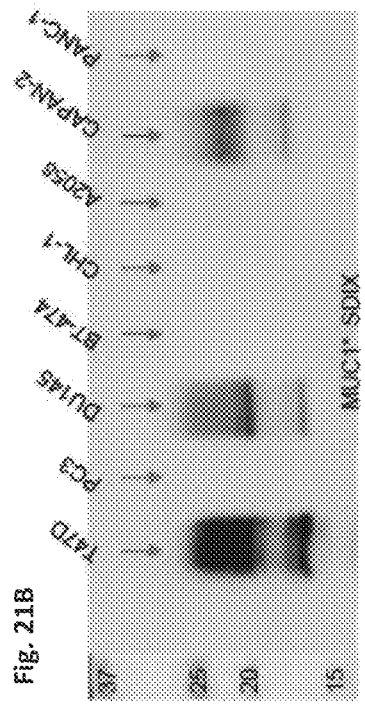
Figures 21A-21C

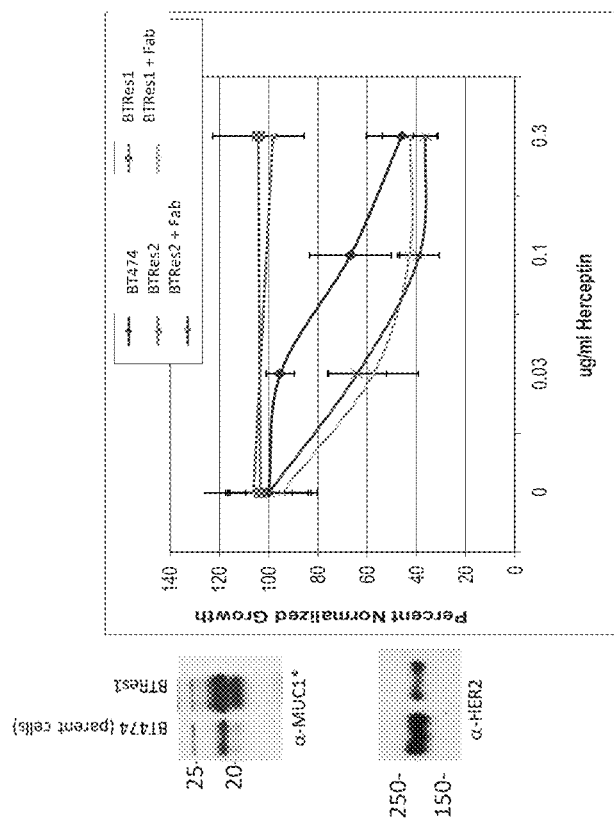
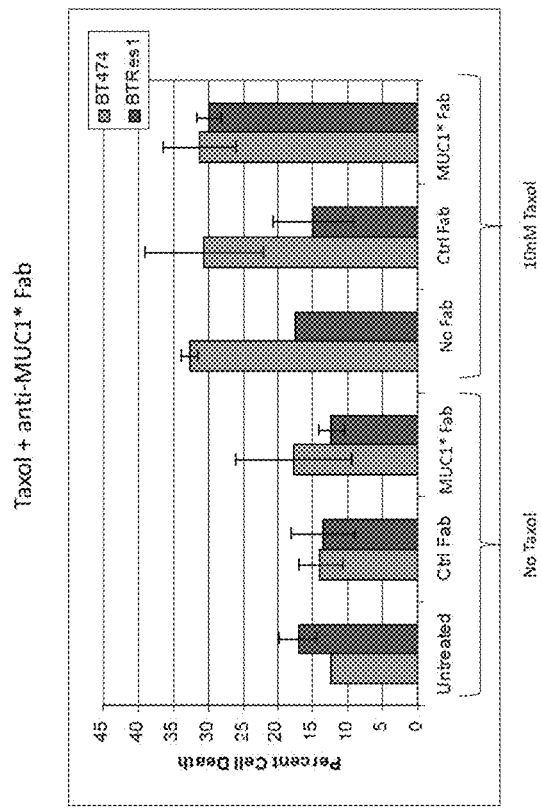
Fig. 21D
Fig. 21E
Fig. 21F
Figures 21D-21F

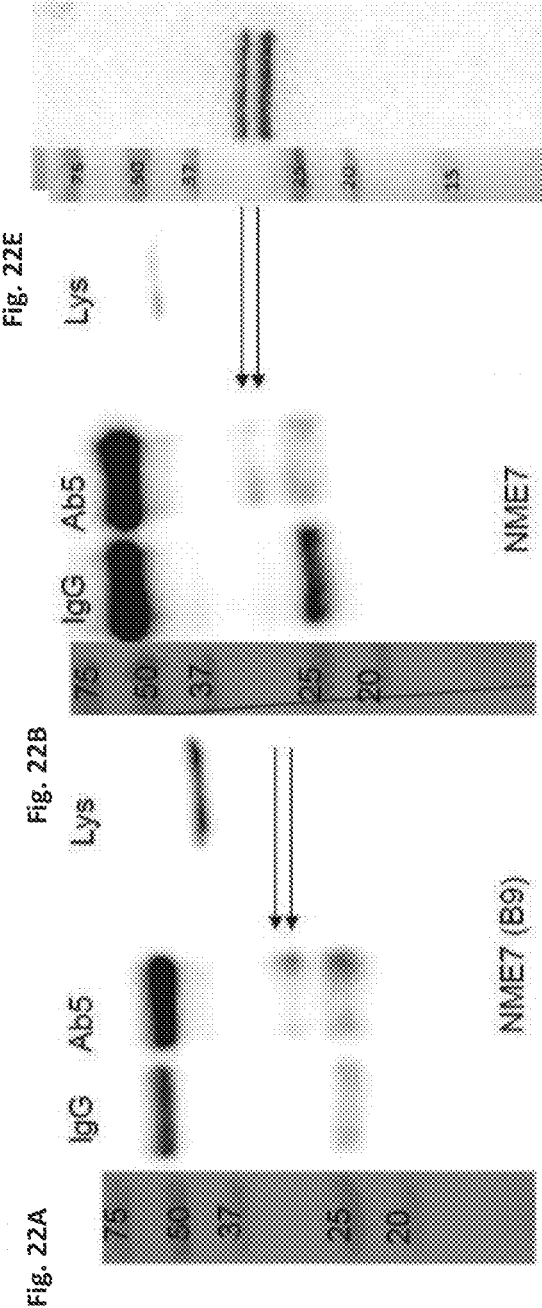
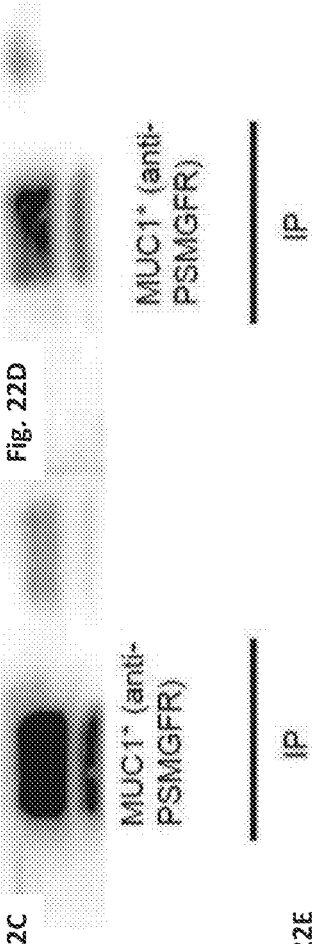
Figures 22A-22E

Onco-embryonic growth factor NME7 transforms cancer cells into metastatic cancer stem cells
Day 6
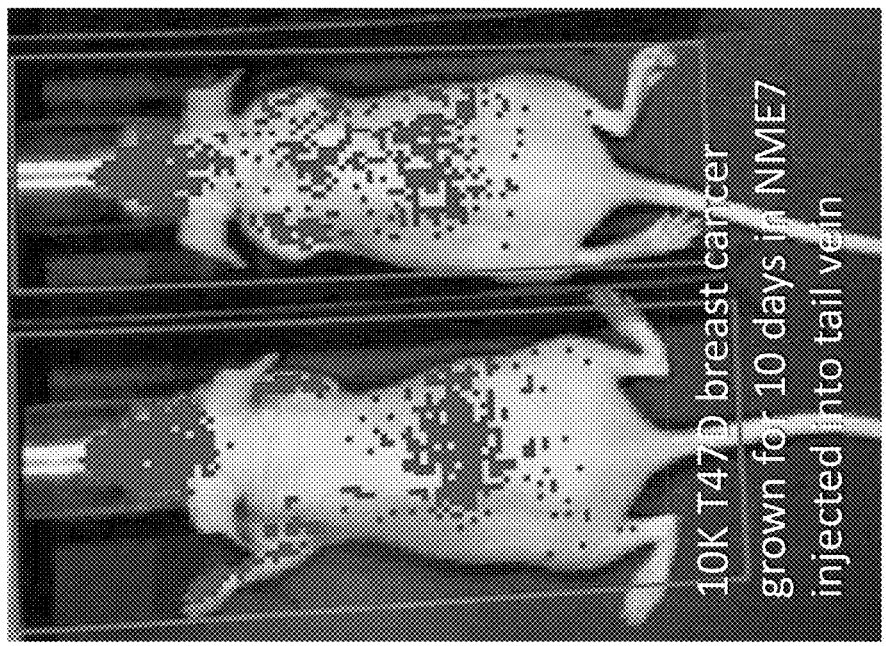
Fig. 33A
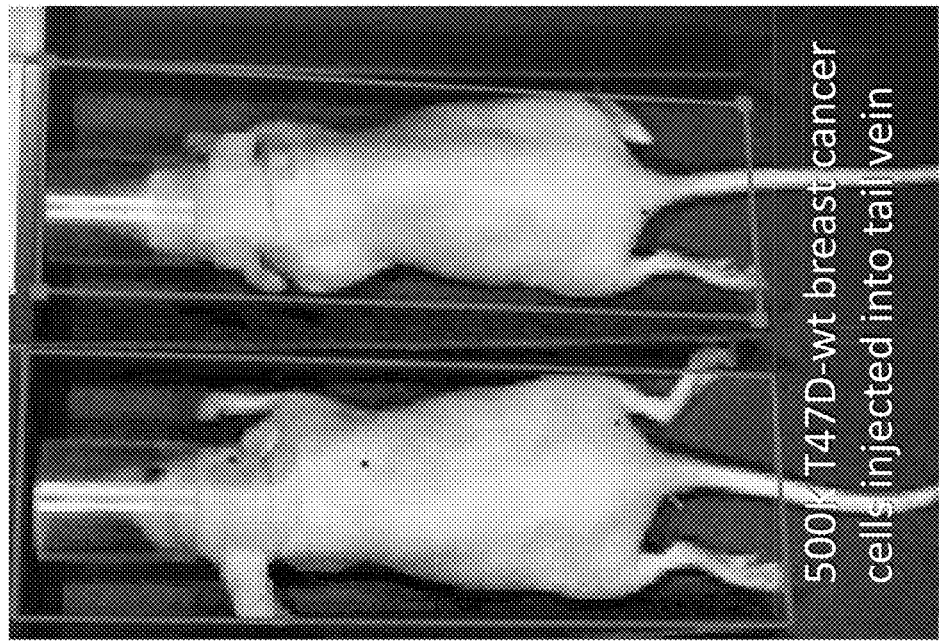
Fig. 33B
Figures 33A-33B Day 14 T47D-CSC @ 10K vs wt @ 500K; CSC mouse had 3 anti-NME7 injections, although 1st injection was at same time as NME7 injection
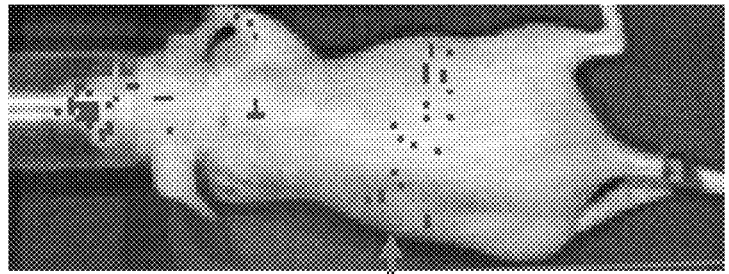
Fig. 36A
T47D-wt
500K i.v.
Day 14
No Antibody
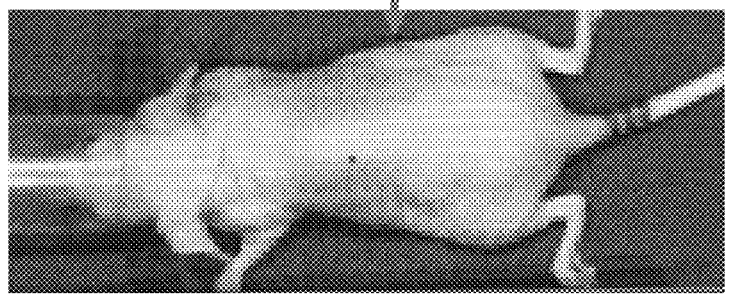
Fig. 36B
Figures 36A-36B Lung
Normal

61

10 ug/ml

61 = Minerva's anti-NME7 antibody

Fig. 39A

Tumor Grade 2

Tumor Grade 3
(T2N0M0) Clinical IB

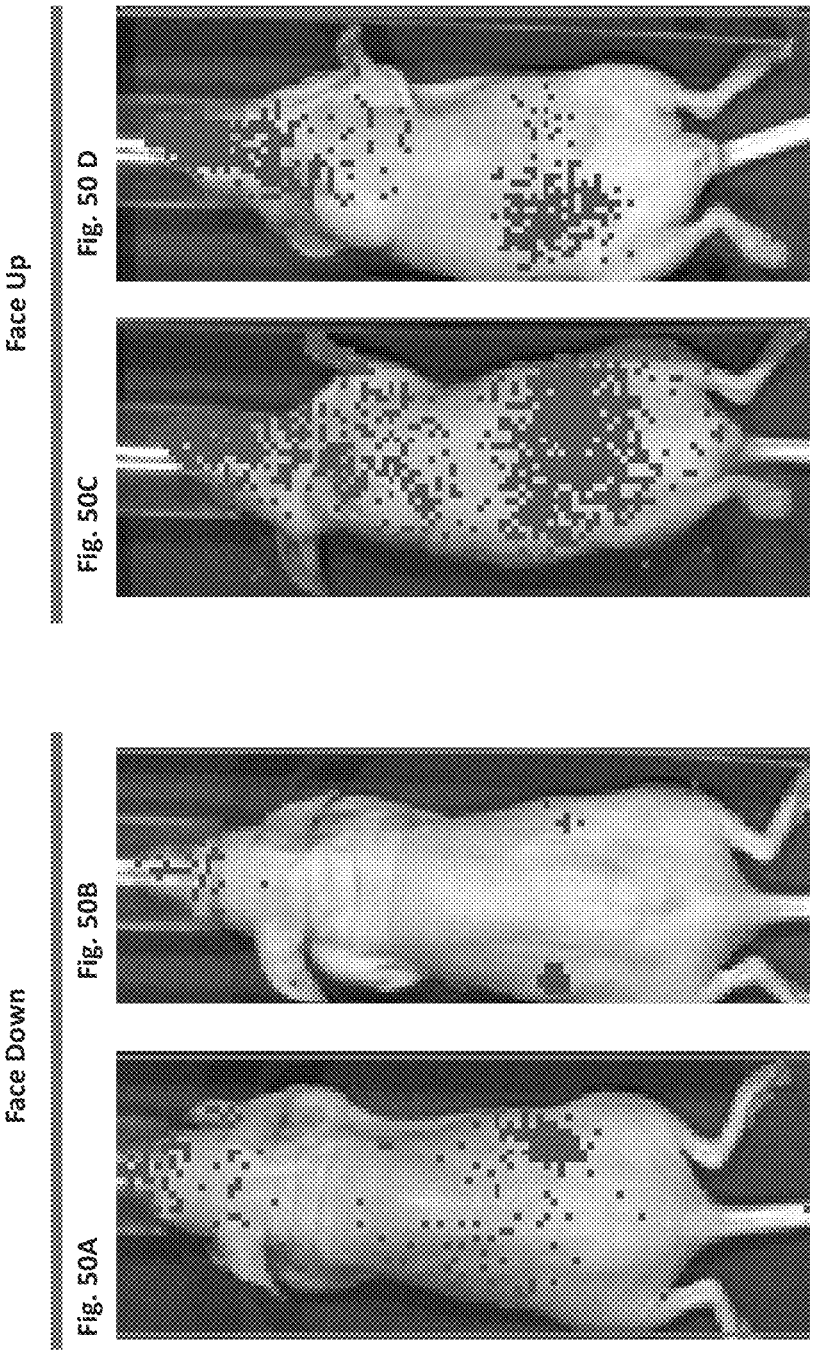
Figures 50A-D

ANTI-NME ANTIBODY AND METHOD OF TREATING CANCER OR CANCER METASTASIS

CROSS REFERENCE

This application is a divisional of U.S. patent application Ser. No. 18/002,832 filed Dec. 21, 2022, which is a National Stage Entry of International Patent Application No. PCT/US2021/039291, filed Jun. 27, 2021, which claims priority to U.S. Patent Application No. 63/046,852, filed Jul. 1, 2020; claims priority to U.S. Patent Application No. 63/044,670, filed Jun. 26, 2020; and is a continuation of International Patent Application No. PCT/US2021/036500, filed Jun. 8, 2021, each of which is incorporated herein by reference in its entirety.

SEQUENCE LISTING

The instant application contains a Sequence Listing which has been submitted electronically in XML format and is hereby incorporated by reference in its entirety. Said XML copy, created on Dec. 10, 2024, is named 56699-744_401SL.xml and is 998,519 bytes in size.

BACKGROUND OF THE INVENTION

1. Field of the Invention

The present application relates to NME proteins, peptides derived from NME proteins, and antibodies generated from the peptides thereof or antibody or antibody fragments selected by virtue of their ability to bind to said peptides. The present application also relates to treating or preventing diseases associated with the expression of NME in a patient.

2. General Background and State of the Art

NDPK (nucleoside diphosphate protein kinase) proteins are a family of proteins grouped together because they all contain an NDPK domain. The first NME proteins discovered, previously called NM23 proteins, were NM23-H1 and NM23-H2. For decades it was unclear whether they induced differentiation or prevented differentiation of hematopoietic cells. The inventors previously discovered that NM23-H1 prevents differentiation when it is a dimer, which binds to the MUC1* growth factor receptor, but at higher concentrations NM23-H1 becomes a hexamer, which does not bind to MUC1*, and it induces differentiation. NM23 used to be called a metastasis suppressor when it was found that it was under-expressed in some very aggressive cancers. The present inventors previously disclosed that NM23-H1 dimers bind to and dimerize the extracellular domain of the MUC1* growth factor receptor that is over expressed on the vast majority of cancers and such binding promotes the growth of cancer cells. Conversely, at higher concentrations, NM23 forms tetramers and hexamers that do not bind to MUC1* and do not promote tumorigenesis. Very recently more NME family proteins (NME 1-10) have been discovered although until now, their functions have not been elucidated, NME7 is a newly discovered NME family protein, but its NDPK domain has no enzymatic activity, unlike other NME family members, NME7 is either not expressed at all in adult tissues or is expressed at extremely low levels.

SUMMARY OF THE INVENTION

The present application is directed to a method of treating or preventing cancer in a subject, comprising administering to the subject an antibody made against a member of the NME family. The NME family may be NME7 family. The antibody may bind to NME7. The antibody may bind to NME7AB or NME7AB-like protein. The antibody may bind to NME7-X1. The antibody may inhibit binding between NME7 and its cognate binding partner. The cognate binding partner may be MUC1*. The cognate binding partner may be PSMGFR portion of the MUC1* extracellular domain. In one aspect, the antibody may be generated or selected for its ability to bind to a peptide selected from those listed in FIGS. 6-9 (SEQ ID NOS: 88 to 145). Preferably, the peptide may be selected from those listed in FIG. 9 (SEQ ID NOS: 141 to 145).

The peptide may be highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS: 88 to 145). In one aspect, the antibody may be selected for its ability to bind to NME7AB or NME7-X1 but not to NME1. The antibody may be polyclonal, monoclonal, bivalent, monovalent, bispecific, an antibody fragment containing the variable region, or an antibody mimic. The antibody may be human or humanized. The antibody may be a single chain scFv.

In another aspect, the invention is directed to a method of treating or preventing cancer in a subject, comprising administering to the subject a peptide that is highly homologous or identical to regions of $NME7_{AB}$. The peptide may be at least 80% homologous to one or more of the peptides listed in FIG. 6. The peptide may be at least 80% homologous to one or more of the peptides listed in FIG. 7. The peptide may be at least 80% homologous to one or more of the peptides listed in FIG. 8. The peptide may be at least 80% homologous to one or more of the peptides listed in FIG. 9. The peptide may be selected from peptides listed in FIG. 6-9 (SEQ ID NOS: 88 to 145). The peptide may be selected from those listed in FIG. 9 (SEQ ID NOS: 141 to 145). Or, the peptide may be highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS: 88 to 145). The peptide may be connected to another peptide via a spacer or linker.

In another aspect, the invention is directed to a chimeric antigen receptor (CAR), for the treatment or prevention of cancer wherein the targeting extracellular portion of the CAR comprises at least a peptide fragment of a member of the NME family, NME family may be NME7 family. The member of the NME7 family may be NME7. Or, the member of the NME7 family may be NME7AB or NME7AB-like protein. The member of the NME7 family may be also NME7-X1. The targeting extracellular portion of the CAR may include a peptide of the peptides listed in FIG. 6-9 (SEQ ID NOS: 88 to 145). The peptide may be selected from those listed in FIG. 9 (SEQ ID NOS: 141 to 145). The peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS: 88 to 145). The peptide may be connected to another peptide via a spacer or linker.

In yet another aspect, the invention is directed to a method of treating or preventing cancer or cancer metastasis, comprising engineering the chimeric antigen receptor according to claim 3, into an immune system cell and administering the cell to a subject in need thereof.

In another aspect, the invention is directed to a chimeric antigen receptor (CAR), for the treatment or prevention of cancer, wherein the targeting extracellular portion of the chimeric antigen receptor comprises a portion of an antibody that binds to $NME7_{AB}$, $NME7_{AB}$-like protein or NME7-X1. The portion of the antibody may be a single chain scFv or may be human or humanized.

In yet another aspect, the invention is directed to a method of vaccinating a person against cancer or metastatic cancer comprising immunizing the person with a peptide fragment of a member of the NME family. The NME family may be NME7 family. The member of the NME7 family may be NME7 or NME7b. The member of the NME7 family may be $NME7_{AB}$ or $NME7_{AB}$-like protein. The NME7 family may be NME7-X1. The immunizing peptide may be a peptide from the peptides listed in FIG. 6-9 (SEQ ID NOS: 88 to 145). Preferably, the peptide may be selected from those listed in FIG. 9 (SEQ ID NOS: 141 to 145). The immunizing peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS: 88 to 145). The immunizing peptide may be connected to another peptide via a spacer or linker.

In yet another aspect, the invention is directed to a method of treating or preventing cancer in a subject, comprising administering to the subject a nucleic acid that inhibits the expression of NME7, NME7b, $NME7_{AB}$-like protein or NME7-X1. The nucleic acid may be an anti-sense nucleic acid that suppresses expression of NME7, $NME7_{AB}$-like protein or NME7-X1. The nucleic acid may be an inhibitory RNA, siRNA, RNAi, or shRNA that inhibits expression of NME7, $NME7_{AB}$-like protein or NME7-X1.

In another aspect, the invention is directed to a method of treating or preventing cancer in a subject, comprising administering to the subject genetically edited nucleic acids that inhibit expression of NME7, NME7b, $NME7_{AB}$-like protein or NME7-X1. The genetically edited nucleic acids that inhibit expression of NME7, NME7b, $NME7_{AB}$-like protein or NME7-X1 may be inserted into cells that may be then administered to the patient. The genetically edited nucleic acids that inhibit expression of NME7, NME7b, $NME7_{AB}$-like protein or NME7-X1 may be inserted into cells using a viral vector. The viral vector may be a lentiviral system.

In another aspect, the invention is directed to a method of growing cancer cells comprising contacting the cells with $NME7_{AB}$, NME7b, $NME7_{AB}$-like protein or NME7-X1, 2i or 5i. The method may include culturing the cells in a medium that contains $NME7_{AB}$, NME7b, $NME7_{AB}$-like protein or NME7-X1, 2i or 5i, or growing cells in an animal that expresses human $NME7_{AB}$, NME7b, $NME7_{AB}$-like protein or NME7-X1, or to which $NME7_{AB}$, NME7b, $NME7_{AB}$-like protein or NME7-X1 is administered. The cancer cells may be breast, prostate, ovarian, colorectal, pancreatic, liver, melanoma or brain cancer cells. Drug candidates may be tested on the cells. The efficacy of the drugs may be assessed by comparing cancer growth to a no drug control or comparing expression levels of metastatic markers or stem cell markers to a no drug control or comparing the ability of the resultant cells to form tumors in animals from low cell copy number compared to a no drug control and determining the efficacy of a candidate drug for the treatment of cancer or metastasis. The cells may be obtained from a patient being assessed for treatment for cancer and drugs that would be effective for that patient are selected based on results using methods described above. The cells may not be obtained from a patient being assessed for treatment for cancer but drugs that would be effective for that patient are selected based on results using the methods described above.

In another aspect, the invention is directed to a method of generating antibodies or antibody-like molecules from peptides or peptide mimics having a sequence derived from the sequence of NME. The NME may be NME7. The peptide may be used as an immunogen to generate antibodies or antibody-like molecules. The peptide may be administered to an animal to generate anti-NME7 antibodies. The peptide may be administered to a human to generate anti-NME7 antibodies. The peptide may have a sequence listed in FIG. 6-9 (SEQ ID NOS: 88 to 145). Preferably, the peptide may be selected from those listed in FIG. 9 (SEQ ID NOS: 141 to 145). The peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS: 88 to 145).

In another aspect, the invention is directed to a method of detecting presence of cancer or the progression of cancer, comprising the steps of:
1) obtaining a sample from a patient having cancer or at risk of developing a cancer;
2) subjecting that sample to an assay capable of detecting or measuring levels of a member of the NME7 family, or levels of nucleic acids encoding a member of the NME7 family;
3) comparing levels of the measured member of the NME7 family or the member of the NME7 family-encoding nucleic acids in the test sample to levels in control patients or control cells;
4) determining that the levels of the member of the NME7 family or nucleic acids encoding the member of the NME7 family are elevated compared to the controls; and
5) concluding that the donor of the test sample has cancer or has had a progression of cancer if the control to which the test was compared came from a donor previously diagnosed with a cancer. In this method, the detection of the member of the NME7 family in circulation or in a tissue may be an indicator of cancer in a patient. The member of the NME7 family may be NME7, NME7b, NME7-X1, or $NME7_{AB}$-like protein.

In yet another aspect, the invention is directed to a method comprising:
  detecting presence of a member of the NME7 family or MUC1* in a patient; and
  administering anti-NME7 or anti-MUC1* antibody or antibodies to the patient exhibiting the member of the NME7 family or MUC1* expression. The member of the NME7 family may be NME7, NME7b, NME7-X1, or $NME7_{AB}$-like protein.

In yet another aspect, the invention is directed to a method for treating or preventing cancer comprising:
1) obtaining a sample from a patient suspected of having a cancer or at risk of developing a cancer or at risk of developing a metastatic cancer;
2) measuring an amount of the member of an NME7 family or a member of the NME7 family encoding nucleic acid, wherein the measured levels are significantly above those measured in a control sample;
3) determining that the patient has a cancer or has developed a more aggressive or a metastatic cancer;
4) administering to the patient an effective amount of a therapeutic agent that suppresses expression of the member of the NME7 family, inhibits cleavage of NME7 or inhibits NME7 binding to its targets. The target of the member of the NME7 family may be MUC1*. The target of the member of the NME7 family may be PSMGFR portion of the MUC1* extracellular domain. The member of the NME7 family may be NME7, NME7b, NME7-X1, or NME7$_{AB}$-like protein.

In any of the methods above regarding cancer, cancer may include breast, prostate, ovarian, colorectal, pancreatic, liver, melanoma or brain cancer.

In one aspect, the invention is directed to an NME7 specific antibody or fragment thereof that binds to the NME7 B3 peptide of SEQ ID NO:145 or SEQ ID NO:169. The antibody may be monoclonal antibody or bivalent, monovalent, an Fab, or a single chain variable fragment antibody (scFv). The antibody may be linked to an antibody drug conjugate. The drug may be linked to a toxin or pro-toxin.

The invention is also directed to an isolated nucleic acid encoding the antibody.

The invention is also directed to an isolated hybridoma expressing the monoclonal antibody discussed above. The antibody may specifically bind to NME7$_{AB}$ or NME7-X1, but not to NME1. The antibody may disrupt interaction between NME7$_{AB}$ and MUC1* extra cellular domain or between NME7-X1 and MUC1* extra cellular domain. Or, the antibody may disrupt binding between NME7$_{AB}$ and PSMGFR or between NME7-X1 and PSMGFR. Further, the antibody may disrupt binding between NME7$_{AB}$ and N-10 or between NME7-X1 and N-10.

In another aspect, the antibody may not disrupt interaction between NME7$_{AB}$ and MUC1* extra cellular domain or between NME7-X1 and MUC1* extra cellular domain. NME7$_{AB}$ or NME7-X1 may bind to the N-10 peptide (SEQ ID NO:170) but not to a C-10 peptide (SEQ ID NO: 171). In particular, the antibody may be 5A1, 4A3, 5D4, or 4P3.

The antibody may comprise an amino acid sequence in the heavy chain variable region comprising the following:
in the CDR1 region YTFTNYGMN (SEQ ID NO:439);
in the CDR2 region WINTYTGEPTYVDDFKG (SEQ ID NO:440); and
in the CDR3 region LRGIRPGPLAY (SEQ ID NO:441); and
an amino acid sequence in the light chain variable region comprising the following:
in the CDR1 region SASSSVSYMN (SEQ ID NO:444);
in the CDR2 region GISNLAS (SEQ ID NO:445); and
in the CDR3 region QQRSSYPPT (SEQ ID NO:446).
An example of such an antibody above is 5A1.

In another aspect, the antibody may comprise an amino acid sequence in the heavy chain variable region comprising the following:
in the CDR1 region NTFTEYTMH (SEQ ID NO:429);
in the CDR2 region GFNPNNGVTNYNQKFKG (SEQ ID NO:430); and
in the CDR3 region RYYHSTYVFYFDS (SEQ ID NO:431); and
an amino acid sequence in the light chain variable region comprising the following:
in the CDR1 region SASQGISNYLN (SEQ ID NO:434);
in the CDR2 region YTSSLHS (SEQ ID NO:435); and
in the CDR3 region QQYSKLPYT (SEQ ID NO:436).
An example of such an antibody above is 5D4.

In another aspect, the antibody may comprise an amino acid sequence in the heavy chain variable region comprising the following:
in the CDR1 region NTFTEYTMH (SEQ ID NO:388);
in the CDR2 region GFNPNNGVTNYNQKFKG (SEQ ID NO:389); and
in the CDR3 region RYYHSLYVFYFDY (SEQ ID NO:390); and
an amino acid sequence in the light chain variable region comprising the following:
in the CDR1 region SASQGISNYLN (SEQ ID NO:434);
in the CDR2 region YTSSLHS (SEQ ID NO:435); and
in the CDR3 region QQYSKLPYT (SEQ ID NO:436).
An example of such an antibody above is 4A3.

In another aspect, the antibody may comprise an amino acid sequence in the heavy chain variable region comprising the following:
in the CDR1 region NTFTEYTMH (SEQ ID NO:388);
in the CDR2 region GFNPNNGVTNYNQKFKG (SEQ ID NO:389); and
in the CDR3 region RYYHSLYVFYFDY (SEQ ID NO:390); and
an amino acid sequence in the light chain variable region comprising the following:
in the CDR1 region ITSTDIDDDMN (SEQ ID NO: 1144);
in the CDR2 region EGNTLRP (SEQ ID NO: 1145); and
in the CDR3 region LQSDNLPLT (SEQ ID NO: 1146).
An example of such an antibody above is 4P3.

The antibody may be human, humanized or an engineered antibody mimic.

The antibody may be non-human, such as murine or camelid.

The invention is also directed to a method of administering to a patient for prevention or treatment of cancer comprising administering to the patient a composition comprising the antibody described above.

The invention is also directed to a method for preventing or treating cancer metastasis in a patient, comprising administering to the patient a composition comprising the antibody described above.

The invention is also directed to a method for diagnosing cancer or cancer metastasis comprising contacting a patient specimen and normal specimen with the antibody above, and comparing the results from both specimen, wherein presence of positive binding to the antibody in the patient specimen indicates the presence of cancer or cancer metastasis in the patient. The antibody may be linked to an imaging agent. The patient specimen may be blood, bodily fluid, tissue, circulating cells, in vitro, in vivo, including intra-operative.

The invention is also directed to a cell that is engineered to express an anti-NME7$_{AB}$ antibody or fragment thereof. The cell may be an immune cell, such as T cell or NK cell, or a stem or progenitor cell, preferably stem or progenitor cell that is then differentiated to become a T cell.

The cell may comprise a chimeric antigen receptor (CAR) that recognizes tumor associated antigen. Expression of the anti-NME7 antibody may be inducible. Nucleic acid encoding an anti-NME7$_{AB}$ antibody may be inserted into the Foxp3 enhancer or promoter. The anti-NME7$_{AB}$ antibody may be in an NFAT-inducible system. NFATc1 response element may be inserted upstream of the antibody sequence that is inserted into Foxp3 enhancer or promoter region.

The anti-NME7$_{AB}$ antibody or fragment thereof may bind to the NME7 B3 peptide, or disrupt binding of NME7$_{AB}$ or NME7-X1 to the PSMGFR peptide of the MUC1* extra cellular domain.

The CAR may recognize a tumor associated antigen and an anti-NME7 antibody. The tumor associated antigen may be MUC1*.

The invention is also directed to an anti-cancer vaccine comprising a composition comprising one or more peptides derived from $NME7_{AB}$ listed in FIG. 6-FIG. 9 or a peptide having at least 80%, 85%, 90%, 95%, 97% sequence identity thereof as the immunogenicity eliciting portion. The peptide may be a peptide of SEQ ID NOS: 141-145 or a peptide having at least 80%, 85%, 90%, 95%, 97% sequence identity thereof. The peptide may be a peptide of SEQ ID NO: 145 or a peptide having at least 80%, 85%, 90%, 95%, 97% sequence identity thereof.

In another aspect, the invention is directed to a BiTE comprising the above-described antibody.

In yet another aspect, the invention is directed to a method of generating anti-$NME7_{AB}$ antibodies wherein Cysteine residue in the NME7 B3 peptide is mutated to avoid disulfide bonding.

In yet another aspect, the invention is directed to a method of generating cells with enhanced metastatic potential comprising culturing the cells with $NME7_{AB}$ or NME7-X1.

The invention is also directed to a cell that is engineered to express $NME7_{AB}$ or NME7-X1, a transgenic animal that expresses $NME7_{AB}$ or NME7-X1, wherein the $NME7_{AB}$ or NME7-X1 may be human, and also wherein expression of $NME7_{AB}$ or NME7-X1 may be inducible.

BRIEF DESCRIPTION OF THE DRAWINGS

The present invention will become more fully understood from the detailed description given herein below, and the accompanying drawings which are given by way of illustration only, and thus are not limitative of the present invention, and wherein:

FIG. 5 is a sequence alignment between human NME1 and human NME7-A or -B domain. Figure discloses SEQ ID NOS 1137, 1140, 1137 and 1143, respectively, in order of appearance.

FIG. 6 lists immunogenic peptides from human NME7 with low sequence identity to NME1 and selected for their ability to generate therapeutic anti-NME7 antibodies for the treatment or prevention of cancers. Figure discloses SEQ ID NOS 88-118, respectively, in order of appearance.

FIG. 7 lists immunogenic peptides from human NME7 that may be important for structural integrity or for binding to MUC1* selected for their ability to generate therapeutic anti-NME7 antibodies for the treatment or prevention of cancers. Figure discloses SEQ ID NOS 122-133, respectively, in order of appearance.

FIG. 8 lists immunogenic peptides from human NME1 that may be important for structural integrity or for binding to MUC1* and selected for their ability to generate therapeutic anti-NME7 antibodies for the treatment or prevention of cancers. Figure discloses SEQ ID NOS 134-140, respectively, in order of appearance.

FIG. 9 lists immunogenic peptides from human NME7 selected for their low sequence identity to NME1 and for their homology to bacterial NME1 proteins that have been implicated in cancers. These peptides are preferred for their ability to generate therapeutic anti-NME7 antibodies for the treatment or prevention of cancers. The peptides shown in this Figure include and added Cysteine covalently bound at the C-terminal end. Figure discloses SEQ ID NOS 141-145, and 169, respectively, in order of appearance.

FIGS. 14A-14B show tables of scientist observations when cancer cells were grown in either $NME7_{AB}$ or 2i inhibitors, which both are able to transform cancer cells to a more metastatic state, and in the presence or absence of NME7 derived peptides A1, A2, B1, B2 and B3. The $NME7_{AB}$ peptides inhibited the transition of adherent cancer cells to the floater cells, which RT-PCR measurements show have increased expression of metastatic markers, especially CXCR4.

FIG. 15A shows PCR graph of CXCR4 expression of T47D cancer cells grown in $NME7_{AB}$ or 2i in the presence or absence of anti-NME7 antibodies. FIG. 15B shows a graph of RT-PCR measurements of CXCR4, CHD1 and SOX2 expression in T47D breast cancer cells that were grown in 2i inhibitors for 72 hours or 144 hours, in the presence of $NME7_{AB}$ immunizing peptides and shows the peptides are themselves inhibitory to the metastatic transformation. Peptides A1, A2 and B1 which were used in the inhibitory Combo 2 and 3 in FIG. 15A are also inhibitory as peptides. Peptide B3 is the most inhibitory and is the immunizing peptide for antibody 61 which was the most inhibitory antibody tested in FIG. 15A. FIG. 15C shows the graph of FIG. 15B with the scale of the Y-axis reduced.

FIGS. 19A-19F show photographs of Western blots in which various cancer cell lines are probed for expression of NME7 species using antibodies generated by immunization with NME7 derived peptides. FIG. 19A shows Western blot wherein antibody 52 that binds to the A1 peptide is used to probe a panel of cells for the presence of full-length NME7, $NME7_{AB}$ or NME7-X1. FIG. 19B shows Western blot wherein antibody 56 that binds to the B1 peptide is used to probe a panel of cells for the presence of full-length NME7, $NME7_{AB}$ or NME7-X1. FIG. 19C shows Western blot wherein antibody 61 that binds to the B3 peptide is used to probe a panel of cells for the presence of full-length NME7, $NME7_{AB}$ or NME7-X1. FIG. 19D shows Western blot wherein commercially available polyclonal antibody H278, raised against both the NME7 A and B domain, is used to probe a panel of cells for the presence of NME7. As the figure shows, antibody H278 also recognizes NME1. FIG. 19E shows a gel published on website for commercially available anti-NME7 antibody B9, showing it binds to a species with an apparent molecular weight of full-length NME7. FIG. 19F shows a Western blot in which we used anti-NME7 antibody B9 to probe a gel that was loaded only with NME1. As can be seen in the figure, antibody B9 recognizes NME1 as well as full-length NME7. This is not surprising because like antibody H278. B9 was raised against both A and B domains of NME7 where the A domain of NME1 is highly homologous to the A domain of $NME7_{AB}$.

FIG. 20A shows SK-OV3, a MUC1-positive ovarian cancer cell line increased expression of metastatic markers CXCR4. CDH1 aka E-cadherin, SOX2 and NME7-X1: FIG. 20B shows OV-90 a MUC1-negative ovarian cancer cell line increased expression of metastatic markers CXCR4 and NME7-X1: FIG. 20C shows MDA-MB a breast cancer cell line that expresses minimal levels of MUC1 increased expression of metastatic markers CDH1 aka E-cadherin and SOX2.

FIGS. 21A-21F show photographs of Western blots and description of cancer cell lines analyzed. For Western blots in FIGS. 21A and 21B, all cancer samples were normalized such that they were loaded onto gel at a concentration of 40 ug/mL. In FIG. 21A, various cancer cell lines are probed for the expression of full-length MUC1 using an anti-tandem repeat monoclonal antibody VU4H5. In FIG. 21B, various cancer cell lines are probed for the expression of cleaved form MUC1* using a polyclonal anti-PSMGFR antibody.

FIG. 21C is a description of the cancer cell lines analyzed. FIG. 21D shows that HER2 positive BT474 breast cancer cells, marked "BT474 (parent cells)" express little to no MUC1 or MUC1* until they acquire resistance to Herceptin and other chemotherapy drugs, marked "BTRes1" in figure. Parent cells were made resistant to Herceptin. Taxol. Doxorubicin and cyclophosphamide by culturing the cells in sub-lethal levels of Herceptin. FIG. 21D shows that the expression level of HER2 has not changed but expression of MUC1* has dramatically increased as the cells acquired resistance to Herceptin. FIG. 21E shows a graph of the growth of the parent BT474 cells compared to the drug resistant metastatic cells in response to treatment with Herceptin in the presence or absence of an anti-MUC1* Fab. As can be seen in the figure, the BT474 parent cells show a Herceptin concentration dependent decrease in cell growth, whereas the two Herceptin resistant cell lines. BTRes 1 and BTRes2, show no decrease in cancer cell growth in response to treatment with Herceptin. However, when treated with an anti-MUC1* Fab, the resistant cell lines show a Herceptin concentration dependent decrease in cancer cell growth. FIG. 21F shows a graph of the percent cell death of the parent BT474 cells compared to the drug resistant BTRes1 cells, in response to treatment with Taxol in the presence or absence of an anti-MUC1* Fab.

FIGS. 22A-22E show photographs of Western blots of a co-immunoprecipitation experiment. T47D breast cancer cell extracts were incubated with an antibody against the MUC1 cytoplasmic tail. Ab-5, or a control antibody. IgG, and co-immunoprecipitated. The gels were blotted with two different commercially available anti-NME7 antibodies B9 (FIG. 22A) and CF7 (FIG. 22B). Both gels show unique NME7 bands at ~33 kDa and ~30 kDa. The gels were stripped and re-probed with an antibody against the extracellular domain of MUC1*, anti-PSMGFR (FIG. 22C) and (FIG. 22D), which shows that the NME7 species and MUC1* interact. A recombinant $NME7_{AB}$ and a recombinant NME7-X1 were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 22E).

FIGS. 33A-33B show IVIS photographs of immune compromised nu/nu mice Day 6 post tail vein injection of cancer cells. FIG. 33A shows IVIS photographs of mice injected with 500,000 T47D-wt breast cancer cells. FIG. 33B shows IVIS photographs of mice injected with 10,000 T47D breast cancer cells that were grown for 10 days in NME7$_{AB}$ in a minimal media. The floating cells were collected. These floating cells are referred to herein as cancer stem cells, CSCs. As can be seen in the figure, the mice injected with wild type cancer cells show no signs of metastasis. However, the mice injected with 50-times less cells, but cancer stem cells, show that the injected cancer cells are clearly metastasizing.

FIG. 34A shows IVIS photographs of mouse injected with 500,000 T47D-wt breast cancer cells. FIG. 34B shows IVIS photographs of mouse injected with 10,000 T47D-CSC (cancer stem cells). FIG. 34C shows IVIS photographs of mouse injected with 10,000 T47D-CSC (cancer stem cells) and injected on Day 7 with anti-NME7 antibody. FIG. 34D shows the hand recording of the IVIS measure of emitted photons. As can be seen in the figure, the mouse chosen for treatment is more metastatic than the comparable T47D-CSC mouse. The efficacy of the first antibody injection may have been blocked by the Day 6 injection of free NME7$_{AB}$. Control mouse injected with 500,000 T47D-wt cells shows some weak emission of photons that may be background or surviving cancer cells.

FIG. 35A shows IVIS photographs of mouse injected with 500,000 T47D-wt breast cancer cells. FIG. 35B shows that mouse injected with 10,000 T47D-CSC (cancer stem cells) that was not treated with anti-NME7 antibody died from excess tumor burden before IVIS photograph could be taken. FIG. 35C shows IVIS photographs of mouse injected with 10,000 T47D-CSC (cancer stem cells) and injected on Day 7 and Day 10 with anti-NME7 antibody. As can be seen in the figure, the mouse treated with anti-NME7 antibody is clearing away the cancer metastases. Control mouse injected with 500,000 T47D-wt cells shows less photon emissions indicating fewer surviving cancer cells or may be background.

FIGS. 36A-36B shows IVIS photographs of immune compromised nu/nu mice Day 14 post tail vein injection of cancer cells. FIG. 36A shows IVIS photographs of mouse injected with 500,000 T47D-wt breast cancer cells. FIG. 36B shows IVIS photographs of mouse injected with 10,000 T47D-CSC (cancer stem cells) and injected on Day 7, Day 10, and Day 12 with anti-NME7 antibody. As can be seen in the figure, the mouse treated with anti-NME7 antibody nearly completely free of cancer cell metastases. Control mouse injected with 500,000 T47D-wt cells shows no photon emissions.

FIGS. 37A, 37C, 37E, 37G, 37I, 37K, 37M and 37O show IVIS photographs of mouse that had been injected Day 0 into the tail vein with 500,000 T47D-wt cells. FIGS. 37B, 37D, 37F, 37H, 37J, 37L, 37N and 37P show IVIS photographs of mouse that had been injected Day 0 into the tail vein with 10,000 T47D cancer stem cells, to which anti-NME7 antibody was administered from Day 7 to Day 17, whereupon treatment was suspended, then resumed on Day 21. FIGS. 37Q, 37R, 37S, 37T, and 37U show enlarged IVIS photographs of the treated mouse between Day 17, when anti-NME7 antibody treatment was suspended, through Day 21, when antibody treatment was resumed to Day 26. FIG. 37V shows the scale bar of the IVIS measurements. As can be seen in this time course, cancer cells that had been grown in NME7 readily metastasize and such metastasis can be effectively treated, prevented or reversed by treatment with an antibody that binds to NME7.

FIG. 38A shows mice that were injected into the tail vein (i.v.). FIG. 38B shows mice that were injected intra-peritonealy (i.p.). FIG. 38C shows mice that were injected sub-cutaneously (s.c.).

FIGS. 39A-39C shows human lung tissue specimens stained with an anti-NME7 antibody that binds to the B3 peptide. The figure shows lack of NME7 expression on normal tissues, increasing expression of NME7 as tumor grade and metastasis increase.

FIGS. 42A-42C show IVIS photographs with animals face down. FIG. 42D-42F show IVIS photographs with animals face up. FIGS. 42A and 42D show control animals injected with phosphate buffered saline solution. FIGS. 42B and 42E show a prevention model in which animals were injected with anti-NME7$_{AB}$ antibody 4A3 24 hrs before injection of the metastatic cancer cells, then approximately every other day for a total of 12 antibody injections over 22 days. FIGS. 42C and 42F show a reversal model in which animals were injected with anti-NME7$_{AB}$ antibody 4A3 24 hrs after injection of the metastatic cancer cells, then approximately every other day for a total of 11 antibody injections over 20 days.

FIGS. 43A-43C show IVIS photographs with animals face down. FIGS. 43D-43F show IVIS photographs with animals face up. FIGS. 43A and 43D show control animals injected with phosphate buffered saline solution. FIGS. 43B, 43E, 43C and 43F show a prevention model in which animals were injected with anti-NME7$_{AB}$ antibodies 24 hours before injection of the metastatic cancer cells, then approximately every other day for a total of 12 antibody injections over 22 days. Images were taken on Day 27.

FIG. 44A shows control animals injected with phosphate buffered saline solution. FIG. 44B shows animals treated with anti-NME7$_{AB}$ monoclonal antibody 8F9A5A1, also known as 5A1. FIG. 44C shows animals treated with anti-NME7$_{AB}$ monoclonal antibody 8F9A4A3, also known as 4A3. FIG. 44D shows animals treated with anti-NME7$_{AB}$ monoclonal antibody 5F3A5D4, also known as 5D4. Green arrows indicate low antibody dosage (5-7 mg/kg) over the indicated period and Red arrows indicate high dosage (15 mg/kg). As can be seen in the figure, animals treated with anti-NME7$_{AB}$ antibodies have less metastases than the control animals even though many of the animals in the groups to be treated with antibody have more metastasis before any treatment. Higher concentrations of anti-NME7$_{AB}$ antibody are more effective than low concentrations. For example between Day 11 and Day 17, animals were treated with high dose and most of the treated animals have cleared metastases by about Day 17. However, 1 low dose of antibody resulted in metastasis recurrence. Animals again respond to high dose treatment by Day 32.

FIG. 45A shows IVIS photographs of control animals. FIG. 45B shows IVIS photographs of animals injected into tail vein with a cocktail of anti-$NME7_{AB}$ antibodies 5A1, 4A3 and 5D4 to a total concentration of 15 mg/kg. Antibodies or PBS were administered 4 times between Day 7 and Day 18. As can be seen in the figure, the anti-$NME7_{AB}$ antibody treated animals show less metastases than the control group. In the treated group. 2 of the 5 animals have primary tumors that are larger than those in the control group. This could be because the anti-$NME7_{AB}$ antibodies prevented the spread of the cancer cells, so they remained concentrated in the primary tumor. In this experiment. PCR analysis showed that after 11 days in culture with $NME7_{AB}$, the T47D breast cancer cells had upregulated CXCR4 by 109-fold. OCT4 by 2-fold, NANOG by 3.5-fold and MUC1 by 2.7-fold.

FIGS. 46A-46B show whole body IVIS photographs of control animals that were injected with only PBS. FIGS. 46C-46D show whole body IVIS photographs of control animals that were injected with the anti-$NME7_{AB}$ antibody 5A1. FIGS. 46E-46F show whole body IVIS photographs of control animals that were injected with the anti-$NME7_{AB}$ antibody 4A3. FIGS. 46G-46H show whole body IVIS photographs of control animals that were injected with the anti-$NME7_{AB}$ antibody 5D4. FIGS. 46A, 46C, 46E, and 46G are IVIS photographs taken at Day 7 before any treatment. FIGS. 46B, 46D, 46F, and 46H are IVIS photographs taken at Day 31 after anti-$NME7_{AB}$ antibody treatment or mock treatment. As can be seen in the figure, animals in the PBS control group show metastasis (blue dots) in the whole body IVIS photographs, while animals treated with anti-$NME7_{AB}$ antibodies do not. FIGS. 46I-46P show photographs and IVIS photographs of livers and lung harvested from animals after sacrifice. FIGS. 46I, 46K, 46M, and 46O are regular photographs. FIGS. 46J, 46L, 46N, and 46P are IVIS photographs, illuminating the cancer cells that have metastasized there. As can be seen in the figure, the anti-$NME7_{AB}$ antibodies greatly inhibited metastasis to the liver, which is a primary site for breast cancer metastasis. FIG. 46Q is a bar graph of the measured photons emitted and enumerated by IVIS instrument for livers harvested from control animals versus the treated animals.

FIG. 47A shows T47D breast cancer cells stained with varying concentrations of anti-$NME7_{AB}$ antibody 5D4. FIG. 47B shows ZR-75-1 breast cancer cells, also known as 1500s, stained with varying concentrations of anti-$NME7_{AB}$ antibody 5D4. FIG. 47C shows H1975 non-small cell lung cancer cells stained with varying concentrations of anti-$NME7_{AB}$ antibody 5D4. FIG. 47D shows H292 non-small cell lung cancer cells stained with varying concentrations of anti-$NME7_{AB}$ antibody 5D4. FIG. 47E shows HPAFII pancreatic cancer cells stained with varying concentrations of anti-$NME7_{AB}$ antibody 5D4. FIG. 47F shows DU145 prostate cancer cells stained with varying concentrations of anti-$NME7_{AB}$ antibody 5D4. As can be seen in the figure, all the cancer cell lines we tested show strong and membranous staining for $NME7_{AB}$. The monoclonal antibody used in these experiments was 5D4. In parallel, $NME7_{AB}$ antibodies 5A1 and 4A3 were used to stain the same cell lines and produced the same results.

FIGS. 48A-48C shows H1975 non-small cell lung cancer cells, which are an adenocarcinoma, stained with varying concentrations of anti-$NME7_{AB}$ antibody 5D4. FIG. 48A is an overlay of DAPI and anti-$NME7_{AB}$ staining. FIG. 48B shows anti-$NME7_{AB}$ staining alone. FIG. 48C is a magnified view of the overlay of DAPI and anti-$NME7_{AB}$ staining. FIGS. 48D-48F shows H292 non-small cell lung cancer cells, which are a mucoepidermoid pulmonary carcinoma, stained with varying concentrations of anti-$NME7_{AB}$ antibody 5D4. FIG. 48D is an overlay of DAPI and anti-$NME7_{AB}$ staining. FIG. 48E shows anti-$NME7_{AB}$ staining alone. FIG. 48F is a magnified view of the overlay of DAPI and anti-$NME7_{AB}$ staining. FIGS. 48G-48I shows H358 non-small cell lung cancer cells, which are a metastatic bronchioalveolar carcinoma, stained with varying concentrations of anti-$NME7_{AB}$ antibody 5D4. FIG. 48G is an overlay of DAPI and anti-$NME7_{AB}$ staining. FIG. 48H shows anti-$NME7_{AB}$ staining alone. FIG. 48I is a magnified view of the overlay of DAPI and anti-$NME7_{AB}$ staining.

FIG. 49A measured breast metastatic marker CXCR4. FIG. 49B measured stem cell marker OCT4. FIG. 49C measured metastatic marker ALDH1. FIG. 49D measured stem cell marker SOX2. FIG. 49E measured stem cell marker NANOG. FIG. 49F measured marker CDH1, also known as E-cadherin. FIG. 49G measured metastatic marker CD133. FIG. 49H measured stem cell marker ZEB2. FIG. 49I measured stem, cancer and metastatic marker MUC1. The floater cells, also known as tumor spheres become able to grow anchorage independently and show markers of metastasis that are more elevated than the adherent cells. Animals injected with cancer stem cells are those injected with the $NME7_{AB}$ grown floater cells. As can be seen in the figure markers of metastasis, stem cell markers, or markers of epithelial to mesenchymal transition (EMT) are elevated after culture in $NME7_{AB}$, indicating a transition to a more metastatic state.

FIG. 50A-50D shows IVIS photographs of NSG mice injected into the tail vein with 10,000 cancer cells that were either NCI-H358 parent cells or NCI-H358 cells after 10 days in culture with $NME7_{AB}$. FIGS. 50A and 50C show IVIS photographs of the mouse that was injected with the NCI-H358 lung cancer cells that had been grown in $NME7_{AB}$ for 10 days. FIGS. 50B and 50D show IVIS photographs of the mouse that was injected with the parental NCI-H358 cells. FIGS. 50A and 50B show the IVIS photographs where mice are imaged face down. FIGS. 50C and 50D show the IVIS photographs where mice are imaged face up. As can be seen in the figure, the $NME7_{AB}$ grown cells have greatly increased metastatic potential.

FIG. 52A shows control animals injected with phosphate buffered saline solution. FIG. 52B shows animals treated with anti-$NME7_{AB}$ humanized 4A3 4.8. FIG. 52C shows animals treated with anti-$NME7_{AB}$ humanized 4A3 12.3. FIG. 52D shows animals treated with anti-$NME7_{AB}$ monoclonal antibody murine 4A3. FIG. 52E shows a graph of the quantification of bioluminescence measurement of tumor volume, taken in an IVIS instrument. Animals were injected with either PBS or an anti-NME7 antibody at 15 mg/kg once every 3 days. Antibody hu 4A3 4.8 denotes that the sequences derived from human heavy chain antibody sequence 1.46 (SEQ ID NO: 1102) and light chain sequence 1.6 (SEQ ID NO: 1104) were used. Antibody hu 4A3 12.3 denotes that the sequences derived from human heavy chain antibody sequence 4.4 (SEQ ID NO: 1106) and light chain sequence 4.1 (SEQ ID NO:1108) were used. Note that half the animals treated with hu 4A3 4.8 were given a partial half dose.

DETAILED DESCRIPTION OF THE PREFERRED EMBODIMENTS

Definitions

Figure 1A:
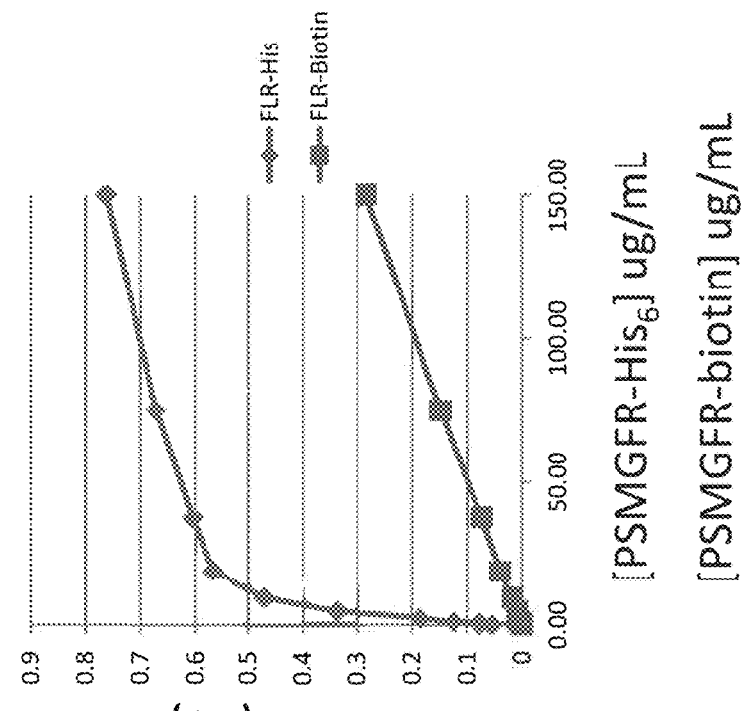
FIGS. 1A-1B show a graph of HRP signal from ELISA sandwich assay showing $NME7_{AB}$ dimerizes MUC1* extra cellular domain peptide.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, "fragments" or "functional derivatives" refers to biologically active amino acid sequence variants and fragments of the polypeptide of the present invention, as well as covalent modifications, including derivatives obtained by reaction with organic derivatizing agents, post-translational modifications, derivatives with nonproteinaceous polymers, and immunoadhesins.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "subject" is a vertebrate, preferably a mammal, more preferably a human.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable, "Treatment" can also mean prolonging survival as compared to expected survival if not receiving treatment, "Treatment" refers to both therapeutic treatment and prophylactic or preventative measures. Those in need of treatment include those already with the disorder as well as those in which the disorder is to be prevented, "Palliating" a disease means that the extent and/or undesirable clinical manifestations of a disease state are lessened and/or the time course of the progression is slowed or lengthened, as compared to a situation without treatment.

As used herein, "A1" peptide, "A2" peptide, "B1" peptide, "B2" peptide and "B3" peptide refer to peptides derived from NME7 that are used to generate or select antibodies that bind to human NME7$_{AB}$, but not (or significantly less) to human NME1. The peptides used to generate these antibodies are common to both NME7$_{AB}$ and NME7-X1, and are set forth as below:

A1 is NME7A peptide 1 (A domain): MLSRKEALDFHVDHQS (SEQ ID NO: 141)

A2 is NME7A peptide 2 (A domain): SGVARTDASES (SEQ ID NO:142)

B1 is NME7B peptide 1 (B domain): DAGFEISAMQMFNMDRVNVE (SEQ ID NO: 143)

B2 is NME7B peptide 2 (B domain): EVYKGVVTEYHDMVTE (SEQ ID NO: 144)

B3 is NME7B peptide 3 (B domain): AIFGKTKIQNAVHCTDLPEDGLLEVQYFF (SEQ ID NO:145)

Further, for the sake of clarity, NME7A (with capital letter "A") refers to the subunit A portion of NME7, NME7a (with small letter "a") refers to the full-length NME7 that is described elsewhere in this application. And, NME7B (with capital letter "B") refers to the subunit B portion of NME7, NME7b (with small letter "b") refers to a species of NME7 that is partially devoid of the DM10 region, which is described elsewhere in this application.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human fabs that are then screened for binding to peptide epitopes from target proteins. The selected Fab regions can then be engineered into a scaffold or framework so that they resemble antibodies.

As used herein, an "effective amount of an agent to inhibit an NME family member protein" refers to the effective amount of the agent in hindering the activating interaction between the NME family member protein and its cognate receptor such as As used herein, "NME derived fragment" refers to a peptide sequence that is either a fragment of the NME or is highly homologous to the peptide sequence that is a fragment of the NME.

As used herein, the "MUC1*" extra cellular domain is defined primarily by the PSMGFR sequence (GTINVHDVETQFNQYKTEAAS-RYNLTISDVSVSDVPFPFSAQSGA (SEQ ID NO:6)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:6). In this regard, the "N-number" as in "N-10 PSMGFR" or simply "N-10", "N-15 PSMGFR" or simply "N-15", or "N-20 PSMGFR" or simply "N-20" refers to the number of amino acid residues that have been deleted at the N-terminal end of PSMGFR. Likewise "C-number" as in "C-10 PSMGFR" or simply "C-10", "C-15 PSMGFR" or simply "C-15", or "C-20 PSMGFR" or simply "C-20" refers to the number of amino acid residues that have been deleted at the C-terminal end of PSMGFR. A mixture of deletions and additions is also possible. For instance. N+20/C-27 refers to a peptide fragment of wild-type MUC1 in which 20 amino acids are added to the PSMGFR at the N-terminus and 27 amino acids are deleted from the C-terminus.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, "high homology" is considered to be at least 30%, 35%, 40%, 45%, 50%, 55%, 60%, 65%, 70%, 75%, 80%, 85%, 90%, 95%, or 97% identity in a designated overlapping region between any two polypeptides.

As used herein, "NME family proteins" or "NME family member proteins", numbered 1-10, are proteins grouped together because they all have at least one NDPK (nucleotide diphosphate kinase) domain. In some cases, the NDPK domain is not functional in terms of being able to catalyze the conversion of ATP to ADP, NME proteins were formerly known as NM23 proteins, numbered H1 and H2. Recently, as many as ten (10) NME family members have been identified. Herein, the terms NM23 and NME are interchangeable. Herein, terms NME1, NME2, NME5, NME6, NME7, NME8 and NME9) are used to refer to the native protein as well as NME variants. In some cases these variants are more soluble, express better in $E.$ $coli$ or are more soluble than the native sequence protein. For example, NME7 as used in the specification can mean the native protein or a variant, such as $NME7_{AB}$ that has superior commercial applicability because variations allow high yield expression of the soluble, properly folded protein in $E,$ $coli$, $NME7_{AB}$ consists primarily of the NME7 A and B domains but is devoid of most of the DM10 domain (SEQ ID NO:39), which is at the N-terminus of the native protein, "NME1" as referred to herein is interchangeable with "NM23-H1". It is also intended that the invention not be limited by the exact sequence of the NME proteins. The mutant NME1-S120G, also called NM23-S120G, are used interchangeably throughout the application. The S120G mutants and the P96S mutant are preferred because of their preference for dimer formation, but may be referred to herein as NM23 dimers, NME1 dimers, or dimeric NME1, or dimeric NM23.

NME7 as referred to herein is intended to mean native NME7 having a molecular weight of about 42 kDa.

A "family of NME7" refers to full length NME7 as well as naturally occurring or artificially created cleaved form having a molecular weight about 30 kDa, 33 kDa, or a cleaved form having a molecular weight of about 25 kDa, a variant devoid or partially devoid of the DM10 leader sequence (SEQ ID NO:162), which is NME7 amino acids 1-91 of NME7 represented by SEQ ID NO:82 or 147, such as NME7b, NME7-X1, $NME7_{AB}$ or a recombinant NME7 protein, or variants thereof whose sequence may be altered to allow for efficient expression or that increase yield, solubility or other characteristics that make the NME7 more effective or commercially more viable. The "family of NME7" may also include "$NME7_{AB}$-like" protein, which is a protein in the range of 30 to 33 kDa that is expressed in cancer cells.

As used herein, an "an agent that maintains stem cells in the naïve state or reverts primed stem cells to the naïve state" refers to a protein, small molecule or nucleic acid that alone or in combination maintains stem cells in the naïve state, resembling cells of the inner cell mass of an embryo. Examples include but are not limited to human NME1 dimers, bacterial, fungal, yeast, viral or parasitic NME proteins that have high sequence identity to human NME proteins, especially NME1, NME7, NME7-X1, $NME7_{AB}$, NME6, 2i (Silva J et al, 2008: Hanna et al, 2010), 5i (Theunissen T W et al, 2014), nucleic acids such as siRNA that suppress expression of MBD3, CHD4 (Rais Yl et al, 2013), BRD4, or JMJD6 (Liu W et al 2013).

As used herein, the terms "$NME7_{AB}$", "NME7AB" and "NME-AB" are used interchangeably.

As used herein, an "an agent that promotes pluripotency" or "reverts somatic cells to a stem-like or cancer-like state" refers to a protein, small molecule or nucleic acid that alone or in combination induces expression of or suppresses expression of certain genes such that the genetic signature shifts to one that more closely resembles stem cells or cancer cells. Examples include but are not limited to NME1 dimers, NME7, NME7-X1, $NME7_{AB}$, 21, 5i, nucleic acids such as siRNA that suppress expression of MBD3, CHD4, BRD4, or JMJD6, microbial NME proteins that have high sequence homology to human NME1, NME2, NME5, NME6, NME7, NME8, or NME9, preferably with the regions that house NDPK domains.

As used herein, in reference to an agent being referred to as a "small molecule", it may be a synthetic chemical or chemically based molecule having a molecular weight between 50 Da and 2000 Da, more preferably between 150 Da and 1000 Da, still more preferably between 200 Da and 750 Da.

As used herein, in reference to an agent being referred to as a "natural product", it may be chemical molecule or a biological molecule, so long as the molecule exists in nature.

As used herein, FGF, FGF-2 or bFGF refer to fibroblast growth factor (Xu R H et al, 2005; Xu C et al, 2005).

As used herein, "Rho associated kinase inhibitors" may be small molecules, peptides or proteins (Rath N, et al, 2012). Rho kinase inhibitors are abbreviated here and elsewhere as ROCi or ROCKi, or Ri. The use of specific rho kinase inhibitors are meant to be exemplary and can be substituted for any other rho kinase inhibitor.

As used herein, the term "cancer stem cells" or "tumor initiating cells" refers to cancer cells that express levels of genes that have been linked to a more metastatic state or more aggressive cancers. The terms "cancer stem cells" or "tumor initiating cells" can also refer to cancer cells for which far fewer cells are required to give rise to a tumor when transplanted into an animal. Cancer stem cells and tumor initiating cells are often resistant to chemotherapy drugs.

As used herein, the terms "stem/cancer", "cancer-like", "stem-like" refers to a state in which cells acquire characteristics of stem cells or cancer cells, share important elements of the gene expression profile of stem cells, cancer cells or cancer stem cells. Stem-like cells may be somatic cells undergoing induction to a less mature state, such as increasing expression of pluripotency genes. Stem-like cells also refers to cells that have undergone some dedifferentiation or are in a meta-stable state from which they can alter their terminal differentiation. Cancer like cells may be cancer cells that have not yet been fully characterized but display morphology and characteristics of cancer cells, such as being able to grow anchorage-independently or being able to give rise to a tumor in an animal.

As used herein, "spacers" or "linkers" of different lengths can be incorporated anywhere in the peptide. Spacer attachment is usually through an amide linkage but other functionalities are possible.

NME, NME7 and Protein Family of NME7

Figure 18:
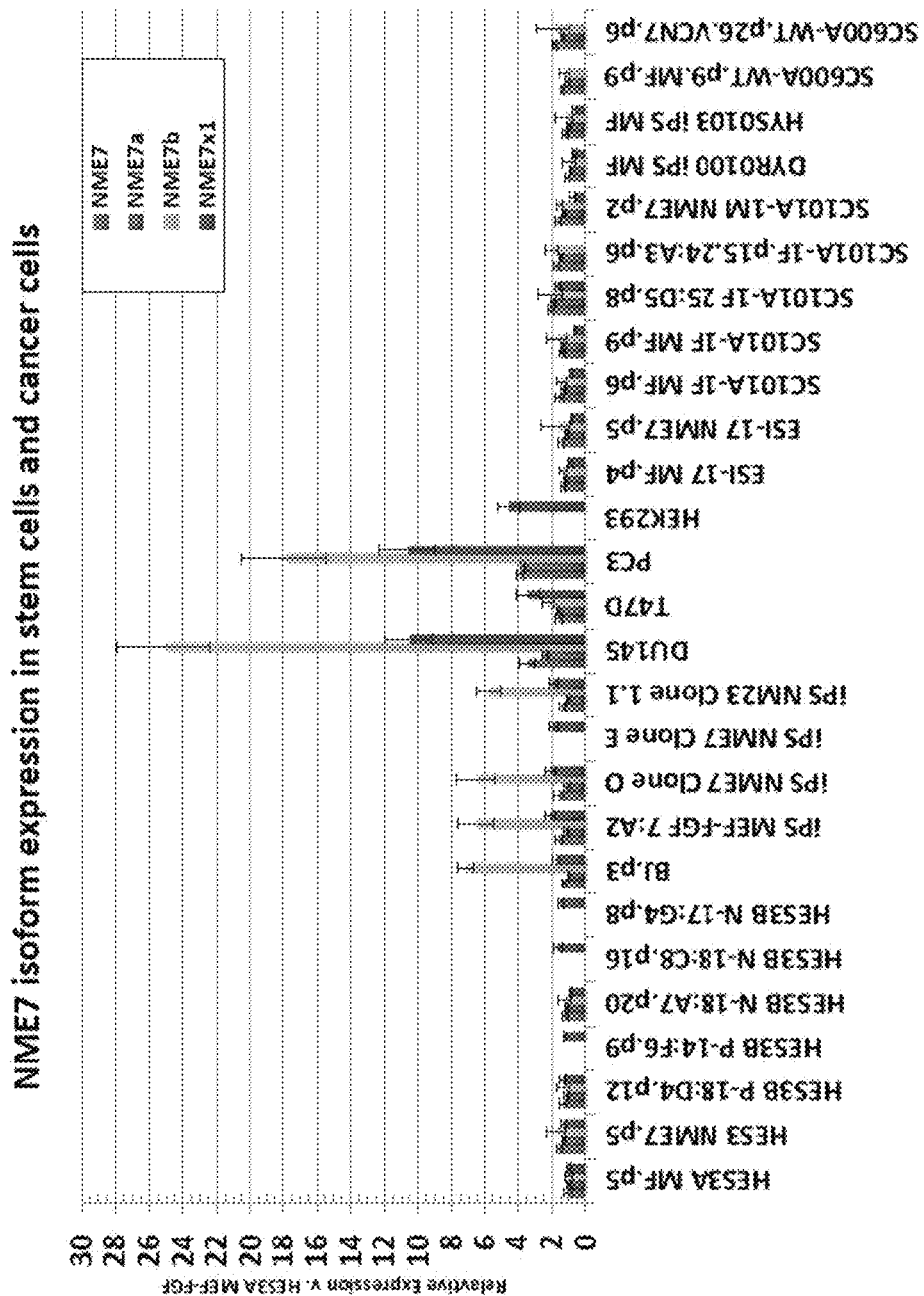
FIG. 18 shows a graph of RT-PCR measurement of the expression of NME7, NME7a, NME7b and NME7-X1 in a panel of human stem cells and cancer cells, NME7a is full-length NME7, NME7b is missing a small portion of the DM10 domain, NME7-X1 is missing all of the DM10 domain and a small portion of the N-terminus of the first NDPK A domain. The bar labeled NME7 means that primers were used that detected both NME7a and NME7b.
Figures 19A, 19B, 19C:
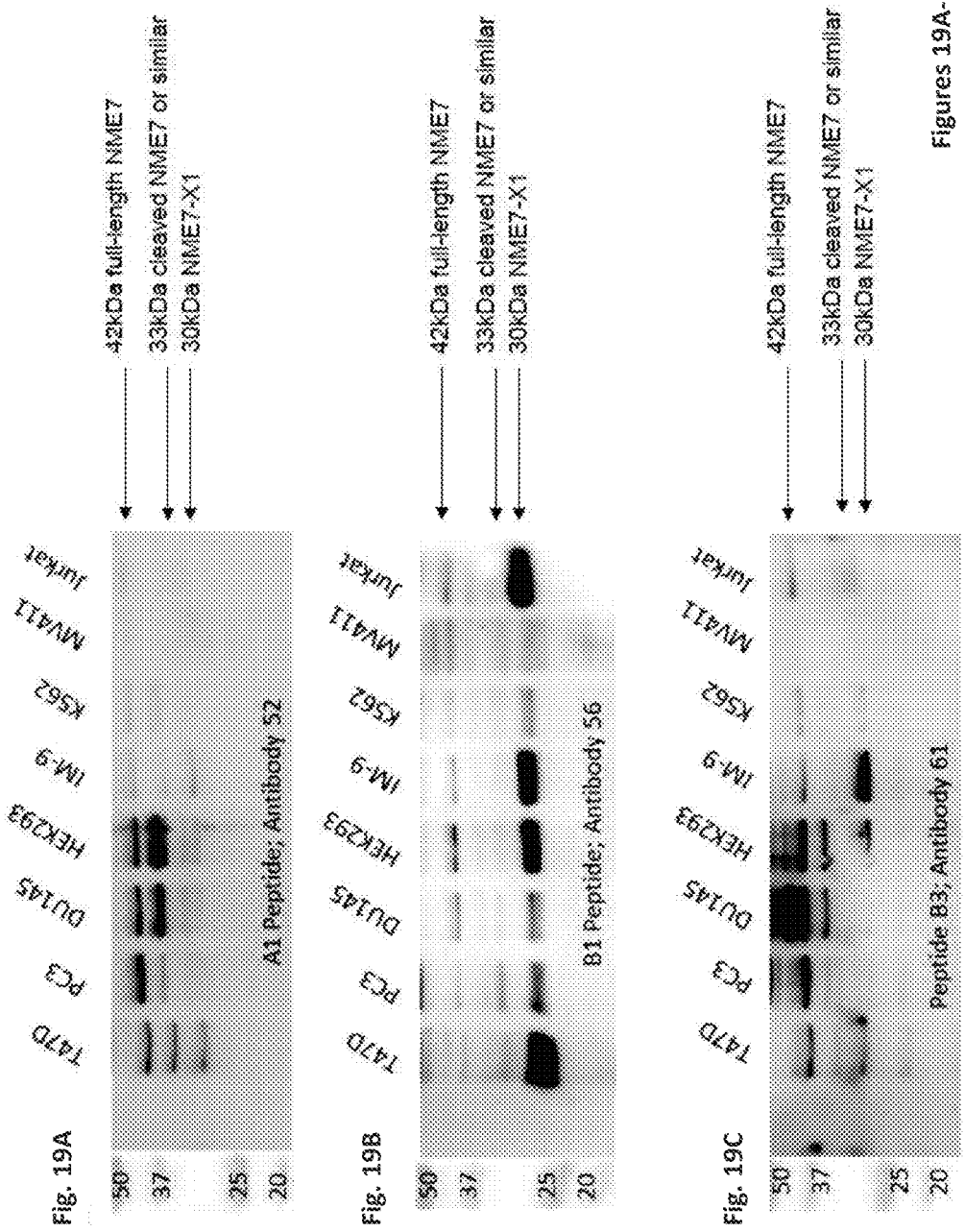
Figures 23A, 23B, 23C:
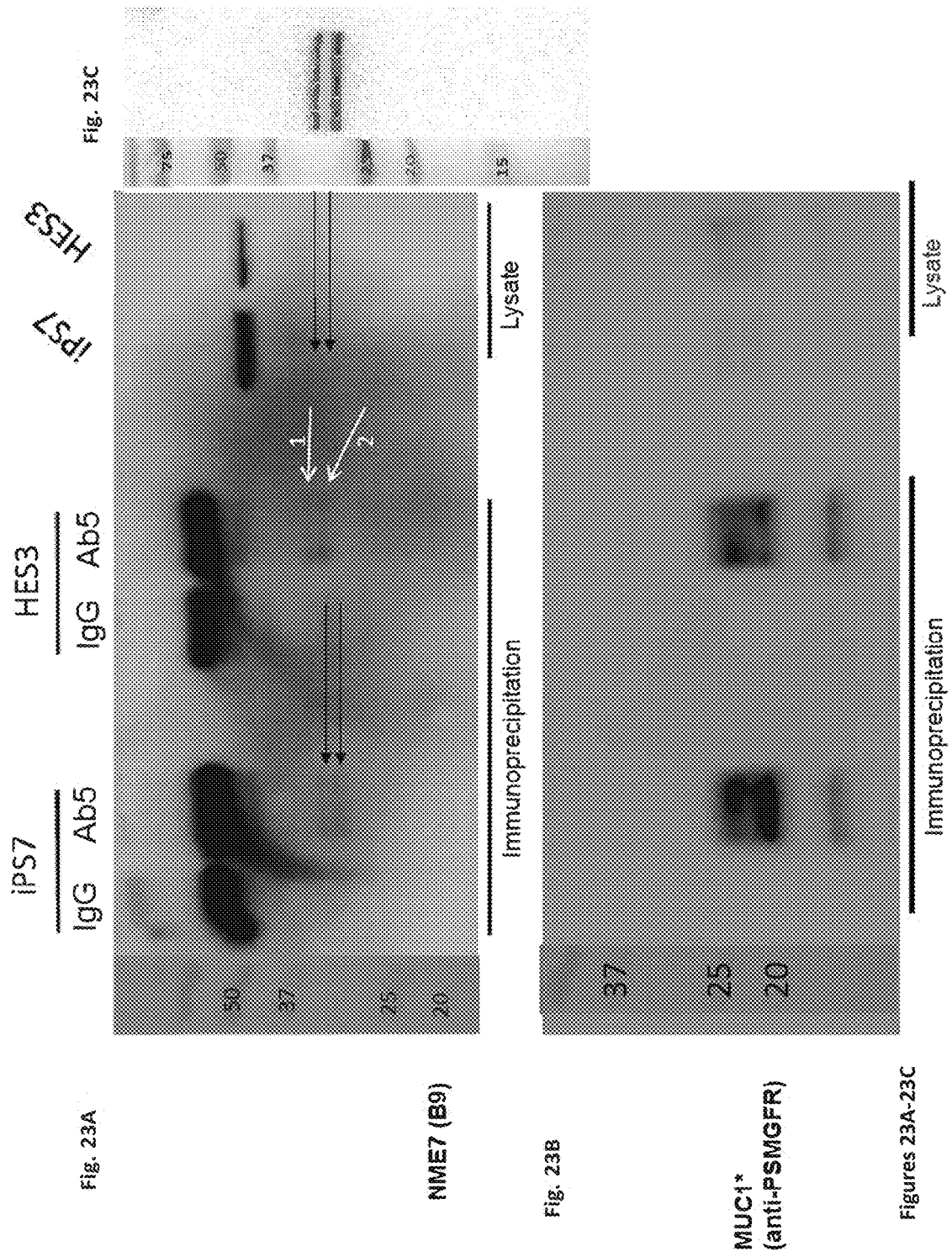
FIGS. 23A-23C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (FIG. 23A). Both cell types show unique NME7 bands at ~33 kDa and ~30 kDa. The gel was stripped and re-probed with an antibody against the extracellular domain of MUC1*, anti-PSMGFR (FIG. 23B), which shows that the NME7 species and MUC1* interact. A recombinant $NME7_{AB}$ and a recombinant NME7-X1 were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 23C).
Figures 40A, 40B, 40C:
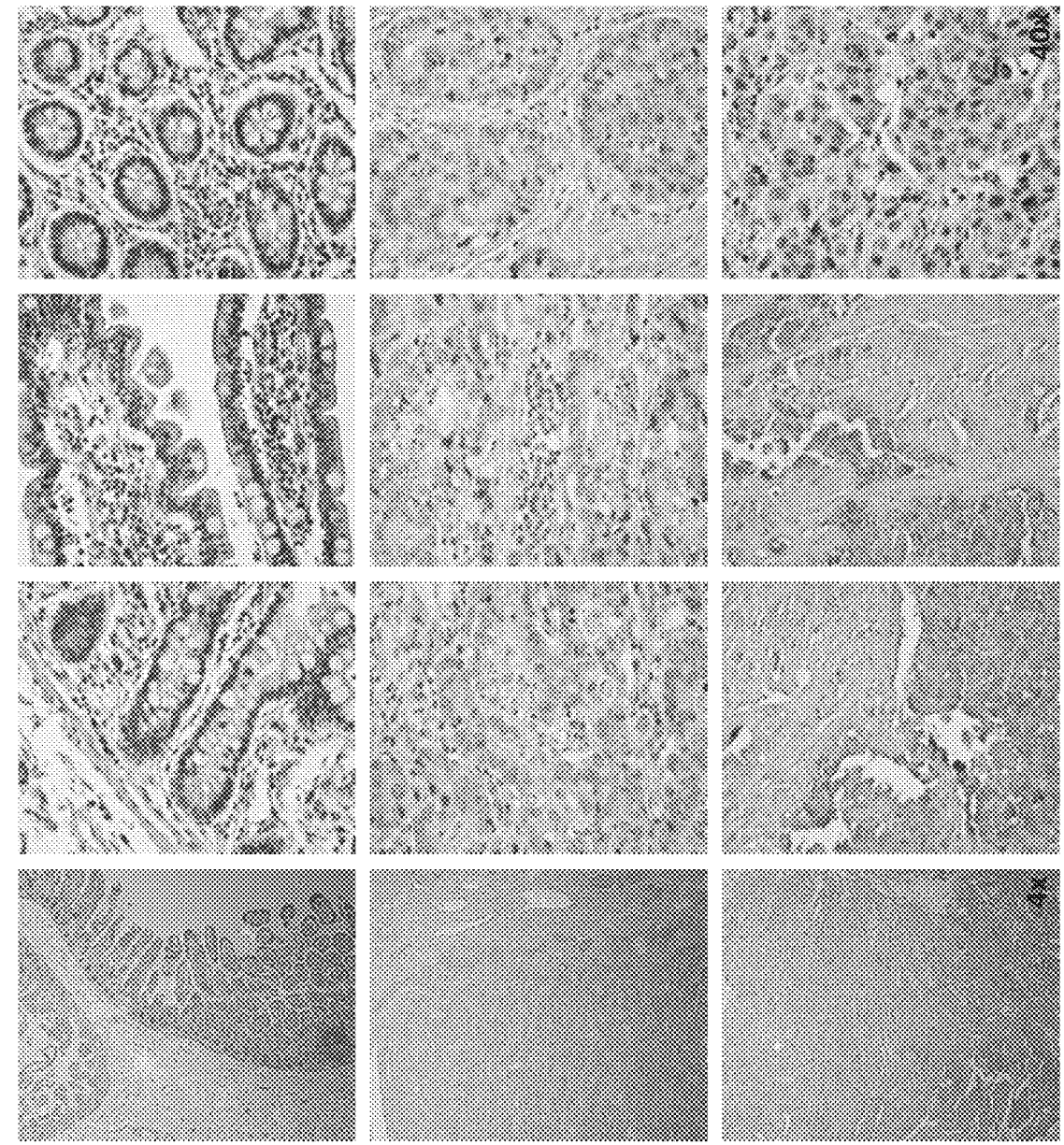
FIGS. 40A-40C shows human small intestine tissue specimens stained with an anti-NME7 antibody that binds to the B3 peptide. The figure shows lack of NME7 expression on normal tissues, increasing expression of NME7 as tumor grade and metastasis increase.
Figures 41A, 41B, 41C, 41D:
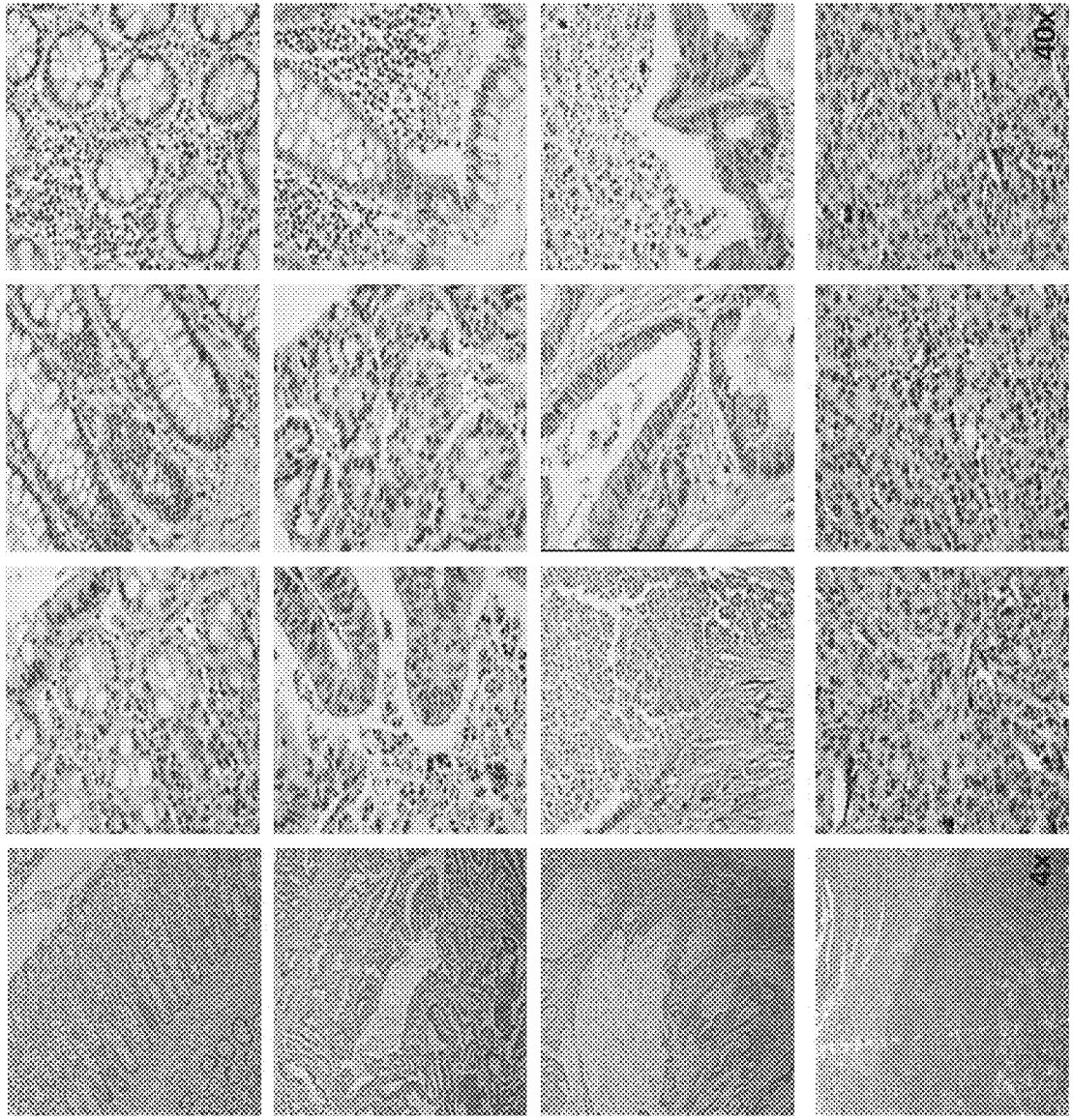
FIGS. 41A-41D show human colon tissue specimens stained with an anti-NME7 antibody that binds to the B3 peptide. The figure shows lack of NME7 expression on normal tissues, increasing expression of NME7 as tumor grade and metastasis increase.

The present inventors discovered that NME7 and NME7-X1 are highly expressed in early human stem cells and also in most cancer cells (FIG. 17, FIG. 18, FIG. 19A-FIG. 19F, FIG. 22, FIG. 23, FIG. 39, FIG. 40, FIG. 41, FIG. 47, FIG. 48, FIG. 17 shows a graph of RT-PCR measurement of the expression of NME7-X1 in a panel of human stem cells and cancer cells. FIG. 18 shows a graph of RT-PCR measurement of the expression of NME7, NME7a. NME7b and NME7-X1 in a panel of human stem cells and cancer cells, NME7a is full-length NME7, NME7b is missing a small portion of the DM10 domain, NME7-X1 is missing all of the DM10 domain and a small portion of the N-terminus of the first NDPK A domain. The bar labeled NME7 means that primers were used that detected both NME7a and NME7b. FIGS. 19A-19F show photographs of Western blots in which various cancer cell lines are probed for expression of NME7 species using antibodies generated by immunization with NME7 derived short peptides. FIG. 19A shows Western probed with antibody of the invention #52 which binds to NME7 derived peptide A1. FIG. 19B shows Western probed with antibody of the invention #56 which binds to NME7 derived peptide B1. FIG. 19C shows Western probed with antibody of the invention #61 which binds to NME7 derived peptide B3. FIGS. 22A-22E show photographs of Western blots of a co-immunoprecipitation experiment. T47D breast cancer cell extracts were incubated with an antibody against the MUC1 cytoplasmic tail. Ab-5, or a control antibody, IgG, and co-immunoprecipitated. The gels were blotted with two different commercially available anti-NME7 antibodies B9 (FIG. 22A) and CF7 (FIG. 22B). Both gels show unique NME7 bands at ~33 kDa and ~30 kDa. The gels were stripped and re-probed with an antibody against the extracellular domain of MUC1*, anti-PSMGFR (FIG. 22C) and (FIG. 22D), which shows that the NME7 species and MUC1* interact. A recombinant $NME7_{AB}$ and a recombinant NME7-X1 were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 22E). FIGS. 23A-23C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (FIG. 23A). Both cell types show unique NME7 bands at ~33 kDa and ~30 kDa. The gel was stripped and re-probed with an antibody against the extracellular domain of MUC1*, anti-PSMGFR (FIG. 23B), which shows that the NME7 species and MUC1* interact. A recombinant $NME7_{AB}$ and a recombinant NME7-X1 were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 23C). FIGS. 39A-39C shows human lung tissue specimens stained with an anti-NME7 antibody that binds to the B3 peptide. The figure shows lack of NME7 expression on normal tissues, increasing expression of NME7 as tumor grade and metastasis increase. FIGS. 40A-40C shows human small intestine tissue specimens stained with an anti-NME7 antibody that binds to the B3 peptide. The figure shows lack of NME7 expression on normal tissues, increasing expression of NME7 as tumor grade and metastasis increase. FIGS. 41A-41D show human colon tissue specimens stained with an anti-NME7 antibody that binds to the B3 peptide. The figure shows lack of NME7 expression on normal tissues, increasing expression of NME7 as tumor grade and metastasis increase. FIG. 47 and FIG. 48 show immunofluorescent photographs showing that NME7 is secreted by and binds to an extra cellular receptor of a wide variety of cancer cell lines.

Figure 1B:
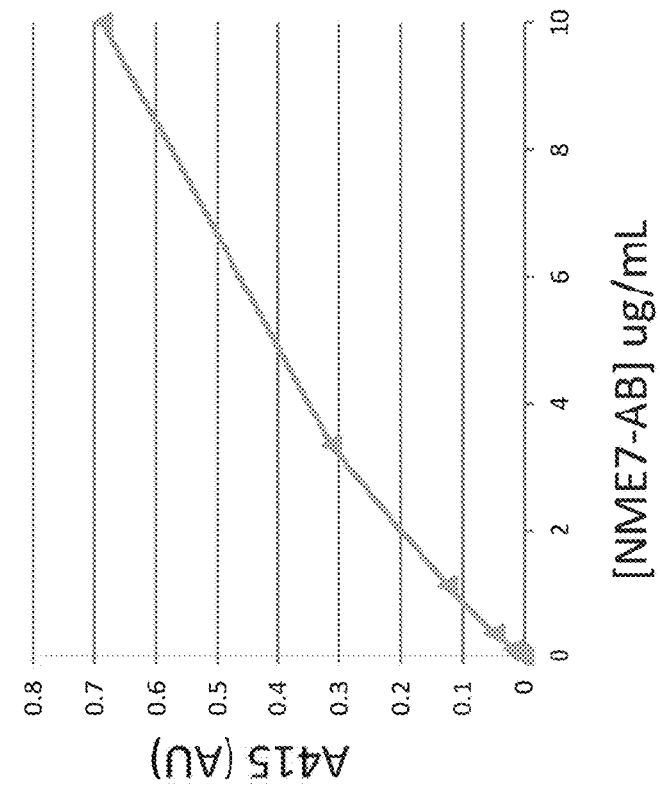

Further, we demonstrated that like NM23-H1, NME7 binds to and dimerizes the MUC1* growth factor receptor on both stem cells and cancer cells (FIG. 1). FIG. 5 shows a sequence alignment of NME1 and NME7 A and B domains.

The inventors recently discovered that NME7 is a primitive form of NME1 (NM23-H1) that is expressed in very early embryonic stem cells, NME7 is either not expressed at all, or is expressed at extremely low levels, in adult tissues. However, the inventors discovered that NME7 is expressed at high levels in cancerous cells and tissues and at even higher levels in metastatic cancer cells and tissues. A cleaved form of NME7 may be a secreted form allowing it to bind to and activate extracellular receptors. We detect full-length NME7, MW 42 kDa, as well as NME7 species that are approximately 33 kDa and 30 kDa. The 33 kDa and 30 kDa species are secreted from cancer cells. Western blots detect full-length NME7 in cell lysates, but smaller 30-33 kDa NME7 species in their conditioned media. Western blots probed with either an antibody that recognizes NME7 or an antibody that only recognizes the DM10 domain show that the lower molecular weight NME7 species that are secreted into the conditioned media are devoid of the DM10 domain. These data are consistent with the idea that naturally occurring NME7 species are comparable to the recombinant $NME7_{AB}$ we generated as they have nearly the same molecular weight, both are secreted and are both devoid of the 91 amino acids of the DM10 domain which may keep the protein retained within the cell.

We discovered a new NME7 isoform, NME7-X1, and also discovered that it is over-expressed in stem cells and cancer cells and is particularly over-expressed in prostate cancers (FIG. 17, FIG. 18, FIG. 19, and FIG. 22), NME7-X1, molecular weight ~30 kDa, comprises NME7 amino acids 125-376, whereas the recombinant $NME7_{AB}$, molecular weight ~33 kDa, that we generated spans amino acids 92-376, so includes 33 more N-terminal amino acids, NME7b spans amino acids 37-376 and is devoid of only 37 amino acids of the DM10 domain is also overexpressed in prostate cancers (FIG. 18). We generated a human recombinant NME7-X1 and show that it is the secreted 30 kDa NME7 species in cancer cells that runs just lower than a naturally occurring ~33 kDa NME7 species that appears to be a naturally occurring "$NME7_{AB}$-like" protein that is a cleavage product or alternative isoform.

We tested a panel of cancer cell lines and found that they express high levels of NME7 and lower molecular weight species that may be truncations similar to $NME7_{AB}$, such as $NME7_{AB}$-like protein, or alternate isoforms such as NME7-X1.

Whereas NM23-H1 (aka NME1) has to be a dimer, NME7 is a monomer with two binding sites for MUC1* extracellular domain. We generated a recombinant human NME7 that is devoid of the DM10 domain, which we call NME7$_{AB}$. A sandwich ELISA binding assay that shows that a recombinant NME7$_{AB}$ simultaneously binds to two PSMGFR peptides wherein the extracellular domain of MUC1* is comprised of most or all of the PSMGFR sequence (FIG. 1). In a nanoparticle binding assay, NME7 was also shown to be able to bind to and dimerize the PSMGFR portion of the MUC1* extracellular domain.

Agents that disable NME7, block its interaction with its binding partners or suppress its expression are potent anti-cancer therapeutics. Such agents may be antibodies, small molecules or nucleic acids. They may act on NME7 directly, on molecules that regulate NME7 expression, or on enzymes that cleave NME7 to cancer-promoting forms.

We discovered that like NM23-H1 dimers, a recombinant NME7$_{AB}$ monomer was fully able to support pluripotent human stem cell growth in the absence of any other growth factor, cytokine or serum. Competitively inhibiting the interaction between NME7 and MUC1* extracellular domain, comprised essentially of the PSMGFR sequence, induced differentiation of stem cells, showing that it is the interaction of NME7 and MUC1* that promotes stem cell growth and inhibits differentiation.

Figure 12:
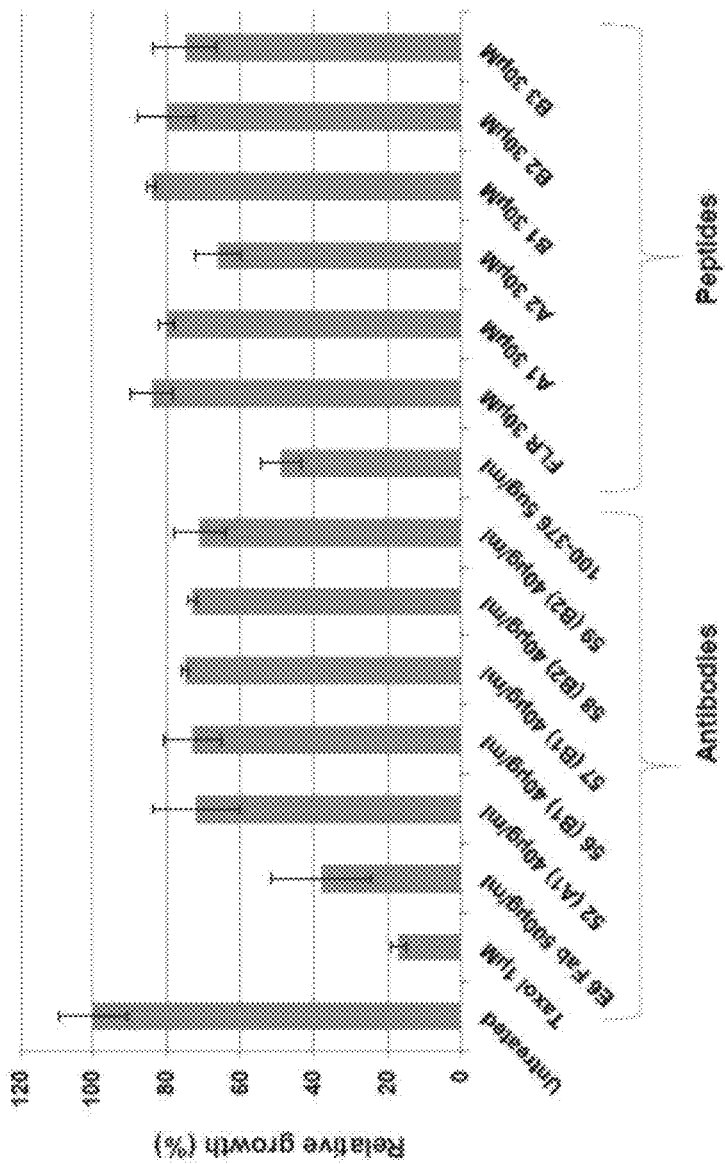
FIG. 12 shows a graph of a cancer cell growth experiment in which breast cancer cells were grown in the presence or absence of NME7 antibodies or short peptides derived from NME7, which were used to generate or select the antibodies. In addition, an antibody generated by immunization with nearly the entire $NME7_{AB}$ peptide, amino acids 100-376, was shown to inhibit cancer cell growth.
Figure 13:
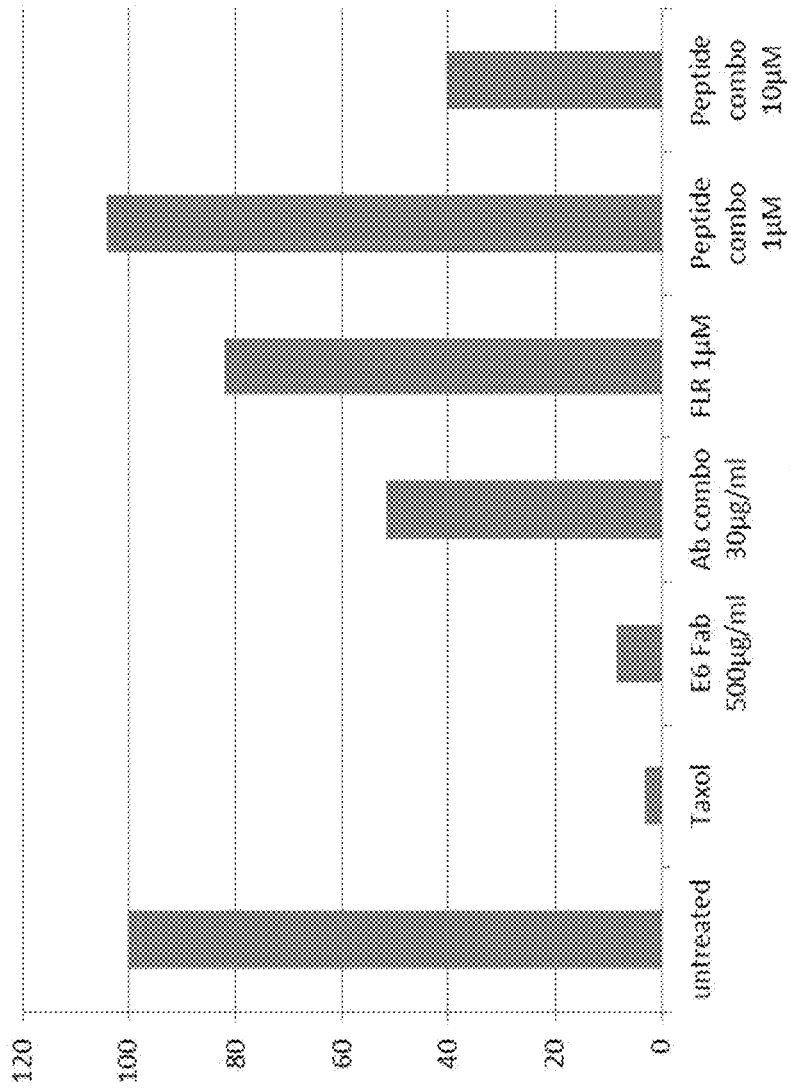
FIG. 13 shows a graph of a cancer cell growth experiment in which breast cancer cells were grown in the presence or absence of combinations of NME7 antibodies or combinations of the short peptides derived from NME7, which were used to generate or select the antibodies. Both antibodies as well as their immunizing $NME7_{AB}$ peptides inhibited growth of cancer cells.
Figure 15A:
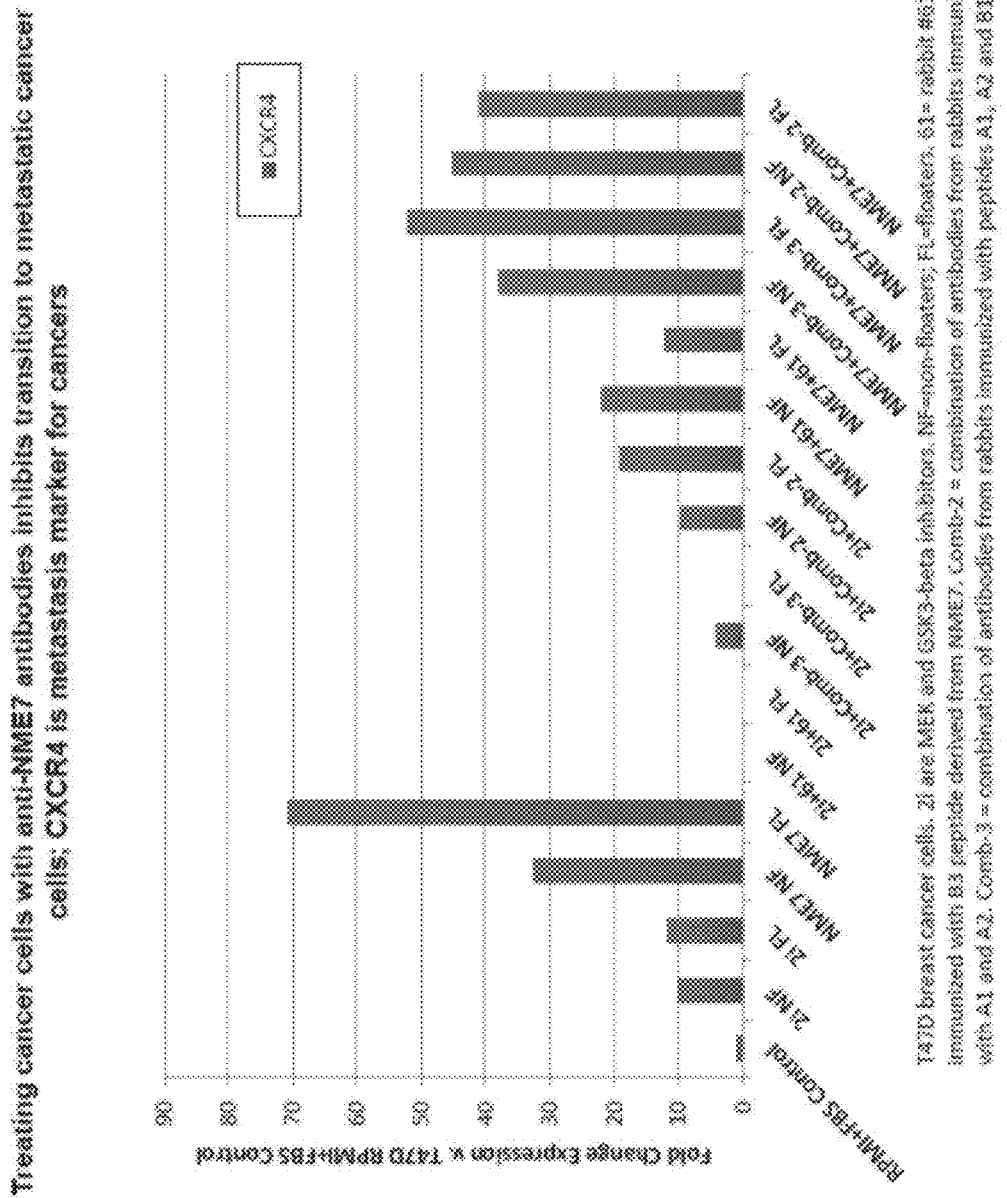
FIGS. 15A-15C show graphs of RT-PCR measurements of expression of CXCR4 and other metastatic markers in T47D breast cancer cells that were grown in either $NME7_{AB}$ or 2i inhibitors, each of which transform cancer cells to a more metastatic state, and the inhibitory effect of anti-NME7 antibodies on the metastatic transformation.
Figure 15B:
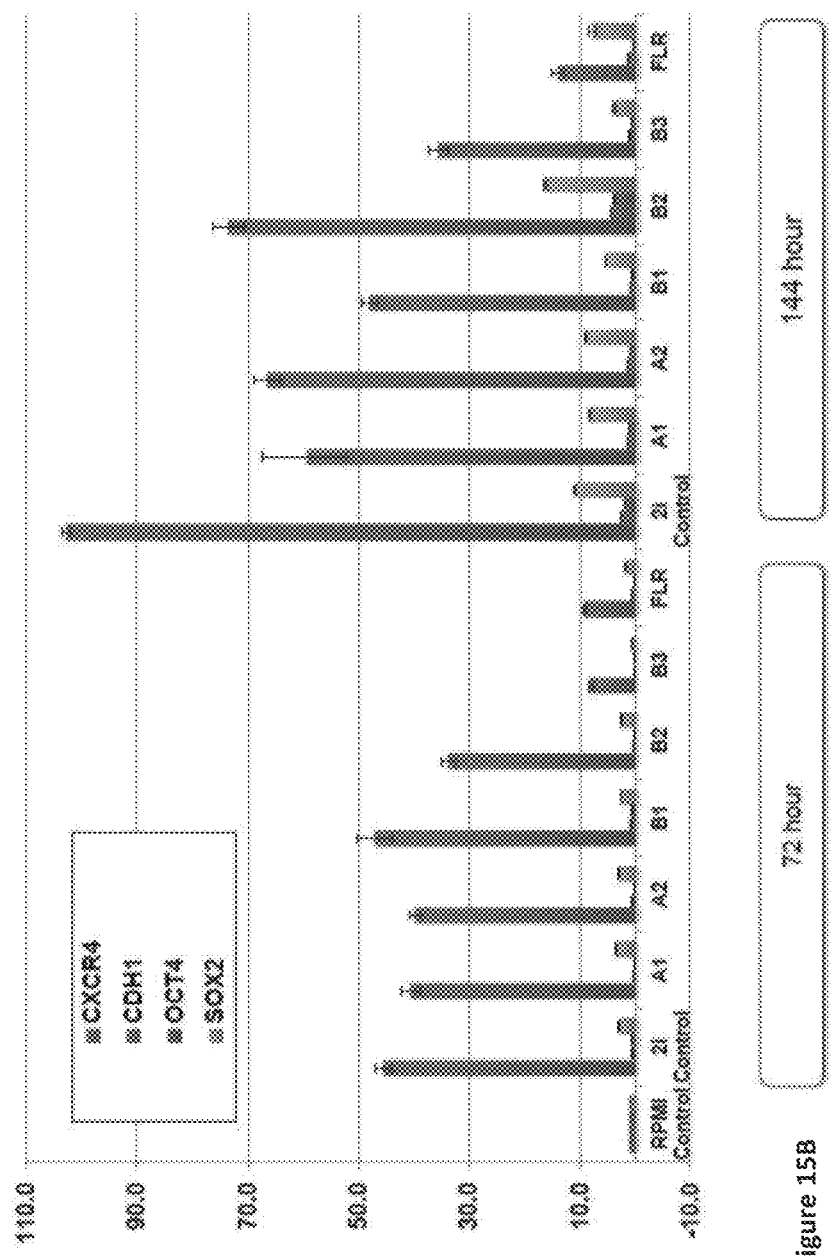
Figure 15C:
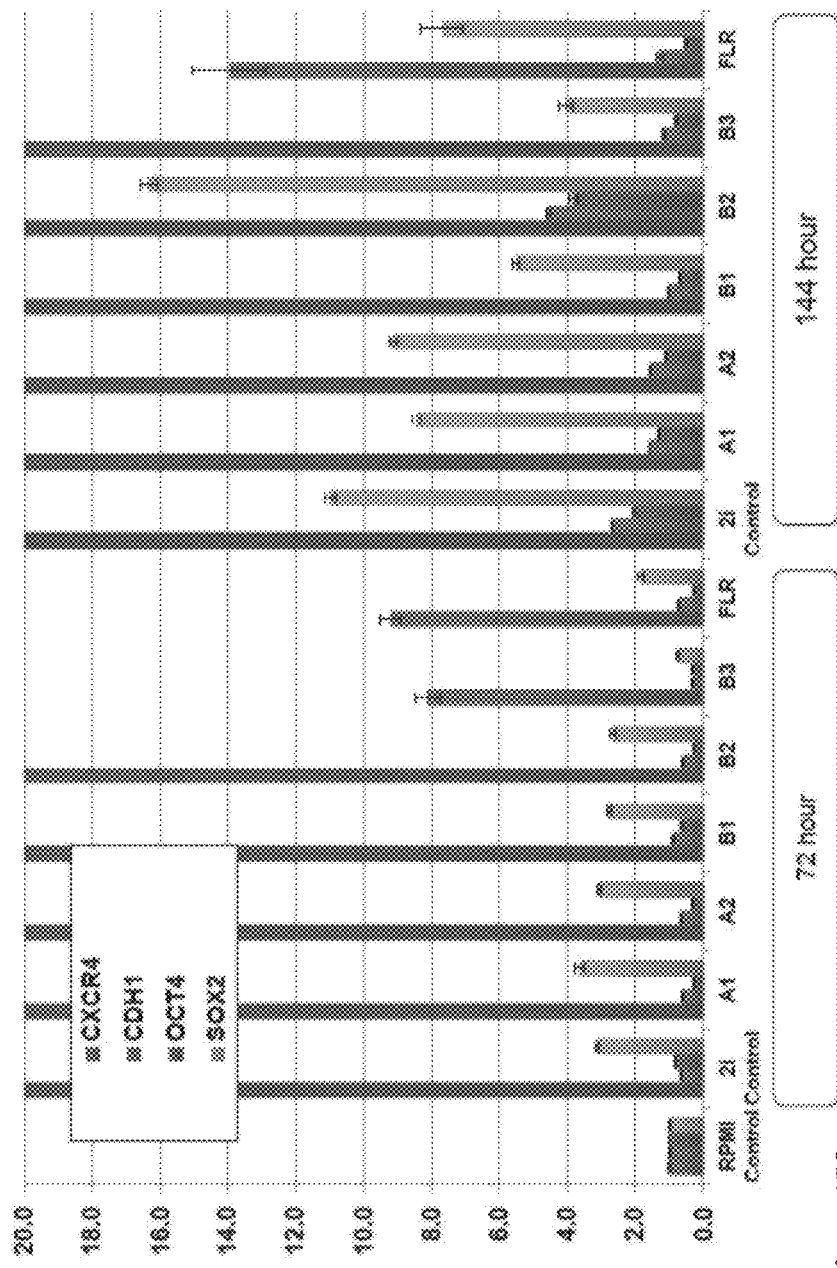
Figure 16:
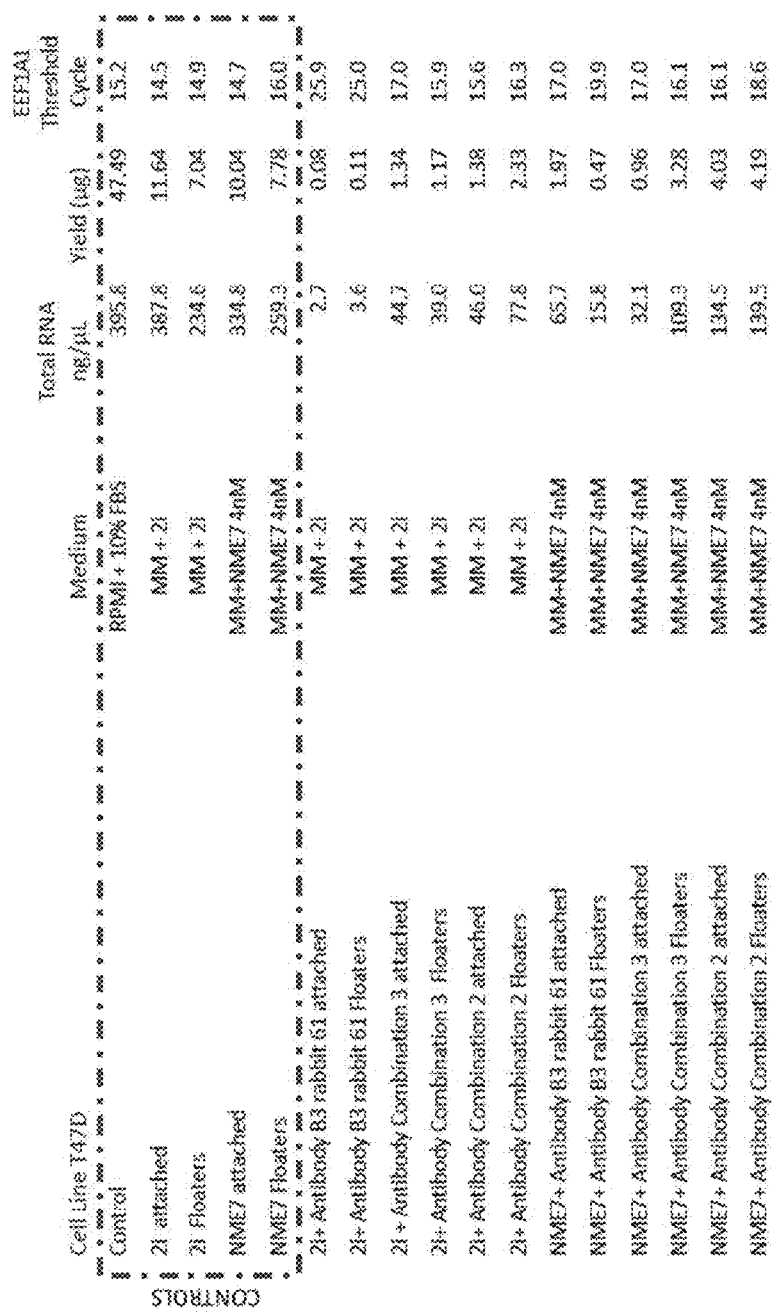
FIG. 16 shows a table of recorded RNA levels in samples that were used for RT-PCR measurement of CXCR4 in FIG. 31 as well as the threshold cycle number for CXCR4 expression as well as for the control housekeeping gene.
Figure 17:
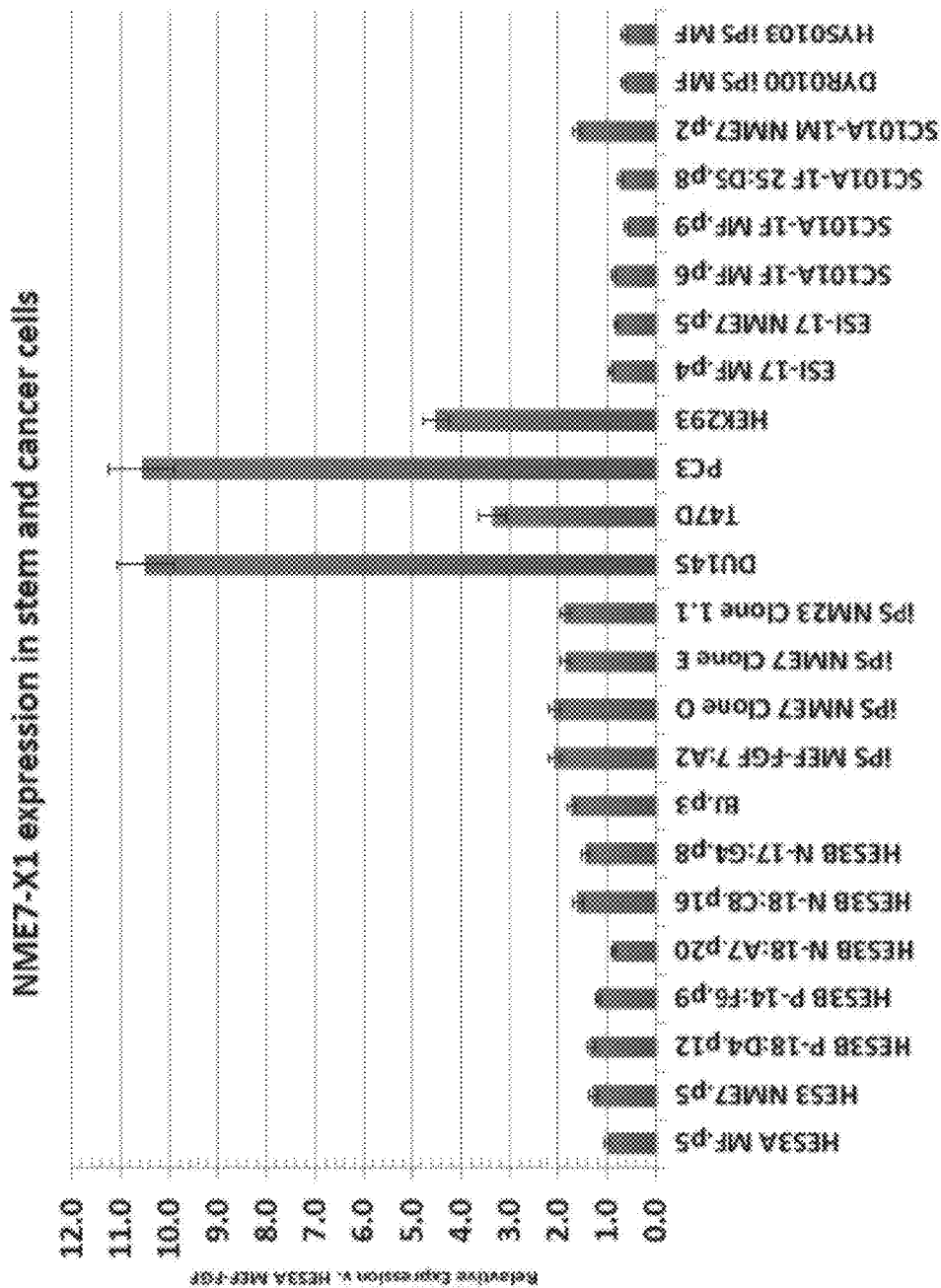
FIG. 17 shows a graph of RT-PCR measurement of the expression of NME7-X1 in a panel of human stem cells and cancer cells.
Figure 29:
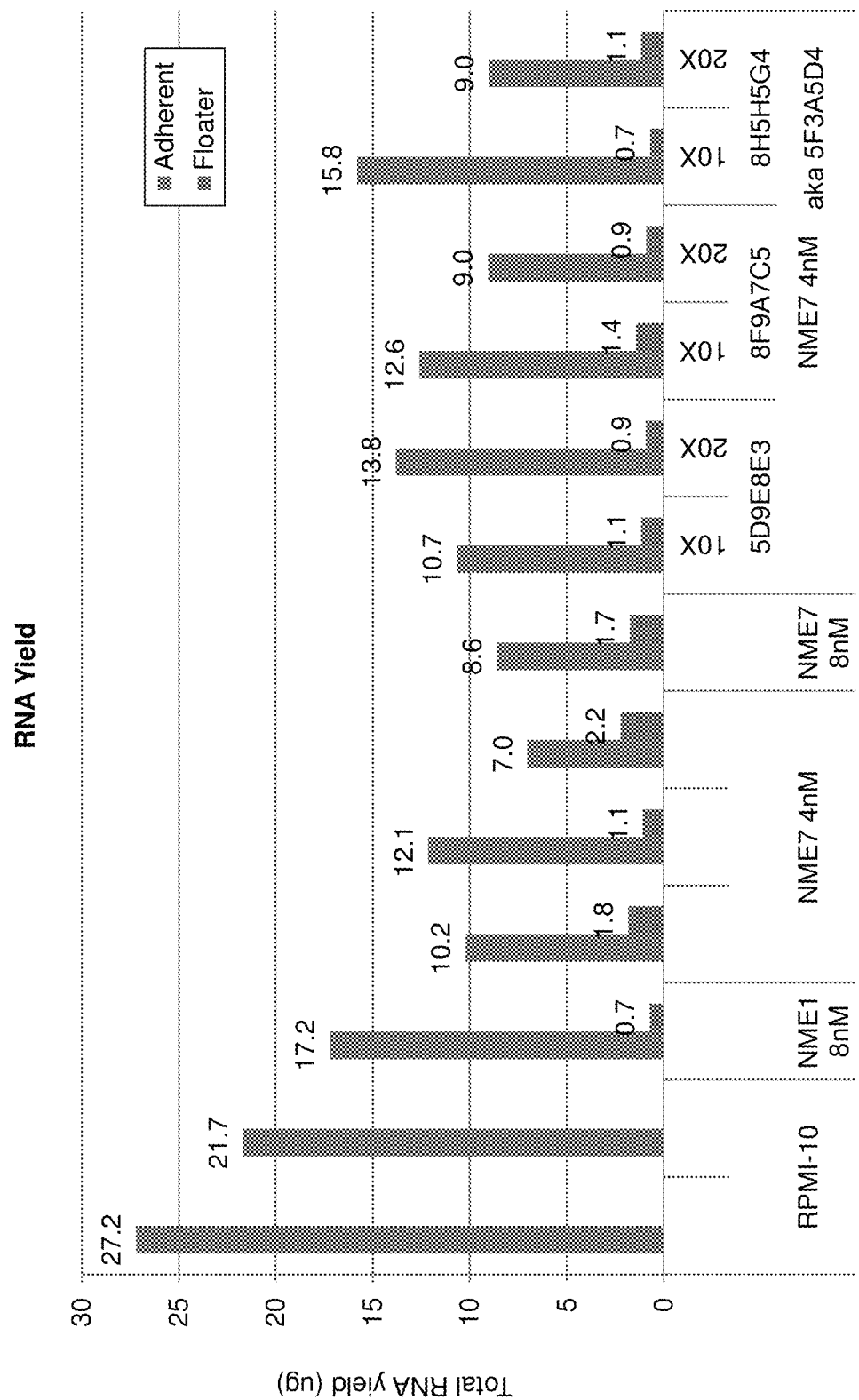
FIG. 29 shows a graph of the amount of RNA present in samples of T47D breast cancer cells were cultured in either their normal recommended media. RMPI, serum-free media containing only NME7$_{AB}$ as the growth factor at 4 nM, which is optimal, or 8 nM, or serum-free media containing only NME1 S120G dimers as the growth factor at 8 nM: because NME1 is a homodimer and NME7$_{AB}$ is a monomer comprised of two pseudo-identical domains, 8 nM NME1 is the molar equivalent of 4 nM NME7$_{AB}$. The cancer cells were cultured in the presence or absence of anti-NME7 B3 antibodies. In this experiment, floating cells were separated from the adherent cells and analyzed separately. Significant data argues that the floater cells are the cancer stem cells. An increase or decrease in the amount of RNA in a sample argues that an agent increased or decreased, respectively, the number of cells in a given population that were generated.
Figure 30:
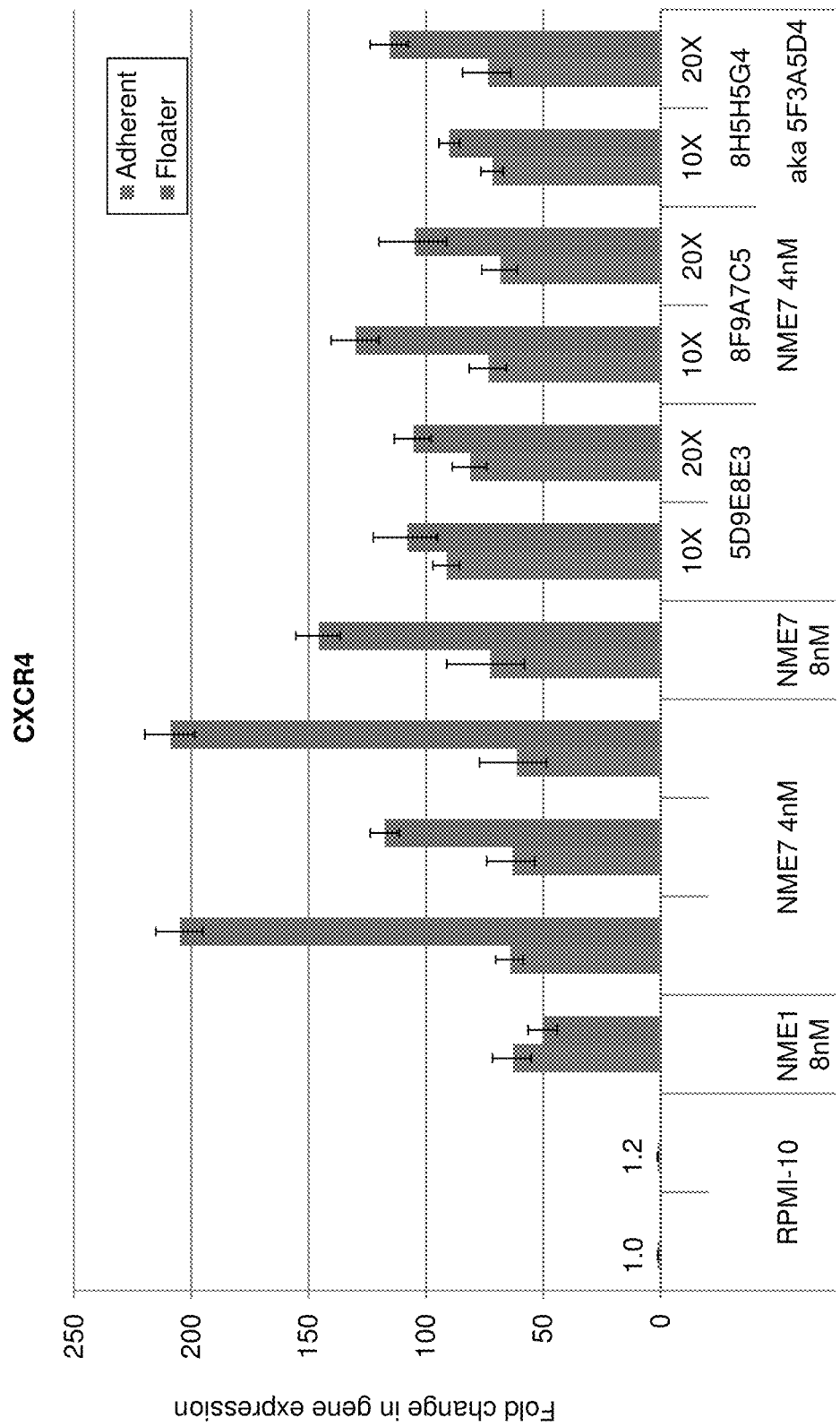
FIG. 30 shows a graph of a PCR measurement of metastatic marker CXCR4 in T47D breast cancer cells that were cultured in either their normal recommended media, RPMI, serum-free media containing only NME7$_{AB}$ as the growth factor at 4 nM, which is optimal, or 8 nM, or serum-free media containing only NME1 S120G dimers as the growth factor at 8 nM; because NME1 is a homodimer and NME7$_{AB}$ is a monomer comprised of two pseudo-identical domains, 8 nM NME1 is the molar equivalent of 4 nM NME7$_{AB}$. The cancer cells were cultured in the presence or absence of anti-NME7 B3 antibodies. In this experiment, floating cells were separated from the adherent cells and analyzed separately. Significant data argues that the floater cells are the cancer stem cells. As can be seen in the figure, growth in NME7$_{AB}$ media increases CXCR4 in the floater population of cells and anti-NME7 B3 antibodies decreased its expression, arguing that anti-NME7 antibodies decreased generation of cancer stem cells.
Figure 31:
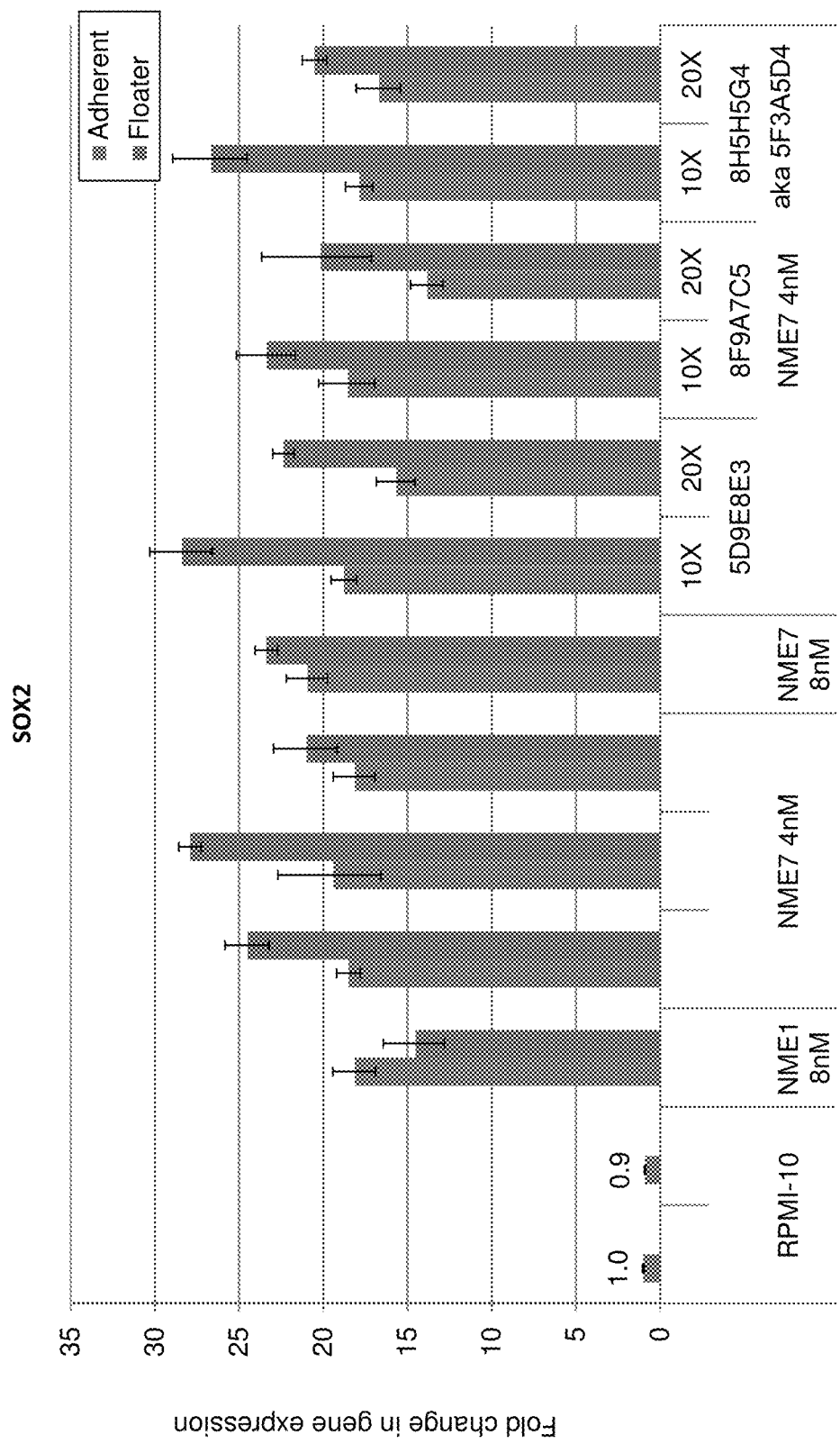
FIG. 31 shows a graph of a PCR measurement of stem cell marker and metastatic marker SOX2 in T47D breast cancer cells that were cultured in either their normal recommended media. RMPI, serum-free media containing only NME7$_{AB}$ as the growth factor at 4 nM, which is optimal, or 8 nM, or serum-free media containing only NME1 S120G dimers as the growth factor at 8 nM: because NME1 is a homodimer and NME7$_{AB}$ is a monomer comprised of two pseudo-identical domains, 8 nM NME1 is the molar equivalent of 4 nM NME7$_{AB}$. The cancer cells were cultured in the presence or absence of anti-NME7 B3 antibodies. In this experiment, floating cells were separated from the adherent cells and analyzed separately. Significant data argues that the floater cells are the cancer stem cells. As can be seen in the figure, growth in NME7$_{AB}$ media increases SOX2 expression in the floater population of cells and anti-NME7 B3 antibodies decreased its expression, arguing that anti-NME7 antibodies decreased generation of cancer stem cells.

Next, we showed that NME7$_{AB}$ alone is also able to fully support human cancer cell growth, NME7$_{AB}$, when added to regular cancer cell growth media, stimulated cancer cell growth and in particular the growth of MUC1-positive and MUC1*-positive cancer cells. Inhibiting the interaction of NME7 with MUC1* inhibited cancer cell growth. Blocking the MUC1* growth factor receptor with an anti-MUC1* Fab potently inhibited cancer cell growth. Similarly, antibodies that bind to NME7 inhibit cancer cell growth. In one example of inhibition of cancer growth by anti-NME7 antibody, the polyclonal antibody was generated from immunizing an animal with the portion of NME7 that spans amino acids 100-376 (FIG. 12 and FIG. 13). However, we found that antibodies generated from immunizing with shorter peptides from NME7$_{AB}$ or from NME7-X1 also inhibit cancer growth. In particular, they inhibit the growth of MUC1 and MUC1*-positive cancers. Anti-NME7 antibodies of the invention inhibited the formation of the non-adherent "floater" cells that are able to form tumor spheres and which can travel from primary tumor and metastasize (FIG. 14, FIG. 16, FIG. 29). Anti-NME7 antibodies of the invention inhibited the upregulation of metastatic and stem cell markers, now believed to also be characteristic of metastasis (FIG. 15, FIG. 30, FIG. 31, FIG. 32). NME7 Causes Cancer Metastasis The inventors further discovered that culturing cancer cells in a minimal media containing NME7$_{AB}$ induced a wide variety of cancer cells to become transformed to a more metastatic state. Evidence of this induced metastatic state include a change from adherent cell growth to non-adherent cell growth, aka, "floater" cells and accompanying up-regulation of specific metastatic markers that were especially upregulated in the floating cells. These metastatic markers that are upregulated after culture in NME7$_{AB}$ include but are not limited to CXCR4, CHD1 aka E-cadherin, MUC1, ALDH1, CD44, and pluripotent stem cell markers such as OCT4, SOX2, NANOG, KLF2/4, FOXa2, TBX3, ZEB2 and c-Myc (FIG. 2, FIG. 3, FIG. 20, FIG. 49, FIG. 51). Cancer cells cultured in NME7$_{AB}$ had dramatically higher engraftment rates when xenografted into test animals, which were over 90%. In addition, very low numbers of implanted cancer cells formed tumors in the test animals, which is evidence that NME7$_{AB}$ had transformed them into cancer stem cells also known as metastatic cancer cells. Cancer cells cultured in NME7$_{AB}$ and injected into the tail vein of NOD/SCID/GAMMA mice bearing estrogen release pellets metastasized in animals from low numbers of cells compared to the parent cells, grown in regular media (FIG. 33-FIG. 38). Because cancer cells make either an NME7 cleavage product or alternative isoform that is essentially equivalent to NME7$_{AB}$, the methods described here are not limited to using NME7$_{AB}$; other NME7 species could work as well. For example, we discovered another NME7 isoform, NME7-X1, is expressed by cancer cells. It is identical to our recombinant NME7$_{AB}$ with the exception that the X1 isoform is missing 33 amino acids from the N-terminus, NME7-X1 is expected to function like NME7$_{AB}$. "NME7$_{AB}$-like" protein has also been detected in cancer cells as being about 33 Da species.

We note that the inventors' previous work showed that NME7$_{AB}$ alone is able to revert human stem cells to an earlier naïve state. We discovered that culturing cancer cells in the presence of other reagents that make stem cells revert to a more naïve state, makes the cancer cells transform to a more metastatic state. We demonstrated that culturing cancer cells NME7$_{AB}$ (FIG. 2), or in dimeric NME1 (FIG. 3), or "2i" inhibitors (FIG. 4), are each able to transform regular cancer cells into metastatic cancer cells, which are also called cancer stem cells "CSCs" or tumor initiating cells "TICs". However, NME7$_{AB}$ induced cancer cells to enter a more metastatic state better than NME1, also known as NM23-H1, which was better than 2i.

2i is the name given to two biochemical inhibitors that researchers found made human stem cells revert to a more naïve state. 2i are MEK and GSK3-beta inhibitors PD0325901 and CHIR99021, which are added to culture medium to final concentrations of about 1 mM and 3 mM, respectively, NME7$_{AB}$ and NME7-X1 are at a final concentration of about 4 nM when added to separate batches of minimal medium to make cancer cells transform to metastatic cells, although lower and higher concentrations also work well in the range of about 1 nM to 16 nM. Human or bacterial NME1 dimers are used at a final concentration of 4 nM to 32 nM, with 16 nM typically used in these experiments, wherein the human NME bears the S120G mutation. Lower concentrations may be required if using wild type. It is not intended that these exact concentrations are important. It is important that the NME1 proteins are dimers and the range of concentrations over which this happens is in the low nanomolar range although certain mutations allow higher concentrations to remain as dimers. Similarly, the concentrations of NME7 proteins can vary, NME7$_{AB}$ and NME7-X1 are monomers and concentrations used to transform cancer cells to metastatic cells should allow the proteins to remain as monomers.

In addition to NME7, NME7$_{AB}$, NME7-X1, and the 2i inhibitors MEKi and GSK3i, other reagents and inhibitors have been shown by others to cause stem cells to revert to a more naïve state. These inhibitors, "i's" include JNKi, p38i, PKCi, ROCKi, BMPi, BRAFi, SRCi as well as growth factors activing and LIF (Gafni et al 2013, Chan et al 2013, Valamehr et al 2014, Ware et al 2014, Theunissen et al 2014). These reagents can also be used to make cancer cells progress to a more metastatic state. Cells that have been induced to transform to a more metastatic state using any single factor or combination of the inhibitors or growth factors, that make stem cells revert to a more naïve state, can then be used as discovery tools to identify or test drugs to treat or prevent cancer metastasis.

Various molecular markers have been proposed as being indicators of metastatic cancer cells. Different cancer types may have different molecules that are up-regulated. For example, the receptor CXCR4 is up-regulated in metastatic breast cancers while E-cadherin, also known as CHD1, is up-regulated more in metastatic prostate cancers. In addition to these specific metastasis markers, typical markers of pluripotency such as OCT4, SOX2, NANOG, and KLF4 are up-regulated as cancers become metastatic. The starting cancer cells and the later metastatic cancer cells are assayed by PCR to measure expression levels of these genes. We demonstrated that these cancer cells, cultured in agents such as $NME7_{AB}$ that cause them to be transformed to a more metastatic state, as evidenced by increased expression of metastatic markers and pluripotent stem cell markers, function as metastatic cancer cells.

A functional test of whether or not a population of cancer cells is metastatic is to implant very low numbers. e.g. 200, of the cells in immuno-compromised mice and see if they develop into a tumor. Typically 5-6 million cancer cells are required to form a tumor in an immuno-compromised mouse. We showed that as few as 50 of the NME-induced metastatic cancer cells formed tumors in mice. In addition, mice that were injected throughout the test period with human $NME7_{AB}$, NME1, or NME7-X1 developed remote metastases.

In one particular experiment. T47D human breast cancer cells were cultured in standard RPMI media for 14 days with media changes every 48 hours and passed by trypsinization when approximately 75% confluent. The cells were then plated into 6-well plates and cultured in minimal stem cell media (see Example 1) that was supplemented with 4 nM $NME7_{AB}$ B. Media was changed every 48 hours. By about Day 4, some cells become detached from the surface and float. Media is carefully changed so as to retain the "floaters" as these are the cells that have the highest metastatic potential as evidence by RT-PCR measurement of metastatic markers. On Day 7 or 8, the floaters are harvested and counted. Samples are retained for RT-PCR measurement. The key marker measured is CXCR4, which is up-regulated by 40-200-times after being briefly cultured in $NME7_{AB}$.

The freshly harvested floater metastatic cells were xenografted into the flank of female nu/nu athymic mice that have been implanted with 90-day slow release estrogen pellets. Floater cells were xenografted with 10,000, 1,000, 100 or 50 cells each. Half of the mice in each group of 6 were also injected daily with 32 nM $NME7_{AB}$ near the original implantation site. The parent T47D cells that were cultured in RPMI media without $NME7_{AB}$ were also implanted into mice at 6 million. 10,000 or 100 as controls. Mice implanted with the NME7-induced floater cells developed tumors even when as few as 50 cells were implanted. Mice that were implanted with the floater cells and that received daily injections of $NME7_{AB}$ also developed remote tumors or remote metastases in various organs. 11 out of the 12 mice, or 92%, that were injected with human $NME7_{AB}$ after implantation of the $NME7_{AB}$ cultured cancer cells developed tumors at the injection site. Only 7 out of the 12 mice, or 58%, that were not injected with human $NME7_{AB}$ after implantation developed tumors. 9 out of the 11 mice, or 82%, that exhibited tumors and were injected with human $NME7_{AB}$ developed multiple tumors remote from the injection site. None of the mice that were not injected with $NME7_{AB}$ developed multiple, visible tumors.

After sacrifice. RT-PCR and Western blots showed that the remote bumps on the mice injected with $NME7_{AB}$ were indeed human breast tumors. Similar analysis of their organs showed that in addition to remote bumps, mice had randomly metastasized to the liver and lung with human breast cancer characteristic of the human breast cancer cells that were implanted. As expected, only the mice implanted with 6 million cells grew tumors.

Figure 2:
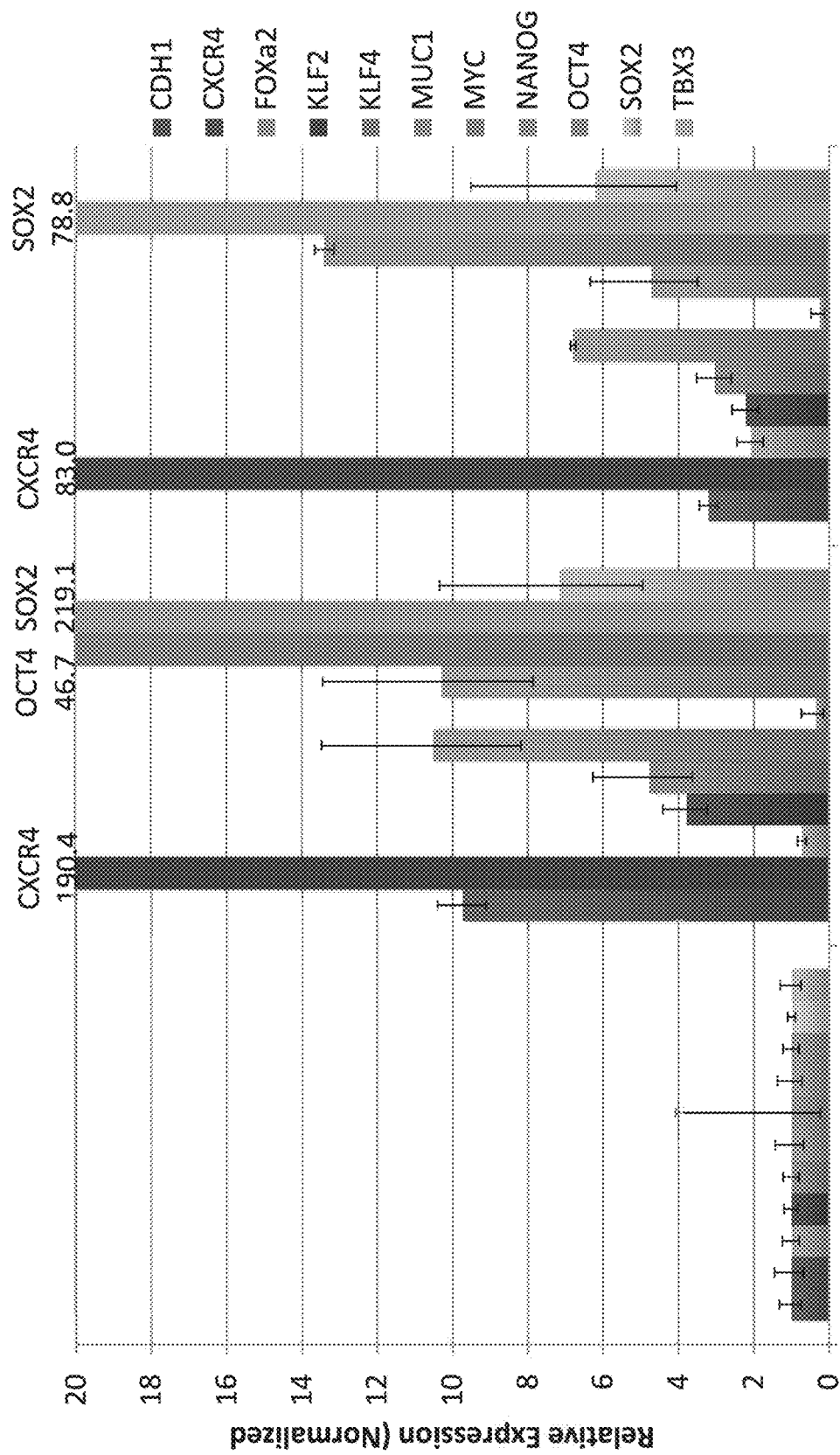
FIG. 2 is a graph of RT-PCR measurements of gene expression for stem cell markers and cancer stem cell markers for T47D cancer cells after being cultured in traditional media or a media containing NME7, wherein cells that became non-adherent (floaters) were analyzed separate from those that remained adherent.

We have demonstrated that human recombinant $NME7_{AB}$ is comparable in size and sequence to NME7-X1 and to a 30-33 kDa NME7 cleavage product. We have shown that $NME7_{AB}$ promotes cancerous growth and causes cancer cells to accelerate to the highly metastatic cancer stem cell (CSC) state also called tumor initiating cells (TIC). Therefore, we conclude that NME7-X1 and an NME7 cleavage product that removes the DM10 domain also promote cancerous growth and causes cancer cells to accelerate to the highly metastatic cancer stem cell (CSC) state also called tumor initiating cells (TIC). In one example, $NME7_{AB}$ Was added to cancer cells in a serum-free media and in the absence of any other growth factors or cytokines. Within 7-10 days, the cancer cells had reverted to the highly metastatic CSCs/TICs as evidenced by more than 100-fold increase in the expression of molecular markers such as CXCR4, which are indicators of metastatic cancer cells. In one example, T47D breast cancer cells were cultured in either standard RPMI media or in a Minimal Stem Cell Media (Example 1) to which was added recombinant $NME7_{AB}$ to a final concentration of 16 nM. After 10 days cells were collected and analyzed by RT-PCR for expression of molecular markers of CSCs which were elevated by 10-200-times (FIG. 2). This is a specific, detailed example of how we transformed one cancer cell type to a more metastatic state. It is not intended that the invention be limited by these details as there are a range of cancer cells that are transformed in this way, a range of reagents that revert stem cells to a more naïve state that also progress cancer cells to a more metastatic state and a range of concentrations over which the added reagents transform the cancer cells. Other types of cancer cells have required longer periods of culture in $NME7_{AB}$ for dramatic upregulation of metastatic markers and ability to form tumors from very low numbers of cancer cells implanted. For example, prostate cancer cells cultured in $NME7_{AB}$, 2i, human NME1 or bacterial NME1 that has high homology to human NME1 or human NME7 showed dramatic increase in metastatic markers after 2-3 passages.

Metastasis marker CXCR4 is particularly elevated in metastatic breast cancer cells, while CHD1 is particularly elevated in metastatic prostate cancer. Here we show that pluripotent stem cell markers such as OCT4, SOX2, NANOG, KLF2/4 and TBX3 are also up-regulated when cancer cells transform to more metastatic cells.

Figure 3:
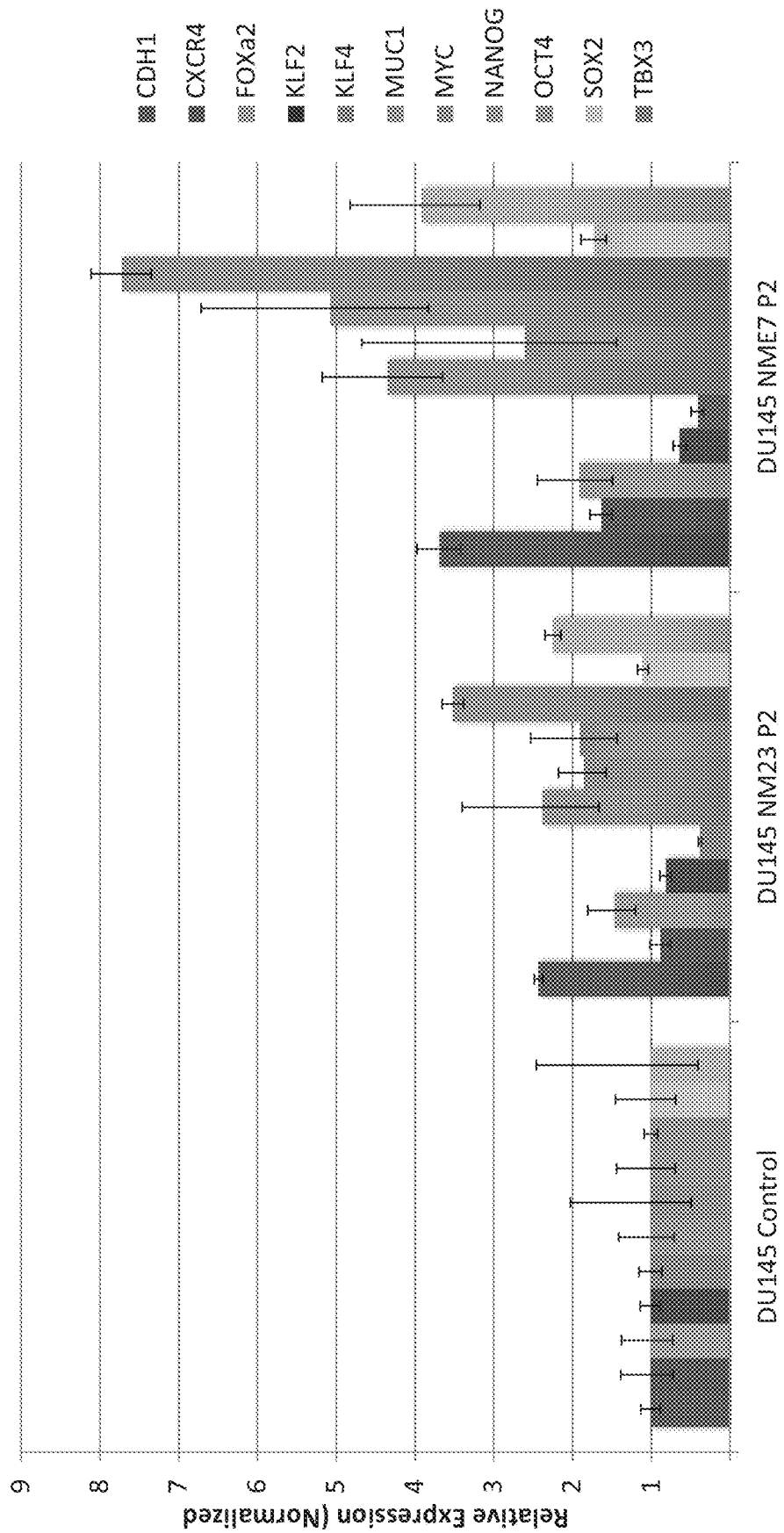
FIG. 3 is a graph of RT-PCR measurements of gene expression for a variety of stem and putative cancer stem cell markers for DU145 prostate cancer cells. Cells were cultured either in traditional media or a media containing NME1 dimers ("NM23") or NME7 ($NME7_{AB}$). Rho kinase inhibitor was not used because by passage 2, cells remained adherent.
Figures 20A, 20B:
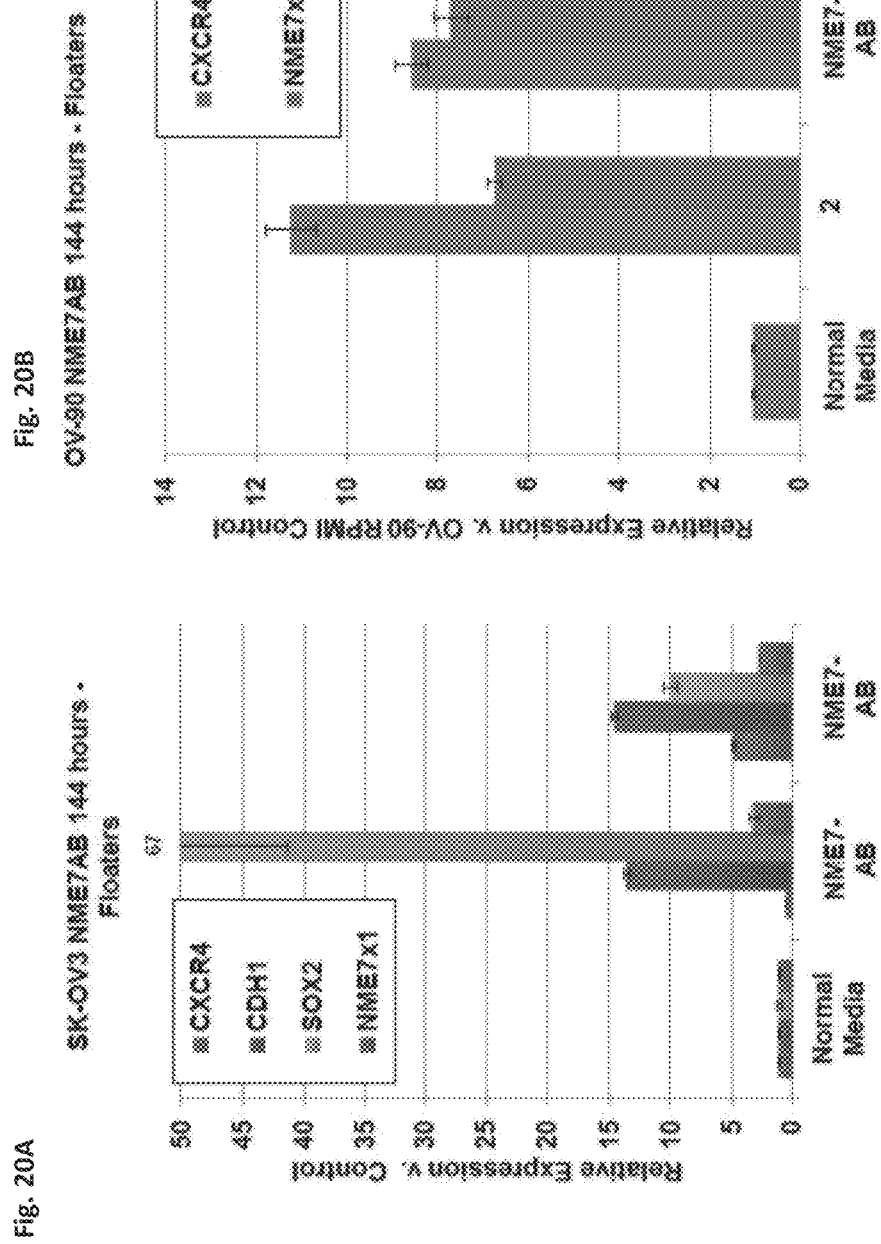
FIGS. 20A-20C show graphs of RT-PCR measurements of metastatic markers in cancer cells after being cultured in a serum-free media containing $NME7_{AB}$ compared to the standard media.
Figure 20C:
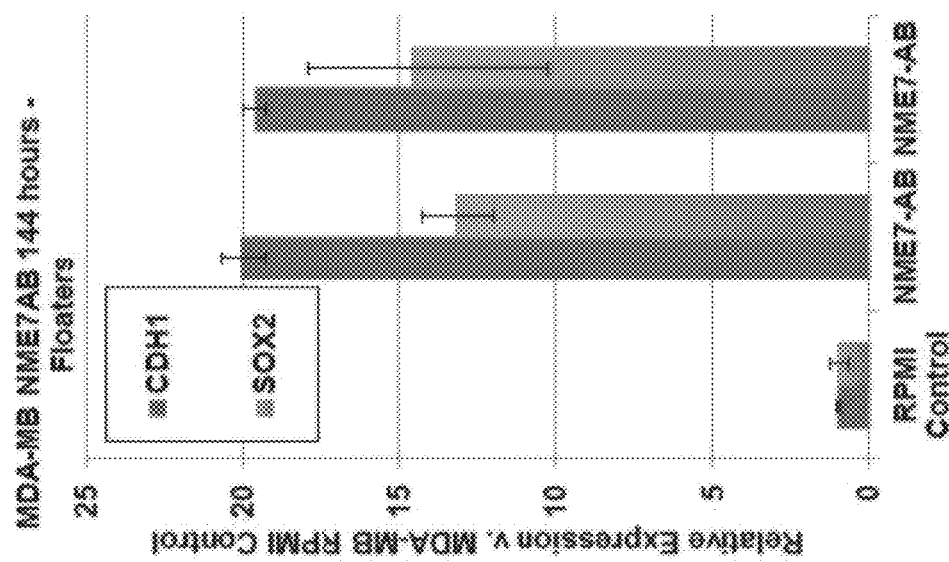

DU145 prostate cancer cells were cultured similarly and those cells cultured in $NME7_{AB}$ also showed dramatic increases in expression of CSC markers (FIG. 3). In prostate cancer cells, CHD1 (aka E-cadherin) and CXCR4 were up-regulated compared to the control cancer cells, which were not grown in $NME7_{AB}$, along with other pluripotent stem cell markers. FIG. 20A-20C shows that ovarian cancer cell lines SK-OV3. OV-90 and breast cancer cell line MDA-MB all transitioned from adherent to non-adherent floater cells and increased expression of metastatic markers after 72 or 144 hours in culture with $NME7_{AB}$. Ovarian, prostate, pancreatic cancer cells and melanoma cells were also cultured in $NME7_{AB}$ and were transformed to a more metastatic state after as few as 3 days in culture. FIG. 21 shows that breast, ovarian, prostate, pancreatic cancer cells and melanoma cells express MUC1 and MUC1*.

Here we have shown that $NME7_{AB}$ transforms a wide range of cancer cells to a more metastatic state. We have also shown that cancer cells express a naturally occurring species that is approximately the same molecular weight as recombinant $NME7_{AB}$ 33 kDa (FIG. 17. FIG. 18. FIG. 19, and FIG. 22 and is also devoid of the DM10 domain like $NME7_{AB}$ and also express an alternative isoform NME7-X1 30 kDa which is the same sequence as $NME7_{AB}$ except is missing 33 amino acids from the N-terminus. A co-immunoprecipitation experiment was performed on T47D breast cancer cells, wherein the cell extracts were incubated with an antibody against the MUC1 cytoplasmic tail. Ab-5, or a control antibody. IgG, and co-immunoprecipitated. The immunoprecipitated species were separated by gel electrophoresis. The gels were blotted with two different commercially available anti-NME7 antibodies. Both gels show unique NME7 bands at ~33 kDa and ~30 kDa (FIG. 22A-22B). The gels were stripped and re-probed with an antibody against the extracellular domain of MUC1*, anti-PSMGFR (FIG. 22C-22D), which shows that the NME7 species and MUC1* interact. A recombinant $NME7_{AB}$ and a recombinant NME7-X1 that we made were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 22E). A similar experiment was carried out in human stem cells. FIG. 23A-23C show photographs of Western blots of a co-immunoprecipitation experiment. Human induced pluripotent stem, iPS7, or embryonic stem. HES3, cell extracts were incubated with an antibody against the MUC1 cytoplasmic tail. Ab-5, or a control antibody, IgG, and co-immunoprecipitated. The gel was blotted with a commercially available anti-NME7 antibody B9 (FIG. 23A). Both cell types show unique NME7 bands at ~33 kDa and ~30 kDa. The gel was stripped and re-probed with an antibody against the extracellular domain of MUC1*, anti-PSMGFR (FIG. 23B), which shows that the NME7 species and MUC1* interact. A recombinant $NME7_{AB}$ and a recombinant NME7-X1 that we made were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 23C). Because $NME7_{AB}$ is a recombinant protein, we do not know if the naturally occurring species may contain an extra 1-15 additional amino acids or devoid of 1-15 additional amino acids than the recombinant $NME7_{AB}$, yet run with the same apparent molecular weight. By "$NME7_{AB}$-like", we mean an NME7 species that runs with an apparent molecular weight of approximately 33 kDa that is able to function the way the recombinant $NME7_{AB}$ does, in that it is able to stimulate cancer cell growth, induce transition of cancer cells to a more metastatic state and is able to fully support pluripotent growth of human stem cells.

We conclude that cancer cell lines and cancer cell populations that express NME7 and lower molecular weight NME7 species contain some cancer cells that are CSCs or metastatic cancer cells. These cancers can be made more metastatic or increase the population of cells that are metastatic by culturing the cells in $NME7_{AB}$, NME7-X1 or lower molecular weight NME7 species. FIG. 19 shows a Western blot of a panel of cancer cells all expressing NME7 as well as lower molecular weight species $NME7_{AB}$-like at 33 kDa and NME7-X1 at 30 kDa. FIG. 21 shows that cancer cell lines T47D breast cancer. PC3 and DU145 prostate cancer. BT-474 breast cancer, CHL-1 and A2058 both melanoma cell lines and CAPAN-2 and PANC-1 both pancreatic cell lines all express MUC1 and MUC1*. In FIG. 21A. BT474 cells appear not to express MUC1 or MUC1* however, we previously showed (Fessler et al 2009) that when these HER2 positive breast cancer cells become resistant to chemotherapy drugs. i.e. metastatic, they do so by increasing expression of MUC1* (FIG. 21D). Blocking the MUC1* receptor with an anti-MUC1* Fab reversed their resistance to Herceptin (FIG. 21E). Taxol (FIG. 21F) as well as other chemo agents. These cancer types and other cancer types that express NME7 and lower molecular weight NME7 species such as 33 kDa. 30 kDa can be made more metastatic or increase the population of cells that are metastatic by culturing the cells in $NME7_{AB}$, NME7-X1 or lower molecular weight NME7 species.

Conversely, the metastatic potential of these and other cancer types that express NME7 and lower molecular weight NME7 species such as 33 kDa or 30 kDa can be reversed by treating the cells with anti-NME7 antibodies. Anti-NME7 antibodies or antibodies that bind to $NME7_{AB}$ or NME7-X1 are administered to a patient for the treatment or prevention of cancers including breast, prostate, ovarian, pancreatic and liver cancers. Because we have shown that $NME7_{AB}$ exerts its tumorigenic effects by binding to and activating the MUC1* growth factor receptor, anti-NME7 antibodies will be effective against any MUC1*-positive cancers, which include but are not limited to breast, lung, liver, pancreatic, gastric colorectal, prostate, brain, melanoma, kidney and others. Anti-NME7, anti-$NME7_{AB}$ or anti-NME7-X1 antibodies are administered to patients for the treatment or prevention of cancers that are $NME7_{AB}$, $NME7_{AB}$-like, or NME7-X1 positive or a MUC1* positive.

Testing Patient Cancer Cells for Effective Therapies $NME7_{AB}$, NME7-X1 as well as 2i and other reagents that revert stem cells to a more naïve state also induce cancer cells to transform to a more metastatic state. After treatment with any one or combination of these reagents, cancer cells have a higher engraftment rate and require up to 100.000-times less cells to cause a tumor to form in a test animal. Therefore, methods described in this disclosure can be used to enable xenografting of a patient's primary tumor cells into a test animal.

Candidate therapeutic agents can then be tested on the recipient animal. Effective therapeutic agents identified in this way can be used to treat the donor patient or other patients with similar cancers. In one embodiment, a method of identifying effective therapeutics for a particular patient or a particular type of cancer comprises the steps of: 1) cancer cells are obtained from a cell line, a patient or a patient to whom the therapeutic being tested will be administered: 2) cancer cells are cultured in $NME7_{AB}$, NME7-X1, human NME1, bacterial NME1 that has high homology to human NME1 or NME7, 2i, or other reagents shown to revert stem cells to a more naïve state: 3) resultant cancer cells are implanted into a test animal to which human $NME7_{AB}$, NME7-X1, human NME1, bacterial NME1 that has high homology to human NME1 or NME7, 2i, or other reagents shown to revert stem cells to a more naïve state may also be administered or animal is transgenic for human $NME7_{AB}$ or NME7-X1; 4) candidate anti-cancer therapeutic agents are administered to the animal; 5) efficacy of the therapeutic agents are assessed; and 6) effective therapeutic agent is administered to the donor patient or to another patient with similar cancer.

Anti-NME7 Antibodies

Anti-NME7 antibodies are potent anti-cancer agents, NME7 is a growth factor that promotes the growth of cancer cells and also promotes their progression to a more metastatic state or a more aggressive state, NME7 and a truncated form of NME7 that is ~ 33 kDa or 30 kDa have been shown to fully support cancer growth even in serum-free media devoid of any other growth factors or cytokines. In pull-down assays. ELISAs and nanoparticle binding experiments, we have shown that the growth factor receptor MUC1* is a binding partner of NME7 and $NME7_{AB}$. Promotion of this interaction by eliminating all other growth factors or cytokines increased expression of cancer stem cell markers. Blocking this interaction even in the presence of serum, using a polyclonal antibody that specifically binds to NME7 actively killed the cancer cells. Thus, anti-NME7 or anti-$NME7_{AB}$ antibodies are potent anti-cancer agents that can be administered to a patient for the treatment or prevention of cancers. More than 75% of all cancers are MUC1* positive. MUC1* is the transmembrane cleavage product of MUC1 wherein most of the extracellular domain has been shed, leaving a portion of the extracellular domain that contains most of the PSMGFR sequence and may contain 9-20 additional amino acids N-terminal to the boundary of the of the PSMGFR sequence.

One aspect of the invention is a method of treating or preventing cancer in a subject, comprising administering to the subject an effective amount of an anti-NME7 antibody. In one instance, the anti-NME7 antibody is able to bind to $NME7_{AB}$. In another instance, the anti-NME7 antibody is able to bind to NME7-X1. In yet another instance, the anti-NME7 antibody that is administered to a patient inhibits or prevents its binding to its target in the promotion of cancers. In one case, the target is the extracellular domain of a cleaved MUC1. More specifically, the NME7 target that promotes cancer is the PSMGFR region of the MUC1* extracellular domain. In one aspect, an effective therapeutic agent is one that disrupts or prevents the interaction between an NME7 species and MUC1* extracellular domain, consisting primarily of the PSMGFR portion of MUC1* or the PSMGFR peptide. Agents for the treatment or prevention of cancers are those agents that directly or indirectly inhibit the expression or function of NME7, an $NME7_{AB}$-like cleavage product or alternative isoform, including NME7-X1. In one case an effective anti-cancer therapeutic agent is one that binds to the NME7 species or disables its tumorigenic activity. An effective therapeutic agent for the treatment or prevention of cancers is an agent that binds to or disables NME7, an $NME7_{AB}$-like cleavage product or alternative isoform, or NME7-X1. In one aspect, the therapeutic agents that binds to the NME7 species is an antibody. The antibody may be polyclonal, monoclonal, bispecific, bivalent, monovalent, single chain, scFv, or an antibody mimic that may be animal in origin, human-animal chimera, humanized or human. The antibody can be generated by inoculation or immunization with an NME7 species or fragment thereof or selected, for example from a library or a pool of antibodies, for their ability to bind to an NME7 species, including NME7, an $NME7_{AB}$-like cleavage product or alternative isoform, including NME7-X1.

Generation of Anti-NME7 Antibodies

Anti-NME7 antibodies can be generated outside of the patient such as in a host animal or in a patient. Antibodies can be generated by immunization of NME7 or NME7 fragments or selected from a library or pool of antibodies that may be natural, synthetic, whole or antibody fragments based on their ability to bind to desired NME7 species such as $NME7_{AB}$ or NME7-X1. In one aspect, the antibody is generated from immunization with, or selected for its ability to bind to, a peptide selected from those listed in FIG. 6-9. In another aspect, the antibody is generated from peptides whose sequences are not identical to those of human NME1 or the antibodies are selected for their ability to bind to NME7 species and their inability to bind to human NME1.

One method used to identify NME7 or NME7-X1 derived peptides that give rise to antibodies that inhibit cancer growth and inhibit transition to metastasis or peptides that are themselves inhibitory is as follows: 1) protein sequences of human NME1, human NME7, human NME7-X1 and several bacterial or fungal NME proteins that have high sequence homology to either human NME1 or human NME7 are aligned; 2) regions of high sequence homology among all the NMEs are identified: 3) peptide sequences that are unique to NME7 or NME7-X1 but are flanking the regions of high sequence homology are identified. The peptides are then synthesized and used to generate antibodies in a human or host animal. The resultant antibodies are selected for therapeutic use if: 1) they bind to $NME7_{AB}$ or NME7-X1, but not to NME1; 2) have the ability to inhibit cancer growth; 3) have the ability to inhibit the transition of cancer cells to a more metastatic state; or 4) inhibit metastasis in vivo. In some cases, antibodies for therapeutic use are selected for their ability to disrupt binding of $NME7_{AB}$ or NME7-X1 to the MUC1* extra cellular domain, to the PSMGFR peptide or to the N-10 peptide.

Use of Anti-NME7 Antibody for Treatment of Cancer

Figure 10A:
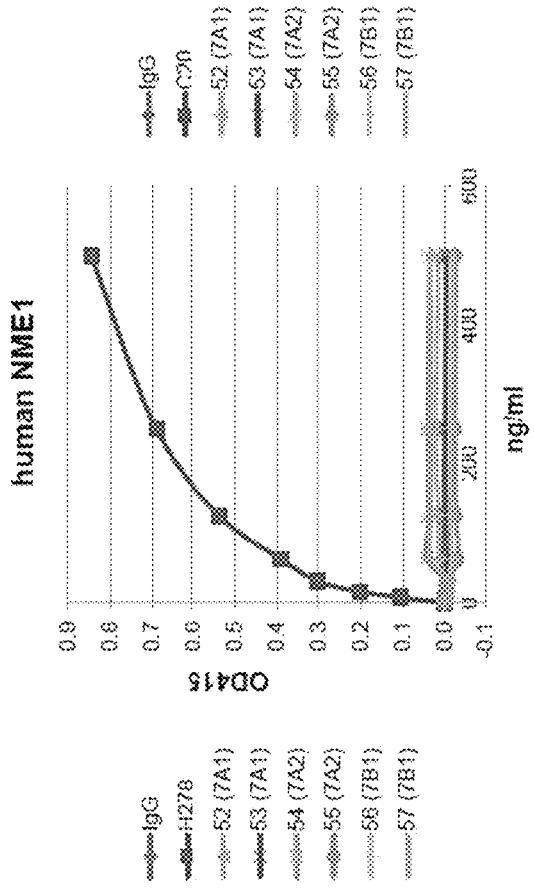
FIGS. 10A-10B show graphs of ELISA assays in which either $NME7_{AB}$ (FIG. 10A) or NME1 (FIG. 10B) is adsorbed to the plate and anti-NME7 antibodies generated by NME7 peptides A1, A2, B1, B2 and B3 are tested for their ability to bind to NME7 but not to NME1. C20 is an anti-NME1 antibody.
Figure 10B:
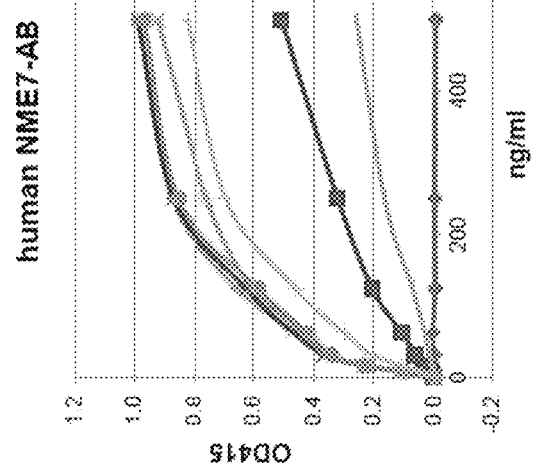
Figure 11:
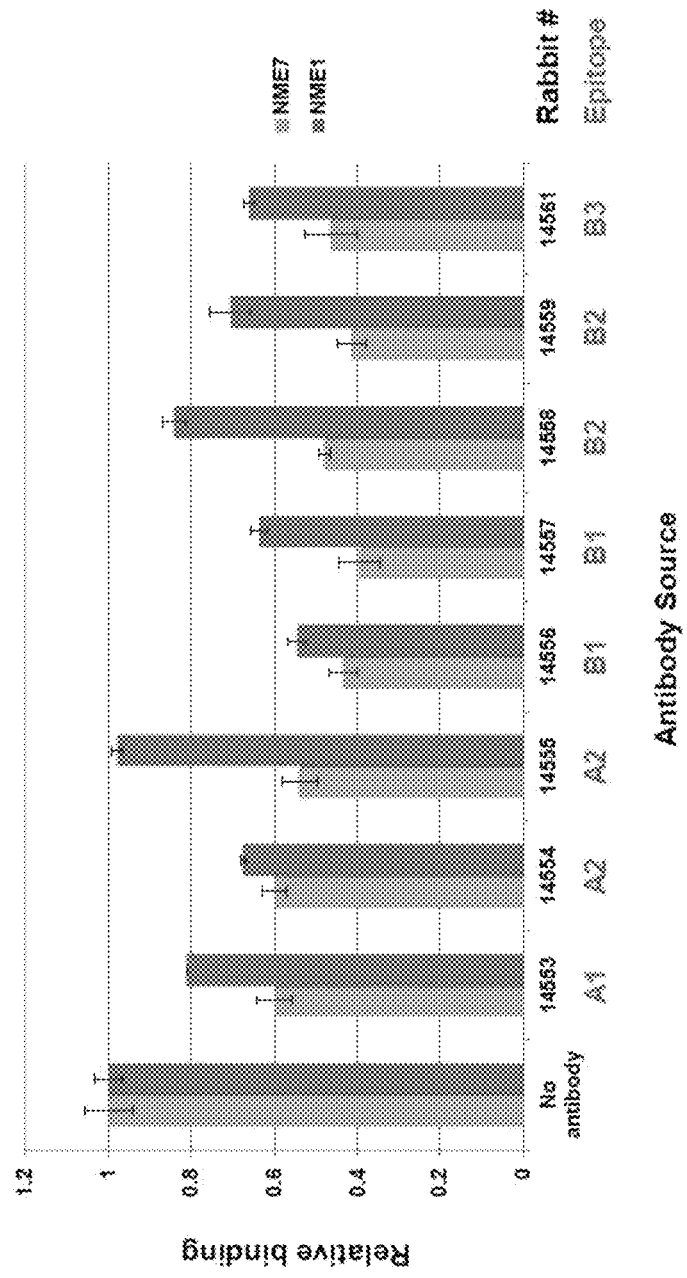
FIG. 11 shows graphs of ELISA assays in which anti-NME7 antibodies generated are tested for their ability to inhibit binding of $NME7_{AB}$ to a surface immobilized MUC1* peptide but not inhibit binding of NME1.

Those antibodies that inhibit cancer growth or transition to a more metastatic state are selected for use as anti-cancer therapeutics and may be administered to a patient for the treatment or prevention of cancers. Selected antibodies may be further optimized for example by engineering or making human chimera antibodies or fully human antibodies. To demonstrate the efficacy of this approach, we selected NME7 peptides from regions of NME7 suspected to be critical to its cancerous function. We then generated antibodies using these peptides and then tested both the resultant antibodies as well as the immunizing peptides for their ability to: a) inhibit cancerous growth; and b) inhibit the induced transition from cancer cells to metastatic cancer cells, NME7 peptides were selected as immunizing agents for antibody production and as inhibitory agents themselves (FIG. 9. Example 7), Peptides A1 (SEQ ID NO:141), A2 (SEQ ID NO:142), B1 (SEQ ID NO:143), B2 (SEQ ID NO:144) and B3 (SEQ ID NO:145), wherein A refers to the domain from which the peptide is derived. i.e. the NDPK A domain and the B denotes that the peptide is derived from the NDPK B domain (FIG. 5). Each peptide was used as an immunogen and injected into 2 rabbits each for production of polyclonal antibodies. The antibodies that were harvested from the blood of the immunized rabbits were purified over a column derivatized with the immunizing peptide. The purified antibodies were then tested for their ability to bind to human NME7. All of the resultant antibodies bound to human NME7 but not human NME1 as desired (FIG. 10A-10B. Example 8). These results show that by choosing peptides whose sequence is found in NME7 but not exactly identical in NME1, antibodies are generated that specifically bind to NME7 but not NME1. Because NME1 has healthy function, it is in most cases desirable to generate antibodies that do not interfere with NME1. The antibodies were also tested for their ability to inhibit the binding of NME7 to a MUC1* extracellular domain peptide. The ELISA experiment shown in FIG. 11 shows that the antibodies inhibited the binding of $NME7_{AB}$ to a MUC1* extracellular domain peptide much more than they inhibited binding of NME1. Recall that each of the NME7 A domain and B domain can bind to a PSMGFR peptide. Therefore, complete inhibition of NME7$_{AB}$ binding to a PSMGFR peptide cannot be accomplished with a single antibody or peptide that is derived from just one domain. These antibodies and their respective immunizing peptides also inhibited cancer cell growth (FIG. 12-13). These antibodies also inhibited the formation of non-adherent "floater" cells that result from growing cancer cells in NME7$_{AB}$ (FIG. 14). As can be seen in the figure, the polyclonal antibody generated by immunization with the B3 peptide reduced the number of metastatic floater cells by 95%, indicating that anti-NME7 antibodies that bind to the B3 peptide are most effective at inhibiting cancer metastasis. Similarly, the antibodies inhibited the expression of metastatic marker CXCR4 (FIG. 15A). Again, the B3 antibodies were most efficient at inhibiting expression of CXCR4: bar labeled NME7 FL (NME7 floater cells) shows 70-fold increase in CXCR4 that B3 antibody 61 decreased to 20-fold (bar labeled NME7+61 FL). In addition, the immunizing peptides themselves inhibited the upregulation of CXCR4 and other metastatic markers when T47D cancer cells were grown in NME7$_{AB}$ or 2i.

This is but one example of selecting peptides that generate antibodies that inhibit the cancerous function of NME7 and NME7 species. Sequence alignment among human NME1, human NME7, human NME7-X1 and bacterial NME proteins that had high sequence homology to human NME1 or NME7 identified five regions of homology. The fact that peptides A1, A2. B1, B2 and B3 all generated antibodies that inhibited cancer growth or their transition to a metastatic state means that the five regions from which these peptides were derived are regions of NME7 that are important for its function in the promotion of cancer. Other peptides from these regions will also give rise to anti-NME7 antibodies that will inhibit cancer growth and metastasis and are therefore potent anti-cancer therapeutics. Antibodies generated from peptides A1, A2. B1. B2 and B3 were shown to inhibit cancer growth and inhibited the transition to a more metastatic state. Monoclonal antibodies generated by immunization with the same or similar peptides and subsequent testing of the monoclonals will identify antibodies that, after humanizing or other engineering known to those skilled in the art, would be administered to a patient for the treatment or prevention of cancers.

In a particular experiment, the antibodies generated by immunization with peptides A1, A2, B1, B2 and B3, as well as the immunizing peptides themselves, were added to cancer cells in culture to see if the addition of the antibodies or the immunizing peptides would inhibit cancer cell growth. At low concentrations and added separately, the antibodies as well as the immunizing peptides inhibited cancer cells growth (FIG. 12 for one example). However, when added at higher concentrations or combined, the antibodies as well as the immunizing peptides robustly inhibited cancer cell growth (FIG. 13). The corresponding human NME7 amino acid numbers of immunizing peptides A1, A2, B1, B2 and B3 are 127-142, 181-191, 263-282, 287-301, 343-371, respectively, from human full-length NME7 having SEQ ID NO:82 or 147.

To clarify, when residue numbers of NME7 are discussed, they refer to the residue numbers of NME7 as set forth in SEQ ID NO:82 or 147.

The antibody used in cancer growth inhibition experiments and one of the antibodies shown in FIG. 12 was generated by immunizing with NME7 peptide corresponding to amino acids 100-376 of NME7 (SEQ ID NO:82 or 147). To generate higher affinity and specific anti-NME7 antibodies, the following steps are followed: immunize animal with a peptide containing human NME7 amino acids 100-376, then: 1) de-select those antibodies that bind to human NME1; 2) select those antibodies that inhibit NME7$_{AB}$, 2i, or other NME induced transition of cancer cells to a more metastatic state: 3) select those antibodies that inhibit the growth of cancer cells: 4) select those antibodies that inhibit the growth of MUC1* positive cancer cells: 5) select those antibodies that inhibit binding of NME7$_{AB}$ or NME7-X1 to MUC1* extracellular domain, essentially inhibit binding to the PSMGFR peptide; and/or 6) select those antibodies that bind to one or more of the peptides listed in FIG. 9—A1, A2, B1, B2 or B3 peptides.

Higher affinity monoclonal antibodies or monoclonal antibodies generated from longer peptides may be more effective antibody therapeutics. Alternatively, combinations of ani-NME7, anti-NME7$_{AB}$ or anti-NME7-X1 antibodies are administered to a patient to increase efficacy.

Anti-NME7 Antibodies Inhibit the Transition of Cancer Cells to Metastatic Cancer Cells.

Anti-NME7 antibodies inhibit transition of cancer cells to metastatic cancer cells also called cancer stem cells (CSCs) or tumor initiating cells (TICs). Recall that we have demonstrated that culturing a wide variety of cancer cells in the presence of NME7$_{AB}$ causes them to transition from regular cancer cells to the metastatic CSCs or TICs. Thus, antibodies that bind to NME7, NME7$_{AB}$ or NME7-X1 will inhibit the progression of cancer cells to a more metastatic state.

Cancer cells transform to a more metastatic state when cultured in the presence of agents that revert stem cells to a more naïve state. We have demonstrated that culturing cancer cells in NME7$_{AB}$, human NME1 dimers, bacterial NME1 dimers or MEK and GSK3-beta inhibitors, called "2i", causes the cells to become more metastatic. As the cells transition to a more metastatic state, they become non-adherent or less adherent and float off of the culture plate. These floating cells, "floaters" were collected separately from those that were adherent and were shown to: a) express much higher levels of metastatic genes; and b) generated tumors when xenografted into mice at very low copy number. RT-PCR measurement of specific metastatic markers such as CXCR4 for breast cancers, CHD1 for prostate cancer, and other pluripotent stem cell markers such as OCT4, SOX2, NANOG, KLF4 and others were dramatically over-expressed in cancer cells that were cultured in NME7$_{AB}$ and most over-expressed in the cells that became non-adherent, called "floaters" here and in figures.

In one example, NME7$_{AB}$ specific antibodies, generated by immunization with NME7-derived peptides A1, A2, B1, B2 and B3, as well as the immunizing peptides themselves, were added into the media along with either NME7$_{AB}$ or 2i to determine if they inhibited the transformation of regular cancer cells to metastatic cancer stem cells. Antibodies and peptides were separately added along with the agent that causes metastatic transformation; in this case NME7$_{AB}$ or the 2i inhibitors PD0325901 and CHIR99021, NME7$_{AB}$ and 2i were separately used to induce the cancer cells to be transformed to a more aggressive metastatic state. 2i was used so that it could not be argued that the antibodies that were added to the media simply sopped up all of the NME7$_{AB}$ so that the causative agent effectively was not there (Example 10).

Visual observation was independently recorded by two scientists as the experiment progressed (FIG. 14). The most striking observation was that the antibodies and the peptides dramatically reduced the number of floater cells, which was the first indication that the antibodies and peptides inhibit the transformation to metastatic cancer cells. In particular, cells to which the antibody generated from immunization with the B3 peptide barely generated any floater cells, mRNA was extracted from both the floater cells, the adherent cells and the control cancer cells. The amount of mRNA, which indicates cell viability and growth, was measured. Cells that were treated with antibody had much less mRNA, indicating less live dividing cells (FIG. 16), which confirms that anti-NME7$_{AB}$ antibodies inhibit cancer cell growth as well as their transition to a more metastatic state. RT-PCR was used to measure expression levels of metastatic markers, including CXCR4. Treatment with the anti-NME7 antibodies greatly reduced the amount of metastatic markers, such as CXCR4, indicating that the anti-NME7 antibodies or peptides inhibit the transition to metastatic cancer (FIG. 15A-15C). These results show that antibodies that bind to NME7$_{AB}$ can be administered to a patient for the treatment or prevention of metastatic cancers.

Peptides Derived from NME7$_{AB}$ or NME7-X1 Competitively Inhibit the Binding of Intact NME7$_{AB}$ and NME7-X1 and are Anti-Cancer Agents.

In another aspect of the invention, therapeutic agents for the treatment or prevention of cancers are peptides derived from the NME7 sequence, which are administered to a patient for the treatment or prevention of cancers. In one aspect, the NME7-derived peptides are administered to a patient so that the peptides, which should be shorter than the entire NME7 and unable to confer the oncogenic activity of NME7, bind to the targets of NME7 and competitively inhibit the interaction of intact NME7 with its targets, wherein such interactions promote cancer. Since NME7$_{AB}$ is fully able to confer oncogenic activity, the sequence of NME7$_{AB}$ is preferred as the source for the shorter peptide(s), wherein it must be confirmed that the peptides themselves are not able to promote cancerous growth or other tumorigenic or oncogenic activity. In a preferred embodiment, one or more peptides having the sequence of a portion of NME7$_{AB}$ and being preferably about 12-56 amino acids in length are administered to a patient. To increase half-life, the peptides may be peptide mimics, such as peptides with unnatural backbone or D-form amino acids for L. In yet another case, the anti-cancer therapeutic agent is a peptide or peptide mimic wherein the peptide has a sequence highly homologous to at least a portion of NME7, NME7$_{AB}$, or NME7-X1 or its target the MUC1* extracellular domain, comprising the PSMGFR peptide, also called "FLR" in some cases herein.

FIG. 6-FIG. 9 provide a listing of preferred amino acid sequences that are predicted to inhibit NME7 binding to its cognate target. In a still more preferred embodiment, the peptides that are chosen for administration to a patient suffering from cancer or at risk of developing cancer are chosen because they bind to an NME7 binding partner and they do not themselves confer tumorigenic activity. In a yet more preferred embodiment, the NME7 binding partner is the extracellular domain of MUC1*. In a still more preferred embodiment, the NME7 binding partner is the PSMGFR peptide.

By the term "conferring tumorigenic activity or oncogenic activity", it is meant that the peptides themselves cannot support or promote the growth of cancers. Another way of testing whether or not a peptide or peptides derived from NME7 can promote tumorigenesis is to test whether or not the peptides can support pluripotent growth of human stem cells, NME proteins and peptides that support pluripotent human stem cell growth also support cancer growth. In yet another method, peptides are de-selected if they can cause somatic cells to revert to a less mature state.

Fragments of NME7$_{AB}$ inhibit cancer cell growth and the transition of cancer cells to a more metastatic state. As a demonstration, NME7 peptides A1, A2, B1, B2 and B3 added separately (FIG. 12) or in combinations (FIG. 13) inhibit the growth of cancer cells. In addition. NME7 peptides A1, A2, B1, B2 and B3 inhibited the transition of cancer cell to a more metastatic state (FIG. 15).

Thus, antibodies generated by immunizing with peptides specific to NME7, and specific to NME7$_{AB}$ or NME7-X1 will block the cancerous action of NME7 species and will be potent anti-cancer agents. Similarly, these results show that the peptides specific to NME7, and specific to NME7$_{AB}$ or NME7-X1 will block the cancerous action of NME7 species. In one aspect of the invention, the peptides are chosen from the list shown in FIG. 6. In one aspect of the invention the peptides are chosen from the list shown in FIG. 7. In one aspect of the invention the peptides are chosen from the list shown in FIG. 8. In yet another aspect of the invention the peptides are chosen from the list shown in FIG. 9. These antibodies may be generated by immunizing or may be generated or selected by other means, then selected for their ability to bind to NME7, NME7$_{AB}$, NME7-X1 or NME7 derived peptides, including but not limited to NME7 derived peptides A1 (SEQ ID NO: 141), A2 (SEQ ID NO: 142), B1 (SEQ ID NO: 143), B2 (SEQ ID NO: 144) or B3 (SEQ ID NO: 145). Such antibodies may be polyclonal, monoclonal, bispecific, bivalent, monovalent, single chain, scFv, human or humanized or may be an antibody mimic such as protein scaffolds that present recognition regions that bind to a specific target.

Anti-NME7 antibodies for use in the treatment or prevention of cancers can be generated by standard methods known to those skilled in the art wherein those methods are used to generate antibodies or antibody-like molecules that recognize NME7, NME7$_{AB}$ or a shorter form of NME7$_{AB}$ wherein an additional 10-25 amino acids form the N-terminus are not present. Such antibodies may be human or humanized. Such antibodies may be polyclonal, monoclonal, bispecific, bivalent, monovalent, single chain, scFv, human or humanized or may be an antibody mimic such as protein scaffolds that present recognition regions that bind to a specific target.

Anti-NME7 antibodies that are generated by immunization with the NME7 derived peptides A1 (SEQ ID NO: 141), A2 (SEQ ID NO: 142), B1 (SEQ ID NO: 143), B2 (SEQ ID NO: 144) or B3 (SEQ ID NO: 145) or antibodies that bind to the A1, A2, B1, B2 or B3 peptides are antibodies that bind to NME7$_{AB}$ and NME7-X1, but resist binding to NME1 which may be required for the function of some healthy cells. Such antibodies inhibit the binding of NME7$_{AB}$ or NME7-X1 to their target receptor, MUC1*. Antibodies that bind to A1, A2, B1, B2 or B3 peptides are antibodies can be administered to a patient diagnosed with or at risk of developing a cancer or metastasis. Such antibodies may be human or humanized. Such antibodies may be polyclonal, monoclonal, bispecific, bivalent, monovalent, single chain, scFv, or may be an antibody mimic such as protein scaffolds that present recognition regions that bind to a specific target.

Anti-NME7 antibodies that are generated by immunization with the B3 peptide or antibodies that bind to the B3 peptide are especially specific for the recognition of NME7$_{AB}$ and NME7-X1. Such antibodies are also very efficient at inhibiting the binding of NME7$_{AB}$ or NME7-X1 to their target receptor, MUC1*. Antibodies that bind to the B3 peptide are also exceptionally efficient at preventing, inhibiting and reversing cancer or cancer metastases. Such antibodies may be human or humanized. Such antibodies may be polyclonal, monoclonal, bispecific, bivalent, monovalent, single chain, scFv, or may be an antibody mimic such as protein scaffolds that present recognition regions that bind to a specific target.

Note that the polyclonal antibody #61, which was generated in rabbits immunized with the B3 peptide, inhibited the transformation of cancer cells to cancer stem cells as evidenced by antibody #61 blocking upregulation of metastatic marker CXCR4 (FIG. 15).

The B3 peptide (SEQ ID NO: 145) derived from NME7 has a Cysteine at position 14, which complicates the generation of anti-NME7 antibodies. We mutated Cysteine 14 to Serine to make AIFGKTKIQNAVHSTDLPEDG-LLEVQYFF (SEQ ID NO:169) and immunized animals to generate anti-NME7 monoclonal antibodies. The resultant antibodies bind to the native B3 sequence as well as the B3Cys14Ser peptide. Seven (7) high affinity and specific monoclonal antibodies were generated: 8F9A5A1, 8F9A4A3, 5F3A5D4, 5D9E2B11, 5D9E10E4, 5D9G2C4, and 8H5H5G4. However, various sequence alignments showed that there are only three (3) unique sequence antibodies: 8F9A5A1, 8F9A4A3, 8F9A4P3 and 5F3A5D4 as seen below. Bolded and underlined regions indicate CDR sequences.

```
HEAVY CHAIN ALIGNMENT
8F9A5A1H    IQLVQSGPELKKPGETVKISCKASGYTFTNYGMNWVKQAPGKGLKWMGWINTYTGEPTYV    60

8F9A4A3H    VQLQQSGPELVKPGASVKISCKTSGNTFTEYTMHWVKQSHGKSLEWIGGFNPNNGVTNYN    60

5D9E2B11H   VQLQQSGPDLVKPGTSVKISCKTSGNTFTEYTMHWVKQSHGKSLEWIGGFNPNNGVTNYN    60

5D9E10E4H   VQLQQSGPDLVKPGTSVKISCKTSGNTFTEYTMHWVKQSHGKSLEWIGGFNPNNGVTNYN    60

5D9G2C4H    VQLQQSGPDLVKPGTSVKISCKTSGNTFTEYTMHWVKQSHGKSLEWIGGFNPNNGVTNYN    60

5F3A5D4H    VQLQQSGPDLVKPGTSVKISCKTSGNTFTEYTMHWVKQSHGKSLEWIGGFNPNNGVTNYN    60

8H5H5G4H    VQLQQSGPDLVKPGTSVKISCKTSGNTFTEYTMHWVKQSHGKSLEWIGGFNPNNGVTNYN    60
            :** ****:* *** :******:** ***:* *:****: **.*:*:* :*  .*  .*

8F9A5A1H    DDFKGRFAFSLETSATCAYLQINNLKNEDTSTYFCARLR--GIRPGPLAYWGQGTLVTVS   118

8F9A4A3H    QKFKGKATLTVDKSSSIAYMELRSLTSEDSAVYYCARRYYHSLYVFYFDYWGQGTTLTVS   120

5D9E2B11H   QKFKGKATLTVDKSSSTAYMELRSLTSEDSAVYYCARRYYHSTYVFYFDSWGQGTT----  116

5D9E10E4H   QKFKGKATLTVDKSSSTAYMELRSLTSEDSAVYYCARRYYHSTYVFYFDSWGQGTTLTVS   120

5D9G2C4H    QKFKGKATLTVDKSSSTAYMELRSLTSEDSAVYYCARRYYHSTYVFYFDSWGQGTTLTVS   120

5F3A5D4H    QKFKGKATLTVDKSSSTAYMELRSLTSEDSAVYYCARRYYHSTYVFYFDSWGQGTTLTVS   120

8H5H5G4H    QKFKGKATLTVDKSSSTAYMELRSLTSEDSAVYYCARRYYHSTYVFYFDSWGQGTTLTVS   120
            :.***: ::::::.*::***:::...*..**::*:***    .    : *****

8F9A5A1H    A                                                             119   (SEQ ID NO: 172)

8F9A4A3H    S                                                             121   (SEQ ID NO: 1205)

5D9E2B11H   -                                                             116   (SEQ ID NO: 174)

5D9E10E4H   S                                                             121   (SEQ ID NO: 175)

5D9G2C4H    S                                                             121   (SEQ ID NO: 176)

5F3A5D4H    S                                                             121   (SEQ ID NO: 177)

8H5H5G4H    S                                                             121   (SEQ ID NO: 178)

8F9A4P3H    VQLQQSGPELVKPGASVKISCKTSGNTFTEYTMHWVKQSHGKSLEWIGGFNPNNGVTNYN    60

8F9A4A3H    VQLQQSGPELVKPGASVKISCKTSGNTFTEYTMHWVKQSHGKSLEWIGGFNPNNGVTNYN    60

5D9E2B11H   VQLQQSGPDLVKPGTSVKISCKTSGNTFTEYTMHWVKQSHGKSLEWIGGFNPNNGVTNYN    60

5D9E10E4H   VQLQQSGPDLVKPGTSVKISCKTSGNTFTEYTMHWVKQSHGKSLEWIGGFNPNNGVTNYN    60

5D9G2C4H    VQLQQSGPDLVKPGTSVKISCKTSGNTFTEYTMHWVKQSHGKSLEWIGGFNPNNGVTNYN    60

5F3A5D4H    VQLQQSGPDLVKPGTSVKISCKTSGNTFTEYTMHWVKQSHGKSLEWIGGFNPNNGVTNYN    60

8H5H5G4H    VQLQQSGPDLVKPGTSVKISCKTSGNTFTEYTMHWVKQSHGKSLEWIGGFNPNNGVTNYN    60
            ********:*****:*********************************************

8F9A4P3H    QKFKGKATLTVDKSSSTAYMELRSLTSEDSAVYYCARRYYHSLYVFYFDYWGQGTTLTVS   120

8F9A4A3H    QKFKGKATLTVDKSSSTAYMELRSLTSEDSAVYYCARRYYHSLYVFYFDYWGQGTTLTVS   120
```

```
5D9E2B11H  QKFKGKATLTVDKSSSTAYMELRSLTSEDSAVYYCARRYYHSTYVFYFDSWGQGTT----     116

5D9E10E4H  QKFKGKATLTVDKSSSTAYMELRSLTSEDSAVYYCARRYYHSTYVFYFDSWGQGTTLTVS     120

5D9G2C4H   QKFKGKATLTVDKSSSTAYMELRSLTSEDSAVYYCARRYYHSTYVFYFDSWGQGTTLTVS     120

5F3A5D4H   QKFKGKATLTVDKSSSTAYMELRSLTSEDSAVYYCARRYYHSTYVFYFDSWGQGTTLTVS     120

8H5H5G4H   QKFKGKATLTVDKSSSTAYMELRSLTSEDSAVYYCARRYYHSTYVFYFDSWGQGTTLTVS     120
           ***********************************************  ******  ******

8F9A4P3H   S                                                                121  (SEQ ID NO: 173)

8F9A4A3H   S                                                                121  (SEQ ID NO: 1205)

5D9E2B11H  -                                                                116  (SEQ ID NO: 174)

5D9E10E4H  S                                                                121  (SEQ ID NO: 175)

5D9G2C4H   S                                                                121  (SEQ ID NO: 176)

5F3A5D4H   S                                                                121  (SEQ ID NO: 177)

8H5H5G4H   S                                                                121  (SEQ ID NO: 178)

LIGHT CHAIN ALIGNMENT
8F9A4P3L   ETTVTQSPASLSMAIGEKVTIRCITSTDIDDDMNWYQQKPGEPPKLLISEGNTLRPGVPS     60

8F9A4A3L   DIQMTQTTSSLSASLGDRVTLSCSASQGISNYLNWYQQKPDGTVELLIFYTSSLHSGVPS     60

5D9E2B11L  DIQMTQTTSSLSASLGDRVTISCSASQGISNYLNWFQQKPDGTIKLLIYYTSSLHSGVPS     60

5D9E10E4L  DIQMTQTTSSLSASLGDRVTISCSASQGISNYLNWFQQKPDGTIKLLIYYTSSLHSGVPS     60

5D9G2C4L   DIQMTQTTSSLSASLGDRVTISCSASQGISNYLNWFQQKPDGTIKLLIYYTSSLHSGVPS     60

5F3A5D4L   DIQMTQTTSSLSASLGDRVTISCSASQGISNYLNWFQQKPDGTIKLLIYYTSSLHSGVPS     60

8H5H5G4L   DIQMTQTTSSLSASLGDRVTISCSASQGISNYLNWFQQKPDGTIKLLIYYTSSLHSGVPS     60

8F9A5A1L   EILLTQSPAIIAASPGEKVTITCSASSSV-SYMNWYQQKPGSSPKIWEYGISNLASGVPA     60
             :**:  : :: :  *:***  * :*  .:    :**:****.    *: *    ..*  ***:

8F9A4P3L   RFSSSGYGTDFVFTIENMLSEDVADYYCLQSDNLPLTFGSGTKLEIKR                 108  (SEQ ID NO: 185)

8F9A4A3L   RFSGSGSGTDYSLTISNLEPEDIATYYCQQYSKLPYTFGGGTKLEIK                  108  (SEQ ID NO: 1109)

5D9E2B11L  RFSGSGSGTDYSLTISNVEPEDIATYYCQQYSKLPYTFGGGTKLEIKR                 108  (SEQ ID NO: 186)

5D9E10E4L  RFSGSGSGTDYSLTISNVEPEDIATYYCQQYSKLPYTFGGGTKLEIKR                 108  (SEQ ID NO: 187)

5D9G2C4L   RFSGSGSGTDYSLTISNVEPEDIATYYCQQYSKLPYTFGGGTKLEIKR                 108  (SEQ ID NO: 188)

5F3A5D4L   RFSGSGSGTDYSLTISNVEPEDIATYYCQQYSKLPYTFGGGTKLEIKR                 108  (SEQ ID NO: 189)

8H5H5G4L   RFSGSGSGTDYSLTISNVEPEDIATYYCQQYSKLPYTFGGGTKLEIKR                 108  (SEQ ID NO: 190)

8F9A5A1L   RFSGSGSGTSFSFTINSMEAEDVATYYCQQRSSYPPTFGGGTKLEIKR                 108  (SEQ ID NO: 191)
           ***.** **.: :**..:  **:* *** *  ..  * ***.********

5D9E2B11L  DIQMTQTTSSLSASLGDRVTISCSASQGISNYLNWFQQKPDGTIKLLIYYTSSLHSGVPS     60

5D9E10E4L  DIQMTQTTSSLSASLGDRVTISCSASQGISNYLNWFQQKPDGTIKLLIYYTSSLHSGVPS     60

5D9G2C4L   DIQMTQTTSSLSASLGDRVTISCSASQGISNYLNWFQQKPDGTIKLLIYYTSSLHSGVPS     60

5F3A5D4L   DIQMTQTTSSLSASLGDRVTISCSASQGISNYLNWFQQKPDGTIKLLIYYTSSLHSGVPS     60

8H5H5G4L   DIQMTQTTSSLSASLGDRVTISCSASQGISNYLNWFQQKPDGTIKLLIYYTSSLHSGVPS     60
           ************************************************************

5D9E2B11L  RFSGSGSGTDYSLTISNVEPEDIATYYCQQYSKLPYTFGGGTKLEIKR                 108  (SEQ ID NO: 192)

5D9E10E4L  RFSGSGSGTDYSLTISNVEPEDIATYYCQQYSKLPYTFGGGTKLEIKR                 108  (SEQ ID NO: 193)

5D9G2C4L   RFSGSGSGTDYSLTISNVEPEDIATYYCQQYSKLPYTFGGGTKLEIKR                 108  (SEQ ID NO: 194)

5F3A5D4L   RFSGSGSGTDYSLTISNVEPEDIATYYCQQYSKLPYTFGGGTKLEIKR                 108  (SEQ ID NO: 195)

8H5H5G4L   RFSGSGSGTDYSLTISNVEPEDIATYYCQQYSKLPYTFGGGTKLEIKR                 108  (SEQ ID NO: 196)
           ************************************************
```

```
8F9A4P3L   ETTVTQSPASLSMAIGEKVTIRCITSTDIDDDMNWYQQKPGEPPKLLISEGNTLRPGVPS        60

8F9A5A1L   EILLTQSPAIIAASPGEKVTITCSASSSV-SYMNWYQQKPGSSPKIWIYGISNLASGVPA        60
           *  :*****  ::  : ******  * :*:..: . *********. **:  *   ...*:  ***:

8F9A4P3L   RFSSSGYGTDFVFTIENMLSEDVADYYCLQSDNLPLTFGSGTKLEIKR                    108 (SEQ ID NO: 197)

8F9A5A1L   RFSGSGSGTSFSFTINSMEAEDVATYYCQQRSSYPPTFGGGTKLEIKR                    108 (SEQ ID NO: 198)
           ***.** **.* ***:.* :**** *** *  ..  * ***.*********
```

Figure 24:
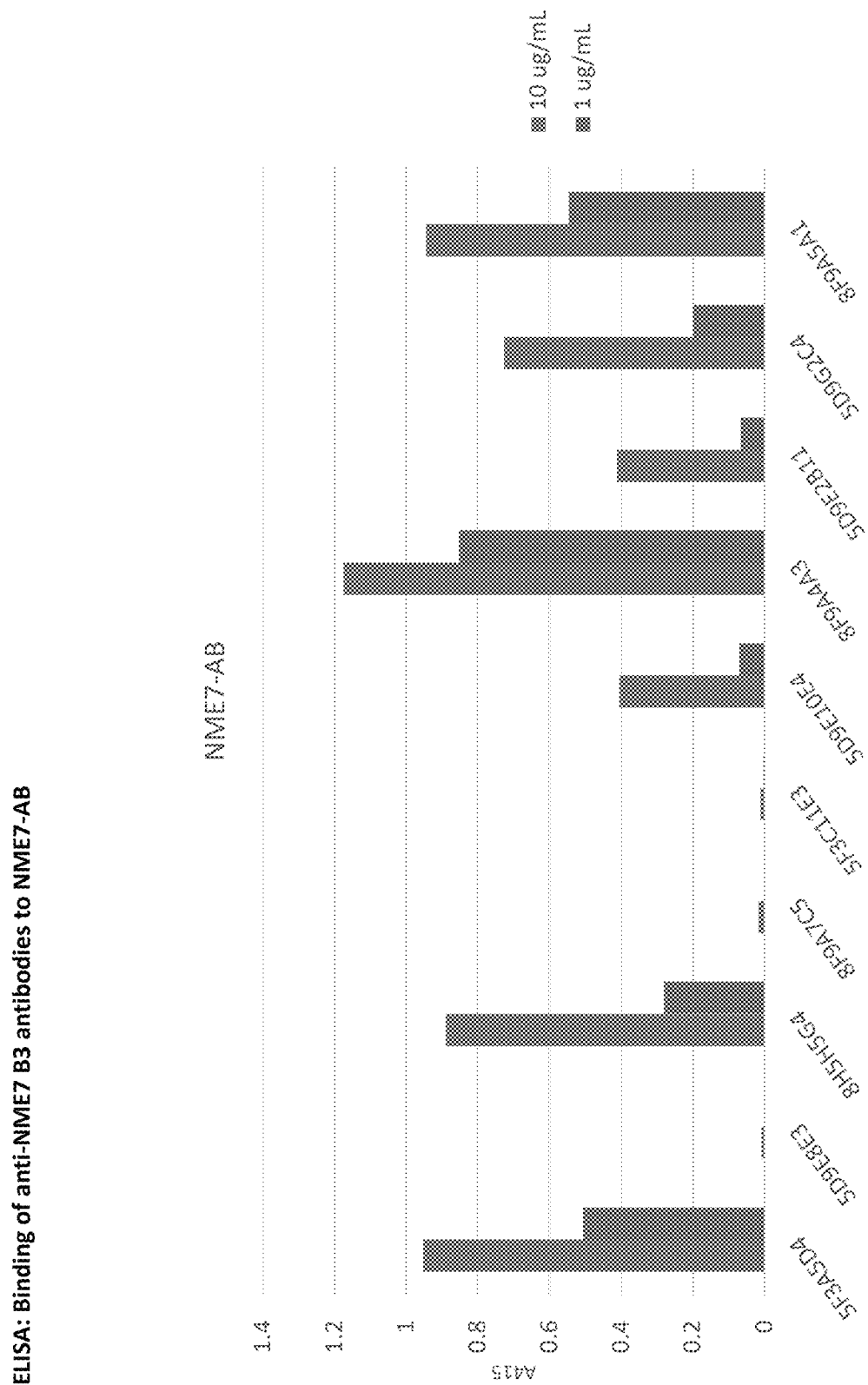
FIG. 24 shows a graph of an ELISA experiment assaying new anti-NME7 antibodies for their ability to bind to $NME7_{AB}$. $NME7_{AB}$ is known to bind to the extra cellular domain of MUC1*. The surface of the multi-well plate was coated with a recombinant $NME7_{AB}$. Anti-$NME7_{AB}$ antibodies were separately added to wells. Standard washes were performed and visualized by adding an HRP-conjugated secondary antibody. As can be seen. 7 of the 10 new anti-NME7 antibodies bound strongly to NME7$_{AB}$.
Figure 25:
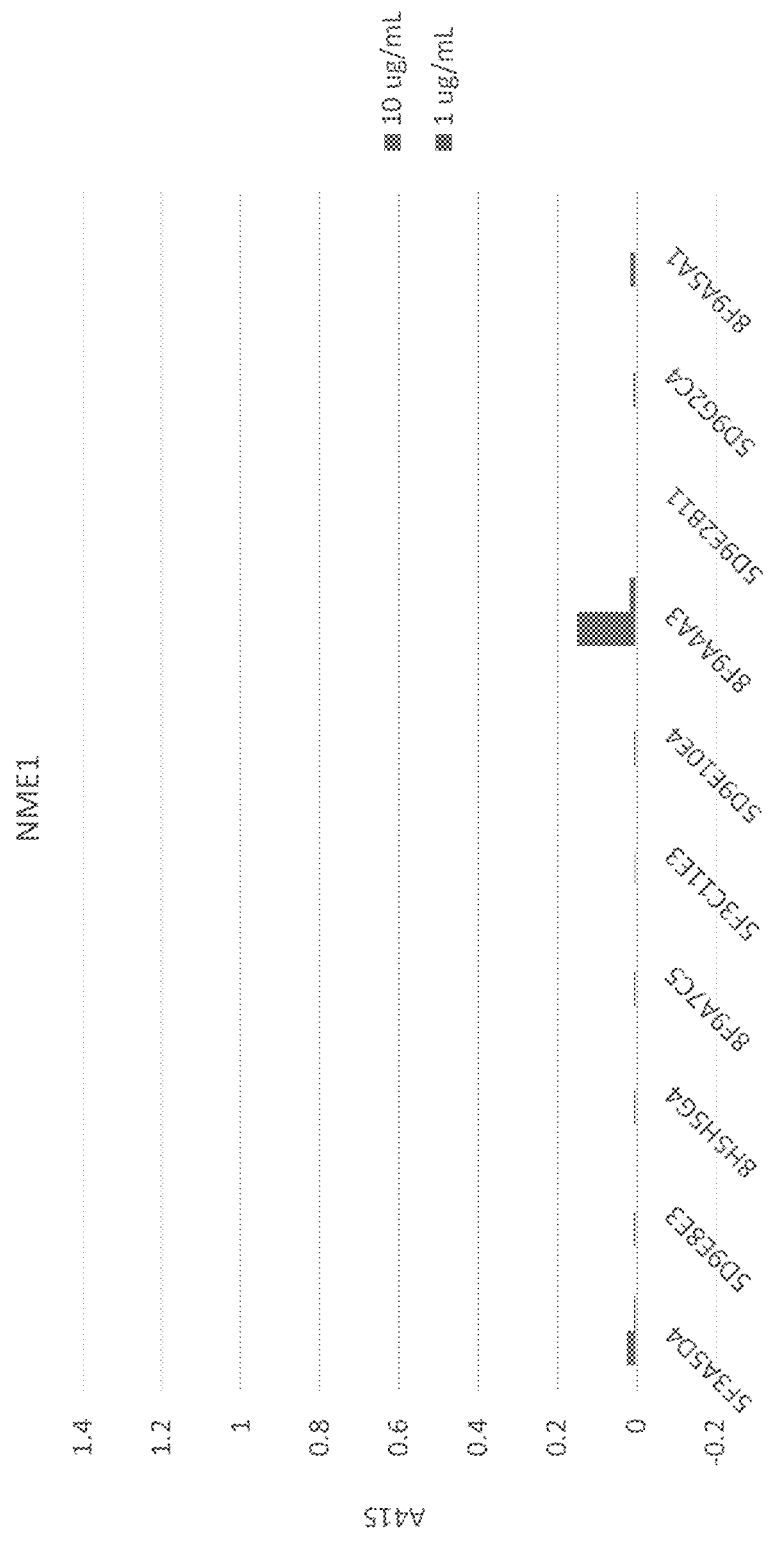
FIG. 25 shows a graph of an ELISA experiment assaying new anti-NME7 antibodies for their ability, or preferably inability, to bind to NME1. The surface of the multi-well plate was coated with a recombinant NME1-S120G dimers, which are also known to bind to the MUC1* extra cellular domain. Anti-NME7$_{AB}$ antibodies were separately added to wells. Standard washes were performed and visualized by adding an HRP-conjugated secondary antibody. As can be seen only one antibody showed just minimal binding to NME1.

Monoclonal antibodies 5D9E2B11, 5D9E10E4, 5D9G2C4, and 8H5H5G4 all have the same sequence as 5F3A5D4, also known as 5D4. Herein, when we refer to antibody 5F3A5D4, aka 5D4, it is understood that it also applies to 5D9E2B11, 5D9E10E4, 5D9G2C4, and 8H5H5G4. As can be seen in FIG. 24 and FIG. 25 anti-NME7 antibodies 8F9A5A1, 8F9A4A3, and 5F3A5D4 all bind to NME7$_{AB}$ but not to NME1. This is important because the A domain of NME7 has high homology to NME1, which is required for normal cell function. For an anti-cancer therapeutic or an anti-metastasis therapeutic it will be imperative to inhibit NME7$_{AB}$ but not NME1.

Figure 26:
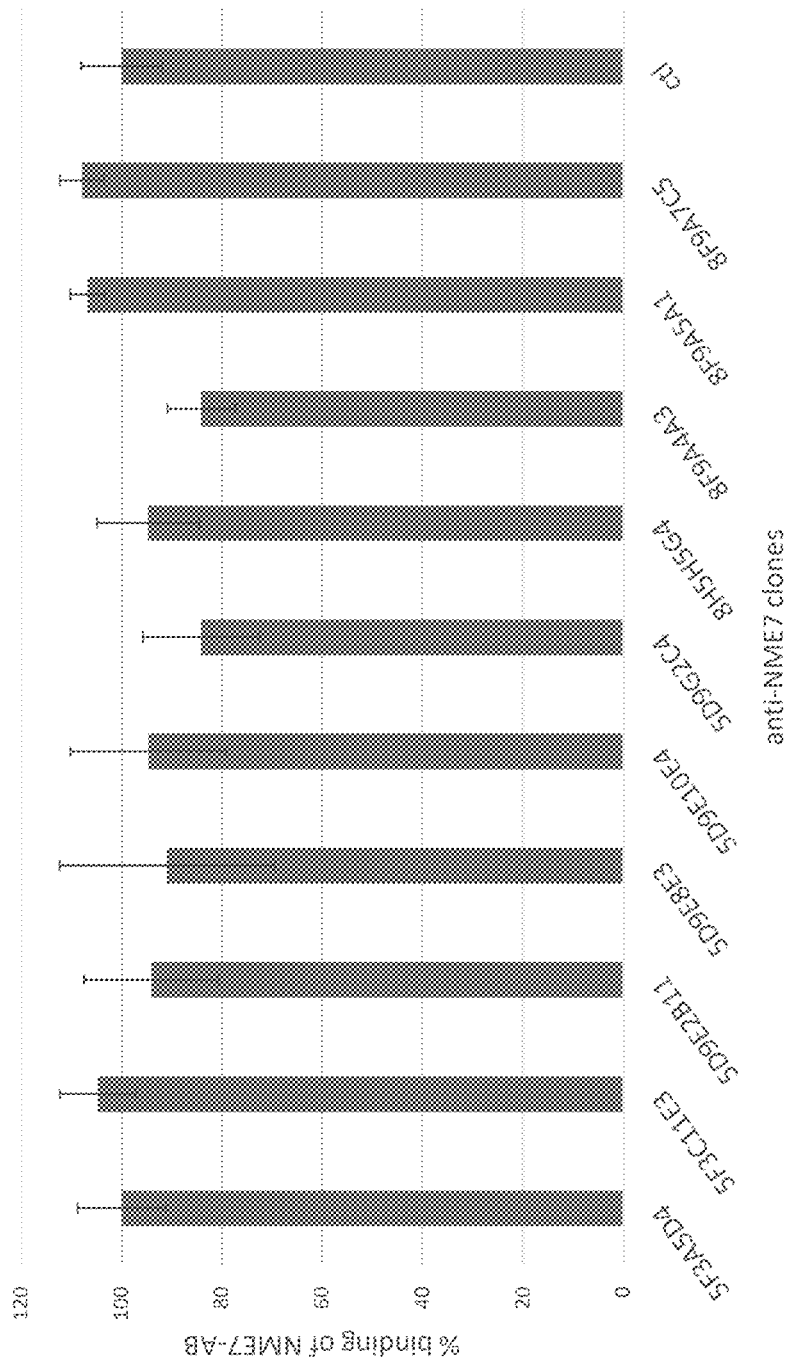
FIG. 26 shows a graph of an ELISA competitive inhibition assay, NME7$_{AB}$/anti-NME7 antibody complexes were made before adding to a multi-well plate coated with MUC1* extra cellular domain peptide. PSMGFR. Recall that NME7$_{AB}$ has two pseudo-identical domains A and B that are each able to bind to MUC1* extra cellular domain. Antibodies that bind to the NME7 B3 peptide, which is in the B domain, do not bind to the NME7 A domain. Therefore, only partial inhibition of the NME7$_{AB}$/MUC1* interaction is expected.
Figure 27:
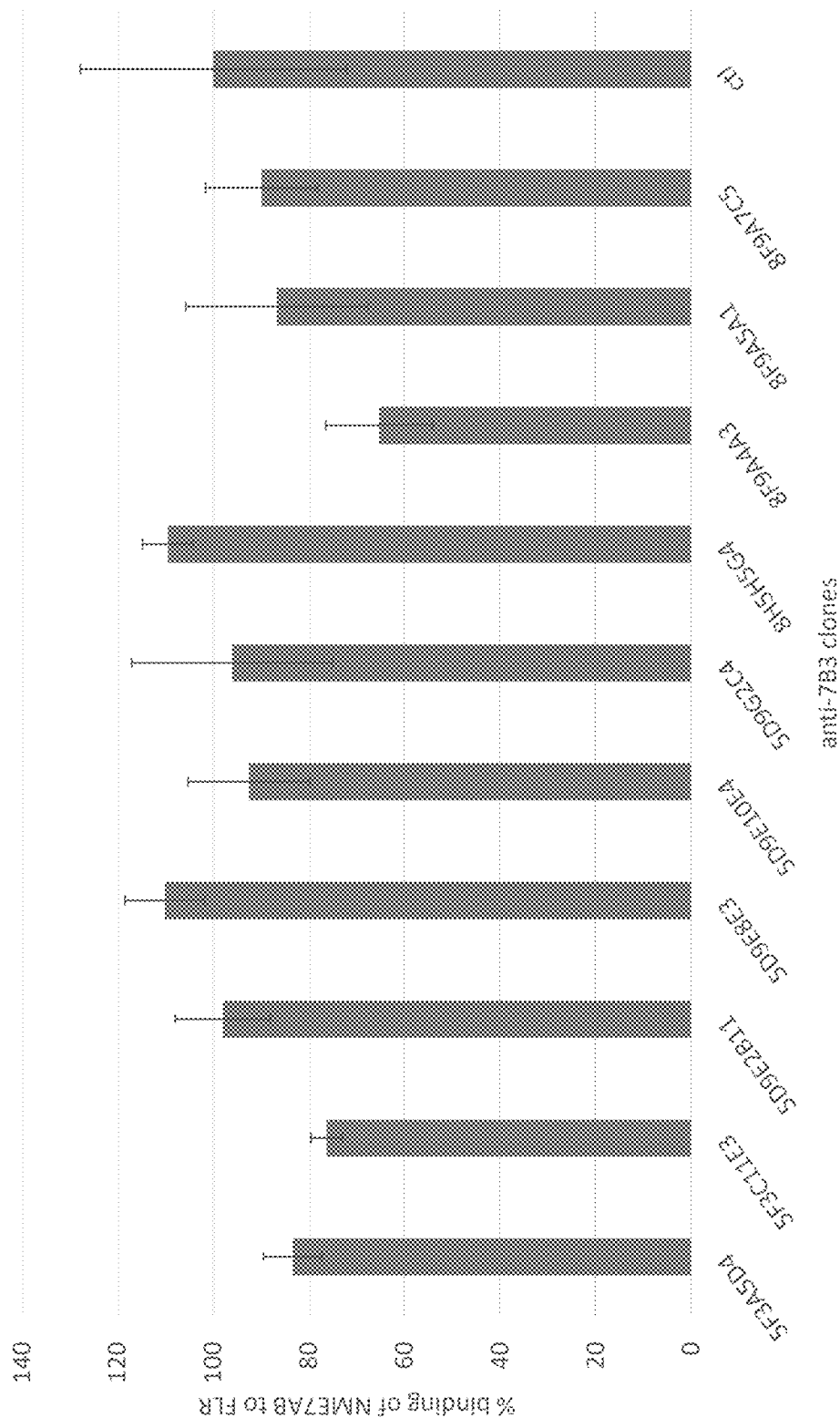
FIG. 27 shows a graph of an ELISA displacement assay, NME7$_{AB}$ was first bound to surface-immobilized MUC1* extra cellular domain peptide on the plate, then disrupted by the addition of anti-NME7 antibodies.
Figure 28:
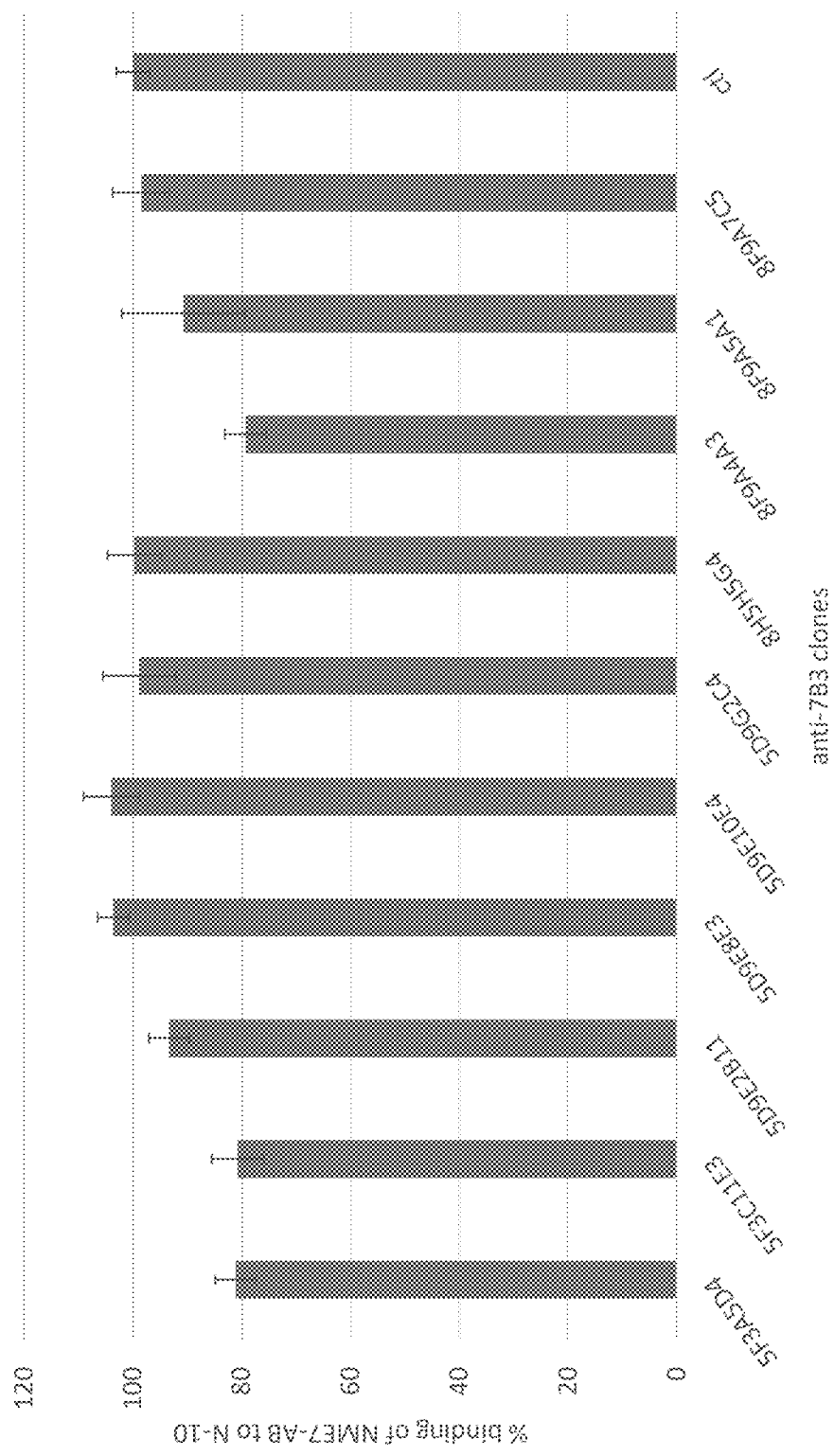
FIG. 28 shows a graph of an ELISA displacement assay. In this case, the multi-well plate was coated with a truncated MUC1* peptide, N-10, which has the 10 N-terminal amino acids missing of the PSMGFR sequence, NME7$_{AB}$ is known to bind to the N-10 peptide. NME7$_{AB}$ was bound to surface-immobilized N-10 peptide on the plate, then disrupted by the addition of anti-NME7 antibodies.

FIG. 26, FIG. 27 and FIG. 28 show that these anti-NME7 antibodies are also able to disrupt the binding of NME7$_{AB}$ to the MUC1* PSMGFR peptide and the N-10 PSMGFR peptide. As can be seen, there is not a total displacement of NME7$_{AB}$ from the MUC1* peptides. However, recall that NME7$_{AB}$ is comprised of an A domain and a B domain, each of which are capable of binding to MUC1*. These antibodies were designed to disrupt binding of the B domain to MUC1*; the A domain of NME7$_{AB}$ would still be able to bind to the MUC1* peptide on the plate surface. For a useful therapeutic, the antibody would only need to disrupt the binding of one domain to MUC1* and in so doing ligand-induced dimerization and activation of MUC1* growth factor receptor would be blocked. Antibodies or antibody mimics that bind to the NME7 B3 peptide or the B3 Cys14Ser peptide (SEQ ID NO: 169) are antibodies can be administered to a patient diagnosed with or at risk of developing a cancer or metastasis.

It is well known in the field that it is difficult to make cancer cells metastasize in an animal model. It is estimated that in a human tumor only about 1 in 100,000 or even 1 in 1,000,000 cancer cells is able to break away from the tumor and implant elsewhere to initiate a metastasis [Al-Hajj et al., 2003]. Some researchers report that T47D breast cancer cells injected into an immune compromised mouse will metastasize after about 12 weeks [Harrell et al 2006]. Other researchers report that AsPC-1 pancreatic cancer cells will metastasize after about 4 weeks [Suzuki et al, 2013].

Here, we show that T47D breast cancer cells grown for 10 days in a serum-free media containing recombinant NME7$_{AB}$ as the only growth factor. It was observed that when grown in NME7$_{AB}$, about 25% of the cancer cells began floating, stopped dividing but were still viable. PCR measurement showed that these "floating" cells greatly upregulated expression of the breast cancer metastatic factor CXCR4.

In some of the figures presented herein, these floater cells are referred to as cancer stem cells (CSCs). Immune compromised female nu/nu mice were implanted with 90-day release estrogen pellets. Either 500,000 T47D-wt cells or 10,000 T47D-CSCs (cancer stem cells) were injected into the tail vein (i.v.), sub-cutaneously (s.c.), or into the intra-peritoneal space (i.p.) of the nu/nu mice. These cancer cells were engineered to express Luciferase. To visualize the tumors or cancer cells, animals are injected with Luciferin, then visualized on an IVIS instrument 10 minutes later. As can be seen in the IVIS measurements of FIG. 33A-FIG. 33B, by Day 6 the 500,000 T47D-wt cells injected into the tail vein show no signs of live cancer cells or cancer cell engraftment.

Figures 34A, 34B, 34C, 34D:
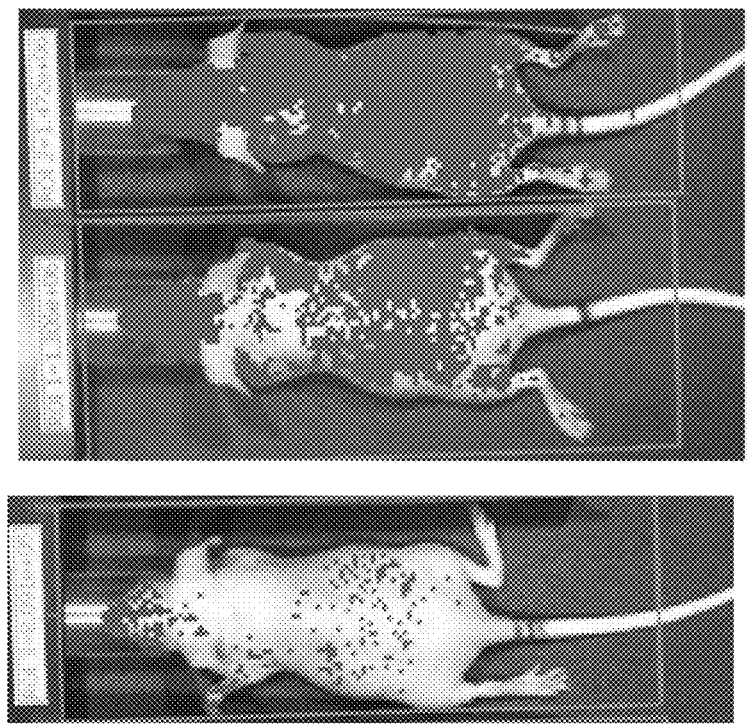
FIGS. 34A-34D show IVIS photographs of immune compromised nu/nu mice Day 10 post tail vein injection of cancer cells.
Figures 35A, 35B, 35C:
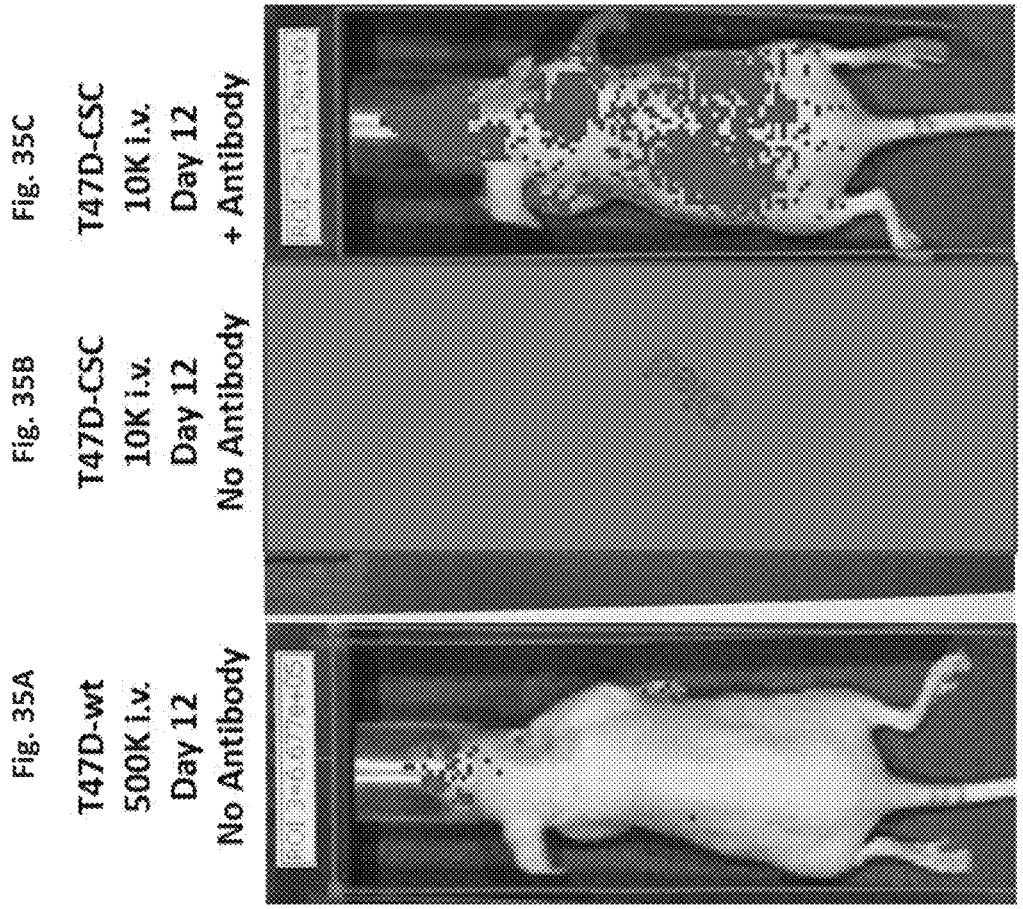
FIG. 35A-35C shows IVIS photographs of immune compromised nu/nu mice Day 12 post tail vein injection of cancer cells.

In stark contrast, the 10,000 T47D-CSC injected into the tail vein have metastasized. Before the Day 6 IVIS measurement, the T47D-CSC mice were injected with 32 nM recombinant NME7$_{AB}$. The next day, one of the two CSC mice was injected with a cocktail of anti-NME7 monoclonal antibodies 8F9A5A1, 8F9A4A3, and 5F3A5D4 in a volume of 200 uL at a concentration that corresponds to 15 mgs/kg. The nearly coincident injection of NME7$_{AB}$ and anti-NME7 antibody likely nullified the effect of the antibody. FIG. 34 shows that by Day 10, the treated mouse is almost entirely metastatic. As can be seen in the figure, the mouse chosen for treatment is more metastatic than the comparable T47D-CSC mouse.

Figures 37A, 37V:
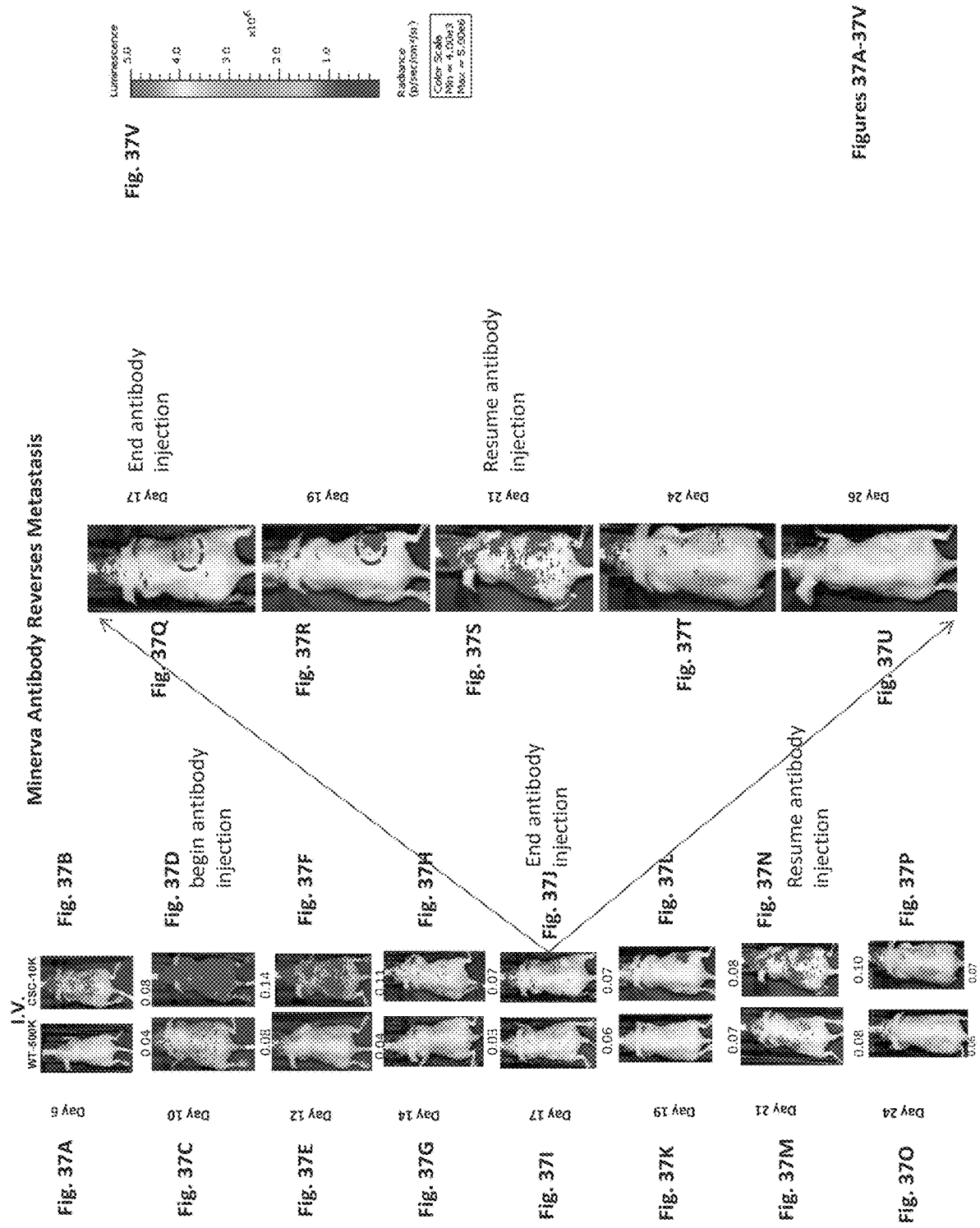
FIGS. 37A-37V shows time course of IVIS photographs of immune compromised nu/nu mice from Day 6 to Day 26 post cancer cell tail vein injection.

That animal was again injected with the anti-NME7 antibodies on Day 10. The IVIS measurement of Day 12 (FIG. 35) shows that the antibody treated mouse is beginning to clear the metastases. By Day 14 (FIG. 36) the untreated mouse has died from rampant metastases and the treated mouse has cleared the metastases. FIG. 37 shows the time course of IVIS measurements for the mouse injected with 500,000 T47D-wt cells and the mouse injected with T47D-CSCs that received anti-NME7 treatment until Day 17 when antibody treatment was suspended. As can be seen, on Day 17 there remained a small cluster of cancer cells, which by Day 19 had grown larger. By Day 21 the metastases had spread and antibody treatment was resumed. As is shown in the figure, after resumption of anti-NME7 antibody treatment, the animal was cleared of all metastases and shows no signs of ill health.

Figures 38A, 38B, 38C:
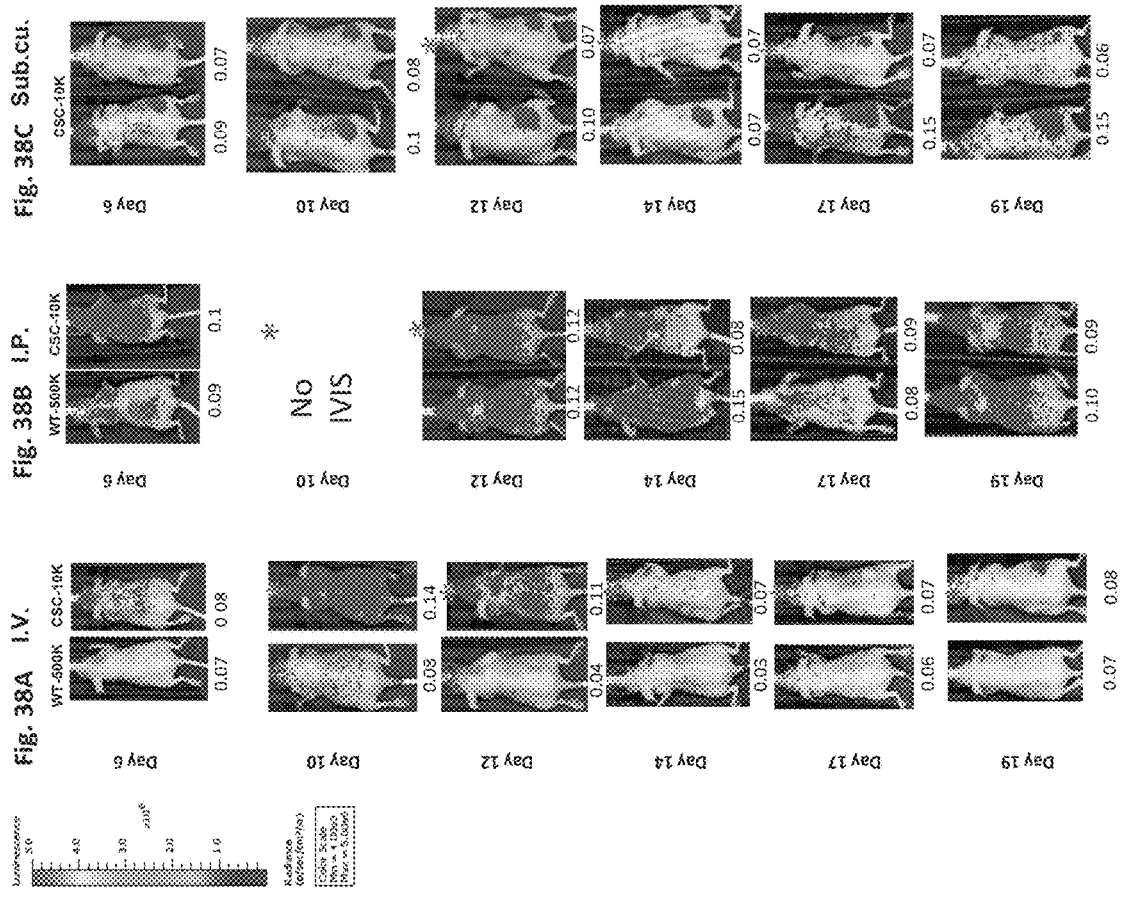
FIG. 38A-38C shows time course of IVIS photographs of immune compromised nu/nu mice from Day 6 to Day 19 post injection with either 500.000 T47D wild type breast cancer cells or 10,000 T47D cancer stem cells.

FIG. 38 shows the IVIS time course for animals that were injected sub-cutaneously or intra-peritoneally. Antibody injections for animals injected with CSCs sub-cutaneously or intra-peritoneally were also injected with anti-NME7 antibodies s.c, or i.p . . . . In these animals, antibody injections stopped at Day 17 and did not resume. FIG. 39-FIG. 40 show that a polyclonal anti-NME7 antibody generated by immunization with the B3 peptide stains advanced cancers and metastatic cancers but not normal tissues or low-grade cancers, where only 1 in 100,000 or 1 in 1,000,000 cancer cells would be a metastatic cancer cells. Taken together, these data show that anti-NME7 antibodies 8F9A5A1, 8F9A4A3, and 5F3A5D4 or 8F9A5A1, or 8F9A4A3, or 5F3A5D4 administered to a patient diagnosed with or at risk of developing a cancer would prevent, inhibit the formation of, or reverse cancer metastases.

Figures 42A, 42B, 42C, 42D, 42E, 42F:
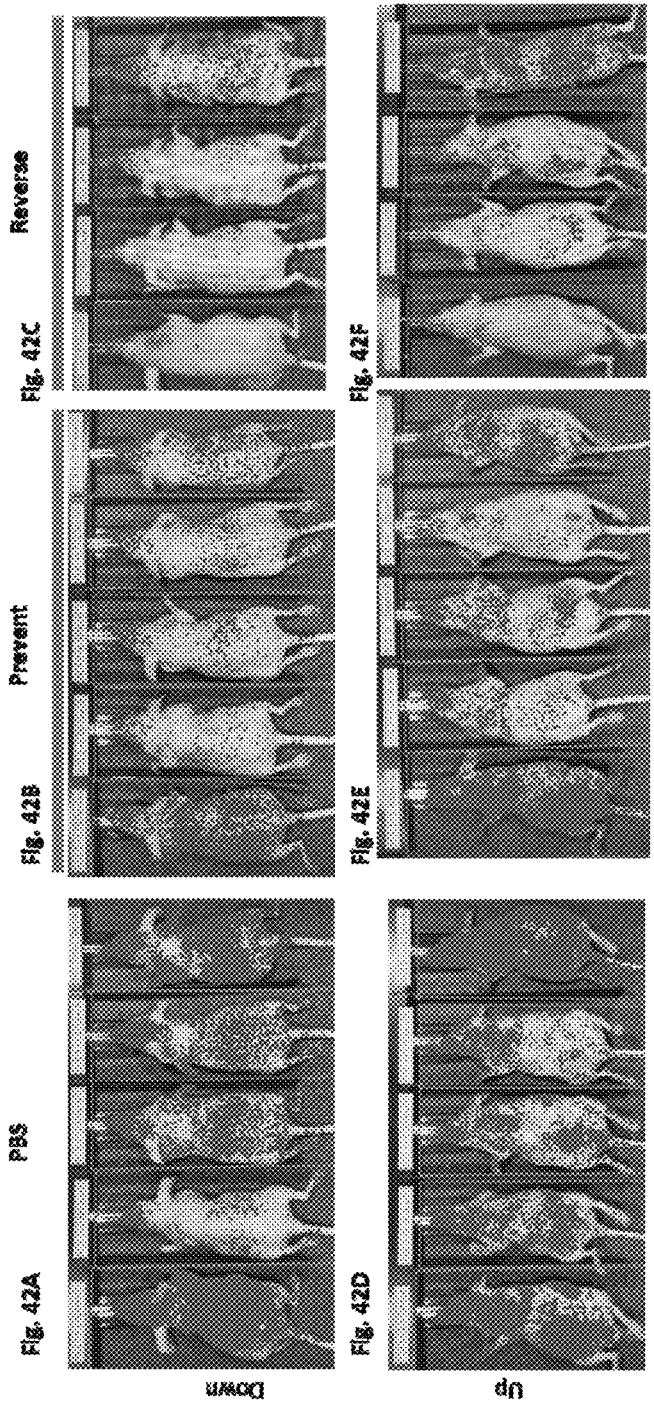
FIGS. 42A-42F shows photographs of female nu/nu mice weighing approximately 20 g each, which were injected into the tail vein with 10,000 Luciferase positive T47D metastatic breast cancer stem cells and treated with the anti-NME7$_{AB}$ antibody 4A3 also known as 8F9A4A3. To image cancer cells, the Luciferase substrate. Luciferin, is intraperitoneally injected 10 minutes before being photographed in IVIS instrument.

In addition to treating metastatic animals with a cocktail of anti-NME7$_{AB}$ antibodies, we also administered monoclonal anti-NME7$_{AB}$ antibodies individually and showed they were capable of preventing as well as reversing cancer metastases. In one demonstration, female nu/nu mice weighing approximately 20 g each, were implanted with 90-day estrogen release pellets between 8-10 weeks of age. Cancer cells were made metastatic by culturing for 10-15 days in a serum-free media supplemented with growth factor $NME7_{AB}$. Both adherent and floating cells show upregulation of metastatic markers and in animals are able to metastasize within 4-7 days. In this case, the floating cells were harvested on Day 11 of in vitro culture and injected into the tail vein of the test animals. To test a prevention model, one group of animals was injected into the tail vein. 24 hours before injection of the metastatic cancer cells, with anti-$NME7_{AB}$ antibody 8F9A4A3 at 15 mg/kg and injected thereafter with the same dosage approximately every 48 hours. FIG. 42A-FIG. 42F shows photographs of female nu/nu mice, which were injected into the tail vein with 10,000 Luciferase positive T47D metastatic breast cancer stem cells and treated with the anti-$NME7_{AB}$ antibody 4A3 also known as 8F9A4A3. To image cancer cells, the Luciferase substrate. Luciferin, is intraperitoneally injected 10 minutes before being photographed in IVIS instrument. FIG. 42A-42C show IVIS photographs with animals face down. FIG. 42D-42F show IVIS photographs with animals face up. FIGS. 42A and 42D show control animals injected with phosphate buffered saline solution. FIGS. 42B and 42E show a prevention model in which animals were injected with anti-$NME7_{AB}$ antibody 4A3 24 hrs before injection of the metastatic cancer cells, then approximately every other day for a total of 12 antibody injections over 22 days. FIGS. 42C and 42F show a reversal model in which animals were injected with anti-$NME7_{AB}$ antibody 4A3 24 hrs after injection of the metastatic cancer cells, then approximately every other day for a total of 11 antibody injections over 20 days. As can be seen in the figure, anti-$NME7_{AB}$ antibody 8F9A4A3 can prevent, as well as reverse an established metastasis.

Figures 43A, 43B, 43C, 43D, 43E, 43F:
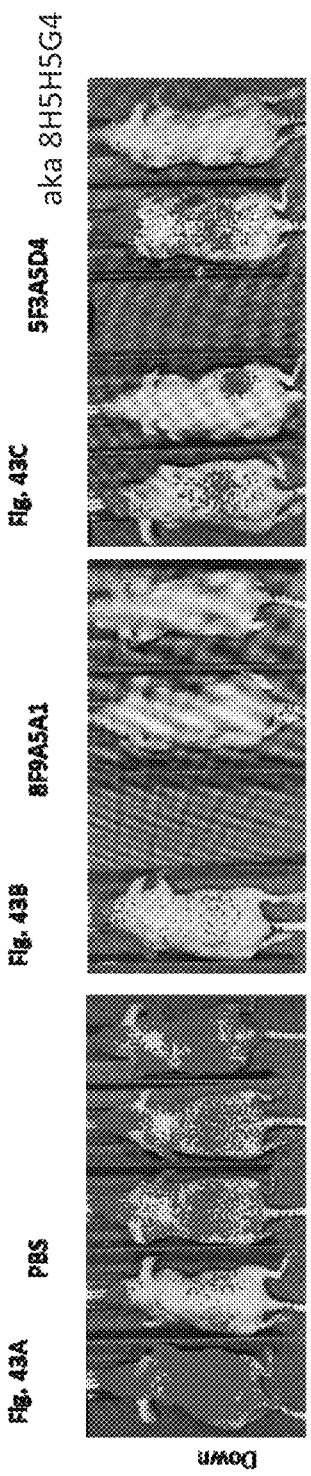
FIGS. 43A-43F shows photographs of female nu/nu mice weighing approximately 20 g each, which were injected into the tail vein with 10,000 Luciferase positive T47D metastatic breast cancer stem cells and treated with the anti-NME7$_{AB}$ antibodies 5A1, also known as 8F9A5A1, or 5D4, also known as 5F3A5D4. To image cancer cells, the Luciferase substrate, Luciferin, is intraperitoneally injected 10 minutes before being photographed in IVIS instrument.

Anti-$NME7_{AB}$ antibodies 5A1 and 5D4 were also tested in a metastasis prevention model and shown to greatly inhibit cancer metastasis. FIG. 43A-43F shows photographs of female nu/nu mice weighing approximately 20 g each, which were injected into the tail vein with 10,000 Luciferase positive T47D metastatic breast cancer stem cells and treated with the anti-$NME7_{AB}$ antibodies 5A1, also known as 8F9A5A1, and 5D4, also known as 5F3A5D4. To image cancer cells, the Luciferase substrate. Luciferin, is intraperitoneally injected 10 minutes before being photographed in IVIS instrument. FIG. 43A-43C show IVIS photographs with animals face down. FIG. 43D-43F show IVIS photographs with animals face up. FIGS. 43A and 43D show control animals injected with phosphate buffered saline solution. FIGS. 43B, 43E, 43C and 43F show a prevention model in which animals were injected with anti-$NME7_{AB}$ antibodies, at 15 mg/kg 24 hours before injection of the metastatic cancer cells, then approximately every other day for a total of 12 antibody injections over 22 days. Photographs were taken either at Day 24 or at Day 27. Specifically, mouse #1 in the group treated with antibody 5A1 was photographed at Day 27 while mouse #2 and #3 were photographed on Day 24 because animals died on Day 26

Anti-$NME7_{AB}$ antibodies 5A1 and 5D4 were also tested in a metastasis reversal model and shown to greatly inhibit established cancer metastases. In this experiment, animals were injected on Day (into the tail vein with 10,000 T47D metastatic cancer cells mixed with $NME7_{AB}$ at a final concentration of 32 nM. Further, animals were injected twice. Day 3 and Day 4, with more $NME7_{AB}$ which our experiments have shown make the metastasis more difficult to reverse. The first antibody injection was on Day 7.

Figures 44A, 44B, 44C, 44D:
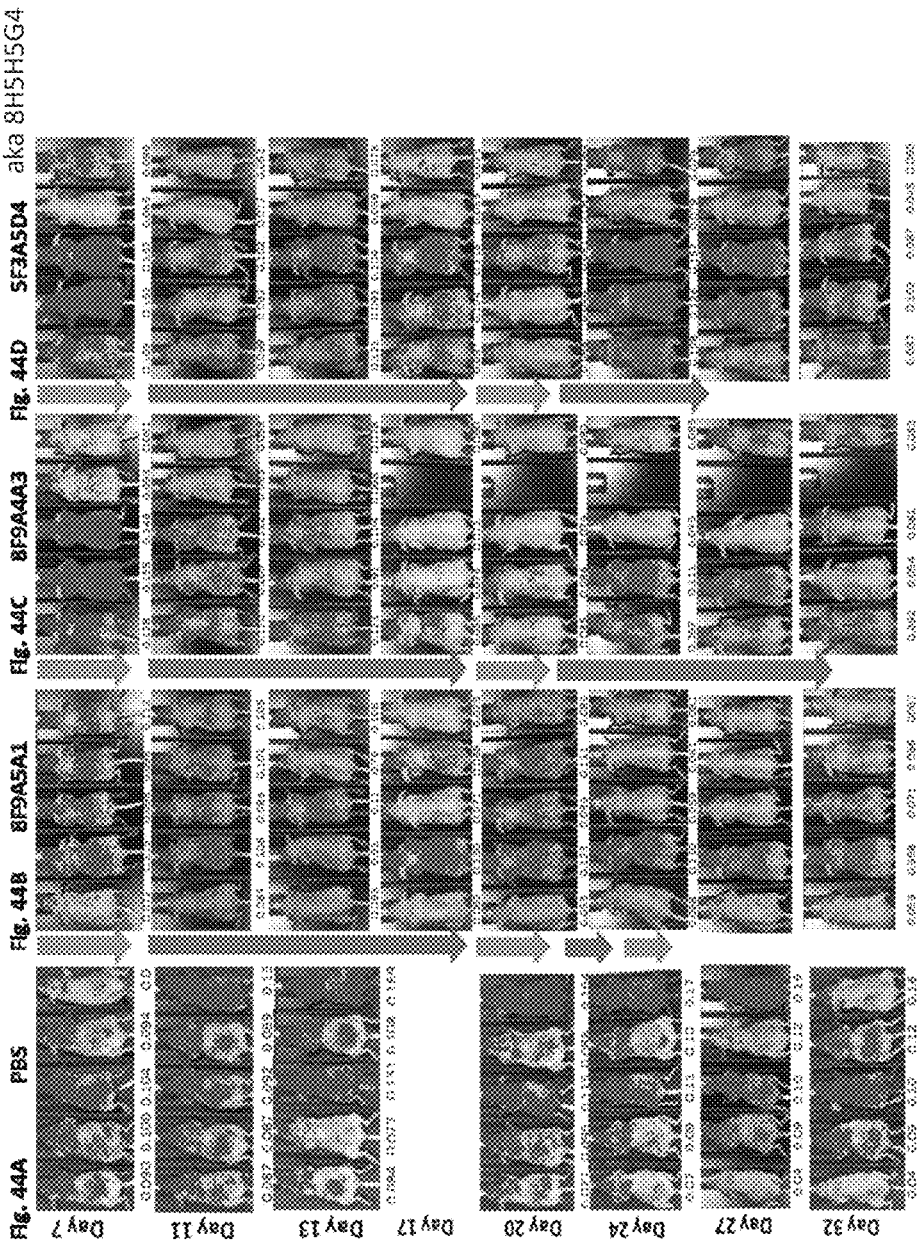
FIGS. 44A-44D shows photographs of female nu/nu mice that on Day (were injected into the tail vein with 10,000 Luciferase positive T47D metastatic breast cancer stem cells mixed with NME7$_{AB}$ to a final concentration of 32 nM. On Day 1 and Day 2 animals were injected into the tail vein with more 32 nM NME7$_{AB}$, which we have shown increases metastases. This is a system to demonstrate reversion of established metastases. On Day 7 animals were treated with individual anti-NME7$_{AB}$ antibodies 8F9A5A1, 8F9A4A3, or 5F3A5D4.

Because the degree of metastasis in each test animal is somewhat variable, we wanted to make certain that the apparent clearance of metastatic cancer cells was due to the anti-$NME7_{AB}$ treatment. We therefore treated the animals with alternating high dose and low doses. As can clearly be seen in FIG. 44, high dose anti-$NME7_{AB}$ results in clearance of the metastasis, which if not completely eradicated comes back and even increases with lower dose. This experiment shows that all three anti-$NME7_{AB}$ antibodies tested. 5A1, 4A3 and 5D4, which are able to bind to the NME7-B3 peptide, inhibit cancer metastasis in a concentration dependent manner. FIG. 44A-44D show photographs of female nu/nu mice that were injected into the tail vein with 10,000 Luciferase positive T47D metastatic breast cancer stem cells mixed with $NME7_{AB}$ at a final concentration of 32 nM. Animals were then injected into the tail vein with 32 nM $NME7_{AB}$ before being treated with individual anti-$NME7_{AB}$ antibodies. FIG. 44A shows control animals injected with phosphate buffered saline solution. FIG. 44B shows animals treated with anti-$NME7_{AB}$ monoclonal antibody 8F9A5A1. FIG. 44C shows animals treated with anti-$NME7_{AB}$ monoclonal antibody 8F9A4A3. FIG. 44D shows animals treated with anti-$NME7_{AB}$ monoclonal antibody 5F3A5D4. Green arrows indicate low antibody dosage (5-7 mg/kg) over the indicated period and Red arrows indicate high dosage (15 mg/kg). As can be seen in the figure, the metastasis clears considerably when antibody is administered at 15 mg/kg.

Figures 45A, 45B:
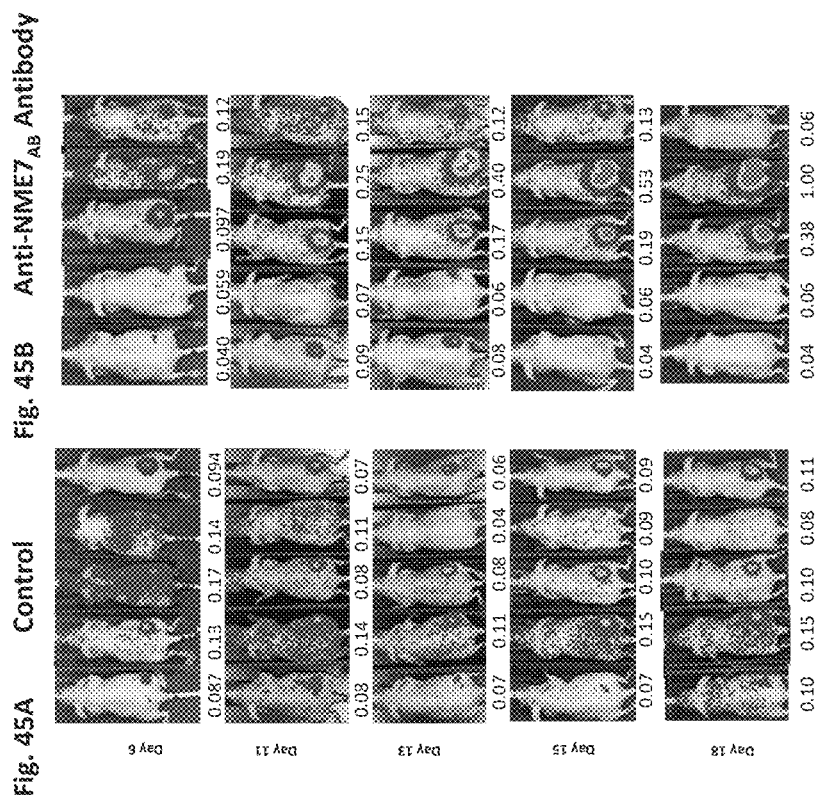
FIGS. 45A-45B shows photographs of female nu/nu mice that on Day 0 were injected sub-cutaneously into the right flank with 10,000 Luciferase positive T47D metastatic breast cancer stem cells, mixed with $NME7_{AB}$ to a final concentration of 32 nM, then mixed in a 1:1 vol:vol with Matrigel. Tumor engraftment was allowed to progress Day 0-Day 6. Animals were then treated i.v, by tail vein injection with anti-$NME7_{AB}$ antibodies. Control animals were injected with PBS.

In addition to demonstrating that the anti-$NME7_{AB}$ antibodies of the invention can inhibit metastasis, we tested their effect on metastasis from a primary tumor, which would more closely mimic the physiology of cancer metastasis. We generated T47D metastatic breast cancer cells, also known as cancer stem cells (CSCs) by culturing the cancer cells in a minimal serum-free media containing $NME7_{AB}$ for 10-15 days. These T47D CSCs were then implanted sub-cutaneously into the right flank of NSG mice into which had been implanted a 90-day estrogen release pellet. The implanted cancer cells were Luciferase positive so that after injection of the Luciferase substrate. Luciferin, the cancer cells emit photons and can be photographed in an IVIS instrument to measure and locate the implanted cancer cells. FIG. 45A-45B shows photographs of female nu/nu mice that on Day 0 were injected sub-cutaneously into the right flank with 10,000 Luciferase positive T47D metastatic breast cancer stem cells, mixed with $NME7_{AB}$ to a final concentration of 32 nM, then mixed in a 1:1 vol:vol with Matrigel. Tumor engraftment was allowed to progress Day 0-Day 6. Animals were then treated i.v, by tail vein injection with anti-$NME7_{AB}$ antibodies. Control animals were injected with PBS. FIG. 45A shows IVIS photographs of control animals. FIG. 45B shows IVIS photographs of animals injected into tail vein with a cocktail of anti-$NME7_{AB}$ antibodies 5A1, 4A3 and 5D4 to a total concentration of 15 mg/kg. Antibodies or PBS were administered 4 times between Day 7 and Day 18. As can be seen in the figure, the anti-$NME7_{AB}$ antibody treated animals show less metastases (blue dots in whole body) than the control group. In the treated group. 2 of the 5 animals have primary tumors that are larger than those in the control group. This could be because the anti-$NME7_{AB}$ antibodies prevented the spread of the cancer cells, so they remained concentrated in the primary tumor. In this experiment. PCR analysis, performed prior to injection of the cancer cells, showed that after 11 days in culture with $NME7_{AB}$, the T47D breast cancer cells had upregulated CXCR4 by 109-fold. OCT4 by 2-fold, NANOG by 3.5-fold and MUC1 by 2.7-fold.

Figures 46A, 46Q:
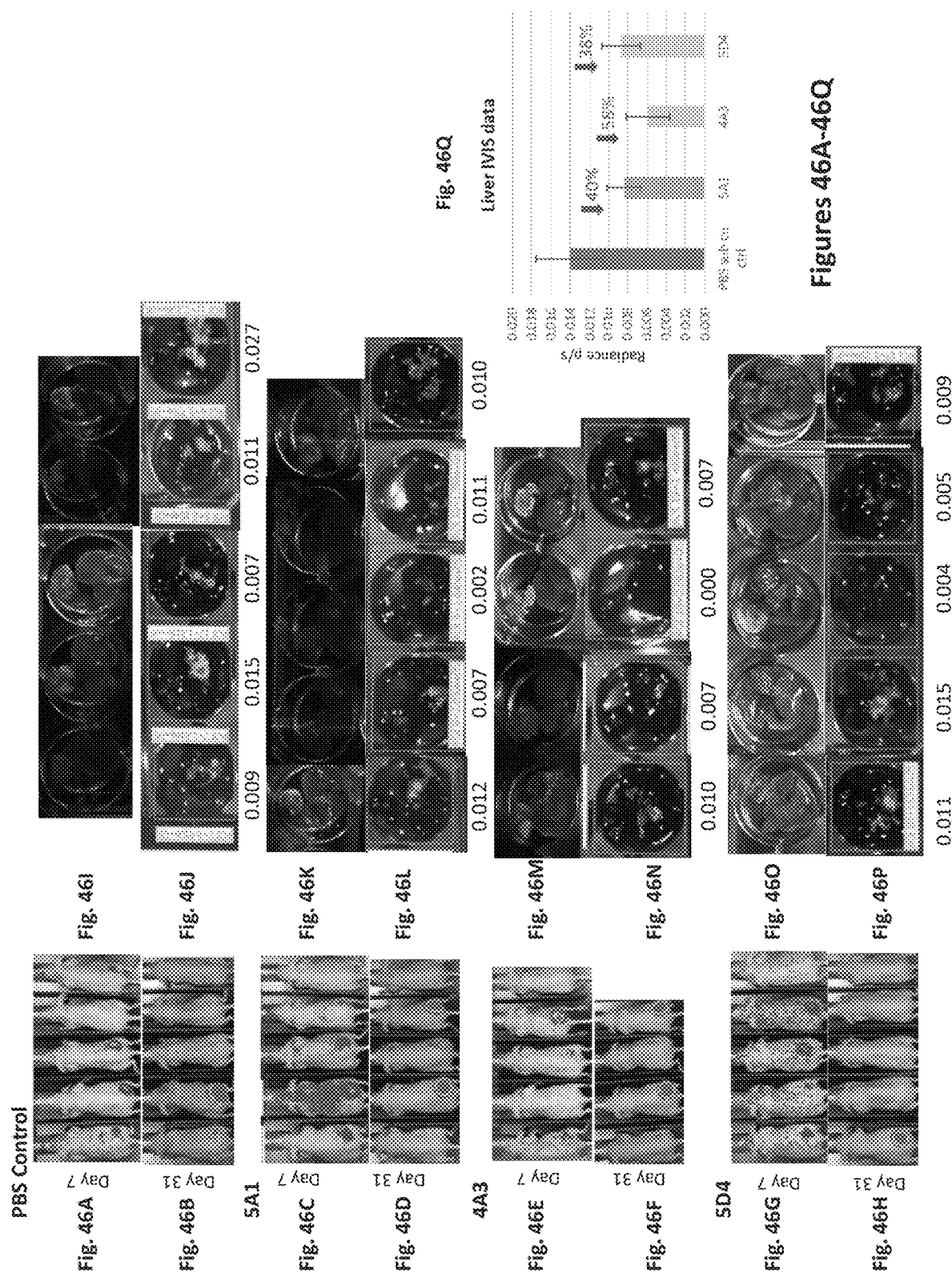
FIGS. 46A-46Q shows photographs of female nu/nu mice that on Day 0 were injected sub-cutaneously into the right flank with 10,000 Luciferase positive T47D metastatic breast cancer stem cells, mixed with $NME7_{AB}$ to a final concentration of 32 nM, then mixed in a 1:1 vol:vol with Matrigel. Tumor engraftment was allowed to progress Day 0-Day 6. Animals were then treated i.v, by tail vein injection, with anti-$NME7_{AB}$ antibodies. Control animals were injected with PBS. On Day 38 animals were sacrificed and livers harvested then analyzed by IVIS to detect cancer cells that had metastasized to the liver.

In another experiment, we tested the effect of anti-NME7$_{AB}$ antibodies of the invention on metastasis from a primary tumor to organs that breast cancers typically metastasize to. Breast cancers commonly metastasize to liver, lung, bone and brain, in that order. We generated T47D metastatic breast cancer cells by culturing in a minimal serum-free media containing NME7$_{AB}$ for 11 days. These T47D CSCs were then implanted sub-cutaneously into the right flank of NSG mice into which had been implanted a 90-day estrogen release pellet. FIG. 46A-46P shows photographs of female nu/nu mice that on Day 0 were injected sub-cutaneously into the right flank with 10,000 Luciferase positive T47D metastatic breast cancer stem cells, mixed with NME7$_{AB}$ to a final concentration of 32 nM, then mixed in a 1:1 vol:vol with Matrigel. Tumor engraftment was allowed to progress Day 0-Day 6. Animals were then treated i.v., by tail vein injection, with anti-NME7$_{AB}$ antibodies. Control animals were injected with PBS. On Day 38 animals were sacrificed and livers harvested then analyzed by IVIS to detect cancer cells that had metastasized to the liver. FIG. 46A-46B show whole body IVIS photographs of control animals that were injected with only PBS. FIG. 46C-46D show whole body IVIS photographs of control animals that were injected with the anti-NME7$_{AB}$ antibody 5A1. FIG. 46E-46F show whole body IVIS photographs of control animals that were injected with the anti-NME7$_{AB}$ antibody 4A3. FIG. 46G-46H show whole body IVIS photographs of control animals that were injected with the anti-NME7$_{AB}$ antibody 5D4. FIGS. 46A, 46C, 46E, and 46G are IVIS photographs taken at Day 7 before any treatment. FIGS. 46B, 46D, 46F, and 46H are IVIS photographs taken at Day 31 after anti-NME7$_{AB}$ antibody treatment or mock treatment. As can be seen in the figure, animals in the PBS control group show metastasis (blue dots) in the whole body IVIS photographs, while animals treated with anti-NME7$_{AB}$ antibodies do not. FIG. 46I-46P show photographs and IVIS photographs of livers and lung harvested from animals after sacrifice. FIGS. 46I, 46K, 46M, and 46O are regular photographs. FIGS. 46J, 46L, 46N, and 46P are IVIS photographs, illuminating the cancer cells that have metastasized there. As can be seen in the figure, the anti-NME7$_{AB}$ antibodies greatly inhibited metastasis to the liver, which is a primary site for breast cancer metastasis. FIG. 46Q is a bar graph of the measured photons emitted and enumerated by IVIS instrument for livers harvested from control animals versus the treated animals. As can be seen in the inserted graph of IVIS measurements, the inhibition of metastasis to the liver follows the rank order of inhibition of metastasis when cells were injected into the tail vein, which also matches the rank order of potency in being able to disrupt the NME7$_{AB}$-MUC1* interaction.

Figures 52A, 52B, 52C, 52D, 52E:
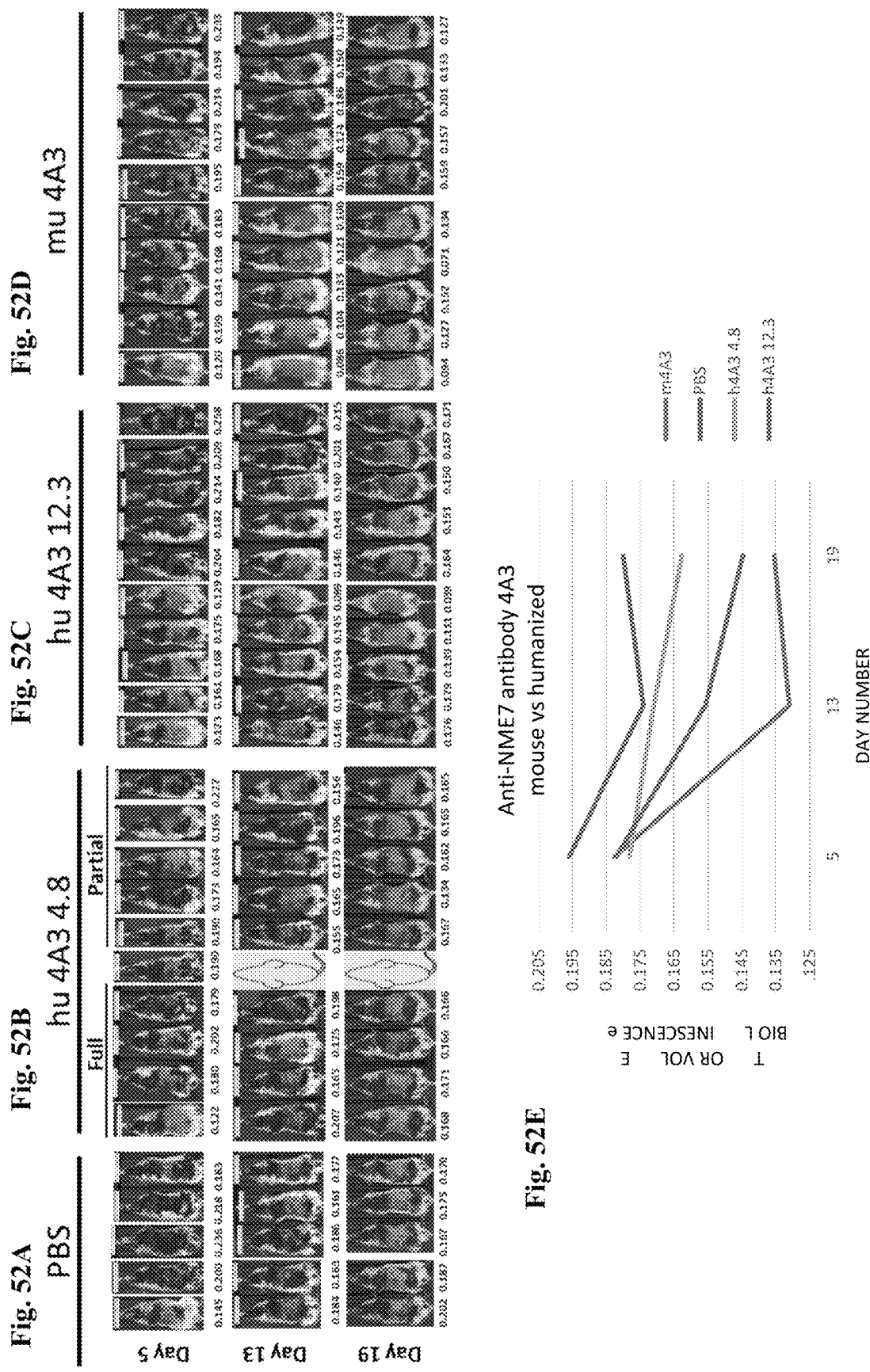
FIGS. 52A-52E shows photographs of female nu/nu mice that on Day (were injected into the tail vein with 10,000 Luciferase positive T47D metastatic breast cancer stem cells mixed with $NME7_{AB}$ to a final concentration of 32 nM. On Day 1 and Day 2 animals were injected into the tail vein with more 32 nM $NME7_{AB}$, which we have shown increases metastases. This is a system to demonstrate reversion of established metastases. On Day 5 animals were injected intravenously with 15 mg/kg of 8F9A4A3, aka 4A3, wherein the antibody was either the murine sequence or humanized 4A3 variant 4.8, or humanized 4A3 variant 12.3.

FIGS. 52A-52E shows photographs of female nu/nu mice that on Day 0 were injected into the tail vein with 10,000 Luciferase positive T47D metastatic breast cancer stem cells mixed with NME7$_{AB}$ to a final concentration of 32 nM. On Day 1 and Day 2 animals were injected into the tail vein with more 32 nM NME7$_{AB}$, which we have shown increases metastases. This is a system to demonstrate reversion of established metastases. On Day 5 animals were injected intravenously with 15 mg/kg of 8F9A4A3, aka 4A3, wherein the antibody was either the murine sequence or humanized 4A3 variant 4.8, or humanized 4A3 variant 12.3. FIG. 52A shows control animals injected with phosphate buffered saline solution. FIG. 52B shows animals treated with anti-NME7$_{AB}$ humanized 4A3 4.8. FIG. 52C shows animals treated with anti-NME7$_{AB}$ humanized 4A3 12.3. FIG. 52D shows animals treated with anti-NME7$_{AB}$ monoclonal antibody murine 4A3. FIG. 52E shows a graph of the quantification of bioluminescence measurement of tumor volume, taken in an IVIS instrument. Animals were injected with either PBS or an anti-NME7 antibody at 15 mg/kg once every 3 days. Antibody hu 4A3 4.8 denotes that the sequences derived from human heavy chain antibody sequence 1.46 (SEQ ID NO: 1102) and light chain sequence 1.6 (SEQ ID NO: 1104) were used. Antibody hu 4A3 12.3 denotes that the sequences derived from human heavy chain antibody sequence 4.4 (SEQ ID NO:1106) and light chain sequence 4.1 (SEQ ID NO:1108) were used. Note that half the animals treated with hu 4A3 4.8 were given a partial half dose.

Humanized 4A3 variant 4.8 was generated from human heavy chain IGHV1-46*0) 1 (IMGT accession number X92343) and from human light chain IGKV1-6*0) 1 (IMGT accession number M64858). Humanized 4A3 variant 4.8 was also caller 4A3 146-16.

Humanized 4A3 variant 12.3 was generated from human heavy chain IGHV4-4*01 (IMGT accession number X05713) and from human light chain IGKV4-1*01 (IMGT accession number Z00023). Humanized 4A3 variant 12.3 was also caller 4A3 44-41.

The accession number are from the IMGT data base (the international ImMunoGeneTics information system).

Figures 47A, 47B, 47C, 47D, 47E, 47F:
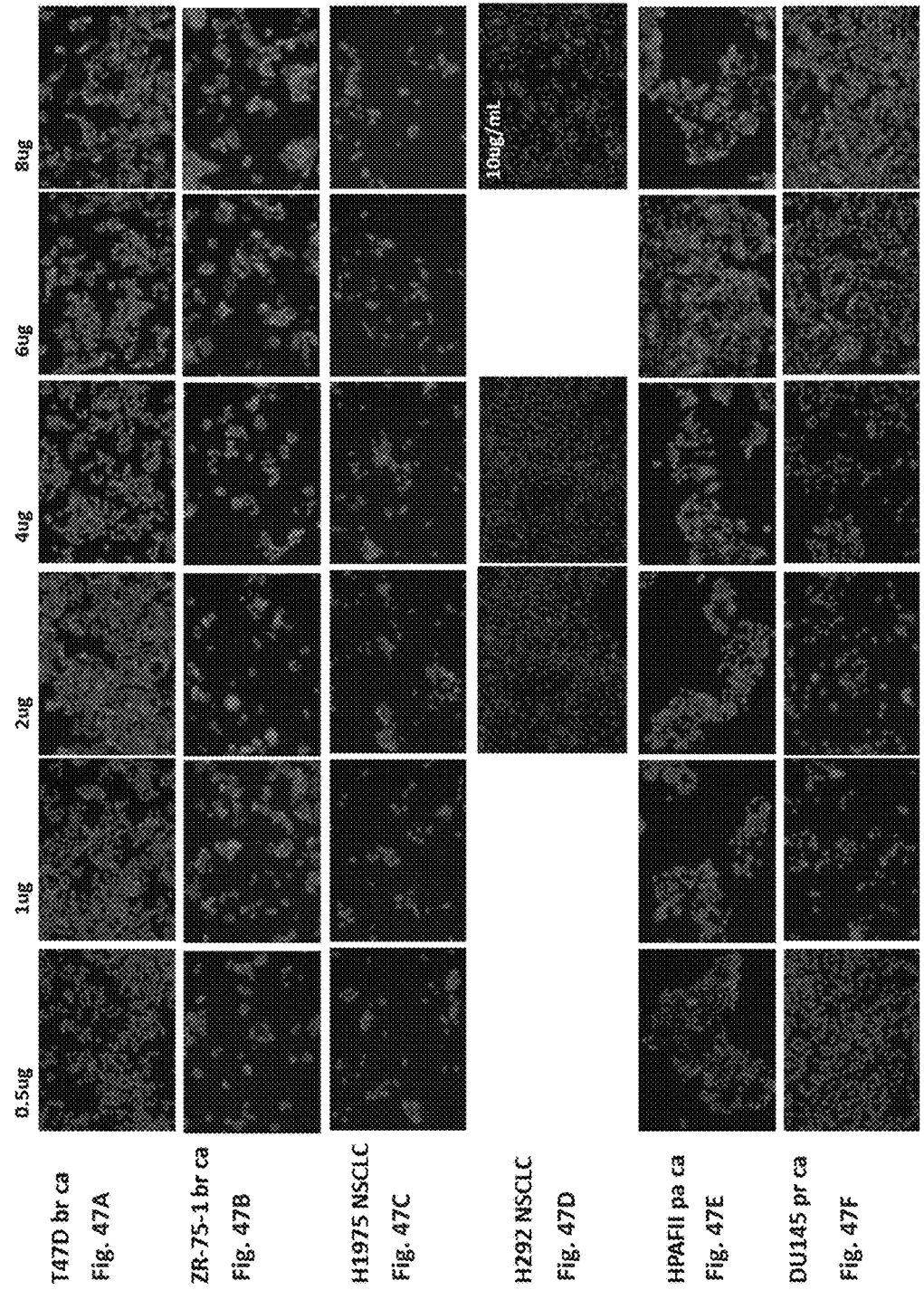
FIGS. 47A-47F shows photographs of immunofluorescent experiments in which various cancer cell lines are stained for the presence of $NME7_{AB}$.

IGHVx-x or IGKVx-x correspond to the IMGT gene name. *x corresponds to the IMGT allele name We performed immunofluorescent imaging of many cancer cell lines to determine if cultured cancer cell lines express NME7AB. As FIG. 47A-47F and FIG. 48A-48I clearly show, each MUC1 positive cancer cell line we tested is positive for NME7AB and its binding is membranous, consistent with NME7$_{AB}$ being secreted from cancer cells whereupon it binds to the extra cellular domain of MUC1*. FIG. 47A-47F shows photographs of immunofluorescent experiments in which various cancer cell lines are stained for the presence of NME7AB. FIG. 47A shows T47D breast cancer cells stained with varying concentrations of anti-NME7AB antibody 5D4. FIG. 47B shows ZR-75-1 breast cancer cells, also known as 1500s, stained with varying concentrations of anti-NME7AB antibody 5D4. FIG. 47C shows H1975 non-small cell lung cancer cells stained with varying concentrations of anti-NME7AB antibody 5D4. FIG. 47D shows H292 non-small cell lung cancer cells stained with varying concentrations of anti-NME7AB antibody 5D4. FIG. 47E shows HPAFII pancreatic cancer cells stained with varying concentrations of anti-NME7AB antibody 5D4. FIG. 47F shows DU145 prostate cancer cells stained with varying concentrations of anti-NME7AB antibody 5D4. As can be seen in the figure, all the cancer cell lines we tested show strong and membranous staining for NME7$_{AB}$. The monoclonal antibody used in these experiments was 5D4. In parallel, NME7$_{AB}$ antibodies 5A1 and 4A3 were used to stain the same cell lines and produced the same results.

Figures 48A, 48B, 48C, 48D, 48E, 48F, 48G, 48H, 48I:
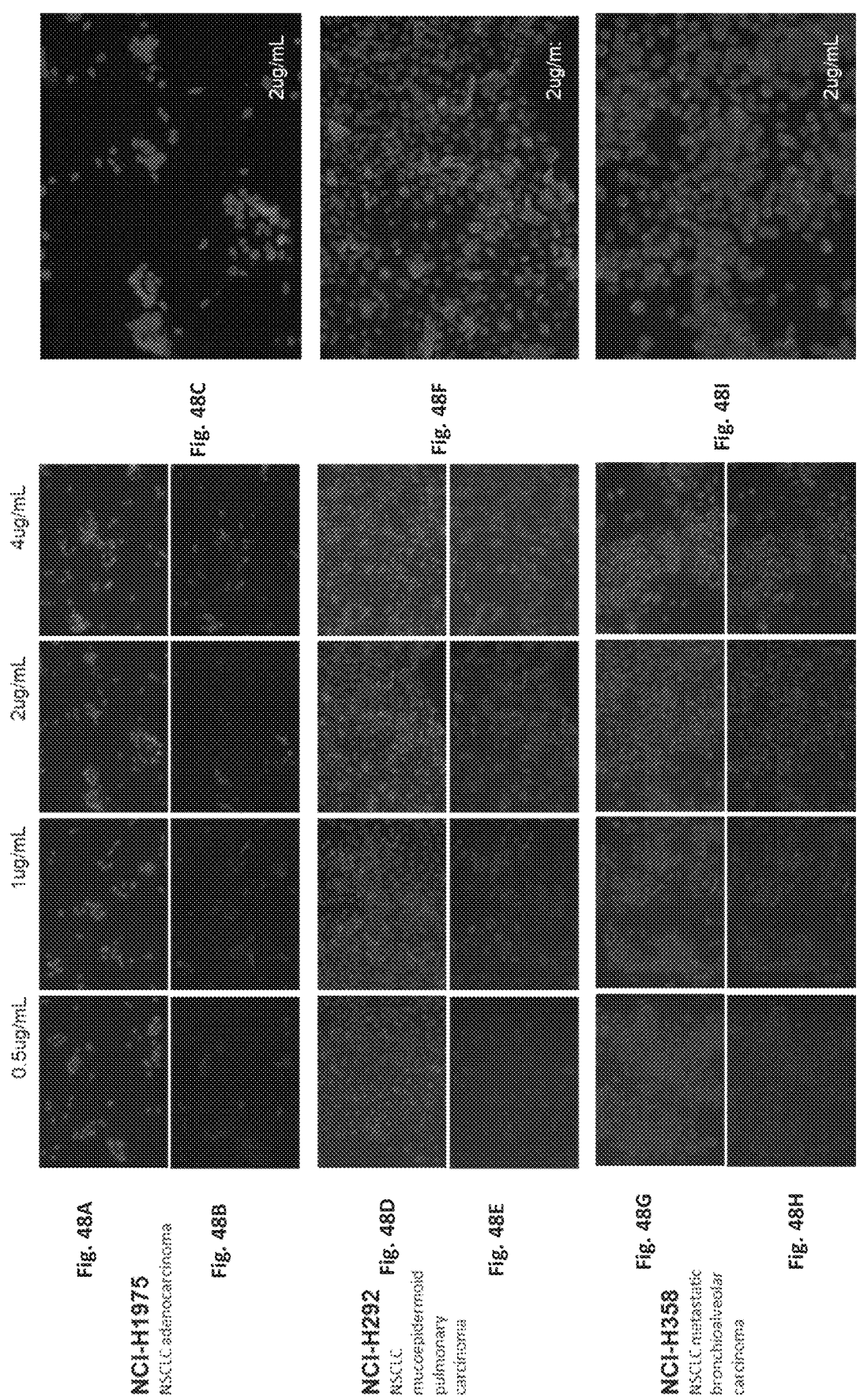
FIGS. 48A-48I shows photographs of immunofluorescent experiments in which various lung cancer cell lines are stained for the presence of $NME7_{AB}$.

FIG. 48A-48I shows photographs of immunofluorescent experiments in which various lung cancer cell lines are stained for the presence of NME7AB. FIG. 48A-48C shows H1975 non-small cell lung cancer cells, which are an adenocarcinoma, stained with varying concentrations of anti-NME7$_{AB}$ antibody 5D4. FIG. 48A is an overlay of DAPI and anti-NME7$_{AB}$ staining. FIG. 48B shows anti-NME7$_{AB}$ staining alone. FIG. 48C is a magnified view of the overlay of DAPI and anti-NME7$_{AB}$ staining. FIG. 48D-48F shows H292 non-small cell lung cancer cells, which are a mucoepidermoid pulmonary carcinoma, stained with varying concentrations of anti-NME7$_{AB}$ antibody 5D4. FIG. 48D is an overlay of DAPI and anti-NME7$_{AB}$ staining. FIG. 48E shows anti-NME7$_{AB}$ staining alone. FIG. 48F is a magnified view of the overlay of DAPI and anti-NME7$_{AB}$ staining. FIG. 48G-48I shows H358 non-small cell lung cancer cells, which are a metastatic bronchioalveolar carcinoma, stained with varying concentrations of anti-NME7$_{AB}$ antibody 5D4. FIG. 48G is an overlay of DAPI and anti-NME7$_{AB}$ staining. FIG. 48H shows anti-NME7$_{AB}$ staining alone. FIG. 48I is a magnified view of the overlay of DAPI and anti-NME7$_{AB}$ staining.

Figures 49A, 49B, 49C, 49D, 49E, 49F:
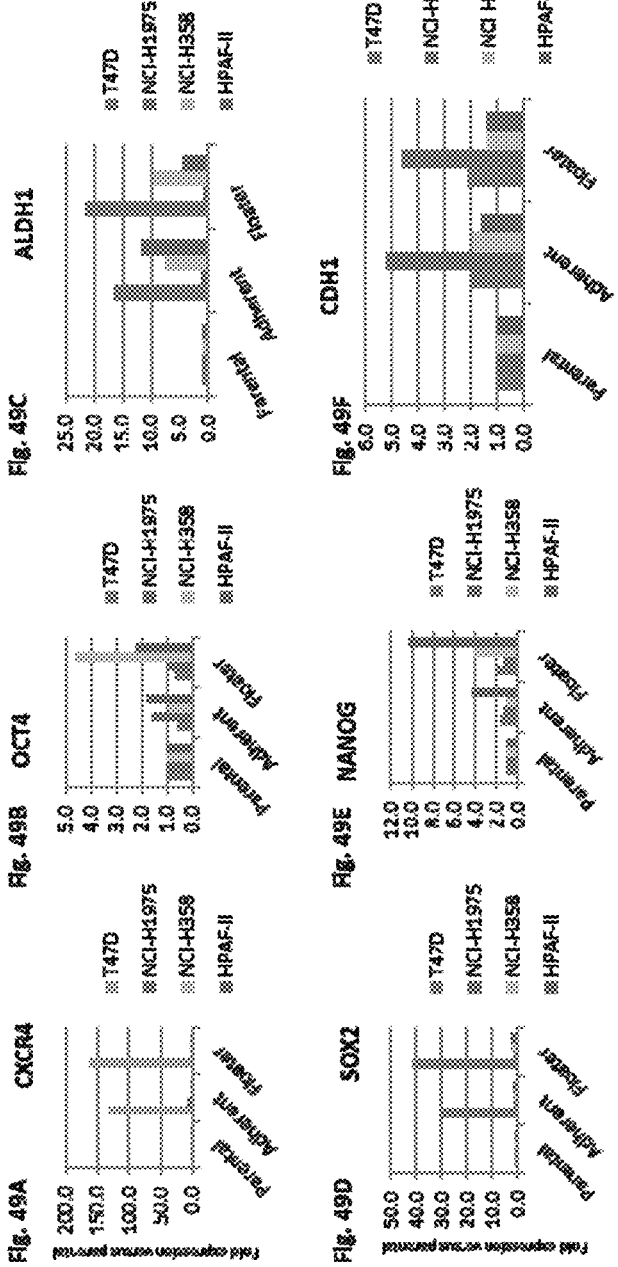
FIG. 49A-49I shows PCR graphs of cancer cell lines, breast T47D, Lung H1975, lung H358 and pancreatic HPAFII before and after culture in $NME7_{AB}$.
Figures 49G, 49H, 49I:
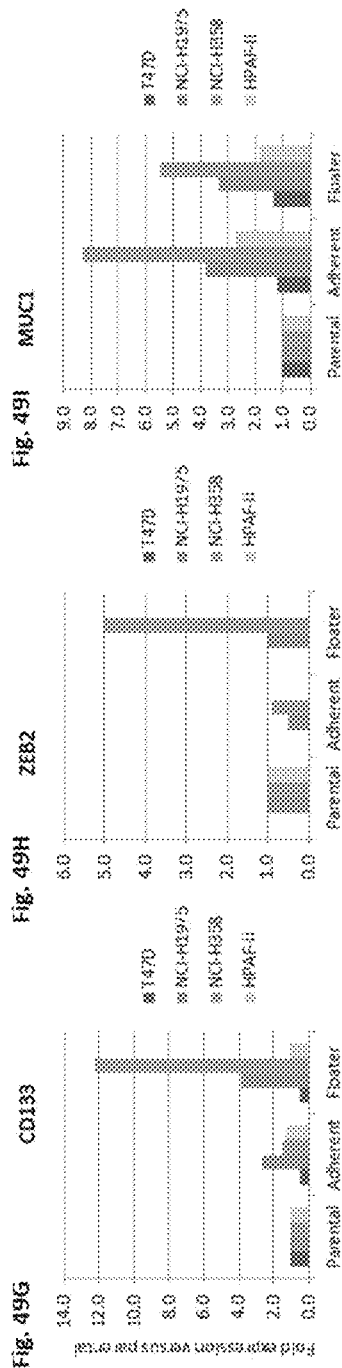

In addition, culturing these cell lines in a serum-free media containing NME7$_{AB}$ even further increased their expression of stem cell and metastatic markers. In particular, the cells that became non-adherent, referred to here as floaters, have even higher expression of stem cell and metastatic markers than their adherent counterparts. FIG. 49A-49I shows PCR graphs of cancer cell lines, breast T47D. Lung H1975, lung H358 and pancreatic HPAFII before and after culture in NME7$_{AB}$. FIG. 49A measured breast metastatic marker CXCR4. FIG. 49B measured stem cell marker OCT4. FIG. 49C measured metastatic marker ALDH1. FIG. 49D measured stem cell marker SOX2. FIG. 49E measured stem cell marker NANOG. FIG. 49F measured marker CDH1, also known as E-cadherin. FIG. 49G measured metastatic marker CD133. FIG. 49H measured stem cell marker ZEB2. FIG. 49I measured stem, cancer and metastatic marker MUC1. The floater cells, also known as tumor spheres become able to grow anchorage independently and show markers of metastasis that are more elevated than the adherent cells. Animals injected with cancer stem cells are those injected with the NME7$_{AB}$ grown floater cells. As can be seen in the figure markers of metastasis, stem cell markers, or markers of epithelial to mesenchymal transition (EMT) are elevated after culture in NME7$_{AB}$, indicating a transition to a more metastatic state. FIG. 50 shows Day 6 IVIS photographs of NSG mice injected into the tail vein with either 10,000 H358 lung cancer parent cells or H358 cells after 10-12 days in culture with NME7$_{AB}$. As can be seen in the figure, the NCI-H358 lung cancer cells grown in NME7$_{AB}$ have greatly increased metastatic potential compared to the parent cells, which are themselves reportedly metastatic cells. The functional increase in metastasis in 6 days from the NCI-H358 NME7$_{AB}$ metastatic cancer stem cells from just 10,000 cells is consistent with FIG. 49, showing that H358 cells greatly increased expression of metastatic markers after culture in NME7$_{AB}$.

Figure 51:
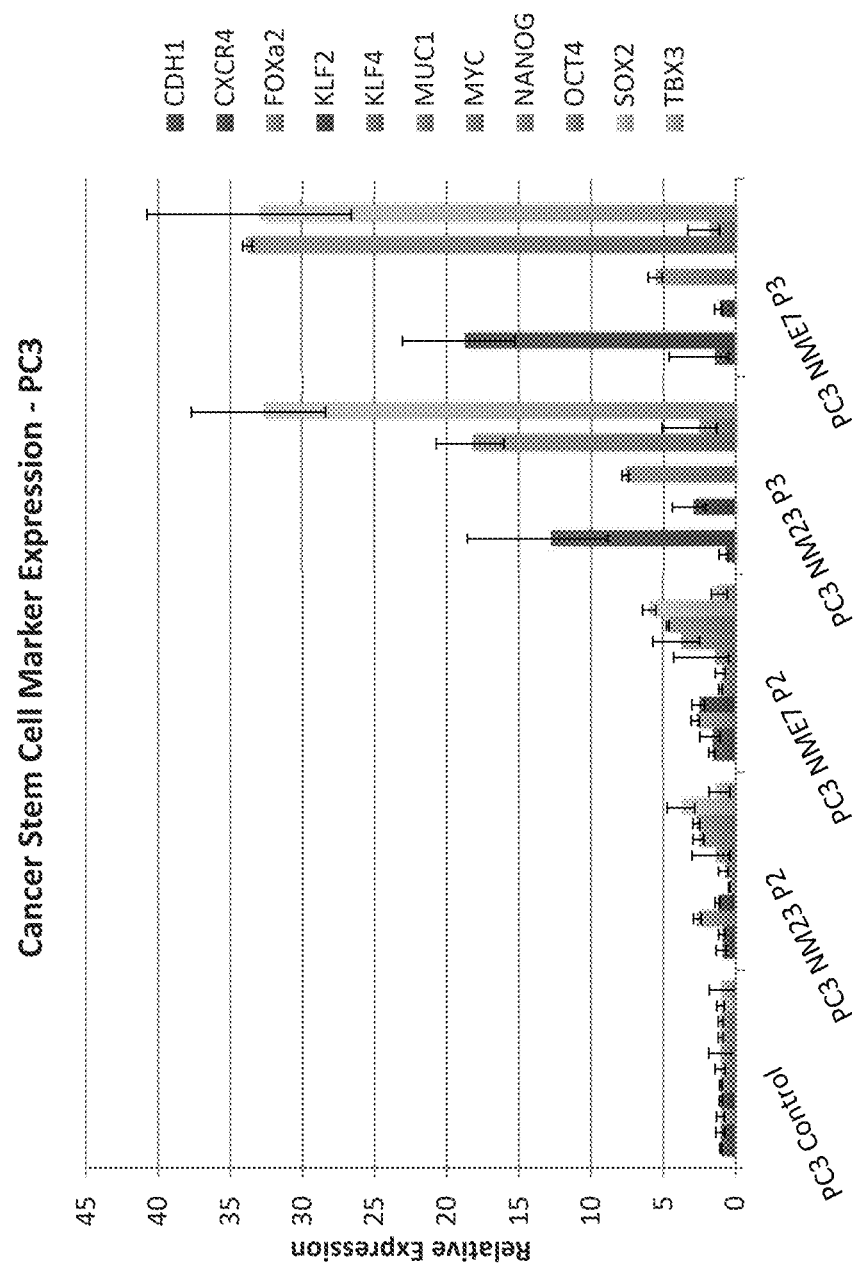
FIG. 51 shows PCR graph of a MUC1 negative prostate cancer line PC3 before and after 2 or 3 passages in culture in either dimeric NM23-H1, also known as NME1, or $NME7_{AB}$. The graph shows the fold difference in markers of stem cells, cancer cells as well as metastatic markers. As can be seen in the figure, repeated culture in NME1 or $NME7_{AB}$ induces upregulation of stem, cancer and metastatic markers but also upregulates expression of MUC1 by 5-8 times.

FIG. 51 shows PCR graph of a MUC1 negative prostate cancer line PC3 before and after 2 or 3 passages in culture in either dimeric NM23-H1, also known as NME1, or NME7$_{AB}$. The graph shows the fold difference in markers of stem cells, cancer cells as well as metastatic markers. As can be seen in the figure, repeated culture in NME1 or NME7$_{AB}$ induces upregulation of stem, cancer and metastatic markers but also upregulates expression of MUC1 by 5-8 times.

Collectively, these data have demonstrated that an NME7 that is devoid of the DM10 domain is secreted by cancer cells and binds to the extra cellular domain of a MUC1 that is devoid of tandem repeat domain, whereupon the NME7 dimerizes the MUC1* extra cellular domain which results in increased cancer cell growth and an increase in the cancer cells metastatic potential. It stands to reason that antibodies that disrupt the interaction between NME7$_{AB}$ and MUC1* extra cellular domain would inhibit cancer cell growth and would inhibit cancer metastasis. Here, we have shown that anti-NME7$_{AB}$ antibodies that inhibit interaction between NME7$_{AB}$ and MUC1* extra cellular domain do in fact inhibit cancer cell growth and cancer metastasis. Therefore, it follows that anti-NME7$_{AB}$ antibodies can be administered to a patient, diagnosed with or at risk of developing a cancer or metastasis, for the treatment or prevention of cancers.

Because NME1 is expressed in the cytoplasm of all cells and can be lethal if knocked out, and importantly the NME1 A domain has high sequence homology to the NME7 A domain, it is critical that anti-NME7$_{AB}$ antibodies for therapeutic use bind to NME7$_{AB}$ or NME7-X1, but not to NME1. In one aspect of the invention antibodies that would be optimal for therapeutic use were selected for their ability to bind to peptides that were unique to NME7$_{AB}$ or NME7-X1 and were not present in the NME1 sequence. FIG. 6-FIG. 9 lists NME7$_{AB}$ unique peptides.

In a preferred embodiment, antibodies suitable for administration to a patient for the treatment or prevention of cancer or cancer metastasis are selected from the group of antibodies that bind to the NME7 B3 peptide. In yet a more preferred embodiment, antibodies suitable for administration to a patient for the treatment or prevention of cancer or cancer metastasis are selected from the group of antibodies that bind to the NME7 B3 peptide, bind to NME7$_{AB}$ but do not bind to NME1. Examples of antibodies suitable for therapeutic use for the treatment or prevention of cancers or cancer metastasis, which have demonstrated such anti-cancer activity and anti-metastatic activity in vitro and in vivo here, include anti-NME7 antibodies 5A1, 4A3 and 5D4. These are but examples and other antibodies generated as described here and selected as described here will have the same anti-cancer and anti-metastatic activity. Such antibodies may be full antibodies or fragment thereof, including scFvs or antibody mimics wherein the variable domains of the antibody are incorporated into a protein scaffold that mimic an antibody. The antibodies may be of human or non-human species, including murine, camelid, llama, human or humanized and may be monoclonal, polyclonal, scFvs or fragments thereof.

Anti-NME7 antibodies for treatment or prevention of cancers or metastases can be used in many different therapeutic formats. For example, any of the antibodies described herein, or a fragment thereof, can be administered to a patient as a stand-alone antibody or antibody fragment, or attached to a toxin such as an antibody drug conjugate (ADC), or incorporated into a bi-specific antibody or incorporated into a BiTE (bispecific T cell engager), or incorporated into a chimeric antigen receptor (CAR) or engineered to be expressed by a cell that also expresses a CAR. The cell may be an immune cell, a T cell, an NK cell or a stem or progenitor cell, which may then be differentiated into a T cell or an NK cell.

Any of the antibodies described herein, or a fragment thereof, can be used as a diagnostic reagent to probe a bodily fluid, cell, tissue or bodily specimen for the presence of NME7$_{AB}$ or NME7-X1, which would be an indicator of cancer or susceptibility to cancers. Antibodies for diagnostic uses may be connected to an imaging agent, a nucleic acid tag, may be of any species including camelid, and can be used in whole body applications or on a bodily fluid, such as blood, cell, or tissue, in vitro, in vivo or intra-operatively.

The selection criteria, for therapeutically useful or diagnostically useful anti-NME7 antibodies, depends on the format or modality of the therapeutic or diagnostic into which the antibody will be incorporated. If the antibody or antibody fragment is to be administered to a patient as a stand-alone agent for the treatment or prevention of cancers or cancer metastases, then the antibody is selected for its ability to: i) bind to NME7$_{AB}$ or NME7-X1, but not to NME1; ii) bind to the PSMGFR peptide; iii) bind to the N-10 peptide and iv) disrupt the interaction between NME7$_{AB}$ or NME7-X1 and the MUC1* extra cellular domain or the interaction between NME7$_{AB}$ or NME7-X1 and the N-10 peptide. The antibody may also be selected for its ability to bind to the NME7 B3 peptide. This therapeutic format also encompasses a cell that has been engineered to express a CAR and a secreted anti-NME7 antibody.

Other modalities require other selection criteria for anti-NME7 antibodies. If the anti-NME7 antibody is to be incorporated into an ADC, the ADC must be internalized by the target cell to trigger killing of the target cell. Recall that NME7$_{AB}$ or NME7-X1 will be bound to the extra cellular domain of MUC1*. If the antibody disrupts binding of the NME to MUC1* extra cellular domain, then the toxin-conjugated antibody will not be internalized and the cell will not be killed. Similarly, if the anti-NME7 antibody is to be incorporated into a CAR or a BiTE, the interaction between NME7$_{AB}$ or NME7-X1 cannot be disrupted or the immune cell will no longer be able to direct its killing agents to the cancer cell. If the anti-NME7 antibody is to be used as a diagnostic reagent, the interaction between NME7$_{AB}$ or NME7-X1 cannot be disrupted or antibody and associated label will be washed away. Therefore, for ADC, CAR T, or CAR-NK, BiTEs or diagnostic applications, the anti-NME7 antibody is selected for its ability to: i) bind to NME7$_{AB}$ or NME7-X1, but not to NME1; ii) bind to the PSMGFR peptide; iii) bind to the N-10 peptide and iv) bind to NME7$_{AB}$ or NME7-X1 without disrupting the interaction with the MUC1* extra cellular domain or the interaction between NME7$_{AB}$ or NME7-X1 and the N-10 peptide. The antibody may also be selected for its ability to bind to the NME7 B3 peptide.

In one aspect of the invention, a cell is engineered to express an anti-NME7$_{AB}$ antibody of the invention or fragment thereof. The cell may be an immune cell, such as a T cell or NK cell or it may be a stem or progenitor cell, which may be differentiated into a more mature immune cell such as a T cell or NK cell. In a preferred embodiment, the cell that is engineered to express an anti-NME7$_{AB}$ antibody is also engineered to express a chimeric antigen receptor (CAR). In a preferred embodiment, the CAR recognizes a tumor associated antigen. In a preferred embodiment, the CAR targets MUC1*. In a more preferred embodiment, the CAR is directed to the tumor by anti-MUC1* antibody MNC2. In another aspect of the invention, cell that is engineered to express a CAR is also engineered to inducibly express an anti-NME7 antibody. In one example, the nucleic acid encoding an anti-NME7$_{AB}$ antibody is inserted into the Foxp3 enhancer or promoter. In another example, the anti-NME7$_{AB}$ antibody is in an NFAT-inducible system. In one aspect, the NFAT-inducible system incorporates NFATc1 response elements inserted upstream of an anti-NME7$_{AB}$ antibody sequence. They may be inserted into an IL-2 promoter, a Foxp3 enhancer or promoter or other suitable promoter or enhancer.

In another aspect of the invention, peptides that are unique to NME7$_{AB}$ or NME7-X1 are incorporated into an entity used to immunize or vaccinate people against cancers or cancer metastases. In a preferred embodiment, the peptide comprises all or part of the NME7 B3 peptide, which may be the NME7 B3 peptide with Cys-14-Ser mutation.

Another aspect of the invention involves a method of generating anti-NME7$_{AB}$ antibodies in a host animal, where the animal is immunized with the NME7 B3 peptide. In a preferred embodiment, the NME7 B3 peptide has Cysteine 14 mutated to Serine (SEQ ID NO: 169) to avoid disulfide bond formation which inhibits NME7 specific antibody generation.

Another aspect of the invention involves a method of generating cells with enhanced metastatic potential involving culturing the cells with NME7$_{AB}$ or NME7-X1. These cells can then be used in many aspects of drug discovery.

Another aspect of the invention involves a cell that is engineered to express NME7$_{AB}$ or NME7-X1. The NME7$_{AB}$ or NME7-X1 may be of human sequence. Their expression may be inducible. In one aspect the cell is an egg which is then developed into an animal that may be a transgenic animal able to express human NME7$_{AB}$ or NME7-X1.

NME7 binds to and dimerizes the extra cellular domain of the MUC1* growth factor receptor. Tissue studies show that MUC1* increases as tumor grade and metastasis increase. Here we show that NME7 expression increases as tumor grade and metastasis increases (FIG. 39-FIG. 41). Here, we have shown that antibodies that inhibit the interaction of NME7 and MUC1* inhibit tumor growth and metastases.

Other NME family members may bind to and dimerize the extra cellular domain of the MUC1* growth factor receptor. For example, we have shown that NME1, NME2 and NME6 can exist as dimers and that they bind to and dimerize the MUC1* extra cellular domain. NME7$_{AB}$ and NME7-X1 have two domains that can bind to the MUC1* extra cellular domain so as monomers they dimerize and activate the MUC1* growth factor receptor. We have now shown that anti-NME7 antibodies inhibit cancer and cancer metastases. Similarly, antibodies or antibody mimics that bind to these other NME proteins may be anti-cancer or anti-metastasis therapeutics that can be administered to a patient diagnosed with or at risk of developing a cancer or a metastasis. In one aspect of the invention, antibodies that can be used therapeutically for the treatment of cancers or metastases are antibodies that bind to NME1, NME2, NME3, NME4, NME5, NME6, NME7, NME8, NME9 or NME10. In one aspect of the invention, the therapeutic antibody or antibody mimic inhibits the binding of the NME protein and its cognate growth factor receptor. In one aspect of the invention, the therapeutic antibody or antibody mimic inhibits the interaction of the NME protein with the extra cellular domain of MUC1*. In another aspect of the invention, the therapeutic antibody or antibody mimic binds to a peptide, derived from NME1, NME2, NME3, NME4, NME5, NME6, NME7, NME8, NME9 or NME10, wherein the peptide is homologous to the NME7 A1, A2, B1, B2 or B3 peptide.

Below is a sequence alignment that shows a homology and identity alignment between NME7 and other NME family members. The underlined or underlined and bolded sequences correspond to NME7 peptides A1 (SEQ ID NO: 141), A2 (SEQ ID NO: 142), B1 (SEQ ID NO: 143), B2 (SEQ ID NO: 144) and B3 (SEQ ID NO: 145).

```
nucleoside diphosphate kinase 7 isoform a [Homo sapiens] (Hu_7)
MNHSERFVFIAEWYDPNASLLRRYELLFYPGDGSVEMHDVKNHRTFLKRTKYDNLHLEDLFIGNKVNVFSRQLVL

IDYGDQYTARQLCSRKEKTLALIKPDAISKAGEIIEIINKAGFTITKLKMMMLSRKEALDFHVDHQSRPFFNELI
```

-continued

QFITTGPIIAMEILRDDAICEWKRLLGPANSGVARTDASESIRALFGTDGIRNAAHGPDSFASAAREMELFFPSS

GGCGPANTAKFTN<u>CTCCEVKPHAVSEGLLGKILMAIRDAGFEISAMQMFNMDRVNVZEFYEVYKGVVTEYHDMVT</u>

<u>EMYSGPCVAMEIQQNNAEKTFREFCGPADPEIARHLRPGTLRAIFGKTKIQNAVHCTDLPEDGLLEVQYFF</u>KILD

N (SEQ ID NO: 1141)

NME2 Theoretical pI/Mw: 8.52/17298.04
MANLERTFIAIKPDGVQRGLVGEIIKRFEQKGFRLVAMKFLRASEEHLKQHYIDLKDRPFFPGLVKYMNSGPVVA

MVWEGLNVVKTGRVMLGETNPADSKPGTIRGDFCIQVGRNIIHGSDSVKSAEKEISLWFKPEELVDYKSCAHDWV

YE (SEQ ID NO: 200)

global/global (N-W) score: 171; 26.5% identity (56.8% similar) in 155 aa
overlap (1-131:1-152)

```
              10        20        30        40        50
7A    ----EKTLALIKPDAISKA--GEIIEIINKAGETITKLKMMMLSRKEALDFHVDHQSRPF
          :.:.  :::::..... ::::: ...  ::   ..  ::..  ...  ..: :::::
2     MANLERTFIAEKPDGVQRGLVGEIIKRFEQKGFRLVAMKFLRASEEHLKQHYIDLKDRPF
              10        20        30        40        50        60

60        70        80        90       100       110
7A    FNELIQFITTGPIIAMEILRDDAICEWKRLLGPANSGVARTDASESIRALFGTDGIRNAA
      :  :.......::.::    ...   . .: .:   :..   .::.  :  . : :
2     FPGLVKYMNSGPVVAMVWEGLNVVKTGRVMLGETNPADSKPG---TIRGDFCIQVGRNII
              70        80        90       100       110

120       130
7A    HGPDSFASAAREMELFF-------------------------- (SEQ ID NO: 199)
      ::  ::   ::  .:.  :.:
2     HGSDSVKSAEKEISLWFKPEELVDYKSCAHDWVYE---------- (SEQ ID NO: 200)
              120       130       140       150
``` global/global (N-W) score: 104; 24.4% identity (51.3% similar) in 156 aa
overlap (1-134:1-152)

```
              10        20        30        40        50
7B    NC----TCCIVKPHAVSEGLLGKILMAIRDAGFEISAMQMFNMDRVNVEEFYEVYKGVVT
       :     ..: .:..:: :.    ...  :::  ::::.  ..   .... :   :
2     MANLERTFIAEKPDGVQRGLVGEIIKRFEQKGFRLVAMKFLRASEEHLKQHYIDLKDR-P
              10        20        30        40        50

60        70        80        90       100       110
7B    EYHDMVTEMYSGPCVAMEIQQNNATKTFREFCGPADPEIARHLRPGTLRAIFGKTKIQNA
        .: : :::  ::: .  :..::  :  :  :  :  .. :::.:      ..:
2     FFPGLVKYMNSGPVVAMVWEGLNVVKTGRVMLGETNPADSK---PGTIRGDFCIQVGRNI
              60        70        80        90       100       110

120       130
7B    VHCTDLPEDGLLEVQYFF------------------ (SEQ ID NO: 201)
       .: .:   ... :::. ::
2     IHGSDSVKSAEKEISLWFKPEELVDYKSCAHDWVYE (SEQ ID NO: 202)
              120       130       140       150
```

>NME3 Theoretical pI/Mw: 5.96/19088.97
MICLVLTIFANLFPSAYSGVNERTFLAVKPDGVQRRLVGEIVRRFERKGFKLVALKLVQASEELLREHYVELRER

PFYSRLVKYMGSPVVAMVWQGLDVVRASRALIGATDPGDATPGTIRGDFCVEVGKNVIHGSDSVESAQREIALW

FREDELLCWEDSAGHWLYE (SEQ ID NO: 206)

```
              10        20        30        40        50
7A    EKTLALIKPDAISK--AGEIIEIINKAGFTITKLKMMMLSRKEALDFHVDHQSRPFFNEL
          :.:. .::::..     .:::::. ...  ::  :::..  .. ..  ..:::::.:
3     ERTFLAVKPDGVQRRLVGEIVRRFERKGFKLVALKLVQASEELLREHYVELRERPFYSRL
              30        40        50        60        70        80

60        70        80        90       100       110
7A    IQFITTGPIIAMEILRDDAICEWKRLLGPANSGVARTDASE-SIRALFGTDGIRNAAHGP
       ....  .::..::   :::   . .:.::   ::   :.   ::. :  ..  .::  ::
3     VKYMGSPVVAMVWQGLDVVRASRALIGATDPG---DATPGTIRGDFCVEVGKNVIHGS
              90       100       110       120       130

120       130
7A    DSFASAAREMELFF (SEQ ID NO: 203)
      ::   ::  ::.: ::.:
3     DSVESAQREIALWF (SEQ ID NO: 204)
              140       150
```

10        20        30

```
                                           -continued
7B  N-C-------------------TCCIVKPHAVSEGLLGKILMAIRDAGFEISAMQMFNM
    :                     :::  :.:. :.:.:.  ..  .:.  :....  .
3   MICLVLTIFANLFPSAYSGVNERTFLAVKPDGVQRRLVGEIVRRFERKGFKLVALKLVQA
               10        20        30        40        50        60

40        50        60        70        80        90
7B  DRVNVFEFYEVYKGVVTEYHDMVTEMYSGPCVAMEIQQNNATKTFREFCGPADPEIARHL
    ..   ..:  : :          : .:  : ::: :::  :  .....  :  . : .::  :
3   SEELLREHY-VELRERPFYSRLVKYMGSPVVAMVWQGLDVVRASRALIGATDPGDAT--
            70        80        90       100       110

100       110       120       130
7B  RPGTLRAIFGKTKIQNAVHCTDLPEDGLLEVQYFF---------------- (SEQ ID NO: 205)
    :::::.: :        .    :: :.    ::.  :.
3   -PGTIRGDFCVEVGKNVIHGSDSVESAQREIALWFREDELLCWEDSAGHWLYE (SEQ ID NO: 206)
           120       130       140       150       160

NME4 Theoretical pI/Mw: 10.30/20658.59
MGGLFWRSALRGLRCGPRAPGPSLLVRHGSGGPSWTRERTLVAVKPDGVQRRLVGDVIQRFERRGFTLVGMKMLQ

APESVLAEHYQDLRRKPFYPALIRYMSSGPVVAMVWEGYNVVRASRAMIGHTDSAEAAPGTIRGDFSVHISRNVI

HASDSVEGAQREIQLWFQSSELVSWADGGQHSSIHPA (SEQ ID NO: 1110)

29.3% identity (68.4% similar) in 133 aa overlap (1-131:56-185)
            10        20        30        40        50
7A  EKTLALIKPDAISK--AGEIIEIINKAGFTITKLKMMMLSRKEALDFHVDHQSRPFFNEL
    :.:. .:::::.   .:..:..  :::.  ::::.   . . :. .::.  :
4   ERTLVAVKPDGVQRRLVGDVIQRFERRGFTLVGMKMLQAPESVLAEHYQDLRRKPFYPAL
           60        70        80        90       100       110

60        70        80        90       100       110
7A  IQFITTGPIIAMEILRDDAICEWKRLLGPANSGVARTDASESIRALFGTDGIRNAAHGPD
    :......:..::      ...    . .  .::..  :  . .::. :...   ::. :.  :
4   IRYMSSGPVVAMVWEGYNVVRASRAMIGHTDSAEA---APGTIRGDFSVHISRNVIHASD
          120       130       140       150       160       170

120       130
7A  SFASAAREMELFF (SEQ ID NO: 207)
    :   .:  ::..:.:
4   SVEGAQREIQLWF (SEQ ID NO: 208)
            180

28.8% identity (56.8% similar) in 132 aa overlap (3-134:40-167)
            10        20        30        40        50        60
7B  TCCIVKPHAVSEGLLGKILMAIRDAGFEISAMQMFNMDRVNVEEFYEVYKGVVTEYHDMV
    :       :::  .::  :.:  ...   ::   ::  ..:.:.:    .. :
4   TLVAVKPDGVQRRLVGDVIQRFERRGFTLVGMKMLQAPESVLAEHYQDLRRK-PFYPALI
          40        50        60        70        80        90

70        80        90       100       110       120
7B  TEMYSCPCVAMEIQQNNATKTFREFCGPADPEIARHLRPGTLRAIFGKTKIQNAVHCTDL
    : ::: :::    . :.....  :  . : .:  :     :::::.: :        .::..:
4   RYMSSGPVVAMVWEGYNVVRASRAMIGHTDSAEAA---PGTIRGDFSVHISRNVIHASDS
          100       110       120       130       140       150

130
7B  PEDGLLEVQYFF (SEQ ID NO: 209)
    :  .  ::.  ::
4   VEGAQREIQLWF (SEQ ID NO: 210)
          160

NME5 Theoretical pI/Mw: 6.08/29296.23
MEISMPPPQIYVEKTLAIIKPDIVDKEEEIQDIILRSGFTIVQRRKLRLSPEQCSNFYVEKYGKMFFPNLTAYMS

SGPLVAMILARHKAISYWLELLGPNNSLVAKETHPDSLRAIYGTDDLRNALHGSNDFAAAEREIRFMFPEVIVEP

IPIGQAAKDYLNLHIMPTLLEGLTELCKQKPADPLFWYMCCRREHWTLRSILLVCMSGIRMSLPHCADYCSFVEG

FEIWLADWLLKNNPNKPKLCHHPIVEEPY (SEQ ID NO: 1111)

44.3% identity (74.8% similar) in 131 aa overlap (1-131:13-143)
7A              10        20        30        40        50        60
    EKTLALIKPDAISKAGEIIEIINKAGFTITKLKMMMLSRKEALDFHVDHQSRPFFNELIQ
    :::::::::::  ..: :: .:. ::::::.   .  .::       .:::..  ..  .:
5   EKTLAIIKPDIVDKEEEIQDIILRSGFTIVQRRKLRLSPEQCSNFYVEKYGKMFFPNLTA
          20        30        40        50        60        70

70        80        90       100       110       120
7A  FITTGPIIAMEILRDDAICEWKRLLGPANSGVARTDASESIRALFGTDGIRNAAHGPDSF
    ..::..:.::  .: .  :  : .::: ::  .:.:::::: :::. ::  ::: ...
```

```
                                             -continued
5    YMSSGPLVAMILARHKAISYWLELLGPNNSLVAKETHPDSLRAIYGTDDLRNALHGSNDF
              80        90       100       110       120       130

130
7A   ASAAREMELFF (SEQ ID NO: 211)
     :.: ::....:
5    AAAEREIRFMF (SEQ ID NO: 212)
         140

28.0% identity (58.3% similar) in 132 aa overlap (3-134:15-143)
             10        20        30        40        50        60
7B   TCCIVKPHAVSEGLLGKILMAIRDAGFEISAMQMFNMDRVNVEEFYEVYKGVVTEYHDMV
      :  :.:: :.. .:  ..:: .. : :: .::..:  .  :..  .::  ::: . ...
5    TLAIIKPDIVDKEE--EIQDIILRSGFTIVQRRKLRLSPEQCSNFY-VEKYGKMFFPNLT
             20        30        40        50        60        70

70        80        90       100       110       120
7B   TEMYSCPCVAMEIQQNNATKTFREFCGPADPEIARHLRPGTLRAIFGKTKIQNAVHCTDL
     . : ::: ::: ..:: :: :   ::  :: .:.. ::  :.:  .:::.:  .::::.:
5    AYMSSGPLVAMILARHKAISYWLELLGPNNSLVAKETHPDSLRAIYGTDDLRNALHGSND
             80        90       100       110       120       130

130
7B   PEDGLLEVQYFF (SEQ ID NO: 213)
      . :.....:
5    FAAAEREIRFMF (SEQ ID NO: 214)
         140
```

NME6 Theoretical pI/Mw: 7.81/22003.16

MTQNLGSEMASILRSPQALQLTLALIKPDAVAHPLILEAVHQQILSNKFLIVRMRELLWRKEDCQRFYREHEGRF

FYQRLVEFMASGPIRAYILAHKDAIQLWRTLMGPTRVFRARHVAPDSIRGSFGLTDTRNTTHGSDSVVSASREIA

AFFPDFSEQRWYEEEEPQLRCGPVCYSPEGGVHYVAGTGGLGPA (SEQ ID NO: 65)

```
37.6% identity (68.4% similar) in 133 aa overlap (3-131:22-153)
             10        20        30        40        50
7A   TLALIKPDAISKAGEIIEIINKA----GFTITKLKMMMLSRKEALDFHVDHQSRPFFNEL
     :::::::::: .      ::.:      ::.   .:.   .: . ..::::. .::::
6    TLALIKPDAVAHP-LILEAVHQQILSNKFLIVRMRELLWRKEDCQRFYREHEGRFFYQRL
             30        40        50        60        70        80

60        70        80        90       100       110
7A   IQFITTGPIIAMEILRDDAICEWKRLLGPANSGVARTDASESIRALFGTDGIRNAAHGPD
     ..:..:::  .  . ::: :. :.::.    ::  : :::: ::::.::..  ::::::
6    VEFMASGPIRAYILAHKDAIQLWRTLMGPTRVFRARHVAPDSIRGSFGLTDTRNTTHGSD
             90       100       110       120       130       140

120       130
7A   SFASAAREMELFF (SEQ ID NO: 215)
     :  .:::::. ::
6    SVVSASREIAAFF (SEQ ID NO: 216)
            150

29.3% identity (57.9% similar) in 133 aa overlap (3-134:22-153)
             10        20        30        40        50        60
7B   TCCIVKPHAVSEGL-LGKILMAIRDAGFEISAMQMFNMDRVNVEEFYEVYKGVVTEYHDM
      :   ..:: :::: ::  :. .  .. .:  .  ::.:  ::: :::  .. . ...:
6    TLALIKPDAVAHPLILEAVHQQILSNKFLIVRMRELLWRKEDCQRFYREHEGRFF-YQRL
             30        40        50        60        70        80

70        80        90       100       110       120
7B   VTEMYSGPCVAMEIQQNNATKTFREFCGPADPEIARHLRPGELRAIFGKTKIQNAVHCTD
     :  : ::: ::: ..:: :: :    :::  :: .:.. ::  :.:  .:::.:  .::::
6    VEFMASGPIRAYILAHKDAIQLWRTLMGPTRVFRARHVAPDSIRGSFGLTDTRNTTHGSD
             90       100       110       120       130       140

130
7B   LPEDGLLEVQYFF (SEQ ID NO: 217)
      .. :. ::
6    SVVSASREIAAFF (SEQ ID NO: 218)
            150
```

NME8 Theoretical pI/Mw: 4.90/67269.94

MASKKREVQLQTVINNQSLWDEMLQNKGLTVIDVYQAWCGPCRAMQPLFRKLKNELNEDEILHFAVAEADNIVTL

QPFRDKCEPVFLFSVNGKIIEKIQGANAPLVNKKVINLIDEERKIAAGEMARPQYPEIPLVDSDSEVSEESPCES

VQELYSIAIIKPDAVISKKVLEIKRKITKAGFIIEAEHKTVLTEEQVVNFYSRIADQCDFEEFVSFMTSGLSYIL

VVSQGSKHNPPSEETEPQTDTEPNERSEDQPEVEAQVTPGMMKNKQDSLQEYLERQHLAQLCDIEEDAANVAKFM

```
DAFFPDFKKMKSMKLEKTLALLRPNLFHERKDDVLRIIKDEDFKILEQRQVVLSEKEAQALCKEYENEDYFNKLI

ENMTSGPSLALVLLRDNGLQYWKQLLGPRTVEEAIEYFPESLCAQFAMDSLPVNQLYGSDSLETAEREIQHFFPL

QSTLGLIKPHATSEQREQILKIVKEAGFDLTQVKKMFLTPEQIEKIYPKVTGKDFYKDLLEMLSVGPSMVMILTK

WNAVAEWRRLMGPTDPEEAKLLSPDSIRAQFGISKLKNIVHGASNAYEAKEVVNRLFEDPEEN (SEQ ID NO: 1112)

36.1% identity (69.2% similar) in 133 aa overlap (1-131:316-448)
            10         20         30         40         50
7A   EKTLALIKPDAIS-KAGEIIEIINKAGFTITKLKMMMLSRKEALDFHVDHQSRPFFNELI
     :::::::::. .     ....::.   :  : ....::.:::  ..... .::.::
8    EKTLALLRPNLFHERKDDVLRIIKDEDFKILEQRQVVLSEKEAQALCKEYENEDYFNKLI
           320        330        340        350        360        370

60         70         80         90        100        110
7A   QFITTGPIIAMEILRDDAICEWKRLLGPANSGVARTDASESIRALFGTDGIR-NAAHGPD
     . .:.:: ..  .::::. ::.::::  .  ::  :: ::..:.. ...  :  .:
8    ENMTSGPSLALVLLRDNGLQYWKQLLGPRTVEEAIEYFPESLCAQFAMDSLPVNQLYGSD
           380        390        400        410        420        430

120        130
7A   SFASAAREMELFF (SEQ ID NO: 219)
     :. .: :::. ::
8    SLETAEREIQHFF (SEQ ID NO: 220)
           440

Waterman-Eggert score: 269;85.9 bits; E(1) < 1.1e-21
33.6% identity (72.7% similar) in 128 aa overlap (1-127:451-577)
7A          10         20         30         40         50
     EKTLALIKPDAISKAGE-IIEIINKAGFTITKLKMMMLSRKEALDFHVDHQSRPFFNELI
     ..:::::::  : :.   : :.:....:::  .::.:  ::. ..   ..  :.....
8    QSTLGLIKPHATSEQREQILKIVKEAGFDLTQVKKMFLTPEQIEKIYPKVTGKDFYKDLL
           460        470        480        490        500        510

60         70         80         90        100        110
7A   QFITTGPIIAMEILRDDAICEWKRLLGPANSGVARTDASESFRALFGTDGIRNAAHGPDS
     ...:.::   ..:::::.::..:.: ::.   ::   :: .:  :. .. ::..::
8    EMLSVGPSMVMILTKWNAVAEWRRLMGPTDPEEAKLLSPDSIRAQFGISKLKNIVHGASN
           520        530        540        550        560        570
     120
7A   FASAAREM (SEQ ID NO: 221)
      :  :.:.
8    -AYEAKEV (SEQ ID NO: 222)

Waterman-Eggert score: 119;40.4 bits; E(1) < 5.3e-08
33.8% identity (73.8% similar) in 65 aa overlap (3-65:156-220)
            10         20         30         40         50         60
7A   TLALIKPDAI--SKAGEIIEIINKAGFTITKLKMMMLSRKEALDFHVDHQSRPFFNELIQ
     ..:::::::     .::  .::  ::  : :.::::   ..  . ..::..    :.:..
8    SIAIIKPDAVISKKVLEIKRKITKAGFIIEAEHKTVLTEEQVVNFYSRIADQCDFEEFVS
           160        170        180        190        200        210

7A   FITTG (SEQ ID NO: 223)
     :.::.:
8    FMTSG (SEQ ID NO: 224)
        220

33.6% identity (65.5% similar) in 116 aa overlap (3-118:453-566)
            10         20         30         40         50         60
7B   TCCIVKPHAVSEGLLGKILMAIRDAGFEISAMQMFNMDRVNVEEFYEVYKGVVTEYHDMV
     :   ..::::::.  .:: ...:.:..    .  .  ..:::.:  :    :.:.:
8    TLGLIKPHATSEQRE-QILKIVKEAGFDLTQVKKMFLTPEQEEKIYPKVTGK-DFYKDLL
           460        470        480        490        500        510

70         80         90        100        110
7B   TEMYSGPCVAMEIQQNNATKTFREFCGPADPEIARHLRPGTLRAIFGKTKIQNAVH (SEQ ID NO: 225)
     .  :: ::.. ::    ..  .   :.:  :. :: :::..:..  ....::..:
8    EMLSVGPSMVMILTKWNAVAEWRRLMGPTDPEEAKLLSPDSIRAQFGISKLKNIVH (SEQ ID NO: 226)
           520        530        540        550        560

Waterman-Eggert score: 128;41.3 bits; E(1) < 2.9e-08
23.3% identity (60.3% similar) in 116 aa overlap (20-134:334-448)
           20         30         40         50         60         70
7B   ILMAIRDAGFEISAMQMFNMDRVNVEEFYEVYKGVVTEYHDMVTEMYSGPCVAMEIQQNN
     .:    ::.::: :.   ::  :  :..:   ... ..::::  .:::: :.:..
8    VLRIIKDEDFKILEQRQVVLSEKEAQALCKEYENE-DYFNKLIENMTSGPSLALVLLRDN
           340        350        360        370        380        390

80         90        100        110        120        130
```

```
7B    ATKTFREFCGPADPEIARHLRPGTLRAIFGKTKIQ-NAVHCCDLPEDGLLEVQYFF (SEQ ID NO: 227)
      . . ..... ::    :  :  .: : :..   ..  :. . . : : :.: : .   :.:::
8     GLQYWKQLLGPRTVEEAIEYFPESLCAQFAMDSLPVNQLYGSDSLETAEREIQHFF (SEQ ID NO: 228)
              400       410       420       430       440

Waterman-Eggert score: 76;26.4 bits; E(1) < 0.00088
23.4% identity (46.8% similar) in ill aa overlap (6-105:159-268)
              10        20        30        40        50        60
7B    IVKPHAVSEGLLGKILMAIRDAGFEISAMQMFNMDRVNVEEFYEVYKGVVTEYHDMVTEM
      :..;  ::    ..     .:   :: :::  : :.    . . .::      ......:
8     IIKPDAVISKKVLEIKRKITKAGFIIEAEHKTVLTEEQVVNFYSRIADQC-DFEEFVSFM
             160       170       180       190       200       210

70        80        90       100
7B    YSGPCVAMEIQQNNATKTFREFCGPA-----------DPEIARHLRPGTLR (SEQ ID NO: 229)
       ::   .  ..:.. .     :  :            .::.  .. :: ..
8     TSGLSYILVVSQGSKHNPPSEETEPQTDTEPNERSEDQPEVEAQVTPGMMK (SEQ ID NO: 230)
             220       230       240       250       260

NME9
MLSSKGLTVVDVYQGWCGPCKPVVSLFQKMRIEVGLDLLHFALAEADRLDVLEKYRGKCE

PTFLFYAIKDEALSDEDECVSHGKNNGEDEDMVSSERTCTLAIIKPDAVAHGKTDEIIMK

IQEAGFEILTNEERTMTEAEVRLFYQHKAGESPSSVRHRNALQCRPWKPGQRRC (SEQ ID NO: 231)

41.3% identity (67.4% similar) in 46 aa overlap (3-46:100-145)
                  10        20        30         40
7A    TLALIKPDAIS--KAGEIIEIINKAGFTITKLKMMMLSRKEALDFH
      :::::::::::.. :. :::  :..::: :    . ... :. ::
9     TLAIIKPDAVAHGKTDEIIMKIQEAGFEILTNEERTMTEAEVRLFY
             100       110       120       130       140

>--
Waterman-Eggert score: 30;13.5 bits; E(1) < 0.85
28.6% identity (71.4% similar) in 14 aa overlap (69-82:100-113)
             70        80
7A    AMEILRDDAICEWK (SEQ ID NO: 232)
      ..  :... ::. .   :
9     TLAIIKPDAVAHGK (SEQ ID NO: 233)
            100       110

Waterman-Eggert score: 29;13.2 bits; E(1) < 0.91
25.8% identity (74.2% similar) in 31 aa overlap (12-42:121-149)
                20        30        40
7A    ISKAGEIIEIINKAGFTITKLKMMMLSRKEA (SEQ ID NO: 234)
      :...::  .::...  :::.  ..  ...:
9     IQEAG--FEILTNEERTMTEAEVRLFYQHKA (SEQ ID NO: 235)
                130       140

39.6% identity (69.8% similar) in 53 aa overlap (1-53:98-150)
              10        20        30        40        50
7B    NCTCCIVKPHAVSEGLLGKILMAIRDAGFEISAMCMFNMDRVNVEEFYEVYKG (SEQ ID NO: 236)
      .::   :.::   ::.. :   ..:: ...::::::  .  ..:::::. . :
9     TCTLAIIKPDAVAHGKTDEIIMKIQEAGFEILTNEERTMTEAEVRLFYQHKAG (SEQ ID NO: 237)
             100       110       120       130       140       150

NME10 NP_008846.2 protein XRP2 [Homo sapiens]
MGCFFSKRRKADKESRPENEEERPKQYSWDQREKVDPKDYMFSGLKDEEVGRLPGTVAGQQFLIQDCENC

NIYIFDHSATVTIDDCTNCIIFLGPVKGSVFFRNCRDCKCTLACQQFRVRDCRKLEVFLCCATQPIIESS

SNIKFGCFQWYYPELAFQFKDAGLSIFNNTWSNIHDFTPVSGELNWSLLPEDAVVQDYVPIPTTEELKAV

RVSTEANRSIVPISRGQRQKSSDESCLVVLFAGDYTIANARKLIDEMVGKGFFLVQTKEVSMKAEDAQRV

FREKAPDFLPLLNKGPVEALEFNGDGAVEVCQLIVNEIFNGTKMFVSESKETASGDVDSFYNFADIQMGI (SEQ ID NO: 238)

23.5% identity (66.2% similar) in 68 aa overlap (11-78:246-308)
              20        30        40        50        60        70
7A    AISKACEIIEEINKAGFTITKLKMMMLSRKEALDFHVDHQSRPFFNELIQFITTGPIIAM
       .:.: ...:. .    :: ... ::  ... : ..  .:  .. ... : ... ::.::
10    TIANARKLIDEMVGKGFFLVQTKEVSMKAEDAQ--RVFREKAP---DFLPLLNKGPVIAL
             250       260       270       280       290       300

7A    EILRDDAI (SEQ ID NO: 239)
      :. : ..
10    EFNGDGAV (SEQ ID NO: 240)
```

-continued

```
Waterman-Eggert score: 30; 15.1 bits; E(1) < 0.73
28.9% identity (57.8% similar) in 45 aa overlap (66-108:200-244)
          70        80        90       100
7A  PIIAMEILRDDAIC-EWKRLLGPANSGVARTDASES-IRALFGTD (SEQ ID NO: 241)
    ::  .  :  :           .      ....::  .....:
10  PIPTTEELKAVRVSTEANRSIVPISRGQRQKSSDESCLVVLFAGD (SEQ ID NO: 242)
        200       210       220       230       240

Waterman-Eggert score: 33;14.4 bits; E(1) < 0.87
14.7% identity (52.0% similar) in 75 aa overlap (7-80:35-109)
          10        20        30        40        50        60
7A  IKPDAISKAGEIIEIINKAGFTITKLKMMMLSRKEALDFHVDHQSRPFFNELIQ-FITTG
     . :        .:  ... :..  ....   ..      :::.    ...    .:  :
10  VDPKDYMFSGLKDETVGRLPGTVAGQQFLIQDCENCNIYIFDHSATVTIDDCTNCIIFLG
         40        50        60        70        80        90

70        80
7A  PIIAMEILRDDAICE (SEQ ID NO: 243)
    :. .   ...:.  ..
10  PVKGSVFFRNCRDCK (SEQ ID NO: 244)
           100

Waterman-Eggert score: 45;17.5 bits; E(1) < 0.22
21.6% identity (58.8% similar) in 51 aa overlap (4-50:130-180)
          10        20        30        40        50
7B  CCIVKP--HAVSEGLLGKILMAIRDAGFEI--SAMQMFNMDRVNVEEFYEV (SEQ ID NO: 245)
    ::  ..:  .. ..  .  .:.      .       .......  :...:   :
10  CCATQPIIESSSNIKFGCFQWYYPELAFQFKDAGLSIFNNTWSNIHDFTPV (SEQ ID NO: 246)
        130       140       150       160       170       180
```

As an example, antibodies or antibody mimics that bind to the NME7 homologous peptides ("homologous peptides") in particular homologous to A1, A2, B1, B2 or B3 peptides, may be administered to a patient diagnosed with or at risk of developing a cancer or cancer metastasis.

Homologous Peptides to A1, A2, B1, B2 or B3 Peptides

Homologous peptides to A1, A2, B1, B2 or B3 peptides may include without limitation the following:

NME2A1
(amino acids) (SEQ ID NO: 247)
RASEEHLKQHYIDLKD

NME2A2
(amino acids) (SEQ ID NO: 248)
PADSKPGT

NME2B1
(amino acids) (SEQ ID NO: 249)
QKGFRLVAMKFLRASEEHLK

NME2B2
(amino acids) (SEQ ID NO: 250)
IDLKDRPFPGLVKY

NME2B3
(amino acids) (SEQ ID NO: 251)
GDFCIQVGRNIIHGSDSVKSAEKEISLWF

NME3A1
(amino acids) (SEQ ID NO: 252)
QASEELLREHYVELRE

NME3A1
(amino acids) (SEQ ID NO: 253)
PGDATPGT

NME3B1
(amino acids) (SEQ ID NO: 254)
RKGFKLVALKLVQASEELLR

NME3B2
(amino acids) (SEQ ID NO: 255)
VELRERPFYSRLVKY

NME3B3
(amino acids) (SEQ ID NO: 256)
GDFCVEVGKNVIHGSDSVESAQREIALWF

NME4A1
(amino acids) (SEQ ID NO: 257)
QAPESVLAEHYQDLRR

NME4A2
(amino acids) (SEQ ID NO: 258)
SAEAAPGT

NME4B1
(amino acids) (SEQ ID NO: 259)
RRGFTLVGMKMLQAPESVLA

NME4B2
(amino acids) (SEQ ID NO: 260)
QDLRRKPFYPALIRY

NME4B3
(amino acids) (SEQ ID NO: 261)
GDFSVHISRNVIHASDSVEGAQREIQLWF

NME5A1
(amino acids) (SEQ ID NO: 262)
RLSPEQCSNFYVEKYG

NME5A2
(amino acids)
(SEQ ID NO: 263)
SLVAKETHPDS

NME5B1
(amino acids)
(SEQ ID NO: 264)
RSGFTIVQRRKLRLSPEQCS

NME5B2
(amino acids)
(SEQ ID NO: 265)
VEKYGKMFFPNLTAY

NME5B3
(amino acids)
(SEQ ID NO: 266)
AIYGTDDLRNALHGSNDFAAAEREIRFMF

NME6A1
(amino acids)
(SEQ ID NO: 267)
LWRKEDCQRFYREHEG

NME6A2
(amino acids)
(SEQ ID NO: 268)
VFRARHVAPDS

NME6B1
(amino acids)
(SEQ ID NO: 269)
SNKFLIVRMRELLWRKEDCQ

NME6B2
(amino acids)
(SEQ ID NO: 270)
REHEGRFFYQRLVEF

NME6B3
(amino acids)
(SEQ ID NO: 271)
GSFGLTDTRNTTHGSDSVVSASREIAAFF

NME8A1
(amino acids)
(SEQ ID NO: 272)
VLSEKEAQALCKEYEN

NME8A2
(amino acids)
(SEQ ID NO: 273)
VEEAIEYFPES

NME8A3
(amino acids)
(SEQ ID NO: 274)
FLTPEQIEKIYPKVTG

NME8A4
(amino acids)
(SEQ ID NO: 275)
PEEAKLLSPDS

NME8A5
(amino acids)
(SEQ ID NO: 276)
VLTEEQVVNFYSRIAD

NME8B1
(amino acids)
(SEQ ID NO: 277)
EAGFDLTQVKKMFLTPEQIE

NME8B2
(amino acids)
(SEQ ID NO: 278)
PKVTGKDFYKDLLEM

NME8B3
(amino acids)
(SEQ ID NO: 279)
AQFGISKLKNIVH

NME8B4
(amino acids)
(SEQ ID NO: 280)
DEDFKILEQRQVVLSEKEAQ

NME8B5
(amino acids)
(SEQ ID NO: 281)
KEYENEDYFNKLIEN

NME8B6
(amino acids)
(SEQ ID NO: 282)
AQFAMDSLPVNQLYGSDSLETAEREIQHFF

NME8B7
(amino acids)
(SEQ ID NO: 283)
KAGFIIEAEHKTVLTEEQVV

NME8B8
(amino acids)
(SEQ ID NO: 284)
SRIADQCDFEEFVSF

NME9A1
(amino acids)
(SEQ ID NO: 285)
TMTEAEVRLFY

NME9B1
(amino acids)
(SEQ ID NO: 286)
EAGFEILTNEERTMTEAEVR

NME10A1
(amino acids)
(SEQ ID NO: 287)
SMKAEDAQRVFREK

NME10A2
(amino acids)
(SEQ ID NO: 288)
GQRQKSSDES

NME10A3
(amino acids)
(SEQ ID NO: 289)
IQDCENCNIYIFDHSA

NME10B1
(SEQ ID NO: 290)
ELAFQFKDAGLSIFNNTWSNIH

In some cases, peptides derived from other NME proteins can be made more homologous to NME7 A1, A2, B1, B2 or B3 peptides by shifting the frame or extending the NME7 peptides such that the extended peptides are more homologous to the NME7 peptides that gave rise to antibodies that inhibit cancer or cancer metastases. As another example, antibodies or antibody mimics that bind to the NME7 homologous extended peptides ("extended peptides") may be administered to a patient diagnosed with or at risk of developing a cancer or cancer metastasis.

Homologous Extended Peptides to A1, A2, B1, B2 or B3 Peptides

Homologous peptides to A1, A2, B1, B2 or B3 peptides that are extended peptides may include without limitation the following:

NME2A1
(amino acids)
(SEQ ID NO: 291)
RASEEHLKQHYIDLKDRPFFPGL

NME2A2
(amino acids)
(SEQ ID NO: 292)
LGETNPADSKPGTIRGDF

NME2B1
(amino acids)
(SEQ ID NO: 293)
GLVGEIIKRFEQKGFRLVAMKFLRASEEHLKQHY

NME2B2
(amino acids)
(SEQ ID NO: 294)
YIDLKDRPFFPGLVKYMNSGPVVAM

NME2B3
(amino acids)
(SEQ ID NO: 295)
PGTIRGDFCIQVGRNIIHGSDSVKSAEKEISLWF

NME3A1
(amino acids)
(SEQ ID NO: 296)
LKLVQASEELLREHYVELRERPFYSRL

NME3A1
(amino acids)
(SEQ ID NO: 297)
LIGATDPGDATPGTIRGDF

NME3B1
(amino acids)
(SEQ ID NO: 298)
LVGEIVRRFERKGFKLVALKLVQASEELLRE

NME3B2
(amino acids)
(SEQ ID NO: 299)
EHY-VELRERPFYSRLVKYMGSGPVVAM

NME3B3
(amino acids)
(SEQ ID NO: 300)
PGTIRGDFCVEVGKNVIHGSDSVESAQREIALWF

NME4A1
(amino acids)
(SEQ ID NO: 301)
GFTLVGMKMLQAPESVLAEHYQDLRRKPF

NME4A2
(amino acids)
(SEQ ID NO: 302)
GHTDSAEAAPGTIRGDF

NME4B1
(amino acids)
(SEQ ID NO: 303)
LVGDVIQRFERRGFTLVGMKMLQAPESVLAEHY

NME4B2
(amino acids)
(SEQ ID NO: 304)
EHYQDLRRKPFYPALIRYMSSGPVVAM

NME4B3
(amino acids)
(SEQ ID NO: 305)
PGTIRGDFSVHISRNVIHASDS VEGAQREIQLWF

NME5A1
(amino acids)
(SEQ ID NO: 306)
GFTIVQRRKLRLSPEQCSNFYVEKYGKMFF

NME5A2
(amino acids)
(SEQ ID NO: 307)
LLGPNNSLVAKETHPDSLRAIYGTD

NME5B1
(amino acids)
(SEQ ID NO: 308)
IQDIILRSGFTIVQRRKLRLSPEQCSNFY

NME5B2
(amino acids)
(SEQ ID NO: 309)
FYVEKYGKMFFPNLTAYMSSGPLVAM

NME5B3
(amino acids)
(SEQ ID NO: 310)
PDSLRAIYGTDDLRNALHGSNDFAAAEREIRFMF

NME6A1
(amino acids)
(SEQ ID NO: 11)
FLIVRMRELLWRKEDCQRFYREHEGRFFYQRL

NME6A2
(amino acids)
(SEQ ID NO: 12)
LMGPTRVFRARHVAPDSIRGSFG

NME6B1
(amino acids)
(SEQ ID NO: 13)
ILSNKFLIVRMRELLWRKEDCQRFY

NME6B2
(amino acids)
(SEQ ID NO: 314)
FYREHEGRFFYQRLVEFMASGPIRA

NME6B3
(amino acids)
(SEQ ID NO: 15)
ARHVAPDSIRGSFGLTDTRNTTHGSDSVVSASREIAAFF

NME8A1
(amino acids)
(SEQ ID NO: 16)
FKILEQRQVVLSEKEAQALCKEYENEDYFNKLI

NME8A2
(amino acids)
(SEQ ID NO: 17)
WKQLLGPRTVEEAIEYFPESLCAQFAMD

NME8A3
(amino acids)
(SEQ ID NO: 18)
AGFDLTQVKKMFLTPEQIEKIYPKVTGKDFYKDL

NME8A4
(amino acids)
(SEQ ID NO: 19)
EWRRLMGPTDPEEAKLLSPDSIRAQFG

NME8A5
(amino acids)
(SEQ ID NO: 320)
KAGFIIEAEHKTVLTEEQVVNFYSRIADQCDFEE

NME8B1
(amino acids)
(SEQ ID NO: 321)
ILKIVKEAGFDLTQVKKMFLTPEQIEKIY

```
NME8B2
(amino acids)
                                       (SEQ ID NO: 322)
YPKVTGKDFYKDLLEMLSVGP NME8B3
(amino acids)
                                       (SEQ ID NO: 323)
DPEEAKLLSPDSIRAQFGISKLKNIVH NME8B4
(amino acids)
                                       (SEQ ID NO: 324)
LRIIKDEDFKILEQRQVVLSEKEAQ NME8B5
(amino acids)
                                       (SEQ ID NO: 325)
KEYENE-DYFNKLIENMTSGPSLA NME8B6
(amino acids)
                                       (SEQ ID NO: 326)
PESLCAQFAMDSLPVNQLYGSDSLETAEREIQHFF NME8B7
(amino acids)
                                       (SEQ ID NO: 327)
IKRKITKAGFIIEAEHKTVLTEEQVVNFY NME8B8
(amino acids)
                                       (SEQ ID NO: 328)
FYSRIADQCDFEEFVSFMTSG NME9A1
(amino acids)
                                       (SEQ ID NO: 329)
AGFEILTNEERTMTEAEVRLFY NME9B1
(amino acids)
                                       (SEQ ID NO: 330)
IIMKIQEAGFEILTNEERTMTEAEVRLFY NME10A1
(amino acids)
                                       (SEQ ID NO: 331)
GFFLVQTKEVSMKAEDAQRVFREKAP NME10A2
(amino acids)
                                       (SEQ ID NO: 332)
EANRSIVPISRGQRQKSSDESCLVVLFAGD NME10A3
(amino acids)
                                       (SEQ ID NO: 333)
IQDCENCNIYIFDHSA NME10B1
                                       (SEQ ID NO: 334)
ELAFQFKDAGLSIFNNTWSNIHDFTPVDCT
```

Some NME proteins exert a function that is necessary for normal cell growth or development. For example, NME1 is thought to be required for normal cell function. Other NME proteins have catalytic domains whose function is required in normal cells or tissues. In these cases, therapeutic antibodies can be selected based on their ability to bind to the targeted, cancer associated NME, but not to a non-targeted NME. For example, the anti-NME7 antibodies presented here, 8F9A5A1, 8F9A4A3, and 5F3A5D4, were selected for their ability to bind to NME7$_{AB}$ but not to NME1; they were further selected based on their ability to inhibit cancer and cancer metastases.

In another aspect of the invention, anti-NME7 antibodies, antibody fragments, for example scFvs, or fragments of antibody mimics are incorporated into chimeric antigen receptors (CARs) which are engineered to be expressed in immune cells. The immune cell can be engineered to express an anti-NME7 CAR, an anti-MUC1* CAR, or both. One of the CARs may be expressed off of an inducible promoter. Alternatively, an immune cell may be engineered to express a CAR such as an anti-MUC1* CAR and an inducible anti-NME7 antibody or antibody fragment. In some instances the inducible promoter may contain NFAT response elements. In one aspect, these engineered species are expressed in T cells, NK cells or dendritic cells. The immune cells may be obtained from the patient or from a donor. In some cases, immune molecules such as MHCs, checkpoint inhibitors or receptors for checkpoint inhibitors are mutated or cut out, for example using CrisPR or CrisPR-like technology. In another aspect. ITAM molecules, Fos, or Jun are mutated or genetically excised via Talens. Sleeping Beauty. CrisPR or CrisPR-like technologies in patient or donor derived immune cells.

In one aspect of the invention, the anti-NME7 antibodies or antibody mimics for use in CAR T format are chosen from among the group of antibodies or antibody mimics that are specific for NME7 but do not disrupt the binding of NME7 to the extra cellular domain of MUC1*. In this way, the anti-NME7 antibody or antibody mimic that targets the CAR T to the tumor will not simply pluck the ligand from the receptor, whereupon the T cell would be unable to inject the target cancer cell with Granzyme B. Such antibodies or antibody mimics are generated by immunizing an animal with an NME7 peptide, such as NME7 peptides A1, A2, B1, B2 or B3 or selected by virtue of their ability to bind to NME7 peptides A1, A2, B1. B2 or B3. Antibodies or antibody mimics can be screened for their ability to specifically bind to NME7, but not to NME1 or NME2, and also for their inability to disrupt binding between NME7 and MUC1* extra cellular domain. For example, in an ELISA setup, the PSMGFR peptide is immobilized to the surface. A labeled NME7$_{AB}$ is allowed to bind to the surface immobilized MUC1* extra cellular domain, and detection of the NME7$_{AB}$ label is measured in the presence or absence of the test antibody or antibody mimic. In one aspect of the invention, an antibody that does not diminish binding between NME7$_{AB}$ and surface-immobilized MUC1* extra cellular domain peptide is selected as an antibody that is incorporated into a CAR and engineered to be expressed in an immune cell and then administered to a patient for the treatment or prevention of cancer or cancer metastases.

In one aspect of the invention, an anti-NME7 antibody or fragment thereof is administered to a patient diagnosed with or at risk of developing a cancer or cancer metastasis. In one aspect, the anti-NME7 antibody or antibody fragment binds to an NME peptide discussed above in particular under sections "Homologous peptides to A1, A2, B1, B2 or B3 peptides" and the "Homologous extended peptides to A1, A2, B1, B2 or B3 peptides".

In another aspect, the antibody, antibody fragment or antibody mimic binds to an NME7 derived peptide chosen from among A1, A2. B1. B2 or B3 (SEQ ID NOS: 141-145). In yet another aspect, the antibody, antibody fragment or antibody mimic binds to an NME7 peptide comprising most or all of the B3 peptide. In one aspect of the invention, the anti-NME7 antibody, antibody fragment or antibody mimic comprises sequences derived from the variable domains of anti-NME7 antibodies 8F9A4A3 ("4A3") (SEQ ID NOS: 1001-1015). 8F9A5A1 ("5A1") (SEQ ID NOS: 1016-1030), or 8H5H5G4 ("5G4") (SEQ ID NOS: 1031-1045) shown below:

Anti-NME7 B3 peptide monoclonal antibodies
Monoclonal antibody 8F9A4A3 "4A3"
Heavy chain variable region sequence (SEQ ID NO: 1138)

Gaggtccagctgcaacagtctggacctgaactggtgaagcctggggcttcagtgaagatatcctgcaagacttctgg aaacacattcactgaatacaccatgcactgggtgaagcagagccatggaaagagccttgagtggattggaggttttaatcctaacaatg gtgttactaactacaaccagaagttcaagggcaaggccacattgactgtagacaagtcctccagcacagcctacatggagctccgcag cctgacatctgaggattctgcagtctattactgtgcaagacggtactaccatagtctctacgtgttttactttgactactggggccaaggca ccactctcacagtctcctca Translated protein, wherein the underlined sequence is the complementarity determining region (CDR):

(SEQ ID NO: 1139)

EVQLQQSGPELVKPGASVKISCKTSG<u>NTFTEYTMH</u>WVKQSHGKSLEWIG

GFNPNNGVTNYNQKFKGKATLTVDKSSSTAYMELRSLTSEDSAVYYCARRYYHSLY

VFYFDYWGQGTTLTVSS

Mouse 8F9A4A3 heavy chain variable domain framework 1 (FR1) sequence (SEQ ID NO: 1113)

gaggtccagctgcaacagtctggacctgaactggtgaagcctggggcttcagtgaagatatcctgcaagacttctgga (SEQ ID NO: 1114)

EVQLQQSGPELVKPGASVKISCKTSG

Heavy chain variable region CDR1:

(SEQ ID NO: 1115)

Aacacattcactgaatacaccatgcac (SEQ ID NO: 388)

NTFTEYTMH

Mouse 8F9A4A3 heavy chain variable domain framework 2 (FR2) sequence (SEQ ID NO: 1116)

Tgggtgaagcagagccatggaaagagccttgagtggattgga (SEQ ID NO: 1117)

WVKQSHGKSLEWIG

Mouse 8F9A4A3 Heavy chain variable region CDR2:

(SEQ ID NO: 1118)

Ggttttaatcctaacaatggtgttactaactacaaccagaagttcaagggc (SEQ ID NO: 389)

GFNPNNGVTNYNQKFKG

Mouse 4A3 heavy chain variable domain framework 3 (FR3) sequence (SEQ ID NO: 1119)

Aaggccacattgactgtagacaagtcctccagcacagcctacatggagctccgcagcctgacatctgaggattctgc agtctattactgtgcaaga (SEQ ID NO: 1120)

KATLTVDKSSSTAYMELRSLTSEDSAVYYCAR

Mouse 8F9A4A3 Heavy chain variable region CDR3:

(SEQ ID NO: 1121)

cggtactaccatagtctctacgtgttttactttgactac (SEQ ID NO: 390)

RYYHSLYVFYFDY

Mouse 8F9A4A3 Light chain variable region sequence (SEQ ID NO: 1136)

gatatccagatgacacagactacatcctccctgtctgcctctctgggagacagagtcaccctcagttgcagtgcaagtc agggcattagcaattatttaaactggtatcagcagaaaccagatggaactgttgaactcctgatcttttacacatcaagtttacactcagga gtcccatcaaggttcagtggcagtgggtctgggacagattattctctcaccatcagcaacctggaacctgaagatattgccacttactatt gtcagcagtatagtaagcttccttacacgttcggaggggggaccaagctggaaataaaa -continued Translated protein, wherein the underlined sequence is the complementarity determining region (CDR):

(SEQ ID NO: 1109)
DIQMTQTTSSLSASLGDRVTLSCSASQGISNYLNWYQQKPDGTVELLIFYT

SSLHSGVPSRFSGSGSGTDYSLTISNLEPEDIATYYCQQYSKLPYTFGGGTKLEIK

Mouse 8F9A4A3 light chain variable domain framework 1 (FR1) sequence (SEQ ID NO: 1122)
gatatccagatgacacagactacatcctccctgtctgcctctctgggagacagagtcaccctcagttgc (SEQ ID NO: 1123)
DIQMTQTTSSLSASLGDRVTLSC Mouse 8F9A4A3 Light chain variable region CDR 1:

(SEQ ID NO: 1124)
Agtgcaagtcagggcattagcaattatttaaac (SEQ ID NO: 393)
SASQGISNYLN Mouse 4A3 light chain variable domain framework 2 (FR2) sequence (SEQ ID NO: 1125)
Tggtatcagcagaaaccagatggaactgttgaactcctgatctttt (SEQ ID NO: 1126)
WYQQKPDGTVELLIF Mouse 8F9A4A3 Light chain variable region CDR2:

(SEQ ID NO: 1127)
Tacacatcaagtttacactca (SEQ ID NO: 394)
YTSSLHS

Mouse 8F9A4A3 light chain variable domain framework 3 (FR3) sequence (SEQ ID NO: 1128)
Ggagtcccatcaaggttcagtggcagtgggtctgggacagattattctctcaccatcagcaacctggaacctgaagat attgccacttactattgt (SEQ ID NO: 1129)
GVPSRFSGSGSGTDYSLTISNLEPEDIATYYC Mouse 8F9A4A3 Light chain variable region CDR3:

(SEQ ID NO: 1130)
Cagcagtatagtaagcttccttacacg (SEQ ID NO: 395)
QQYSKLPYT

Humanized 8F9A4A3 H-ori heavy chain variable domain sequence (SEQ ID NO: 1131)
Caggttcagctggttcagtctggtgcagaagtgaagaaacctggcgcctctgtgaaggtgtcctgcaaggtgtccgg aaataccttcaccgagtacaccatgcactgggtccgacaggcccctggcaaaggacttgaatggatgggcggcttcaaccccaacaa cggcgtgaccaactacaaccagaaattcaaggccgcgtgaccatgaccgaggacacaagcacagacaccgcctacatggaactg agcagcctgagaagcgaggacaccgccgtgtactactgcgccagaaggtactaccacagcctgtacgtgttctacttcgactactggg gccagggcaccctggtcacagtttcttct (SEQ ID NO: 1206)
QVQLVQSGAEVKKPGASVKVSCKVSGNTFTEYTMHWVRQAPGKGLEW

MGGFNPNNGVTNYNQKFKGRVTMTEDTSTDTAYMELSSLRSEDTAVYYCARRYYH

SLYVFYFDYWGQGTLVTVSS

Humanized 8F9A4A3 H-1.46 heavy chain variable domain sequence (SEQ ID NO: 1101)
caagtgcagctggtgcagagcggcgccgaggtgaagaaacctggcgccagcgtgaaagtgtcctgcaaggccag cggcaatacattcaccgagtacacaatgcactgggtcagacaggcccccggccagggcctggaatggatcggcggatttaaccca acaacggcgtgacaaactacaaccagaagttcaagggcaaggtgaccatcacaagagacaccagcagcagcaccgtgtacatgga actgtcttctctgcggagcgaggataccgccgtgtactattgtgccagacgtactaccacagcctgtacgtgttctacttcgactactgg ggacagggcaccctggttaccgtgtcctct (SEQ ID NO: 1102)
QVQLVQSGAEVKKPGASVKVSCKASGNTFTEYTMHWVRQAPGQGLEWI

GGFNPNNGVTNYNQKFKGKVTITRDTSSSTVYMELSSLRSEDTAVYYCARRYYHSL

YVFYFDYWGQGTLVTVSS

Humanized 8F9A4A3 H-3.15 heavy chain variable domain sequence (SEQ ID NO: 1132)
Gaggtgcagctggtggaaagcggcggcggcctggttaagcctggcggatctctgagactgagctgtgccgcttctg gcaataccttcaccgagtacaccatgcactgggtgcggcaggcccctggaaaaggcctggaatggatcggcggatttaaccccaac aacggcgtgacaaattacaaccagaaattcaagggcaagttcaccatcacaagagataagagcaagaacaccctgtacctgcaaatg aacagcctgaagtccgaggacaccgccgtgtactactgcgccagacggtactaccacagcctctatgtgttctacttcgactactgggg ccagggcacactggtcaccgtgtccagc (SEQ ID NO: 1133)
EVQLVESGGGLVKPGGSLRLSCAASGNTFTEYTMHWVRQAPGKGLEWIG

GFNPNNGVTNYNQKFKGKFTITRDKSKNTLYLQMNSLKSEDTAVYYCARRYYHSLY

VFYFDYWGQGTLVTVSS

Humanized 8F9A4A3 H-4.4 heavy chain variable domain sequence (SEQ ID NO: 1105)
caagtgcagctgcaggagagcggacctggcctggttaagcctggaggcaccctgtctctgacatgtgctgtgtctgg caataccttttaccgagtacaccatgcactgggtgcggcagcctccaggcaagggcctggaatggatcggcggcttcaaccccaacaa cggcgtgacaaattacaaccagaaattcaagggaaaagtgaccatcaccgtggataagtccaagaacaccttcagcctcaagctgag cagcgtgacagccgccgacaccgccgtgtactactgcgccagaagatactatcacagcctgtacgtgttctacttcgactactggggc cagggcacactggtcaccgtgtccagc (SEQ ID NO: 1106)
QVQLQESGPGLVKPGGTLSLTCAVSGNTFTEYTMHWVRQPPGKGLEWIG

GFNPNNGVTNYNQKFKGKVTITVDKSKNTFSLKLSSVTAADTAVYYCARRYYHSLY

VFYFDYWGQGTLVTVSS

Humanized 8F9A4A3 L-1.6 light chain variable domain sequence (SEQ ID NO: 1103)
gatatccagatgacacagagccctagctccctgagcgccagcgtgggcgaccgggtcaccattacatgcagcgctt ctcagggcatctccaactacctgaactggtaccagcagaaacccggcaaggcccctaagctgctgatcttctacaccagctctctgca cagcggcgtgccatctagattcagcggatctggcagcggcaccgactacaccctgaccatcagctccctccagcctgaggacttcgc cacctactactgtcagcaatacagcaagctgccttataccttggcggcggaacaaaggtggaaatcaag (SEQ ID NO: 1104)
DIQMTQSPSSLSASVGDRVTITCSASQGISNYLNWYQQKPGKAPKLLIFYT

SSLHSGVPSRFSGSGSGTDYTLTISSLQPEDFATYYCQQYSKLPYTFGGGTKVEIK

Humanized 8F9A4A3 L-3.15 light chain variable domain sequence (SEQ ID NO: 1134)
Gagatcgtgatgacccagagcccagctacacttagtgtgagtccaggtgaacgggctaccctgtcctgcagcgcca gccagggcatcagcaactacctgaactggtaccagcagaaacctggccaggcccctagactgctgatcttctacaccagcagcctgc acagcggcatccccgccagattcagcggcagcggctctggaacagactacaccctgacaatctctagcctgcagtctgaagattttgc cgtctactactgtcagcaatacagcaagctgccttataccttcggcggcggaaccaaggtggaaattaag (SEQ ID NO: 1135)
EIVMTQSPATLSVSPGERATLSCSASQGISNYLNWYQQKPGQAPRLLIFYT

SSLHSGIPARFSGSGSGTDYTLTISSLQSEDFAVYYCQQYSKLPYTFGGGTKVEIK

Humanized 8F9A4A3 L-4.1 light chain variable domain sequence (SEQ ID NO: 1107)
gatatcgtgatgacccagagcccagcagcctggcagtgagtctgggtgagcgtgctacaatcaactgcagcgcca gccagggcatctccaactacctgaattggtatcagcagaaacctggccaggctcctaagctgctgatcttctacaccagcagcctgcac -continued agcggcgtgccagatagattcagcggcagcggatctggcaccgactacacactgaccatttcttctctccaggccgaggacgtggcc gtctactactgtcagcaatacagcaagctgccttacacctttggcggaggcacaaaggtggaaatcaag (SEQ ID NO: 1108)
DIVMTQSPDSLAVSLGERATINCSASQGISNYLNWYQQKPGQAPKLLIFYT

SSLHSGVPDRFSGSGSGTDYTLTISSLQAEDVAVYYCQQYSKLPYTFGGGTKVEIK

Monoclonal antibody 5F3A5D4
Heavy chain variable region sequence
H-2,3,4,13,15

(SEQ ID NO: 427)
gtccagctgcaacagtctggacctgatctggtgaagcctgggacttcagtgaagatatcctgtaagacttctggaaaca cattcactgaatacaccatgcactgggtgaagcagagccatggaaagagccttgagtggattggaggttttaatcctaacaatggtgtta ctaactacaaccagaagttcaagggcaaggccacattgactgtagacaagtcctccagcacagcctacatggagctccgcagcctga catctgaggattctgcagtctattactgtgcaagacgttactaccatagtacctacgtgttctactttgactcctggggccaaggcaccact ctcacagtctcctca Translated protein, wherein the underlined sequence is the complementarity
determining region (CDR):

(SEQ ID NO: 428)
VQLQQSGPDLVKPGTSVKISCKTSGNTFTEYTMHWVKQSHGKSLEWIGGF

NPNNGVTNYNQKFKGKATLTVDKSSSTAYMELRSLTSEDSAVYYCARRYYHSTYVF

YFDSWGQGTTLTVSS

Heavy chain variable region CDR1:

(SEQ ID NO: 429)
NTFTEYTMH

Heavy chain variable region CDR2:

(SEQ ID NO: 430)
GFNPNNGVTNYNQKFKG

Heavy chain variable region CDR3:

(SEQ ID NO: 431)
RYYHSTYVFYFDS

Light chain variable region sequence
K-1,2,3,4,9

(SEQ ID NO: 432)
gatatccagatgacacagactacatcctcccctgtctgcctctctgggagacagagtcaccatcagttgcagtgcaagtc agggcattagcaattatttaaactggtttcagcagaaaccagatggaactattaagctcctgatctattacacatcaagtttacattcagga gtcccatcaaggttcagtggcagtgggtctgggacagattattctctcaccatcagtaatgtggaacctgaagatattgccacttactattg tcagcagtatagtaagcttccttacacgttcggaggggggaccaagctggagataaaacgg Translated protein, wherein the underlined sequence is the complementarity
determining region (CDR):

(SEQ ID NO: 433)
DIQMTQTTSSLSASLGDRVTISCSASQGISNYLNWFQQKPDGTIKLLIYYTS

SLHSGVPSRFSGSGSGTDYSLTISNVEPEDIATYYCQQYSKLPYTFGGGTKLEIKR

Light chain variable region CDR 1:

(SEQ ID NO: 434)
SASQGISNYLN

Light chain variable region CDR2:

(SEQ ID NO: 435)
YTSSLHS

Light chain variable region CDR3:

(SEQ ID NO: 436)
QQYSKLPYT

Mouse 5F3A5D4-V2 heavy chain variable domain sequence:
(DNA)

(SEQ ID NO: 1155)
Gaggtccagctgcaacagtctggacctgatctggtgaagcctgggacttcagtgaagatatcctgtaagacttctgga aacacattcactgaatacaccatgcactgggtgaagcagagccatggaaagagccttgagtggattggaggttttaatcctaacaatgg tgttactaactacaaccagaagttcaagggcaaggccacattgactgtagacaagtcctccagcacagcctacatggagctccgcagc ctgacatctgaggattctgcagtctattactgtgcaagacgttactaccatagtacctacgtgttctactttgactcctggggccaaggcac cactctcacagtctcctca (amino acids)
(SEQ ID NO: 1172)
EVQLQQSGPDLVKPGTSVKISCKTSGNTFTEYTMHWVKQSHGKSLEWIG

GFNPNNGVTNYNQKFKGKATLTVDKSSSTAYMELRSLTSEDSAVYYCARRYYHSTY

VFYFDSWGQGTTLTVSS

Mouse 5F3A5D4-V2 heavy chain variable domain framework 1 (FR1)
sequence
(DNA)
(SEQ ID NO: 1173)
Gaggtccagctgcaacagtctggacctgatctggtgaagcctgggacttcagtgaagatatcctgtaagacttctgga (amino acids)
(SEQ ID NO: 1174)
EVQLQQSGPDLVKPGTSVKISCKTSG Mouse 5F3A5D4-V2 heavy chain variable domain Complementarity-
determining region 1 (CDR1) sequence
(DNA)
(SEQ ID NO: 1187)
Aacacattcactgaatacaccatgcac (amino acids)
(SEQ ID NO: 429)
NTFTEYTMH Mouse 5F3A5D4-V2 heavy chain variable domain framework 2 (FR2)
sequence
(DNA)
(SEQ ID NO: 1188)
Tgggtgaagcagagccatggaaagagccttgagtggattgga (amino acids)
(SEQ ID NO: 1189)
WVKQSHGKSLEWIG Mouse 5F3A5D4-V2 heavy chain variable domain Complementarity-
determining region 2 (CDR2) sequence
(DNA)
(SEQ ID NO: 1190)
Ggttttaatcctaacaatggtgttactaactacaaccagaagttcaagggc (amino acids)
(SEQ ID NO: 430)
GFNPNNGVTNYNQKFKG Mouse 5F3A5D4-V2 heavy chain variable domain framework 3 (FR3)
sequence
(DNA)
(SEQ ID NO: 1191)
Aaggccacattgactgtagacaagtcctccagcacagcctacatggagctccgcagcctgacatctgaggattctgc agtctattactgtgcaaga (amino acids)
(SEQ ID NO: 1175)
KATLTVDKSSSTAYMELRSLTSEDSAVYYCAR Mouse 5F3A5D4-V2 heavy chain variable domain Complementarity-
determining region 3 (CDR3) sequence
(DNA)
(SEQ ID NO: 1176)
Cgttactaccatagtacctacgtgttctactttgactcc (amino acids)
(SEQ ID NO: 431)
RYYHSTYVFYFDS -continued Mouse 5F3A5D4-V2 heavy chain variable domain framework 4 (FR4) sequence
(DNA)
(SEQ ID NO: 1177)
Tggggccaaggcaccactctcacagtctcctca (amino acids)
(SEQ ID NO: 1178)
WGQGTTLTVSS Mouse 5F3A5D4-2 light chain variable domain sequence
(DNA)
(SEQ ID NO: 1179)
gatatccagatgacacagactacatcctccctgtctgcctctctgggagacagagtcaccatcagttgcagtgcaagtc agggcattagcaattatttaaactggtttcagcagaaaccagatggaactattaagctcctgatctattacacatcaagtttacattcagga gtcccatcaaggttcagtggcagtgggtctgggacagattattctctcaccatcagtaatgtggaacctgaagatattgccacttactattg tcagcagtatagtaagcttccttacacgttcggaggggggaccaagctggagataaaa (amino acids)
(SEQ ID NO: 1180)
DIQMTQTTSSLSASLGDRVTISCSASQGISNYLNWFQQKPDGTIKLLIYYTS

SLHSGVPSRFSGSGSGTDYSLTISNVEPEDIATYYCQQYSKLPYTFGGGTKLEIK

Mouse 5F3A5D4-2 light chain variable domain framework 1 (FR1) sequence
(DNA)
(SEQ ID NO: 1171)
gatatccagatgacacagactacatcctccctgtctgcctctctgggagacagagtcaccatcagttgc (amino acids)
(SEQ ID NO: 1147)
DIQMTQTTSSLSASLGDRVTISC Mouse 5F3A5D4-2 light chain variable domain Complementarity-determining region 1 (CDR) sequence
(DNA)
(SEQ ID NO: 1193)
agtgcaagtcagggcattagcaattatttaaac (amino acids)
(SEQ ID NO: 1208)
SASQGISNYLN Mouse 5F3A5D4-2 light chain variable domain framework 2 (FR2) sequence
(DNA)
(SEQ ID NO: 1148)
tggtttcagcagaaaccagatggaactattaagctcctgatctat (amino acids)
(SEQ ID NO: 1149)
WFQQKPDGTIKLLIY Mouse 5F3A5D4-2 light chain variable domain Complementarity-determining region 2 (CDR2) sequence
(DNA)
(SEQ ID NO: 1150)
tacacatcaagtttacattca (amino acids)
(SEQ ID NO: 1210)
YTSSLHS Mouse 5F3A5D4-2 light chain variable domain framework 3 (FR3) sequence
(DNA)
(SEQ ID NO: 1151)
ggagtcccatcaaggttcagtggcagtgggtctgggacagattattctctcaccatcagtaatgtggaacctgaagata ttgccacttactattgt (amino acids)
(SEQ ID NO: 1152)
GVPSRFSGSGSGTDYSLTISNVEPEDIATYYC -continued Mouse 5F3A5D4-2 light chain variable domain Complementarity-determining region 3 (CDR3) sequence
(DNA)
(SEQ ID NO: 1200)
cagcagtatagtaagcttccttacacg (amino acids)
(SEQ ID NO: 1212)
QQYSKLPYT Mouse 5F3A5D4-2 light chain variable domain framework 4 (FR4) sequence
(DNA)
(SEQ ID NO: 1153)
ttcggagggggaccaagctggagataaaa (amino acids)
(SEQ ID NO: 1154)
FGGGTKLEIK Mouse 5F3A5D4-3 light chain variable domain sequence
(DNA)
(SEQ ID NO: 1204)
gatatccagatgacacagactacatcctccctgtctgcctctctgggagacagagtcaccctcagttgcagtgcaagtc agggcattagcaattatttaaactggtatcagcagaaaccagatggaactgttgaactcctgatcttttacacatcaagtttacactcagga gtcccatcaaggttcagtggcagtgggtctgggacagattattctctcaccatcagcaacctggaacctgaagatattgccacttactatt gtcagcagtatagtaagcttccttacacgttcggaggggggaccaagctggaaataaaa (amino acids)
(SEQ ID NO: 1186)
DIQMTQTTSSLSASLGDRVTLSCSASQGISNYLNWYQQKPDGTVELLIFYT

SSLHSGVPSRFSGSGSGTDYSLTISNLEPEDIATYYCQQYSKLPYTFGGGTKLEIK

Mouse 5F3A5D4-3 light chain variable domain framework 1 (FR1) sequence
(DNA)
(SEQ ID NO: 1156)
gatatccagatgacacagactacatcctccctgtctgcctctctgggagacagagtcaccctcagttgc (amino acids)
(SEQ ID NO: 1192)
DIQMTQTTSSLSASLGDRVTLSC Mouse 5F3A5D4-3 light chain variable domain Complementarity-determining region 1 (CDR1) sequence
(DNA)
(SEQ ID NO: 1194)
agtgcaagtcagggcattagcaattatttaaac (amino acids)
(SEQ ID NO: 1209)
SASQGISNYLN Mouse 5F3A5D4-3 light chain variable domain framework 2 (FR2) sequence
(DNA)
(SEQ ID NO: 1195)
tggtatcagcagaaaccagatggaactgttgaactcctgatctttt (amino acids)
(SEQ ID NO: 1196)
WYQQKPDGTVELLIF Mouse 5F3A5D4-3 light chain variable domain Complementarity-determining region 2 (CDR2) sequence
(DNA)
(SEQ ID NO: 1197)
tacacatcaagtttacactca (amino acids)
(SEQ ID NO: 1211)
YTSSLHS Mouse 5F3A5D4-3 light chain variable domain framework 3 (FR3) sequence
(DNA)
(SEQ ID NO: 1198)
ggagtcccatcaaggttcagtggcagtgggtctgggacagattattctctcaccatcagcaacctggaacctgaagat attgccacttactattgt (amino acids)

(SEQ ID NO: 1199)

GVPSRFSGSGSGTDYSLTISNLEPEDIATYYC

Mouse 5F3A5D4-3 light chain variable domain Complementarity-determining
region 3 (CDR3) sequence
(DNA)

(SEQ ID NO: 1201)

cagcagtatagtaagcttccttacacg (amino acids)

(SEQ ID NO: 1213)

QQYSKLPYT

Mouse 5F3A5D4-3 light chain variable domain framework 4 (FR4) sequence
(DNA)

(SEQ ID NO: 1157)

ttcggagggggaccaagctggaaataaaa (amino acids)

(SEQ ID NO: 1207)

FGGGTKLEIK

Humanized 5F3A5D4-V2 H-1.27 heavy chain variable domain sequence
(DNA)

(SEQ ID NO: 1158)

caagtgcagctggtccagagcggcgccgaggtgaaaaagcctggcgccagcgtgaaggtgtcctgcaaggtgtct ggcaataccttcaccgagtacaccatgcactgggtgcggcaggcccctggaaaaggcctggaatggatcggcggatttaaccccaa caacggcgtgaccaactacaaccagaagttcaagggcaaggttacactgaccgtggacaccagctcttctaccgcctacatggaact gagcagcctgagaagcgaggatacagccgtgtactattgtgccagaagatactaccacagcacctacgtgttctacttcgacagctgg ggccagggcacactggtgacagtgtccagc (amnio acids)

(SEQ ID NO: 1181)

QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHST

YVFYFDSWGQGTLVTVSS

Humanized 5F3A5D4-V2 H-1.46 heavy chain variable domain sequence
(DNA)

(SEQ ID NO: 1159)

caagtgcagctggtgcagagcggagccgaggtgaaaaagcccggcgcttctgtgaaggtgtcttgtaaagccagc ggcaacaccttcaccgagtacaccatgcactgggtgcggcaggcccctggccagggcctggaatggatcggcggctttaatcctaac aacggcgtgacaaactacaaccagaagttcaagggcaaggttacaatcaccagagataccagcagctctaccgtgtacatggaactg agcagcctgagaagcgaggacaccgccgtgtattactgcgccagacggtactaccacagcacctacgtgttctacttcgacagctgg ggcagggaacactggtcacagtgtcctcc (amino acids)

(SEQ ID NO: 1160)

QVQLVQSGAEVKKPGASVKVSCKASGNTFTEYTMHWVRQAPGQGLEWI

GGFNPNNGVTNYNQKFKGKVTITRDTSSSTVYMELSSLRSEDTAVYYCARRYYHST

YVFYFDSWGQGTLVTVSS

Humanized 5F3A5D4-V2 H-3.15 heavy chain variable domain sequence
(DNA)

(SEQ ID NO: 1161)

gaggtgcagctggtggaaagcggaggaggcctggttaagcctggaggcagcctgagactgagctgtgccgcttct ggcaataccttcaccgagtacaccatgcactgggtgcggcaggcccctggcaaaggcctggaatggatcggcggcttcaaccccaa caacggcgtgacaaattacaaccagaaattcaagggcaagtttacaatcaccagagataagtctaagaacacactctatctgcaaatga -continued acagcctgaagtccgaggacaccgccgtgtactactgcgccagacggtactaccacagcacatacgtgttctacttcgacagctggg gccagggcaccctggtcaccgtgtccagc (amino acids)

(SEQ ID NO: 1162)

EVQLVESGGGLVKPGGSLRLSCAASGNTFTEYTMHWVRQAPGKGLEWIG

GFNPNNGVTNYNQKFKGKFTITRDKSKNTLYLQMNSLKSEDTAVYYCARRYYHSTY

VFYFDSWGQGTLVTVSS

Humanized 5F3A5D4-V2 H-4.4 heavy chain variable domain sequence
(DNA)

(SEQ ID NO: 1163)

caagtgcagctgcaggagagcggacctggcctggtcaagcctggcggcaccctgagcctcacctgtgctgtttctg gcaataccttcaccgagtacaccatgcactgggtgcggcagcctccaggcaaaggcctggaatggatcggcggatttaaccccaaca acggcgtgacaaattacaaccagaaattcaagggcaaggtgaccatcacagtggataagtccaagaacaccttcagcctgaagctgt ctagcgtgacagccgccgacaccgccgtgtactactgcgccagaagatactatcacagcacctacgtgttctacttcgacagctgggg acagggcacactggtgacagtgtccagc (amino acids)

(SEQ ID NO: 1164)

QVQLQESGPGLVKPGGTLSLTCAVSGNTFTEYTMHWVRQPPGKGLEWIG

GFNPNNGVTNYNQKFKGKVTITVDKSKNTFSLKLSSVTAADTAVYYCARRYYHSTY

VFYFDSWGQGTLVTVSS

Humanized 5F3A5D4-2 L-1.6 light chain variable domain sequence
(DNA)

(SEQ ID NO: 1165)

gatatccagatgacacagagccctagctccctgagcgccagcgtgggcgaccgggtcaccattacatgcagcgctt ctcagggcatctccaactacctgaactggtttcagcagaaacccggcaaggcccctaagctgctgatctattacaccagctctctgcac agcggcgtgccatctagattcagcggatctggcagcggcaccgactacaccctgaccatcagctccctccagcctgaggacttcgcc acctactactgtcagcaatacagcaagctgccttatacctttggcggcggaacaaaggtggaaatcaag (amino acids)

(SEQ ID NO: 1166)

DIQMTQSPSSLSASVGDRVTITCSASQGISNYLNWFQQKPGKAPKLLIYYT

SSLHSGVPSRFSGSGSGTDYTLTISSLQPEDFATYYCQQYSKLPYTFGGGTKVEIK

Humanized 5F3A5D4-2 L-3.15 light chain variable domain sequence
(DNA)

(SEQ ID NO: 1167)

gagatcgtgatgacccagagcccagctacacttagtgtgagtccaggtgaacgggctaccctgtcctgcagcgcca gccagggcatcagcaactacctgaactggtttcagcagaaacctggccaggcccctagactgctgatctattacaccagcagcctgca cagcggcatccccgccagattcagcggcagcggctctggaacagactacaccctgacaatctctagcctgcagtctgaagattttgcc gtctactactgtcagcaatacagcaagctgccttatacctttcggggcggaaccaaggtggaaattaag (amino acids)

(SEQ ID NO: 1168)

EIVMTQSPATLSVSPGERATLSCSASQGISNYLNWFQQKPGQAPRLLIYYT

SSLHSGIPARFSGSGSGTDYTLTISSLQSEDFAVYYCQQYSKLPYTFGGGTKVEIK

Humanized 5F3A5D4-2 L-4.1 light chain variable domain sequence
(DNA)

(SEQ ID NO: 1169)

gatatcgtgatgacccagagcccagacagcctggcagtgagtctgggtgagcgtgctacaatcaactgcagcgcca gccagggcatctccaactacctgaattggtttcagcagaaacctggccaggctcctaagctgctgatctattacaccagcagcctgcac -continued agcggcgtgccagatagattcagcggcagcggatctggcaccgactacacactgaccatttcttctctccaggccgaggacgtggcc gtctactactgtcagcaatacagcaagctgccttacacctttggcggaggcacaaaggtggaaatcaag (amino acids)

(SEQ ID NO: 1170)

DIVMTQSPDSLAVSLGERATINCSASQGISNYLNWFQQKPGQAPKLLIYYT

SSLHSGVPDRFSGSGSGTDYTLTISSLQAEDVAVYYCQQYSKLPYTFGGGTKVEIK

Humanized 5F3A5D4-3 L-1.6 light chain variable domain sequence
(DNA)

(SEQ ID NO: 1182)

gatatccagatgacacagagccctagctccctgagcgccagcgtgggcgaccgggtcaccattacatgcagcgctt ctcagggcatctccaactacctgaactggtaccagcagaaacccggcaaggcccctaagctgctgatcttctacaccagctctctgca cagcggcgtgccatctagattcagcggatctggcagcggcaccgactacaccctgaccatcagctccctccagcctgaggacttcgc cacctactactgtcagcaatacagcaagctgccttatacctttggcggcggaacaaaggtggaaatcaag (amino acids)

(SEQ ID NO: 1183)

DIQMTQSPSSLSASVGDRVTITCSASQGISNYLNWYQQKPGKAPKLLIFYT

SSLHSGVPSRFSGSGSGTDYTLTISSLQPEDFATYYCQQYSKLPYTFGGGTKVEIK

Humanized 5F3A5D4-3 L-3.15 light chain variable domain sequence
(DNA)

(SEQ ID NO: 1202)

gagatcgtgatgacccagagcccagctacacttagtgtgagtccaggtgaacgggctaccctgtcctgcagcgcca gccagggcatcagcaactacctgaactggtaccagcagaaacctggccaggcccctagactgctgatcttctacaccagcagcctgc acagcggcatccccgccagattcagcggcagcggctctggaacagactacaccctgacaatctctagcctgcagtctgaagattttgc cgtctactactgtcagcaatacagcaagctgccttataccttcggcggcggaaccaaggtggaaattaag (amino acids)

(SEQ ID NO: 1203)

EIVMTQSPATLSVSPGERATLSCSASQGISNYLNWYQQKPGQAPRLLIFYT

SSLHSGIPARFSGSGSGTDYTLTISSLQSEDFAVYYCQQYSKLPYTFGGGTKVEIK

Humanized 5F3A5D4-3 L-4.1 light chain variable domain sequence
(DNA)

(SEQ ID NO: 1184)

gatatcgtgatgacccagagcccagacagcctggcagtgagtctgggtgagcgtgctacaatcaactgcagcgcca gccagggcatctccaactacctgaattggtatcagcagaaacctggccaggctcctaagctgctgatcttctacaccagcagcctgcac agcggcgtgccagatagattcagcggcagcggatctggcaccgactacacactgaccatttcttctctccaggccgaggacgtggcc gtctactactgtcagcaatacagcaagctgccttacacctttggcggaggcacaaaggtggaaatcaag (amino acids)

(SEQ ID NO: 1185)

DIVMTQSPDSLAVSLGERATINCSASQGISNYLNWYQQKPGQAPKLLIFYT

SSLHSGVPDRFSGSGSGTDYTLTISSLQAEDVAVYYCQQYSKLPYTFGGGTKVEIK

Monoclonal antibody 8F9A5A1
Heavy chain variable region sequence
H-3,4,6,10,11

(SEQ ID NO: 437)

atccagttggtgcagtctggacctgagctgaagaagcctggagagacagtcaagatctcctgcaaggcttctgggtat accttcacaaactatggaatgaactgggtgaagcaggctccaggaaagggtttaaagtggatgggctggataaacacctacactgga gagccaacatatgttgatgacttcaagggacggtttgccttctcttttggaaacctctgccaccactgcctatttgcagatcaacaacctca aaaatgaggacacgtctacatatttctgtgcaagattgaggggatacgaccgggtcccttggcttactggggccaagggactctggtc actgtctctgca -continued Translated protein, wherein the underlined sequence is the complementarity determining region (CDR):

(SEQ ID NO: 438)
IQLVQSGPELKKPGETVKISCKASG<u>YTFTNYGMN</u>WVKQAPGKGLKWMG

<u>WINTYTGEPTYVDDFKG</u>RFAFSLETSATTAYLQINNLKNEDTSTYFCAR<u>LRGIRPGPL</u>

<u>AY</u>WGQGTLVTVSA

Heavy chain variable region CDR1:

(SEQ ID NO: 439)
YTFTNYGMN

Heavy chain variable region CDR2:

(SEQ ID NO: 440)
WINTYTGEPTYVDDFKG

Heavy chain variable region CDR3:

(SEQ ID NO: 441)
LRGIRPGPLAY

Light chain variable region sequence
K-1,2,3,4,5

(SEQ ID NO: 442)
gaaattttgctcacccagtctccagcaatcatagctgcatctcctggggagaaggtcaccatcacctgcagtgccagct caagtgtaagttacatgaactggtaccagcagaaaccaggatcctcccccaaaatatggatttatggtatatccaacctggcttctggag ttcctgctcgcttcagtggcagtgggtctgggacatctttctctttcacaatcaacagcatggaggctgaagatgttgccacttattactgtc agcaaaggagtagttacccacccacgttcggaggggggaccaagctggaaataaaacgg Translated protein, wherein the underlined sequence is the complementarity determining region (CDR):

(SEQ ID NO: 443)
EILLTQSPAIIAASPGEKVTITC<u>SASSSVSYMN</u>WYQQKPGSSPKIWIY<u>GISNL</u>

<u>AS</u>GVPARFSGSGSGTSFSFTINSMEAEDVATYYC<u>QQRSSYPPT</u>FGGGTKLEIKR

Light chain variable region CDR 1:

(SEQ ID NO: 444)
SASSSVSYMN

Light chain variable region CDR2:

(SEQ ID NO: 445)
GISNLAS

Light chain variable region CDR3:

(SEQ ID NO: 446)
QQRSSYPPT

8F9A4P3 Heavy chain variable region sequence mouse (SEQ ID NO: 335)
Gtccagctgcaacagtctggacctgaactggtgaagcctggggcttcagtgaagatatcctgcaagacttctggaaa cacattcactgaatacaccatgcactgggtgaagcagagccatggaaagagccttgagtggattggaggttttaatcctaacaatggtg ttactaactacaaccagaagttcaagggcaaggccacattgactgtagacaagtcctccagcacagcctacatggagctccgcagcct gacatctgaggattctgcagtctattactgtgcaagacggtactaccatagtctctacgtgttttactttgactactggggccaaggcacca ctctcacagtctcctca (SEQ ID NO: 1001)
VQLQQSGPELVKPGASVKISCKTSGNTFTEYTMHWVKQSHGKSLEWIGGF

NPNNGVTNYNQKFKGKATLTVDKSSSTAYMELRSLTSEDSAVYYCARRYYHSLYVF

YFDYWGQGTTLTVSS

IGHV1-24*01 V-REGION sequence human (closest match hu antibody sequence)

(SEQ ID NO: 336)
Caggtccagctggtacagtctggggctgaggtgaagaagcctggggcctcagtgaaggtctcctgcaaggtttccg gatacacccctcactgaattatccatgcactgggtgcgacaggctcctggaaaagggcttgagtggatgggaggttttgatcctgaagat ggtgaaacaatctacgcacagaagttccagggcagagtcaccatgaccgaggacacatctacagacacagcctacatggagctgag cagcctgagatctgaggacacggccgtgtattactgtgcaaca

```
                                                                    (SEQ ID NO: 1002)
QVQLVQSGAEVKKPGASVKVSCKVSGYTLTELSMHWVRQAPGKGLEW

MGGFDPEDGETIYAQKFQGRVTMTEDTSTDTAYMELSSLRSEDTAVYYCAT human (closest match hu antibody sequence)
IGHJ4*01 J-REGION sequence
                                                                    (SEQ ID NO: 337)
tactttgactactggggccaaggaaccctggtcaccgtctcctca (SEQ ID NO: 1003)
YFDYWGQGTLVTVSS humanized heavy chain variable seq (SEQ ID NO: 1001 + SEQ ID NO: 1002 + SEQ ID NO: 1003)
humanized 8F9A4P3 Heavy chain variable region sequence
(DNA)
                                                                    (SEQ ID NO: 338)
caggtccagctggtacagtctggggctgaggtgaagaagcctggggcctcagtgaaggtctcctgcaaggtttccg gaaacacattcactgaatacaccatgcactgggtgcgacaggctcctggaaaagggcttgagtggatgggaggttttaatcctaacaat ggtgttactaactacaaccagaagttcaagggcagagtcaccatgaccgaggacacatctacagacacagcctacatggagctgagc agcctgagatctgaggacacggccgtgtattactgtgcaagacggtactaccatagtctctacgtgttttactttgactactggggccaag gaaccctggtcaccgtctcctca (SEQ ID NO: 1004)
QVQLVQSGAEVKKPGASVKVSCKVSGNTFTEYTMHWVRQAPGKGLEW

MGGFNPNNGVTNYNQKFKGRVTMTEDTSTDTAYMELSSLRSEDTAVYYCARRYYH

SLYVFYFDYWGQGTLVTVSS humanized heavy chain variable seq (codon optimized version of 1004)
humanized 8F9A4P3 Heavy chain variable region sequence (codon optimized)
(DNA)
                                                                    (SEQ ID NO: 339)
caggttcagctggttcagtctggcgccgaagtgaagaaacctggcgcctctgtgaaggtgtcctgcaaggtgtccgg aaataccttcaccgagtacaccatgcactgggtccgacaggcccctggcaaaggacttgaatggatgggcggcttcaaccccaacaa cggcgtgaccaactacaaccagaaattcaagggccgcgtgaccatgaccgaggacacaagcacagacaccgcctacatggaactg agcagcctgagaagcgaggacaccgccgtgtactactgcgccagaaggtactaccacagcctgtacgtgttctacttcgactactggg gccagggcaccctggtcacagtttcttct (SEQ ID NO: 1005)
QVQLVQSGAEVKKPGASVKVSCKVSGNTFTEYTMHWVRQAPGKGLEW

MGGFNPNNGVTNYNQKFKGRVTMTEDTSTDTAYMELSSLRSEDTAVYYCARRYYH

SLYVFYFDYWGQGTLVTVSS humanized heavy chain variable seq ("modified" SEQ ID NO: 1005 sequence,
where modified means certain amino acids that are thought to be critical for binding or
structure have been reverted to the mouse sequence).
Modified humanized 8F9A4P3 Heavy chain variable region sequence
                                                                    (SEQ ID NO: 340)
caggtccagctggtacagtctggggctgaggtgaagaagcctggggcctcagtgaaggtctcctgcaaggtttccg gaaacacattcactgaatacaccatgcactgggtgcgacaggctcctggaaaagggcttgagtggattggaggttttaatcctaacaat ggtgttactaactacaaccagaagttcaagggcaaagtcaccctgaccgtggacacatctagcagcacagcctacatggagctgagc agcctgagatctgaggacacggccgtgtattactgtgcaagacggtactaccatagtctctacgtgttttactttgactactggggccaag gaaccctggtcaccgtctcctca (SEQ ID NO: 1006)
QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHSL

YVFYFDYWGQGTLVTVSS
```

-continued humanized heavy chain variable seq (SEQ ID NO: 1006 codon optimized)
Modified humanized 8F9A4P3 Heavy chain variable region sequence (codon optimized)

(SEQ ID NO: 341)
caggttcagctggttcagtctggcgccgaagtgaagaaacctggcgcctctgtgaaggtgtcctgcaaggtgtccgg aaataccttcaccgagtacaccatgcactgggtccgacaggcccctggcaaggactggaatggatcggcggcttcaaccccaaca acggcgtgaccaactacaaccagaaattcaagggcaaagtgaccctgaccgtggacaccagcagcagcacagcctacatggaact gagcagcctgagaagcgaggacaccgccgtgtactactgcgccagaaggtactaccacagcctgtacgtgttctacttcgactactgg ggccagggcaccctggtcacagtttcttct (SEQ ID NO: 1007)
QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHSL

YVFYFDYWGQGTLVTVSS

8F9A4P3 Light chain variable region sequence mouse (SEQ ID NO: 342)
gaaacaactgtgacccagtctccagcatccctgtccatggctataggagaaaaagtcaccatcagatgcataaccag cactgatattgatgatgatatgaactggtaccagcagaagccaggggaacctcctaagctccttatttcagaaggcaatactcttcgtcct ggagtcccatcccgattctccagcagtggctatggtacagattttgttttacaattgaaaacatgctctcagaagatgttgcagattactac tgtttgcaaagtgataacttgcctctcacgttcggctcggggacaaagttggaaataaaacgg (SEQ ID NO: 1008)
ETTVTQSPASLSMAIGEKVTIRCITSTDIDDDMNWYQQKPGEPPKLLISEGN

TLRPGVPSRFSSSGYGTDFVFTIENMLSEDVADYYCLQSDNLPLTFGSGTKLEIKR human (closest match hu antibody sequence)
IGKV5-2*01 V-REGION sequence (SEQ ID NO: 343)
gaaacgacactcacgcagtctccagcattcatgtcagcgactccaggagacaaagtcaacatctcctgcaaagccag ccaagacattgatgatgatatgaactggtaccaacagaaaccaggagaagctgctattttcattattcaagaagctactactctcgttcct ggaatcccacctcgattcagtggcagcgggtatggaacagattttaccctcacaattaataacatagaatctgaggatgctgcatattact tctgt (SEQ ID NO: 1009)
ETTLTQSPAFMSATPGDKVNISCKASQDIDDDMNWYQQKPGEAAIFIIQEA

TTLVPGIPPRFSGSGYGTDFTLTINNIESEDAAYYFC human (closest match hu antibody sequence)
IGKJ4*02 J-REGION sequence (SEQ ID NO: 344)
ctcacgttcggcggagggaccaaggtggagatcaaa (SEQ ID NO: 1010)
LTFGGGTKVEIK humanized light chain variable seq (SEQ ID NO: 1008 + SEQ ID NO: 1009 + SEQ ID NO: 1)
humanized 8F9A4P3 Light chain variable region sequence (SEQ ID NO: 345)
gaaacgacactcacgcagtctccagcattcatgtcagcgactccaggagacaaagtcaacatctcctgcataaccag cactgatattgatgatgatatgaactggtaccaacagaaaccaggagaagctgctattttcattattcaagaaggcaatactcttcgtcctg gaatcccacctcgattcagtggcagcgggtatggaacagattttaccctcacaattaataacatagaatctgaggatgctgcatattactt ctgtttgcaaagtgataacttgcctctcacgttcggcggagggaccaaggtggagatcaaacgg (SEQ ID NO: 1011)
ETTLTQSPAFMSATPGDKVNISCITSTDIDDDMNWYQQKPGEAAIFIIQEGN

TLRPGIPPRFSGSGYGTDFTLTINNIESEDAAYYFCLQSDNLPLTFGGGTKVEIKR

-continued humanized light chain variable seq (codon optimized version of SEQ ID NO: 1011)
humanized 8F9A4P3 Light chain variable region sequence (codon optimized)

(SEQ ID NO: 346)

Gagacaaccctgacacagagccctgccttcatgtctgccacacctggcgacaaagtgaacatcagctgcatcacca gcaccgacatcgacgacgacatgaactggtatcagcagaagcctggcgaggccgccatcttcatcatccaagagggcaacacactg cggcctggcatccctcctagattttctggcagcggctacggcaccgacttcaccctgaccatcaacaacatcgagagcgaggacgcc gcctactacttctgcctgcaaagcgacaacctgcctctgacctttggcggaggcaccaaggtggaaatcaagcgg (SEQ ID NO: 1012)

ETTLTQSPAFMSATPGDKVNISCITSTDIDDDMNWYQQKPGEAAIFIIQEGN

TLRPGIPPRFSGSGYGTDFTLTINNIESEDAAYYFCLQSDNLPLTFGGGTKVEIKR humanized light chain variable seq ("modified" SEQ ID NO: 1012 sequence,
where modified means certain amino acids that are thought to be critical for binding or
structure have been reverted to the mouse sequence).
Modified humanized 8F9A4P3 Light chain variable region sequence (SEQ ID NO: 347)

gaaacgacagtgacgcagtctccagcattcatgtcagcgactccaggagacaaagtcaccatctcctgcataaccag cactgatattgatgatgatatgaactggtaccaacagaaaccaggagaagctgctattctgctgattagcgaaggcaatactcttcgtcct ggaatcccacctcgattcagtagcagcgggtatggaacagattttaccctcacaattaataacatagaatctgaggatgctgcatattact tctgtttgcaaagtgataacttgcctctcacgttcggcggagggaccaaggtggagatcaaacgg (SEQ ID NO: 1013)

ETTVTQSPAFMSATPGDKVTISCITSTDIDDDMNWYQQKPGEAAILLISEG

NTLRPGIPPRFSSSGYGTDFTLTINNIESEDAAYYFCLQSDNLPLTFGGGTKVEIKR humanized light chain variable seq
Modified humanized 8F9A4P3 Light chain variable region sequence (codon
optimized)

(SEQ ID NO: 348)

gagacaaccgtgacacagagccctgccttcatgtctgccacacctggcgacaaagtgaccatcagctgcatcacca gcaccgacatcgacgacgacatgaactggtatcagcagaagcctggcgaggccgccatcctgcttatctctgagggaaacacactgc ggcctggcatccctcctagattttccagcagcggctacggcaccgacttcaccctgaccatcaacaacatcgagagcgaggacgccg cctactacttctgcctgcaaagcgacaacctgcctctgacctttggcggaggcaccaaggtggaaatcaagcgg (SEQ ID NO: 1014)

ETTVTQSPAFMSATPGDKVTISCITSTDIDDDMNWYQQKPGEAAILLISEG

NTLRPGIPPRFSSSGYGTDFTLTINNIESEDAAYYFCLQSDNLPLTFGGGTKVEIKR humanized heavy and light chains joined via a flexible linker.
Modified humanized 8F9A4P3 sequence (codon optimized)

(SEQ ID NO: 349)

Caggttcagctggttcagtctggcgccgaagtgaagaaacctggcgcctctgtgaaggtgtcctgcaaggtgtccgg aaataccttcaccgagtacaccatgcactgggtccgacaggcccctggcaaaggactggaatggatcggcggcttcaaccccaaca acggcgtgaccaactacaaccagaaattcaagggcaaagtgaccctgaccgtggacaccagcagcagcacagcctacatggaact gagcagcctgagaagcgaggacaccgccgtgtactactgcgccagaaggtactaccacagcctgtacgtgttctacttcgactactgg ggccagggcaccctggtcacagttcttctggcggtggcggaagcggaggcggtggctccggtggcggaggcagcgaaacgaca gtgacgcagtctccagcattcatgtcagcgactccaggagacaaagtcaccatctcctgcataaccagcactgatattgatgatgatatg aactggtaccaacagaaaccaggagaagctgctattctgctgattagcgaaggcaatactcttcgtcctggaatcccacctcgattcagt agcagcgggtatggaacagattttaccctcacaattaataacatagaatctgaggatgctgcatattacttctgtttgcaaagtgataactt gcctctcacgttcggcggagggaccaaggtggagatcaaacgg (SEQ ID NO: 1015)

QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHSL

YVFYFDYWGQGTLVTVSSGGGGSGGGGSGGGGSETTVTQSPAFMSATPGDKVTISCI

TSTDIDDDMNWYQQKPGEAAILLISEGNTLRPGIPPRFSSSGYGTDFTLTINNIESEDA

AYYFCLQSDNLPLTFGGGTKVEIKR

8F9A5A1 Heavy chain variable region sequence (SEQ ID NO: 350)

atccagttggtgcagtctggacctgagctgaagaagcctggagagacagtcaagatctcctgcaaggcttctgggtat accttcacaaactatggaatgaactgggtgaagcaggctccaggaaagggtttaaagtggatgggctggataaacacctacactgga gagccaacatatgttgatgacttcaagggacggtttgccttctctttggaaacctctgccaccactgcctatttgcagatcaacaacctca aaaatgaggacacgtctacatatttctgtgcaagattgaggggatacgaccgggtcccttggcttactggggccaagggactctggtc actgtctctgca (SEQ ID NO: 1016)

IQLVQSGPELKKPGETVKISCKASGYTFTNYGMNWVKQAPGKGLKWMG

WINTYTGEPTYVDDFKGRFAFSLETSATTAYLQINNLKNEDTSTYFCARLRGIRPGPL

AYWGQGTLVTVSA

IGHV7-81*01 V-REGION sequence (SEQ ID NO: 351)

caggtgcagctggtgcagtctggccatgaggtgaagcagcctggggcctcagtgaaggtctcctgcaaggcttctg gttacagtttcaccacctatggtatgaattgggtgccacaggcccctggacaagggcttgagtggatgggatggttcaacacctacact gggaacccaacatatgcccagggcttcacaggacggtttgtcttctccatggacacctctgccagcacagcatacctgcagatcagca gcctaaaggctgaggacatggccatgtattactgtgcgaga (SEQ ID NO: 1017)

QVQLVQSGHEVKQPGASVKVSCKASGYSFTTYGMNWVPQAPGQGLEW

MGWFNTYTGNPTYAQGFTGRFVFSMDTSASTAYLQISSLKAEDMAMYYCAR

IGHJ4*03 J-REGION sequence (SEQ ID NO: 352)

tactttgactactggggccaagggaccctggtcaccgtctcctca (SEQ ID NO: 1018)

YFDYWGQGTLVTVSS humanized 8F9A5A1 Heavy chain variable region sequence (SEQ ID NO: 353)

Caggtgcagctggtgcagtctggccatgaggtgaagcagcctggggcctcagtgaaggtctcctgcaaggcttctg ggtataccttcacaaactatggaatgaactgggtgccacaggcccctggacaagggcttgagtggatgggatggataaacacctaca ctggagagccaacatatgttgatgacttcaagggacggtttgtcttctccatggacacctctgccagcacagcatacctgcagatcagc agcctaaaggctgaggacatggccatgtattactgtgcaagattgaggggatacgaccgggtcccttggcttactggggccaaggg accctggtcaccgtctcctca (SEQ ID NO: 1019)

QVQLVQSGHEVKQPGASVKVSCKASGYTFTNYGMNWVPQAPGQGLEW

MGWINTYTGEPTYVDDFKGRFVFSMDTSASTAYLQISSLKAEDMAMYYCARLRGIR

PGPLAYWGQGTLVTVSS humanized 8F9A5A1 Heavy chain variable region sequence (codon optimized)

(SEQ ID NO: 354)

caggttcagctggtgcagtctggccacgaagtgaaacagcctggcgcctctgtgaaggtgtcctgtaaagccagcg gctacacctttaccaactacggcatgaactgggtgccccaggctcctggacaaggcttggaatggatgggctggatcaacacctacac cggcgagcctacctacgtggacgacttcaagggcagattcgtgttcagcatggacaccagcgccagcacagcctacctgcagatca gctctctgaaggccgaggatatggccatgtactactgcgccagactgagaggcatcagacctggacctctggcctattgggacagg gcacactggtcacagtgtcctct

```
                                                                                (SEQ ID NO: 1020)
QVQLVQSGHEVKQPGASVKVSCKASGYTFTNYGMNWVPQAPGQGLEW

MGWINTYTGEPTYVDDFKGRFVFSMDTSASTAYLQISSLKAEDMAMYYCARLRGIR

PGPLAYWGQGTLVTVSS

Modified humanized 8F9A5A1 Heavy chain variable region sequence
                                                                                (SEQ ID NO: 355)
cagatccagctggtgcagtctggccccgaggtgaagcagcctgggggcctcagtgaaggtctcctgcaaggcttctg ggtataccttcacaaactatggaatgaactgggtgaagcaggcccctggacaagggcttgagtggatgggatggataaacacctaca ctggagagccaacatatgttgatgacttcaagggacggtttgccttctccatggacacctctgccagcacagcatacctgcagatcagc agcctaaaggctgaggacaccgccacctattactgtgcaagattgaggggatacgacccgggtcccttggcttactggggccaaggg accctggtcaccgtctcctca
                                                                                (SEQ ID NO: 1021)
QIQLVQSGPEVKQPGASVKVSCKASGYTFTNYGMNWVKQAPGQGLEWM

GWINTYTGEPTYVDDFKGRFAFSMDTSASTAYLQISSLKAEDTATYYCARLRPG

PLAYWGQGTLVTVSS

Modified humanized 8F9A5A1 Heavy chain variable region sequence (codon
optimized)
                                                                                (SEQ ID NO: 356)
cagattcagctggtgcagtctggccccgaagtgaaacaacctggcgcctctgtgaaggtgtcctgcaaggccagcg gctacacctttaccaactacgcatgaactgggtcaagcaggcccctggacaaggcctggaatggatgggctggatcaacacctaca ccggcgagcctacctacgtggacgacttcaagggcagattcgccttcagcatggacaccagcgccagcacagcctacctgcagatc agctctctgaaggccgaggacaccgccacctactactgtgccagactgagaggcatcagacccggacctctggcctattggggaca gggaacactggtcaccgtgtcctct
                                                                                (SEQ ID NO: 1022)
QIQLVQSGPEVKQPGASVKVSCKASGYTFTNYGMNWVKQAPGQGLEWM

GWINTYTGEPTYVDDFKGRFAFSMDTSASTAYLQISSLKAEDTATYYCARLRPG

PLAYWGQGTLVTVSS

8F9A5A1 Light chain variable region sequence
                                                                                (SEQ ID NO: 357)
gaaattttgctcacccagtctccagcaatcatagctgcatctcctggggagaaggtcaccatcacctgcagtgccagct caagtgtaagttacatgaactggtaccagcagaaaccaggatcctcccccaaaatatggatttatggtatatccaacctggcttctggag ttcctgctcgcttcagtggcagtgggtctgggacatcttctctttcacaatcaacagcatggaggctgaagatgttgccacttattactgtc agcaaaggagtagttacccacccacgttcggaggggggaccaagctggaaataaaacgg
                                                                                (SEQ ID NO: 1023)
EILLTQSPANIAASPGEKVTITCSASSSVSYMNWYQQKPGSSPKIWIYGISNL

ASGVPARFSGSGSGTSFSFTINSMEAEDVATYYCQQRSSYPPTFGGGTKLEIKR

IGKV3D-15*02 V-REGION sequence
                                                                                (SEQ ID NO: 358)
gaaatagtgatgatgcagtctccagccacccctgtctgtgtctccaggggaaagagccaccctctcctgcagggccag
tcagagtgttagcagcaacttagcctggtaccagcagaaacctggccaggctcccaggctcctcatctatggtgcatccaccagggcc
actggcatcccagccaggttcagtggcagtgggtctgggacagagttcactctcaccatcagcagcctgcagtctgaagattttgcagt ttattactgtcagcagtataataac
                                                                                (SEQ ID NO: 1024)
EIVMMQSPATLSVSPGERATLSCRASQSVSSNLAWYQQKPGQAPRLLIYG

ASTRATGIPARFSGSGSGTEFTLTISSLQSEDFAVYYCQQYNN

IGKJ4*02 J-REGION sequence
                                                                                (SEQ ID NO: 359)
ctcacgttcggcggagggaccaaggtggagatcaaa
                                                                                (SEQ ID NO: 1025)
LTFGGGTKVEIK
```

-continued humanized 8F9A5A1 Light chain variable region sequence
(SEQ ID NO: 360)
gaaatagtgatgatgcagtctccagccaccctgtctgtgtctccaggggaaagagccaccctctcctgcagtgccagc tcaagtgtaagttacatgaactggtaccagcagaaacctggccaggctcccaggctcctcatctatggtatatccaacctggcttctggc atcccagccaggttcagtggcagtgggtctgggacagagttcactctcaccatcagcagcctgcagtctgaagattttgcagtttattact gtcagcaaaggagtagttacccacccacgttcggcggagggaccaaggtggagatcaaacgg (SEQ ID NO: 1026)
EIVMMQSPATLSVSPGERATLSCSASSSVSYMNWYQQKPGQAPRLLIYGIS

NLASGIPARFSGSGSGTEFTLTISSLQSEDFAVYYCQQRSSYPPTFGGGTKVEIKR humanized 8F9A5A1 Light chain variable region sequence (codon optimized)
(SEQ ID NO: 361)
gagatcgtgatgatgcagagccccgccacactgagtgtgtctccaggcgaaagagccacactgtcctgtagcgcca gcagcagcgtgtcctacatgaactggtatcagcagaagcccggacaggcccctagactgctgatctacggcatcagcaatctggcca gcggcatccctgccagattttctggctctggctccggcaccgagttcaccctgacaatctctagcctgcagagcgaggacttcgccgtg tactactgccagcagagaagcagctaccctcctacctttggcggaggcaccaaggtggaaatcaagcgg (SEQ ID NO: 1027)
EIVMMQSPATLSVSPGERATLSCSASSSVSYMNWYQQKPGQAPRLLIYGIS

NLASGIPARFSGSGSGTEFTLTISSLQSEDFAVYYCQQRSSYPPTFGGGTKVEIKR

Modified humanized 8F9A5A1 Light chain variable region sequence
(SEQ ID NO: 362)
gaaatagtgctgacccagtctccagccaccctgtctgtgtctccaggggaaagagccaccctctcctgcagtgccag ctcaagtgtaagttacatgaactggtaccagcagaaacctggccaggctcccaggctctggatctatggtatatccaacctggcttctgg catcccagccaggttcagtggcagtgggtctgggacaagcttcagcctcaccatcagcagcctgcagtctgaagattttgcagtttatta ctgtcagcaaaggagtagttacccacccacgttcggcggagggaccaaggtggagatcaaacgg (SEQ ID NO: 1028)
EIVLTQSPATLSVSPGERATLSCSASSSVSYMNWYQQKPGQAPRLWIYGIS

NLASGIPARFSGSGSGTSFSLTISSLQSEDFAVYYCQQRSSYPPTFGGGTKVEIKR

Modified humanized 8F9A5A1 Light chain variable region sequence (codon optimized)
(SEQ ID NO: 363)
gagatcgtgctgacacagtctcccgccacactgagtgtgtctccaggcgaaagagccacactgtcctgtagcgccag cagcagcgtgtcctacatgaactggtatcagcagaagcccggacaggcccctagactgtggatctacggcatcagcaatctggccag cggcatccctgccagattttctggctctggctccggcaccagcttcagcctgacaatcagcagcctgcagagcgaggacttcgccgtg tactactgccagcagagaagcagctaccctcctacctttggcggaggcaccaaggtggaaatcaagcgg (amino acids)
(SEQ ID NO: 1029)
EIVLTQSPATLSVSPGERATLSCSASSSVSYMNWYQQKPGQAPRLWIYGIS

NLASGIPARFSGSGSGTSFSLTISSLQSEDFAVYYCQQRSSYPPTFGGGTKVEIKR

Modified humanized 8F9A5A1 scFV sequence (codon optimized)
(SEQ ID NO: 364)
Cagattcagctggtgcagtctggccccgaagtgaaacaacctggcgcctctgtgaaggtgtcctgcaaggccagcg gctacaccttaccaactacggcatgaactgggtcaagcaggcccctggacaaggcctggaatggatgggctggatcaacacctaca ccggcgagcctacctacgtggacgacttcaagggcagattcgccttcagcatggacaccagcgccagcacagcctacctgcagatc agctctctgaaggccgaggacaccgccacctactactgtgccagactgagaggcatcagaccggacctctggcctattgggaca gggaacactggtcaccgtgtcctctggcggtggcggaagcggaggcggtggctccggtggcggaggcagcgagatcgtgctgac acagtctcccgccacactgagtgtgtctccaggcgaaagagccacactgtcctgtagcgccagcagcagcgtgtcctacatgaactg gtatcagcagaagcccggacaggcccctagactgtggatctacggcatcagcaatctggccagcggcatccctgccagattttctggc tctggctccggcaccagcttcagcctgacaatcagcagcctgcagagcgaggacttcgccgtgtactactgccagcagagaagcag ctaccctcctacctttggcggaggcaccaaggtggaaatcaagcgg (SEQ ID NO: 1030)
QIQLVQSGPEVKQPGASVKVSCKASGYTFTNYGMNWVKQAPGQGLEWM
GWINTYTGEPTYVDDFKGRFAFSMDTSASTAYLQISSLKAEDTATYYCARLRGIRPG
PLAYWGQGTLVTVSSGGGGSGGGGSGGGGSEIVLTQSPATLSVSPGERATLSCSASS
SVSYMNWYQQKPGQAPRLWIYGISNLASGIPARFSGSGSGTSFSLTISSLQSEDFAVY
YCQQRSSYPPTFGGGTKVEIKR 8H5H5G4 Heavy chain variable region sequence (SEQ ID NO: 365)
gtccagctgcaacagtctggacctgatctggtgaagcctgggacttcagtgaagatatcctgtaagacttctggaaaca
cattcactgaatacaccatgcactgggtgaagcagagccatggaaagagccttgagtggattggaggttttaatcctaacaatggtgtta
ctaactacaaccagaagttcaagggcaaggccacattgactgtagacaagtcctccagcacagcctacatggagctccgcagcctga
catctgaggattctgcagtctattactgtgcaagacgttactaccatagtacctacgtgttctactttgactcctggggccaaggcaccact
ctcacagtctcctca (SEQ ID NO: 1031)
VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS IGHV1-24*01 V-REGION sequence
(DNA)
(SEQ ID NO: 366)
caggtccagctggtacagtctggggctgaggtgaagaagcctggggcctcagtgaaggtctcctgcaaggtttccg
gatacacccctcactgaattatccatgcactgggtgcgacaggctcctggaaaagggcttgagtggatgggaggttttgatcctgaagat
ggtgaaacaatctacgcacagaagttccaggcagagtcaccatgaccgaggacacatctacagacacagcctacatggagctgag
cagcctgagatctgaggacacggccgtgtattactgtgcaaca (amino acids)
(SEQ ID NO: 1032)
QVQLVQSGAEVKKPGASVKVSCKVSGYTLTELSMHWVRQAPGKGLEW
MGGFDPEDGETIYAQKFQGRVTMTEDTSTDTAYMELSSLRSEDTAVYYCAT IGHJ4*03 J-REGION sequence
(DNA)
(SEQ ID NO: 367)
tactttgactactggggccaagggaccctggtcaccgtctcctca (amino acids)
(SEQ ID NO: 1033)
YFDYWGQGTLVTVSS Humanized 8H5H5G4 Heavy chain variable region sequence
(DNA)
(SEQ ID NO: 368)
caggtccagctggtacagtctggggctgaggtgaagaagcctggggcctcagtgaaggtctcctgcaaggtttccg
gaaacacattcactgaatacaccatgcacTgggtgcgacaggctcctggaaaagggcttgagtggatgggaggttttaatcctaacaa
tggtgttactaactacaaccagaagttcaagggcAgagtcaccatgaccgaggacacatctacagacacagcctacatggagctgag
cagcctgagatctgaggacacggccgtgtattactgtGcaagacgttactaccatagtacctacgtgttctactttgactcctggggcca
agggaccctggtcaccgtctcctca (amino acids)
(SEQ ID NO: 1034)
QVQLVQSGAEVKKPGASVKVSCKVSGNTFTEYTMHWVRQAPGKGLEW
MGGFNPNNGVTNYNQKFKGRVTMTEDTSTDTAYMELSSLRSEDTAVYYCARRYYH
STYVFYFDSWGQGTLVTVSS Humanized 8H5H5G4 Heavy chain variable region sequence (codon optimized)
(DNA)
(SEQ ID NO: 369)

caggttcagctggttcagtctggcgccgaagtgaagaaacctggcgcctctgtgaaggtgtcctgcaaggtgtccgg aaataccttcaccgagtacaccatgcactgggtccgacaggcccctggcaaaggacttgaatggatgggcggcttcaaccccaacaa cggcgtgaccaactacaaccagaaattcaaggccgcgtgaccatgaccgaggacacaagcacagacaccgcctacatggaactg agcagcctgagaagcgaggacaccgccgtgtactactgcgccagaaggtactaccacagcacctacgtgttctacttcgacagctgg ggccagggcacactggtcacagtttcttct (amino acids)
(SEQ ID NO: 1035)

QVQLVQSGAEVKKPGASVKVSCKVSGNTFTEYTMHWVRQAPGKGLEW

MGGFNPNNGVTNYNQKFKGRVTMTEDTSTDTAYMELSSLRSEDTAVYYCARRYYH

STYVFYFDSWGQGTLVTVSS

Modified Humanized 8H5H5G4 Heavy chain variable region sequence
(DNA)
(SEQ ID NO: 370)

caggtccagctggtacagtctggggctgaggtgaagaagcctggggcctcagtgaaggtctcctgcaaggtttccg gaaacacattcactgaatacaccatgcactgggtgcgacaggctcctggaaaagggcttgagtggatcggaggttttaatcctaacaat ggtgttactaactacaaccagaagttcaagggcaaggtcaccctgaccgtggacacatctagcagcacagcctacatggagctgagc agcctgagatctgaggacacggccgtgtattactgtgcaagacgttactaccatagtacctacgtgttctactttgactcctggggccaa gggaccctggtcaccgtctcctca (amino acids)
(SEQ ID NO: 1036)

QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHST

YVFYFDSWGQGTLVTVSS

Modified Humanized 8H5H5G4 Heavy chain variable region sequence (codon optimized)
(DNA)
(SEQ ID NO: 371)

caggttcagctggttcagtctggcgccgaagtgaagaaacctggcgcctctgtgaaggtgtcctgcaaggtgtccgg aaataccttcaccgagtacaccatgcactgggtccgacaggcccctggcaaaggactggaatggatcggcggcttcaacccccaaca acggcgtgaccaactacaaccagaaattcaagggcaaagtgaccctgaccgtggacaccagcagcagcacagcctacatggaact gagcagcctgagaagcgaggacaccgccgtgtactactgcgccagaaggtactaccacagcacctacgtgttctacttcgacagctg gggccagggcacactggtcacagtttcttct (amino acids)
(SEQ ID NO: 1037)

QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHST

YVFYFDSWGQGTLVTVSS

8H5H5G4 Light chain variable region sequence
(DNA)
(SEQ ID NO: 372)

gatatccagatgacacagactacatcctccctgtctgcctctctgggagacagagtcaccatcagttgcagtgcaagtc agggcattagcaattatttaaactggtttcagcagaaaccagatggaactattaagctcctgatctattacacatcaagtttacattcagga gtcccatcaaggttcagtggcagtgggtctgggacagattattctctcaccatcagtaatgtggaacctgaagatattgccacttactattg tcagcagtatagtaagcttccttacacgttcggaggggggaccaagctggagataaaacgg (amino acids)
(SEQ ID NO: 1038)

DIQMTQTTSSLSASLGDRVTISCSASQGISNYLNWFQQKPDGTIKLLIYYTS

SLHSGVPSRFSGSGSGTDYSLTISNVEPEDIATYYCQQYSKLPYTFGGGTKLEIKR

-continued

IGKV1-27*01 V-REGION sequence
(DNA)
(SEQ ID NO: 373)
gacatccagatgacccagtctccatcctccctgtctgcatctgtaggagacagagtcaccatcacttgccgggcgagt cagggcattagcaattatttagcctggtatcagcagaaaccagggaaagttcctaagctcctgatctatgctgcatccactttgcaatcag gggtcccatctcggttcagtggcagtggatctgggacagatttcactctcaccatcagcagcctgcagcctgaagatgttgcaacttatt actgtcaaaagtataacagtgcccct (amino acids)
(SEQ ID NO: 1039)
DIQMTQSPSSLSASVGDRVTITCRASQGISNYLAWYQQKPGKVPKLLIYAA

STLQSGVPSRFSGSGSGTDFTLTISSLQPEDVATYYCQKYNSAP

IGKJ4*02 J-REGION sequence
(DNA)
(SEQ ID NO: 374)
ctcacgttcggcggagggaccaaggtggagatcaaa (amino acids)
(SEQ ID NO: 1040)
LTFGGGTKVEIK humanized 8H5H5G4 Light chain variable region sequence
(DNA)
(SEQ ID NO: 375)
gacatccagatgacccagtctccatcctccctgtctgcatctgtaggagacagagtcaccatcacttgcagtgcaagtc agggcattagcaattatttaaacTggtatcagcagaaaccagggaaagttcctaagctcctgatctattacacatcaagtttacattcagg ggtcccatctcggttcagtggcagtggatctgggacagatttcactctcaccatcagcagcctgcagcctgaagatgttgcaacttatta ctgtcagcagtatagtaagcttccttacacgttcggcggagggaccaaggtggagatcaaacgg (amino acids)
(SEQ ID NO: 1041)
DIQMTQSPSSLSASVGDRVTITCSASQGISNYLNWYQQKPGKVPKLLIYYT

SSLHSGVPSRFSGSGSGTDFTLTISSLQPEDVATYYCQQYSKLPYTFGGGTKVEIKR humanized 8H5H5G4 Light chain variable region sequence (codon optimized)
(DNA)
(SEQ ID NO: 376)
gacatccagatgacacagagccctagcagcctgtctgccagcgtgggagacagagtgaccatcacatgtagcgcca gccagggcatcagcaactacctgaactggtatcagcagaaacccggcaaggtgcccaagctgctgatctactacaccagcagcctg cacagcggcgtgccaagcagattttctggcagcggctctggcaccgacttcaccctgaccatatctagcctgcagcctgaggacgtg gccacctactactgtcagcagtacagcaagctgccctacacctttggcggaggcaccaaggtggaaatcaagcgg (amino acids)
(SEQ ID NO: 1042)
DIQMTQSPSSLSASVGDRVTITCSASQGISNYLNWYQQKPGKVPKLLIYYT

SSLHSGVPSRFSGSGSGTDFTLTISSLQPEDVATYYCQQYSKLPYTFGGGTKVEIKR

Modified humanized 8H5H5G4 Light chain variable region sequence
(DNA)
(SEQ ID NO: 377)
gacatccagatgacccagtctccatcctccctgtctgcatctgtaggagacagagtcaccatcacttgcagtgcaagtc agggcattagcaattatttaaactggtatcagcagaaaccagggaaagttcctaagctcctgatctattacacatcaagtttacattcagg ggtcccatctcggttcagtggcagtggatctgggacagattacactctcaccatcagcagcctgcagcctgaagatgttgcaacttatta ctgtcagcagtatagtaagcttccttacacgttcggcggagggaccaaggtggagatcaaacgg (amino acids)
(SEQ ID NO: 1043)
DIQMTQSPSSLSASVGDRVTITCSASQGISNYLNWYQQKPGKVPKLLIYYT

SSLHSGVPSRFSGSGSGTDYTLTISSLQPEDVATYYCQQYSKLPYTFGGGTKVEIKR

-continued

Modified humanized 8H5H5G4 Light chain variable region sequence (codon optimized)
(DNA)
(SEQ ID NO: 378)

gacatccagatgacacagagccctagcagcctgtctgccagcgtgggagacagagtgaccatcacatgtagcgcca gccagggcatcagcaactacctgaactggtatcagcagaaacccggcaaggtgcccaagctgctgatctactacaccagcagcctg cacagcggcgtgccaagcagatttctggcagcggctctggcaccgactacaccctgaccatatctagcctgcagcctgaggacgtg gccacctactactgtcagcagtacagcaagctgccctacacctttggcggaggcaccaaggtggaaatcaagcgg (amino acids)
(SEQ ID NO: 1044)
DIQMTQSPSSLSASVGDRVTITCSASQGISNYLNWYQQKPGKVPKLLIYYT

SSLHSGVPSRFSGSGSGTDYTLTISSLQPEDVATYYCQQYSKLPYTFGGGTKVEIKR

Modified humanized 8H5H5G4 scFV sequence (codon optimized)
(DNA)
(SEQ ID NO: 379)

Caggttcagctggttcagtctggcgccgaagtgaagaaacctggcgcctctgtgaaggtgtcctgcaaggtgtccgg aaataccttcaccgagtacaccatgcactgggtccgacaggcccctggcaaaggactggaatggatcggcggcttcaaccccaaca acggcgtgaccaactacaaccagaaattcaagggcaaagtgaccctgaccgtggacaccagcagcagcacagcctacatggaact gagcagcctgagaagcgaggacaccgccgtgtactactgcgccagaaggtactaccacagcacctacgtgttctacttcgacagctg gggccagggcacactggtcacagtttcttctggcggtggcggaagcggaggcggtggctccggtggcggaggcagcgacatcca gatgacacagagccctagcagcctgtctgccagcgtgggagacagagtgaccatcacatgtagcgccagccagggcatcagcaact acctgaactggtatcagcagaaacccggcaaggtgcccaagctgctgatctactacaccagcagcctgcacagcggcgtgccaagc agatttctggcagcggctctggcaccgactacaccctgaccatatctagcctgcagcctgaggacgtggccacctactactgtcagca gtacagcaagctgccctacacctttggcggaggcaccaaggtggaaatcaagcgg (amino acids)
(SEQ ID NO: 1045)
QVQLVQSGAEVKKPGASVKVSCKVSGNTFTEYTMHWVRQAPGKGLEWI

GGFNPNNGVTNYNQKFKGKVTLTVDTSSSTAYMELSSLRSEDTAVYYCARRYYHST

YVFYFDSWGQGTLVTVSSGGGGSGGGGSGGGGSDIQMTQSPSSLSASVGDRVTITCS

ASQGISNYLNWYQQKPGKVPKLLIYYTSSLHSGVPSRFSGSGSGTDYTLTISSLQPED

VATYYCQQYSKLPYTFGGGTKVEIKR

Human IgG1 heavy chain constant region sequence: (for making full antibody -
pair with either kappa or lambda constant region; 2 plasmids, express together)
(DNA)
(SEQ ID NO: 380)

gctagcaccaagggcccatcggtcttccccctggcaccctcctccaagagcacctctgggggcacagcggccctgg gctgcctggtcaaggactacttccccgaaccggtgacggtgtcgtggaactcaggcgccctgaccagcggcgtgcacaccttcccg gctgtcctacagtcctcaggactctactccctcagcagcgtggtgacagtgccctccagcagcttgggcacccagacctacatctgca acgtgaatcacaagcccagcaacaccaaggtggacaagaaagttgagcccaaatcttgtgacaaaactcacacatgcccaccgtgcc cagcacctgaactcctggggggaccgtcagtcttcctcttccccccaaaacccaaggacaccctcatgatctcccggacccctgaggt cacatgcgtggtggtggacgtgagccacgaagaccctgaggtcaagttcaactggtacgtggacggcgtggaggtgcataatgcca agacaaagccgcgggaggagcagtacaacagcacgtaccgtgtggtcagcgtcctcaccgtcctgcaccaggactggctgaatgg caaggagtacaagtgcaaggtctccaacaaagccctcccagccccatcgagaaaaccatctccaaagccaaagggcagccccga gaaccacaggtgtacaccctgcccccatcccgggaggagatgaccaagaaccaggtcagcctgacctgcctggtcaaaggcttctat -continued cccagcgacatcgccgtggagtgggagagcaatgggcagccggagaacaactacaagaccacgcctcccgtgctggactccgac ggctccttcttcctctacagcaagctcaccgtggacaagagcaggtggcagcaggggaacgtcttctcatgctccgtgatgcatgagg ctctgcacaaccactacacgcagaagagcctctccctgtctccgggtaaatga (amino acids)   (SEQ ID NO: 1046)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSPGK

Human IgG2 heavy chain constant region sequence: (for making full antibody -
pair with either kappa or lambda constant region; 2 plasmids, express together)
(DNA)   (SEQ ID NO: 381)

gcctccaccaagggcccatcggtcttccccctggcgccctgctccaggagcacctccgagagcacagccgccctg ggctgcctggtcaaggactacttccccgaaccggtgacggtgtcgtggaactcaggcgctctgaccagcggcgtgcacaccttccca gctgtcctacagtcctcaggactctactccctcagcagcgtggtgaccgtgccctccagcaacttcggcacccagacctacacctgca acgtagatcacaagcccagcaacaccaaggtggacaagacagttgagcgcaaatgttgtgtcgagtgcccaccgtgcccagcacca cctgtggcaggaccgtcagtcttcctcttccccccaaaacccaaggacaccctcatgatctcccggacccctgaggtcacgtgcgtgg tggtggacgtgagccacgaagaccccgaggtccagttcaactggtacgtggacggcgtggaggtgcataatgccaagacaaagcc acgggaggagcagttcaacagcacgttccgtgtggtcagcgtcctcaccgttgtgcaccaggactggctgaacggcaaggagtaca agtgcaaggtctccaacaaaggcctcccagcccccatcgagaaaaccatctccaaaaccaaagggcagccccgagaaccacaggt gtacaccctgcccccatcccgggaggagatgaccaagaaccaggtcagcctgacctgcctggtcaaaggcttctaccccagcgaca tcgccgtggagtgggagagcaatgggcagccggagaacaactacaagaccacacctcccatgctggactccgacggctccttcttc ctctacagcaagctcaccgtggacaagagcaggtggcagcaggggaacgtcttctcatgctccgtgatgcatgaggctctgcacaac cactacacgcagaagagcctctccctgtctccgggtaaatag (amino acids)   (SEQ ID NO: 1047)

ASTKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERKCCVECPP

CPAPPVAGPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK

Human Kappa light chain constant region sequence:
(DNA)   (SEQ ID NO: 382)

aggacggtggctgcaccatctgtcttcatcttcccgccatctgatgagcagttgaaatctggaactgcctctgttgtgtg cctgctgaataacttctatcccagagaggccaaagtacagtggaaggtggataacgccctccaatcgggtaactcccaggagagtgtc acagagcaggacagcaaggacagcacctacagcctcagcagcaccctgacgctgagcaaagcagactacgagaaacacaaagtc tacgcctgcgaagtcacccatcagggcctgagctcgcccgtcacaaagagcttcaacaggggagagtgttag (amino acids)   (SEQ ID NO: 1048)

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC

-continued

Human Lambda light chain constant region sequence:
(DNA)

(SEQ ID NO: 383)

ggtcagcccaaggctgccccctcggtcactctgttcccgccctcctctgaggagcttcaagccaacaaggccacact ggtgtgtctcataagtgacttctacccgggagccgtgacagtggcctggaaggcagatagcagccccgtcaaggcgggagtggaga ccaccacaccctccaaacaaagcaacaacaagtacgcggccagcagctatctgagcctgacgcctgagcagtggaagtcccacag aagctacagctgccaggtcacgcatgaagggagcaccgtggagaagacagtggcccctacagaatgttcatag (amino acids)

(SEQ ID NO: 1049)

GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTVAPTECS

Human IgG1 Fc region sequence: (to be fused to scFv for homo-dimerizes)
(DNA)

(SEQ ID NO: 384)

gagcccaaatcttgtgacaaaactcacacatgcccaccgtgcccagcacctgaactcctggggggaccgtcagtctt cctcttccccccaaaacccaaggacaccctcatgatctcccggacccctgaggtcacatgcgtggtggtggacgtgagccacgaaga ccctgaggtcaagttcaactggtacgtggacggcgtggaggtgcataatgccaagacaaagccgcgggaggagcagtacaacagc acgtaccgtgtggtcagcgtcctcaccgtcctgcaccaggactggctgaatggcaaggagtacaagtgcaaggtctccaacaaagcc ctcccagcccccatcgagaaaaccatctccaaagccaaagggcagccccgagaaccacaggtgtacaccctgcccccatcccggg aggagatgaccaagaaccaggtcagcctgacctgcctggtcaaaggcttctatcccagcgacatcgccgtggagtgggagagcaat gggcagccggagaacaactacaagaccacgcctcccgtgctggactccgacggctccttcttcctctacagcaagctcaccgtggac aagagcaggtggcagcaggggaacgtcttctcatgctccgtgatgcatgaggctctgcacaaccactacacgcagaagagcctctcc ctgtctccgggtaaatga (amino acids)

(SEQ ID NO: 1050)

EPKSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNH

YTQKSLSLSPGK*

Human IgG2 Fc region sequence:
(DNA)

(SEQ ID NO: 385)

gagcgcaaatgttgtgtcgagtgcccaccgtgcccagcaccacctgtggcaggaccgtcagtcttcctcttccccccca aaacccaaggacaccctcatgatctcccggacccctgaggtcacgtgcgtggtggtggacgtgagccacgaagaccccgaggtcca gttcaactggtacgtggacggcgtggaggtgcataatgccaagacaaagccacgggaggagcagttcaacagcacgttccgtgtgg tcagcgtcctcaccgttgtgcaccaggactggctgaacggcaaggagtacaagtgcaaggtctccaacaaaggcctcccagccccc atcgagaaaaccatctccaaaaccaaagggcagcccgagaaccacaggtgtacaccctgcccccatcccgggaggagatgacca agaaccaggtcagcctgacctgcctggtcaaaggcttctaccccagcgacatcgccgtggagtgggagagcaatgggcagccgga gaacaactacaagaccacacctcccatgctggactccgacggctccttcttcctctacagcaagctcaccgtggacaagagcaggtg gcagcaggggaacgtcttctcatgctccgtgatgcatgaggctctgcacaaccactacacgcagaagagcctctccctgtctccgggt aaatag (amino acids)

(SEQ ID NO: 1051)

ERKCCVECPPCPAPPVAGPSVFLFPPKPKDTLMISRTPEVTCVVVDVSHED

PEVQFNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSDIAVEWES

NGQPENNYKTTPPMLDSDGSFFLYSKLTVDKSRWQQGNVFSCSVMHEALHNHYTQ

KSLSLSPGK*

In another aspect of the invention, an immune cell engineered to express a CAR is administered to a patient diagnosed with or at risk of developing a cancer or cancer metastasis, wherein the immune cell is also engineered to express an anti-NME7 antibody or antibody fragment, which may be expressed off of an inducible promoter. In one aspect, the CAR is guided by an anti-MUC1* antibody fragment. In one case, the CAR is huMNC2-CAR44. In one aspect, the anti-NME7 antibody or antibody fragment binds to an NME peptide listed under sections "Homologous peptides to A1, A2, B1, B2 or B3 peptides" and the "Homologous extended peptides to A1, A2, B1, B2 or B3 peptides" above. In another aspect, the antibody or antibody fragment binds to an NME7 derived peptide chosen from among A1, A2, B1, B2 or B3 (SEQ ID NOS: 141-145). In yet another aspect, the antibody, antibody fragment or antibody mimic binds to an NME7 peptide comprising the B3 peptide. In one aspect of the invention, the anti-NME7 antibody, antibody fragment or antibody mimic comprises sequences derived from the variable domains of anti-NME7 antibodies 8F9A4A3, 8F9A5A1, or 8H5H5G4.

Such antibodies may be human or humanized. Such antibodies may be polyclonal, monoclonal, bispecific, bivalent, monovalent, single chain, scFv, or may be an antibody mimic such as protein scaffolds that present recognition regions that bind to a specific target. As is appreciated by those skilled in the art, antibodies can be of non-human origin, human or humanized. Methods for humanizing antibodies include fusing all or some of the mouse variable regions to V- and J-regions of a closest match human antibody sequence, for example, as shown in sequences listed as SEQ ID NOS: 1001-1045. Full antibodies, rather than single chain constructs, can also be made. For example, the heavy chain variable mouse sequence is fused to human V- and J-regions then fused to the human heavy chain constant regions of IgG1, IgG2 or IgG3. Similarly, the light chain variable mouse sequences are fused to human V- and J-regions then fused to either the human Kappa or Lambda constant regions of IgG1, IgG2 or lgG3. Plasmids are expressed together and associate to form the full antibody (SEQ ID NOS: 1047-1051).

In another aspect of the invention, small molecules are anti-cancer agents that are selected for their ability to inhibit the tumorigenic effects of NME7, NME7$_{AB}$ or NME7-X1. For example, a high throughput screen identifies small molecules that will treat cancer. In a multi-well plate, small molecules are separately added to wells in which cancer cells are cultured in a medium containing NME7$_{AB}$. If the small molecule diminishes the amount of cells that become floaters and/or reduces the expression of metastatic markers such as CXCR4, CHD1 or pluripotent stem cell markers, then that small molecule is an anti-cancer drug candidate. Another method of identifying small molecules that are anti-cancer agents is to select those small molecules that bind to NME7, NME7$_{AB}$ or NME7-X1 or suppresses expression of the NME7 species. Yet another high throughput screen is to select for small molecules that inhibit the binding of NME7$_{AB}$ to the PSMGFR peptide of the MUC1* extracellular domain and those small molecules will be anti-cancer agents.

The sequences of NME7$_{AB}$ and NME7-X1 differ only in that NME7-X1 is missing some of the N-terminal sequence that NME7$_{AB}$ has. Experiments show that there is a naturally occurring NME7 species that is nearly identical to NME7$_{AB}$, which we call NME7$_{AB}$-like species. Antibodies that bind to NME7-X1 may also bind to the naturally occurring species that mimics NME7$_{AB}$, unless there are conformational differences that an antibody can differentiate. Therefore, if it is desired to inhibit NME7-X1 but not NME7$_{AB}$-like species, or vice versa, siRNA, anti-sense nucleic acids, or genetic editing techniques can be used to inhibit expression of one but not the other.

In one case, the anti-cancer therapeutic agent is a nucleic acid that directly or indirectly suppresses specific expression of NME7, NME7-X1 or NME7$_{AB}$-like species. Such nucleic acids can be siRNA. RNAi, anti-sense nucleic acids and the like that directly suppress the NME7 species. In another aspect of the invention, the nucleic acid can indirectly suppress the NME7 species for example by altering the expression of a molecule that regulates it. For example, the super enhancer BRD4 suppresses expression of NME7. Therefore, an effective therapeutic for the treatment or prevention of cancer is an agent that increases expression of BRD4. An effective therapeutic may be an agent that increases expression of BRD4's co-factor. JMJD6.

Peptides derived from NME7$_{AB}$ or NME7-X1, or the entire protein, are used to generate anti-NME7 or anti-NME7-X1 antibodies in animals that we have demonstrated inhibit cancer growth and inhibit transition of cancer cells to metastatic cancer cells. Similarly, NME7 derived peptides can be administered to a human such that they generate antibodies that treat or prevent cancer or inhibit transition of cancer cells to metastatic cancer cells, NME7 peptides or proteins are administered to a person as a type of vaccine to stimulate the production of anti-NME7, anti-NME7$_{AB}$ or anti-NME7-X1 antibodies in the recipient. The results shown in FIG. 12 and FIG. 13 indicate that immunizing a person with a collection of peptides derived from NME7, especially in the NME7-X1 or NME7$_{AB}$ sequences may be a more effective vaccine than immunizing with a single peptide. Said peptides or proteins may further be conjugated to a carrier protein or other adjuvant, known to those skilled in the art to aid in the stimulation of an immune response.

NME7 peptides that lie outside of the DM10 domain are preferred to generate antibodies for the treatment or prevention of cancer. Peptides that can be administered to a patient for the prevention of cancer or metastasis contain sequences of the peptides listed in FIG. 6-FIG. 9. A1, A2, B1, B2 and B3 are examples of peptides that generate antibodies that bind to NME7$_{AB}$ and NME7-X1 and are administered to a patient for the treatment or prevention of cancer. The invention is not limited to peptides of the exact sequence as is naturally occurring in NME7 or NME7-X1. As is known to those skilled in the art, substitution of several amino acids of a peptide sequence can still give rise to antibodies that specifically recognize the natural protein sequence. It is not intended that the invention be limited to the peptides demonstrated herein to inhibit cancer growth or inhibit the transition of regular cancer cells to metastatic cancer cells. The methods used here to identify peptides A1, A2, B1, B2 and B3 can also be used to identify other peptide sequences that could be equally or more effective than the peptides demonstrated here.

Chimeric antigen receptor molecules comprising portions of human $NME7_{AB}$ or NME7-X1 or comprising an antibody fragment that binds to $NME7_{AB}$ or NME7-X1 are anticancer therapeutics and are administered to a patient for the treatment or prevention of cancers or cancer metastases.

In one instance, the recognition units or variable regions of anti-NME7 antibodies are fused to molecules of T cells using the technology known as CAR (chimeric antigen receptor) technology or CAR T technology. The salient feature of antibodies or fragments thereof that can be used therapeutically to treat or prevent cancers is the identification of antibody-like variable regions that recognize NME7 and prevent its interaction with targets that promote cancers. In one case, the target is the PSMGFR region of MUC1*.

Antibodies, antibody fragments or single chain antibodies can be engineered into chimeric molecules, including chimeric antigen receptors, also known as CARs, which molecules are then transfected or transduced into an immune system cell, such as a T cell, and administered to a patient. The humanized antibodies or antibody fragments, typically an scFv, comprises much of the extracellular domain of a CAR. The antibody fragment is biochemically fused to immune system signaling molecules, such as CD8 as the transmembrane domain and cytoplasmic signaling motifs such as T cell receptor signaling molecules also called activation domains, or co-stimulatory domains including but not limited to CD3-zeta. CD28, 41bb, OX40. CARs can be transfected into T cells or other cells, preferably immune system cells and administered to a patient. Here we describe CARs in which the extracellular portion contains an anti-NME7, anti-$NME7_{AB}$ or anti-NME7-X1 antibody, antibody fragment or single chain, scFv antibody fragment. In a preferred embodiment, the antibody or antibody fragment is human or humanized.

Effective anti-NME7 or anti-NME7-X1 antibodies or fragments will have the ability to bind to native NME7, $NME7_{AB}$ or NME7-X1. In practice, the parent antibody, from which the extracellular domain of the CAR is engineered, is generated by immunizing an animal with an NME7, $NME7_{AB}$ or NME7-X1 derived peptide. In one aspect of the invention, the immunizing peptide is comprised of NME7 amino acids 1-376. In one aspect of the invention, the immunizing peptide is comprised of NME7 amino acids 92-376. In another aspect of the invention, the immunizing peptide is comprised of NME7 amino acids 125-376. In yet another aspect of the invention, the immunizing peptide is made up of sequences listed in FIG. 6-FIG. 8. In another aspect of the invention, the immunizing peptide is made up of sequences listed in FIG. 9. Alternatively, the parent antibody or the antibody fragment is selected from a library or pool of antibodies, which may be natural, synthetic or fragments of either, wherein they are selected for their ability to bind to NME7, $NME7_{AB}$ or NME7-X1, peptides listed in FIG. 6-FIG. 8, or peptides listed in FIG. 9.

The targeting portion of a CAR need not be an antibody or antibody fragment. Here we describe a CAR wherein the extracellular domain contains an NME7 fragment, NME7-derived peptide(s) are engineered into a different sort of CAR wherein the targeting portion of the extracellular domain is a protein fragment or peptide rather than an antibody or antibody fragment. The peptide CARs are transfected or transduced into an immune system cell, typically a T cell. The NME7 fragments or NME7 derived peptides are selected for their ability to bind to their cognate binding partners but should not be able to function as intact NME7. $NME7_{AB}$ or NME7-X1 and confer tumorigenic activity, NME7 fragments or NME7 derived peptides are biochemically fused to immune system signaling molecules, such as CD8 as the transmembrane domain and cytoplasmic signaling motifs such as T cell receptor signaling molecules also called activation domains, or co-stimulatory domains including but not limited to CD3-zeta, CD28, 41bb, OX40.

In one aspect of the invention, the NME7 fragment is most or all of the NME7 NDPK B domain. In another aspect of the invention, the NME7 fragment is an NME7 peptide that contains one or more of the peptide sequences listed in FIG. 6-FIG. 9. Experiments indicate that, for strategies that use NME7 or fragments of NME7, $NME7_{AB}$, or NME7-X1 as the targeting portion of a chimeric antigen receptor (CAR) for engineered immune cell therapeutics, fairly large fragments of $NME7_{AB}$ or NME7-X1 would be more effective than shorter peptides, for example peptides less than 15 amino acids in length. Alternatively, a collection of CARs, each bearing a different $NME7_{AB}$ derived peptide can collectively be transfected or transduced into an immune system cell and administered to a patient for the treatment or prevention of cancers. Experiments shown in FIG. 12-FIG. 13 support the validity of this approach.

CARs that contain an NME7 fragment in its extracellular domain are transfected or transduced into an immune system cell, typically a T cell, and administered to a patient for the treatment or prevention of cancers. In one aspect, the cancer is a MUC1*-positive cancer. In another aspect, the cancer is a metastatic cancer.

Agents that inhibit an enzyme that cleaves NME7 can be used to treat or prevent cancers. Some forms of NME7 are sequestered within the cell and therefore are not secreted from the cell whereupon they can act as growth factors to promote cancers. Full-length NME7 is 42 kDa. However, we found that a ~33 kDa NME7 species that is devoid of the DM10 domain and appears to be essentially identical to the recombinant $NME7_{AB}$ that we generated, is secreted from cancer cells and stem cells. This ~33 kDa NME7 species and another ~25 kDa NME7 species may be cleavage products that would be eliminated by an agent that inhibited cleavage of NME7.

The detection of elevated levels of NME7, or an ~33 kDa NME7 species, which we call $NME7_{AB}$-like species, or NME7-X1 in a patient sample is diagnostic of the presence of cancer or its progression to a more aggressive or metastatic state. The inventors have discovered that both early stage, naïve stem cells and cancer cells, especially MUC1*-positive cancer cells, express high levels of a ~33 kDa NME7 that is devoid of the DM10 domain and NME7-X1.

NME7-X1 was recently listed in a protein database as being a theoretical alternative isoform of NME7, however, it had never been detected in tissues or cells. We designed primers that differentiate NME7-X1 from NME7 by PCR. The expression levels of human NME7. NME7a, NME7b and NME7-X1 were measured by PCR in a panel of cells that included fibroblast cells, human embryonic stem cells, human iPS cells. T47D human breast cancer cells. DU145 human prostate cancer cells. PC3 human prostate cancer cells. HEK295 human fetal liver cells, and other human stem cell lines, NME7 is expressed at higher levels in cancer cells than in stem cells. Particularly, NME7-X1 is expressed 10-fold higher in prostate cancer cells and 3-fold higher in breast cancer cells, than it is in fibroblast cells or stem cells, NME7-X1 is expressed ~5-fold higher in HEK293 fetal liver cells than it is in fibroblast cells or stem cells and therefore predicts that NME7-X1 is elevated in liver cancers, NME7b is expressed 17-25-times higher in prostate cancer cells than in stem cells.

Detection of elevated levels of NME7 species in a patient sample will be indicators that the patient has a cancer or is at risk of developing a cancer. Levels of NME7 species levels can be measured or assessed by PCR, hybridization schemes, cycling probe technologies. FISH, immunocytochemistry, IHC, Western blot, immunoprecipitation, sandwich assays. ELISA assays and the like. The patient sample may be a fluid sample, a blood sample, milk, urine, cells, liquid biopsy, biopsy and the like. In a patient diagnosed with cancer, elevated levels of NME7 species are indicators of increased metastatic potential. Elevated levels of NME7-X1 are indicators of prostate cancer. Antibodies of the invention are used to detect and distinguish NME7 species and are used as a diagnostic tool.

Because adult cells and tissues do not express significant levels of NME7 or secrete NME7, an effective way to diagnose cancer or to diagnose a more aggressive or metastatic form, or a shift to a more aggressive form, is to measure levels of NME7 in a sample from a patient, from a collection of cells or tissues or from cultured cells, compared to NME7 levels in a healthy sample or compared to levels of NME7 known to exist in healthy adult cells or tissues. Increased levels of NME7 indicate the presence of cancer, the presence of a metastatic cancer or the onset of metastasis. Increased levels of NME7 is also indicative of a MUC1*-positive cancer. The sample assayed for the presence of NME7 may be a collection of cells that may be cultured cell lines or cells from a patient, a bodily fluid, a blood sample, a tissue specimen, or a biopsy specimen. Therefore, a diagnostic assay that will detect the presence of cancer or the progression of cancer, comprises the steps of: 1) obtaining a sample from a patient having cancer or at risk of developing a cancer: 2) subjecting that sample to an assay capable of detecting or measuring levels of NME7, or levels of nucleic acids encoding NME7; 3) comparing levels of the measured NME7 protein or NME7-encoding nucleic acids in the test sample to levels in control patients or control cells: 4) determining that the levels of NME7 or nucleic acids encoding NME7 are elevated compared to the controls; and 5) concluding that the donor of the test sample has cancer or has had a progression of cancer if the control to which the test was compared came from a donor previously diagnosed with a cancer.

In this assay, the control sample to which the test sample is compared can be non-cancerous cells, cultured cells, a sample from a healthy donor, a non-cancerous sample from the donor, or a sample from the donor of the test sample wherein the control sample was taken from the donor at a previous point in time. The source of such samples may be any specimen taken from the patient being tested for the presence or progression of cancer, including bodily fluids, cerebrospinal fluid, bone marrow samples, blood, tissues, cells, biopsy tissues or cells, cultured cells derived from a patient's cells and the like. The source of the sample to which the test sample is compared can be bodily fluids, cerebrospinal fluid, bone marrow samples, blood, tissues, cells, biopsy tissues or cells, or cultured cells that may be derived from a healthy donor or the test patient wherein the samples were taken at a previous point in time. The measured levels to which the test sample is compared may be from previously recorded data and compiled into lists for comparison to test samples.

Theranostics

Patients diagnosed with elevated levels of NME7 protein or nucleic acids encoding NME7 are then treated with therapeutic agents that suppress expression of NME7, inhibit cleavage of NME7 or inhibit NME7 binding to its targets, wherein such interaction promotes cancers. An important target of NME7 or a cleavage product of NME7, is MUC1*, NME7 binds to and dimerizes the extracellular domain of MUC1*. Therefore, patients diagnosed with elevated levels of NME7 will benefit from treatment with therapeutic agents that inhibit NME7 and/or therapeutic agents that inhibit the dimerization of a cleaved form of MUC1, whose extracellular domain is comprised of some or all of the PSMGFR sequence. Thus assessing suitability of cancer treatments and administration of an effective amount of a therapeutic for the treatment or prevention of cancers would consists of the steps of: 1) obtaining a sample from a patient suspected of having a cancer or at risk of developing a cancer or at risk of developing a metastatic cancer: 2) measuring an amount of NME7 or a cleavage product thereof or an NME7 encoding nucleic acid wherein the measured levels are significantly above those measured in a control sample: 3) determining that the patient has a cancer or has developed a more aggressive or a metastatic cancer: 4) administering to the patient an effective amount of a therapeutic agent that suppresses expression of NME7, inhibits cleavage of NME7 or inhibits NME7 binding to its targets and/or administering to the patient an effective amount of a therapeutic agent that suppresses expression of MUC1, inhibits cleavage of MUC1 to MUC1* or inhibits MUC1* binding to its targets. In a preferred embodiment, the therapeutic agent that inhibits NME7 binding to its targets, inhibits its interaction with MUC1*. In a more preferred embodiments, it inhibits its interaction with the extracellular domain of MUC1* comprised essentially of the PSMGFR sequence. In a preferred embodiment, the therapeutic agent that inhibits MUC1* binding to its targets, inhibits the interaction between MUC1* and NME7. In a more preferred embodiment, the therapeutic agent that inhibits the interaction between MUC1* and NME7 inhibits the binding of MUC1* to the portion of NME7 that is comprised essentially of the sequence of $NME7_{AB}$.

Chemically Modified Peptides

Polypeptide or antibody therapeutics may suffer from short circulating half-life, and proteolytic degradation and low solubility. To improve the pharmacokinetics and pharmacodynamics properties of the inventive biopharmaceuticals, methods such as manipulation of the amino acid sequence may be made to decrease or increase immunogenicity and decrease proteolytic cleavage: fusion or conjugation of the peptides to immunoglobulins and serum proteins, such as albumin may be made: incorporation into drug delivery vehicles for the biopharmaceuticals such as the inventive peptides and antibodies for protection and slow release may also be made; and conjugating to natural or synthetic polymers are also contemplated. In particular, for synthetic polymer conjugation, pegylation or acylation, such as N-acylation. S-acylation and so forth are also contemplated.

Nucleic Acid Constructs

Also provided is an expression vector comprising a nucleic acid molecule of the invention as described herein, wherein the nucleic acid molecule is operatively linked to an expression control sequence. Also provided is a host-vector system for the production of a polypeptide which comprises the expression vector of the invention which has been introduced into a host cell suitable for expression of the polypeptide. The suitable host cell may be a bacterial cell such as E, coli, a yeast cell, such as Pichia pastoris, an insect cell, such as Spodoptera frugiperda, or a mammalian cell, such as a COS, HEK or CHO cell.

The present invention also provides for methods of producing the polypeptides of the invention by growing cells of the host-vector system described herein, under conditions permitting production of the polypeptide and recovering the polypeptide so produced. The polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, polypeptide includes functionally equivalent molecules in which amino acid residues are substituted for residues within the sequence resulting in a silent or conservative change. For example, one or more amino acid residues within the sequence can be substituted by another amino acid of a similar polarity, which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. The potential glycosylation amino acids include serine, threonine, and asparagine. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Any of the methods known to one skilled in the art for the insertion of DNA fragments into a vector may be used to construct expression vectors encoding the polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the polypeptides of the invention may be regulated by a second nucleic acid sequence so that the polypeptide is expressed in a host transformed with the recombinant DNA molecule. For example, expression of the polypeptides described herein may be controlled by any promoter/enhancer element known in the art. Promoters which may be used to control expression of the polypeptide include, but are not limited to the long terminal repeat as described in Squinto et al., (1991, Cell 65:1-20): the SV40 early promoter region (Bernoist and Chambon, 1981, Nature 290:304-310), the CMV promoter, the M-MuLV 5' terminal repeat the promoter contained in the 3'long terminal repeat of Rous sarcoma virus (Yamamoto, et al., 1980, Cell 22:787-797), the herpes thymidine kinase promoter (Wagner et al., 1981. Proc. Natl. Acad. Sci. U.S.A. 78:144-1445), the regulatory sequences of the met-allothionein gene (Brinster et al., 1982, Nature 296:39-42): prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American. 1980, 242:74-94: promoter elements from yeast or other fungi such as the Gal 4 promoter, the ADH (alcohol dehydrogenase) promoter. PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987. Mol. Cell. Biol. 7:1436-1444), mouse mammary tumor virus control region which is active in testicular, breast, lymphoid and mast cells (Leder et al., 1986, Cell 45:485-495), Sendai virus, lenti virus, albumin gene control region which is active in liver (Pinkert et al., 1987. Genes and Devel. 1:268-276), alpha-fetoprotein gene control region which is active in liver (Krumlauf et al., 1985. Mol. Cell. Biol. 5:1639-1648: Hammer et al., 1987. Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985. Nature 315:338-340); Kollias et al., 1986, Cell 46:89-94); myelin basic protein gene control region which is active in oligodendrocyte cells in the brain (Readhead et al., 1987, Cell 48:703-712): myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a polypeptide as described herein, are used to transfect the host and thereby direct expression of such nucleic acid to produce polypeptides which may then be recovered in biologically active form. As used herein, a biologically active form includes a form capable of binding to the relevant receptor and causing a differentiated function and/or influencing the phenotype of the cell expressing the receptor.

Expression vectors containing the nucleic acid inserts can be identified by without limitation, at least three general approaches: (a) DNA-DNA hybridization. (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The polypeptide, in particular modified of the present invention, may be expressed in the host cells transiently, constitutively or permanently.

Effective doses useful for treating the diseases or disorders indicated in the present application may be determined using methods known to one skilled in the art (see, for example. Fingl, et al., The Pharmacological Basis of Therapeutics, Goodman and Gilman, eds. Macmillan Publishing Co, New York, pp. 1-46 (1975). Pharmaceutical compositions for use according to the invention include the polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions, which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Lentiviral vectors, such as retroviral vectors, and other vectors such as adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes: blood cells such as T-lymphocytes. B-lymphocytes, monocytes, macrophages, neutrophils, eosinophils, megakaryocytes, granulocytes: various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

The formulation of therapeutic compounds is generally known in the art and reference can conveniently be made to Remington's Pharmaceutical Sciences. 17th ed., Mack Publishing Co., Easton. Pa., USA. For example, from about 0.05 ng to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intra ocular, intradermal or suppository routes or implanting (eg using slow release molecules by the intraperitoneal route or by using cells e.g. monocytes or dendrite cells sensitized in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like: a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, intra ocular, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Sequence Listing Free Text

As regards the use of nucleotide symbols other than a, g, c, t, they follow the convention set forth in WIPO Standard ST.25, Appendix 2, Table 1, wherein k represents t or g: n represents a, c, t or g: m represents a or c: r represents a or g; s represents c or g; w represents a or t and y represents c or t.

```
                                                   (SEQ ID NO: 1)
MTPGTQSPFF  LLLLLTVLTV  VTGSGHASST  PGGEKETSAT

QRSSVPSSTE  KNAVSMTSSV  LSSHSPGSGS  STTQGQDVTL

APATEPASGS  AATWGQDVTS  VPVTRPALGS  TTPPAHDVTS

APDNKPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS

APDTRPAPGS  TAPPAHGVTS  APDTRPAPGS  TAPPAHGVTS
```

```
APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDNRPALGS TAPPVHNVTS

ASGSASGSAS TLVHNGTSAR ATTTPASKST PFSIPSHHSD

TPTTLASHST KTDASSTHHS SVPPLTSSNH STSPQLSTGV

SFFFLSFHIS NLQFNSSLED PSTDYYQELQ RDISEMFLQI

YKQGGFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL
describes full-length MUC1 Receptor (Mucin 1
precursor, Genbank Accession number: P15941).

(SEQ ID NO: 2)
MTPGTQSPFFLLLLLTVLT (SEQ ID NO: 3)
MTPGTQSPFFLLLLLTVLT VVTA (SEQ ID NO: 4)
MTPGTQSPFFLLLLLTVLT VVTG
```

SEQ ID NOS: 2, 3 and 4 describe N-terminal MUC-1 signaling sequence for directing MUC1 receptor and truncated isoforms to cell membrane surface. Up to 3 amino acid residues may be absent at C-terminal end as indicated by variants in SEQ ID NOS: 2, 3 and 4.

GTINVHDVETQFNQYKTEAAS-RYNLTISDVSVSDVPFPFSAQSGAGVPGW GIALL-VLVCVLVALAIVYLIALA-VCQCRRKNYGQLDIFPARDTYHPMSEYPTYHTHG RYVPPSSTDRSPYEKVSAGNGGSSLSYTN-PAVAAASANL (SEQ ID NO:5) describes a truncated MUC1 receptor isoform having nat-PSMGFR at its N-terminus and including the transmembrane and cytoplasmic sequences of a full-length MUC1 receptor.

GTINVHDVETQFNQYKTEAAS-RYNLTISDVSVSDVPFPFSAQSGA (SEQ ID NO: 6) describes the extracellular domain of Native Primary Sequence of the MUC1 Growth Factor Receptor (nat-PSMGFR—an example of "PSMGFR"):

TINVHDVETQFNQYKTEAAS-RYNLTISDVSVSDVPFPFSAQSGA (SEQ ID NO: 7) describes the extracellular domain of Native Primary Sequence of the MUC1 Growth Factor Receptor (nat-PSMGFR—An example of "PSMGFR"), having a single amino acid deletion at the N-terminus of SEQ ID NO:6).

GTINVHDVETQFNQYK-TEAASPYNLTISDVSVSDVPFPFSAQSGA (SEQ ID NO: 8) describes the extracellular domain of "SPY" functional variant of the native Primary Sequence of the MUC1 Growth Factor Receptor having enhanced stability (var-PSMGFR—An example of "PSMGFR").

TINVHDVETQFNQYK-TEAASPYNLTISDVSVSDVPFPFSAQSGA (SEQ ID NO: 9) describes the extracellular domain of "SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO: 8).

```
describes MUC1 cytoplasmic domain nucleotide sequence
                                                                                (SEQ ID NO: 10)
tgtcagtgccgccgaaagaactacgggcagctggacatctttccagcccgggatacctaccatcctatgagcgagta ccccacctaccacacccatgggcgctatgtgcccctagcagtaccgatcgtagcccctatgagaaggtttctgcaggtaacggtggc agcagcctctcttacacaaacccagcagtggcagccgcttctgccaacttg.

describes MUC1 cytoplasmic domain amino acid sequence
                                                                                (SEQ ID NO: 11)
CQCRRKNYGQLDIFPARDTYHPMSEYPTYHTHGRYVPPSSTDRSPYEKVS

AGNGGSSLSYTNPAVAAASANL.

describes NME7 nucleotide sequence (NME7: GENBANK ACCESSION AB209049)
                                                                                (SEQ ID NO: 12)
gagatcctgagacaatgaatcatagtgaaagattcgttttcattgcagagtggtatgatccaaatgcttcacttcttcgac gttatgagctttatttttacccaggggatggatctgttgaaatgcatgatgtaaagaatcatcgcacctttttaaagcggaccaaatatgata acctgcacttggaagatttatttataggcaacaaagtgaatgtcttttctcgacaactggtattaattgactatggggatcaatatacagctc gccagctgggcagtaggaaagaaaaaacgctagccctaattaaaccagatgcaatatcaaaggctggagaaataattgaaataataa acaaagctggatttactataaccaaactcaaaatgatgatgctttcaaggaaagaagcattggattttcatgtagatcaccagtcaagacc cttttcaatgagctgatccagtttattacaactggtcctattattgccatgagattttaagagatgatgctatatgtgaatggaaaagactg ctgggacctgcaaactctggagtggcacgcacagatgcttctgaaagcattagagccctctttggaacagatggcataagaaatgcag cgcatggccctgattcttttgcttctgcggccagagaaatggagttgttttttccttcaagtggaggttgtgggccggcaaacactgctaa atttactaattgtacctgttgcattgttaaacccccatgctgtcagtgaaggtatgttgaatacactatattcagtacattttgttaataggagag caatgtttattttcttgatgtactttatgtatagaaaataa.
```

```
describes NME7 amino acid sequence (NME7: GENBANK ACCESSION AB209049)
                                                                                    (SEQ ID NO: 13)
DPETMNHSERFVFIAEWYDPNASLLRRYELLFYPGDGSVEMHDVKNHRT

FLKRTKYDNLHLEDLFIGNKVNVFSRQLVLIDYGDQYTARQLGSRKEKTLALIKPDAI

SKAGEIIEIINKAGFTITKLKMMMLSRKEALDFHVDHQSRPFFNELIQFITTGPIIAMEIL

RDDAICEWKRLLGPANSGVARTDASESIRALFGTDGIRNAAHGPDSFASAAREMELF

FPSSGGCGPANTAKFTNCTCCIVKPHAVSEGMLNTLYSVHFVNRRAMFIFLMYFMY

RK.

describes NM23-H1 nucleotide sequence (NM23-H1: GENBANK
ACCESSION AF487339)
                                                                                    (SEQ ID NO: 14)
atggtgctactgtctactttagggatcgtctttcaaggcgaggggcctcctatctcaagctgtgatacaggaaccatggc caactgtgagcgtaccttcattgcgatcaaaccagatggggtccagcggggtcttgtgggagagattatcaagcgttttgagcagaaag gattccgccttgttggtctgaaattcatgcaagcttccgaagatcttctcaaggaacactacgttgacctgaaggaccgtccattctttgcc ggcctggtgaaatacatgcactcagggccggtagttgccatggtctgggaggggctgaatgtggtgaagacgggccgagtcatgctc ggggagaccaaccctgcagactccaagcctgggaccatccgtggagacttctgcatacaagttggcaggaacattatacatggcagt gattctgtggagagtgcagagaaggagatcggcttgtggtttcaccctgaggaactggtagattacacgagctgtgctcagaactggat ctatgaatga.

NM23-H1 describes amino acid sequence (NM23-H1:
GENBANK ACCESSION AF487339)
                                                                                    (SEQ ID NO: 15)
MVLLSTLGIVFQGEGPPISSCDTGTMANCERTFIAIKPDGVQRGLVGEIIKR

FEQKGFRLVGLKFMQASEDLLKEHYVDLKDRPFFAGLVKYMHSGPVVAMVWEGL

NVVKTGRVMLGETNPADSKPGTIRGDFCIQVGRNIIHGSDSVESAEKEIGLWFHPEEL

VDYTSCAQNWIYE.

describes NM23-H1 S120G mutant nucleotide sequence (NM23-
H1: GENBANK ACCESSION AF487339)
                                                                                    (SEQ ID NO: 16)
atggtgctactgtctactttagggatcgtctttcaaggcgaggggcctcctatctcaagctgtgatacaggaaccatggc caactgtgagcgtaccttcattgcgatcaaaccagatggggtccagcggggtcttgtgggagagattatcaagcgttttgagcagaaag gattccgccttgttggtctgaaattcatgcaagcttccgaagatcttctcaaggaacactacgttgacctgaaggaccgtccattctttgcc ggcctggtgaaatacatgcactcagggccggtagttgccatggtctgggaggggctgaatgtggtgaagacgggccgagtcatgctc ggggagaccaaccctgcagactccaagcctgggaccatccgtggagacttctgcatacaagttggcaggaacattatacatggcggt gattctgtggagagtgcagagaaggagatcggcttgtggtttcaccctgaggaactggtagattacacgagctgtgctcagaactggat ctatgaatga.

describes NM23-H1 S120G mutant amino acid
sequence (NM23-H1: GENBANK ACCESSION AF487339)
                                                                                    (SEQ ID NO: 17)
MVLLSTLGIVFQGEGPPISSCDTGTMANCERTFIAIKPDGVQRGLVGEIIKR

FEQKGFRLVGLKFMQASEDLLKEHYVDLKDRPFFAGLVKYMHSGPVVAMVWEGL

NVVKTGRVMLGETNPADSKPGTIRGDFCIQVGRNIIHGGDSVESAEKEIGLWFHPEEL

VDYTSCAQNWIYE.

describes NM23-H2 nucleotide sequence
(NM23-H2: GENBANK ACCESSION AK313448)
                                                                                    (SEQ ID NO: 18)
atggccaacctggagcgcaccttcatcgccatcaagccggacggcgtgcagcgcggcctggtgggcgagatcatc aagcgcttcgagcagaagggattccgcctcgtggccatgaagttcctccgggcctctgaagaacacctgaagcagcactacattgac ctgaaagaccgaccattcttccctgggctggtgaagtacatgaactcagggccggttgtggccatgtctgggaggggctgaacgtg gtgaagacaggccgagtgatgcttggggagaccaatccagcagattcaaagccaggcaccattcgtgggggacttctgcattcaggtt
```

-continued ggcaggaacatcattcatggcagtgattcagtaaaaagtgctgaaaaagaaatcagcctatggtttaagcctgaagaactggttgacta caagtcttgtgctcatgactgggtctatgaataa.

describes NM23-H2 amino acid sequence (NM23-H2: GENBANK ACCESSION AK313448)
(SEQ ID NO: 19)

MANLERTFIAIKPDGVQRGLVGEIIKRFEQKGFRLVAMKFLRASEEHLKQH

YIDLKDRPFFPGLVKYMNSGPVVAMVWEGLNVVKTGRVMLGETNPADSKPGTIRG

DFCIQVGRNIIHGSDSVKSAEKEISLWFKPEELVDYKSCAHDWVYE.

Human NM23-H7-2 sequence optimized for E. coli expression:
(DNA)
(SEQ ID NO: 20)

atgcatgacgttaaaaatcaccgtaccttctgaaacgcacgaaatatgataatctgcatctggaagacctgtttattggc aacaaagtcaatgtgttctctcgtcagctggtgctgatcgattatggcgaccagtacaccgcgcgtcaactgggtagtcgcaaagaaaa aacgctggccctgattaaaccggatgcaatctccaaagctggcgaaattatcgaaattatcaacaaagcgggtttcaccatcacgaaac tgaaaatgatgatgctgagccgtaaagaagccctggattttcatgtcgaccaccagtctcgcccgttttttcaatgaactgattcaattcatc accacgggtccgattatcgcaatggaaattctgcgtgatgacgctatctgcgaatggaaacgcctgctgggcccggcaaactcaggtg ttgcgcgtaccgatgccagtgaatccattcgcgctctgtttggcaccgatggtatccgtaatgcagcacatggtccggactcattcgcat cggcagctcgtgaaatggaactgttttttcccgagctctggcggttgcggtccggcaaacaccgccaaatttaccaattgtacgtgctgta ttgtcaaaccgcacgcagtgtcagaaggcctgctgggtaaaattctgatggcaatccgtgatgctggctttgaaatctcggccatgcag atgttcaacatggaccgcgttaacgtcgaagaattctacgaagtttacaaaggcgtggttaccgaatatcacgatatggttacgaaatg tactccggtccgtgcgtcgcgatggaaattcagcaaaacaatgccaccaaaacgtttcgtgaattctgtggtccggcagatccggaaat cgcacgtcatctgcgtccgggtaccctgcgcgcaatttttggtaaaacgaaaatccagaacgctgtgcactgtaccgatctgccggaa gacggtctgctggaagttcaatacttttttcaaaattctggataattga (amino acids)
(SEQ ID NO: 21)

MHDVKNHRTFLKRTKYDNLHLEDLFIGNKVNVFSRQLVLIDYGDQYTAR

QLGSRKEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIR

DAGFEISAMQMFNMDRVNVEEFYEVYKGVVTEYHDMVTEMYSGPCVAMEIQQNN

ATKTFREFCGPADPEIARHLRPGTLRAIFGKTKIQNAVHCTDLPEDGLLEVQYFFKILD

N-

Human NME7-A:
(DNA)
(SEQ ID NO: 22)

atggaaaaaacgctagccctaattaaaccagatgcaatatcaaaggctggagaaataattgaaataataaacaaagct ggatttactataaccaaactcaaaatgatgatgctttcaaggaaagaagcattggattttcatgtagatcaccagtcaagacccttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctctttggaacagatggcataagaaatgcagcgcatggc cctgattcttttgcttctgcggccagagaaatggagttgttttttttga (amino acids)
(SEQ ID NO: 23)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFF-

Human NME7-A1:
(DNA)

(SEQ ID NO: 24)

atggaaaaaacgctagccctaattaaaccagatgcaatatcaaaggctggagaaataattgaaataataaacaaagct ggatttactataaccaaactcaaaatgatgatgctttcaaggaaagaagcattggattttcatgtagatcaccagtcaagacccttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctctttggaacagatggcataagaaatgcagcgcatggc cctgattcttttgcttctgcggccagagaaatggagttgtttttccttcaagtggaggttgtgggccggcaaacactgctaaatttacttga (amino acids)

(SEQ ID NO: 25)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFT-

Human NME7-A2:
(DNA)

(SEQ ID NO: 26)

atgaatcatagtgaaagattcgttttcattgcagagtggtatgatccaaatgcttcacttcttcgacgttatgagcttttatttt acccaggggatggatctgttgaaatgcatgatgtaaagaatcatcgcaccttttaaagcggaccaaatatgataacctgcacttggaag atttatttataggcaacaaagtgaatgtcttttctcgacaactggtattaattgactatgggatcaatatacagctcgccagctgggcagta ggaaagaaaaaacgctagccctaattaaaccagatgcaatatcaaaggctggagaaataattgaaataataaacaaagctggatttact ataaccaaactcaaaatgatgatgctttcaaggaaagaagcattggattttcatgtagatcaccagtcaagacccttttcaatgagctgat ccagtttattacaactggtcctattattgccatggagattttaagagatgatgctatatgtgaatggaaaagactgctgggacctgcaaact ctggagtggcacgcacagatgcttctgaaagcattagagccctctttggaacagatggcataagaaatgcagcgcatggccctgattct tttgcttctgcggccagagaaatggagttgtttttttga (amino acids)

(SEQ ID NO: 27)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFF-

Human NME7-A3:
(DNA)

(SEQ ID NO: 28)

atgaatcatagtgaaagattcgttttcattgcagagtggtatgatccaaatgcttcacttcttcgacgttatgagcttttatttt acccaggggatggatctgttgaaatgcatgatgtaaagaatcatcgcaccttttaaagcggaccaaatatgataacctgcacttggaag atttatttataggcaacaaagtgaatgtcttttctcgacaactggtattaattgactatgggatcaatatacagctcgccagctgggcagta ggaaagaaaaaacgctagccctaattaaaccagatgcaatatcaaaggctggagaaataattgaaataataaacaaagctggatttact ataaccaaactcaaaatgatgatgctttcaaggaaagaagcattggattttcatgtagatcaccagtcaagacccttttcaatgagctgat ccagtttattacaactggtcctattattgccatggagattttaagagatgatgctatatgtgaatggaaaagactgctgggacctgcaaact ctggagtggcacgcacagatgcttctgaaagcattagagccctctttggaacagatggcataagaaatgcagcgcatggccctgattct tttgcttctgcggccagagaaatggagttgtttttccttcaagtggaggttgtgggccggcaaacactgctaaatttacttga (amino acids)

(SEQ ID NO: 29)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFT-

Human NME7-B:
(DNA)
(SEQ ID NO: 30)

atgaattgtacctgttgcattgttaaacccatgctgtcagtgaaggactgttgggaaagatcctgatggctatccgaga tgcaggttttgaaatctcagctatgcagatgttcaatatggatcgggttaatgttgaggaattctatgaagtttataaaggagtagtgaccg aatatcatgacatggtgacagaaatgtattctggcccttgtgtagcaatggagattcaacagaataatgctacaaagacatttcgagaatttt tgtggacctgctgatcctgaaattgcccggcatttacgccctggaactctcagagcaatctttggtaaaactaagatccagaatgctgttc actgtactgatctgccagaggatggcctattagaggttcaatacttcttctga (amino acids)
(SEQ ID NO: 31)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFF-

Human NME7-B1:
(DNA)
(SEQ ID NO: 32)

atgaattgtacctgttgcattgttaaacccatgctgtcagtgaaggactgttgggaaagatcctgatggctatccgaga tgcaggttttgaaatctcagctatgcagatgttcaatatggatcgggttaatgttgaggaattctatgaagtttataaaggagtagtgaccg aatatcatgacatggtgacagaaatgtattctggcccttgtgtagcaatggagattcaacagaataatgctacaaagacatttcgagaattt tgtggacctgctgatcctgaaattgcccggcatttacgccctggaactctcagagcaatctttggtaaaactaagatccagaatgctgttc actgtactgatctgccagaggatggcctattagaggttcaatacttcttcaagatcttggataattagtga (amino acids)
(SEQ ID NO: 33)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFFKILDN-

Human NME7-B2:
(DNA)
(SEQ ID NO: 34)

atgccttcaagtggaggttgtgggccggcaaacactgctaaatttactaattgtacctgttgcattgttaaacccatgct gtcagtgaaggactgttgggaaagatcctgatggctatccgagatgcaggttttgaaatctcagctatgcagatgttcaatatggatcgg gttaatgttgaggaattctatgaagtttataaaggagtagtgaccgaatatcatgacatggtgacagaaatgtattctggcccttgtgtagc aatggagattcaacagaataatgctacaaagacatttcgagaattttgtggacctgctgatcctgaaattgcccggcatttacgccctgga actctcagagcaatctttggtaaaactaagatccagaatgctgttcactgtactgatctgccagaggatggcctattagaggttcaatactt cttctga (amino acids)
(SEQ ID NO: 35)

MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFF-

Human NME7-B3:
(DNA)
(SEQ ID NO: 36)

atgccttcaagtggaggttgtgggccggcaaacactgctaaatttactaattgtacctgttgcattgttaaacccatgct gtcagtgaaggactgttgggaaagatcctgatggctatccgagatgcaggttttgaaatctcagctatgcagatgttcaatatggatcgg gttaatgttgaggaattctatgaagtttataaaggagtagtgaccgaatatcatgacatggtgacagaaatgtattctggcccttgtgtagc -continued aatggagattcaacagaataatgctacaaagacatttcgagaattttgtggacctgctgatcctgaaattgcccggcatttacgccctgga actctcagagcaatctttggtaaaactaagatccagaatgctgttcactgtactgatctgccagaggatggcctattagaggttcaatactt cttcaagatcttggataattagtga (amino acids)

(SEQ ID NO: 37)

MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFFKILDN--

Human NME7$_{AB}$, also known as NME7$_{AB}$:
(DNA)

(SEQ ID NO: 38)

atggaaaaaacgctagccctaattaaaccagatgcaatatcaaaggctggagaaataattgaaataataaacaaagct ggatttactataaccaaactcaaaatgatgatgctttcaaggaaagaagcattggattttcatgtagatcaccagtcaagacccttttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctcttttggaacagatggcataagaaatgcagcgcatggc cctgattcttttgcttctgcggccagagaaatggagttgtttttcctcaagtggaggttgtgggccggcaaacactgctaaatttactaatt gtacctgttgcattgttaaacccatgctgtcagtgaaggactgttgggaaagatcctgatggctatccgagatgcaggttttgaaatctc agctatgcagatgttcaatatggatcgggttaatgttgaggaattctatgaagtttataaaggagtagtgaccgaatatcatgacatggtga cagaaatgtattctggcccttgtgtagcaatggagattcaacagaataatgctacaaagacatttcgagaattttgtggacctgctgatcct gaaattgcccggcatttacgccctggaactctcagagcaatctttggtaaaactaagatccagaatgctgttcactgtactgatctgccag aggatggcctattagaggttcaatacttcttcaagatcttggataattagtga (amino acids)

(SEQ ID NO: 39)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDN--

Human NME7$_{AB}$1:
(DNA)

(SEQ ID NO: 40)

atggaaaaaacgctagccctaattaaaccagatgcaatatcaaaggctggagaaataattgaaataataaacaaagct ggatttactataaccaaactcaaaatgatgatgctttcaaggaaagaagcattggattttcatgtagatcaccagtcaagacccttttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctcttttggaacagatggcataagaaatgcagcgcatggc cctgattcttttgcttctgcggccagagaaatggagttgtttttcctcaagtggaggttgtgggccggcaaacactgctaaatttactaatt gtacctgttgcattgttaaacccatgctgtcagtgaaggactgttgggaaagatcctgatggctatccgagatgcaggttttgaaatctc agctatgcagatgttcaatatggatcgggttaatgttgaggaattctatgaagtttataaaggagtagtgaccgaatatcatgacatggtga cagaaatgtattctggcccttgtgtagcaatggagattcaacagaataatgctacaaagacatttcgagaattttgtggacctgctgatcct gaaattgcccggcatttacgccctggaactctcagagcaatctttggtaaaactaagatccagaatgctgttcactgtactgatctgccag aggatggcctattagaggttcaatacttcttctga (amino acids)

(SEQ ID NO: 41)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFF-

Human NME7-A sequence optimized for *E. coli* expression:
(DNA)

(SEQ ID NO: 42)

atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgcctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgtttttctga (amino acids)

(SEQ ID NO: 43)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFF-

Human NME7-A1 sequence optimized for *E. coli* expression:
(DNA)

(SEQ ID NO: 44)

atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgcctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgtttttcccgagctctggcggttgcggtccggcaaacaccgccaaatt tacctga (amino acids)

(SEQ ID NO: 45)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFT-

Human NME7-A2 sequence optimized for *E. coli* expression:
(DNA)

(SEQ ID NO: 46)

atgaatcactccgaacgctttgtttttatcgccgaatggtatgacccgaatgcttccctgctgcgccgctacgaactgct gttttatccgggcgatggtagcgtggaaatgcatgacgttaaaaatcaccgtaccttttctgaaacgcacgaaatatgataatctgcatctg gaagacctgtttattggcaacaaagtcaatgtgttctctcgtcagctggtgctgatcgattatggcgaccagtacaccgcgcgtcaactg ggtagtcgcaaagaaaaaacgctggccctgattaaaccggatgcaatctccaaagctggcgaaattatcgaaattatcaacaaagcgg gtttcaccatcacgaaactgaaaatgatgatgctgagccgtaaagaagccctggattttcatgtcgaccaccagtctcgcccgttttcaa tgaactgattcaattcatcaccacgggtccgattatcgcaatggaaattctgcgtgatgacgctatctgcgaatggaaacgcctgctggg cccggcaaactcaggtgttgcgcgtaccgatgccagtgaatccattcgcgctctgtttggcaccgatggtatccgtaatgcagcacatg gtccggactcattcgcatcggcagctcgtgaaatggaactgtttttctga (amino acids)

(SEQ ID NO: 47)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFF-

-continued

Human NME7-A3 sequence optimized for *E. coli* expression:
(DNA)

(SEQ ID NO: 48)

atgaatcactccgaacgctttgtttttatcgccgaatggtatgacccgaatgcttccctgctgcgccgctacgaactgct gttttatccgggcgatggtagcgtggaaatgcatgacgttaaaaatcaccgtacctttctgaaacgcacgaaatatgataatctgcatctg gaagacctgtttattggcaacaaagtcaatgtgttctctcgtcagctggtgctgatcgattatggcgaccagtacaccgcgcgtcaactg ggtagtcgcaaagaaaaaacgctggccctgattaaaccggatgcaatctccaaagctggcgaaattatcgaaattatcaacaaagcgg gttttcaccatcacgaaactgaaatgatgatgctgagccgtaaagaagccctggattttcatgtcgaccaccagtctcgcccgttttt caa tgaactgattcaattcatcaccacgggtccgattatcgcaatggaaattctgcgtgatgacgctatctgcgaatggaaacgcctgctggg cccggcaaactcaggtgttgcgcgtaccgatgccagtgaatccattcgcgctctgtttggcaccgatggtatccgtaatgcagcacatg gtccggactcattcgcatcggcagctcgtgaaatggaactgttttttcccgagctctggcggttgcggtccggcaaacaccgccaaattt acctga (amino acids)

(SEQ ID NO: 49)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFT-

Human NME7-B sequence optimized for *E. coli* expression:
(DNA)

(SEQ ID NO: 50)

atgaattgtacgtgctgtattgtcaaaccgcacgcagtgtcagaaggcctgctgggtaaaattctgatggcaatccgtg atgctggctttgaaatctcggccatgcagatgttcaacatggaccgcgttaacgtcgaagaattctacgaagtttacaaaggcgtggtta ccgaatatcacgatatggttacggaaatgtactccggtccgtgcgtcgcgatggaaattcagcaaaacaatgccaccaaaacgtttcgt gaattctgtggtccggcagatccggaaatcgcacgtcatctgcgtccgggtaccctgcgcgcaattttttggtaaaacgaaaatccagaa cgctgtgcactgtaccgatctgccggaagacggtctgctggaagttcaatactttttctga (amino acids)

(SEQ ID NO: 51)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFF-

Human NME7-B1 sequence optimized for *E. coli* expression:
(DNA)

(SEQ ID NO: 52)

atgaattgtacgtgctgtattgtcaaaccgcacgcagtgtcagaaggcctgctgggtaaaattctgatggcaatccgtg atgctggctttgaaatctcggccatgcagatgttcaacatggaccgcgttaacgtcgaagaattctacgaagtttacaaaggcgtggtta ccgaatatcacgatatggttacggaaatgtactccggtccgtgcgtcgcgatggaaattcagcaaaacaatgccaccaaaacgtttcgt gaattctgtggtccggcagatccggaaatcgcacgtcatctgcgtccgggtaccctgcgcgcaattttttggtaaaacgaaaatccagaa cgctgtgcactgtaccgatctgccggaagacggtctgctggaagttcaatacttttt caaaattctggataattga (amino acids)

(SEQ ID NO: 53)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFFKILDN-

Human NME7-B2 sequence optimized for *E. coli* expression:
(DNA)

(SEQ ID NO: 54)

atgccgagctctggcggttgcggtccggcaaacaccgccaaatttaccaattgtacgtgctgtattgtcaaaccgcac gcagtgtcagaaggcctgctgggtaaaattctgatggcaatccgtgatgctggctttgaaatctcggccatgcagatgttcaacatggac -continued cgcgttaacgtcgaagaattctacgaagtttacaaaggcgtggttaccgaatatcacgatatggttacggaaatgtactccggtccgtgc gtcgcgatggaaattcagcaaaacaatgccaccaaaacgtttcgtgaattctgtggtccggcagatccggaaatcgcacgtcatctgcg tccgggtaccctgcgcgcaattttttggtaaaacgaaaatccagaacgctgtgcactgtaccgatctgccggaagacggtctgctggaa gttcaatacttttctga (amino acids)

(SEQ ID NO: 55)

MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFF-

Human NME7-B3 sequence optimized for *E. coli* expression:
(DNA)

(SEQ ID NO: 56)

atgccgagctctggcggttgcggtccggcaaacaccgccaaatttaccaattgtacgtgctgtattgtcaaaccgcac gcagtgtcagaaggcctgctgggtaaaattctgatggcaatccgtgatgctggctttgaaatctcggccatgcagatgttcaacatggac cgcgttaacgtcgaagaattctacgaagtttacaaaggcgtggttaccgaatatcacgatatggttacggaaatgtactccggtccgtgc gtcgcgatggaaattcagcaaaacaatgccaccaaaacgtttcgtgaattctgtggtccggcagatccggaaatcgcacgtcatctgcg tccgggtaccctgcgcgcaattttttggtaaaacgaaaatccagaacgctgtgcactgtaccgatctgccggaagacggtctgctggaa gttcaatacttttcaaaattctggataattga (amino acids)

(SEQ ID NO: 57)

MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFFKILDN-

Human NME7$_{AB}$, also known as NME7$_{AB}$ sequence optimized for *E. coli* expression:
(DNA)

(SEQ ID NO: 58)

atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgcctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgttttttcccgagctctggcggttgcggtccggcaaacaccgccaaatt taccaattgtacgtgctgtattgtcaaaccgcacgcagtgtcagaaggcctgctgggtaaaattctgatggcaatccgtgatgctggcttt gaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttttggtaaaacgaaaatccagaacgctgtgcact gtaccgatctgccggaagacggtctgctggaagttcaatacttttcaaaattctggataattga (amino acids)

(SEQ ID NO: 59)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDN-

-continued

Human NME7$_{AB}$1, also known as NME7$_{AB}$1 sequence optimized for *E. coli* expression:
(DNA)

(SEQ ID NO: 60)

Atggaaaaaacgctggccctgattaaaccggatgcaatctccaaagctggcgaaattatcgaaattatcaacaaagc gggtttcaccatcacgaaactgaaaatgatgatgctgagccgtaaagaagccctggattttcatgtcgaccaccagtctcgcccgttttc aatgaactgattcaattcatcaccacgggtccgattatcgcaatggaaattctgcgtgatgacgctatctgcgaatggaaacgcctgctg ggcccggcaaactcaggtgttgcgcgtaccgatgccagtgaatccattcgcgctctgtttggcaccgatggtatccgtaatgcagcaca tggtccggactcattcgcatcggcagctcgtgaaatggaactgttttccccgagctctggcggttgcggtccggcaaacaccgccaaat ttaccaattgtacgtgctgtattgtcaaaccgcacgcagtgtcagaaggcctgctgggtaaaattctgatggcaatccgtgatgctggctt tgaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttggtaaaacgaaaatccagaacgctgtgcact gtaccgatctgccggaagacggtctgctggaagttcaatacttttctga (amino acids)

(SEQ ID NO: 61)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFF-

Mouse NME6
(DNA)

(SEQ ID NO: 62)

Atgacctccatcttgcgaagtccccaagctcttcagctcacactagccctgatcaagcctgatgcagttgcccaccca ctgatcctggaggctgttcatcagcagattctgagcaacaagttcctcattgtacgaacgagggaactgcagtggaagctggaggact gccggaggttttaccgagagcatgaagggcgttttttctatcagcggctggtggagttcatgacaagtgggccaatccgagcctatatc cttgcccacaaagatgccatccaactttggaggacactgatgggaccccaccagagtatttcgagcacgctatatagcccagattcaat tcgtggaagtttgggcctcactgacacccgaaatactacccatggctcagactccgtggtttccgccagcagagagattgcagccttctt ccctgacttcagtgaacagcgctggtatgaggaggaggaaccccagctgcggtgtggtcctgtgcactacagtccagaggaaggtat ccactgtgcagctgaaacaggaggccacaaacaacctaacaaaacctag (amino acids)

(SEQ ID NO: 63)

MTSILRSPQALQLTLALIKPDAVAHPLILEAVHQQILSNKFLIVRTRELQWK

LEDCRRFYREHEGRFFYQRLVEFMTSGPIRAYILAHKDAIQLWRTLMGPTRVFRARY

IAPDSIRGSLGLTDTRNTTHGSDSVVSASREIAAFFPDFSEQRWYEEEEPQLRCGPVHY

SPEEGIHCAAETGGHKQPNKT-

Human NME6:
(DNA)

(SEQ ID NO: 64)

Atgacccagaatctggggagtgagatggcctcaatcttgcgaagccctcaggctctccagctcactctagccctgat caagcctgacgcagtcgcccatccactgattctggaggctgttcatcagcagattctaagcaacaagttcctgattgtacgaatgagag aactactgtggagaaaggaagattgccagaggttttaccgagagcatgaagggcgttttttctatcagaggctggtggagttcatggcc agcgggccaatccgagcctacatccttgcccacaaggatgccatccagctctggaggacgctcatgggacccaccagagtgttccga gcacgccatgtggccccagattctatccgtgggagtttcggcctcactgacacccgcaacaccaccatggttcggactctgtggtttc -continued agccagcagagagattgcagccttcttccctgacttcagtgaacagcgctggtatgaggaggaagagccccagttgcgctgtggccct gtgtgctatagcccagagggaggtgtccactatgtagctggaacaggaggcctaggaccagcctga (amino acids) (SEQ ID NO: 65)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPVCYSPEGGVHYVAGTGGLGPA-

Human NME6 1:
(DNA) (SEQ ID NO: 66)

Atgacccagaatctggggagtgagatggcctcaatcttgcgaagccctcaggctctccagctcactctagccctgat caagcctgacgcagtcgcccatccactgattctggaggctgttcatcagcagattctaagcaacaagttcctgattgtacgaatgagag aactactgtggagaaaggaagattgccagaggttttaccgagagcatgaaggggcgttttttctatcagaggctggtggagttcatggcc agcgggccaatccgagcctacatccttgcccacaaggatgccatccagctctggaggacgctcatgggacccaccagagtgttccga gcacgccatgtggccccagattctatccgtgggagtttcggcctcactgacacccgcaacaccacccatggttcggactctgtggtttc agccagcagagagattgcagccttcttccctgacttcagtgaacagcgctggtatgaggaggaagagccccagttgcgctgtggccct gtgtga (amino acids) (SEQ ID NO: 67)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPV-

Human NME6 2:
(DNA) (SEQ ID NO: 68)

Atgctcactctagccctgatcaagcctgacgcagtcgcccatccactgattctggaggctgttcatcagcagattctaa gcaacaagttcctgattgtacgaatgagagaactactgtggagaaaggaagattgccagaggttttaccgagagcatgaaggggcgtttt ttctatcagaggctggtggagttcatggccagcgggccaatccgagcctacatccttgcccacaaggatgccatccagctctggagga cgctcatgggacccaccagagtgttccgagcacgccatgtggccccagattctatccgtgggagtttcggcctcactgacacccgcaa caccacccatggttcggactctgtggtttcagccagcagagagattgcagccttcttccctgacttcagtgaacagcgctggtatgagg aggaagagccccagttgcgctgtggccctgtgtga (amino acids) (SEQ ID NO: 69)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPV-

Human NME6 3:
(DNA) (SEQ ID NO: 70)

Atgctcactctagccctgatcaagcctgacgcagtcgcccatccactgattctggaggctgttcatcagcagattctaa gcaacaagttcctgattgtacgaatgagagaactactgtggagaaaggaagattgccagaggttttaccgagagcatgaaggggcgtttt ttctatcagaggctggtggagttcatggccagcgggccaatccgagcctacatccttgcccacaaggatgccatccagctctggagga cgctcatgggacccaccagagtgttccgagcacgccatgtggccccagattctatccgtgggagtttcggcctcactgacacccgcaa caccacccatggttcggactctgtggtttcagccagcagagagattgcagccttcttccctgacttcagtgaacagcgctggtatgagg aggaagagccccagttgcgctgtggccctgtgtgctatagcccagagggaggtgtccactatgtagctggaacaggaggcctagga ccagcctga (amino acids)

(SEQ ID NO: 71)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPVCYSPEGGVHY

VAGTGGLGPA-

Human NME6 sequence optimized for *E. coli* expression:
(DNA)

(SEQ ID NO: 72)

Atgacgcaaaatctgggctcggaaatggcaagtatcctgcgctccccgcaagcactgcaactgaccctggctctgat caaaccggacgctgttgctcatccgctgattctggaagcggtccaccagcaaattctgagcaacaaatttctgatcgtgcgtatgcgcg aactgctgtggcgtaaagaagattgccagcgttttttatcgcgaacatgaaggccgtttcttttatcaacgcctggttgaattcatggcctct ggtccgattcgcgcatatatcctggctcacaaagatgcgattcagctgtggcgtaccctgatgggtccgacgcgcgtctttcgtgcacgt catgtggcaccggactcaatccgtggctcgttcggtctgaccgatacgcgcaataccacgcacggtagcgactctgttgttagtgcgtc ccgtgaaatcgcggccttttttcccggacttctccgaacagcgttggtacgaagaagaagaaccgcaactgcgctgtggcccggtctgtt attctccggaaggtggtgtccattatgtggcgggcacgggtggtctgggtccggcatga (amino acids)

(SEQ ID NO: 73)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPVCYSPEGGVHYVAGTGGLGPA-

Human NME6 1 sequence optimized for *E. coli* expression:
(DNA)

(SEQ ID NO: 74)

Atgacgcaaaatctgggctcggaaatggcaagtatcctgcgctccccgcaagcactgcaactgaccctggctctgat caaaccggacgctgttgctcatccgctgattctggaagcggtccaccagcaaattctgagcaacaaatttctgatcgtgcgtatgcgcg aactgctgtggcgtaaagaagattgccagcgttttttatcgcgaacatgaaggccgtttcttttatcaacgcctggttgaattcatggcctct ggtccgattcgcgcatatatcctggctcacaaagatgcgattcagctgtggcgtaccctgatgggtccgacgcgcgtctttcgtgcacgt catgtggcaccggactcaatccgtggctcgttcggtctgaccgatacgcgcaataccacgcacggtagcgactctgttgttagtgcgtc ccgtgaaatcgcggccttttttcccggacttctccgaacagcgttggtacgaagaagaagaaccgcaactgcgctgtggcccggtctga (amino acids)

(SEQ ID NO: 75)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPV-

Human NME6 2 sequence optimized for *E. coli* expression:
(DNA)

(SEQ ID NO: 76)

Atgctgaccctggctctgatcaaaccggacgctgttgctcatccgctgattctggaagcggtccaccagcaaattctg agcaacaaatttctgatcgtgcgtatgcgcgaactgctgtggcgtaaagaagattgccagcgttttttatcgcgaacatgaaggccgtttct tttatcaacgcctggttgaattcatggcctctggtccgattcgcgcatatatcctggctcacaaagatgcgattcagctgtggcgtaccctg atgggtccgacgcgcgtctttcgtgcacgtcatgtggcaccggactcaatccgtggctcgttcggtctgaccgatacgcgcaataccac gcacggtagcgactctgttgttagtgcgtcccgtgaaatcgcggccttttttcccggacttctccgaacagcgttggtacgaagaagaag aaccgcaactgcgctgtggcccggtctga (amino acids) (SEQ ID NO: 77)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPV-

Human NME6 3 sequence optimized for *E. coli* expression:
(DNA) (SEQ ID NO: 78)

Atgctgaccctggctctgatcaaaccggacgctgttgctcatccgctgattctggaagcggtccaccagcaaattctg agcaacaaatttctgatcgtgcgtatgcgcgaactgctgtggcgtaaagaagattgccagcgttttatcgcgaacatgaaggccgtttct tttatcaacgcctggttgaattcatggcctctggtccgattcgcgcatatatcctggctcacaaagatgcgattcagctgtggcgtaccctg atgggtccgacgcgcgtctttcgtgcacgtcatgtggcaccggactcaatccgtggctcgttcggtctgaccgatacgcgcaataccac gcacggtagcgactctgttgttagtgcgtcccgtgaaatcgcggccttttcccggacttctccgaacagcgttggtacgaagaagaag aaccgcaactgcgctgtggcccggtctgttattctccggaaggtggtgtccattatgtggggcacgggtggtctgggtccggcatg a (amino acids) (SEQ ID NO: 79)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPVCYSPEGGVHY

VAGTGGLGPA-

OriGene-NME7-1 full length
(DNA) (SEQ ID NO: 80)

gacgttgtatacgactcctatagggcggccgggaattcgtcgactggatccggtaccgaggagatctgccgccgcg atcgccatgaatcatagtgaaagattcgttttcattgcagagtggtatgatccaaatgcttcacttcttcgacgttatgagcttttattttaccc aggggatggatctgttgaaatgcatgatgtaaagaatcatcgcacctttttaaagcggaccaaatatgataacctgcacttggaagattta tttataggcaacaaagtgaatgtcttctctcgacaactggtattaattgactatggggatcaatatacagctcgccagctgggcagtagga agaaaaaaacgctagccctaattaaaccagatgcaatatcaaaggctggagaaataattgaaataataaacaaagctggatttactataa ccaaactcaaaatgatgatgctttcaaggaaagaagcattggattttcatgtagatcaccagtcaagacccttttttcaatgagctgatcca gtttattacaactggtcctattattgccatggagattttaagagatgatgctatatgtgaatggaaaagactgctgggacctgcaaactctg gagtggcacgcacagatgcttctgaaagcattagagccctctttggaacagatggcataagaaatgcagcgcatggccctgattcttttt gcttctgcggccagagaaatggagttgttttttccttcaagtggaggttgtgggccggcaaacactgctaaatttactaattgtacctgttg cattgttaaacccatgctgtcagtgaaggactgttgggaaagatcctgatggctatccgagatgcaggttttgaaatctcagctatgcag atgttcaatatggatcgggttaatgttgaggaattctatgaagtttataaaggagtagtgaccgaatatcatgacatggtgacagaaatgta ttctggcccttgtgtagcaatggagattcaacagaataatgctacaaagacatttcgagaattttgtggacctgctgatcctgaaattgccc ggcatttacgccctggaactctcagagcaatctttggtaaaactaagatccagaatgctgttcactgtactgatctgccagaggatggcct attagaggttcaatacttcttcaagatcttggataatacgcgtacgcggccgctcgagcagaaactcatctcagaagaggatctggcag caaatgatatcctggattacaaggatgacgacgataaggtttaa (amino acids) (SEQ ID NO: 81)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

-continued

PGTLRAIFGKTKIQNAVHCTDLPEDGLLEVQYFFKILDNTRTRRLEQKLISEEDLAAN

DILDYKDDDDKV

Abnova NME7-1 Full length
(amino acids)
(SEQ ID NO: 82)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

PGTLRAIFGKTKIQNAVHCTDLPEDGLLEVQYFFKILDN

Abnova Partial NME7-B
(amino acids)
(SEQ ID NO: 83)

DRVNVEEFYEVYKGVVTEYHDMVTEMYSGPCVAMEIQQNNATKTFREF

CGPADPEIARHLRPGTLRAIFGKTKIQNAVHCTDLPEDGLLEVQYFFKIL

Histidine Tag
(SEQ ID NO: 84)
(ctcgag)caccaccaccaccaccactga

Strept II Tag
(SEQ ID NO: 85)
(accggt)tggagccatcctcagttcgaaaagtaatga

N-10 peptide:
(SEQ ID NO: 86)
QFNQYKTEAASRYNLTISDVSVSDVPFPFSAQSGA

C-10 peptide
(SEQ ID NO: 87)
GTINVHDVETQFNQYKTEAASRYNLTISDVSVSDV (SEQ ID NO: 88)
LALIKPDA (SEQ ID NO: 89)
MMMLSRKEALDFHVDHQS (SEQ ID NO: 90)
ALDFHVDHQS (SEQ ID NO: 91)
EILRDDAICEWKRL (SEQ ID NO: 92)
FNELIQFITTGP (SEQ ID NO: 93)
RDDAICEW (SEQ ID NO: 94)
SGVARTDASESIRALFGTDGIRNAA (SEQ ID NO: 95)
ELFFPSSGG (SEQ ID NO: 96)
KFTNCTCCIVKPHAVSEGLLGKILMA (SEQ ID NO: 97)
LMAIRDAGFEISAMQMFNMDRVNVEEFYEVYKGVVT (SEQ ID NO: 98)
EFYEVYKGVVTEYHD (SEQ ID NO: 99)
EIQQNNATKTFREFCGPADPEIARHLRPGTLRAIFGKTKIQNA -continued

```
                                                   (SEQ ID NO: 100)
YSGPCVAM (SEQ ID NO: 101)
FREFCGP (SEQ ID NO: 102)
VHCTDLPEDGLLEVQYFFKILDN (SEQ ID NO: 103)
IQNAVHCTD (SEQ ID NO: 104)
TDLPEDGLLEVQYFFKILDN (SEQ ID NO: 105)
PEDGLLEVQYFFK (SEQ ID NO: 106)
EIINKAGFTITK (SEQ ID NO: 107)
MLSRKEALDFHVDHQS (SEQ ID NO: 108)
NELIQFITT (SEQ ID NO: 109)
EILRDDAICEWKRL (SEQ ID NO: 110)
SGVARTDASESIRALFGTDGI (SEQ ID NO: 111)
SGVARTDASES (SEQ ID NO: 112)
ALFGTDGI (SEQ ID NO: 113)
NCTCCIVKPHAVSE (SEQ ID NO: 114)
LGKILMAIRDA (SEQ ID NO: 115)
EISAMQMFNMDRVNVE (SEQ ID NO: 116)
EVYKGVVT (SEQ ID NO: 117)
EYHDMVTE (SEQ ID NO: 118)
EFCGPADPEIARHLR (SEQ ID NO: 119)
AIFGKTKIQNAV (SEQ ID NO: 120)
LPEDGLLEVQYFFKILDN (SEQ ID NO: 121)
GPDSFASAAREMELFFP

Immunizing peptides derived from human NME7
                                                   (SEQ ID NO: 122)
ICEWKRL (SEQ ID NO: 123)
LGKILMAIRDA (SEQ ID NO: 124)
HAVSEGLLGK (SEQ ID NO: 125)
VTEMYSGP (SEQ ID NO: 126)
NATKTFREF
```

AIRDAGFEI (SEQ ID NO: 127)

AICEWKRLLGPAN (SEQ ID NO: 128)

DHQSRPFF (SEQ ID NO: 129)

AICEWKRLLGPAN (SEQ ID NO: 130)

VDHQSRPF (SEQ ID NO: 131)

PDSFAS (SEQ ID NO: 132)

KAGEIIEIINKAGFTITK (SEQ ID NO: 133)

Immunizing peptides derived from human NME1

MANCERTFIAIKPDGVQRGLVGEIIKRFE (SEQ ID NO: 134)

VDLKDRPF (SEQ ID NO: 135)

HGSDSVESAEKEIGLWF (SEQ ID NO: 136)

ERTFIAIKPDGVQRGLVGEIIKRFE (SEQ ID NO: 137)

VDLKDRPFFAGLVKYMHSGPVVAMVWEGLN (SEQ ID NO: 138)

NIIHGSDSVESAEKEIGLWFHPEELV (SEQ ID NO: 139)

KPDGVQRGLVGEII (SEQ ID NO: 140)

Immunizing peptide derived from human NME7, but which does not bind NME1
peptide A1

MLSRKEALDFHVDHQS (SEQ ID NO: 141)

peptide A2

SGVARTDASES (SEQ ID NO: 142)

peptide B1

DAGFEISAMQMFNMDRVNVE (SEQ ID NO: 143)

peptide B2

EVYKGVVTEYHDMVTE (SEQ ID NO: 144)

peptide B3

AIFGKTKIQNAVHCTDLPEDGLLEVQYFF (SEQ ID NO: 145)

Human NME7 a
(DNA)

(SEQ ID NO: 146)

atgaatcatagtgaaagattcgttttcattgcagagtggtatgatccaaatgcttcacttcttcgacgttatgagctttatttt acccaggggatggatctgttgaaatgcatgatgtaaagaatcatcgcacctttttaaagcggaccaaatatgataacctgcacttggaag atttatttataggcaacaaagtgaatgtctttctcgacaactggtattaattgactatggggatcaatatacagctcgccagctgggcagta ggaaagaaaaaacgctagccctaattaaaccagatgcaatatcaaaggctggagaaataattgaaataataaacaaagctggatttact ataaccaaactcaaatgatgatgctttcaaggaaagaagcattggatttcatgtagatcaccagtcaagacccttttttcaatgagctgat ccagtttattacaactggtcctattattgccatgagattttaagagatgatgctatatgtgaatggaaaagactgctgggacctgcaaact ctggagtggcacgcacagatgcttctgaaagcattagagccctcttttggaacagatggcataagaaatgcagcgcatggccctgattct -continued tttgcttctgcggccagagaaatggagttgttttttccttcaagtggaggttgtgggccggcaaacactgctaaatttactaattgtacctgtt
gcattgttaaaccccatgctgtcagtgaaggactgttgggaaagatcctgatggctatccgagatgcaggttttgaaatctcagctatgca
gatgttcaatatggatcgggttaatgttgaggaattctatgaagtttataaaggagtagtgaccgaatatcatgacatggtgacagaaatgt
attctggcccttgtgtagcaatggagattcaacagaataatgctacaaagacatttcgagaattttgtggacctgctgatcctgaaattgcc
cggcatttacgccctggaactctcagagcaatctttggtaaaactaagatccagaatgctgttcactgtactgatctgccagaggatggc
ctattagaggttcaatacttcttcaagatcttggataattag (amino acids) (SEQ ID NO: 147)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALIKPDAISKA
GEIIEIINKAGFTITKLKMMMLSRKEALDFHVDHQSRPFFNELIQFITTGPIIAMEILRDD
AICEWKRLLGPANSGVARTDASESIRALFGTDGIRNAAHGPDSFASAAREMELFFPSS
GGCGPANTAKFTNCTCCIVKPHAVSEGLLGKILMAIRDAGFEISAMQMFNMDRVNV
EEFYEVYKGVVTEYHDMVTEMYSGPCVAMEIQQNNATKTFREFCGPADPEIARHLR
PGTLRAIFGKTKIQNAVHCTDLPEDGLLEVQYFFKILDN Human NME7 b
(DNA) (SEQ ID NO: 148)
atgcatgatgtaaagaatcatcgcaccttttaaagcggaccaaatatgataacctgcacttggaagatttatttataggc
aacaaagtgaatgtcttttctcgacaactggtattaattgactatggggatcaatatacagctcgccagctgggcagtaggaagaaaaa
acgctagccctaattaaaccagatgcaatatcaaaggctggagaaataattgaaataataaacaaagctggatttactataaccaaactc
aaaatgatgatgctttcaaggaaagaagcattggattttcatgtagatcaccagtcaagaccctttttcaatgagctgatccagtttattaca
actggtcctattattgccatggagattttaagagatgatgctatatgtgaatggaaaagactgctgggacctgcaaactctggagtggca
cgcacagatgcttctgaaagcattagagccctctttggaacagatggcataagaaatgcagcgcatggccctgattcttttgcttctgcg
gccagagaaatggagttgttttttccttcaagtggaggttgtgggccggcaaacactgctaaatttactaattgtacctgttgcattgttaaa
ccccatgctgtcagtgaaggactgttgggaaagatcctgatggctatccgagatgcaggttttgaaatctcagctatgcagatgttcaata
tggatcgggttaatgttgaggaattctatgaagtttataaaggagtagtgaccgaatatcatgacatggtgacagaaatgtattctggccct
tgtgtagcaatggagattcaacagaataatgctacaaagacatttcgagaattttgtggacctgctgatcctgaaattgcccggcatttac
gccctggaactctcagagcaatctttggtaaaactaagatccagaatgctgttcactgtactgatctgccagaggatggcctattagagg
ttcaatacttcttcaagatcttggataattag (amino acids) (SEQ ID NO: 149)
MHDVKNHRTFLKRTKYDNLHLEDLFIGNKVNVFSRQLVLIDYGDQYTAR
QLGSRKEKTLALIKPDAISKAGEIIEIINKAGFTITKLKMMMLSRKEALDFHVDHQSRP
FFNELIQFITTGPIIAMEILRDDAICEWKRLLGPANSGVARTDASESIRALFGTDGIRNA
AHGPDSFASAAREMELFFPSSGGCGPANTAKFTNCTCCIVKPHAVSEGLLGKILMAIR
DAGFEISAMQMFNMDRVNVEEFYEVYKGVVTEYHDMVTEMYSGPCVAMEIQQNN
ATKTFREFCGPADPEIARHLRPGTLRAIFGKTKIQNAVHCTDLPEDGLLEVQYFFKILD
N Human NME7$_{AB}$ also known as NME7$_{AB}$
(DNA) (SEQ ID NO: 150)
atggaaaaaacgctagccctaattaaaccagatgcaatatcaaaggctggagaaataattgaaataataaacaaagct
ggatttactataaccaaactcaaaatgatgatgctttcaaggaaagaagcattggattttcatgtagatcaccagtcaagaccctttttcaat
gagctgatccagtttattacaactggtcctattattgccatggagattttaagagatgatgctatatgtgaatggaaaagactgctgggacc -continued tgcaaactctggagtggcacgcacagatgcttctgaaagcattagagccctctttggaacagatggcataagaaatgcagcgcatggc cctgattcttttgcttctgcggccagagaaatggagttgttttttccttcaagtggaggttgtgggccggcaaacactgctaaatttactaatt gtacctgttgcattgttaaacccatgctgtcagtgaaggactgttgggaaagatcctgatggctatccgagatgcaggttttgaaatctc agctatgcagatgttcaatatggatcgggttaatgttgaggaattctatgaagtttataaaggagtagtgaccgaatatcatgacatggtga cagaaatgtattctggcccttgtgtagcaatggagattcaacagaataatgctacaaagacatttcgagaattttgtggacctgctgatcct gaaattgcccggcatttacgccctggaactctcagagcaatctttggtaaaactaagatccagaatgctgttcactgtactgatctgccag aggatggcctattagaggttcaatacttcttcaagatcttggataattag (amino acids)

(SEQ ID NO: 151)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDN

Human NME7-X1
(DNA)

(SEQ ID NO: 152)

atgatgatgctttcaaggaaagaagcattggattttcatgtagatcaccagtcaagacccttttttcaatgagctgatccag tttattacaactggtcctattattgccatggagattttaagagatgatgctatatgtgaatggaaaagactgctgggacctgcaaactctgg agtggcacgcacagatgcttctgaaagcattagagccctctttggaacagatggcataagaaatgcagcgcatggccctgattcttttgc ttctgcggccagagaaatggagttgttttttccttcaagtggaggttgtgggccggcaaacactgctaaatttactaattgtacctgttgcat tgttaaacccatgctgtcagtgaaggactgtgggaaagatcctgatggctatccgagatgcaggttttgaaatctcagctatgcagat gttcaatatggatcgggttaatgttgaggaattctatgaagtttataaaggagtagtgaccgaatatcatgacatggtgacagaaatgtatt ctggcccttgtgtagcaatggagattcaacagaataatgctacaaagacatttcgagaattttgtggacctgctgatcctgaaattgcccg gcatttacgccctggaactctcagagcaatctttggtaaaactaagatccagaatgctgttcactgtactgatctgccagaggatggccta ttagaggttcaatacttcttcaagatcttggataattag (amino acids)

(SEQ ID NO: 153)

MMMLSRKEALDFHVDHQSRPFFNELIQFITTGPIIAMEILRDDAICEWKRL

LGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYK

GVVTEYHDMVTEMYSGPCVAMEIQQNNATKTFREFCGPADPEIARHLRPGTLRAIFG

KTKIQNAVHCTDLPEDGLLEVQYFFKILDN*

Human NME7 a (optimized for E coli expression)
(DNA)

(SEQ ID NO: 154)

atgaatcactccgaacgctttgttttatcgccgaatggtatgaccgaatgcttccctgctgcgccgctacgaactgct gttttatccgggcgatggtagcgtggaaatgcatgacgttaaaaatcaccgtacctttctgaaacgcacgaaatatgataatctgcatctg gaagacctgtttattggcaacaaagtcaatgtgttctctcgtcagctggtgctgatcgattatggcgaccagtacaccgcgcgtcaactg ggtagtcgcaaagaaaaaacgctggccctgattaaaccggatgcaatctccaaagctggcgaaattatcgaaattatcaacaaagcgg gttttcaccatcacgaaactgaaaatgatgatgctgagccgtaaagaagccctggattttcatgtcgaccaccagtctcgcccgttttttcaa tgaactgattcaattcatcaccacgggtccgattatcgcaatggaaattctgcgtgatgacgctatctgcgaatggaaacgcctgctggg cccggcaaactcaggtgttgcgcgtaccgatgccagtgaatccattcgcgctctgtttggcaccgatggtatccgtaatgcagcacatg gtccggactcattcgcatcggcagctcgtgaaatggaactgttttttcccgagctctggcggttgcggtccggcaaacaccgccaaattt accaattgtacgtgctgtattgtcaaaccgcacgcagtgtcagaaggcctgctgggtaaaattctgatggcaatccgtgatgctggcttt -continued gaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttggtaaaacgaaaatccagaacgctgtgcact gtaccgatctgccggaagacggtctgctggaagttcaatacttttcaaaattctggataat (amino acids)
(SEQ ID NO: 155)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

PGTLRAIFGKTKIQNAVHCTDLPEDGLLEVQYFFKILDNTG

Human NME7 b (optimized for *E coli* expression)
(DNA)
(SEQ ID NO: 156)

atgcatgacgttaaaaatcaccgtacctttctgaaacgcacgaaatatgataatctgcatctggaagacctgtttattggc aacaaagtcaatgtgttctctcgtcagctggtgctgatcgattatggcgaccagtacaccgcgcgtcaactgggtagtcgcaaagaaaa aacgctggccctgattaaaccggatgcaatctccaaagctggcgaaattatcgaaattatcaacaaagcgggtttcaccatcacgaaac tgaaaatgatgatgctgagccgtaaagaagccctggattttcatgtcgaccaccagtctcgcccgttttt caatgaactgattcaattcatc accacgggtccgattatcgcaatggaaattctgcgtgatgacgctatctgcgaatggaaacgctgctgggcccggcaaactcaggtg ttgcgcgtaccgatgccagtgaatccattcgcgctctgtttggcaccgatggtatccgtaatgcagcacatggtccggactcattcgcat cggcagctcgtgaaatggaactgttttttcccgagctctggcggttgcggtccggcaaacaccgccaaatttaccaattgtacgtgctgta ttgtcaaaccgcacgcagtgtcagaaggcctgctgggtaaaattctgatggcaatccgtgatgctggctttgaaatctcggccatgcag atgttcaacatggaccgcgttaacgtcgaagaattctacgaagtttacaaaggcgtggttaccgaatatcacgatatggttacggaaatg tactccggtccgtgcgtcgcgatggaaattcagcaaaacaatgccaccaaaacgtttcgtgaattctgtggtccggcagatccggaaat cgcacgtcatctgcgtccgggtaccctgcgcgcaattttggtaaaacgaaaatccagaacgctgtgcactgtaccgatctgccggaa gacggtctgctggaagttcaatacttttcaaaattctggataat (amino acids)
(SEQ ID NO: 157)

MHDVKNHRTFLKRTKYDNLHLEDLFIGNKVNVFSRQLVLIDYGDQYTAR

QLGSRKEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIR

DAGFEISAMQMFNMDRVNVEEFYEVYKGVVTEYHDMVTEMYSGPCVAMEIQQNN

ATKTFREFCGPADPEIARHLRPGTLRAIFGKTKIQNAVHCTDLPEDGLLEVQYFFKILD

NTG

Human NME7$_{AB}$ also known as NME7$_{AB}$ (optimized for *E coli* expression)
(DNA)
(SEQ ID NO: 158)

atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgtttttca atgaactgattcaattcatcaccacgggtccgattatcgcaatggaaattctgcgtgatgacgctatctgcgaatggaaacgctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgttttttcccgagctctggcggttgcggtccggcaaacaccgccaaatt -continued

```
taccaattgtacgtgctgtattgtcaaaccgcacgcagtgtcagaaggcctgctgggtaaaattctgatggcaatccgtgatgctggcttt gaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttttggtaaaacgaaaatccagaacgctgtgcact gtaccgatctgccggaagacggtctgctggaagttcaatacttttttcaaaattctggataat
```

(amino acids)

(SEQ ID NO: 159)

```
MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDNTG
```

Human NME7-X1 (optimized for *E coli* expression) (DNA)

(SEQ ID NO: 160)

```
atgatgatgctgagccgtaaagaagccctggattttcatgtcgaccaccagtctcgcccgttttttcaatgaactgattcaa ttcatcaccacgggtccgattatcgcaatggaaattctgcgtgatgacgctatctgcgaatggaaacgcctgctgggcccggcaaactc aggtgttgcgcgtaccgatgccagtgaatccattcgcgctctgtttggcaccgatggtatccgtaatgcagcacatggtccggactcatt cgcatcggcagctcgtgaaatggaactgttttttcccgagctctggcggttgcggtccggcaaacaccgccaaatttaccaattgtacgt gctgtattgtcaaaccgcacgcagtgtcagaaggcctgctgggtaaaattctgatggcaatccgtgatgctggctttgaaatctcggcca tgcagatgttcaacatggaccgcgttaacgtcgaagaattctacgaagtttacaaaggcgtggttaccgaatatcacgatatggttacgg aaatgtactccggtccgtgcgtcgcgatggaaattcagcaaaacaatgccaccaaaacgtttcgtgaattctgtggtccggcagatccg gaaatcgcacgtcatctgcgtccgggtaccctgcgcgcaattttttggtaaaacgaaaatccagaacgctgtgcactgtaccgatctgcc ggaagacggtctgctggaagttcaatacttttttcaaaattctggataat
```

(amino acids)

(SEQ ID NO: 161)

```
MMMLSRKEALDFHVDHQSRPFFNELIQFITTGPIIAMEILRDDAICEWKRL

LGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYK

GVVTEYHDMVTEMYSGPCVAMEIQQNNATKTFREFCGPADPEIARHLRPGTLRAIFG

KTKIQNAVHCTDLPEDGLLEVQYFFKILDNTG
```

DM10 domain of NME7 (amino acids)

(SEQ ID NO: 162)

```
MNHSERFVFIAEWYDPNASLLRRYELLFYPGDGSVEMHDVKNHRTFLKR

TKYDNLHLEDLFIGNKVNVFSRQLVLIDYGDQYTARQLGSRK
``` a fragment or variation of PSMGFR peptide (SEQ ID NO: 163)

SNIKFRPGSVVVQLTLAFREGTINVHDVETQFNQYKTEAASRY;

a fragment or variation of PSMGFR peptide (SEQ ID NO: 164)

SVVVQLTLAFREGTINVHDVETQFNQYKTEAASRY;

a fragment or variation of PSMGFR peptide (SEQ ID NO: 165)

VQLTLAFREGTINVHDVETQFNQY;

a fragment or variation of PSMGFR peptide (SEQ ID NO: 166)

SNIKFRPGSVVVQLTLAFREGTIN;

a fragment or variation of PSMGFR peptide (SEQ ID NO: 167)

SNIKFRPGSVVVQLTLAFREGTINVHDVETQFNQYKTE;

a fragment or variation of PSMGFR peptide (SEQ ID NO: 168)

VQLTLAFREGTINVHDVETQFNQYKTEAASRYNLTISDVSVSDVP.

Cys at residue 14 is mutated to Ser of NME7B peptide 3 (B domain):

(SEQ ID NO: 169)

AIFGKTKIQNAVHSTDLPEDGLLEVQYFF

N-10 peptide (SEQ ID NO: 170)

QFNQYKTEAASRYNLTISDVSVSDVPFPFSAQSGA

C-10 peptide (SEQ ID NO: 171)

GTINVHDVETQFNQYKTEAASRYNLTISDVSVSDV

EXAMPLES

Example 1—Components of Minimal Serum-Free Base ("MM") (500 Mls)

400 ml DME/F12/GlutaMAX I (Invitrogen #10565-018)
100 ml Knockout Serum Replacement (KO-SR, Invitrogen #10828-028)
5 ml 100×MEM Non-essential Amino Acid Solution (Invitrogen #11140-050)
0.9 ml (0.1 mM) β-mercaptoethanol (55 mM stock, Invitrogen #21985-023.

Example 2—Generation of Protein Constructs

For generating recombinant NME7, first, constructs were made to make a recombinant NME7 that could be expressed efficiently and in soluble form. The first approach was to make a construct that would encode the native NME7 (a) or an alternative splice variant NME7 (b), which has an N-terminal deletion. In some cases, the constructs carried a histidine tag or a strep tag to aid in purification, NME7-a, full-length NME7 expressed poorly in E, coli and NME7-b did not express at all in E, coli. However, a novel construct was made in which the DM10 sequence was deleted and the NME7 comprised essentially the NDPK A and B domains having a calculated molecular weight of 33 kDa.

This novel NME7$_{AB}$ expressed very well in E, coli and existed as the soluble protein, NME7$_{AB}$ was first purified over an NTA-Ni column and then further purified by size exclusion chromatography (FPLC) over a Sephadex 200 column. Fractions were collected and tested by SDS-PAGE to identify fractions with the highest and purest expression of NME7$_{AB}$. The FPLC trace for the combined fractions that were the most pure were combined. The purified NME7$_{AB}$ protein was then tested and shown to fully support the growth of human stem cells and further reverts them to the most naïve, pre-X-inactivation state. The purified NME7$_{AB}$ was also shown to accelerate the growth of cancer cells.

Example 3—ELISA Assay Showing NME7$_{AB}$ Simultaneously Binds to Two MUC1* Extra Cellular Domain Peptides Results are shown in FIG. 1. The PSMGFR peptide bearing a C-terminal Cysteine (PSMGFR-Cys) was covalently coupled to BSA using Imject Maleimide activated BSA kit (Thermo Fisher). PSMGFR-Cys coupled BSA was diluted to 10 ug/mL in 0.1M carbonate/bicarbonate buffer pH 9.6 and 50 uL was added to each well of a 96 well plate. After overnight incubation at 4° C., the plate was washed twice with PBS-T and a 3% BSA solution was added to block remaining binding site on the well. After 1 h at RT the plate was washed twice with PBS-T and NME7, diluted in PBS-T+1% BSA, was added at different concentrations. After 1h at RT the plate was washed 3× with PBS-T and anti-NM23-H7 (B-9). Santa Cruz. Biotechnology), diluted in PBS-T+1% BSA, was added at 1/500 dilution. After 1 h at RT the plate was washed 3× with PBS-T and goat anti mouse-HRP, diluted in PBS-T+1% BSA, was added at 1/3333 dilution. After 1 h at RT the plate was washed 3× with PBS-T and binding of NME7 was measured at 415 nm using ABTS solution (Pierce).

ELISA MUC1* dimerization: The protocol for NME7 binding was used, and NME7 was used at 11.6 ug/mL.

After 1 h at RT the plate was washed 3× with PBS-T and His-Tagged PSMGFR peptide (PSMGFR-His) or biotinylated PSMGFR peptide (PSMGFR-biotin), diluted in PBS-T+1% BSA, was added at different concentration. After 1 h at RT the plate was washed 3× with PBS-T and anti-Histag-HRP (Abcam) or streptavidin-HRP (Pierce), diluted in PBS-T+1% BSA, was added at a concentration of 1/5000. After 1 h at RT the plate was washed 3× with PBS-T and binding of PSMGFR peptide to NME7 already bound to another PSMGFR peptide (which could not signal by anti-His antibody or by streptavidin) coupled BSA was measured at 415 nm using a ABTS solution (Pierce).

Example 4—Functional Testing of Human Recombinant NME7$_{AB}$

For testing recombinant NME7$_{AB}$ for ability to maintain pluripotency and inhibit differentiation, a soluble variant of NME7, NME7$_{AB}$, was generated and purified. Human stem cells (iPS cat #SC101a-1, System Biosciences) were grown per the manufacturer's directions in 4 ng/ml bFGF over a layer of mouse fibroblast feeder cells for four passages. These source stem cells were then plated into 6-well cell culture plates (Vita™, Thermo Fisher) that had been coated with 12.5 ug/well of a monoclonal anti-MUC1* antibody. MN-C3. Cells were plated at a density of 300,000 cells per well. The base media was Minimal Stem Cell Media consisting of: 400 ml DME/F12/GlutaMAX I (Invitrogen #10565-018), 100 ml Knockout Serum Replacement (KO-SR. Invitrogen #10828-028), 5 ml 100×MEM Non-essential Amino Acid Solution (Invitrogen #11140-050) and 0.9 ml (0.1 mM) β-mercaptoethanol (55 mM stock, Invitrogen #21985-023). The base media can be any media. In a preferred embodiment, the base media is free of other growth factors and cytokines. To the base media was added either 8 nM of NME7$_{AB}$ or 8 nM NM23-H1 refolded and purified as stable dimers. Media was changed every 48 hours and due to accelerated growth, had to be harvested and passaged at Day 3 post-plating. Comparable pluripotent stem cell growth was achieved when stem cells were grown in NM23-H1 dimers or in NME7 monomers.

NME7 and NM23-H1 (NME1) dimers both grew pluripotently and had no differentiation even when 100% confluent. As can be seen in the photos, NME7 cells grew faster than the cells grown in NM23-H1 dimers. Cell counts at the first harvest verified that culture in NME7 produced 1.4-times more cells than culture in NM23-H1 dimers. ICC staining for the typical pluripotent markers confirmed that NME7$_{AB}$ fully supported human stem cell growth, pluripotency, and resisted differentiation.

The NME7 species of ~30-33 kDa may be an alternative splice isoform or a post translational modification such as cleavage, which may enable secretion from the cell.

Example 5—Inducing Transition of Cancer Cells to Metastatic Cancer Cells by Culturing Cells Under Conditions that Revert Stem Cells to a More Naïve State Cancer cells are normally cultured in a serum-containing media such as RPMI. We discovered that culturing cancer cells in the presence of reagents that make stem cells revert to a more naïve state, makes the cancer cells transform to a more metastatic state.

We demonstrated that NME7$_{AB}$, human NME1 dimers, bacterial NME1 dimers. NME7-X1 and "2i" inhibitors were each able to transform regular cancer cells into metastatic cancer cells, which are also called cancer stem cells "CSCs" or tumor initiating cells "TICs". 2i is the name given to two biochemical inhibitors that researchers found made human stem cells revert to a more naïve state. 2i are MEK and GSK3-beta inhibitors PD0325901 and CHIR99021, which are added to culture medium to final concentrations of about 1 mM and 3 mM, respectively.

NME7$_{AB}$ and NME7-X1 are at a final concentration of about 4 nM when added to separate batches of minimal medium to make cancer cells transform to metastatic cells, although lower and higher concentrations also work well in the range of about 1 nM to 16 nM. Human or bacterial NME1 dimers are used at a final concentration of 4 nM to 32 nM, with 16 nM typically used in these experiments, wherein the human NME bears the S120G mutation. Lower concentrations may be required if using wild type. It is not intended that these exact concentrations are important. It is important that the NME1 proteins are dimers and the range of concentrations over which this happens is in the low nanomolar range although certain mutations allow higher concentrations to remain as dimers.

Similarly, the concentrations of NME7 proteins can vary, NME7$_{AB}$ and NME7-X1 are monomers and concentrations used to transform cancer cells to metastatic cells should allow the proteins to remain as monomers. Various molecular markers have been proposed as being indicators of metastatic cancer cells. Different cancer types may have different molecules that are up-regulated. For example, the receptor CXCR4 is up-regulated in metastatic breast cancers while E-cadherin, also known as CHD1, is up-regulated more in metastatic prostate cancers.

In addition to these specific metastasis markers, typical markers of pluripotency such as OCT4, SOX2, NANOG, and KLF4 are up-regulated as cancers become metastatic. The starting cancer cells and the later metastatic cancer cells can be assayed by PCR to measure expression levels of these genes.

FIG. 2 shows a graph of RT-PCR measurements of T47D breast cancer cells that were cultured in a media that contained NME7$_{AB}$. A rho I kinase inhibitor, ROCi, ROCKi or Ri, was added to prevent the transformed cells from floating off the plate. Expression levels of various metastatic markers as well as pluripotent stem cell markers were measured for the parent cells and for the NME7$_{AB}$ cultured cells. The results show that the floater cells express higher amounts of metastatic and pluripotency markers compared to the cells that received ROCi. We reasoned it was because those measurements were the average of cells that did not transform and those that did but the ROCi made them remain adherent. This can clearly be seen in figures wherein "—Ri" means adherent cells that did not receive ROCi and so were not mixed with the highly metastatic cells that float.

Prostate cancer cells also transitioned to a more metastatic state when cultured in media containing NM23, aka NME1, or NME7$_{AB}$. Here we show that for every cell line tested so far, culture in NME7$_{AB}$, human NME1 dimers, or bacterial NMEs that have high sequence homology to human, induces transition to a more metastatic state.

Figure 4:
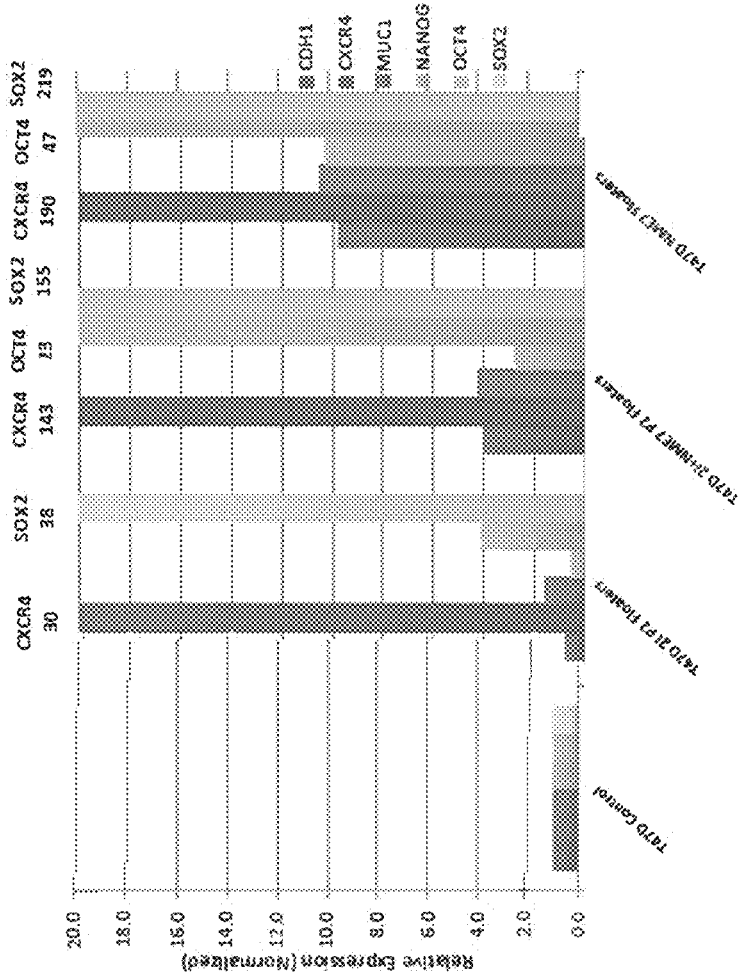
FIG. 4 is a graph of RT-PCR measurement of the metastatic markers and pluripotent stem cell markers showing that the 2i inhibitors (GSK3-beta and MEK inhibitors), which were previously shown to revert stem cells to a more naïve state, also induce cancer cells to a more metastatic state although not as well as $NME7_{AB}$.

FIG. 4 shows a graph of RT-PCR measurements of expression levels of metastatic and pluripotency markers for breast cancer cells that are cultured in media containing either 2i inhibitors, NME7$_{AB}$ or both. As can be seen. 2i inhibitors are also able to induce the transition of cancer cells to a more metastatic state. Ovarian cancer cell lines SK-OV3. OV-90, pancreatic cancer cell lines CAPAN-2 and PANC-1, breast cancer cell line MDA-MB all displayed the morphological transition of going from adherent to non-adherent when cultured in NME7$_{AB}$ and or 2i inhibitors.

FIG. 20 shows graphs of RT-PCR measurement of metastatic or pluripotency markers for various cancer cell lines cultured for 72 or 144 hours in NME7$_{AB}$. FIG. 20A shows that SK-OV3 cells increase expression of metastatic markers CHD1, SOX2 and NME7-X1 when cultured in NME7$_{AB}$. FIG. 20B shows that OV-90 cells increase expression of metastatic markers CXCR4 and NME7-X1 after culture in NME7$_{AB}$.

Example 6—Demonstration that Cancer Cells Cultured in NME7 Become Metastatic

A functional test of whether or not a population of cancer cells is metastatic is to implant very low numbers. e.g. 200, of the cells in immuno-compromised mice and see if they develop into a tumor. Typically 5-6 million cancer cells are required to form a tumor in an immuno-compromised mouse. We showed that as few as 50 of the NME-induced metastatic cancer cells formed tumors in mice. In addition, mice that were injected throughout the test period with human NME7$_{AB}$, NME1, or NME7-X1 developed remote metastases.

T47D human breast cancer cells were cultured in standard RPMI media for 14 days with media changes every 48 hours and passed by trypsinization when approximately 75% confluent. The cells were then plated into 6-well plates and cultured in minimal stem cell media (see Example 1) that was supplemented with 4 nM NME7$_{AB}$. Media was changed every 48 hours. By about Day 4, some cells become detached from the surface and float. Media is carefully changed so as to retain the "floaters" as these are the cells that have the highest metastatic potential as evidenced by RT-PCR measurement of metastatic markers. On Day 7 or 8, the floaters are harvested and counted. Samples are retained for RT-PCR measurement. The key marker measured is CXCR4 which is up-regulated by 40-200 times after being briefly cultured in NME7$_{AB}$.

The freshly harvested floater metastatic cells are xenografted into the flank of female nu/nu athymic mice that have been implanted with 90-day slow release estrogen pellets. Floater cells were xenografted as 10,000, 1,000, 100 or 50 cells each. Half of the mice in each group of 6 were also injected daily with 32 nM NME7$_{AB}$ near the original implantation site. The parent T47D cells that were cultured in RPMI media without NME7$_{AB}$ were also implanted into mice as 6 million. 10,000 or 100 as controls. Mice implanted with the NME7-induced floater cells developed tumors even when as few as 50 cells were implanted. Mice that were implanted with the floater cells and that received daily injections of NME7$_{AB}$ also developed remote tumors or remote metastases in various organs. 11 out of the 12 mice, or 92%, that were injected with human NME7$_{AB}$ after implantation of the NME7$_{AB}$ cultured cancer cells, developed tumors at the injection site. Only 7 out of the 12 mice, or 58%, that were not injected with human NME7$_{AB}$ after implantation developed tumors. 9 out of the 11 mice, or 82%, that got tumors and were injected with human NME7$_{AB}$ developed multiple tumors remote from the injection site. None of the mice that were not injected with NME7$_{AB}$ developed multiple, visible tumors.

After sacrifice. RT-PCR and Western blots showed that the remote bumps on the mice injected with NME7$_{AB}$ were indeed human breast tumors. Similar analysis of their organs showed that in addition to remote bumps, mice had randomly metastasized to the liver and lung with human breast cancer characteristic of the human breast cancer cells that were implanted. As expected, only the mice implanted with 6 million cells grew tumors.

Several experiments like the one described above were performed with essentially the same results. In each experiment, there were either 24 or 52 mice, including all proper controls.

Example 7—Peptides Selected Because their Sequence is Unique to NME7, A1, A2, B1, B2 and B3, Inhibit the Binding of NME7 Species to MUC1* Extracellular Domain Peptide NME7 peptides were selected as immunizing agents for antibody production. NME7 peptides A1, A2, B1, B2 and B3 (FIG. 9) were chosen using a process of sequence alignment among human NME1, human NME7 and several bacterial NMEs that were homologous to human NME1 or human NME7. Five regions that had high sequence homology among all were identified. However, to prevent selecting peptides that would give rise to antibodies that would inhibit human NME1 as well as human NME7, we chose NME7 sequences that were adjacent to the homologous regions wherein those peptides had sequences that were different from human NME1. We did ELISA assays to see if the peptides on their own could bind to a synthetic MUC1* peptide on the surface and inhibit the binding of human NME7 or human NME1 to the immobilized peptide (FIG. 11). FIG. 11 shows that the peptides inhibited the binding of NME7 and NME1 to the immobilized PSMGFR peptide. Recall that each of the NME7 A domain and B domain can bind to a PSMGFR peptide. Therefore complete inhibition of NME7$_{AB}$ binding to a PSMGFR peptide cannot be accomplished with a single antibody or peptide that is derived from just one domain. This showed that those regions from which the peptides were derived were the regions that interacted with MUC1* and would give rise to antibodies that would bind to those regions of NME7 and inhibit its binding to MUC1* receptor.

In another experiment, the free peptides A1, A2, B1, B2 and B3 were added to cancer cells in culture that were undergoing transition to a more metastatic state by culturing in either NME7$_{AB}$ or 2i. FIG. 14 shows a table of scientist observations when cancer cells are grown in either NME7$_{AB}$ or 2i inhibitors, and shows that the free peptides inhibited the morphological change from adherent cells to floaters, which for breast cancer cells is directly correlated to increased expression of metastatic markers, especially CXCR4. RT-PCR measurements confirm that the NME7$_{AB}$ peptides inhibited the increase in expression of metastasis marker CXCR4.

Figure 32:
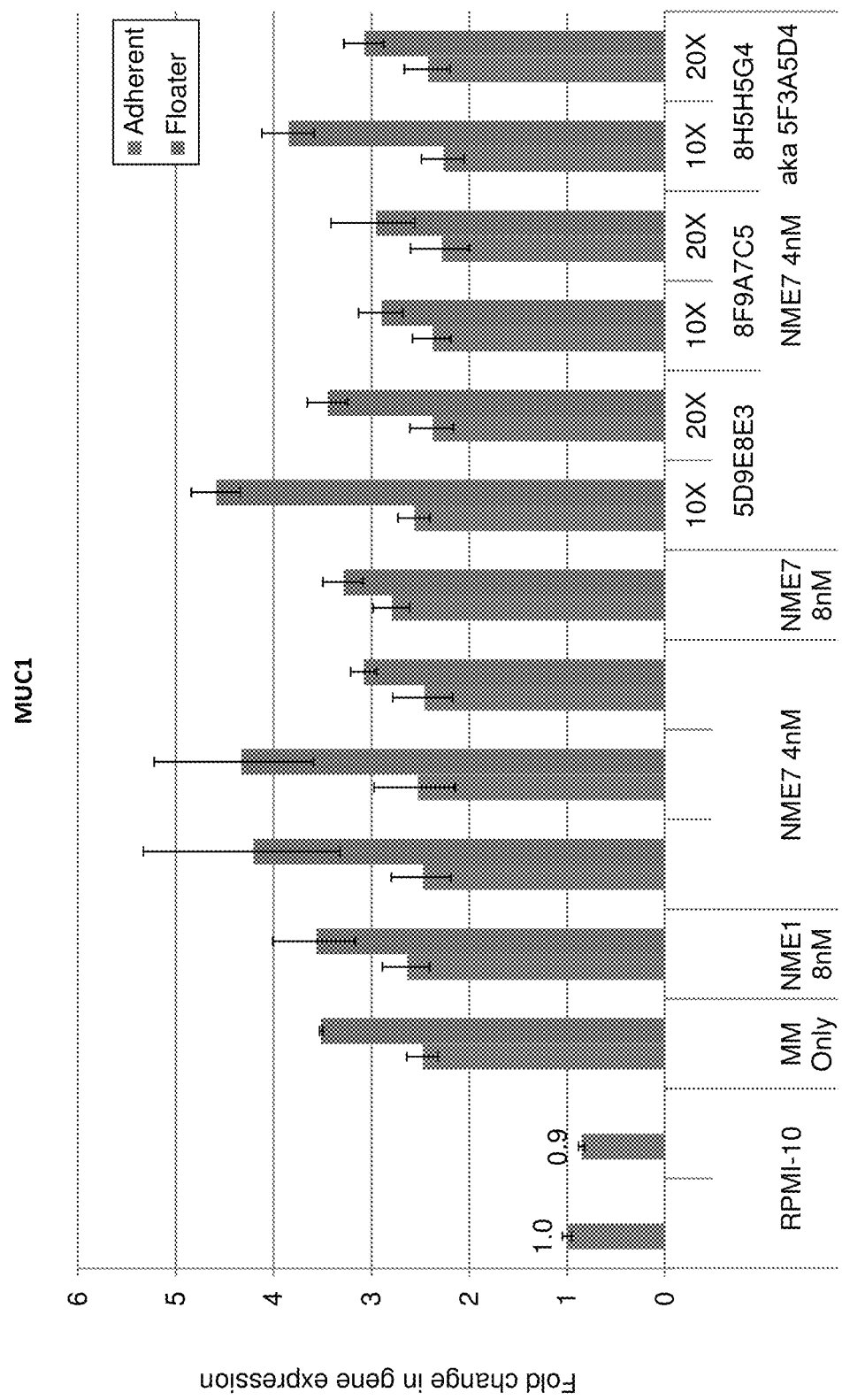
FIG. 32 shows a graph of a PCR measurement of stem cell marker and metastatic growth factor receptor MUC1 in T47D breast cancer cells that were cultured in either their normal recommended media. RMPI, serum-free media containing only NME7$_{AB}$ as the growth factor at 4 nM, which is optimal, or 8 nM, or serum-free media containing only NME1 S120G dimers as the growth factor at 8 nM: because NME1 is a homodimer and NME7$_{AB}$ is a monomer comprised of two pseudo-identical domains, 8 nM NME1 is the molar equivalent of 4 nM NME7$_{AB}$. The cancer cells were cultured in the presence or absence of anti-NME7 B3 antibodies. In this experiment, floating cells were separated from the adherent cells and analyzed separately. Significant data argues that the floater cells are the cancer stem cells. As can be seen in the figure, growth in NME7$_{AB}$ media increases MUC1 expression in the floater population of cells and anti-NME7 B3 antibodies decreased its expression, arguing that anti-NME7 antibodies decreased generation of cancer stem cells.

FIG. 15 shows a graph of RT-PCR measurements of CXCR4 expression in T47D breast cancer cells that were grown in either NME7$_{AB}$ or 2i inhibitors, each of which transform cancer cells to a more metastatic state, and the inhibitory effect of NME7-derived peptides, A1, A2, B1, B2 and B3, on the metastatic transformation. FIG. 32 shows a table of recorded RNA levels in samples that were used for RT-PCR measurement of CXCR4 in FIG. 15 as well as the threshold cycle number for CXCR4 expression as well as for the control housekeeping gene.

Example 8—Anti-NME7 Antibodies Specifically Bind to Human NME7 but not to Human NME1

A standard ELISA assay was performed to determine whether or not the NME7 antibodies we generated by immunization with NME7$_{AB}$ peptides A1, A2, B1, B2, and B3 would bind specifically to NME7$_{AB}$, but not to human NME1 as it has healthy functions and it may be detrimental to a human to block it with an antibody. The ELISAs of FIG. 24-25 show that all of the NME7 antibodies that were generated from peptides A1, A2, B1, B2, and B3 bind to human NME7$_{AB}$ (FIG. 24) but not to human NME1 (FIG. 25). The peptides used to generate these antibodies are common to both NME7$_{AB}$ and NME7-X1. This assays show that the antibodies generated from peptides A1, A2, B1, B2, and B3 specifically bind to NME7$_{AB}$ and by extension will bind to NME7-X1.

NME7A peptide 1 (A domain): MLSRKEALDFHVDHQS (SEQ ID NO:141)
NME7A peptide 2 (A domain): SGVARTDASES (SEQ ID NO:142)
NME7B peptide 1 (B domain): DAGFEISAMQMFNMDRVNVE (SEQ ID NO: 143)
NME7B peptide 2 (B domain): EVYKGVVTEYHDMVTE (SEQ ID NO:144)
NME7B peptide 3 (B domain): AIFGKTKIQNAVHCTDLPEDGLLEVQYFF (SEQ ID NO:145)

Example 9—Anti-NME7 Specific Antibodies and the Peptides that Generated them Inhibit Cancer Cell Growth Rabbits were immunized with NME7 peptides A1, A2, B1, B2, and B3 and antibodies were generated, collected and purified over a column to which the immunizing peptide had been conjugated. T47D breast cancer cells were plated and cultured according to ATCC protocols in RPMI media supplemented with serum. Antibodies generated from immunization with peptides A1, A2, B1, B2, and B3 were added at the concentrations indicated in FIG. 12. Immunizing peptides A1, A2, B1, B2, and B3, and the PSMGFR extracellular domain peptide of MUC1*, "FLR" here, were also added separately to growing T47D breast cancer cells. Taxol and the E6 anti-MUC1* Fab were added as controls. The graph of FIG. 12 shows that the antibodies generated, as well as the free peptides, potently inhibited the growth of the cancer cells. Note the comparison to inhibition using Taxol, which is a chemotherapy agent that kills healthy and cancer cells alike. Also, for comparison, a polyclonal antibody generated using a large stretch of NME7 from amino acid 100 to 376 is shown. Although this antibody is a potent inhibitor of cancer growth it could have non-specific effects since it can bind to NME1 as well as to NME7.

In a similar experiment, combinations of the antibodies generated from immunization with peptides A1, A2, B1, B2, and B3 as well as the peptides themselves were added to growing cancer cells at the concentrations indicated. The graphs of cell growth shown in FIG. 13 show that the combinations of antibodies and peptides potently inhibited the growth of cancer cells. In these two experiments, the cells were MUC1* positive breast cancer cells.

Example 10—Anti-NME7 Antibodies Inhibit the Transition of Cancer Cells to Metastatic Cancer Cells Cancer cells transform to a more metastatic state when cultured in the presence of agents that revert stem cells to a more naïve state. We have demonstrated that culturing cancer cells in NME7$_{AB}$, human NME1 dimers, bacterial NME1 dimers or MEK and GSK3-beta inhibitors, called "2i", causes the cells to become more metastatic. As the cells transition to a more metastatic state, they become non-adherent and float off of the culture plate. These floating cells, "floaters" were collected separately from those that were adherent and were shown to: a) express much higher levels of metastatic genes; and b) when xenografted into mice, the floater cells were able to generate tumors when implanted at very low numbers. RT-PCR measurement of specific metastatic markers such as CXCR4 in breast cancers, CHD1 in prostate cancer, and other pluripotent stem cell markers such as OCT4, SOX2, NANOG, KLF4, c-Myc and others were dramatically over-expressed in cancer cells that were cultured in NME7$_{AB}$ and most over-expressed in the cells that became non-adherent, called "floaters" here and in figures.

Here we show that the NME7-specific antibodies, generated by immunization with NME7-derived peptides A1, A2. B1. B2 and B3, as well as the peptides themselves, inhibit the transition from cancer cell to metastatic cancer cells. In the first of these experiments, the antibodies generated by immunization with A1, A2. B1. B2 and B3 were tested for their ability to inhibit the metastatic transition induced by culture of T47D breast cancer cells in NME7$_{AB}$ or in 2i inhibitors. The most striking observation was that the antibodies and the peptides dramatically reduced the number of floater cells, which was the first indication that the antibodies and peptides had inhibited the transformation to metastatic cancer cells. In particular, cells to which the antibody generated from immunization with the B3 peptide barely generated any floater cells.

FIG. 14 shows the recorded observations of the percentage of floater cells visible for each antibody relative to the control wells that did not receive any antibody treatment. mRNA was extracted from both the floater cells and the adherent cells. RT-PCR was used to measure expression levels of metastatic markers, including CXCR4. Treatment with the anti-NME7 antibodies greatly reduced the amount of metastatic markers, such as CXCR4, indicating the antibodies inhibited the transition to metastatic cancer. (See FIG. 15). Notably, the antibody generated by immunization with peptide B3, aka antibody #61, essentially completely inhibited the transition to a more metastatic state. FIG. 15B shows that breast cancer cells that were treated with the NME7$_{AB}$ peptides. A1, A2, B1, B2 and B3, alone were able to potently inhibit the transition to a more metastatic state induced by culturing the cells in a media containing the 2i inhibitors. Peptide B3 was especially effective as was antibody #61 that it generated. FIG. 15C shows the same graph but with the Y-axis expanded to show the peptide inhibition of metastatic markers. The amount of mRNA, which indicates cell viability and growth, was measured. Cells that were treated with antibody had much less mRNA, indicating that in addition to inhibiting the transition to a more metastatic state, the anti-NME7$_{AB}$ antibodies inhibited the growth of the cancer cells. FIG. 16 shows a table of the amounts of RNA recovered for the inhibition experiment shown in FIG. 15A.

Example 11—Anti-NME7 Antibodies Generated with NME7-Derived Peptides A1, A2, B1, B2 and B3 Identify Novel NME7 Species not Detectable Using any Commercially Available Antibodies As is known to those skilled in the art, some antibodies recognize a linear portion of the target protein and can be used in Western blot assays while other antibodies recognize a non-linear conformational motif and can be used in pull-down or immunoprecipitation assays. Previous to this application, cleaved NME7 or isoform NME7-X1 was not known to exist. Using antibodies that were commercially available at the time of filing shows that existing antibodies could not specifically detect these important NME7 species. B9 (Santa Cruz Biotechnology) is a monoclonal antibody raised against NME7 amino acids 100-376. FIG. 19D-19F shows that it only detects full-length 42 kDa NME7. Another commercially available antibody. H278, is a rabbit polyclonal raised against NME7 amino acids 100-376, which includes amino acid sequences that are not unique to NME7. FIG. 19D-19F shows that this antibody also stains NME1, which is 17 kDa as well as full-length NME7 and other bands that do not appear to be specific to NME7$_{AB}$.

NME7 antibodies generated by immunization with NME7$_{AB}$ peptides A1, A2, B1. B2 or B3 identify new NME7 species including the full-length 42 k Da protein, a ~33 kDa NME7 species that may be a cleavage product or alternative isoform, a ~30 kDa NME7 species that may be a cleavage product or alternative isoform, wherein the ~30 kDa species appears to be NME7-X1. FIG. 19A-C shows that antibodies generated by peptides A1, B1 and B3 identify the secreted forms of NME7, NME7$_{AB}$ and NME7-X1 in a wide range of cancer cell lines, including T47D breast cancer cells, PC3 and DU145 prostate cancer cells. HEK293 fetal liver cells, and leukemia cells IM-9, K562, and MV411.

Example 12—Generation of Anti-NME7 Antibodies

A synthetic peptide having the sequence of the B3 region of NME7. AIFGKTKIQNAVHCTDLPEDGLLEVQYFFC (SEQ ID NO: 1142), was used to immunize rabbits. Antibodies that resulted from immunization with NME7 peptide B3 inhibited the growth of MUC1* positive cancer cells and also inhibited the formation of cancer stem cells, which are characterized by upregulation of metastatic markers, ability to grow anchorage independently, and are able to form tumors in animals from as few as 200 cells, whereas regular cancer cells typically require implantation of about 4 million cells for tumor engraftment.

In some cases, the NME7 B3 peptide was made with a C14A or C14V mutation. This sequence more reproducibly generated anti-NME7 antibodies.

Monoclonal antibodies were generated in mice according to standard methods by immunizing with NME7 B3, B3 with C14A mutation, or B3 with C14V mutation. The antibodies listed were selected because of their ability to bind to NME7, NME7-X1, $NME7_{AB}$, but importantly did not bind to NME1, which is thought to be required for some normal cellular functions. These antibodies also bind to the NME7 derived peptides B3, B3 with C14A mutation, and B3 with C14V mutation.

Experiments showed that these anti-NME7 antibodies inhibited the binding of NME7 to the MUC1* extra cellular domain, but did not block the binding of NME1 to the MUC1* extra cellular domain peptide. Further, the antibodies inhibited the formation of cancer stem cells.

CITED REFERENCES LIST

Al-Hajj et al. (2003) Prospective identification of tumorigenic breast cancer cells. PNAS. April 1; 100(7):3983-3988.

Clarke M F, Dick J E, Dirks P B, Eaves C J, Jamieson C H, Jones D L, Visvader J, Weissman I L, Wahl G M. (2006) Cancer stem cells—perspectives on current status and future directions: AACR Workshop on cancer stem cell. Cancer Res. October 1; 66(19):9339-44. Epub 2006 Sep. 21.

Chen K, Huang Y H, Chen J L, (2013) Understanding and targeting cancer stem cells: therapeutic implications and challenges. Acta Pharmacologica Sinica 34: 732-740; Review Darash-Yahana M, Pikarsky E, Abramovitch R, Zeira E, Pal B, Karplus R, Beider K, Avniel S, Kasem S, Galun E, Peled A (2004) Role of high expression levels of CXCR4 in tumor growth, vascularization, and metastasis. FASEB J 18 (11): 1240-1242

Mahanta S, Fessler S, Park J, Bamdad C. A Minimal Fragment of MUC1 Mediates Growth of Cancer Cells, 2008 PloS ONE 3:e2054-2065.

Hikita S, Clegg O, Kosik K, Bamdad C. MUC1* Mediates the Growth of Human Pluripotent Stem Cells. 2008 PloS ONE 3:e3312-3325.

Kumar S M, Liu S, Lu H, Zhang H, Zhang P J, Gimotty P A, Guerra M, Guo W, Xu X. (2012) Acquired cancer stem cell phenotypes through Oct4-mediated dedifferentiation. Oncogene. November 22; 31(47):4898-911.

Liu K, Lin B, Zhao M, Yang X, Chen M, Gao A, Liu F, Que J, Lan X, (2013) The multiple roles for Sox2 in stem cell maintenance and tumorigenesis. Cellular Signaling May; 25(5):1264-71. Review Wang M L, Chiou S H, Wu C W. (2013) Targeting cancer stem cells: emerging role of Nanog transcription factor. Onco targets and Therapy. September 4; 6:1207-20. Review.

Xu C, Rosler E, Jiang J, Lebkowski J S, Gold J D, et al. (2005) Basic Fibroblast Growth Factor Supports Undifferentiated Human Embryonic Stem Cell Growth Without Conditioned Medium. STEM CELLS 23:315-323.

Fessler S, Wotkowicz M, Mahanta S, Bamdad C (2009) MUC1* is a determinant of trastuzumab (Herceptin) resistance in breast cancer cells. Breast Cancer Res Treat 118:113-124 DOI 10.1007/s10549-009-0412-3

Miki J, Furusato B, Li H, Gu Y, Takahashi H, Egawa S, Sesterhenn I A, McLeod D G, Srivastava S, Rhim J S, Identification of putative stem cell markers. CD133 and CXCR4, in hTERT-immortalized primary nonmalignant and malignant tumor-derived human prostate epithelial cell lines and in prostate cancer specimens. Cancer Res. 2007 Apr. 1; 67(7):3153-61.

Jeter C R, Liu B, Liu X, Chen X, Liu C, Calhoun-Davis T, Repass J, Zaehres H, Shen J J, Tang D G. NANOG promotes cancer stem cell characteristics and prostate cancer resistance to androgen deprivation. Oncogene. 2011 Sep. 8; 30(36):3833-45. PMCID:

Faber A, Goessler U R, Hoermann K, Schultz, J D, Umbreit C, Stern-Straeter J. SDF-1-CXCR4 axis: cell trafficking in the cancer stem cell niche of head and neck squamous cell carcinoma. Oncol. Rep. 2013 June; 29(6):2325-31.

Mukherjee D, Zhao J. The Role of chemokine receptor CXCR4 in breast cancer metastasis. Am J Cancer Res. 2013; 3(1):46-57. PMCID: PMC3555200)

Herreros-Villanueva M, Zhang J-S, Koenig A, Abel E V, Smyrk T C, Bamlet W R, de Narvajas AA-M. Gomez T S, Simeone D M, Bujanda L, Billadeau D D, SOX2 promotes dedifferentiation and imparts stem cell-like features to pancreatic cancer cells. Oncogenesis. 2013; 2:e61. PMCID: PMC3759123

Hanna J, Cheng A W, Saha K, Kim J, Lengner C J, et al. (2010) Human embryonic stem cells with biological and epigenetic characteristics similar to those of mouse ESCs. Proc Natl Acad Sci USA 107:9222-9227.

Smagghe, B. J. Stewart A. K., Carter M. G., Shelton L. S., Bernier K. J., Hartman E. J., Calhoun A. K., Hatziioannou V. M., Lillacci G., Kirk B. A., DiNardo B. A., Kosik K. S., Bamdad C. (2013) MUC1* Ligand. NM23-H1. Is a Novel Growth Factor That Maintains Human Stem Cells in a More Naïve State. PloS ONE 8 (3): e58601

Theunissen T W, Powell B E, Wang H, Mitalipova M, Faddah D A, Reddy J, Fan Z P, Maetzel D, Ganz K, Shi L, Lungjangwa T, Imsoonthornruksa S, Stelzer Y, Rangarajan S, D'Alessio A, Zhang J, Gao Q, Dawlaty M M, Young R A, Gray N S, Jaenisch R. (2014) Systematic Identification of Culture Conditions for Induction and Maintenance of Naive Human Pluripotency. Cell Stem Cell. 2014 Jul. 24, S1934-5909(14)00298-7.

Rais Y1, Zviran A, Geula S, Gafni O, Chomsky E, Viukov S, Mansour A A, Caspi I, Krupalnik V, Zerbib M, Maza I, Mor N, Baran D, Weinberger L, Jaitin D A, Lara-Astiaso D, Blecher-Gonen R, Shipony Z, Mukamel Z, Hagai T, Gilad S, Amann-Zalcenstein D, Tanay A, Amit I, Novershtern N, Hanna J H (2013) Deterministic direct reprogramming of somatic cells to pluripotency. 502 (7469): 65-70.

Xu R H, Peck R M, Li D S, Feng X, Ludwig T, et al. (2005) Basic FGF and suppression of BMP signaling sustain undifferentiated proliferation of human ES cells. Nat Methods 2: 185-190.

Liu W, Ma Q, Wong K, Li W, Ohgi K, Zhang J, Aggarwal A K, Rosenfeld M G. Brd4 and JMJD6-Associated Anti-Pause Enhancers in Regulation of Transcriptional Pause Release. Cell. 2013 Dec. 19; 155(7):1581-95. PMCID: PMC3886918.

Silva J, Barrandon O, Nichols J, Kawaguchi J, Theunissen T W, Smith A. Promotion of reprogramming to ground state pluripotency by signal inhibition. PLOS Biol. 2008 Oct. 21; 6(10):e253. PMCID: PMC2570424

Takahashi K and Yamanaka S (2006) Induction of pluripotent stem cells from mouse embryonic and adult fibroblast cultures by defined factors. Cell 126(4):663-676.

Porter D et al. (2011) Chimeric antigen receptor-modified T cells in chronic lymphoid leukemia. N Engl J Med 365: 725-733 DOI: 10.1056/NEJMoa1103849

Tiller T et al. (2013) A fully synthetic human Fab antibody library based on fixed VH/VL framework pairings with favorable biophysical properties. MABs 9:5(3) PMID: 23571156

Webb P A, Perisic O, Mendola C E, Backer J M and Williams R L. The crystal structure of a human nucleoside diphosphate kinase. NM23-H2. J Mol Biol. 1995, 251: 574-587.

Min K, Song H K, Chang C, Kim S Y, Lee K J and Suh S W. Crystal structure of human nucleoside diphosphate kinase A, a metastasis suppressor. Proteins. 2002, 46:340-342.

Okabe-Kado et al., "A new function of Nm23/NDP kinase as a differentiation inhibitory factor, which does not require it's kinase activity", FEBS Letters 363:311-315, 1995

Lombardi et al., "nm23: Unraveling Its Biological Function in Cell Differentiation" JOURNAL OF CELLULAR PHYSIOLOGY 182:144-149 (2000)

Harrell et al., Estrogen Receptor Positive Breast Cancer Metastasis: Altered Hormonal Sensitivity and Tumor Aggressiveness in Lymphatic Vessels and Lymph Nodes. Cancer Res 2006; 66: (18). Sep. 15, 2006.

Suzuki et al., Combined effect of dehydroxymethylepoxyquinomicin and gemcitabine in a mouse model of liver metastasis of pancreatic cancer. Clin Exp Metastasis (2013) 30:381-392.

Those skilled in the art will recognize, or be able to ascertain using no more than routine experimentation, many equivalents to the specific embodiments of the invention specifically described herein. Such equivalents are intended to be encompassed in the scope of the claims.

SEQUENCE LISTING

```
Sequence total quantity: 1213
SEQ ID NO: 1           moltype = AA  length = 1255
FEATURE                Location/Qualifiers
REGION                 1..1255
                       note = MUC1 Receptor - Mucin 1 precursor, Genbank Accession
                        number: P15941
source                 1..1255
                       mol_type = protein
                       organism = synthetic construct
SEQUENCE: 1
MTPGTQSPFF LLLLLTVLTV VTGSGHASST PGGEKETSAT QRSSVPSSTE KNAVSMTSSV   60
LSSHSPGSGS STTQGQDVTL APATEPASGS AATWGQDVTS VPVTRPALGS TTPPAHDVTS  120
APDNKPAPGS TAPPAHGVTS APDTRPAPGS TAPPAHGVTS APDTRPAPGS TAPPAHGVTS  180
APDTRPAPGS TAPPAHGVTS APDTRPAPGS TAPPAHGVTS APDTRPAPGS TAPPAHGVTS  240
APDTRPAPGS TAPPAHGVTS APDTRPAPGS TAPPAHGVTS APDTRPAPGS TAPPAHGVTS  300
APDTRPAPGS TAPPAHGVTS APDTRPAPGS TAPPAHGVTS APDTRPAPGS TAPPAHGVTS  360
APDTRPAPGS TAPPAHGVTS APDTRPAPGS TAPPAHGVTS APDTRPAPGS TAPPAHGVTS  420
APDTRPAPGS TAPPAHGVTS APDTRPAPGS TAPPAHGVTS APDTRPAPGS TAPPAHGVTS  480
APDTRPAPGS TAPPAHGVTS APDTRPAPGS TAPPAHGVTS APDTRPAPGS TAPPAHGVTS  540
APDTRPAPGS TAPPAHGVTS APDTRPAPGS TAPPAHGVTS APDTRPAPGS TAPPAHGVTS  600
APDTRPAPGS TAPPAHGVTS APDTRPAPGS TAPPAHGVTS APDTRPAPGS TAPPAHGVTS  660
APDTRPAPGS TAPPAHGVTS APDTRPAPGS TAPPAHGVTS APDTRPAPGS TAPPAHGVTS  720
APDTRPAPGS TAPPAHGVTS APDTRPAPGS TAPPAHGVTS APDTRPAPGS TAPPAHGVTS  780
APDTRPAPGS TAPPAHGVTS APDTRPAPGS TAPPAHGVTS APDTRPAPGS TAPPAHGVTS  840
APDTRPAPGS TAPPAHGVTS APDTRPAPGS TAPPAHGVTS APDTRPAPGS TAPPAHGVTS  900
APDTRPAPGS TAPPAHGVTS APDTRPAPGS TAPPAHGVTS APDNRPALGS TAPPVHNVTS  960
ASGSASGSAS TLVHNGTSAR ATTTPASKST PFSIPSHHSD TPTTLASHST KTDASSTHHS 1020
SVPPLTSSNH STSPQLSTGV SFFFLSFHIS NLQFNSSLED PSTDYYQELQ RDISEMFLQI 1080
YKQGGFLGLS NIKFRPGSVV VQLTLAFREG TINVHDVETQ FNQYKTEAAS RYNLTISDVS 1140
VSDVPFPFSA QSGAGVPGWG IALLVLVCVL VALAIVYLIA LAVCQCRRKN YGQLDIFPAR 1200
DTYHPMSEYP TYHTHGRYVP PSSTDRSPYE KVSAGNGGSS LSYTNPAVAA ASANL      1255

SEQ ID NO: 2           moltype = AA  length = 19
FEATURE                Location/Qualifiers
REGION                 1..19
                       note = N-terminal MUC-1 signaling sequence
source                 1..19
                       mol_type = protein
                       organism = synthetic construct
SEQUENCE: 2
MTPGTQSPFF LLLLLTVLT                                               19

SEQ ID NO: 3           moltype = AA  length = 23
FEATURE                Location/Qualifiers
REGION                 1..23
                       note = N-terminal MUC-1 signaling sequence
source                 1..23
                       mol_type = protein
                       organism = synthetic construct
SEQUENCE: 3
MTPGTQSPFF LLLLLTVLTV VTA                                          23

SEQ ID NO: 4           moltype = AA  length = 23
FEATURE                Location/Qualifiers
```

```
REGION                  1..23
                        note = N-terminal MUC-1 signaling sequence
source                  1..23
                        mol_type = protein
                        organism = synthetic construct
SEQUENCE: 4
MTPGTQSPFF LLLLLTVLTV VTG                                                 23

SEQ ID NO: 5            moltype = AA   length = 146
FEATURE                 Location/Qualifiers
REGION                  1..146
                        note = Truncated MUC1 receptor isoform having nat-PSMGFR at
                         its N-terminus and including the transmembrane and
                         cytoplasmic sequences of a full-length MUC1 receptor
source                  1..146
                        mol_type = protein
                        organism = synthetic construct
SEQUENCE: 5
GTINVHDVET QFNQYKTEAA SRYNLTISDV SVSDVPFPFS AQSGAGVPGW GIALLVLVCV          60
LVALAIVYLI ALAVCQCRRK NYGQLDIFPA RDTYHPMSEY PTYHTHGRYV PPSSTDRSPY         120
EKVSAGNGGS SLSYTNPAVA AASANL                                             146

SEQ ID NO: 6            moltype = AA   length = 45
FEATURE                 Location/Qualifiers
REGION                  1..45
                        note = PSMGFR sequence
source                  1..45
                        mol_type = protein
                        organism = synthetic construct
SEQUENCE: 6
GTINVHDVET QFNQYKTEAA SRYNLTISDV SVSDVPFPFS AQSGA                          45

SEQ ID NO: 7            moltype = AA   length = 44
FEATURE                 Location/Qualifiers
REGION                  1..44
                        note = PSMGFR sequence
source                  1..44
                        mol_type = protein
                        organism = synthetic construct
SEQUENCE: 7
TINVHDVETQ FNQYKTEAAS RYNLTISDVS VSDVPFPFSA QSGA                           44

SEQ ID NO: 8            moltype = AA   length = 45
FEATURE                 Location/Qualifiers
REGION                  1..45
                        note = PSMGFR sequence
source                  1..45
                        mol_type = protein
                        organism = synthetic construct
SEQUENCE: 8
GTINVHDVET QFNQYKTEAA SPYNLTISDV SVSDVPFPFS AQSGA                          45

SEQ ID NO: 9            moltype = AA   length = 44
FEATURE                 Location/Qualifiers
REGION                  1..44
                        note = PSMGFR sequence
source                  1..44
                        mol_type = protein
                        organism = synthetic construct
SEQUENCE: 9
TINVHDVETQ FNQYKTEAAS PYNLTISDVS VSDVPFPFSA QSGA                           44

SEQ ID NO: 10           moltype = DNA   length = 216
FEATURE                 Location/Qualifiers
misc_feature            1..216
                        note = MUC1 cytoplasmic domain nucleotide sequence
source                  1..216
                        mol_type = other DNA
                        organism = synthetic construct
SEQUENCE: 10
tgtcagtgcc gccgaaagaa ctacgggcag ctggacatct ttccagcccg ggatacctac          60
catcctatga gcgagtaccc cacctaccac acccatgggc gctatgtgcc ccctagcagt         120
accgatcgta gccctatga gaaggtttct gcaggtaacg gtggcagcag cctctcttac         180
acaaacccag cagtggcagc cgcttctgcc aacttg                                  216

SEQ ID NO: 11           moltype = AA   length = 72
FEATURE                 Location/Qualifiers
REGION                  1..72
                        note = MUC1 cytoplasmic domain amino acid sequence
```

```
source                  1..72
                        mol_type = protein
                        organism = synthetic construct
SEQUENCE: 11
CQCRRKNYGQ LDIFPARDTY HPMSEYPTYH THGRYVPPSS TDRSPYEKVS AGNGGSSLSY    60
TNPAVAAASA NL                                                       72

SEQ ID NO: 12           moltype = DNA  length = 854
FEATURE                 Location/Qualifiers
misc_feature            1..854
                        note = NME7 nucleotide sequence (NME7: GENBANK ACCESSION
                        AB209049)
source                  1..854
                        mol_type = other DNA
                        organism = synthetic construct
SEQUENCE: 12
gagatcctga gacaatgaat catagtgaaa gattcgtttt cattgcagag tggtatgatc    60
caaatgcttc acttcttcga cgttatgagc ttttatttta cccaggggat ggatctgttg   120
aaatgcatga tgtaaagaat catcgcacct ttttaaagcg gaccaaatat gataacctgc   180
acttggaaga tttatttata ggcaacaaag tgaatgtctt ttctcgacaa ctggtattaa   240
ttgactatgg ggatcaatat acagctcgcc agctgggcag taggaaagaa aaaacgctag   300
ccctaattaa accagatgca atatcaaagg ctggagaaat aataaacaaag   360
ctggatttac tataaccaaa ctcaaaatga tgatgctttc aaggaaagaa gcattggatt   420
ttcatgtaga tcaccagtca agacccttt tcaatgagct gatccagttt attacaactg   480
gtcctattat tgccatggag attttaagag atgatgctat atgtgaatgg aaaagactgc   540
tgggacctgc aaactctgga gtggcacgca cagatgcttc tgaaagcatt agagccctct   600
ttggaacaga tggcataaga aatgcagcgc atggccctga ttcttttgct tctgcggcca   660
gagaaatgga gttgtttttt ccttcaagtg gaggttgtgg gccggcaaac actgctaaat   720
ttactaattg tacctgttgc attgttaaac cccatgctgt cagtgaaggt atgttgaata   780
cactatattc agtacatttt gttaatagga gcaatgtt tattttcttg atgtacttta   840
tgtatagaaa ataa                                                    854

SEQ ID NO: 13           moltype = AA  length = 283
FEATURE                 Location/Qualifiers
REGION                  1..283
                        note = NME7 amino acid sequence (NME7: GENBANK ACCESSION
                        AB209049)
source                  1..283
                        mol_type = protein
                        organism = synthetic construct
SEQUENCE: 13
DPETMNHSER FVFIAEWYDP NASLLRRYEL LFYPGDGSVE MHDVKNHRTF LKRTKYDNLH    60
LEDLFIGNKV NVFSRQLVLI DYGDQYTARQ LGSRKEKTLA LIKPDAISKA GEIIEIINKA   120
GFTITKLKMM MLSRKEALDF HVDHQSRPFF NELIQFITTG PIIAMEILRD DAICEWKRLL   180
GPANSGVART DASESIRALF GTDGIRNAAH GPDSFASAAR EMELFFPSSG GCGPANTAKF   240
TNCTCCIVKP HAVSEGMLNT LYSVHFVNRR AMFIFLMYFM YRK                     283

SEQ ID NO: 14           moltype = DNA  length = 534
FEATURE                 Location/Qualifiers
misc_feature            1..534
                        note = NM23-H1 nucleotide sequence (NM23-H1: GENBANK
                        ACCESSION AF487339)
source                  1..534
                        mol_type = other DNA
                        organism = synthetic construct
SEQUENCE: 14
atggtgctac tgtctacttt agggatcgtc tttcaaggcg aggggcctcc tatctcaagc    60
tgtgatacag gaaccatggc caactgtgag cgtaccttca ttgcgatcaa accagatggg   120
gtccagcggg gtcttgtggg agagattatc aagcgttttg agcagaaagg attccgcctt   180
gttggtctga aattcatgca agcttccgaa gatctgctca aggaacacta cgttgacctg   240
aaggaccgtc cattctttgc cggcctggtg aaatacatgc actcagggcc ggtagttgcc   300
atggtctggg aggggctgaa tgtggtgaag acgggccgag tcatgctcgg ggagaccaac   360
cctgcagact ccaagcctgg gaccatccgt ggagacttct gcatacaagt ggcaggaac   420
attatacatg gcagtgattc tgtggagagt gcagagaagg agatcggctt gtggtttcac   480
cctgaggaac tggtagatta cacgagctgt gctcagaact ggatctatga atga        534

SEQ ID NO: 15           moltype = AA  length = 177
FEATURE                 Location/Qualifiers
REGION                  1..177
                        note = NM23-H1 describes amino acid sequence (NM23-H1:
                        GENBANK ACCESSION AF487339)
source                  1..177
                        mol_type = protein
                        organism = synthetic construct
SEQUENCE: 15
MVLLSTLGIV FQGEGPPISS CDTGTMANCE RTFIAIKPDG VQRGLVGEII KRFEQKGFRL    60
VGLKFMQASE DLLKEHYVDL KDRPFFAGLV KYMHSGPVVA MVWEGLNVVK TGRVMLGETN   120
PADSKPGTIR GDFCIQVGRN IIHGSDSVES AEKEIGLWFH PEELVDYTSC AQNWIYE      177
```

| SEQ ID NO: 16 | moltype = DNA  length = 534 |
| --- | --- |
| FEATURE | Location/Qualifiers |
| misc_feature | 1..534 |
| | note = NM23-H1 S120G mutant nucleotide sequence (NM23-H1: GENBANK ACCESSION AF487339) |
| source | 1..534 |
| | mol_type = other DNA |
| | organism = synthetic construct |

SEQUENCE: 16

```
atggtgctac tgtctacttt agggatcgtc tttcaaggcg aggggcctcc tatctcaagc   60
tgtgatacag gaaccatggc caactgtgag cgtaccttca ttgcgatcaa accagatggg  120
gtccagcggg gtcttgtggg agagattatc aagcgttttg agcagaaagg attccgcctt  180
gttggtctga aattcatgca agcttccgaa gatcttctca ggaacactac cgttgacctg  240
aaggaccgtc cattctttgc cggcctggtg aaatacatgc actcagggcc ggtagttgcc  300
atggtctggg aggggctgaa tgtggtgaag acgggccgag tcatgctcgg ggagaccaac  360
cctgcagact ccaagcctgg gaccatccgt ggagacttct gcatacaagt tggcaggaac  420
attatacatg gcggtgattc tgtggagagt gcagagaagg agatcggctt gtggtttcac  480
cctgaggaac tggtagatta cacgagctgt gctcagaact ggatctatga atga         534
```

| SEQ ID NO: 17 | moltype = AA  length = 177 |
| --- | --- |
| FEATURE | Location/Qualifiers |
| REGION | 1..177 |
| | note = NM23-H1 S120G mutant amino acid sequence (NM23-H1: GENBANK ACCESSION AF487339) |
| source | 1..177 |
| | mol_type = protein |
| | organism = synthetic construct |

SEQUENCE: 17

```
MVLLSTLGIV FQGEGPPISS CDTGTMANCE RTFIAIKPDG VQRGLVGEII KRFEQKGFRL   60
VGLKFMQASE DLLRNTTVDL KDRPFFAGLV KYMHSGPVVA MVWEGLNVVK TGRVMLGETN  120
PADSKPGTIR GDFCIQVGRN IIHGGDSVES AEKEIGLWFH PEELVDYTSC AQNWIYE     177
```

| SEQ ID NO: 18 | moltype = DNA  length = 459 |
| --- | --- |
| FEATURE | Location/Qualifiers |
| misc_feature | 1..459 |
| | note = NM23-H2 nucleotide sequence (NM23-H2: GENBANK ACCESSION AK313448) |
| source | 1..459 |
| | mol_type = other DNA |
| | organism = synthetic construct |

SEQUENCE: 18

```
atggccaacc tggagcgcac cttcatcgcc atcaagccgg acggcgtgca gcgcggcctg   60
gtgggcgaga tcatcaagcg cttcgagcag aagggattcc gcctcgtggc catgaagttc  120
ctccgggcct ctgaagaaca cctgaagcag cactacattg acctgaaaga ccgaccattc  180
ttccctgggc tggtgaagta catgaactca gggccggttg tggccatggt ctgggagggg  240
ctgaacgtgg tgaagacagg ccgagtgatg cttggggaga ccaatccagc agattcaaag  300
ccaggcacca ttcgtgggga cttctgcatt caggttgcgg gaacatcat tcatggcagt  360
gattcagtaa aaagtgctga aaaagaaatc agcctatggt ttaagcctga agaactggtt  420
gactacaagt cttgtgctca tgactgggtc tatgaataa                         459
```

| SEQ ID NO: 19 | moltype = AA  length = 152 |
| --- | --- |
| FEATURE | Location/Qualifiers |
| REGION | 1..152 |
| | note = NM23-H2 amino acid sequence (NM23-H2: GENBANK ACCESSION AK313448) |
| source | 1..152 |
| | mol_type = protein |
| | organism = synthetic construct |

SEQUENCE: 19

```
MANLERTFIA IKPDGVQRGL VGEIIKRFEQ KGFRLVAMKF LRASEEHLKQ HYIDLKDRPF   60
FPGLVKYMNS GPVVAMVWEG LNVVKTGRVM LGETNPADSK PGTIRGDFCI QVGRNIIHGS  120
DSVKSAEKEI SLWFKPEELV DYKSCAHDWV YE                                152
```

| SEQ ID NO: 20 | moltype = DNA  length = 1023 |
| --- | --- |
| FEATURE | Location/Qualifiers |
| misc_feature | 1..1023 |
| | note = Human NM23-H7-2 sequence optimized for E. coli expression |
| source | 1..1023 |
| | mol_type = other DNA |
| | organism = synthetic construct |

SEQUENCE: 20

```
atgcatgacg ttaaaaatca ccgtaccttt ctgaaacgca cgaaaatatga taatctgcat   60
ctggaagacc tgtttattgg caacaaagtc aatgtgttct ctcgtcagct ggtgctgatc  120
gattatggcg accagtacac cgcgcgtcaa ctgggtagtc gcaaagaaaa aacgctggcc  180
ctgattaaac cggatgcaat ctccaaagct ggcgaaatta cgaaattat caacaaagcg  240
gtttcacca tcacgaaact gaaaatgatg atgctgagcc gtaaagaagc cctgattttt  300
catgtcgacc accagtctcg cccgttttc aatgaactga ttcaattcat caccacgggt  360
ccgattatcg caatgaaaat tctgcgtgat gacgctatct gcgaatggaa acgcctgctg  420
```

```
ggcccggcaa actcaggtgt tgcgcgtacc gatgccagtg aatccattcg cgctctgttt    480
ggcaccgatg gtatccgtaa tgcagcacat ggtccggact cattcgcatc ggcagctcgt    540
gaaatggaac tgttttttcc gagctctggc ggttgcggtc cggcaaacac cgccaaattt    600
accaattgta cgtgctgtat tgtcaaaccg cacgcagtgt cagaaggcct gctgggtaaa    660
attctgatgg caatccgtga tgctggcttt gaaatctacg ccatgcagat gttcaacatg    720
gaccgcgtta acgtcgaaga attctacgaa gtttacaaag gcgtggttac cgaatatcac    780
gatatggtta cggaaatgta ctccggtccg tgcgtcgcga tggaaattca gcaaaacaat    840
gccaccaaaa cgtttcgtga attctgtggt ccggcagatc cggaaatcgc acgtcatctg    900
cgtccgggta ccctgcgcgc aatttttggt aaaacgaaaa tccagaacgc tgtgcactgt    960
accgatctgc cggaagacgg tctgctggaa gttaatact  ttttcaaaat tctggataat   1020
tga                                                                 1023

SEQ ID NO: 21             moltype = AA  length = 340
FEATURE                   Location/Qualifiers
REGION                    1..340
                          note = Human NM23-H7-2 sequence optimized for E. coli
                          expression
source                    1..340
                          mol_type = protein
                          organism = synthetic construct
SEQUENCE: 21
MHDVKNHRTF LKRTKYDNLH LEDLFIGNKV NVFSRQLVLI DYGDQYTARQ LGSRKEKTLA    60
LIKPDAISKA GEIIEIINKA GFTITKLKMM MLSRKEALDF HVDHQSRPFF NELIQFITTG   120
PIIAMEILRD DAICEWKRLL GPANSGVART DASESIRALF GTDGIRNAAH GPDSFASAAR   180
EMELFFPSSG GCGPANTAKF TNCTCCIVKP HAVSEGLLGK ILMAIRDAGF EISAMQMFNM   240
DRVNVEEFYE VYKGVVTEYH DMVTEMYSGP CVAMEIQQNN ATKTFREFCG PADPEIARHL   300
RPGTLRAIFG KTKIQNAVHC TDLPEDGLLE VQYFFKILDN                        340

SEQ ID NO: 22             moltype = DNA  length = 399
FEATURE                   Location/Qualifiers
misc_feature              1..399
                          note = Human NME7-A
source                    1..399
                          mol_type = other DNA
                          organism = synthetic construct
SEQUENCE: 22
atggaaaaaa cgctagccct aattaaacca gatgcaatat caaaggctgg agaaataatt     60
gaataataa acaaagctgg atttactata accaaactca aatgatgat gctttcaagg    120
aaagaagcat tggattttca tgtagatcac cagtcaagac cctttttcaa tgagctgatc    180
cagtttatta caactggtcc tattattgcc atggagattt taagagatga tgctatatgt    240
gaatggaaaa gactgctggg acctgcaaac tctggagtgg cacgcacaga tgcttctgaa    300
agcattagag ccctctttgg aacagatggc ataagaaatg cagcgcatgg ccctgattct    360
tttgcttctg cggccagaga aatggagttg ttttttttga                         399

SEQ ID NO: 23             moltype = AA  length = 132
FEATURE                   Location/Qualifiers
REGION                    1..132
                          note = Human NME7-A
source                    1..132
                          mol_type = protein
                          organism = synthetic construct
SEQUENCE: 23
MEKTLALIKP DAISKAGEII EIINKAGFTI TKLKMMMLSR KEALDFHVDH QSRPFFNELI     60
QFITTGPIIA MEILRDDAIC EWKRLLGPAN SGVARTDASE SIRALFGTDG IRNAAHGPDS   120
FASAAREMEL FF                                                      132

SEQ ID NO: 24             moltype = DNA  length = 444
FEATURE                   Location/Qualifiers
misc_feature              1..444
                          note = Human NME7-A1
source                    1..444
                          mol_type = other DNA
                          organism = synthetic construct
SEQUENCE: 24
atggaaaaaa cgctagccct aattaaacca gatgcaatat caaaggctgg agaaataatt     60
gaataataa acaaagctgg atttactata accaaactca aatgatgat gctttcaagg    120
aaagaagcat tggattttca tgtagatcac cagtcaagac cctttttcaa tgagctgatc    180
cagtttatta caactggtcc tattattgcc atggagattt taagagatga tgctatatgt    240
gaatggaaaa gactgctggg acctgcaaac tctggagtgg cacgcacaga tgcttctgaa    300
agcattagag ccctctttgg aacagatggc ataagaaatg cagcgcatgg ccctgattct    360
tttgcttctg cggccagaga aatggagttg ttttttcctt caagtggagg ttgtgggccg    420
gcaaacactg ctaaatttac ttga                                         444

SEQ ID NO: 25             moltype = AA  length = 147
FEATURE                   Location/Qualifiers
REGION                    1..147
                          note = Human NME7-A1
source                    1..147
                          mol_type = protein
```

```
                       organism = synthetic construct
SEQUENCE: 25
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FFPSSGGCGP ANTAKFT                                      147

SEQ ID NO: 26          moltype = DNA  length = 669
FEATURE                Location/Qualifiers
misc_feature           1..669
                       note = Human NME7-A2
source                 1..669
                       mol_type = other DNA
                       organism = synthetic construct
SEQUENCE: 26
atgaatcata gtgaaagatt cgttttcatt gcagagtggt atgatccaaa tgcttcactt    60
cttcgacgtt atgagctttt attttaccca ggggatggat ctgttgaaat gcatgatgta   120
aagaatcatc gcaccttttt aaagcggacc aaatatgata acctgcactt ggaagattta   180
tttataggca acaaagtgaa tgtctttttct cgacaactgg tattaattga ctatggggat   240
caatatacag ctcgccagct gggcagtagg aaagaaaaaa cgctagccct aattaaacca   300
gatgcaatat caaaggctgg agaaataatt gaaataataa acaaagctgg atttactata   360
accaaactca aaatgatgat gctttcaagg aagaagcat tggattttca gtagatcac    420
cagtcaagac cctttttcaa tgagctgatc cagtttatta caactggtcc tattattgcc   480
atggagattt taagagatga tgctatatgt gaatggaaaa gactgctggg acctgcaaac   540
tctgagtgg cacgcacaga tgcttctgaa agcattagag ccctcttgg aacagatggc    600
ataagaaatg cagcgcatgg ccctgattct tttgcttctg cggccagaga aatggagttg   660
ttttttga                                                           669

SEQ ID NO: 27          moltype = AA   length = 222
FEATURE                Location/Qualifiers
REGION                 1..222
                       note = Human NME7-A2
source                 1..222
                       mol_type = protein
                       organism = synthetic construct
SEQUENCE: 27
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FF                     222

SEQ ID NO: 28          moltype = DNA  length = 714
FEATURE                Location/Qualifiers
misc_feature           1..714
                       note = Human NME7-A3
source                 1..714
                       mol_type = other DNA
                       organism = synthetic construct
SEQUENCE: 28
atgaatcata gtgaaagatt cgttttcatt gcagagtggt atgatccaaa tgcttcactt    60
cttcgacgtt atgagctttt attttaccca ggggatggat ctgttgaaat gcatgatgta   120
aagaatcatc gcaccttttt aaagcggacc aaatatgata acctgcactt ggaagattta   180
tttataggca acaaagtgaa tgtctttttct cgacaactgg tattaattga ctatggggat   240
caatatacag ctcgccagct gggcagtagg aaagaaaaaa cgctagccct aattaaacca   300
gatgcaatat caaaggctgg agaaataatt gaaataataa acaaagctgg atttactata   360
accaaactca aaatgatgat gctttcaagg aagaagcat tggattttca gtagatcac    420
cagtcaagac cctttttcaa tgagctgatc cagtttatta caactggtcc tattattgcc   480
atggagattt taagagatga tgctatatgt gaatggaaaa gactgctggg acctgcaaac   540
tctgagtgg cacgcacaga tgcttctgaa agcattagag ccctcttgg aacagatggc    600
ataagaaatg cagcgcatgg ccctgattct tttgcttctg cggccagaga aatggagttg   660
ttttttcctt caagtggagg ttgtgggccg gcaaacactg ctaaatttac ttga         714

SEQ ID NO: 29          moltype = AA   length = 237
FEATURE                Location/Qualifiers
REGION                 1..237
                       note = Human NME7-A3
source                 1..237
                       mol_type = protein
                       organism = synthetic construct
SEQUENCE: 29
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FFPSSGGCGP ANTAKFT      237

SEQ ID NO: 30          moltype = DNA  length = 408
FEATURE                Location/Qualifiers
misc_feature           1..408
                       note = Human NME7-B
source                 1..408
```

```
                        mol_type = other DNA
                        organism = synthetic construct
SEQUENCE: 30
atgaattgta cctgttgcat tgttaaaccc catgctgtca gtgaaggact gttgggaaag    60
atcctgatgg ctatccgaga tgcaggtttt gaaatctcag ctatgcagat gttcaatatg   120
gatcgggtta atgttgagga attctatgaa gtttataaag gagtagtgac cgaatatcat   180
gacatggtga cagaaatgta ttctggcccc tgtgtagcaa tggagattca acagaataat   240
gctacaaaga catttcgaga attttgtgga cctgctgatc ctgaaattgc ccggcattta   300
cgccctggaa ctctcagagc aatctttggt aaaactaaga tccagaatgc tgttcactgt   360
actgatctgc cagaggatgg cctattagag gttcaatact tcttctga               408

SEQ ID NO: 31          moltype = AA  length = 135
FEATURE                Location/Qualifiers
REGION                 1..135
                       note = Human NME7-B
source                 1..135
                       mol_type = protein
                       organism = synthetic construct
SEQUENCE: 31
MNCTCCIVKP HAVSEGLLGK ILMAIRDAGF EISAMQMFNM DRVNVEEFYE VYKGVVTEYH    60
DMVTEMYSGP CVAMEIQQNN ATKTFREFCG PADPEIARHL RPGTLRAIFG KTKIQNAVHC   120
TDLPEDGLLE VQYFF                                                   135

SEQ ID NO: 32          moltype = DNA  length = 426
FEATURE                Location/Qualifiers
misc_feature           1..426
                       note = Human NME7-B1
source                 1..426
                       mol_type = other DNA
                       organism = synthetic construct
SEQUENCE: 32
atgaattgta cctgttgcat tgttaaaccc catgctgtca gtgaaggact gttgggaaag    60
atcctgatgg ctatccgaga tgcaggtttt gaaatctcag ctatgcagat gttcaatatg   120
gatcgggtta atgttgagga attctatgaa gtttataaag gagtagtgac cgaatatcat   180
gacatggtga cagaaatgta ttctggcccc tgtgtagcaa tggagattca acagaataat   240
gctacaaaga catttcgaga attttgtgga cctgctgatc ctgaaattgc ccggcattta   300
cgccctggaa ctctcagagc aatctttggt aaaactaaga tccagaatgc tgttcactgt   360
actgatctgc cagaggatgg cctattagag gttcaatact tcttcaagat cttggataat   420
tagtga                                                             426

SEQ ID NO: 33          moltype = AA  length = 140
FEATURE                Location/Qualifiers
REGION                 1..140
                       note = Human NME7-B1
source                 1..140
                       mol_type = protein
                       organism = synthetic construct
SEQUENCE: 33
MNCTCCIVKP HAVSEGLLGK ILMAIRDAGF EISAMQMFNM DRVNVEEFYE VYKGVVTEYH    60
DMVTEMYSGP CVAMEIQQNN ATKTFREFCG PADPEIARHL RPGTLRAIFG KTKIQNAVHC   120
TDLPEDGLLE VQYFFKILDN                                              140

SEQ ID NO: 34          moltype = DNA  length = 453
FEATURE                Location/Qualifiers
misc_feature           1..453
                       note = Human NME7-B2
source                 1..453
                       mol_type = other DNA
                       organism = synthetic construct
SEQUENCE: 34
atgccttcaa gtggaggttg tgggccggca aacactgcta aatttactaa ttgtacctgt    60
tgcattgtta aacccatgc tgtcagtgaa ggactgttgg gaaagatcct gatggctatc   120
cgagatgcag gttttgaaat ctcagctatg cagatgttca atatggatcg ggttaatgtt   180
gaggaattct atgaagttta taaggagta gtgaccgaat atcatgacat ggtgacagaa   240
atgtattctg gcccttgtgt agcaatggag attcaacaga ataatgctac aaagacattt   300
cgagaatttt gtggacctgc tgatcctgaa attgcccggc atttacgccc tggaactctc   360
agagcaatct ttggtaaaac taagatccag aatgctgttc actgtactga tctgccagag   420
gatggcctat tagaggttca atacttcttc tga                               453

SEQ ID NO: 35          moltype = AA  length = 150
FEATURE                Location/Qualifiers
REGION                 1..150
                       note = Human NME7-B2
source                 1..150
                       mol_type = protein
                       organism = synthetic construct
SEQUENCE: 35
MPSSGGCGPA NTAKFTNCTC CIVKPHAVSE GLLGKILMAI RDAGFEISAM QMFNMDRVNV    60
EEFYEVYKGV VTEYHDMVTE MYSGPCVAME IQQNNATKTF REFCGPADPE IARHLRPGTL   120
```

RAIFGKTKIQ NAVHCTDLPE DGLLEVQYFF                                  150

SEQ ID NO: 36           moltype = DNA   length = 471
FEATURE                 Location/Qualifiers
misc_feature            1..471
                        note = Human NME7-B3
source                  1..471
                        mol_type = other DNA
                        organism = synthetic construct
SEQUENCE: 36
atgccttcaa gtggaggttg tgggccggca acactgcta aatttactaa ttgtacctgt    60
tgcattgtta aacccatgc tgtcagtgaa ggactgttgg gaaagatcct gatggctatc   120
cgagatgcag gttttgaaat ctcagctatg cagatgttca atatggatcg ggttaatgtt   180
gaggaattct atgaagttta taaggagta gtgaccgaat atcatgacat ggtgacagaa   240
atgtattctg gcccttgtgt agcaatggag attcaacaga ataatgctac aaagacttt   300
cgagaatttt gtggacctgc tgatcctgaa attgcccggc atttacgccc tggaactctc   360
agagcaatct ttggtaaaac taagatccag aatgctgttc actgtactga tctgccagag   420
gatggcctat tagaggttca atacttcttc aagatcttgg ataattagtg a            471

SEQ ID NO: 37           moltype = AA    length = 155
FEATURE                 Location/Qualifiers
REGION                  1..155
                        note = Human NME7-B3
source                  1..155
                        mol_type = protein
                        organism = synthetic construct
SEQUENCE: 37
MPSSGGCGPA NTAKFTNCTC CIVKPHAVSE GLLGKILMAI RDAGFEISAM QMFNMDRVNV    60
EEFYEVYKGV VTEYHDMVTE MYSGPCVAME IQQNNATKTF REFCGPADPE IARHLRPGTL   120
RAIFGKTKIQ NAVHCTDLPE DGLLEVQYFF KILDN                               155

SEQ ID NO: 38           moltype = DNA   length = 864
FEATURE                 Location/Qualifiers
misc_feature            1..864
                        note = Human NME7-AB, also known as NME7AB
source                  1..864
                        mol_type = other DNA
                        organism = synthetic construct
SEQUENCE: 38
atggaaaaaa cgctagccct aattaaacca gatgcaatat caaaggctgg agaaataatt    60
gaaataataa acaaagctgg atttactata accaaactca aatgatgat gctttcaagg   120
aaagaagcat tggattttca tgtagatcac cagtcaagac ccttttcaa tgagctgatc   180
cagtttatta caactggtcc tattattgcc atggagatt taagagatga tgctatatgt   240
gaatggaaaa gactgctggg acctgcaaac tctggagtgg cacgcacaga tgcttctgaa   300
agcattagag ccctctttgg aacagatggc ataagaaatg cagcgcatgg ccctgattct   360
tttgcttctg cggccagaga aatggagttg ttttttcctt caagtggagg ttgtgggccg   420
gcaaacactg ctaaatttac taattgtacc tgttgcattg ttaaacccca tgctgtcagt   480
gaaggactgt tgggaaagat cctgatggct atccgagatg caggtttga atctctcagct   540
atgcagatgt tcaatatgga tcgggttaat gttgaggaat tctatgaagt ttataaagga   600
gtagtgaccg aatatcatga catggtgaca gaaatgtatt ctggcccttg tgtagcaatg   660
gagattcaac agaataatgc tacaaagaca tttcgagaat tttgtggacc tgctgatcct   720
gaaattgccc ggcatttacg ccctggaact ctcagagcaa tctttggtaa aactaagatc   780
cagaatgctg ttcactgtac tgatctgcca gaggatggcc tattagaggt tcaatacttc   840
ttcaagatct tggataatta gtga                                           864

SEQ ID NO: 39           moltype = AA    length = 286
FEATURE                 Location/Qualifiers
REGION                  1..286
                        note = Human NME7-AB, also known as NME7AB
source                  1..286
                        mol_type = protein
                        organism = synthetic construct
SEQUENCE: 39
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FFPSSGGCGP ANTAKFTNCT CCIVKPHAVS EGLLGKILMA IRDAGFEISA   180
MQMFNMDRVN VEEFYEVYKG VVTEYHDMVT EMYSGPCVAM EIQQNNATKT FREFCGPADP   240
EIARHLRPGT LRAIFGKTKI QNAVHCTDLP EDGLLEVQYF FKILDN                  286

SEQ ID NO: 40           moltype = DNA   length = 846
FEATURE                 Location/Qualifiers
misc_feature            1..846
                        note = Human NME7-AB1
source                  1..846
                        mol_type = other DNA
                        organism = synthetic construct
SEQUENCE: 40
atggaaaaaa cgctagccct aattaaacca gatgcaatat caaaggctgg agaaataatt    60
gaaataataa acaaagctgg atttactata accaaactca aatgatgat gctttcaagg   120

```
aaagaagcat tggattttca tgtagatcac cagtcaagac ccttttcaa tgagctgatc    180
cagtttatta caactggtcc tattattgcc atggagattt taagagatga tgctatatgt   240
gaatggaaaa gactgctggg acctgcaaac tctggagtgg cacgcacaga tgcttctgaa   300
agcattagag ccctctttgg aacagatggc ataagaaatg cagcgcatgg ccctgattct   360
tttgcttctg cggccagaga aatggagttg tttttccctt caagtggagg ttgtgggccg   420
gcaaacactg ctaaatttac taattgtacc tgttgcattg ttaaaccca tgctgtcagt    480
gaaggactgt tgggaaagat cctgatggct atccgagatg caggttttga aatctcagct   540
atgcagatgt tcaatatgga tcgggttaat gttgaggaat ctatgaagt ttataaagga    600
gtagtgaccg aatatcatga catggtgaca gaaatgtatt ctggcccttg tgtagcaatg   660
gagattcaac agaataatgc tacaaagaca tttcgagaat tttgtggacc tgctgatcct   720
gaaattgccc ggcatttacg ccctggaact ctcagagcaa tctttggtaa aactaagatc   780
cagaatgctg ttcactgtac tgatctgcca gaggatggcc tattagaggt tcaatacttc   840
ttctga                                                              846

SEQ ID NO: 41        moltype = AA  length = 281
FEATURE              Location/Qualifiers
REGION               1..281
                     note = Human NME7-AB1
source               1..281
                     mol_type = protein
                     organism = synthetic construct
SEQUENCE: 41
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FFPSSGGCGP ANTAKFTNCT CCIVKPHAVS EGLLGKILMA IRDAGFEISA   180
MQMFNMDRVN VEEFYEVYKG VVTEYHDMVT EMYSGPCVAM EIQQNNATKT FREFCGPADP   240
EIARHLRPGT LRAIFGKTKI QNAVHCTDLP EDGLLEVQYF F                       281

SEQ ID NO: 42        moltype = DNA  length = 399
FEATURE              Location/Qualifiers
misc_feature         1..399
                     note = Human NME7-A sequence optimized for E. coli
                        expression
source               1..399
                     mol_type = other DNA
                     organism = synthetic construct
SEQUENCE: 42
atggaaaaaa cgctggccct gattaaaccg gatgcaatct ccaaagctgg cgaaattatc    60
gaaattatca acaaagcggg tttcaccatc acgaaactga aaatgatgat gctgagccgt   120
aaagaagccc tggattttca tgtcgaccac cagtctcgcc cgttttttcaa tgaactgatt  180
caattcatca ccacgggtcc gattatcgca atggaaattc tgcgtgatga cgctatctgc   240
gaatggaaac gcctgctggg cccggcaaac tcaggtgttg cgcgtaccga tgccagtgaa   300
tccattcgcg ctctgtttgg caccgatggt atccgtaatg cagcacatgg tccggactca   360
ttcgcatcgg cagctcgtga aatggaactg tttttctga                          399

SEQ ID NO: 43        moltype = AA  length = 132
FEATURE              Location/Qualifiers
REGION               1..132
                     note = Human NME7-A sequence optimized for E. coli
                        expression
source               1..132
                     mol_type = protein
                     organism = synthetic construct
SEQUENCE: 43
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FF                                                       132

SEQ ID NO: 44        moltype = DNA  length = 444
FEATURE              Location/Qualifiers
misc_feature         1..444
                     note = Human NME7-A1 sequence optimized for E. coli
                        expression
source               1..444
                     mol_type = other DNA
                     organism = synthetic construct
SEQUENCE: 44
atggaaaaaa cgctggccct gattaaaccg gatgcaatct ccaaagctgg cgaaattatc    60
gaaattatca acaaagcggg tttcaccatc acgaaactga aaatgatgat gctgagccgt   120
aaagaagccc tggattttca tgtcgaccac cagtctcgcc cgttttttcaa tgaactgatt  180
caattcatca ccacgggtcc gattatcgca atggaaattc tgcgtgatga cgctatctgc   240
gaatggaaac gcctgctggg cccggcaaac tcaggtgttg cgcgtaccga tgccagtgaa   300
tccattcgcg ctctgtttgg caccgatggt atccgtaatg cagcacatgg tccggactca   360
ttcgcatcgg cagctcgtga aatggaactg ttttttccga gctctggcgg ttgcggtccg   420
gcaaacaccg ccaaatttac ctga                                          444

SEQ ID NO: 45        moltype = AA  length = 147
FEATURE              Location/Qualifiers
REGION               1..147
```

```
                        note = Human NME7-A1 sequence optimized for E. coli
                            expression
source                  1..147
                        mol_type = protein
                        organism = synthetic construct
SEQUENCE: 45
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FFPSSGGCGP ANTAKFT                                       147

SEQ ID NO: 46           moltype = DNA  length = 669
FEATURE                 Location/Qualifiers
misc_feature            1..669
                        note = Human NME7-A2 sequence optimized for E. coli
                            expression
source                  1..669
                        mol_type = other DNA
                        organism = synthetic construct
SEQUENCE: 46
atgaatcact ccgaacgctt tgttttatc gccgaatggt atgacccgaa tgcttccctg     60
ctgcgccgct acgaactgct gttttatccg ggcgatggta gcgtggaaat gcatgacgtt   120
aaaaatcacc gtacctttct gaaacgcacg aaatatgata atctgcatct ggaagacctg   180
tttattggca acaaagtcaa tgtgttctct cgtcagctgg tgctgatcga ttatggcgac   240
cagtacaccg cgcgtcaact gggtagtcgc aagaaaaaa cgctggccct gattaaaccg    300
gatgcaatct ccaaagctgg cgaaattatc gaaattatca caaagcggg tttccaccatc   360
acgaaactga aaatgatgat gctgagccgt aagaagccc tggattttca tgtcgaccac    420
cagtctcgcc cgttttttcaa tgaactgatt caattcatca ccacgggtcc gattatcgca  480
atggaaattc tgcgtgatga cgctatctgc gaatggaaac gcctgctggg cccggcaaac   540
tcaggtgttg cgcgtaccga tgccagtgaa tccattcgcg ctctgtttgg caccgatggt   600
atccgtaatg cagcacatgg tccggactca ttcgcatcgg cagctcgtga atggaactg    660
ttttttctga                                                          669

SEQ ID NO: 47           moltype = AA  length = 222
FEATURE                 Location/Qualifiers
REGION                  1..222
                        note = Human NME7-A2 sequence optimized for E. coli
                            expression
source                  1..222
                        mol_type = protein
                        organism = synthetic construct
SEQUENCE: 47
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FF                      222

SEQ ID NO: 48           moltype = DNA  length = 714
FEATURE                 Location/Qualifiers
misc_feature            1..714
                        note = Human NME7-A3 sequence optimized for E. coli
                            expression
source                  1..714
                        mol_type = other DNA
                        organism = synthetic construct
SEQUENCE: 48
atgaatcact ccgaacgctt tgttttatc gccgaatggt atgacccgaa tgcttccctg     60
ctgcgccgct acgaactgct gttttatccg ggcgatggta gcgtggaaat gcatgacgtt   120
aaaaatcacc gtacctttct gaaacgcacg aaatatgata atctgcatct ggaagacctg   180
tttattggca acaaagtcaa tgtgttctct cgtcagctgg tgctgatcga ttatggcgac   240
cagtacaccg cgcgtcaact gggtagtcgc aagaaaaaa cgctggccct gattaaaccg    300
gatgcaatct ccaaagctgg cgaaattatc gaaattatca caaagcggg tttccaccatc   360
acgaaactga aaatgatgat gctgagccgt aagaagccc tggattttca tgtcgaccac    420
cagtctcgcc cgttttttcaa tgaactgatt caattcatca ccacgggtcc gattatcgca  480
atggaaattc tgcgtgatga cgctatctgc gaatggaaac gcctgctggg cccggcaaac   540
tcaggtgttg cgcgtaccga tgccagtgaa tccattcgcg ctctgtttgg caccgatggt   600
atccgtaatg cagcacatgg tccggactca ttcgcatcgg cagctcgtga atggaactg    660
ttttttcccga gctctggcgg ttgcggtccg caaacaccg ccaaatttac ctga          714

SEQ ID NO: 49           moltype = AA  length = 237
FEATURE                 Location/Qualifiers
REGION                  1..237
                        note = Human NME7-A3 sequence optimized for E. coli
                            expression
source                  1..237
                        mol_type = protein
                        organism = synthetic construct
SEQUENCE: 49
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
```

```
TKLKMMMLSR KEALDFHVDH QSRPFFNELI QFITTGPIIA MEILRDDAIC EWKRLLGPAN    180
SGVARTDASE SIRALFGTDG IRNAAHGPDS FASAAREMEL FFPSSGGCGP ANTAKFT       237

SEQ ID NO: 50             moltype = DNA  length = 408
FEATURE                   Location/Qualifiers
misc_feature              1..408
                          note = Human NME7-B sequence optimized for E. coli
                            expression
source                    1..408
                          mol_type = other DNA
                          organism = synthetic construct
SEQUENCE: 50
atgaattgta cgtgctgtat tgtcaaaccg cacgcagtgt cagaaggcct gctgggtaaa    60
attctgatgg caatccgtga tgctggcttt gaaatctcgg ccatgcagat gttcaacatg    120
gaccgcgtta acgtcgaaga attctacgaa gtttacaaag cgtggttac cgaatatcac    180
gatatggtta cggaaatgta ctccggtccg tgcgtcgcga tggaaattca gcaaaacaat    240
gccaccaaaa cgtttcgtga attctgtggt ccggcagatc cggaaatcgc acgtcatctg    300
cgtccgggta ccctgcgcgc aatttttggt aaaacgaaaa tccagaacgc tgtgcactgt    360
accgatctgc cggaagacgg tctgctggaa gttcaatact ttttctga                408

SEQ ID NO: 51             moltype = AA  length = 135
FEATURE                   Location/Qualifiers
REGION                    1..135
                          note = Human NME7-B sequence optimized for E. coli
                            expression
source                    1..135
                          mol_type = protein
                          organism = synthetic construct
SEQUENCE: 51
MNCTCCIVKP HAVSEGLLGK ILMAIRDAGF EISAMQMFNM DRVNVEEFYE VYKGVVTEYH    60
DMVTEMYSGP CVAMEIQQNN ATKTFREFCG PADPEIARHL RPGTLRAIFG KTKIQNAVHC    120
TDLPEDGLLE VQYFF                                                    135

SEQ ID NO: 52             moltype = DNA  length = 423
FEATURE                   Location/Qualifiers
misc_feature              1..423
                          note = Human NME7-B1 sequence optimized for E. coli
                            expression
source                    1..423
                          mol_type = other DNA
                          organism = synthetic construct
SEQUENCE: 52
atgaattgta cgtgctgtat tgtcaaaccg cacgcagtgt cagaaggcct gctgggtaaa    60
attctgatgg caatccgtga tgctggcttt gaaatctcgg ccatgcagat gttcaacatg    120
gaccgcgtta acgtcgaaga attctacgaa gtttacaaag cgtggttac cgaatatcac    180
gatatggtta cggaaatgta ctccggtccg tgcgtcgcga tggaaattca gcaaaacaat    240
gccaccaaaa cgtttcgtga attctgtggt ccggcagatc cggaaatcgc acgtcatctg    300
cgtccgggta ccctgcgcgc aatttttggt aaaacgaaaa tccagaacgc tgtgcactgt    360
accgatctgc cggaagacgg tctgctggaa gttcaatact ttttcaaaat tctggataat    420
tga                                                                 423

SEQ ID NO: 53             moltype = AA  length = 140
FEATURE                   Location/Qualifiers
REGION                    1..140
                          note = Human NME7-B1 sequence optimized for E. coli
                            expression
source                    1..140
                          mol_type = protein
                          organism = synthetic construct
SEQUENCE: 53
MNCTCCIVKP HAVSEGLLGK ILMAIRDAGF EISAMQMFNM DRVNVEEFYE VYKGVVTEYH    60
DMVTEMYSGP CVAMEIQQNN ATKTFREFCG PADPEIARHL RPGTLRAIFG KTKIQNAVHC    120
TDLPEDGLLE VQYFFKILDN                                               140

SEQ ID NO: 54             moltype = DNA  length = 453
FEATURE                   Location/Qualifiers
misc_feature              1..453
                          note = Human NME7-B2 sequence optimized for E. coli
                            expression
source                    1..453
                          mol_type = other DNA
                          organism = synthetic construct
SEQUENCE: 54
atgccgagct ctggcggttg cggtccggca aacaccgcca aatttaccaa ttgtacgtgc    60
tgtattgtca aaccgcacgc agtgtcagaa ggcctgctgg gtaaaattct gatggcaatc    120
cgtgatgctg gctttgaaat ctcggccatg cagatgttca acatggaccg cgttaacgtc    180
gaagaattct acgaagttta caaaggcgtg gttaccgaat atcacgatat ggttacggaa    240
atgtactccg gtccgtgcgt cgcgatggaa attcagcaaa acaatgccac caaaacgttt    300
cgtgaattct gtggtccggc agatccggaa atcgcacgtc atctgcgtcc gggtaccctg    360
```

```
cgcgcaattt ttggtaaaac gaaaatccag aacgctgtgc actgtaccga tctgccggaa    420
gacggtctgc tggaagttca atactttttc tga                                 453

SEQ ID NO: 55           moltype = AA  length = 150
FEATURE                 Location/Qualifiers
REGION                  1..150
                        note = Human NME7-B2 sequence optimized for E. coli
                         expression
source                  1..150
                        mol_type = protein
                        organism = synthetic construct
SEQUENCE: 55
MPSSGGCGPA NTAKFTNCTC CIVKPHAVSE GLLGKILMAI RDAGFEISAM QMFNMDRVNV     60
EEFYEVYKGV VTEYHDMVTE MYSGPCVAME IQQNNATKTF REFCGPADPE IARHLRPGTL    120
RAIFGKTKIQ NAVHCTDLPE DGLLEVQYFF                                     150

SEQ ID NO: 56           moltype = DNA  length = 468
FEATURE                 Location/Qualifiers
misc_feature            1..468
                        note = Human NME7-B3 sequence optimized for E. coli
                         expression
source                  1..468
                        mol_type = other DNA
                        organism = synthetic construct
SEQUENCE: 56
atgccgagct ctggcggttg cggtccggca aacaccgcca aatttaccaa ttgtacgtgc     60
tgtattgtca aaccgcacgc agtgtcagaa ggcctgctgg gtaaaattct gatggcaatc    120
cgtgatgctg gctttgaaat ctcggccatg cagatgttca acatggaccg cgttaacgtc    180
gaagaattct acgaagttta caaggcgtg gttaccgaat atcacgatat ggttacgaaa    240
atgtactccg gtccgtgcgt cgcgatgaaa attcagcaaa acaatgccac caaaacgttt    300
cgtgaattct gtggtccggc agatccggaa atcgcacgtc atctgcgtcc gggtacccctg    360
cgcgcaattt ttggtaaaac gaaaatccag aacgctgtgc actgtaccga tctgccggaa    420
gacggtctgc tggaagttca atactttttc aaaattctgg ataattga                468

SEQ ID NO: 57           moltype = AA  length = 155
FEATURE                 Location/Qualifiers
REGION                  1..155
                        note = Human NME7-B3 sequence optimized for E. coli
                         expression
source                  1..155
                        mol_type = protein
                        organism = synthetic construct
SEQUENCE: 57
MPSSGGCGPA NTAKFTNCTC CIVKPHAVSE GLLGKILMAI RDAGFEISAM QMFNMDRVNV     60
EEFYEVYKGV VTEYHDMVTE MYSGPCVAME IQQNNATKTF REFCGPADPE IARHLRPGTL    120
RAIFGKTKIQ NAVHCTDLPE DGLLEVQYFF KILDN                               155

SEQ ID NO: 58           moltype = DNA  length = 861
FEATURE                 Location/Qualifiers
misc_feature            1..861
                        note = Human NME7-AB, also known as NME7AB sequence
                         optimized for E. coli expression
source                  1..861
                        mol_type = other DNA
                        organism = synthetic construct
SEQUENCE: 58
atggaaaaaa cgctggccct gattaaaccg gatgcaatct ccaaagctgg cgaaattatc     60
gaaattatca caaagcgggg tttcaccatc acgaaactga aatgatgat gctgagccgt    120
aaagaagccc tggattttca tgtcgaccac cagtctcgcc cgttttttcaa tgaactgatt    180
caattcatca ccacgggtcc gattatcgca atggaaattc tgcgtgatga cgctatctgc    240
gaatggaaac gcctgctggg cccggcaaac tcaggtgttg cgcgtaccga tgccagtgaa    300
tccattcgcg ctctgtttgg caccgatggt atccgtaatg cagcacatgg tccggactca    360
ttcgcatcgc agctcgtga atggaactg ttttttcccga gctctggcgg ttgcggtccg    420
gcaaacaccg ccaaatttac caattgtacg tgctgtatgtca caaccgca cgcagtgtca    480
gaaggcctgc tgggtaaaat tctgatggca atccgtgatg ctggctttga atctcggcc    540
atgcagatgt tcaacatgga ccgcgttaac gtcgaagaat tctacgaagt ttacaaggc    600
gtggttaccg aatatcacga tatggttacg gaaatgtact ccggtccgtg cgtcgcgatg    660
gaaattcagc aaaacaatgc caccaaaacg tttcgtgaat tctgtggtcc ggcagatccg    720
gaaatcgcac gtcatctgcg tccgggtacc ctgcgcgcaa ttttttggtaa aacgaaaatc    780
cagaacgctg tgcactgtac cgatctgccg gaagacggtc tgctggaagt tcaatacttt    840
ttcaaaattc tggataattg a                                              861

SEQ ID NO: 59           moltype = AA  length = 286
FEATURE                 Location/Qualifiers
REGION                  1..286
                        note = Human NME7-AB, also known as NME7AB sequence
                         optimized for E. coli expression
source                  1..286
                        mol_type = protein
```

```
                        organism = synthetic construct
SEQUENCE: 59
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FFPSSGGCGP ANTAKFTNCT CCIVKPHAVS EGLLGKILMA IRDAGFEISA   180
MQMFNMDRVN VEEFYEVYKG VVTEYHDMVT EMYSGPCVAM EIQQNNATKT FREFCGPADP   240
EIARHLRPGT LRAIFGKTKI QNAVHCTDLP EDGLLEVQYF FKILDN                  286

SEQ ID NO: 60           moltype = DNA   length = 846
FEATURE                 Location/Qualifiers
misc_feature            1..846
                        note = Human NME7-AB1, also known as NME7AB1 sequence
                         optimized for E. coli expression
source                  1..846
                        mol_type = other DNA
                        organism = synthetic construct
SEQUENCE: 60
atggaaaaaa cgctggccct gattaaaccg gatgcaatct ccaaagctgg cgaaattatc    60
gaaattatca acaaagcggg tttcaccatc acgaaactga aaatgatgat gctgagccgt   120
aaagaagccc tggattttca tgtcgaccac cagtctcgcc gttttttcaa tgaactgatt   180
caattcatca ccacgggtcc gattatcgca atggaaattc tgcgtgatga cgctatctgc   240
gaatggaaac gcctgctggg cccggcaaac tcaggtgttg cgcgtaccga tgccagtgaa   300
tccattcgcg ctctgtttgg caccgatggt atccgtaatg cagcacatgg tccggactca   360
ttcgcatcgg cagctcgtga atggaactg ttttcccga gctctggcgg ttgcggtccg    420
gcaaacaccg ccaaatttac caattgtacg tgctgtattg tcaaaccgca cgcagtgtca   480
gaaggcctgc tgggtaaaat tctgatgcca atcgtgacg ctggctttaa aatctcggcc    540
atgcagatgt tcaacatgga ccgcgttaac gtcgaagaat tctacgaagt ttacaaaggc   600
gtggttaccg aatatcacga tatggttacg gaaatgtact ccggtccgtg cgtcgcgatg   660
gaaattcagc aaaacaatgc caccaaaacg tttcgtgaat tctgtggtcc ggcagatccg   720
gaaatcgcac gtcatctgcg tccgggtacc ctgcgcgcaa ttttggtaa aacgaaaatc   780
cagaacgctg tgcactgtac cgatctgccg gaagacggtc tgctggaagt tcaatacttt   840
ttctga                                                              846

SEQ ID NO: 61           moltype = AA   length = 281
FEATURE                 Location/Qualifiers
REGION                  1..281
                        note = Human NME7-AB1, also known as NME7AB1 sequence
                         optimized for E. coli expression
source                  1..281
                        mol_type = protein
                        organism = synthetic construct
SEQUENCE: 61
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS   120
FASAAREMEL FFPSSGGCGP ANTAKFTNCT CCIVKPHAVS EGLLGKILMA IRDAGFEISA   180
MQMFNMDRVN VEEFYEVYKG VVTEYHDMVT EMYSGPCVAM EIQQNNATKT FREFCGPADP   240
EIARHLRPGT LRAIFGKTKI QNAVHCTDLP EDGLLEVQYF F                       281

SEQ ID NO: 62           moltype = DNA   length = 570
FEATURE                 Location/Qualifiers
misc_feature            1..570
                        note = Mouse NME6
source                  1..570
                        mol_type = other DNA
                        organism = synthetic construct
SEQUENCE: 62
atgacctcca tcttgcgaag tccccaagct cttcagctca cactagccct gatcaagcct    60
gatgcagttg cccacccact gatcctggag gctgttcatc agcagattct gagcaacaag   120
ttcctcattg tacgaacgag ggaactgcag tggaagctgg aggactgccg gaggttttac   180
cgagagcatg aagggcgttt tttctatcag cggctggtgg agttcatgac aagtgggcca   240
atccgagcct atatccttgc ccacaaagat gccatccaac tttggaggac actgatggga   300
cccaccagag tatttcgagc acgctatata gccccagatt caattcgtgg aagtttgggc   360
ctcactgaca cccgaaatac tacccatggc tcagactccg tggtttccgc cagcagagag   420
attgcagcct tcttccctga cttcagtgaa cagcgctggt atgaggagga ggaacccag    480
ctgcggtgtg gtcctgtgca ctacagtcca gaggaaggta tccactgtgc agctgaaaca   540
ggaggccaca acaacctaa caaaacctag                                     570

SEQ ID NO: 63           moltype = AA   length = 189
FEATURE                 Location/Qualifiers
REGION                  1..189
                        note = Mouse NME6
source                  1..189
                        mol_type = protein
                        organism = synthetic construct
SEQUENCE: 63
MTSILRSPQA LQLTLALIKP DAVAHPLILE AVHQQILSNK FLIVRTRELQ WKLEDCRRFY    60
REHEGRFFYQ RLVEFMTSGP IRAYILAHKD AIQLWRTLMG PTRVFRARYI APDSIRGSLG   120
LTDTRNTTHG SDSVVSASRE IAAFFPDFSE QRWYEEEEPQ LRCGPVHYSP EEGIHCAAET   180
GGHKQPNKT                                                           189
```

```
SEQ ID NO: 64           moltype = DNA  length = 585
FEATURE                 Location/Qualifiers
misc_feature            1..585
                        note = Human NME6
source                  1..585
                        mol_type = other DNA
                        organism = synthetic construct
SEQUENCE: 64
atgacccaga atctggggag tgagatggcc tcaatcttgc aagcccctca ggctctccag   60
ctcactctag ccctgatcaa gcctgacgca gtcgcccatc cactgattct ggaggctgtt  120
catcagcaga ttctaagcaa caagttcctg attgtacgaa tgagagaact actgtggaga  180
aaggaagatt gccagaggtt ttaccgagag catgaagggc gttttttcta tcagaggctg  240
gtggagttca tggccagcgg gccaatccga gcctacatcc ttgcccacaa ggatgccatc  300
cagctctgga ggacgctcat gggacccacc agagtgttcc gagcacgcca tgtggcccca  360
gattctatcc gtgggagttt cggcctcact gacacccgca acaccaccca tggttcggac  420
tctgtggttt cagccagcag agagattgca gccttcttcc ctgacttcag tgaacagcgc  480
tggtatgagg aggaagagcc ccagttgcgc tgtggccctg tgtgctatag cccagaggga  540
ggtgtccact atgtagctgg aacaggaggc ctaggaccag cctga                  585

SEQ ID NO: 65           moltype = AA  length = 194
FEATURE                 Location/Qualifiers
REGION                  1..194
                        note = Human NME6
source                  1..194
                        mol_type = protein
                        organism = synthetic construct
SEQUENCE: 65
MTQNLGSEMA SILRSPQALQ LTLALIKPDA VAHPLILEAV HQQILSNKFL IVRMRELLWR   60
KEDCQRFYRE HEGRFFYQRL VEFMASGPIR AYILAHKDAI QLWRTLMGPT RVFRARHVAP  120
DSIRGSFGLT DTRNTTHGSD SVVSASREIA AFFPDFSEQR WYEEEEPQLR CGPVCYSPEG  180
GVHYVAGTGG LGPA                                                    194

SEQ ID NO: 66           moltype = DNA  length = 525
FEATURE                 Location/Qualifiers
misc_feature            1..525
                        note = Human NME6 1
source                  1..525
                        mol_type = other DNA
                        organism = synthetic construct
SEQUENCE: 66
atgacccaga atctggggag tgagatggcc tcaatcttgc aagcccctca ggctctccag   60
ctcactctag ccctgatcaa gcctgacgca gtcgcccatc cactgattct ggaggctgtt  120
catcagcaga ttctaagcaa caagttcctg attgtacgaa tgagagaact actgtggaga  180
aaggaagatt gccagaggtt ttaccgagag catgaagggc gttttttcta tcagaggctg  240
gtggagttca tggccagcgg gccaatccga gcctacatcc ttgcccacaa ggatgccatc  300
cagctctgga ggacgctcat gggacccacc agagtgttcc gagcacgcca tgtggcccca  360
gattctatcc gtgggagttt cggcctcact gacacccgca acaccaccca tggttcggac  420
tctgtggttt cagccagcag agagattgca gccttcttcc ctgacttcag tgaacagcgc  480
tggtatgagg aggaagagcc ccagttgcgc tgtggccctg tgtga                  525

SEQ ID NO: 67           moltype = AA  length = 174
FEATURE                 Location/Qualifiers
REGION                  1..174
                        note = Human NME6 1
source                  1..174
                        mol_type = protein
                        organism = synthetic construct
SEQUENCE: 67
MTQNLGSEMA SILRSPQALQ LTLALIKPDA VAHPLILEAV HQQILSNKFL IVRMRELLWR   60
KEDCQRFYRE HEGRFFYQRL VEFMASGPIR AYILAHKDAI QLWRTLMGPT RVFRARHVAP  120
DSIRGSFGLT DTRNTTHGSD SVVSASREIA AFFPDFSEQR WYEEEEPQLR CGPV        174

SEQ ID NO: 68           moltype = DNA  length = 468
FEATURE                 Location/Qualifiers
misc_feature            1..468
                        note = Human NME6 2
source                  1..468
                        mol_type = other DNA
                        organism = synthetic construct
SEQUENCE: 68
atgctcactc tagccctgat caagcctgac gcagtcgccc atccactgat tctggaggct   60
gttcatcagc agattctaag caacaagttc ctgattgtac gaatgagaga actactgtgg  120
agaaaggaag attgccagag gttttaccga gagcatgaag ggcgtttttt ctatcagagg  180
ctggtggagt tcatggccag cgggccaatc cgagcctaca tccttgccca caaggatgcc  240
atccagctct ggaggacgct catgggaccc accagagtgt tccgagcacg ccatgtggcc  300
ccagattcta tccgtgggag tttcggcctc actgacaccc gcaacaccac ccatggttcg  360
gactctgtgg tttcagccag cagagagatt gcagccttct ccctgacttc agtgaacag   420
cgctggtatg aggaggaaga gccccagttg cgctgtggcc ctgtgtga               468
```

```
SEQ ID NO: 69              moltype = AA   length = 155
FEATURE                    Location/Qualifiers
REGION                     1..155
                           note = Human NME6 2
source                     1..155
                           mol_type = protein
                           organism = synthetic construct
SEQUENCE: 69
MLTLALIKPD AVAHPLILEA VHQQILSNKF LIVRMRELLW RKEDCQRFYR EHEGRFFYQR    60
LVEFMASGPI RAYILAHKDA IQLWRTLMGP TRVFRARHVA PDSIRGSFGL TDTRNTTHGS   120
DSVVSASREI AAFFPDFSEQ RWYEEEEPQL RCGPV                              155

SEQ ID NO: 70              moltype = DNA   length = 528
FEATURE                    Location/Qualifiers
misc_feature               1..528
                           note = Human NME6 3
source                     1..528
                           mol_type = other DNA
                           organism = synthetic construct
SEQUENCE: 70
atgctcactc tagccctgat caagcctgac gcagtcgccc atccactgat tctggaggct    60
gttcatcagc agattctaag caacaagttc ctgattgtac gaatgagaga actactgtgg   120
agaaaggaag attgccagag gttttaccga gagcatgaag gcgttttttt ctatcagagg   180
ctggtggagt tcatggccag cgggccaatc cgagcctaca tccttgccca caaggatgcc   240
atccagctct ggaggacgct catgggaccc accagagtgt tccgagcacg ccatgtggcc   300
ccagattcta tccgtgggag tttcggcctc actgacaccc gcaacaccac ccatggttca   360
gactctgtgg tttcagccag cagagagatt gcagccttct tccctgactt cagtgaacag   420
cgctggtatg aggaggaaga gccccagttg cgctgtggcc ctgtgtgcta tagcccagag   480
ggaggtgtcc actatgtagc tggaacagga ggcctagcac agcctga                528

SEQ ID NO: 71              moltype = AA   length = 175
FEATURE                    Location/Qualifiers
REGION                     1..175
                           note = Human NME6 3
source                     1..175
                           mol_type = protein
                           organism = synthetic construct
SEQUENCE: 71
MLTLALIKPD AVAHPLILEA VHQQILSNKF LIVRMRELLW RKEDCQRFYR EHEGRFFYQR    60
LVEFMASGPI RAYILAHKDA IQLWRTLMGP TRVFRARHVA PDSIRGSFGL TDTRNTTHGS   120
DSVVSASREI AAFFPDFSEQ RWYEEEEPQL RCGPVCYSPE GGVHYVAGTG GLGPA        175

SEQ ID NO: 72              moltype = DNA   length = 585
FEATURE                    Location/Qualifiers
misc_feature               1..585
                           note = Human NME6 sequence optimized for E. coli expression
source                     1..585
                           mol_type = other DNA
                           organism = synthetic construct
SEQUENCE: 72
atgacgcaaa atctgggctc ggaaatggca gtatcctgc gctccccgca agcactgcaa    60
ctgaccctgg ctctgatcaa accggacgct gttgctcatc cgctgattct ggaagcggtc   120
caccagcaaa ttctgagcaa caaatttctg atcgtgcgta tgcgcgaact gctgtggcgt   180
aaagaagatt gccagcgttt ttatcgcgaa catgaaggcc gttttttca tcaacgcctg   240
gttgaattca tggcctctgg tccgattcgc gcatatatcc tggctcacaa agatgcgatt   300
cagctgtggc gtaccctgat gggtccgacg cgcgtctttc gtgcacgtca tgtggcaccg   360
gactcaatcc gtggctcgtt cggtctgacc gatacgcgca ataccacgca cggtagcgac   420
tctgttgtta gtgcgtcccg tgaaatcgcg gcctttttcc cggacttctc cgaacagcgt   480
tggtacgaag aagaagaacc gcaactgcgc tgtggcccgg tctgttattc tccggaaggt   540
ggtgtccatt atgtggcggg cacgggtggt ctgggtccgg catga                  585

SEQ ID NO: 73              moltype = AA   length = 194
FEATURE                    Location/Qualifiers
REGION                     1..194
                           note = Human NME6 sequence optimized for E. coli expression
source                     1..194
                           mol_type = protein
                           organism = synthetic construct
SEQUENCE: 73
MTQNLGSEMA SILRSPQALQ LTLALIKPDA VAHPLILEAV HQQILSNKFL IVRMRELLWR    60
KEDCQRFYRE HEGRFFYQRL VEFMASGPIR AYILAHKDAI QLWRTLMGPT RVFRARHVAP   120
DSIRGSFGLT DTRNTTHGSD SVVSASREIA AFFPDFSEQR WYEEEEPQLR CGPVCYSPEG   180
GVHYVAGTGG LGPA                                                    194

SEQ ID NO: 74              moltype = DNA   length = 525
FEATURE                    Location/Qualifiers
misc_feature               1..525
                           note = Human NME6 1 sequence optimized for E. coli
```

```
                        expression
source                  1..525
                        mol_type = other DNA
                        organism = synthetic construct
SEQUENCE: 74
atgacgcaaa atctgggctc ggaaatggca agtatcctgc gctccccgca agcactgcaa    60
ctgaccctgg ctctgatcaa accggacgct gttgctcatc cgctgattct ggaagcggtc   120
caccagcaaa ttctgagcaa caaatttctg atcgtgcgta tgcgcgaact gctgtggcgt   180
aaagaagatt gccagcgttt ttatcgcgaa catgaaggcc gtttcttta tcaacgcctg   240
gttgaattca tggcctctgg tccgattcgc gcatatatcc tggctcacaa agatgcgatt   300
cagctgtggc gtaccctgat gggtccgacg cgcgtctttc gtgcacgtca tgtggccacg   360
gactcaatcc gtggctcgtt cggtctgacc gatacgcgca ataccacgca cggtagcgac   420
tctgttgtta gtgcgtcccg tgaaatcgcg gccttttcc cggacttctc cgaacagcgt   480
tggtacgaag aagaagaacc gcaactgcgc gtgggcccgg tctga                  525

SEQ ID NO: 75           moltype = AA  length = 174
FEATURE                 Location/Qualifiers
REGION                  1..174
                        note = Human NME6 1 sequence optimized for E. coli
                        expression
source                  1..174
                        mol_type = protein
                        organism = synthetic construct
SEQUENCE: 75
MTQNLGSEMA SILRSPQALQ LTLALIKPDA VAHPLILEAV HQQILSNKFL IVRMRELLWR    60
KEDCQRFYRE HEGRFFYQRL VEFMASGPIR AYILAHKDAI QLWRTLMGPT RVFRARHVAP   120
DSIRGSFGLT DTRNTTHGSD SVVSASREIA AFFPDFSEQR WYEEEEPQLR CGPV         174

SEQ ID NO: 76           moltype = DNA  length = 468
FEATURE                 Location/Qualifiers
misc_feature            1..468
                        note = Human NME6 2 sequence optimized for E. coli
                        expression
source                  1..468
                        mol_type = other DNA
                        organism = synthetic construct
SEQUENCE: 76
atgctgaccc tggctctgat caaaccggac gctgttgctc atccgctgat tctggaagcg    60
gtccaccagc aaattctgag caacaaattt ctgatcgtgc gtatgcgcga actgctgtgg   120
cgtaaagaag attgccagcg ttttatcgc gaacatgaag gccgtttctt ttatcaacgc   180
ctggttgaat tcatggcctc tggtccgatt cgcgcatata tcctggctca aagatgcg    240
attcagctgt ggcgtaccct gatgggtccg acgcgcgtct ttcgtgcacg tcatgtggca   300
ccggactcaa tccgtggctc gttcggtctg accgatacgc gcaataccac gcacggtagc   360
gactctgttg ttagtgcgtc ccgtgaaatc gcggcctttt ccggactt ctccgaacag    420
cgttggtacg aagaagaaga accgcaactg cgctgtggcc cggtctga               468

SEQ ID NO: 77           moltype = AA  length = 155
FEATURE                 Location/Qualifiers
REGION                  1..155
                        note = Human NME6 2 sequence optimized for E. coli
                        expression
source                  1..155
                        mol_type = protein
                        organism = synthetic construct
SEQUENCE: 77
MLTLALIKPD AVAHPLILEA VHQQILSNKF LIVRMRELLW RKEDCQRFYR EHEGRFFYQR    60
LVEFMASGPI RAYILAHKDA IQLWRTLMGP TRVFRARHVA PDSIRGSFGL TDTRNTTHGS   120
DSVVSASREI AAFFPDFSEQ RWYEEEEPQL RCGPV                              155

SEQ ID NO: 78           moltype = DNA  length = 528
FEATURE                 Location/Qualifiers
misc_feature            1..528
                        note = Human NME6 3 sequence optimized for E. coli
                        expression
source                  1..528
                        mol_type = other DNA
                        organism = synthetic construct
SEQUENCE: 78
atgctgaccc tggctctgat caaaccggac gctgttgctc atccgctgat tctggaagcg    60
gtccaccagc aaattctgag caacaaattt ctgatcgtgc gtatgcgcga actgctgtgg   120
cgtaaagaag attgccagcg ttttatcgc gaacatgaag gccgtttctt ttatcaacgc   180
ctggttgaat tcatggcctc tggtccgatt cgcgcatata tcctggctca aagatgcg    240
attcagctgt ggcgtaccct gatgggtccg acgcgcgtct ttcgtgcacg tcatgtggca   300
ccggactcaa tccgtggctc gttcggtctg accgatacgc gcaataccac gcacggtagc   360
gactctgttg ttagtgcgtc ccgtgaaatc gcggcctttt ccggactt ctccgaacag    420
cgttggtacg aagaagaaga accgcaactg cgctgtggcc cggtctgtta ttctccggaa   480
ggtggtgtcc attatgtggc gggcacgggg ggtctgggtc cggcatga              528

SEQ ID NO: 79           moltype = AA  length = 175
```

```
FEATURE                 Location/Qualifiers
REGION                  1..175
                        note = Human NME6 3 sequence optimized for E. coli
                         expression
source                  1..175
                        mol_type = protein
                        organism = synthetic construct
SEQUENCE: 79
MLTLALIKPD AVAHPLILEA VHQQILSNKF LIVRMRELLW RKEDCQRFYR EHEGRFFYQR    60
LVEFMASGPI RAYILAHKDA IQLWRTLMGP TRVFRARHVA PDSIRGSFGL TDTRNTTHGS   120
DSVVSASREI AAFFPDFSEQ RWYEEEEPQL RCGPVCYSPE GGVHYVAGTG GLGPA        175

SEQ ID NO: 80           moltype = DNA  length = 1306
FEATURE                 Location/Qualifiers
misc_feature            1..1306
                        note = OriGene-NME7-1 full length
source                  1..1306
                        mol_type = other DNA
                        organism = synthetic construct
SEQUENCE: 80
gacgttgtat acgactccta tagggcggcc gggaattcgt cgactggatc cggtaccgag     60
gagatctgcc gccgcgatcg ccatgaatca tagtgaaaga ttcgttttca ttgcagagtg    120
gtatgatcca aatgcttcac ttcttcgacg ttatgagctt ttattttacc caggggatgg    180
atctgttgaa atgcatgatg taaagaatca tcgcaccttt ttaaagcgga ccaaatatga    240
taacctgcac ttggaagatt tatttatagg caacaaagtg aatgtcttct ctcgacaact    300
ggtattaatt gactatgggg atcaatatac agctcgacag ctgggcagta ggaaagaaaa    360
aacgctagcc ctaattaaac cagatgcaat atcaaaggct ggagaaataa ttgaaataat    420
aaacaaagct ggatttacta taaccaaact caaaatgatg atgctttcaa ggaaagaagc    480
attggatttt catgtagatc accagtcaag accctttttc aatgagctga tccagtttat    540
tacaactggt cctattattg ccatgggaga tttaagagat gatgctatat gtgaatggaa    600
aagactgctg ggacctgcaa actctggagt ggcacgcaca gatgcttctg aaaagcattag    660
agccctcttt ggaacagatg gcataagaaa tgcagcgcat ggcccgtgat cttttgcttc    720
tgcggccaga gaaatggagt tgtttttttcc ttcaagtgga ggttgtgggc cggcaaacac    780
tgctaaatttt actaattgta cctgttgcat tgttaaaccc tgtcatgtca gtgaaggact    840
gttgggaaag atcctgatgg ctatccgaga tgcaggtttt gaaatctcag ctatgcagat    900
gttcaatatg gatcgggtta atgttgagga attctatgaa gtttataaag gagtagtgac    960
cgaatatcat gacatggtga cagaaatgta ttctggcccct tgtgtagcaa tggagattca   1020
acagaataat gctacaaaga catttcgaga attttgtgga cctgctgatc ctgaaattgc   1080
ccggcattta cgccctggaa ctctcagagc aatctttggt aaaactaaga tccagaatgc   1140
tgttcactgt actgatctgc cagaggatgg cctattagag gttaatact tcttcaagat   1200
cttggataat acgcgtacgc ggccgctcga gcagaaactc atctcagaag aggatctggc   1260
agcaaatgat atcctggatt acaaggatga cgacgataag gtttaa              1306

SEQ ID NO: 81           moltype = AA  length = 407
FEATURE                 Location/Qualifiers
REGION                  1..407
                        note = OriGene-NME7-1 full length
source                  1..407
                        mol_type = protein
                        organism = synthetic construct
SEQUENCE: 81
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FFPSSGGCGP ANTAKFTNCT   240
CCIVKPHAVS EGLLGKILMA IRDAGFEISA MQMFNMDRVN VEEFYEVYKG VVTEYHDMVT   300
EMYSGPCVAM EIQQNNATKT FREFCGPADP EIARHLRPGT LRAIFGKTKI QNAVHCTDLP   360
EDGLLEVQYF FKILDNTRTR RLEQKLISEE DLAANDILDY KDDDDKV                407

SEQ ID NO: 82           moltype = AA  length = 376
FEATURE                 Location/Qualifiers
REGION                  1..376
                        note = Abnova NME7-1 Full length
source                  1..376
                        mol_type = protein
                        organism = synthetic construct
SEQUENCE: 82
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FFPSSGGCGP ANTAKFTNCT   240
CCIVKPHAVS EGLLGKILMA IRDAGFEISA MQMFNMDRVN VEEFYEVYKG VVTEYHDMVT   300
EMYSGPCVAM EIQQNNATKT FREFCGPADP EIARHLRPGT LRAIFGKTKI QNAVHCTDLP   360
EDGLLEVQYF FKILDN                                                  376

SEQ ID NO: 83           moltype = AA  length = 98
FEATURE                 Location/Qualifiers
REGION                  1..98
                        note = Abnova Partial NME7-B
```

```
                        source           1..98
                                         mol_type = protein
                                         organism = synthetic construct
SEQUENCE: 83
DRVNVEEFYE VYKGVVTEYH DMVTEMYSGP CVAMEIQQNN ATKTFREFCG PADPEIARHL    60
RPGTLRAIFG KTKIQNAVHC TDLPEDGLLE VQYFFKIL                            98

SEQ ID NO: 84           moltype = DNA    length = 27
FEATURE                 Location/Qualifiers
misc_feature            1..27
                        note = Histidine Tag
source                  1..27
                        mol_type = other DNA
                        organism = synthetic construct
SEQUENCE: 84
ctcgagcacc accaccacca ccactga                                        27

SEQ ID NO: 85           moltype = DNA    length = 36
FEATURE                 Location/Qualifiers
misc_feature            1..36
                        note = Strept II Tag
source                  1..36
                        mol_type = other DNA
                        organism = synthetic construct
SEQUENCE: 85
accggttgga gccatcctca gttcgaaaag taatga                              36

SEQ ID NO: 86           moltype = AA     length = 35
FEATURE                 Location/Qualifiers
REGION                  1..35
                        note = N-10 peptide
source                  1..35
                        mol_type = protein
                        organism = synthetic construct
SEQUENCE: 86
QFNQYKTEAA SRYNLTISDV SVSDVPFPFS AQSGA                               35

SEQ ID NO: 87           moltype = AA     length = 35
FEATURE                 Location/Qualifiers
REGION                  1..35
                        note = C-10 peptide
source                  1..35
                        mol_type = protein
                        organism = synthetic construct
SEQUENCE: 87
GTINVHDVET QFNQYKTEAA SRYNLTISDV SVSDV                               35

SEQ ID NO: 88           moltype = AA     length = 8
FEATURE                 Location/Qualifiers
REGION                  1..8
                        note = Peptide of NME7AB
source                  1..8
                        mol_type = protein
                        organism = synthetic construct
SEQUENCE: 88
LALIKPDA                                                              8

SEQ ID NO: 89           moltype = AA     length = 18
FEATURE                 Location/Qualifiers
REGION                  1..18
                        note = Peptide of NME7AB
source                  1..18
                        mol_type = protein
                        organism = synthetic construct
SEQUENCE: 89
MMMLSRKEAL DFHVDHQS                                                  18

SEQ ID NO: 90           moltype = AA     length = 10
FEATURE                 Location/Qualifiers
REGION                  1..10
                        note = Peptide of NME7AB
source                  1..10
                        mol_type = protein
                        organism = synthetic construct
SEQUENCE: 90
ALDFHVDHQS                                                           10

SEQ ID NO: 91           moltype = AA     length = 14
FEATURE                 Location/Qualifiers
```

```
REGION                   1..14
                         note = Peptide of NME7AB
source                   1..14
                         mol_type = protein
                         organism = synthetic construct
SEQUENCE: 91
EILRDDAICE WKRL                                                             14

SEQ ID NO: 92            moltype = AA   length = 12
FEATURE                  Location/Qualifiers
REGION                   1..12
                         note = Peptide of NME7AB
source                   1..12
                         mol_type = protein
                         organism = synthetic construct
SEQUENCE: 92
FNELIQFITT GP                                                               12

SEQ ID NO: 93            moltype = AA   length = 8
FEATURE                  Location/Qualifiers
REGION                   1..8
                         note = Peptide of NME7AB
source                   1..8
                         mol_type = protein
                         organism = synthetic construct
SEQUENCE: 93
RDDAICEW                                                                    8

SEQ ID NO: 94            moltype = AA   length = 25
FEATURE                  Location/Qualifiers
REGION                   1..25
                         note = Peptide of NME7AB
source                   1..25
                         mol_type = protein
                         organism = synthetic construct
SEQUENCE: 94
SGVARTDASE SIRALFGTDG IRNAA                                                 25

SEQ ID NO: 95            moltype = AA   length = 9
FEATURE                  Location/Qualifiers
REGION                   1..9
                         note = Peptide of NME7AB
source                   1..9
                         mol_type = protein
                         organism = synthetic construct
SEQUENCE: 95
ELFFPSSGG                                                                   9

SEQ ID NO: 96            moltype = AA   length = 26
FEATURE                  Location/Qualifiers
REGION                   1..26
                         note = Peptide of NME7AB
source                   1..26
                         mol_type = protein
                         organism = synthetic construct
SEQUENCE: 96
KFTNCTCCIV KPHAVSEGLL GKILMA                                                26

SEQ ID NO: 97            moltype = AA   length = 36
FEATURE                  Location/Qualifiers
REGION                   1..36
                         note = Peptide of NME7AB
source                   1..36
                         mol_type = protein
                         organism = synthetic construct
SEQUENCE: 97
LMAIRDAGFE ISAMQMFNMD RVNVEEFYEV YKGVVT                                     36

SEQ ID NO: 98            moltype = AA   length = 15
FEATURE                  Location/Qualifiers
REGION                   1..15
                         note = Peptide of NME7AB
source                   1..15
                         mol_type = protein
                         organism = synthetic construct
SEQUENCE: 98
EFYEVYKGVV TEYHD                                                            15

SEQ ID NO: 99            moltype = AA   length = 43
```

```
FEATURE                 Location/Qualifiers
REGION                  1..43
                        note = Peptide of NME7AB
source                  1..43
                        mol_type = protein
                        organism = synthetic construct
SEQUENCE: 99
EIQQNNATKT FREFCGPADP EIARHLRPGT LRAIFGKTKI QNA                         43

SEQ ID NO: 100          moltype = AA  length = 8
FEATURE                 Location/Qualifiers
REGION                  1..8
                        note = Peptide of NME7AB
source                  1..8
                        mol_type = protein
                        organism = synthetic construct
SEQUENCE: 100
YSGPCVAM                                                                8

SEQ ID NO: 101          moltype = AA  length = 7
FEATURE                 Location/Qualifiers
REGION                  1..7
                        note = Peptide of NME7AB
source                  1..7
                        mol_type = protein
                        organism = synthetic construct
SEQUENCE: 101
FREFCGP                                                                 7

SEQ ID NO: 102          moltype = AA  length = 23
FEATURE                 Location/Qualifiers
REGION                  1..23
                        note = Peptide of NME7AB
source                  1..23
                        mol_type = protein
                        organism = synthetic construct
SEQUENCE: 102
VHCTDLPEDG LLEVQYFFKI LDN                                              23

SEQ ID NO: 103          moltype = AA  length = 9
FEATURE                 Location/Qualifiers
REGION                  1..9
                        note = Peptide of NME7AB
source                  1..9
                        mol_type = protein
                        organism = synthetic construct
SEQUENCE: 103
IQNAVHCTD                                                               9

SEQ ID NO: 104          moltype = AA  length = 20
FEATURE                 Location/Qualifiers
REGION                  1..20
                        note = Peptide of NME7AB
source                  1..20
                        mol_type = protein
                        organism = synthetic construct
SEQUENCE: 104
TDLPEDGLLE VQYFFKILDN                                                  20

SEQ ID NO: 105          moltype = AA  length = 13
FEATURE                 Location/Qualifiers
REGION                  1..13
                        note = Peptide of NME7AB
source                  1..13
                        mol_type = protein
                        organism = synthetic construct
SEQUENCE: 105
PEDGLLEVQY FFK                                                         13

SEQ ID NO: 106          moltype = AA  length = 12
FEATURE                 Location/Qualifiers
REGION                  1..12
                        note = Peptide of NME7AB
source                  1..12
                        mol_type = protein
                        organism = synthetic construct
SEQUENCE: 106
EIINKAGFTI TK                                                          12
```

```
SEQ ID NO: 107          moltype = AA  length = 16
FEATURE                 Location/Qualifiers
REGION                  1..16
                        note = Peptide of NME7AB
source                  1..16
                        mol_type = protein
                        organism = synthetic construct
SEQUENCE: 107
MLSRKEALDF HVDHQS                                                        16

SEQ ID NO: 108          moltype = AA  length = 9
FEATURE                 Location/Qualifiers
REGION                  1..9
                        note = Peptide of NME7AB
source                  1..9
                        mol_type = protein
                        organism = synthetic construct
SEQUENCE: 108
NELIQFITT                                                                 9

SEQ ID NO: 109          moltype = AA  length = 14
FEATURE                 Location/Qualifiers
REGION                  1..14
                        note = Peptide of NME7AB
source                  1..14
                        mol_type = protein
                        organism = synthetic construct
SEQUENCE: 109
EILRDDAICE WKRL                                                          14

SEQ ID NO: 110          moltype = AA  length = 21
FEATURE                 Location/Qualifiers
REGION                  1..21
                        note = Peptide of NME7AB
source                  1..21
                        mol_type = protein
                        organism = synthetic construct
SEQUENCE: 110
SGVARTDASE SIRALFGTDG I                                                  21

SEQ ID NO: 111          moltype = AA  length = 11
FEATURE                 Location/Qualifiers
REGION                  1..11
                        note = Peptide of NME7AB
source                  1..11
                        mol_type = protein
                        organism = synthetic construct
SEQUENCE: 111
SGVARTDASE S                                                             11

SEQ ID NO: 112          moltype = AA  length = 8
FEATURE                 Location/Qualifiers
REGION                  1..8
                        note = Peptide of NME7AB
source                  1..8
                        mol_type = protein
                        organism = synthetic construct
SEQUENCE: 112
ALFGTDGI                                                                  8

SEQ ID NO: 113          moltype = AA  length = 14
FEATURE                 Location/Qualifiers
REGION                  1..14
                        note = Peptide of NME7AB
source                  1..14
                        mol_type = protein
                        organism = synthetic construct
SEQUENCE: 113
NCTCCIVKPH AVSE                                                          14

SEQ ID NO: 114          moltype = AA  length = 11
FEATURE                 Location/Qualifiers
REGION                  1..11
                        note = Peptide of NME7AB
source                  1..11
                        mol_type = protein
                        organism = synthetic construct
SEQUENCE: 114
LGKILMAIRD A                                                             11
```

```
SEQ ID NO: 115          moltype = AA   length = 16
FEATURE                 Location/Qualifiers
REGION                  1..16
                        note = Peptide of NME7AB
source                  1..16
                        mol_type = protein
                        organism = synthetic construct
SEQUENCE: 115
EISAMQMFNM DRVNVE                                                       16

SEQ ID NO: 116          moltype = AA   length = 8
FEATURE                 Location/Qualifiers
REGION                  1..8
                        note = Peptide of NME7AB
source                  1..8
                        mol_type = protein
                        organism = synthetic construct
SEQUENCE: 116
EVYKGVVT                                                                 8

SEQ ID NO: 117          moltype = AA   length = 8
FEATURE                 Location/Qualifiers
REGION                  1..8
                        note = Peptide of NME7AB
source                  1..8
                        mol_type = protein
                        organism = synthetic construct
SEQUENCE: 117
EYHDMVTE                                                                 8

SEQ ID NO: 118          moltype = AA   length = 15
FEATURE                 Location/Qualifiers
REGION                  1..15
                        note = Peptide of NME7AB
source                  1..15
                        mol_type = protein
                        organism = synthetic construct
SEQUENCE: 118
EFCGPADPEI ARHLR                                                        15

SEQ ID NO: 119          moltype = AA   length = 12
FEATURE                 Location/Qualifiers
REGION                  1..12
                        note = Peptide of NME7AB
source                  1..12
                        mol_type = protein
                        organism = synthetic construct
SEQUENCE: 119
AIFGKTKIQN AV                                                           12

SEQ ID NO: 120          moltype = AA   length = 18
FEATURE                 Location/Qualifiers
REGION                  1..18
                        note = Peptide of NME7AB
source                  1..18
                        mol_type = protein
                        organism = synthetic construct
SEQUENCE: 120
LPEDGLLEVQ YFFKILDN                                                     18

SEQ ID NO: 121          moltype = AA   length = 17
FEATURE                 Location/Qualifiers
REGION                  1..17
                        note = Peptide of NME7AB
source                  1..17
                        mol_type = protein
                        organism = synthetic construct
SEQUENCE: 121
GPDSFASAAR EMELFFP                                                      17

SEQ ID NO: 122          moltype = AA   length = 7
FEATURE                 Location/Qualifiers
REGION                  1..7
                        note = Immunizing peptides derived from human NME7
source                  1..7
                        mol_type = protein
                        organism = synthetic construct
SEQUENCE: 122
```

```
ICEWKRL                                                                           7

SEQ ID NO: 123          moltype = AA  length = 11
FEATURE                 Location/Qualifiers
REGION                  1..11
                        note = Immunizing peptides derived from human NME7
source                  1..11
                        mol_type = protein
                        organism = synthetic construct
SEQUENCE: 123
LGKILMAIRD A                                                                      11

SEQ ID NO: 124          moltype = AA  length = 10
FEATURE                 Location/Qualifiers
REGION                  1..10
                        note = Immunizing peptides derived from human NME7
source                  1..10
                        mol_type = protein
                        organism = synthetic construct
SEQUENCE: 124
HAVSEGLLGK                                                                        10

SEQ ID NO: 125          moltype = AA  length = 8
FEATURE                 Location/Qualifiers
REGION                  1..8
                        note = Immunizing peptides derived from human NME7
source                  1..8
                        mol_type = protein
                        organism = synthetic construct
SEQUENCE: 125
VTEMYSGP                                                                          8

SEQ ID NO: 126          moltype = AA  length = 9
FEATURE                 Location/Qualifiers
REGION                  1..9
                        note = Immunizing peptides derived from human NME7
source                  1..9
                        mol_type = protein
                        organism = synthetic construct
SEQUENCE: 126
NATKTFREF                                                                         9

SEQ ID NO: 127          moltype = AA  length = 9
FEATURE                 Location/Qualifiers
REGION                  1..9
                        note = Immunizing peptides derived from human NME7
source                  1..9
                        mol_type = protein
                        organism = synthetic construct
SEQUENCE: 127
AIRDAGFEI                                                                         9

SEQ ID NO: 128          moltype = AA  length = 13
FEATURE                 Location/Qualifiers
REGION                  1..13
                        note = Immunizing peptides derived from human NME7
source                  1..13
                        mol_type = protein
                        organism = synthetic construct
SEQUENCE: 128
AICEWKRLLG PAN                                                                    13

SEQ ID NO: 129          moltype = AA  length = 8
FEATURE                 Location/Qualifiers
REGION                  1..8
                        note = Immunizing peptides derived from human NME7
source                  1..8
                        mol_type = protein
                        organism = synthetic construct
SEQUENCE: 129
DHQSRPFF                                                                          8

SEQ ID NO: 130          moltype = AA  length = 13
FEATURE                 Location/Qualifiers
REGION                  1..13
                        note = Immunizing peptides derived from human NME7
source                  1..13
                        mol_type = protein
                        organism = synthetic construct
```

```
SEQUENCE: 130
AICEWKRLLG PAN                                                          13

SEQ ID NO: 131          moltype = AA  length = 8
FEATURE                 Location/Qualifiers
REGION                  1..8
                        note = Immunizing peptides derived from human NME7
source                  1..8
                        mol_type = protein
                        organism = synthetic construct
SEQUENCE: 131
VDHQSRPF                                                                 8

SEQ ID NO: 132          moltype = AA  length = 6
FEATURE                 Location/Qualifiers
REGION                  1..6
                        note = Immunizing peptides derived from human NME7
source                  1..6
                        mol_type = protein
                        organism = synthetic construct
SEQUENCE: 132
PDSFAS                                                                   6

SEQ ID NO: 133          moltype = AA  length = 18
FEATURE                 Location/Qualifiers
REGION                  1..18
                        note = Immunizing peptides derived from human NME7
source                  1..18
                        mol_type = protein
                        organism = synthetic construct
SEQUENCE: 133
KAGEIIEIIN KAGFTITK                                                     18

SEQ ID NO: 134          moltype = AA  length = 29
FEATURE                 Location/Qualifiers
REGION                  1..29
                        note = Immunizing peptides derived from human NME1
source                  1..29
                        mol_type = protein
                        organism = synthetic construct
SEQUENCE: 134
MANCERTFIA IKPDGVQRGL VGEIIKRFE                                         29

SEQ ID NO: 135          moltype = AA  length = 8
FEATURE                 Location/Qualifiers
REGION                  1..8
                        note = Immunizing peptides derived from human NME1
source                  1..8
                        mol_type = protein
                        organism = synthetic construct
SEQUENCE: 135
VDLKDRPF                                                                 8

SEQ ID NO: 136          moltype = AA  length = 17
FEATURE                 Location/Qualifiers
REGION                  1..17
                        note = Immunizing peptides derived from human NME1
source                  1..17
                        mol_type = protein
                        organism = synthetic construct
SEQUENCE: 136
HGSDSVESAE KEIGLWF                                                      17

SEQ ID NO: 137          moltype = AA  length = 25
FEATURE                 Location/Qualifiers
REGION                  1..25
                        note = Immunizing peptides derived from human NME1
source                  1..25
                        mol_type = protein
                        organism = synthetic construct
SEQUENCE: 137
ERTFIAIKPD GVQRGLVGEI IKRFE                                             25

SEQ ID NO: 138          moltype = AA  length = 30
FEATURE                 Location/Qualifiers
REGION                  1..30
                        note = Immunizing peptides derived from human NME1
source                  1..30
                        mol_type = protein
```

```
                        organism = synthetic construct
SEQUENCE: 138
VDLKDRPFFA GLVKYMHSGP VVAMVWEGLN                                       30

SEQ ID NO: 139          moltype = AA  length = 26
FEATURE                 Location/Qualifiers
REGION                  1..26
                        note = Immunizing peptides derived from human NME1
source                  1..26
                        mol_type = protein
                        organism = synthetic construct
SEQUENCE: 139
NIIHGSDSVE SAEKEIGLWF HPEELV                                           26

SEQ ID NO: 140          moltype = AA  length = 14
FEATURE                 Location/Qualifiers
REGION                  1..14
                        note = Immunizing peptides derived from human NME1
source                  1..14
                        mol_type = protein
                        organism = synthetic construct
SEQUENCE: 140
KPDGVQRGLV GEII                                                        14

SEQ ID NO: 141          moltype = AA  length = 16
FEATURE                 Location/Qualifiers
REGION                  1..16
                        note = NME7A peptide 1 (A domain)
source                  1..16
                        mol_type = protein
                        organism = synthetic construct
SEQUENCE: 141
MLSRKEALDF HVDHQS                                                      16

SEQ ID NO: 142          moltype = AA  length = 11
FEATURE                 Location/Qualifiers
REGION                  1..11
                        note = NME7A peptide 2 (A domain)
source                  1..11
                        mol_type = protein
                        organism = synthetic construct
SEQUENCE: 142
SGVARTDASE S                                                           11

SEQ ID NO: 143          moltype = AA  length = 20
FEATURE                 Location/Qualifiers
REGION                  1..20
                        note = NME7B peptide 1 (B domain)
source                  1..20
                        mol_type = protein
                        organism = synthetic construct
SEQUENCE: 143
DAGFEISAMQ MFNMDRVNVE                                                  20

SEQ ID NO: 144          moltype = AA  length = 16
FEATURE                 Location/Qualifiers
REGION                  1..16
                        note = NME7B peptide 2 (B domain)
source                  1..16
                        mol_type = protein
                        organism = synthetic construct
SEQUENCE: 144
EVYKGVVTEY HDMVTE                                                      16

SEQ ID NO: 145          moltype = AA  length = 29
FEATURE                 Location/Qualifiers
REGION                  1..29
                        note = NME7B peptide 3 (B domain)
source                  1..29
                        mol_type = protein
                        organism = synthetic construct
SEQUENCE: 145
AIFGKTKIQN AVHCTDLPED GLLEVQYFF                                        29

SEQ ID NO: 146          moltype = DNA  length = 1131
FEATURE                 Location/Qualifiers
misc_feature            1..1131
                        note = Human NME7 a
source                  1..1131
```

```
                        mol_type = other DNA
                        organism = synthetic construct
SEQUENCE: 146
atgaatcata gtgaaagatt cgttttcatt gcagagtggt atgatccaaa tgcttcactt    60
cttcgacgtt atgagctttt attttaccca ggggatggat ctgttgaaat gcatgatgta   120
aagaatcatc gcacctttt aaagcggacc aaatatgata acctgcactt ggaagattta   180
tttataggca acaaagtgaa tgtcttttct cgacaactgg tattaattga ctatggggat   240
caatatacag ctcgccagct gggcagtagg aagaaaaaa cgctagccct aattaaacca   300
gatgcaatat caaaggctgg agaaataatt gaaataataa acaaagctgg atttactata   360
accaaactca aaatgatgat gctttcaagg aaagaagcat tggattttca tgtagatcac   420
cagtcaagac cctttttcaa tgagctgatc cagtttatta caactggtcc tattattgcc   480
atggagattt taagagatga tgctatatgt gaatggaaaa gactgctggg acctgcaaac   540
tctggagtgg cacgcacaga tgcttctgaa agcattagag ccctctttgg aacagatggc   600
ataagaaatg cagcgctgg ccctgattc tttgcttctg cggccagaga aatggagttg   660
tttttccctt caagtggagg ttgtgggccg gcaaacactg ctaaatttac taattgtacc   720
tgttgcattg ttaaacccca tgctgtcagt gaaggactgt tgggaaagat cctgatggct   780
atccgagatg caggttttga atctcagct atgcagatgt caatatgga tcgggttaat   840
gttgaggaat tctatgaagt ttataaagga gtagtgaccg aatatcatga tgtgaca    900
gaaatgtatt ctggcccttg tgtagcaatg gagattcaac agaataatgc tacaaagaca   960
tttcgagaat tttgtggacc tgctgatcct gaaattgccc ggcatttacg ccctggaact  1020
ctcagagcaa tctttggtaa aactaagatc cagaatgctg ttcactgtac tgatctgcca  1080
gaggatggcc tattagaggt tcaatacttc ttcaagatct tggataatta g          1131

SEQ ID NO: 147           moltype = AA  length = 376
FEATURE                  Location/Qualifiers
REGION                   1..376
                         note = Human NME7 a
source                   1..376
                         mol_type = protein
                         organism = synthetic construct
SEQUENCE: 147
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FFPSSGGCGP ANTAKFTNCT   240
CCIVKPHAVS EGLLGKILMA IRDAGFEISA MQMFNMDRVN VEEFYEVYKG VVTEYHDMVT   300
EMYSGPCVAM EIQQNNATKT FREFCGPADP EIARHLRPGT LRAIFGKTKI QNAVHCTDLP   360
EDGLLEVQYF FKILDN                                                  376

SEQ ID NO: 148           moltype = DNA  length = 1023
FEATURE                  Location/Qualifiers
misc_feature             1..1023
                         note = Human NME7 b
source                   1..1023
                         mol_type = other DNA
                         organism = synthetic construct
SEQUENCE: 148
atgcatgatg taaagaatca tcgcaccttt ttaaagcgga ccaaatatga taacctgcac    60
ttggaagatt tatttatagg caacaaagtg aatgtctttt ctcgacaact ggtattaatt   120
gactatgggg atcaatatac agctcgccag ctgggcagta ggaagaaaa aacgctagcc   180
ctaattaaac cagatgcaat atcaaaggct ggagaaataa ttgaaataat aaacaaagct   240
ggatttacta taaccaaact caaaatgatg atgctttcaa ggaaagaagc attggatttt   300
catgtagatc accagtcaag acccttttc aatgagctga tccagtttat tacaactggt   360
cctattattg ccatggagat tttaagagat gatgctatat gtgaatggaa aagactgctg   420
ggacctgcaa actctggagt ggcacgcaca gatgcttctg aaagcattag agccctgatt   480
ggaacagatg gcataagaaa tgcagcgcat ggcccctgatt cttttgcttc tgcggccaga   540
gaaatggagt tgtttttcc ttcaagtgga ggttgtgggc cggcaaacac tgctaaattt   600
actaattgta cctgttgcat tgttaaaccc catgctgtca gtgaaggact gttgggaaag   660
atcctgatgg ctatccgaga tgcaggtttt gaaatctcag ctatgcagat gttcaatatg   720
gatcgggtta atgttgagga attctatgaa gtttataaag gagtagtgac cgaatatcat   780
gacatggtga cagaaatgta ttctggcccc tgtgtagcaa tggagattca acagaataat   840
gctacaaaga catttcgaga attttgtgga cctgctgatc ctgaaattgc cggcattta   900
cgcccctgaa ctctcagagc aatctttggt aaaactaaga tccagaatgc tgttcactgt   960
actgatctgc cagaggatgg cctattagag gttcaatact tcttcaagat cttggataat  1020
tag                                                                1023

SEQ ID NO: 149           moltype = AA  length = 340
FEATURE                  Location/Qualifiers
REGION                   1..340
                         note = Human NME7 b
source                   1..340
                         mol_type = protein
                         organism = synthetic construct
SEQUENCE: 149
MHDVKNHRTF LKRTKYDNLH LEDLFIGNKV NVFSRQLVLI DYGDQYTARQ LGSRKEKTLA    60
LIKPDAISKA GEIIEIINKA GFTITKLKMM MLSRKEALDF HVDHQSRPFF NELIQFITTG   120
PIIAMEILRD DAICEWKRLL GPANSGVART DASESIRALF GTDGIRNAAH GPDSFASAAR   180
EMELFFPSSG GCGPANTAKF TNCTCCIVKP HAVSEGLLGK ILMAIRDAGF EISAMQMFNM   240
DRVNVEEFYE VYKGVVTEYH DMVTEMYSGP CVAMEIQQNN ATKTFREFCG PADPEIARHL   300
```

RPGTLRAIFG KTKIQNAVHC TDLPEDGLLE VQYFFKILDN                               340

SEQ ID NO: 150           moltype = DNA   length = 861
FEATURE                  Location/Qualifiers
misc_feature             1..861
                         note = Human NME7-AB also known as NME7AB
source                   1..861
                         mol_type = other DNA
                         organism = synthetic construct
SEQUENCE: 150
atggaaaaaa cgctagccct aattaaacca gatgcaatat caaaggctgg agaaataatt      60
gaaataataa acaaagctgg atttactata accaaactca aaatgatgat gctttcaagg     120
aaagaagcat tggattttca tgtagatcac cagtcaagac ccttttcaa tgagctgatc      180
cagtttatta caactggtcc tattattgcc atggagattt taagagatga tgctatatgt    240
gaatggaaaa gactgctggg acctgcaaac tctggagtgg cacgcacaga tgcttctgaa    300
agcattagag ccctctttgg aacagatggc ataagaaatg cagcgcatgg ccctgattct    360
tttgcttctg cggccagaga aatggagttg ttttttcctt caagtggagg ttgtgggccg    420
gcaaacactg ctaaatttac taattgtacc tgttgcattg ttaaacccca tgctgtcagt    480
gaaggactgt tgggaaagat cctgatggct atccgagatg caggttttga aatctctcagct  540
atgcagatgt tcaatatgga tcgggttaat gttgaggaat ctatgaagt ttataaagga     600
gtagtgaccg aatatcatga catggtgaca gaaatgtatt ctggcccttg tgtagcaatg    660
gagattcaac agaataatgc tacaaagaca tttcgagacc tgctgatcct                720
gaaattgccc ggcatttacg ccctggaact ctcagagcaa tctttggtaa aactaagatc    780
cagaatgctg ttcactgtac tgatctgcca gaggatggcc tattagaggt tcaatacttc    840
ttcaagatct tggataatta g                                               861

SEQ ID NO: 151           moltype = AA   length = 286
FEATURE                  Location/Qualifiers
REGION                   1..286
                         note = Human NME7-AB also known as NME7AB
source                   1..286
                         mol_type = protein
                         organism = synthetic construct
SEQUENCE: 151
MEKTLALIKP DAISKAGEII EIINKAGFTI TKLKMMMLSR KEALDFHVDH QSRPFFNELI       60
QFITTGPIIA MEILRDDAIC EWKRLLGPAN SGVARTDASE SIRALFGTDG IRNAAHGPDS      120
FASAAREMEL FFPSSGGCGP ANTAKFTNCT CCIVKPHAVS EGLLGKILMA IRDAGFEISA      180
MQMFNMDRVN VEEFYEVYKG VVTEYHDMVT EMYSGPCVAM EIQQNNATKT FREFCGPADP      240
EIARHLRPGT LRAIFGKTKI QNAVHCTDLP EDGLLEVQYF FKILDN                     286

SEQ ID NO: 152           moltype = DNA   length = 759
FEATURE                  Location/Qualifiers
misc_feature             1..759
                         note = Human NME7-X1
source                   1..759
                         mol_type = other DNA
                         organism = synthetic construct
SEQUENCE: 152
atgatgatgc tttcaaggaa agaagcattg gattttcatg tagatcacca gtcaagaccc       60
ttttcaatg agctgatcca gtttattaca actggtccta ttattgccat ggagatttta      120
agagatgatg ctatatgtga atggaaaaga ctgctggaac ctgcaaactc tggagtggca    180
cgcacagatg cttctgaaag cattagagcc ctctttggaa cagatggcat aagaaatgca    240
gcgcatggcc ctgattcttt tgcttctgcg gccagagaaa tggagttgtt ttttccttca    300
agtggaggtt gtgggccggc aaacactgct aaatttacta attgtacctg ttgcattgtt    360
aaaccccatg ctgtcagtga aggactgttg gaaagatcc tgatggctat ccgagatgca    420
ggttttgaaa tctcagctat gcagatgttc aatatggatc gggttaatgt tgaggaattc    480
tatgaagttt ataaaggagt agtgaccgaa tatcatgaca tggtgacaga aatgtattct    540
ggcccttgtg tagcaatgga gattcaacag aataatgcta caaagacatt tcgagaattt    600
tgtggacctg ctgatcctga aattgcccgg catttacgcc ctggaactct cagagcaatc    660
tttggtaaaa ctaagatcca gaatgctgtt cactgtactg atctgccaga ggatggccta    720
ttagaggttc aatacttctt caagatcttg gataattag                             759

SEQ ID NO: 153           moltype = AA   length = 252
FEATURE                  Location/Qualifiers
REGION                   1..252
                         note = Human NME7-X1
source                   1..252
                         mol_type = protein
                         organism = synthetic construct
SEQUENCE: 153
MMMLSRKEAL DFHVDHQSRP FFNELIQFIT TGPIIAMEIL RDDAICEWKR LLGPANSGVA       60
RTDASESIRA LFGTDGIRNA AHGPDSFASA AREMELFFPS SGGCGPANTA KFTNCTCCIV      120
KPHAVSEGLL GKILMAIRDA GFEISAMQMF NMDRVNVEEF YEVYKGVVTE YHDMVTEMYS      180
GPCVAMEIQQ NNATKTFREF CGPADPEIAR HLRPGTLRAI FGKTKIQNAV HCTDLPEDGL      240
LEVQYFFKIL DN                                                          252

SEQ ID NO: 154           moltype = DNA   length = 1128
FEATURE                  Location/Qualifiers
misc_feature             1..1128 note = Human NME7 a (optimized for E coli expression)
source                      1..1128
                            mol_type = other DNA
                            organism = synthetic construct
SEQUENCE: 154
atgaatcact ccgaacgctt tgtttttatc gccgaatggt atgacccgaa tgcttccctg   60
ctgcgccgct acgaactgct gttttatccg ggcgatggta gcgtggaaat gcatgacgtt  120
aaaaatcacc gtacctttct gaaacgcacg aaatatgata tctgcatct  ggaagacctg  180
tttattggca acaaagtcaa tgtgttctct cgtcagctgg tgctgatcga ttatggcgac  240
cagtacaccg cgcgtcaact gggtagtcgc aagaaaaaa cgctggccct  gattaaaccg  300
gatgcaatct ccaaagctgg cgaaattatc gaaattatca acaaagcggg tttcaccatc  360
acgaaactga aatgatgat gctgagccgt aagaagccc tggattttca tgtcgaccac  420
cagtctcgcc cgttttcaa tgaactgatt caattcatca ccacgggtcc gattatcgca  480
atggaaattc tgcgtgatga cgctatctgc gaatggaaac gcctgctggg cccggcaaac  540
tcaggtgttg cgcgtaccga tgccagtgaa tccattcgcg ctctgtttgg caccgatggt  600
atccgtaatg cagcacatgg tccggactca ttcgcatcgg cagctcgtga atggaactg   660
ttttcccga gctctggcgg ttgcggtccg gcaaacaccg ccaaatttac caattgtacg  720
tgctgtattg tcaaaccgca cgcagtgtca gaaggcctgc tgggtaaaat tctgatggca  780
atccgtgatg ctggctttga aatctccggc catgcagatg tcaacatgga ccgcgttaac  840
gtcgaagaat tctacgaagt ttacaaaggc gtggttaccg aatatcacga tatggttacg  900
gaaatgtact ccggtccgtg cgtcgcgatg gaaattcagc aaaacaatgc caccaaaacg  960
tttcgtgaat tctgtggtcc ggcagatccg gaaatcgcag gtcatcgaa tccgggtacc 1020
ctgcgcgcaa ttttttggta aacgaaaatc cagaacgctg tgcactgtac cgatctgccg 1080
gaagacggtc tgctggaagt tcaatacttt ttcaaaattc tggataat              1128

SEQ ID NO: 155              moltype = AA   length = 378
FEATURE                     Location/Qualifiers
REGION                      1..378
                            note = Human NME7 a (optimized for E coli expression)
source                      1..378
                            mol_type = protein
                            organism = synthetic construct
SEQUENCE: 155
MNHSERFVFI AEWYDPNASL LRRYELLFYP GDGSVEMHDV KNHRTFLKRT KYDNLHLEDL   60
FIGNKVNVFS RQLVLIDYGD QYTARQLGSR KEKTLALIKP DAISKAGEII EIINKAGFTI  120
TKLKMMMLSR KEALDFHVDH QSRPFFNELI QFITTGPIIA MEILRDDAIC EWKRLLGPAN  180
SGVARTDASE SIRALFGTDG IRNAAHGPDS FASAAREMEL FFPSSGGCGP ANTAKFTNCT  240
CCIVKPHAVS EGLLGKILMA IRDAGFEISA MQMFNMDRVN VEEFYEVYKG VVTEYHDMVT  300
EMYSGPCVAM EIQQNNATKT FREFCGPADP EIARHLRPGT LRAIFGKTKI QNAVHCTDLP  360
EDGLLEVQYF FKILDNTG                                                378

SEQ ID NO: 156              moltype = DNA   length = 1020
FEATURE                     Location/Qualifiers
misc_feature                1..1020
                            note = Human NME7 b (optimized for E coli expression)
source                      1..1020
                            mol_type = other DNA
                            organism = synthetic construct
SEQUENCE: 156
atgcatgacg ttaaaaatca ccgtaccttt ctgaaacgca cgaaatatga taatctgcat   60
ctggaagacc tgtttattgg caacaaagtc aatgtgttct ctcgtcagct ggtgctgatc  120
gattatggcg accagtacac cgcgcgtcaa ctgggtagtc gcaaagaaaa aacgctggcc  180
ctgattaaac cggatgcaat ctccaaagct ggcgaaatta tcgaaattat caacaaagcg  240
ggtttcacca tcacgaaact gaaatgatg atgctgagcc gtaagaagc cctggatttt  300
catgtcgaca ccagtctcg cccgtttttc aatgaactga ttcaattcat caccacgggt  360
ccgattatcg caatggaaat tctgcgtgat gacgctatct gcgaatggaa acgcctgctg  420
ggcccggcaa actcaggtgt tgcgcgtacc gatgccagtg aatccattcg cgctctgttt  480
ggcaccgatg gtatccgtaa tgcagcacat ggtccggact cattcgcatc ggcagctcgt  540
gaaatgaac tgttttttccc gagctctggc ggttgcggtc cggcaaacac cgccaaattt  600
accaattgta cgtgctgtat tgtcaaaccg cacgcagtgt cagaaggcct gctgggtaaa  660
attctgatgg caatccgtga tgctggcttt gaaatctcgg ccatgcagat gttcaacatg  720
gaccgcgtta acgtcgaaga attctacgaa gtttacaaag gcgtggttac cgaatatcac  780
gatatggtta cggaaatgta ctccggtccg tgcgtcgcga tggaaattca gcaaaacaat  840
gccaccaaaa cgtttcgtga attctgtggt ccggcagatc cggaaatcgc acgtcatctg  900
cgtccgggta ccctgcgcgc aatttttggt aaaacgaaaa tccagaacgc tgtgcactgt  960
accgatctgc cggaagacgg tctgctggaa gttcaatact ttttcaaaat tctggataat 1020

SEQ ID NO: 157              moltype = AA   length = 342
FEATURE                     Location/Qualifiers
REGION                      1..342
                            note = Human NME7 b (optimized for E coli expression)
source                      1..342
                            mol_type = protein
                            organism = synthetic construct
SEQUENCE: 157
MHDVKNHRTF LKRTKYDNLH LEDLFIGNKV NVFSRQLVLI DYGDQYTARQ LGSRKEKTLA   60
LIKPDAISKA GEIIEIINKA GFTITKLKMM MLSRKEALDF HVDHQSRPFF NELIQFITTG  120
PIIAMEILRD DAICEWKRLL GPANSGVART DASESIRALF GTDGIRNAAH GPDSFASAAR  180
EMELFFPSSG GCGPANTAKF TNCTCCIVKP HAVSEGLLGK ILMAIRDAGF EISAMQMFNM  240

```
DRVNVEEFYE VYKGVVTEYH DMVTEMYSGP CVAMEIQQNN ATKTFREFCG PADPEIARHL    300
RPGTLRAIFG KTKIQNAVHC TDLPEDGLLE VQYFFKILDN TG                      342

SEQ ID NO: 158         moltype = DNA  length = 858
FEATURE                Location/Qualifiers
misc_feature           1..858
                       note = Human NME7-AB also known as NME7AB (optimized for E
                         coli expression)
source                 1..858
                       mol_type = other DNA
                       organism = synthetic construct
SEQUENCE: 158
atggaaaaaa cgctggccct gattaaaccg gatgcaatct ccaaagctgg cgaaattatc    60
gaaattatca acaaagcggg tttcaccatc acgaaactga aaatgatgat gctgagccgt    120
aaagaagccc tggattttca tgtcgaccac cagtctcgcc cgttttttca tgaactgatt    180
caattcatca ccacgggtcc gattatcgca atggaaattc tgcgtgatga cgctatctgc    240
gaatggaaac gcctgctggg cccggcaaac tcaggtgttg cgcgtaccga tgccagtgaa    300
tccattgcgc ctctgtttgg caccgatggt atccgtaatg cagcacatgg tccggactca    360
ttcgcatcgg cagctcgtga atggaactgt tttttcccga gctctggcgg ttgcggtccg    420
gcaaacaccg ccaaatttac caattgtacg tgctgtattg tcaaaccgca cgcagtgtca    480
gaaggcctgc tgggtaaaat tctgatggca atccgtgatg ctggctttga aatctcggcc    540
atgcagatgt tcaacatgga ccgcgttaac gtcgaagaat tctacgaagt ttacaaaggc    600
gtggttaccg aatatcacga tatggttacg gaaatgtact ccggtccgtg cgtcgcgatg    660
gaaattcagc aaaacaatgc caccaaaacg tttcgtgaat tctgtggtcc ggcagatccg    720
gaaatcgcac gtcatctgcg tccgggtacc ctgcgcgcaa ttttggtaa aacgaaaatc    780
cagaacgctg tgcactgtac cgatctgccg gaagacggtc tgctggaagt tcaatacttt    840
ttcaaaattc tggataat                                                 858

SEQ ID NO: 159         moltype = AA  length = 288
FEATURE                Location/Qualifiers
REGION                 1..288
                       note = Human NME7-AB also known as NME7AB (optimized for E
                         coli expression)
source                 1..288
                       mol_type = protein
                       organism = synthetic construct
SEQUENCE: 159
MEKTLALIKP DAISKAGEII EIINKAGFTI TKLKMMMLSR KEALDFHVDH QSRPFFNELI    60
QFITTGPIIA MEILRDDAIC EWKRLLGPAN SGVARTDASE SIRALFGTDG IRNAAHGPDS    120
FASAAREMEL FFPSSGGCGP ANTAKFTNCT CCIVKPHAVS EGLLGKILMA IRDAGFEISA    180
MQMFNMDRVN VEEFYEVYKG VVTEYHDMVT EMYSGPCVAM EIQQNNATKT FREFCGPADP    240
EIARHLRPGT LRAIFGKTKI QNAVHCTDLP EDGLLEVQYF FKILDNTG                288

SEQ ID NO: 160         moltype = DNA  length = 756
FEATURE                Location/Qualifiers
misc_feature           1..756
                       note = Human NME7-X1 (optimized for E coli expression)
source                 1..756
                       mol_type = other DNA
                       organism = synthetic construct
SEQUENCE: 160
atgatgatgc tgagccgtaa agaagccctg gattttcatg tcgaccacca gtctcgcccg    60
ttttttcaatg aactgattca attcatcacc acgggtccga ttatcgcaat ggaaattctg    120
cgtgatgacg ctatctgcga atggaaacgc ctgctgggcc cggcaaactc aggtgttgcg    180
cgtaccgatg ccagtgaatc cattcgcgct ctgtttggca ccgatggtat ccgtaatgca    240
gcacatggtc cggactcatt cgcatcggca gctcgtgaaa tggaactgtt tttcccgagc    300
tctggcggtt gcggtccggc aaacaccgcc aaatttacca attgtacgtg ctgtattgtc    360
aaaccgcacg cagtgtcaga aggcctgctg gtaaaattc tgatggcaat ccgtgatgct    420
ggctttgaaa tctcggccat gcagatgttc aacatggacc gcgttaacgt cgaagaattc    480
tacgaagttt acaaaggcgt ggttaccgaa tatcacgata tggttacgga aatgtactcc    540
ggtccgtgcg tcgcgatgga aattcagcaa aacaatgcca ccaaaacgtt tcgtgaattc    600
tgtggtccgg cagatccgga aatcgcacgt catctgcgtc cgggtaccct gcgcgcaatt    660
tttggtaaaa cgaaaatcca gaacgctgtg cactgtaccg atctgccgga agacggtctg    720
ctggaagttc aatactttt caaaattctg gataat                              756

SEQ ID NO: 161         moltype = AA  length = 254
FEATURE                Location/Qualifiers
REGION                 1..254
                       note = Human NME7-X1 (optimized for E coli expression)
source                 1..254
                       mol_type = protein
                       organism = synthetic construct
SEQUENCE: 161
MMMLSRKEAL DFHVDHQSRP FFNELIQFIT TGPIIAMEIL RDDAICEWKR LLGPANSGVA    60
RTDASESIRA LFGTDGIRNA AHGPDSFASA AREMELFFPS SGGCGPANTA KFTNCTCCIV    120
KPHAVSEGLL GKILMAIRDA GFEISAMQMF NMDRVNVEEF YEVYKGVVTE YHDMVTEMYS    180
GPCVAMEIQQ NNATKTFREF CGPADPEIAR HLRPGTLRAI FGKTKIQNAV HCTDLPEDGL    240
LEVQYFFKIL DNTG                                                     254
```

```
SEQ ID NO: 162          moltype = AA  length = 91
FEATURE                 Location/Qualifiers
REGION                  1..91
                        note = DM10 domain of NME7
source                  1..91
                        mol_type = protein
                        organism = synthetic construct
SEQUENCE: 162
MNHSERFVFI AEWYDPNASL LRRYELLFYP GDGSVEMHDV KNHRTFLKRT KYDNLHLEDL   60
FIGNKVNVFS RQLVLIDYGD QYTARQLGSR K                                 91

SEQ ID NO: 163          moltype = AA  length = 43
FEATURE                 Location/Qualifiers
REGION                  1..43
                        note = Fragment or variation of PSMGFR peptide
source                  1..43
                        mol_type = protein
                        organism = synthetic construct
SEQUENCE: 163
SNIKFRPGSV VVQLTLAFRE GTINVHDVET QFNQYKTEAA SRY                    43

SEQ ID NO: 164          moltype = AA  length = 35
FEATURE                 Location/Qualifiers
REGION                  1..35
                        note = Fragment or variation of PSMGFR peptide
source                  1..35
                        mol_type = protein
                        organism = synthetic construct
SEQUENCE: 164
SVVVQLTLAF REGTINVHDV ETQFNQYKTE AASRY                             35

SEQ ID NO: 165          moltype = AA  length = 24
FEATURE                 Location/Qualifiers
REGION                  1..24
                        note = Fragment or variation of PSMGFR peptide
source                  1..24
                        mol_type = protein
                        organism = synthetic construct
SEQUENCE: 165
VQLTLAFREG TINVHDVETQ FNQY                                         24

SEQ ID NO: 166          moltype = AA  length = 24
FEATURE                 Location/Qualifiers
REGION                  1..24
                        note = Fragment or variation of PSMGFR peptide
source                  1..24
                        mol_type = protein
                        organism = synthetic construct
SEQUENCE: 166
SNIKFRPGSV VVQLTLAFRE GTIN                                         24

SEQ ID NO: 167          moltype = AA  length = 38
FEATURE                 Location/Qualifiers
REGION                  1..38
                        note = Fragment or variation of PSMGFR peptide
source                  1..38
                        mol_type = protein
                        organism = synthetic construct
SEQUENCE: 167
SNIKFRPGSV VVQLTLAFRE GTINVHDVET QFNQYKTE                          38

SEQ ID NO: 168          moltype = AA  length = 45
FEATURE                 Location/Qualifiers
REGION                  1..45
                        note = Fragment or variation of PSMGFR peptide
source                  1..45
                        mol_type = protein
                        organism = synthetic construct
SEQUENCE: 168
VQLTLAFREG TINVHDVETQ FNQYKTEAAS RYNLTISDVS VSDVP                  45

SEQ ID NO: 169          moltype = AA  length = 29
FEATURE                 Location/Qualifiers
REGION                  1..29
                        note = Ser of NME7B peptide 3 (B domain)
source                  1..29
                        mol_type = protein
                        organism = synthetic construct
SEQUENCE: 169
```

```
AIFGKTKIQN AVHSTDLPED GLLEVQYFF                                              29

SEQ ID NO: 170          moltype = AA  length = 35
FEATURE                 Location/Qualifiers
REGION                  1..35
                        note = N-10 peptide
source                  1..35
                        mol_type = protein
                        organism = synthetic construct
SEQUENCE: 170
QFNQYKTEAA SRYNLTISDV SVSDVPFPFS AQSGA                                       35

SEQ ID NO: 171          moltype = AA  length = 35
FEATURE                 Location/Qualifiers
REGION                  1..35
                        note = C-10 peptide
source                  1..35
                        mol_type = protein
                        organism = synthetic construct
SEQUENCE: 171
GTINVHDVET QFNQYKTEAA SRYNLTISDV SVSDV                                       35

SEQ ID NO: 172          moltype = AA  length = 119
FEATURE                 Location/Qualifiers
REGION                  1..119
                        note = 8F9A5A1H heavy chain
source                  1..119
                        mol_type = protein
                        organism = synthetic construct
SEQUENCE: 172
IQLVQSGPEL KKPGETVKIS CKASGYTFTN YGMNWVKQAP GKGLKWMGWI NTYTGEPTYV            60
DDFKGRFAFS LETSATTAYL QINNLKNEDT STYFCARLRG IRPGPLAYWG QGTLVTVSA             119

SEQ ID NO: 173          moltype = AA  length = 121
FEATURE                 Location/Qualifiers
REGION                  1..121
                        note = 8F9A4P3H heavy chain
source                  1..121
                        mol_type = protein
                        organism = synthetic construct
SEQUENCE: 173
VQLQQSGPEL VKPGASVKIS CKTSGNTFTE YTMHWVKQSH GKSLEWIGGF NPNNGVTNYN            60
QKFKGKATLT VDKSSSTAYM ELRSLTSEDS AVYYCARRYY HSLYVFYFDY WGQGTTLTVS            120
S                                                                           121

SEQ ID NO: 174          moltype = AA  length = 116
FEATURE                 Location/Qualifiers
REGION                  1..116
                        note = 5D9E2B11H
source                  1..116
                        mol_type = protein
                        organism = synthetic construct
SEQUENCE: 174
VQLQQSGPDL VKPGTSVKIS CKTSGNTFTE YTMHWVKQSH GKSLEWIGGF NPNNGVTNYN            60
QKFKGKATLT VDKSSSTAYM ELRSLTSEDS AVYYCARRYY HSTYVFYFDS WGQGTT                116

SEQ ID NO: 175          moltype = AA  length = 121
FEATURE                 Location/Qualifiers
REGION                  1..121
                        note = 5D9E10E4H
source                  1..121
                        mol_type = protein
                        organism = synthetic construct
SEQUENCE: 175
VQLQQSGPDL VKPGTSVKIS CKTSGNTFTE YTMHWVKQSH GKSLEWIGGF NPNNGVTNYN            60
QKFKGKATLT VDKSSSTAYM ELRSLTSEDS AVYYCARRYY HSTYVFYFDS WGQGTTLTVS            120
S                                                                           121

SEQ ID NO: 176          moltype = AA  length = 121
FEATURE                 Location/Qualifiers
REGION                  1..121
                        note = 5D9G2C4H
source                  1..121
                        mol_type = protein
                        organism = synthetic construct
SEQUENCE: 176
VQLQQSGPDL VKPGTSVKIS CKTSGNTFTE YTMHWVKQSH GKSLEWIGGF NPNNGVTNYN            60
QKFKGKATLT VDKSSSTAYM ELRSLTSEDS AVYYCARRYY HSTYVFYFDS WGQGTTLTVS            120
S                                                                           121
```

```
SEQ ID NO: 177          moltype = AA   length = 121
FEATURE                 Location/Qualifiers
REGION                  1..121
                        note = 5F3A5D4H
source                  1..121
                        mol_type = protein
                        organism = synthetic construct
SEQUENCE: 177
VQLQQSGPDL VKPGTSVKIS CKTSGNTFTE YTMHWVKQSH GKSLEWIGGF NPNNGVTNYN   60
QKFKGKATLT VDKSSSTAYM ELRSLTSEDS AVYYCARRYY HSTYVFYFDS WGQGTTLTVS  120
S                                                                 121

SEQ ID NO: 178          moltype = AA   length = 121
FEATURE                 Location/Qualifiers
REGION                  1..121
                        note = 8H5H5G4H
source                  1..121
                        mol_type = protein
                        organism = synthetic construct
SEQUENCE: 178
VQLQQSGPDL VKPGTSVKIS CKTSGNTFTE YTMHWVKQSH GKSLEWIGGF NPNNGVTNYN   60
QKFKGKATLT VDKSSSTAYM ELRSLTSEDS AVYYCARRYY HSTYVFYFDS WGQGTTLTVS  120
S                                                                 121

SEQ ID NO: 179          moltype = AA   length = 121
FEATURE                 Location/Qualifiers
REGION                  1..121
                        note = 8F9A4A3H
source                  1..121
                        mol_type = protein
                        organism = synthetic construct
SEQUENCE: 179
VQLQQSGPEL VKPGASVKIS CKTSGNTFTE YTMHWVKQSH GKSLEWIGGF NPNNGVTNYN   60
QKFKGKATLT VDKSSSTAYM ELRSLTSEDS AVYYCARRYY HSLYVFYFDY WGQGTTLTVS  120
S                                                                 121

SEQ ID NO: 180          moltype = AA   length = 116
FEATURE                 Location/Qualifiers
REGION                  1..116
                        note = 5D9E2B11H
source                  1..116
                        mol_type = protein
                        organism = synthetic construct
SEQUENCE: 180
VQLQQSGPDL VKPGTSVKIS CKTSGNTFTE YTMHWVKQSH GKSLEWIGGF NPNNGVTNYN   60
QKFKGKATLT VDKSSSTAYM ELRSLTSEDS AVYYCARRYY HSTYVFYFDS WGQGTT     116

SEQ ID NO: 181          moltype = AA   length = 121
FEATURE                 Location/Qualifiers
REGION                  1..121
                        note = 5D9E10E4H
source                  1..121
                        mol_type = protein
                        organism = synthetic construct
SEQUENCE: 181
VQLQQSGPDL VKPGTSVKIS CKTSGNTFTE YTMHWVKQSH GKSLEWIGGF NPNNGVTNYN   60
QKFKGKATLT VDKSSSTAYM ELRSLTSEDS AVYYCARRYY HSTYVFYFDS WGQGTTLTVS  120
S                                                                 121

SEQ ID NO: 182          moltype = AA   length = 121
FEATURE                 Location/Qualifiers
REGION                  1..121
                        note = 5D9G2C4H
source                  1..121
                        mol_type = protein
                        organism = synthetic construct
SEQUENCE: 182
VQLQQSGPDL VKPGTSVKIS CKTSGNTFTE YTMHWVKQSH GKSLEWIGGF NPNNGVTNYN   60
QKFKGKATLT VDKSSSTAYM ELRSLTSEDS AVYYCARRYY HSTYVFYFDS WGQGTTLTVS  120
S                                                                 121

SEQ ID NO: 183          moltype = AA   length = 121
FEATURE                 Location/Qualifiers
REGION                  1..121
                        note = 5F3A5D4H
source                  1..121
                        mol_type = protein
                        organism = synthetic construct
```

```
SEQUENCE: 183
VQLQQSGPDL VKPGTSVKIS CKTSGNTFTE YTMHWVKQSH GKSLEWIGGF NPNNGVTNYN    60
QKFKGKATLT VDKSSSTAYM ELRSLTSEDS AVYYCARRYY HSTYVFYFDS WGQGTTLTVS   120
S                                                                   121

SEQ ID NO: 184          moltype = AA  length = 121
FEATURE                 Location/Qualifiers
REGION                  1..121
                        note = 8H5H5G4H
source                  1..121
                        mol_type = protein
                        organism = synthetic construct
SEQUENCE: 184
VQLQQSGPDL VKPGTSVKIS CKTSGNTFTE YTMHWVKQSH GKSLEWIGGF NPNNGVTNYN    60
QKFKGKATLT VDKSSSTAYM ELRSLTSEDS AVYYCARRYY HSTYVFYFDS WGQGTTLTVS   120
S                                                                   121

SEQ ID NO: 185          moltype = AA  length = 108
FEATURE                 Location/Qualifiers
REGION                  1..108
                        note = 8F9A4P3L
source                  1..108
                        mol_type = protein
                        organism = synthetic construct
SEQUENCE: 185
ETTVTQSPAS LSMAIGEKVT IRCITSTDID DDMNWYQQKP GEPPKLLISE GNTLRPGVPS    60
RFSSSGYGTD FVFTIENMLS EDVADYYCLQ SDNLPLTFGS GTKLEIKR                108

SEQ ID NO: 186          moltype = AA  length = 108
FEATURE                 Location/Qualifiers
REGION                  1..108
                        note = 5D9E2B11L
source                  1..108
                        mol_type = protein
                        organism = synthetic construct
SEQUENCE: 186
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 187          moltype = AA  length = 108
FEATURE                 Location/Qualifiers
REGION                  1..108
                        note = 5D9E10E4L
source                  1..108
                        mol_type = protein
                        organism = synthetic construct
SEQUENCE: 187
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 188          moltype = AA  length = 108
FEATURE                 Location/Qualifiers
REGION                  1..108
                        note = 5D9G2C4L
source                  1..108
                        mol_type = protein
                        organism = synthetic construct
SEQUENCE: 188
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 189          moltype = AA  length = 108
FEATURE                 Location/Qualifiers
REGION                  1..108
                        note = 5F3A5D4L
source                  1..108
                        mol_type = protein
                        organism = synthetic construct
SEQUENCE: 189
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 190          moltype = AA  length = 108
FEATURE                 Location/Qualifiers
REGION                  1..108
                        note = 8H5H5G4L
source                  1..108
                        mol_type = protein
                        organism = synthetic construct
```

```
SEQUENCE: 190
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 191         moltype = AA  length = 107
FEATURE                Location/Qualifiers
REGION                 1..107
                       note = 8F9A5A1L
source                 1..107
                       mol_type = protein
                       organism = synthetic construct
SEQUENCE: 191
EILLTQSPAI IAASPGEKVT ITCSASSSVS YMNWYQQKPG SSPKIWIYGI SNLASGVPAR    60
FSGSGSGTSF SFTINSMEAE DVATYYCQQR SSYPPTFGGG TKLEIKR                 107

SEQ ID NO: 192         moltype = AA  length = 108
FEATURE                Location/Qualifiers
REGION                 1..108
                       note = 5D9E2B11L
source                 1..108
                       mol_type = protein
                       organism = synthetic construct
SEQUENCE: 192
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 193         moltype = AA  length = 108
FEATURE                Location/Qualifiers
REGION                 1..108
                       note = 5D9E10E4L
source                 1..108
                       mol_type = protein
                       organism = synthetic construct
SEQUENCE: 193
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 194         moltype = AA  length = 108
FEATURE                Location/Qualifiers
REGION                 1..108
                       note = 5D9G2C4L
source                 1..108
                       mol_type = protein
                       organism = synthetic construct
SEQUENCE: 194
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 195         moltype = AA  length = 108
FEATURE                Location/Qualifiers
REGION                 1..108
                       note = 5F3A5D4L
source                 1..108
                       mol_type = protein
                       organism = synthetic construct
SEQUENCE: 195
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 196         moltype = AA  length = 108
FEATURE                Location/Qualifiers
REGION                 1..108
                       note = 8H5H5G4L
source                 1..108
                       mol_type = protein
                       organism = synthetic construct
SEQUENCE: 196
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 197         moltype = AA  length = 108
FEATURE                Location/Qualifiers
REGION                 1..108
                       note = 8F9A4P3L
source                 1..108
                       mol_type = protein
                       organism = synthetic construct
SEQUENCE: 197
ETTVTQSPAS LSMAIGEKVT IRCITSTDID DDMNWYQQKP GEPPKLLISE GNTLRPGVPS    60
```

```
RFSSSGYGTD FVFTIENMLS EDVADYYCLQ SDNLPLTFGS GTKLEIKR                108

SEQ ID NO: 198         moltype = AA   length = 107
FEATURE                Location/Qualifiers
REGION                 1..107
                       note = 8F9A5A1L
source                 1..107
                       mol_type = protein
                       organism = synthetic construct
SEQUENCE: 198
EILLTQSPAI IAASPGEKVT ITCSASSSVS YMNWYQQKPG SSPKIWIYGI SNLASGVPAR   60
FSGSGSGTSF SFTINSMEAE DVATYYCQQR SSYPPTFGGG TKLEIKR                107

SEQ ID NO: 199         moltype = AA   length = 131
FEATURE                Location/Qualifiers
REGION                 1..131
                       note = NME7A partial sequence
source                 1..131
                       mol_type = protein
                       organism = synthetic construct
SEQUENCE: 199
EKTLALIKPD AISKAGEIIE IINKAGFTIT KLKMMMLSRK EALDFHVDHQ SRPFFNELIQ   60
FITTGPIIAM EILRDDAICE WKRLLGPANS GVARTDASES IRALFGTDGI RNAAHGPDSF   120
ASAAREMELF F                                                        131

SEQ ID NO: 200         moltype = AA   length = 152
FEATURE                Location/Qualifiers
REGION                 1..152
                       note = NME2 partial sequence
source                 1..152
                       mol_type = protein
                       organism = synthetic construct
SEQUENCE: 200
MANLERTFIA IKPDGVQRGL VGEIIKRFEQ KGFRLVAMKF LRASEEHLKQ HYIDLKDRPF   60
FPGLVKYMNS GPVVAMVWEG LNVVKTGRVM LGETNPADSK PGTIRGDFCI QVGRNIIHGS   120
DSVKSAEKEI SLWFKPEELV DYKSCAHDWV YE                                 152

SEQ ID NO: 201         moltype = AA   length = 134
FEATURE                Location/Qualifiers
REGION                 1..134
                       note = NME7B partial sequence
source                 1..134
                       mol_type = protein
                       organism = synthetic construct
SEQUENCE: 201
NCTCCCIVKPH AVSEGLLGKI LMAIRDAGFE ISAMQMFNMD RVNVEEFYEV YKGVVTEYHD  60
MVTEMYSGPC VAMEIQQNNA TKTFREFCGP ADPEIARHLR PGTLRAIFGK TKIQNAVHCT   120
DLPEDGLLEV QYFF                                                     134

SEQ ID NO: 202         moltype = AA   length = 152
FEATURE                Location/Qualifiers
REGION                 1..152
                       note = NME2 partial sequence
source                 1..152
                       mol_type = protein
                       organism = synthetic construct
SEQUENCE: 202
MANLERTFIA IKPDGVQRGL VGEIIKRFEQ KGFRLVAMKF LRASEEHLKQ HYIDLKDRPF   60
FPGLVKYMNS GPVVAMVWEG LNVVKTGRVM LGETNPADSK PGTIRGDFCI QVGRNIIHGS   120
DSVKSAEKEI SLWFKPEELV DYKSCAHDWV YE                                 152

SEQ ID NO: 203         moltype = AA   length = 131
FEATURE                Location/Qualifiers
REGION                 1..131
                       note = NME7A partial sequence
source                 1..131
                       mol_type = protein
                       organism = synthetic construct
SEQUENCE: 203
EKTLALIKPD AISKAGEIIE IINKAGFTIT KLKMMMLSRK EALDFHVDHQ SRPFFNELIQ   60
FITTGPIIAM EILRDDAICE WKRLLGPANS GVARTDASES IRALFGTDGI RNAAHGPDSF   120
ASAAREMELF F                                                        131

SEQ ID NO: 204         moltype = AA   length = 130
FEATURE                Location/Qualifiers
REGION                 1..130
                       note = NME3 partial sequence
source                 1..130
                       mol_type = protein
```

```
                          organism = synthetic construct
SEQUENCE: 204
ERTFLAVKPD GVQRRLVGEI VRRFERKGFK LVALKLVQAS EELLREHYVE LRERPFYSRL    60
VKYMGSPVV AMVWQGLDVV RASRALIGAT DPGDATPGTI RGDFCVEVGK NVIHGSDSVE   120
SAQREIALWF                                                          130

SEQ ID NO: 205         moltype = AA  length = 134
FEATURE                Location/Qualifiers
REGION                 1..134
                       note = NME7B partial sequence
source                 1..134
                       mol_type = protein
                       organism = synthetic construct
SEQUENCE: 205
NCTCCIVKPH AVSEGLLGKI LMAIRDAGFE ISAMQMFNMD RVNVEEFYEV YKGVVTEYHD    60
MVTEMYSGPC VAMEIQQNNA TKTFREFCGP ADPEIARHLR PGTLRAIFGK TKIQNAVHCT   120
DLPEDGLLEV QYFF                                                     134

SEQ ID NO: 206         moltype = AA  length = 169
FEATURE                Location/Qualifiers
REGION                 1..169
                       note = NME3 partial sequence
source                 1..169
                       mol_type = protein
                       organism = synthetic construct
SEQUENCE: 206
MICLVLTIFA NLFPSAYSGV NERTFLAVKP DGVQRRLVGE IVRRFERKGF KLVALKLVQA    60
SEELLREHYV ELRERPFYSR LVKYMGSPV VAMVWQGLDV VRASRALIGA TDPGDATPGT   120
IRGDFCVEVG KNVIHGSDSV ESAQREIALW FREDELLCWE DSAGHWLYE              169

SEQ ID NO: 207         moltype = AA  length = 131
FEATURE                Location/Qualifiers
REGION                 1..131
                       note = NME7A partial sequence
source                 1..131
                       mol_type = protein
                       organism = synthetic construct
SEQUENCE: 207
EKTLALIKPD AISKAGEIIE IINKAGFTIT KLKMMMLSRK EALDFHVDHQ SRPFFNELIQ    60
FITTGPIIAM EILRDDAICE WKRLLGPANS GVARTDASES IRALFGTDGI RNAAHGPDSF   120
ASAAREMELF F                                                        131

SEQ ID NO: 208         moltype = AA  length = 130
FEATURE                Location/Qualifiers
REGION                 1..130
                       note = NME4 partial sequence
source                 1..130
                       mol_type = protein
                       organism = synthetic construct
SEQUENCE: 208
ERTLVAVKPD GVQRRLVGDV IQRFERRGFT LVGMKMLQAP ESVLAEHYQD LRRKPFYPAL    60
IRYMSSGPVV AMVWEGYNVV RASRAMIGHT DSAEAAPGTI RGDFSVHISR NVIHASDSVE   120
GAQREIQLWF                                                          130

SEQ ID NO: 209         moltype = AA  length = 132
FEATURE                Location/Qualifiers
REGION                 1..132
                       note = NME7B partial sequence
source                 1..132
                       mol_type = protein
                       organism = synthetic construct
SEQUENCE: 209
TCCIVKPHAV SEGLLGKILM AIRDAGFEIS AMQMFNMDRV NVEEFYEVYK GVVTEYHDMV    60
TEMYSGPCVA MEIQQNNATK TFREFCGPAD PEIARHLRPG TLRAIFGKTK IQNAVHCTDL   120
PEDGLLEVQY FF                                                       132

SEQ ID NO: 210         moltype = AA  length = 128
FEATURE                Location/Qualifiers
REGION                 1..128
                       note = NME4 partial sequence
source                 1..128
                       mol_type = protein
                       organism = synthetic construct
SEQUENCE: 210
TLVAVKPDGV QRRLVGDVIQ RFERRGFTLV GMKMLQAPES VLAEHYQDLR RKPFYPALIR    60
YMSSGPVVAM VWEGYNVVRA SRAMIGHTDS AEAAPGTIRG DFSVHISRNV IHASDSVEGA   120
QREIQLWF                                                            128

SEQ ID NO: 211         moltype = AA  length = 131
```

```
FEATURE              Location/Qualifiers
REGION               1..131
                     note = NME7A partial sequence
source               1..131
                     mol_type = protein
                     organism = synthetic construct
SEQUENCE: 211
EKTLALIKPD AISKAGEIIE IINKAGFTIT KLKMMMLSRK EALDFHVDHQ SRPFFNELIQ     60
FITTGPIIAM EILRDDAICE WKRLLGPANS GVARTDASES IRALFGTDGI RNAAHGPDSF    120
ASAAREMELF F                                                         131

SEQ ID NO: 212       moltype = AA  length = 131
FEATURE              Location/Qualifiers
REGION               1..131
                     note = NME5 partial sequence
source               1..131
                     mol_type = protein
                     organism = synthetic construct
SEQUENCE: 212
EKTLAIIKPD IVDKEEEIQD IILRSGFTIV QRRKLRLSPE QCSNFYVEKY GKMFFPNLTA     60
YMSSGPLVAM ILARHKAISY WLELLGPNNS LVAKETHPDS LRAIYGTDDL RNALHGSNDF    120
AAAEREIRFM F                                                         131

SEQ ID NO: 213       moltype = AA  length = 132
FEATURE              Location/Qualifiers
REGION               1..132
                     note = NME7B partial sequence
source               1..132
                     mol_type = protein
                     organism = synthetic construct
SEQUENCE: 213
TCCIVKPHAV SEGLLGKILM AIRDAGFEIS AMQMFNMDRV NVEEFYEVYK GVVTEYHDMV     60
TEMYSGPCVA MEIQQNNATK TFREFCGPAD PEIARHLRPG TLRAIFGKTK IQNAVHCTDL    120
PEDGLLEVQY FF                                                        132

SEQ ID NO: 214       moltype = AA  length = 129
FEATURE              Location/Qualifiers
REGION               1..129
                     note = NME5 partial sequence
source               1..129
                     mol_type = protein
                     organism = synthetic construct
SEQUENCE: 214
TLAIIKPDIV DKEEEIQDII LRSGFTIVQR RKLRLSPEQC SNFYVEKYGK MFFPNLTAYM     60
SSGPLVAMIL ARHKAISYWL ELLGPNNSLV AKETHPDSLR AIYGTDDLRN ALHGSNDFAA    120
AEREIRFMF                                                            129

SEQ ID NO: 215       moltype = AA  length = 129
FEATURE              Location/Qualifiers
REGION               1..129
                     note = NME7A partial sequence
source               1..129
                     mol_type = protein
                     organism = synthetic construct
SEQUENCE: 215
TLALIKPDAI SKAGEIIEII NKAGFTITKL KMMMLSRKEA LDFHVDHQSR PFFNELIQFI     60
TTGPIIAMEI LRDDAICEWK RLLGPANSGV ARTDASESIR ALFGTDGIRN AAHGPDSFAS    120
AAREMELFF                                                            129

SEQ ID NO: 216       moltype = AA  length = 132
FEATURE              Location/Qualifiers
REGION               1..132
                     note = NME6 partial sequence
source               1..132
                     mol_type = protein
                     organism = synthetic construct
SEQUENCE: 216
TLALIKPDAV AHPLILEAVH QQILSNKFLI VRMRELLWRK EDCQRFYREH EGRFFYQRLV     60
EFMASGPIRA YILAHKDAIQ LWRTLMGPTR VFRARHVAPD SIRGSFGLTD TRNTTHGSDS    120
VVSASREIAA FF                                                        132

SEQ ID NO: 217       moltype = AA  length = 132
FEATURE              Location/Qualifiers
REGION               1..132
                     note = NME7B partial sequence
source               1..132
                     mol_type = protein
                     organism = synthetic construct
SEQUENCE: 217
```

```
TCCIVKPHAV SEGLLGKILM AIRDAGFEIS AMQMFNMDRV NVEEFYEVYK GVVTEYHDMV    60
TEMYSGPCVA MEIQQNNATK TFREFCGPAD PEIARHLRPG TLRAIFGKTK IQNAVHCTDL   120
PEDGLLEVQY FF                                                      132

SEQ ID NO: 218          moltype = AA   length = 132
FEATURE                 Location/Qualifiers
REGION                  1..132
                        note = NME6 partial sequence
source                  1..132
                        mol_type = protein
                        organism = synthetic construct
SEQUENCE: 218
TLALIKPDAV AHPLILEAVH QQILSNKFLI VRMRELLWRK EDCQRFYREH EGRFFYQRLV    60
EFMASGPIRA YILAHKDAIQ LWRTLMGPTR VFRARHVAPD SIRGSFGLTD TRNTTHGSDS   120
VVSASREIAA FF                                                      132

SEQ ID NO: 219          moltype = AA   length = 131
FEATURE                 Location/Qualifiers
REGION                  1..131
                        note = NME7A partial sequence
source                  1..131
                        mol_type = protein
                        organism = synthetic construct
SEQUENCE: 219
EKTLALIKPD AISKAGEIIE IINKAGFTIT KLKMMMLSRK EALDFHVDHQ SRPFFNELIQ    60
FITTGPIIAM EILRDDAICE WKRLLGPANS GVARTDASES IRALFGTDGI RNAAHGPDSF   120
ASAAREMELF F                                                       131

SEQ ID NO: 220          moltype = AA   length = 133
FEATURE                 Location/Qualifiers
REGION                  1..133
                        note = NME8 partial sequence
source                  1..133
                        mol_type = protein
                        organism = synthetic construct
SEQUENCE: 220
EKTLALLRPN LFHERKDDVL RIIKDEDFKI LEQRQVVLSE KEAQALCKEY ENEDYFNKLI    60
ENMTSGPSLA LVLLRDNGLQ YWKQLLGPRT VEEAIEYFPE SLCAQFAMDS LPVNQLYGSD   120
SLETAEREIQ HFF                                                     133

SEQ ID NO: 221          moltype = AA   length = 127
FEATURE                 Location/Qualifiers
REGION                  1..127
                        note = NME7A partial sequence
source                  1..127
                        mol_type = protein
                        organism = synthetic construct
SEQUENCE: 221
EKTLALIKPD AISKAGEIIE IINKAGFTIT KLKMMMLSRK EALDFHVDHQ SRPFFNELIQ    60
FITTGPIIAM EILRDDAICE WKRLLGPANS GVARTDASES IRALFGTDGI RNAAHGPDSF   120
ASAAREM                                                            127

SEQ ID NO: 222          moltype = AA   length = 127
FEATURE                 Location/Qualifiers
REGION                  1..127
                        note = NME8 partial sequence
source                  1..127
                        mol_type = protein
                        organism = synthetic construct
SEQUENCE: 222
QSTLGLIKPH ATSEQREQIL KIVKEAGFDL TQVKKMFLTP EQIEKIYPKV TGKDFYKDLL    60
EMLSVGPSMV MILTKWNAVA EWRRLMGPTD PEEAKLLSPD SIRAQFGISK LKNIVHGASN   120
AYEAKEV                                                            127

SEQ ID NO: 223          moltype = AA   length = 63
FEATURE                 Location/Qualifiers
REGION                  1..63
                        note = NME7A partial sequence
source                  1..63
                        mol_type = protein
                        organism = synthetic construct
SEQUENCE: 223
TLALIKPDAI SKAGEIIEII NKAGFTITKL KMMMLSRKEA LDFHVDHQSR PFFNELIQFI    60
TTG                                                                 63

SEQ ID NO: 224          moltype = AA   length = 65
FEATURE                 Location/Qualifiers
REGION                  1..65
                        note = NME8 partial sequence
```

```
source                  1..65
                        mol_type = protein
                        organism = synthetic construct
SEQUENCE: 224
SIAIIKPDAV ISKKVLEIKR KITKAGFIIE AEHKTVLTEE QVVNFYSRIA DQCDFEEFVS    60
FMTSG                                                                65

SEQ ID NO: 225          moltype = AA   length = 116
FEATURE                 Location/Qualifiers
REGION                  1..116
                        note = NME7B partial sequence
source                  1..116
                        mol_type = protein
                        organism = synthetic construct
SEQUENCE: 225
TCCIVKPHAV SEGLLGKILM AIRDAGFEIS AMQMFNMDRV NVEEFYEVYK GVVTEYHDMV    60
TEMYSGPCVA MEIQQNNATK TFREFCGPAD PEIARHLRPG TLRAIFGKTK IQNAVH       116

SEQ ID NO: 226          moltype = AA   length = 114
FEATURE                 Location/Qualifiers
REGION                  1..114
                        note = NME8 partial sequence
source                  1..114
                        mol_type = protein
                        organism = synthetic construct
SEQUENCE: 226
TLGLIKPHAT SEQREQILKI VKEAGFDLTQ VKKMFLTPEQ IEKIYPKVTG KDFYKDLLEM    60
LSVGPSMVMI LTKWNAVAEW RRLMGPTDPE EAKLLSPDSI RAQFGISKLK NIVH         114

SEQ ID NO: 227          moltype = AA   length = 115
FEATURE                 Location/Qualifiers
REGION                  1..115
                        note = NME7B partial sequence
source                  1..115
                        mol_type = protein
                        organism = synthetic construct
SEQUENCE: 227
ILMAIRDAGF EISAMQMFNM DRVNVEEFYE VYKGVVTEYH DMVTEMYSGP CVAMEIQQNN    60
ATKTFREFCG PADPEIARHL RPGTLRAIFG KTKIQNAVHC TDLPEDGLLE VQYFF        115

SEQ ID NO: 228          moltype = AA   length = 115
FEATURE                 Location/Qualifiers
REGION                  1..115
                        note = NME8 partial sequence
source                  1..115
                        mol_type = protein
                        organism = synthetic construct
SEQUENCE: 228
VLRIIKDEDF KILEQRQVVL SEKEAQALCK EYENEDYFNK LIENMTSGPS LALVLLRDNG    60
LQYWKQLLGP RTVEEAIEYF PESLCAQFAM DSLPVNQLYG SDSLETAERE IQHFF        115

SEQ ID NO: 229          moltype = AA   length = 100
FEATURE                 Location/Qualifiers
REGION                  1..100
                        note = NME7B partial sequence
source                  1..100
                        mol_type = protein
                        organism = synthetic construct
SEQUENCE: 229
IVKPHAVSEG LLGKILMAIR DAGFEISAMQ MFNMDRVNVE EFYEVYKGVV TEYHDMVTEM    60
YSGPCVAMEI QQNNATKTFR EFCGPADPEI ARHLRPGTLR                        100

SEQ ID NO: 230          moltype = AA   length = 110
FEATURE                 Location/Qualifiers
REGION                  1..110
                        note = NME8 partial sequence
source                  1..110
                        mol_type = protein
                        organism = synthetic construct
SEQUENCE: 230
IIKPDAVISK KVLEIKRKIT KAGFIIEAEH KTVLTEEQVV NFYSRIADQC DFEEFVSFMT    60
SGLSYILVVS QGSKHNPPSE ETEPQTDTEP NERSEDQPEV EAQVTPGMMK             110

SEQ ID NO: 231          moltype = AA   length = 174
FEATURE                 Location/Qualifiers
REGION                  1..174
                        note = NME9
source                  1..174
                        mol_type = protein
```

```
                         organism = synthetic construct
SEQUENCE: 231
MLSSKGLTVV DVYQGWCGPC KPVVSLFQKM RIEVGLDLLH FALAEADRLD VLEKYRGKCE    60
PTFLFYAIKD EALSDEDECV SHGKNNGEDE DMVSSERTCT LAIIKPDAVA HGKTDEIIMK   120
IQEAGFEILT NEERTMTEAE VRLFYQHKAG ESPSSVRHRN ALQCRPWKPG QRRC         174

SEQ ID NO: 232           moltype = AA   length = 58
FEATURE                  Location/Qualifiers
REGION                   1..58
                         note = NME7A partial sequence
source                   1..58
                         mol_type = protein
                         organism = synthetic construct
SEQUENCE: 232
TLALIKPDAI SKAGEIIEII NKAGFTITKL KMMMLSRKEA LDFHAMEILR DDAICEWK      58

SEQ ID NO: 233           moltype = AA   length = 60
FEATURE                  Location/Qualifiers
REGION                   1..60
                         note = NME9 partial sequence
source                   1..60
                         mol_type = protein
                         organism = synthetic construct
SEQUENCE: 233
TLAIIKPDAV AHGKTDEIIM KIQEAGFEIL TNEERTMTEA EVRLFYTLAI IKPDAVAHGK    60

SEQ ID NO: 234           moltype = AA   length = 31
FEATURE                  Location/Qualifiers
REGION                   1..31
                         note = NME7A partial sequence
source                   1..31
                         mol_type = protein
                         organism = synthetic construct
SEQUENCE: 234
ISKAGEIIEI INKAGFTITK LKMMMLSRKE A                                   31

SEQ ID NO: 235           moltype = AA   length = 29
FEATURE                  Location/Qualifiers
REGION                   1..29
                         note = NME9 partial sequence
source                   1..29
                         mol_type = protein
                         organism = synthetic construct
SEQUENCE: 235
IQEAGFEILT NEERTMTEAE VRLFYQHKA                                      29

SEQ ID NO: 236           moltype = AA   length = 53
FEATURE                  Location/Qualifiers
REGION                   1..53
                         note = NME7B partial sequence
source                   1..53
                         mol_type = protein
                         organism = synthetic construct
SEQUENCE: 236
NCTCCIVKPH AVSEGLLGKI LMAIRDAGFE ISAMQMFNMD RVNVEEFYEV YKG            53

SEQ ID NO: 237           moltype = AA   length = 53
FEATURE                  Location/Qualifiers
REGION                   1..53
                         note = NME9 partial sequence
source                   1..53
                         mol_type = protein
                         organism = synthetic construct
SEQUENCE: 237
TCTLAIIKPD AVAHGKTDEI IMKIQEAGFE ILTNEERTMT EAEVRLFYQH KAG            53

SEQ ID NO: 238           moltype = AA   length = 350
FEATURE                  Location/Qualifiers
REGION                   1..350
                         note = NME10
source                   1..350
                         mol_type = protein
                         organism = synthetic construct
SEQUENCE: 238
MGCFFSKRRK ADKESRPENE EERPKQYSWD QREKVDPKDY MFSGLKDETV GRLPGTVAGQ    60
QFLIQDCENC NIYIFDHSAT VTIDDCTNCI IFLGPVKGSV FFRNCRDCKC TLACQQFRVR   120
DCRKLEVFLC CATQPIIESS SNIKFGCFQW YYPELAFQFK DAGLSIFNNT WSNIHDFTPV   180
SGELNWSLLP EDAVVQDYVP IPTTEELKAV RVSTEANRSI VPISRGQRQK SSDESCLVVL   240
FAGDYTIANA RKLIDEMVGK GFFLVQTKEV SMKAEDAQRV FREKAPDFLP LLNKGPVIAL   300
```

```
EFNGDGAVEV CQLIVNEIFN GTKMFVSESK ETASGDVDSF YNFADIQMGI          350

SEQ ID NO: 239          moltype = AA   length = 68
FEATURE                 Location/Qualifiers
REGION                  1..68
                        note = NME7A partial sequence
source                  1..68
                        mol_type = protein
                        organism = synthetic construct
SEQUENCE: 239
AISKAGEIIE IINKAGFTIT KLKMMMLSRK EALDFHVDHQ SRPFFNELIQ FITTGPIIAM  60
EILRDDAI                                                          68

SEQ ID NO: 240          moltype = AA   length = 63
FEATURE                 Location/Qualifiers
REGION                  1..63
                        note = NME10 partial sequence
source                  1..63
                        mol_type = protein
                        organism = synthetic construct
SEQUENCE: 240
TIANARKLID EMVGKGFFLV QTKEVSMKAE DAQRVFREKA PDFLPLLNKG PVIALEFNGD  60
GAV                                                               63

SEQ ID NO: 241          moltype = AA   length = 43
FEATURE                 Location/Qualifiers
REGION                  1..43
                        note = NME7A partial sequence
source                  1..43
                        mol_type = protein
                        organism = synthetic construct
SEQUENCE: 241
PIIAMEILRD DAICEWKRLL GPANSGVART DASESIRALF GTD                   43

SEQ ID NO: 242          moltype = AA   length = 45
FEATURE                 Location/Qualifiers
REGION                  1..45
                        note = NME10 partial sequence
source                  1..45
                        mol_type = protein
                        organism = synthetic construct
SEQUENCE: 242
PIPTTEELKA VRVSTEANRS IVPISRGQRQ KSSDESCLVV LFAGD                 45

SEQ ID NO: 243          moltype = AA   length = 74
FEATURE                 Location/Qualifiers
REGION                  1..74
                        note = NME7A partial sequence
source                  1..74
                        mol_type = protein
                        organism = synthetic construct
SEQUENCE: 243
IKPDAISKAG EIIEIINKAG FTITKLKMMM LSRKEALDFH VDHQSRPFFN ELIQFITTGP  60
IIAMEILRDD AICE                                                   74

SEQ ID NO: 244          moltype = AA   length = 75
FEATURE                 Location/Qualifiers
REGION                  1..75
                        note = NME10 partial sequence
source                  1..75
                        mol_type = protein
                        organism = synthetic construct
SEQUENCE: 244
VDPKDYMFSG LKDETVGRLP GTVAGQQFLI QDCENCNIYI FDHSATVTID DCTNCIIFLG  60
PVKGSVFFRN CRDCK                                                  75

SEQ ID NO: 245          moltype = AA   length = 47
FEATURE                 Location/Qualifiers
REGION                  1..47
                        note = NME7B partial sequence
source                  1..47
                        mol_type = protein
                        organism = synthetic construct
SEQUENCE: 245
CCIVKPHAVS EGLLGKILMA IRDAGFEISA MQMFNMDRVN VEEFYEV               47

SEQ ID NO: 246          moltype = AA   length = 51
FEATURE                 Location/Qualifiers
REGION                  1..51
```

```
                    note = NME10 partial sequence
source              1..51
                    mol_type = protein
                    organism = synthetic construct
SEQUENCE: 246
CCATQPIIES SSNIKFGCFQ WYYPELAFQF KDAGLSIFNN TWSNIHDFTP V          51

SEQ ID NO: 247      moltype = AA  length = 16
FEATURE             Location/Qualifiers
REGION              1..16
                    note = NME2A1
source              1..16
                    mol_type = protein
                    organism = synthetic construct
SEQUENCE: 247
RASEEHLKQH YIDLKD                                                 16

SEQ ID NO: 248      moltype = AA  length = 8
FEATURE             Location/Qualifiers
REGION              1..8
                    note = NME2A2
source              1..8
                    mol_type = protein
                    organism = synthetic construct
SEQUENCE: 248
PADSKPGT                                                          8

SEQ ID NO: 249      moltype = AA  length = 20
FEATURE             Location/Qualifiers
REGION              1..20
                    note = NME2B1
source              1..20
                    mol_type = protein
                    organism = synthetic construct
SEQUENCE: 249
QKGFRLVAMK FLRASEEHLK                                             20

SEQ ID NO: 250      moltype = AA  length = 14
FEATURE             Location/Qualifiers
REGION              1..14
                    note = NME2B2
source              1..14
                    mol_type = protein
                    organism = synthetic construct
SEQUENCE: 250
IDLKDRPFPG LVKY                                                   14

SEQ ID NO: 251      moltype = AA  length = 29
FEATURE             Location/Qualifiers
REGION              1..29
                    note = NME2B3
source              1..29
                    mol_type = protein
                    organism = synthetic construct
SEQUENCE: 251
GDFCIQVGRN IIHGSDSVKS AEKEISLWF                                   29

SEQ ID NO: 252      moltype = AA  length = 16
FEATURE             Location/Qualifiers
REGION              1..16
                    note = NME3A1
source              1..16
                    mol_type = protein
                    organism = synthetic construct
SEQUENCE: 252
QASEELLREH YVELRE                                                 16

SEQ ID NO: 253      moltype = AA  length = 8
FEATURE             Location/Qualifiers
REGION              1..8
                    note = NME3A1
source              1..8
                    mol_type = protein
                    organism = synthetic construct
SEQUENCE: 253
PGDATPGT                                                          8

SEQ ID NO: 254      moltype = AA  length = 20
FEATURE             Location/Qualifiers
```

```
REGION                      1..20
                            note = NME3B1
source                      1..20
                            mol_type = protein
                            organism = synthetic construct
SEQUENCE: 254
RKGFKLVALK LVQASEELLR                                              20

SEQ ID NO: 255              moltype = AA  length = 15
FEATURE                     Location/Qualifiers
REGION                      1..15
                            note = NME3B2
source                      1..15
                            mol_type = protein
                            organism = synthetic construct
SEQUENCE: 255
VELRERPFYS RLVKY                                                   15

SEQ ID NO: 256              moltype = AA  length = 29
FEATURE                     Location/Qualifiers
REGION                      1..29
                            note = NME3B3
source                      1..29
                            mol_type = protein
                            organism = synthetic construct
SEQUENCE: 256
GDFCVEVGKN VIHGSDSVES AQREIALWF                                    29

SEQ ID NO: 257              moltype = AA  length = 16
FEATURE                     Location/Qualifiers
REGION                      1..16
                            note = NME4A1
source                      1..16
                            mol_type = protein
                            organism = synthetic construct
SEQUENCE: 257
QAPESVLAEH YQDLRR                                                  16

SEQ ID NO: 258              moltype = AA  length = 8
FEATURE                     Location/Qualifiers
REGION                      1..8
                            note = NME4A2
source                      1..8
                            mol_type = protein
                            organism = synthetic construct
SEQUENCE: 258
SAEAAPGT                                                            8

SEQ ID NO: 259              moltype = AA  length = 20
FEATURE                     Location/Qualifiers
REGION                      1..20
                            note = NME4B1
source                      1..20
                            mol_type = protein
                            organism = synthetic construct
SEQUENCE: 259
RRGFTLVGMK MLQAPESVLA                                              20

SEQ ID NO: 260              moltype = AA  length = 15
FEATURE                     Location/Qualifiers
REGION                      1..15
                            note = NME4B2
source                      1..15
                            mol_type = protein
                            organism = synthetic construct
SEQUENCE: 260
QDLRRKPFYP ALIRY                                                   15

SEQ ID NO: 261              moltype = AA  length = 29
FEATURE                     Location/Qualifiers
REGION                      1..29
                            note = NME4B3
source                      1..29
                            mol_type = protein
                            organism = synthetic construct
SEQUENCE: 261
GDFSVHISRN VIHASDSVEG AQREIQLWF                                    29

SEQ ID NO: 262              moltype = AA  length = 16
```

```
FEATURE                 Location/Qualifiers
REGION                  1..16
                        note = NME5A1
source                  1..16
                        mol_type = protein
                        organism = synthetic construct
SEQUENCE: 262
RLSPEQCSNF YVEKYG                                                       16

SEQ ID NO: 263          moltype = AA  length = 11
FEATURE                 Location/Qualifiers
REGION                  1..11
                        note = NME5A2
source                  1..11
                        mol_type = protein
                        organism = synthetic construct
SEQUENCE: 263
SLVAKETHPD S                                                            11

SEQ ID NO: 264          moltype = AA  length = 20
FEATURE                 Location/Qualifiers
REGION                  1..20
                        note = NME5B1
source                  1..20
                        mol_type = protein
                        organism = synthetic construct
SEQUENCE: 264
RSGFTIVQRR KLRLSPEQCS                                                   20

SEQ ID NO: 265          moltype = AA  length = 15
FEATURE                 Location/Qualifiers
REGION                  1..15
                        note = NME5B2
source                  1..15
                        mol_type = protein
                        organism = synthetic construct
SEQUENCE: 265
VEKYGKMFFP NLTAY                                                        15

SEQ ID NO: 266          moltype = AA  length = 29
FEATURE                 Location/Qualifiers
REGION                  1..29
                        note = NME5B3
source                  1..29
                        mol_type = protein
                        organism = synthetic construct
SEQUENCE: 266
AIYGTDDLRN ALHGSNDFAA AEREIRFMF                                         29

SEQ ID NO: 267          moltype = AA  length = 16
FEATURE                 Location/Qualifiers
REGION                  1..16
                        note = NME6A1
source                  1..16
                        mol_type = protein
                        organism = synthetic construct
SEQUENCE: 267
LWRKEDCQRF YREHEG                                                       16

SEQ ID NO: 268          moltype = AA  length = 11
FEATURE                 Location/Qualifiers
REGION                  1..11
                        note = NME6A2
source                  1..11
                        mol_type = protein
                        organism = synthetic construct
SEQUENCE: 268
VFRARHVAPD S                                                            11

SEQ ID NO: 269          moltype = AA  length = 20
FEATURE                 Location/Qualifiers
REGION                  1..20
                        note = NME6B1
source                  1..20
                        mol_type = protein
                        organism = synthetic construct
SEQUENCE: 269
SNKFLIVRMR ELLWRKEDCQ                                                   20
```

```
SEQ ID NO: 270            moltype = AA  length = 15
FEATURE                   Location/Qualifiers
REGION                    1..15
                          note = NME6B2
source                    1..15
                          mol_type = protein
                          organism = synthetic construct
SEQUENCE: 270
REHEGRFFYQ RLVEF                                                          15

SEQ ID NO: 271            moltype = AA  length = 29
FEATURE                   Location/Qualifiers
REGION                    1..29
                          note = NME6B3
source                    1..29
                          mol_type = protein
                          organism = synthetic construct
SEQUENCE: 271
GSFGLTDTRN TTHGSDSVVS ASREIAAFF                                           29

SEQ ID NO: 272            moltype = AA  length = 16
FEATURE                   Location/Qualifiers
REGION                    1..16
                          note = NME8A1
source                    1..16
                          mol_type = protein
                          organism = synthetic construct
SEQUENCE: 272
VLSEKEAQAL CKEYEN                                                         16

SEQ ID NO: 273            moltype = AA  length = 11
FEATURE                   Location/Qualifiers
REGION                    1..11
                          note = NME8A2
source                    1..11
                          mol_type = protein
                          organism = synthetic construct
SEQUENCE: 273
VEEAIEYFPE S                                                              11

SEQ ID NO: 274            moltype = AA  length = 16
FEATURE                   Location/Qualifiers
REGION                    1..16
                          note = NME8A3
source                    1..16
                          mol_type = protein
                          organism = synthetic construct
SEQUENCE: 274
FLTPEQIEKI YPKVTG                                                         16

SEQ ID NO: 275            moltype = AA  length = 11
FEATURE                   Location/Qualifiers
REGION                    1..11
                          note = NME8A4
source                    1..11
                          mol_type = protein
                          organism = synthetic construct
SEQUENCE: 275
PEEAKLLSPD S                                                              11

SEQ ID NO: 276            moltype = AA  length = 16
FEATURE                   Location/Qualifiers
REGION                    1..16
                          note = NME8A5
source                    1..16
                          mol_type = protein
                          organism = synthetic construct
SEQUENCE: 276
VLTEEQVVNF YSRIAD                                                         16

SEQ ID NO: 277            moltype = AA  length = 20
FEATURE                   Location/Qualifiers
REGION                    1..20
                          note = NME8B1
source                    1..20
                          mol_type = protein
                          organism = synthetic construct
SEQUENCE: 277
EAGFDLTQVK KMFLTPEQIE                                                     20
```

```
SEQ ID NO: 278          moltype = AA   length = 15
FEATURE                 Location/Qualifiers
REGION                  1..15
                        note = NME8B2
source                  1..15
                        mol_type = protein
                        organism = synthetic construct
SEQUENCE: 278
PKVTGKDFYK DLLEM                                                        15

SEQ ID NO: 279          moltype = AA   length = 13
FEATURE                 Location/Qualifiers
REGION                  1..13
                        note = NME8B3
source                  1..13
                        mol_type = protein
                        organism = synthetic construct
SEQUENCE: 279
AQFGISKLKN IVH                                                          13

SEQ ID NO: 280          moltype = AA   length = 20
FEATURE                 Location/Qualifiers
REGION                  1..20
                        note = NME8B4
source                  1..20
                        mol_type = protein
                        organism = synthetic construct
SEQUENCE: 280
DEDFKILEQR QVVLSEKEAQ                                                   20

SEQ ID NO: 281          moltype = AA   length = 15
FEATURE                 Location/Qualifiers
REGION                  1..15
                        note = NME8B5
source                  1..15
                        mol_type = protein
                        organism = synthetic construct
SEQUENCE: 281
KEYENEDYFN KLIEN                                                        15

SEQ ID NO: 282          moltype = AA   length = 30
FEATURE                 Location/Qualifiers
REGION                  1..30
                        note = NME8B6
source                  1..30
                        mol_type = protein
                        organism = synthetic construct
SEQUENCE: 282
AQFAMDSLPV NQLYGSDSLE TAEREIQHFF                                        30

SEQ ID NO: 283          moltype = AA   length = 20
FEATURE                 Location/Qualifiers
REGION                  1..20
                        note = NME8B7
source                  1..20
                        mol_type = protein
                        organism = synthetic construct
SEQUENCE: 283
KAGFIIEAEH KTVLTEEQVV                                                   20

SEQ ID NO: 284          moltype = AA   length = 15
FEATURE                 Location/Qualifiers
REGION                  1..15
                        note = NME8B8
source                  1..15
                        mol_type = protein
                        organism = synthetic construct
SEQUENCE: 284
SRIADQCDFE EFVSF                                                        15

SEQ ID NO: 285          moltype = AA   length = 11
FEATURE                 Location/Qualifiers
REGION                  1..11
                        note = NME9A1
source                  1..11
                        mol_type = protein
                        organism = synthetic construct
SEQUENCE: 285
```

```
TMTEAEVRLF Y                                                                    11

SEQ ID NO: 286          moltype = AA  length = 20
FEATURE                 Location/Qualifiers
REGION                  1..20
                        note = NME9B1
source                  1..20
                        mol_type = protein
                        organism = synthetic construct
SEQUENCE: 286
EAGFEILTNE ERTMTEAEVR                                                           20

SEQ ID NO: 287          moltype = AA  length = 14
FEATURE                 Location/Qualifiers
REGION                  1..14
                        note = NME10A1
source                  1..14
                        mol_type = protein
                        organism = synthetic construct
SEQUENCE: 287
SMKAEDAQRV FREK                                                                 14

SEQ ID NO: 288          moltype = AA  length = 10
FEATURE                 Location/Qualifiers
REGION                  1..10
                        note = NME10A2
source                  1..10
                        mol_type = protein
                        organism = synthetic construct
SEQUENCE: 288
GQRQKSSDES                                                                      10

SEQ ID NO: 289          moltype = AA  length = 16
FEATURE                 Location/Qualifiers
REGION                  1..16
                        note = NME10A3
source                  1..16
                        mol_type = protein
                        organism = synthetic construct
SEQUENCE: 289
IQDCENCNIY IFDHSA                                                               16

SEQ ID NO: 290          moltype = AA  length = 22
FEATURE                 Location/Qualifiers
REGION                  1..22
                        note = NME10B1
source                  1..22
                        mol_type = protein
                        organism = synthetic construct
SEQUENCE: 290
ELAFQFKDAG LSIFNNTWSN IH                                                        22

SEQ ID NO: 291          moltype = AA  length = 23
FEATURE                 Location/Qualifiers
REGION                  1..23
                        note = NME2A1
source                  1..23
                        mol_type = protein
                        organism = synthetic construct
SEQUENCE: 291
RASEEHLKQH YIDLKDRPFF PGL                                                       23

SEQ ID NO: 292          moltype = AA  length = 18
FEATURE                 Location/Qualifiers
REGION                  1..18
                        note = NME2A2
source                  1..18
                        mol_type = protein
                        organism = synthetic construct
SEQUENCE: 292
LGETNPADSK PGTIRGDF                                                             18

SEQ ID NO: 293          moltype = AA  length = 34
FEATURE                 Location/Qualifiers
REGION                  1..34
                        note = NME2B1
source                  1..34
                        mol_type = protein
                        organism = synthetic construct
```

```
SEQUENCE: 293
GLVGEIIKRF EQKGFRLVAM KFLRASEEHL KQHY                                34

SEQ ID NO: 294          moltype = AA  length = 25
FEATURE                 Location/Qualifiers
REGION                  1..25
                        note = NME2B2
source                  1..25
                        mol_type = protein
                        organism = synthetic construct
SEQUENCE: 294
YIDLKDRPFF PGLVKYMNSG PVVAM                                         25

SEQ ID NO: 295          moltype = AA  length = 34
FEATURE                 Location/Qualifiers
REGION                  1..34
                        note = NME2B3
source                  1..34
                        mol_type = protein
                        organism = synthetic construct
SEQUENCE: 295
PGTIRGDFCI QVGRNIIHGS DSVKSAEKEI SLWF                               34

SEQ ID NO: 296          moltype = AA  length = 27
FEATURE                 Location/Qualifiers
REGION                  1..27
                        note = NME3A1
source                  1..27
                        mol_type = protein
                        organism = synthetic construct
SEQUENCE: 296
LKLVQASEEL LREHYVELRE RPFYSRL                                       27

SEQ ID NO: 297          moltype = AA  length = 19
FEATURE                 Location/Qualifiers
REGION                  1..19
                        note = NME3A1
source                  1..19
                        mol_type = protein
                        organism = synthetic construct
SEQUENCE: 297
LIGATDPGDA TPGTIRGDF                                                19

SEQ ID NO: 298          moltype = AA  length = 31
FEATURE                 Location/Qualifiers
REGION                  1..31
                        note = NME3B1
source                  1..31
                        mol_type = protein
                        organism = synthetic construct
SEQUENCE: 298
LVGEIVRRFE RKGFKLVALK LVQASEELLR E                                  31

SEQ ID NO: 299          moltype = AA  length = 27
FEATURE                 Location/Qualifiers
REGION                  1..27
                        note = NME3B2
source                  1..27
                        mol_type = protein
                        organism = synthetic construct
SEQUENCE: 299
EHYVELRERP FYSRLVKYMG SGPVVAM                                       27

SEQ ID NO: 300          moltype = AA  length = 34
FEATURE                 Location/Qualifiers
REGION                  1..34
                        note = NME3B3
source                  1..34
                        mol_type = protein
                        organism = synthetic construct
SEQUENCE: 300
PGTIRGDFCV EVGKNVIHGS DSVESAQREI ALWF                               34

SEQ ID NO: 301          moltype = AA  length = 29
FEATURE                 Location/Qualifiers
REGION                  1..29
                        note = NME4A1
source                  1..29
                        mol_type = protein
```

```
                        organism = synthetic construct
SEQUENCE: 301
GFTLVGMKML QAPESVLAEH YQDLRRKPF                                  29

SEQ ID NO: 302          moltype = AA   length = 17
FEATURE                 Location/Qualifiers
REGION                  1..17
                        note = NME4A2
source                  1..17
                        mol_type = protein
                        organism = synthetic construct
SEQUENCE: 302
GHTDSAEAAP GTIRGDF                                               17

SEQ ID NO: 303          moltype = AA   length = 33
FEATURE                 Location/Qualifiers
REGION                  1..33
                        note = NME4B1
source                  1..33
                        mol_type = protein
                        organism = synthetic construct
SEQUENCE: 303
LVGDVIQRFE RRGFTLVGMK MLQAPESVLA EHY                             33

SEQ ID NO: 304          moltype = AA   length = 27
FEATURE                 Location/Qualifiers
REGION                  1..27
                        note = NME4B2
source                  1..27
                        mol_type = protein
                        organism = synthetic construct
SEQUENCE: 304
EHYQDLRRKP FYPALIRYMS SGPVVAM                                    27

SEQ ID NO: 305          moltype = AA   length = 34
FEATURE                 Location/Qualifiers
REGION                  1..34
                        note = NME4B3
source                  1..34
                        mol_type = protein
                        organism = synthetic construct
SEQUENCE: 305
PGTIRGDFSV HISRNVIHAS DSVEGAQREI QLWF                            34

SEQ ID NO: 306          moltype = AA   length = 30
FEATURE                 Location/Qualifiers
REGION                  1..30
                        note = NME5A1
source                  1..30
                        mol_type = protein
                        organism = synthetic construct
SEQUENCE: 306
GFTIVQRRKL RLSPEQCSNF YVEKYGKMFF                                 30

SEQ ID NO: 307          moltype = AA   length = 25
FEATURE                 Location/Qualifiers
REGION                  1..25
                        note = NME5A2
source                  1..25
                        mol_type = protein
                        organism = synthetic construct
SEQUENCE: 307
LLGPNNSLVA KETHPDSLRA IYGTD                                      25

SEQ ID NO: 308          moltype = AA   length = 29
FEATURE                 Location/Qualifiers
REGION                  1..29
                        note = NME5B1
source                  1..29
                        mol_type = protein
                        organism = synthetic construct
SEQUENCE: 308
IQDIILRSGF TIVQRRKLRL SPEQCSNFY                                  29

SEQ ID NO: 309          moltype = AA   length = 26
FEATURE                 Location/Qualifiers
REGION                  1..26
                        note = NME5B2
source                  1..26
```

```
                        mol_type = protein
                        organism = synthetic construct
SEQUENCE: 309
FYVEKYGKMF FPNLTAYMSS GPLVAM                                        26

SEQ ID NO: 310          moltype = AA  length = 34
FEATURE                 Location/Qualifiers
REGION                  1..34
                        note = NME5B3
source                  1..34
                        mol_type = protein
                        organism = synthetic construct
SEQUENCE: 310
PDSLRAIYGT DDLRNALHGS NDFAAAEREI RFMF                               34

SEQ ID NO: 311          moltype = AA  length = 32
FEATURE                 Location/Qualifiers
REGION                  1..32
                        note = NME6A1
source                  1..32
                        mol_type = protein
                        organism = synthetic construct
SEQUENCE: 311
FLIVRMRELL WRKEDCQRFY REHEGRFFYQ RL                                 32

SEQ ID NO: 312          moltype = AA  length = 23
FEATURE                 Location/Qualifiers
REGION                  1..23
                        note = NME6A2
source                  1..23
                        mol_type = protein
                        organism = synthetic construct
SEQUENCE: 312
LMGPTRVFRA RHVAPDSIRG SFG                                           23

SEQ ID NO: 313          moltype = AA  length = 25
FEATURE                 Location/Qualifiers
REGION                  1..25
                        note = NME6B1
source                  1..25
                        mol_type = protein
                        organism = synthetic construct
SEQUENCE: 313
ILSNKFLIVR MRELLWRKED CQRFY                                         25

SEQ ID NO: 314          moltype = AA  length = 25
FEATURE                 Location/Qualifiers
REGION                  1..25
                        note = NME6B2
source                  1..25
                        mol_type = protein
                        organism = synthetic construct
SEQUENCE: 314
FYREHEGRFF YQRLVEFMAS GPIRA                                         25

SEQ ID NO: 315          moltype = AA  length = 39
FEATURE                 Location/Qualifiers
REGION                  1..39
                        note = NME6B3
source                  1..39
                        mol_type = protein
                        organism = synthetic construct
SEQUENCE: 315
ARHVAPDSIR GSFGLTDTRN TTHGSDSVVS ASREIAAFF                          39

SEQ ID NO: 316          moltype = AA  length = 33
FEATURE                 Location/Qualifiers
REGION                  1..33
                        note = NME8A1
source                  1..33
                        mol_type = protein
                        organism = synthetic construct
SEQUENCE: 316
FKILEQRQVV LSEKEAQALC KEYENEDYFN KLI                                33

SEQ ID NO: 317          moltype = AA  length = 28
FEATURE                 Location/Qualifiers
REGION                  1..28
                        note = NME8A2
```

```
source                  1..28
                        mol_type = protein
                        organism = synthetic construct
SEQUENCE: 317
WKQLLGPRTV EEAIEYFPES LCAQFAMD                                    28

SEQ ID NO: 318          moltype = AA   length = 34
FEATURE                 Location/Qualifiers
REGION                  1..34
                        note = NME8A3
source                  1..34
                        mol_type = protein
                        organism = synthetic construct
SEQUENCE: 318
AGFDLTQVKK MFLTPEQIEK IYPKVTGKDF YKDL                             34

SEQ ID NO: 319          moltype = AA   length = 27
FEATURE                 Location/Qualifiers
REGION                  1..27
                        note = NME8A4
source                  1..27
                        mol_type = protein
                        organism = synthetic construct
SEQUENCE: 319
EWRRLMGPTD PEEAKLLSPD SIRAQFG                                     27

SEQ ID NO: 320          moltype = AA   length = 34
FEATURE                 Location/Qualifiers
REGION                  1..34
                        note = NME8A5
source                  1..34
                        mol_type = protein
                        organism = synthetic construct
SEQUENCE: 320
KAGFIIEAEH KTVLTEEQVV NFYSRIADQC DFEE                             34

SEQ ID NO: 321          moltype = AA   length = 29
FEATURE                 Location/Qualifiers
REGION                  1..29
                        note = NME8B1
source                  1..29
                        mol_type = protein
                        organism = synthetic construct
SEQUENCE: 321
ILKIVKEAGF DLTQVKKMFL TPEQIEKIY                                   29

SEQ ID NO: 322          moltype = AA   length = 21
FEATURE                 Location/Qualifiers
REGION                  1..21
                        note = NME8B2
source                  1..21
                        mol_type = protein
                        organism = synthetic construct
SEQUENCE: 322
YPKVTGKDFY KDLLEMLSVG P                                           21

SEQ ID NO: 323          moltype = AA   length = 27
FEATURE                 Location/Qualifiers
REGION                  1..27
                        note = NME8B3
source                  1..27
                        mol_type = protein
                        organism = synthetic construct
SEQUENCE: 323
DPEEAKLLSP DSIRAQFGIS KLKNIVH                                     27

SEQ ID NO: 324          moltype = AA   length = 25
FEATURE                 Location/Qualifiers
REGION                  1..25
                        note = NME8B4
source                  1..25
                        mol_type = protein
                        organism = synthetic construct
SEQUENCE: 324
LRIIKDEDFK ILEQRQVVLS EKEAQ                                       25

SEQ ID NO: 325          moltype = AA   length = 23
FEATURE                 Location/Qualifiers
REGION                  1..23
```

-continued

```
                        note = NME8B5
source                  1..23
                        mol_type = protein
                        organism = synthetic construct
SEQUENCE: 325
KEYENEDYFN KLIENMTSGP SLA                                       23

SEQ ID NO: 326          moltype = AA  length = 35
FEATURE                 Location/Qualifiers
REGION                  1..35
                        note = NME8B6
source                  1..35
                        mol_type = protein
                        organism = synthetic construct
SEQUENCE: 326
PESLCAQFAM DSLPVNQLYG SDSLETAERE IQHFF                          35

SEQ ID NO: 327          moltype = AA  length = 29
FEATURE                 Location/Qualifiers
REGION                  1..29
                        note = NME8B7
source                  1..29
                        mol_type = protein
                        organism = synthetic construct
SEQUENCE: 327
IKRKITKAGF IIEAEHKTVL TEEQVVNFY                                 29

SEQ ID NO: 328          moltype = AA  length = 21
FEATURE                 Location/Qualifiers
REGION                  1..21
                        note = NME8B8
source                  1..21
                        mol_type = protein
                        organism = synthetic construct
SEQUENCE: 328
FYSRIADQCD FEEFVSFMTS G                                         21

SEQ ID NO: 329          moltype = AA  length = 22
FEATURE                 Location/Qualifiers
REGION                  1..22
                        note = NME9A1
source                  1..22
                        mol_type = protein
                        organism = synthetic construct
SEQUENCE: 329
AGFEILTNEE RTMTEAEVRL FY                                        22

SEQ ID NO: 330          moltype = AA  length = 29
FEATURE                 Location/Qualifiers
REGION                  1..29
                        note = NME9B1
source                  1..29
                        mol_type = protein
                        organism = synthetic construct
SEQUENCE: 330
IIMKIQEAGF EILTNEERTM TEAEVRLFY                                 29

SEQ ID NO: 331          moltype = AA  length = 26
FEATURE                 Location/Qualifiers
REGION                  1..26
                        note = NME10A1
source                  1..26
                        mol_type = protein
                        organism = synthetic construct
SEQUENCE: 331
GFFLVQTKEV SMKAEDAQRV FREKAP                                    26

SEQ ID NO: 332          moltype = AA  length = 30
FEATURE                 Location/Qualifiers
REGION                  1..30
                        note = NME10A2
source                  1..30
                        mol_type = protein
                        organism = synthetic construct
SEQUENCE: 332
EANRSIVPIS RGQRQKSSDE SCLVVLFAGD                                30

SEQ ID NO: 333          moltype = AA  length = 16
FEATURE                 Location/Qualifiers
```

```
REGION                      1..16
                            note = NME10A3
source                      1..16
                            mol_type = protein
                            organism = synthetic construct
SEQUENCE: 333
IQDCENCNIY IFDHSA                                                         16

SEQ ID NO: 334              moltype = AA  length = 30
FEATURE                     Location/Qualifiers
REGION                      1..30
                            note = NME10B1
source                      1..30
                            mol_type = protein
                            organism = synthetic construct
SEQUENCE: 334
ELAFQFKDAG LSIFNNTWSN IHDFTPVDCT                                          30

SEQ ID NO: 335              moltype = DNA  length = 363
FEATURE                     Location/Qualifiers
misc_feature                1..363
                            note = 8F9A4P3 Heavy chain variable region sequence mouse
source                      1..363
                            mol_type = other DNA
                            organism = synthetic construct
SEQUENCE: 335
gtccagctgc aacagtctgg acctgaactg gtgaagcctg gggcttcagt gaagatatcc         60
tgcaagactt ctggaaacac attcactgaa tacaccatgc actgggtgaa gcagagccat        120
ggaaagagcc ttgagtggat tggaggtttt aatcctaaca atggtgttac taactacaac        180
cagaagttca agggcaaggc cacattgact gtagacaagt cctccagcac agcctacatg        240
gagctccgca gcctgacatc tgaggattct gcagtctatt actgtgcaag acggtactac        300
catagtctct acgtgtttta ctttgactac tggggccaag gcaccactct cacagtctcc        360
tca                                                                     363

SEQ ID NO: 336              moltype = DNA  length = 294
FEATURE                     Location/Qualifiers
misc_feature                1..294
                            note = IGHV1-24*01 V-REGION sequence human (closest match
                             hu antibody sequence)
source                      1..294
                            mol_type = other DNA
                            organism = synthetic construct
SEQUENCE: 336
caggtccagc tggtacagtc tggggctgag gtgaagaagc ctggggcctc agtgaaggtc         60
tcctgcaagg tttccggata cacccctcact gaattatcca tgcactgggt gcgacaggct       120
cctgaaaaag gcttgagtg gatgggaggt tttgatcctg aagatggtga acaatactac         180
gcacagaagt tccagggcag agtcaccatg accgaggaca catctacaga cacagcctac        240
atggagctga gcagcctgag atctgaggac acggccgtgt attactgtgc aaca              294

SEQ ID NO: 337              moltype = DNA  length = 45
FEATURE                     Location/Qualifiers
misc_feature                1..45
                            note = IGHJ4*01 J-REGION sequence human (closest match hu
                             antibody sequence)
source                      1..45
                            mol_type = other DNA
                            organism = synthetic construct
SEQUENCE: 337
tactttgact actggggcca aggaaccctg gtcaccgtct cctca                         45

SEQ ID NO: 338              moltype = DNA  length = 366
FEATURE                     Location/Qualifiers
misc_feature                1..366
                            note = humanized 8F9A4P3 Heavy chain variable region
                             sequence
source                      1..366
                            mol_type = other DNA
                            organism = synthetic construct
SEQUENCE: 338
caggtccagc tggtacagtc tggggctgag gtgaagaagc ctggggcctc agtgaaggtc         60
tcctgcaagg tttccggaaa cacattcact gaatacacca tgcactgggt gcgacaggct        120
cctgaaaaag gcttgagtg gatgggaggt tttaatccta acaatggtgt tactaactac         180
aaccagaagt tcaagggcag agtcaccatg accgaggaca catctacaga cacagcctac        240
atggagctga gcagcctgag atctgaggac acggccgtgt attactgtgc aagacggtac        300
taccatagtc tctacgtgtt ttactttgac tactggggcc aaggaaccct ggtcaccgtc        360
tcctca                                                                  366

SEQ ID NO: 339              moltype = DNA  length = 366
FEATURE                     Location/Qualifiers
```

```
misc_feature           1..366
                       note = humanized 8F9A4P3 Heavy chain variable region
                         sequence (codon optimized)
source                 1..366
                       mol_type = other DNA
                       organism = synthetic construct
SEQUENCE: 339
caggttcagc tggttcagtc tggcgccgaa gtgaagaaac ctggcgcctc tgtgaaggtg     60
tcctgcaagg tgtccggaaa taccttcacc gagtacacca tgcactgggt ccgacaggcc    120
cctgcaaag gacttgaatg gatgggcggc ttcaacccca acaacggcgt gaccaactac    180
aaccagaaat tcaagggccg cgtgaccatg accgagaca caagcacaga caccgcctac    240
atggaactga gcagcctgag aagcgaggac accgccgtgt actactgcgc cagaaggtac    300
taccacagcc tgtacgtgtt ctacttcgac tactggggcc agggcaccct ggtcacagtt    360
tcttct                                                               366

SEQ ID NO: 340         moltype = DNA   length = 366
FEATURE                Location/Qualifiers
misc_feature           1..366
                       note = Modified humanized 8F9A4P3 Heavy chain variable
                         region sequence
source                 1..366
                       mol_type = other DNA
                       organism = synthetic construct
SEQUENCE: 340
caggtccagc tggtacagtc tggggctgag gtgaagaagc ctggggcctc agtgaaggtc     60
tcctgcaagg tttccggaaa cacattcact gaatacacca tgcactgggt gcgacaggct    120
cctggaaaag ggcttgagtg gattggaggt tttaatccta acaatggtgt tactaactac    180
aaccagaagt tcaagggcaa agtcaccctg accgtggaca catctagcag cacagcctac    240
atggagctga gcagcctgag atctgaggac acggccgtgt attactgtgc aagacggtac    300
taccatagtc tctacgtgtt ttactttgac tactggggcc aaggaaccct ggtcaccgtc    360
tcctca                                                               366

SEQ ID NO: 341         moltype = DNA   length = 366
FEATURE                Location/Qualifiers
misc_feature           1..366
                       note = Modified humanized 8F9A4P3 Heavy chain variable
                         region sequence (codon optimized)
source                 1..366
                       mol_type = other DNA
                       organism = synthetic construct
SEQUENCE: 341
caggttcagc tggttcagtc tggcgccgaa gtgaagaaac ctggcgcctc tgtgaaggtg     60
tcctgcaagg tgtccggaaa taccttcacc gagtacacca tgcactgggt ccgacaggcc    120
cctggcaaag gactggaatg gatcggcggc ttcaacccca acaacggcgt gaccaactac    180
aaccagaaat tcaagggcaa agtgaccctg accgtggaca ccagcagcag cacagcctac    240
atggaactga gcagcctgag aagcgaggac accgccgtgt actactgcgc cagaaggtac    300
taccacagcc tgtacgtgtt ctacttcgac tactggggcc agggcaccct ggtcacagtt    360
tcttct                                                               366

SEQ ID NO: 342         moltype = DNA   length = 324
FEATURE                Location/Qualifiers
misc_feature           1..324
                       note = 8F9A4P3 Light chain variable region sequence mouse
source                 1..324
                       mol_type = other DNA
                       organism = synthetic construct
SEQUENCE: 342
gaaacaactg tgacccagtc tccagcatcc ctgtccatgg ctataggaga aaaagtcacc     60
atcagatgca taaccagcac tgatattgat gatgatatga actggtacca gcagaagcca    120
ggggaacctc ctaagctcct tatttcagaa ggcaatactc ttcgtcctgg agtcccatcc    180
cgattctcca gcagtggcta tggtacagat tttgttttta caattgaaaa catgctctca    240
gaagatgttg cagattacta ctgtttgcaa agtgataact gcctctcac gttcggctcg    300
gggacaaagt tggaaataaa acgg                                           324

SEQ ID NO: 343         moltype = DNA   length = 264
FEATURE                Location/Qualifiers
misc_feature           1..264
                       note = IGKV5-2*01 V-REGION sequence human (closest match hu
                         antibody sequence)
source                 1..264
                       mol_type = other DNA
                       organism = synthetic construct
SEQUENCE: 343
gaaacgacac tcacgcagtc tccagcattc atgtcagcga ctccaggaga caaagtcaac     60
atctcctgca aagccagcca agacattgat gatgatatga actggtacca acagaaacca    120
ggagaagctg ctatttcat tattcaagaa gctactactc tcgttcctgg aatcccacct    180
cgattcagtg cagcgggta tggaacagat tttaccctca caattaataa catagaatct    240
gaggatgctg catattactt ctgt                                           264
```

-continued

```
SEQ ID NO: 344          moltype = DNA   length = 36
FEATURE                 Location/Qualifiers
misc_feature            1..36
                        note = IGKJ4*02 J-REGION sequence human (closest match hu
                         antibody sequence)
source                  1..36
                        mol_type = other DNA
                        organism = synthetic construct
SEQUENCE: 344
ctcacgttcg gcggagggac caaggtggag atcaaa                                   36

SEQ ID NO: 345          moltype = DNA   length = 324
FEATURE                 Location/Qualifiers
misc_feature            1..324
                        note = humanized 8F9A4P3 Light chain variable region
                         sequence
source                  1..324
                        mol_type = other DNA
                        organism = synthetic construct
SEQUENCE: 345
gaaacgacac tcacgcagtc tccagcattc atgtcagcga ctccaggaga caaagtcaac         60
atctcctgca taaccagcac tgatattgat gatgatatga ctggtaccaa acagaaacca        120
ggagaagctg ctattttcat tattcaagaa ggcaatactc ttcgtcctgg aatcccacct        180
cgattcagtg gcagcgggta tggaacagat tttaccctca caattaataa catagaatct        240
gaggatgctg catattactt ctgtttgcaa agtgataact tgcctctcac gttcggcgga        300
gggaccaagg tggagatcaa acgg                                              324

SEQ ID NO: 346          moltype = DNA   length = 324
FEATURE                 Location/Qualifiers
misc_feature            1..324
                        note = humanized 8F9A4P3 Light chain variable region
                         sequence (codon optimized)
source                  1..324
                        mol_type = other DNA
                        organism = synthetic construct
SEQUENCE: 346
gagacaaccc tgacacagag ccctgccttc atgtctgcca cacctggcga caaagtgaac         60
atcagctgca tcaccagcac cgacatcgac gacgacatga actggtatca gcagaagcct        120
ggcgaggccg ccatcttcat catccaagag ggcaacacc tgcggcctgg catccctcct         180
agattttctg gcagcggcta cggcaccgac ttcacccctg accatcaaca catcgagagc        240
gaggacgccg cctactactt ctgcctgcaa agcgacaacc tgcctctgac ctttggcgga        300
ggcaccaagg tggaaatcaa gcgg                                              324

SEQ ID NO: 347          moltype = DNA   length = 324
FEATURE                 Location/Qualifiers
misc_feature            1..324
                        note = Modified humanized 8F9A4P3 Light chain variable
                         region sequence
source                  1..324
                        mol_type = other DNA
                        organism = synthetic construct
SEQUENCE: 347
gaaacgacag tgacgcagtc tccagcattc atgtcagcga ctccaggaga caaagtcacc         60
atctcctgca taaccagcac tgatattgat gatgatatga actggtacca acagaaacca        120
ggagaagctg ctattctgct gattagcgaa ggcaatactc ttcgtcctgg aatcccacct        180
cgattcagta gcagcgggta tggaacagat tttaccctca caattaataa catagaatct        240
gaggatgctg catattactt ctgtttgcaa agtgataact tgcctctcac gttcggcgga        300
gggaccaagg tggagatcaa acgg                                              324

SEQ ID NO: 348          moltype = DNA   length = 324
FEATURE                 Location/Qualifiers
misc_feature            1..324
                        note = Modified humanized 8F9A4P3 Light chain variable
                         region sequence (codon optimized)
source                  1..324
                        mol_type = other DNA
                        organism = synthetic construct
SEQUENCE: 348
gagacaaccg tgacacagag ccctgccttc atgtctgcca cacctggcga caaagtgacc         60
atcagctgca tcaccagcac cgacatcgac gacgacatga actggtatca gcagaagcct        120
ggcgaggccg ccatcctgct tatctctgag ggaaacacac tgcggcctgg catccctcct        180
agattttcca gcagcggcta cggcaccgac ttcacccctg accatcaaca catcgagagc        240
gaggacgccg cctactactt ctgcctgcaa agcgacaacc tgcctctgac ctttggcgga        300
ggcaccaagg tggaaatcaa gcgg                                              324

SEQ ID NO: 349          moltype = DNA   length = 735
FEATURE                 Location/Qualifiers
misc_feature            1..735
                        note = Modified humanized 8F9A4P3 sequence (codon
```

```
                        optimized) - humanized heavy and light chains joined via a
                        flexible linker
source                  1..735
                        mol_type = other DNA
                        organism = synthetic construct
SEQUENCE: 349
caggttcagc tggttcagtc tggcgccgaa gtgaagaaac ctggcgcctc tgtgaaggtg   60
tcctgcaagg tgtccggaaa taccttcacc gagtacacca tgcactgggt ccgacaggcc  120
cctggcaaag gactggaatg gatcggcggc ttcaacccca caacggcgt gaccaactac  180
aaccagaaat tcaagggcaa agtgaccctg accgtggaca ccagcagcag cacagcctac  240
atggaactga gcagcctgag aagcgaggac accgccgtgt actactgcgc cagaaggtac  300
taccacagcc tgtacgtgtt ctacttcgac tactggggcc agggcaccct ggtcacagtt  360
tcttctggcg gtggcggaag cggaggcggt ggctccggtg gcggaggcag cgaaacgaca  420
gtgacgcagt ctccagcatt catgtcagcg actccaggac acaaagtcac catctcctgc  480
ataaccagca ctgatattga tgatgatatg aactggtacc aacagaaacc aggagaagct  540
gctattctgc tgattagcga aggcaatact cttcgtcctg gaatcccacc tcgattcagt  600
agcagcgggt atggaacaga ttttaccctc acaattaata acatagaatc tgaggatgct  660
gcatattact tctgtttgca aagtgataac ttgcctctca cgttcggcgg agggaccaag  720
gtggagatca aacgg                                                   735

SEQ ID NO: 350          moltype = DNA  length = 357
FEATURE                 Location/Qualifiers
misc_feature            1..357
                        note = 8F9A5A1 Heavy chain variable region sequence
source                  1..357
                        mol_type = other DNA
                        organism = synthetic construct
SEQUENCE: 350
atccagttgg tgcagtctgg acctgagctg aagaagcctg gagagacagt caagatctcc   60
tgcaaggctt ctgggtatac cttcacaaac tatggaatga actgggtgaa gcaggctcca  120
ggaaagggtt taaagtggat gggctgagata aacacctaca ctggagagcc aacatatgtt  180
gatgacttca agggacggtt tgccttctct ttggaaacct ctgccaccac tgcctatttg  240
cagatcaaca acctcaaaaa tgaggacacg tctacatatt tctgtgcaag attgaggggg  300
atacgaccgg tcccttggc ttactggggc aagggactg tggtcactgt ctctgca      357

SEQ ID NO: 351          moltype = DNA  length = 294
FEATURE                 Location/Qualifiers
misc_feature            1..294
                        note = IGHV7-81*01 V-REGION sequence
source                  1..294
                        mol_type = other DNA
                        organism = synthetic construct
SEQUENCE: 351
caggtgcagc tggtgcagtc tggccatgag gtgaagcagc tggggcctc agtgaaggtc    60
tcctgcaagg cttctggtta cagtttcacc acctatggta tgaattgggt gccacaggcc  120
cctggacaag gcttgagtg gatgggatgg ttcaacacct acactgggaa cccaacatat  180
gcccaggct tcacaggacg gtttgtcttc tccatggaca cctctgccag cacagcatac  240
ctgcagatca gcagcctaaa ggctgaggac atggccatgt attactgtgc gaga         294

SEQ ID NO: 352          moltype = DNA  length = 45
FEATURE                 Location/Qualifiers
misc_feature            1..45
                        note = IGHJ4*03 J-REGION sequence
source                  1..45
                        mol_type = other DNA
                        organism = synthetic construct
SEQUENCE: 352
tactttgact actgggggcca agggaccctg gtcaccgtct cctca                   45

SEQ ID NO: 353          moltype = DNA  length = 360
FEATURE                 Location/Qualifiers
misc_feature            1..360
                        note = humanized 8F9A5A1 Heavy chain variable region
                        sequence
source                  1..360
                        mol_type = other DNA
                        organism = synthetic construct
SEQUENCE: 353
caggtgcagc tggtgcagtc tggccatgag gtgaagcagc tggggcctc agtgaaggtc    60
tcctgcaagg cttctgggta accttcaca aactatggaa tgaactgggt gccacaggcc   120
cctggacaag gcttgagtg gatgggatgg ataaacacct acactggaga gccaacatat   180
gttgatgact caagggacg gtttgtcttc tccatggaca cctctgccag cacagcatac   240
ctgcagatca gcagcctaaa ggctgaggac atggccatgt attactgtgc aagattgagg   300
gggatacgac cgggtccctt ggcttactgg ggccaaggga ccctggtcac cgtctcctca   360

SEQ ID NO: 354          moltype = DNA  length = 360
FEATURE                 Location/Qualifiers
misc_feature            1..360
                        note = humanized 8F9A5A1 Heavy chain variable region
```

```
                           sequence (codon optimized)
source                     1..360
                           mol_type = other DNA
                           organism = synthetic construct
SEQUENCE: 354
caggttcagc tggtgcagtc tggccacgaa gtgaaacagc ctggcgcctc tgtgaaggtg    60
tcctgtaaag ccagcggcta cacctttacc aactacggca tgaactgggt gccccaggct   120
cctggacaag gcttggaatg gatgggctgg atcaacacct acaccggcga gcctacctac   180
gtggacgact tcaagggcag attcgtgttc agcatggaca ccagcgccag cacagcctac   240
ctgcagatca gctctctgaa ggccgaggat atggccatgt actactgcgc cagactgaga   300
ggcatcagac ctggaccctct ggcctattgg ggacaggyca cactggtcgc agagtgtcctct   360

SEQ ID NO: 355             moltype = DNA  length = 360
FEATURE                    Location/Qualifiers
misc_feature               1..360
                           note = Modified humanized 8F9A5A1 Heavy chain variable
                           region sequence
source                     1..360
                           mol_type = other DNA
                           organism = synthetic construct
SEQUENCE: 355
cagatccagc tggtgcagtc tggccccgag gtgaagcagc ctggggcctc agtgaaggtc    60
tcctgcaagg cttctgggta taccttcaca aactatgaa tgaactgggt gaagcaggcc   120
cctggacaag gcttgagtg gatgggatgg ataaacacct acactggaga gccaacatat   180
gttgatgact tcaagggacg gtttgccttc tccatggaca cctctgccag cacagcatac   240
ctgcagatca gcagcctaaa ggctgaggac accgccacct attactgtgc aagattgagg   300
gggatacgac cgggtcccctt ggcttactgg ggccaaggga ccctggtcac cgtctcctca   360

SEQ ID NO: 356             moltype = DNA  length = 360
FEATURE                    Location/Qualifiers
misc_feature               1..360
                           note = Modified humanized 8F9A5A1 Heavy chain variable
                           region sequence (codon optimized)
source                     1..360
                           mol_type = other DNA
                           organism = synthetic construct
SEQUENCE: 356
cagattcagc tggtgcagtc tggccccgaa gtgaaacaac ctggcgcctc tgtgaaggtg    60
tcctgcaagg ccagcggcta cacctttacc aactacgca tgaactgggt caagcaggcc   120
cctggacaag gcctggaatg gatgggctgg atcaacacct acaccggcga gcctacctac   180
gtggacgact tcaagggcag attcgccttc agcatggaca ccagcgccag cacagcctac   240
ctgcagatca gctctctgaa ggccgaggac accgccacct actactgtgc cagactgaga   300
ggcatcagac ccggaccctct ggcctattgg ggacaggaa cactggtcac cgtgtcctct   360

SEQ ID NO: 357             moltype = DNA  length = 321
FEATURE                    Location/Qualifiers
misc_feature               1..321
                           note = 8F9A5A1 Light chain variable region sequence
source                     1..321
                           mol_type = other DNA
                           organism = synthetic construct
SEQUENCE: 357
gaaattttgc tcacccagtc tccagcaatc atagctgcat ctcctgggga aaggtcacc    60
atcacctgca gtgccagctc aagtgtaagt tacatgaact ggtaccagca gaaaccagga   120
tcctccccca aaatatggat ttatggtata tccaacctgg cttctggagt tcctgctcgc   180
ttcagtggca gtgggtctgg gacatctttc tctttcacaa tcaacagcag ggaggctgaa   240
gatgttgcca cttattactg tcagcaaagg agtagttacc cacccacgtt cggagggggg   300
accaagctgg aaataaaacg g                                             321

SEQ ID NO: 358             moltype = DNA  length = 279
FEATURE                    Location/Qualifiers
misc_feature               1..279
                           note = IGKV3D-15*02 V-REGION sequence
source                     1..279
                           mol_type = other DNA
                           organism = synthetic construct
SEQUENCE: 358
gaaatagtga tgatgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg catcccagcc   180
aggttcagtg gcagtgggtc tgggacagag ttcactctca ccatcagcag cctgcagtct   240
gaagattttg cagtttatta ctgtcagcag tataataac                          279

SEQ ID NO: 359             moltype = DNA  length = 36
FEATURE                    Location/Qualifiers
misc_feature               1..36
                           note = IGKJ4*02 J-REGION sequence
source                     1..36
                           mol_type = other DNA
```

```
                        organism = synthetic construct
SEQUENCE: 359
ctcacgttcg gcggagggac caaggtggag atcaaa                                36

SEQ ID NO: 360          moltype = DNA  length = 321
FEATURE                 Location/Qualifiers
misc_feature            1..321
                        note = humanized 8F9A5A1 Light chain variable region
                         sequence
source                  1..321
                        mol_type = other DNA
                        organism = synthetic construct
SEQUENCE: 360
gaaatagtga tgatgcagtc tccagccacc ctgtctgtgt ctccagggga aagagccacc        60
ctctcctgca gtgccagctc aagtgtaagt tacatgaact ggtaccagca gaaacctggc      120
caggctccca ggctcctcat ctatggtata tccaacctgg cttctggcat cccagccagg      180
ttcagtggca gtgggtctgg gacagagttc actctcacca tcagcagcct gcagtctgaa      240
gattttgcag tttattactg tcagcaaagg agtagttacc acccacgtt cggcggaggg       300
accaaggtgg agatcaaacg g                                                321

SEQ ID NO: 361          moltype = DNA  length = 321
FEATURE                 Location/Qualifiers
misc_feature            1..321
                        note = humanized 8F9A5A1 Light chain variable region
                         sequence (codon optimized)
source                  1..321
                        mol_type = other DNA
                        organism = synthetic construct
SEQUENCE: 361
gagatcgtga tgatgcagag ccccgccaca ctgagtgtgt ctccaggcga aagagccaca        60
ctgtcctgta gcgccagcag cagcgtgtcc tacatgaact ggtatcagca gaagcccgga      120
caggcccta gactgctgat ctacggcatc agcaatctgg ccagcggcat ccctgccaga       180
ttttctggct ctggctccgg caccgagttc accctgacaa tctctagcct gcagagcgag      240
gacttcgccg tgtactactg ccagcagaga agcagctacc ctcctacctt tggcggaggc      300
accaaggtgg aaatcaagcg g                                                321

SEQ ID NO: 362          moltype = DNA  length = 321
FEATURE                 Location/Qualifiers
misc_feature            1..321
                        note = Modified humanized 8F9A5A1 Light chain variable
                         region sequence
source                  1..321
                        mol_type = other DNA
                        organism = synthetic construct
SEQUENCE: 362
gaaatagtgc tgacccagtc tccagccacc ctgtctgtgt ctccagggga aagagccacc        60
ctctcctgca gtgccagctc aagtgtaagt tacatgaact ggtaccagca gaaacctggc      120
caggctccca ggctctggat ctatggtata tccaacctgg cttctggcat cccagccagg      180
ttcagtggca gtgggtctgg gacaagcttc agcctcacca tcagcagcct gcagtctgaa      240
gattttgcag tttattactg tcagcaaagg agtagttacc acccacgtt cggcggaggg       300
accaaggtgg agatcaaacg g                                                321

SEQ ID NO: 363          moltype = DNA  length = 321
FEATURE                 Location/Qualifiers
misc_feature            1..321
                        note = Modified humanized 8F9A5A1 Light chain variable
                         region sequence (codon optimized)
source                  1..321
                        mol_type = other DNA
                        organism = synthetic construct
SEQUENCE: 363
gagatcgtgc tgacacagtc tcccgccaca ctgagtgtgt ctccaggcga aagagccaca        60
ctgtcctgta gcgccagcag cagcgtgtcc tacatgaact ggtatcagca gaagcccgga      120
caggccccta gactgtggat ctacggcatc agcaatctgg ccagcggcat ccctgccaga       180
ttttctggct ctggctccgg caccagcttc agcctgacaa tcagcagcct gcagagcgag      240
gacttcgccg tgtactactg ccagcagaga agcagctacc ctcctacctt tggcggaggc      300
accaaggtgg aaatcaagcg g                                                321

SEQ ID NO: 364          moltype = DNA  length = 726
FEATURE                 Location/Qualifiers
misc_feature            1..726
                        note = Modified humanized 8F9A5A1 scFV sequence (codon
                         optimized)
source                  1..726
                        mol_type = other DNA
                        organism = synthetic construct
SEQUENCE: 364
cagattcagc tggtgcagtc tggccccgaa gtgaaacaac tggcgcctc tgtgaaggtg        60
tcctgcaagg ccagcggcta caccttacc aactacggca tgaactgggt caagcaggcc       120
```

```
cctggacaag gcctggaatg gatgggctgg atcaacacct acaccggcga gcctacctac    180
gtggacgact tcaagggcag attcgccttc agcatggaca ccagcgccag cacagcctac    240
ctgcagatca gctctctgaa ggccgaggac accgccacct actactgtgc agactgaga     300
ggcatcagac ccggacctct ggcctattgg ggacagggaa cactggtcac cgtgtcctct    360
ggcggtggcg gaagcggagg cggtggctcc ggtggctgga gcagcgagat cgtgctgaca    420
cagtctcccg ccacactgag tgtgtctcca ggcgaaagag ccacactgtc ctgtagcgcc    480
agcagcagcg tgtcctacat gaactggtat cagcagaagc ccggacaggc ccctagactg    540
tggatctacg gcatcagcaa tctggccagc ggcatccctg ccagattttc tggctctggc    600
tccggcacca gcttcagcct gacaatcagc agcctgcaga gcgaggactt cgccgtgtac    660
tactgccagc agagaagcag ctaccctcct acctttggcg gaggcaccaa ggtggaaatc    720
aagcgg                                                               726

SEQ ID NO: 365         moltype = DNA   length = 363
FEATURE                Location/Qualifiers
misc_feature           1..363
                       note = 8H5H5G4 Heavy chain variable region sequence
source                 1..363
                       mol_type = other DNA
                       organism = synthetic construct
SEQUENCE: 365
gtccagctgc aacagtctgg acctgatctg gtgaagcctg ggacttcagt gaagatatcc     60
tgtaagactt ctggaaacac attcactgaa tacaccagc actgggtgaa gcagagccat    120
ggaaagagcc ttgagtggat tggaggtttt aatcctaaca atggtgttac taactacaac    180
cagaagttca agggcaaggc cacattgact gtagacaagt cctccagcac agcctacatg    240
gagctccgca gcctgacatc tgaggattct gcagtctatt actgtgcaag acgttactac    300
catagtacct acgtgttcta ctttgactcc tggggccaag gcaccactct cacagtctcc    360
tca                                                                  363

SEQ ID NO: 366         moltype = DNA   length = 294
FEATURE                Location/Qualifiers
misc_feature           1..294
                       note = IGHV1-24*01 V-REGION sequence
source                 1..294
                       mol_type = other DNA
                       organism = synthetic construct
SEQUENCE: 366
caggtccagc tggtacagtc tggggctgag gtgaagaagc ctggggcctc agtgaaggtc     60
tcctgcaagg tttccggata caccctcact gaattatcca tgcactgggt gcgacaggct    120
cctggacaag ggcttgagtg gatgggaggt tttgatccta aagatggtga aacaatctac    180
gcacagaagt tccagggcag agtcaccatg accgaggaca catctacaga cacagcctac    240
atggagctga gcagcctgag atctgaggac acggccgtgt attactgtgc aaca          294

SEQ ID NO: 367         moltype = DNA   length = 45
FEATURE                Location/Qualifiers
misc_feature           1..45
                       note = IGHJ4*03 J-REGION sequence
source                 1..45
                       mol_type = other DNA
                       organism = synthetic construct
SEQUENCE: 367
tactttgact actggggcca agggaccctg gtcaccgtct cctca                     45

SEQ ID NO: 368         moltype = DNA   length = 366
FEATURE                Location/Qualifiers
misc_feature           1..366
                       note = Humanized 8H5H5G4 Heavy chain variable region
                         sequence
source                 1..366
                       mol_type = other DNA
                       organism = synthetic construct
SEQUENCE: 368
caggtccagc tggtacagtc tggggctgag gtgaagaagc ctggggcctc agtgaaggtc     60
tcctgcaagg tttccggaaa cacattcact gaatacacca tgcactgggt gcgacaggct    120
cctggaaaag ggcttgagtg gatgggaggt tttaatccta acaatggtgt tactaactac    180
aaccagaagt tcaagggcag agtcaccatg accgaggaca catctacaga cacagcctac    240
atggagctga gcagcctgag atctgaggac acggccgtgt attactgtgc aagacgttac    300
taccatagta cctacgtgtt ctactttgac tcctggggcc aagggaccct ggtcaccgtc    360
tcctca                                                               366

SEQ ID NO: 369         moltype = DNA   length = 366
FEATURE                Location/Qualifiers
misc_feature           1..366
                       note = Humanized 8H5H5G4 Heavy chain variable region
                         sequence (codon optimized)
source                 1..366
                       mol_type = other DNA
                       organism = synthetic construct
SEQUENCE: 369
caggttcagc tggttcagtc tggcgccgaa gtgaagaaac ctggcgcctc tgtgaaggtg     60
```

```
tcctgcaagg tgtccggaaa taccttcacc gagtacacca tgcactgggc ccgacaggcc    120
cctggcaaag gacttgaatg gatgggcggc ttcaacccca acaacggcgt gaccaactac    180
aaccagaaat tcaagggccg cgtgaccatg accgaggaca caagcacaga cacccgcctac   240
atggaactga gcagcctgag aagcgaggac accgccgtgt actactgcgc cagaaggtac    300
taccacagca cctacgtgtt ctacttcgac agctggggcc agggcacact ggtcacagtt    360
tcttct                                                               366

SEQ ID NO: 370           moltype = DNA  length = 366
FEATURE                  Location/Qualifiers
misc_feature             1..366
                         note = Modified Humanized 8H5H5G4 Heavy chain variable
                          region sequence
source                   1..366
                         mol_type = other DNA
                         organism = synthetic construct
SEQUENCE: 370
caggtccagc tggtacagtc tggggctgag gtgaagaagc ctggggcctc agtgaaggtc    60
tcctgcaagg tttccggaaa cacattcact gaatacacca tgcactgggt gcgacaggct    120
cctggaaaag ggcttgagtg gatcggaggt tttaatccta acaatggtgt tactaactac    180
aaccagaagt tcaagggcaa ggtcaccctg accggacaca catcagcag cacagcctac    240
atggagctga gcagcctgag atctgaggac acggccgtgt attactgtgc aagacgttac    300
taccatagta cctacgtgtt ctactttgac tcctggggcc aagggaccct ggtcaccgtc    360
tcctca                                                               366

SEQ ID NO: 371           moltype = DNA  length = 366
FEATURE                  Location/Qualifiers
misc_feature             1..366
                         note = Modified Humanized 8H5H5G4 Heavy chain variable
                          region sequence (codon optimized)
source                   1..366
                         mol_type = other DNA
                         organism = synthetic construct
SEQUENCE: 371
caggttcagc tggttcagtc tggcgccgaa gtgaagaaac ctggcgcctc tgtgaaggtg    60
tcctgcaagg tgtccggaaa taccttcacc gagtacacca tgcactgggt ccgacaggcc    120
cctggcaaag gactggaatg gatcggcggc ttcaacccca acaacggcgt gaccaactac    180
aaccagaaat tcaagggcaa agtgaccctg accgtggaca ccagcagcag cacagcctac    240
atggaactga gcagcctgag aagcgaggac accgccgtgt actactgcgc cagaaggtac    300
taccacagca cctacgtgtt ctacttcgac agctggggcc agggcacact ggtcacagtt    360
tcttct                                                               366

SEQ ID NO: 372           moltype = DNA  length = 324
FEATURE                  Location/Qualifiers
misc_feature             1..324
                         note = 8H5H5G4 Light chain variable region sequence
source                   1..324
                         mol_type = other DNA
                         organism = synthetic construct
SEQUENCE: 372
gatatccaga tgacacagac tacatcctcc ctgtctgcct ctctgggaga cagagtcacc    60
atcagttgca gtgcaagtca gggcattagc aattatttaa actggtttca gcagaaacca    120
gatggaacta ttaagctcct gatctattac acatcaagtt tacattcagg agtcccatca    180
aggttcagtg gcagtgggtc tgggacagat tattctctca ccatcagtaa tgtgaaacct    240
gaagatattg ccacttacta ttgtcagcag tatagtaagc ttccttacac gttcggaggg    300
gggaccaagc tggagataaa acgg                                           324

SEQ ID NO: 373           moltype = DNA  length = 285
FEATURE                  Location/Qualifiers
misc_feature             1..285
                         note = IGKV1-27*01 V-REGION sequence
source                   1..285
                         mol_type = other DNA
                         organism = synthetic construct
SEQUENCE: 373
gacatccaga tgacccagtc tccatcctcc ctgtctgcat ctgtaggaga cagagtcacc    60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg ccct                    285

SEQ ID NO: 374           moltype = DNA  length = 36
FEATURE                  Location/Qualifiers
misc_feature             1..36
                         note = IGKJ4*02 J-REGION sequence
source                   1..36
                         mol_type = other DNA
                         organism = synthetic construct
SEQUENCE: 374
ctcacgttcg gcggagggac caaggtggag atcaaa                              36
```

```
SEQ ID NO: 375          moltype = DNA  length = 324
FEATURE                 Location/Qualifiers
misc_feature            1..324
                        note = humanized 8H5H5G4 Light chain variable region
                          sequence
source                  1..324
                        mol_type = other DNA
                        organism = synthetic construct
SEQUENCE: 375
gacatccaga tgacccagtc tccatcctcc ctgtctgcat ctgtaggaga cagagtcacc   60
atcacttgca gtgcaagtca gggcattagc aattatttaa actggtatca gcagaaacca  120
gggaaagttc ctaagctcct gatctattac acatcaagtt tacattcagg ggtcccatct  180
cggttcagtg gcagtggatc tgggacagat ttcactctca ccatcagcag cctgcagcct  240
gaagatgttg caacttatta ctgtcagcag tatagtaagc ttccttacac gttcggcgga  300
gggaccaagg tggagatcaa acgg                                         324

SEQ ID NO: 376          moltype = DNA  length = 324
FEATURE                 Location/Qualifiers
misc_feature            1..324
                        note = humanized 8H5H5G4 Light chain variable region
                          sequence (codon optimized)
source                  1..324
                        mol_type = other DNA
                        organism = synthetic construct
SEQUENCE: 376
gacatccaga tgacacagag ccctagcagc ctgtctgcca gcgtgggaga cagagtgacc   60
atcacatgta gcgccagcca gggcatcagc aactacctga actggtatca gcagaaaccc  120
ggcaaggtgc ccaagctgct gatctactac accagcagcc tgcacagcgg cgtgccaagc  180
agattttctg gcagcggctc tggcaccgac ttcaccctga ccatatctag cctgcagcct  240
gaggacgtgg ccacctacta ctgtcagcag tacagcaagc tgccctacac ctttggcgga  300
ggcaccaagg tggaaatcaa gcgg                                         324

SEQ ID NO: 377          moltype = DNA  length = 324
FEATURE                 Location/Qualifiers
misc_feature            1..324
                        note = Modified humanized 8H5H5G4 Light chain variable
                          region sequence
source                  1..324
                        mol_type = other DNA
                        organism = synthetic construct
SEQUENCE: 377
gacatccaga tgacccagtc tccatcctcc ctgtctgcat ctgtaggaga cagagtcacc   60
atcacttgca gtgcaagtca gggcattagc aattatttaa actggtatca gcagaaacca  120
gggaaagttc ctaagctcct gatctattac acatcaagtt tacattcagg ggtcccatct  180
cggttcagtg gcagtggatc tgggacagat tacactctca ccatcagcag cctgcagcct  240
gaagatgttg caacttatta ctgtcagcag tatagtaagc ttccttacac gttcggcgga  300
gggaccaagg tggagatcaa acgg                                         324

SEQ ID NO: 378          moltype = DNA  length = 324
FEATURE                 Location/Qualifiers
misc_feature            1..324
                        note = Modified humanized 8H5H5G4 Light chain variable
                          region sequence (codon optimized)
source                  1..324
                        mol_type = other DNA
                        organism = synthetic construct
SEQUENCE: 378
gacatccaga tgacacagag ccctagcagc ctgtctgcca gcgtgggaga cagagtgacc   60
atcacatgta gcgccagcca gggcatcagc aactacctga actggtatca gcagaaaccc  120
ggcaaggtgc ccaagctgct gatctactac accagcagcc tgcacagcgg cgtgccaagc  180
agattttctg gcagcggctc tggcaccgac tacaccctga ccatatctag cctgcagcct  240
gaggacgtgg ccacctacta ctgtcagcag tacagcaagc tgccctacac ctttggcgga  300
ggcaccaagg tggaaatcaa gcgg                                         324

SEQ ID NO: 379          moltype = DNA  length = 735
FEATURE                 Location/Qualifiers
misc_feature            1..735
                        note = Modified humanized 8H5H5G4 scFV sequence (codon
                          optimized)
source                  1..735
                        mol_type = other DNA
                        organism = synthetic construct
SEQUENCE: 379
caggttcagc tggttcagtc tggcgccgaa gtgaagaaac tggcgcctc tgtgaaggtg    60
tcctgcaagg tgtccggaaa taccttcacc gagtacacca tgcactgggt ccgacaggcc  120
cctggcaaag gactggaatg gatcggcggc ttcaacccca caacggcgt gaccaactac  180
aaccagaaat tcaagggcaa agtgaccctg accgtggaca ccagcagcag cacagcctac  240
atggaactga gcagcctgag aagcgaggac accgccgtgt actactgcgc cagaaggtac  300
```

```
taccacagca cctacgtgtt ctacttcgac agctgggggcc agggcacact ggtcacagtt    360
tcttctggcg gtggcggaag cggaggcgg ggctccggtg gcggaggcag cgacatccag    420
atgacacaga gccctagcag cctgtctgcc agcgtgggag acagagtgac catcacatgt    480
agcgccagcc agggcatcag caactacctg aactggtatc agcagaaacc cggcaaggtg    540
cccaagctgc tgatctacta caccagcagc ctgcacagcg gctgccaaga cagatttct    600
ggcagcggct ctggcaccga ctacaccctg accatatcta gcctgcagcc tgaggacgtg    660
gccacctact actgtcagca gtacagcaag ctgccctaca cctttggcgg aggcaccaag    720
gtggaaatca agcgg                                                     735

SEQ ID NO: 380        moltype = DNA  length = 993
FEATURE               Location/Qualifiers
misc_feature          1..993
                      note = Human IgG1 heavy chain constant region sequence:
                       (for making full antibody - pair with either kappa or
                       lambda constant region; 2 plasmids, express together)
source                1..993
                      mol_type = other DNA
                      organism = synthetic construct
SEQUENCE: 380
gctagcacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgaca gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993

SEQ ID NO: 381        moltype = DNA  length = 981
FEATURE               Location/Qualifiers
misc_feature          1..981
                      note = Human IgG2 heavy chain constant region sequence:
                       (for making full antibody - pair with either kappa or
                       lambda constant region; 2 plasmids, express together)
source                1..981
                      mol_type = other DNA
                      organism = synthetic construct
SEQUENCE: 381
gcctccacca agggcccatc ggtcttcccc ctggcgccct gctccaggag cacctccgag    60
agcacagccg ccctgggctg cctggtcaag gactacttcc ccgaaccggt gacggtgtcg    120
tggaactcag gcgctctgac cagcggcgtg cacaccttcc cagctgtcct acagtcctca    180
ggactctact ccctcagcag cgtggtgacc gtgccctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagccccc atcgagaaaa ccatctccaa accaaagg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg gcagccgga gaacaactac aagaccacac ctcccatgct ggactccgac    840
ggctccttct cctctacag caagctcacc gtggacaaga gcaggtggca gcaggggaac    900
gtcttctcat gctccgtgat gcatgaggct ctgcacaacc actacacgca gaagagcctc    960
tccctgtctc cgggtaaata g                                              981

SEQ ID NO: 382        moltype = DNA  length = 324
FEATURE               Location/Qualifiers
misc_feature          1..324
                      note = Human Kappa light chain constant region sequence
source                1..324
                      mol_type = other DNA
                      organism = synthetic construct
SEQUENCE: 382
aggacggtgg ctgcaccatc tgtcttcatc ttcccgccat ctgatgagca gttgaaatct    60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                           324
```

| SEQ ID NO: 383 | moltype = DNA length = 321 |
| --- | --- |
| FEATURE | Location/Qualifiers |
| misc_feature | 1..321 |
| | note = Human Lambda light chain constant region sequence |
| source | 1..321 |
| | mol_type = other DNA |
| | organism = synthetic construct |

SEQUENCE: 383

```
ggtcagccca aggctgcccc ctcggtcact ctgttcccgc cctcctctga ggagcttcaa  60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tatctgagcc tgacgcctga gcagtggaag 240
tcccacagaa gctacagctg ccaggtcacg catgaaggga gcaccgtgga aagacagtg  300
gcccctacag aatgttcata g                                           321
```

| SEQ ID NO: 384 | moltype = DNA length = 699 |
| --- | --- |
| FEATURE | Location/Qualifiers |
| misc_feature | 1..699 |
| | note = Human IgG1 Fc region sequence: (to be fused to scFv for homo-dimerizes) |
| source | 1..699 |
| | mol_type = other DNA |
| | organism = synthetic construct |

SEQUENCE: 384

```
gagcccaaat cttgtgacaa aactcacaca tgcccaccgt gcccagcacc tgaactcctg  60
gggggaccgt cagtcttcct cttcccccca aaacccaagg acaccctcat gatctcccgg 120
acccctgagg tcacatgcgt ggtggtggac gtgagccacg aagaccctga ggtcaagttc 180
aactggtacg tggacggcgt ggaggtgcat aatgccaaga caaagccgcg ggaggagcag 240
tacaacagca cgtaccgtgt ggtcagcgtc ctcaccgtcc tgcaccagga ctggctgaat 300
ggcaaggagt acaagtgcaa ggtctccaac aaagccctcc cagccccat cgagaaaacc  360
atctccaaag ccaaagggca gccccgagaa ccacaggtgt acaccctgcc cccatcccgg 420
gaggagatga ccaagaacca ggtcagcctg acctgcctgg tcaaaggctt ctatcccagc 480
gacatcgccg tggagtggga gagcaatggg cagccggaga acaactacaa gaccacgcct 540
cccgtgctgg actccgacgg ctccttcttc ctctacagca agctcaccgt ggacaagagc 600
aggtggcagc aggggaacgt cttctcatgc tccgtgatgc atgaggctct gcacaaccac 660
tacacgcaga agagcctctc cctgtctccg ggtaaatga                        699
```

| SEQ ID NO: 385 | moltype = DNA length = 687 |
| --- | --- |
| FEATURE | Location/Qualifiers |
| misc_feature | 1..687 |
| | note = Human IgG2 Fc region sequence |
| source | 1..687 |
| | mol_type = other DNA |
| | organism = synthetic construct |

SEQUENCE: 385

```
gagcgcaaat gttgtgtcga gtgcccaccg tgcccagcac cacctgtggc aggaccgtca  60
gtcttcctct tccccccaaa acccaaggac accctcatga tctcccggac ccctgaggtc 120
acgtgcgtgg tggtggacgt gagccacgaa gaccccgagg tccagttcaa ctggtacgtg 180
gacggcgtgg aggtgcataa tgccaagaca aagccacggg aggagcagtt caacagcacg 240
ttccgtgtgg tcagcgtcct caccgttgtg caccaggact ggctgaacgg caaggagtac 300
aagtgcaagg tctccaacaa aggcctccca gcccccatcg agaaaaccat ctccaaaacc 360
aaagggcagc cccgagaacc acaggtgtac accctgcccc catcccggga ggagatgacc 420
aagaaccagg tcagcctgac ctgcctggtc aaaggcttct accccagcga catcgccgtg 480
gagtgggaga gcaatgggca gccggagaac aactacaaga ccacacctcc catgctggac 540
tccgacggct ccttcttcct ctacagcaag ctcaccgtgg acaagagcag gtggcagcag 600
gggaacgtct tctcatgctc cgtgatgcat gaggctctgc acaaccacta cacgcagaag 660
agcctctccc tgtctccggg taaatag                                     687
```

| SEQ ID NO: 386 | moltype = DNA length = 363 |
| --- | --- |
| FEATURE | Location/Qualifiers |
| misc_feature | 1..363 |
| | note = Monoclonal antibody 8F9A4A3 - Heavy chain variable region sequence - H-1,8,9,10,11 |
| source | 1..363 |
| | mol_type = other DNA |
| | organism = synthetic construct |

SEQUENCE: 386

```
gtccagctgc aacagtctgg acctgaactg gtgaagcctg gggcttcagt gaagatatcc  60
tgcaagactt ctggaaacac attcactgaa tacaccatgc actgggtgaa gcagagccat 120
ggaaagagcc ttgagtggat tggaggtttt aatcctaaca atggtgttac taactacaac 180
cagaagttca gggcaaggc cacattgact gtagacaagt cctccagcac agcctacatg 240
gagctccgca gcctgacatc tgaggattct gcagtctatt actgtgcaag acggtactac 300
catagtctct acgtgtttta ctttgactac tggggccaag gcaccactct cacagtctcc 360
tca                                                               363
```

| SEQ ID NO: 387 | moltype = AA length = 121 |
| --- | --- |
| FEATURE | Location/Qualifiers |
| REGION | 1..121 |

```
                        note = Monoclonal antibody 8F9A4A3 Translated protein,
                         wherein the underlined sequence is the complementarity
                         determining region (CDR)
source                  1..121
                        mol_type = protein
                        organism = synthetic construct
SEQUENCE: 387
VQLQQSGPEL VKPGASVKIS CKTSGNTFTE YTMHWVKQSH GKSLEWIGGF NPNNGVTNYN   60
QKFKGKATLT VDKSSSTAYM ELRSLTSEDS AVYYCARRYY HSLYVFYFDY WGQGTTLTVS  120
S                                                                 121

SEQ ID NO: 388          moltype = AA   length = 9
FEATURE                 Location/Qualifiers
REGION                  1..9
                        note = Monoclonal antibody 8F9A4A3 Heavy chain variable
                         region CDR1
source                  1..9
                        mol_type = protein
                        organism = synthetic construct
SEQUENCE: 388
NTFTEYTMH                                                            9

SEQ ID NO: 389          moltype = AA   length = 17
FEATURE                 Location/Qualifiers
REGION                  1..17
                        note = Monoclonal antibody 8F9A4A3 Heavy chain variable
                         region CDR2
source                  1..17
                        mol_type = protein
                        organism = synthetic construct
SEQUENCE: 389
GFNPNNGVTN YNQKFKG                                                  17

SEQ ID NO: 390          moltype = AA   length = 13
FEATURE                 Location/Qualifiers
REGION                  1..13
                        note = Monoclonal antibody 8F9A4A3 Heavy chain variable
                         region CDR3
source                  1..13
                        mol_type = protein
                        organism = synthetic construct
SEQUENCE: 390
RYYHSLYVFY FDY                                                      13

SEQ ID NO: 391          moltype = DNA   length = 324
FEATURE                 Location/Qualifiers
misc_feature            1..324
                        note = Monoclonal antibody 8F9A4A3 Light chain variable
                         region sequence - K-3,4,9,10,11
source                  1..324
                        mol_type = other DNA
                        organism = synthetic construct
SEQUENCE: 391
gaaacaactg tgacccagtc tccagcatcc ctgtccatgg ctataggaga aaaagtcacc   60
atcagatgca taaccagcac tgatattgat gatgatatga actggtacca gcagaagcca  120
ggggaacctc ctaagctcct tatttcagaa ggcaatactc ttcgtcctgg agtcccatcc  180
cgattctcca gcagtggcta tggtacagat tttgttttta caattgaaaa catgctctca  240
gaagatgttg cagattacta ctgtttgcaa agtgataact gcctctcac gttcggctcg   300
gggacaaagt tggaaataaa acgg                                          324

SEQ ID NO: 392          moltype = AA   length = 108
FEATURE                 Location/Qualifiers
REGION                  1..108
                        note = Monoclonal antibody 8F9A4A3 Translated protein,
                         wherein the underlined sequence is the complementarity
                         determining region (CDR)
source                  1..108
                        mol_type = protein
                        organism = synthetic construct
SEQUENCE: 392
ETTVTQSPAS LSMAIGEKVT IRCITSTDID DDMNWYQQKP GEPPKLLISE GNTLRPGVPS   60
RFSSSGYGTD FVFTIENMLS EDVADYYCLQ SDNLPLTFGS GTKLEIKR               108

SEQ ID NO: 393          moltype = AA   length = 11
FEATURE                 Location/Qualifiers
REGION                  1..11
                        note = Monoclonal antibody 8F9A4A3 Light chain variable
                         region CDR1
source                  1..11
```

```
                        mol_type = protein
                        organism = synthetic construct
SEQUENCE: 393
SASQGISNYL N                                                         11

SEQ ID NO: 394          moltype = AA   length = 7
FEATURE                 Location/Qualifiers
REGION                  1..7
                        note = Monoclonal antibody 8F9A4A3 Light chain variable
                         region CDR2
source                  1..7
                        mol_type = protein
                        organism = synthetic construct
SEQUENCE: 394
YTSSLHS                                                              7

SEQ ID NO: 395          moltype = AA   length = 9
FEATURE                 Location/Qualifiers
REGION                  1..9
                        note = Monoclonal antibody 8F9A4A3 Light chain variable
                         region CDR3
source                  1..9
                        mol_type = protein
                        organism = synthetic construct
SEQUENCE: 395
QQYSKLPYT                                                            9

SEQ ID NO: 396          moltype = DNA   length = 363
FEATURE                 Location/Qualifiers
misc_feature            1..363
                        note = Monoclonal antibody 5D9E2B11 - Heavy chain variable
                         region sequence - H-1,4,7,8,12
source                  1..363
                        mol_type = other DNA
                        organism = synthetic construct
SEQUENCE: 396
gtccagctgc aacagtctgg acctgatctg gtgaagcctg ggacttcagt gaagatatcc    60
tgtaagactt ctggaaacac attcactgaa tacaccatgc actgggtgaa gcagagccat   120
ggaaagagcc ttgagtggat tggaggtttt aatcctaaca atggtgttac taactacaac   180
cagaagttca aggcaaggc cacattgact gtagacaagt cctccagcac agcctacatg   240
gagctccgca gcctgacatc tgaggattct gcagtctatt actgtgcaag acgttactac   300
catagtacct acgtgttcta ctttgactcc tggggccaag gcaccactct cacagtctcc   360
tca                                                                363

SEQ ID NO: 397          moltype = AA   length = 121
FEATURE                 Location/Qualifiers
REGION                  1..121
                        note = Monoclonal antibody 5D9E2B11 Translated protein,
                         wherein the underlined sequence is the complementarity
                         determining region (CDR)
source                  1..121
                        mol_type = protein
                        organism = synthetic construct
SEQUENCE: 397
VQLQQSGPDL VKPGTSVKIS CKTSGNTFTE YTMHWVKQSH GKSLEWIGGF NPNNGVTNYN    60
QKFKGKATLT VDKSSSTAYM ELRSLTSEDS AVYYCARRYY HSTYVFYFDS WGQGTTLTVS   120
S                                                                  121

SEQ ID NO: 398          moltype = AA   length = 9
FEATURE                 Location/Qualifiers
REGION                  1..9
                        note = Monoclonal antibody 5D9E2B11 Heavy chain variable
                         region CDR1
source                  1..9
                        mol_type = protein
                        organism = synthetic construct
SEQUENCE: 398
NTFTEYTMH                                                            9

SEQ ID NO: 399          moltype = AA   length = 17
FEATURE                 Location/Qualifiers
REGION                  1..17
                        note = Monoclonal antibody 5D9E2B11 Heavy chain variable
                         region CDR2
source                  1..17
                        mol_type = protein
                        organism = synthetic construct
SEQUENCE: 399
GFNPNNGVTN YNQKFKG                                                  17
```

```
SEQ ID NO: 400          moltype = AA   length = 13
FEATURE                 Location/Qualifiers
REGION                  1..13
                        note = Monoclonal antibody 5D9E2B11 Heavy chain variable
                         region CDR3
source                  1..13
                        mol_type = protein
                        organism = synthetic construct
SEQUENCE: 400
RYYHSTYVFY FDS                                                          13

SEQ ID NO: 401          moltype = DNA   length = 324
FEATURE                 Location/Qualifiers
misc_feature            1..324
                        note = Monoclonal antibody 5D9E2B11 Light chain variable
                         region sequence - K-3,4,5,6,12
source                  1..324
                        mol_type = other DNA
                        organism = synthetic construct
SEQUENCE: 401
gatatccaga tgacacagac tacatcctcc ctgtctgcct ctctgggaga cagagtcacc    60
atcagttgca gtgcaagtca gggcattagc aattatttaa actggtttca gcagaaacca   120
gatggaacta ttaagctcct gatctattac acatcaagtt tacattcagg agtcccatca   180
aggttcagtg gcagtgggtc tgggacagat tattctctca ccatcagtaa tgtggaacct   240
gaagatattg ccacttacta ttgtcagcag tatagtaagc ttccttacac gttcggaggg   300
gggaccaagc tggagataaa acgg                                          324

SEQ ID NO: 402          moltype = AA   length = 108
FEATURE                 Location/Qualifiers
REGION                  1..108
                        note = Monoclonal antibody 5D9E2B11 Translated protein
source                  1..108
                        mol_type = protein
                        organism = synthetic construct
SEQUENCE: 402
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 403          moltype = AA   length = 108
FEATURE                 Location/Qualifiers
REGION                  1..108
                        note = Monoclonal antibody 5D9E2B11 Translated protein,
                         wherein the underlined sequence is the complementarity
                         determining region (CDR)
source                  1..108
                        mol_type = protein
                        organism = synthetic construct
SEQUENCE: 403
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 404          moltype = AA   length = 11
FEATURE                 Location/Qualifiers
REGION                  1..11
                        note = Monoclonal antibody 5D9E2B11 Light chain variable
                         region CDR 1
source                  1..11
                        mol_type = protein
                        organism = synthetic construct
SEQUENCE: 404
SASQGISNYL N                                                            11

SEQ ID NO: 405          moltype = AA   length = 7
FEATURE                 Location/Qualifiers
REGION                  1..7
                        note = Monoclonal antibody 5D9E2B11 Light chain variable
                         region CDR2
source                  1..7
                        mol_type = protein
                        organism = synthetic construct
SEQUENCE: 405
YTSSLHS                                                                  7

SEQ ID NO: 406          moltype = AA   length = 9
FEATURE                 Location/Qualifiers
REGION                  1..9
                        note = Monoclonal antibody 5D9E2B11 Light chain variable
                         region CDR3
```

```
source                          1..9
                                mol_type = protein
                                organism = synthetic construct
SEQUENCE: 406
QQYSKLPYT                                                                    9

SEQ ID NO: 407                  moltype = DNA   length = 363
FEATURE                         Location/Qualifiers
misc_feature                    1..363
                                note = Monoclonal antibody 5D9E10E4 - Heavy chain variable
                                  region sequence - H-2,4,7,10,12
source                          1..363
                                mol_type = other DNA
                                organism = synthetic construct
SEQUENCE: 407
gtccagctgc aacagtctgg acctgatctg gtgaagcctg ggacttcagt gaagatatcc       60
tgtaagactt ctggaaacac attcactgaa tacaccatgc actgggtgaa gcagagccat      120
ggaaagagcc ttgagtggat tggaggtttt aatcctaaca atggtgttac taactacaac      180
cagaagttca gggcaaggc cacattgact gtagacaagt cctccagcac agcctacatg       240
gagctccgca gcctgacatc tgaggattct gcagtctatt actgtgcaag acgttactac      300
catagtacct acgtgttcta ctttgactcc tggggccaag gcaccactct cacagtctcc      360
tca                                                                     363

SEQ ID NO: 408                  moltype = AA   length = 121
FEATURE                         Location/Qualifiers
REGION                          1..121
                                note = Monoclonal antibody 5D9E10E4 Translated protein,
                                  wherein the underlined sequence is the complementarity
                                  determining region (CDR)
source                          1..121
                                mol_type = protein
                                organism = synthetic construct
SEQUENCE: 408
VQLQQSGPDL VKPGTSVKIS CKTSGNTFTE YTMHWVKQSH GKSLEWIGGF NPNNGVTNYN        60
QKFKGKATLT VDKSSSTAYM ELRSLTSEDS AVYYCARRYY HSTYVFYFDS WGQGTTLTVS       120
S                                                                      121

SEQ ID NO: 409                  moltype = AA   length = 9
FEATURE                         Location/Qualifiers
REGION                          1..9
                                note = Monoclonal antibody 5D9E10E4 Heavy chain variable
                                  region CDR1
source                          1..9
                                mol_type = protein
                                organism = synthetic construct
SEQUENCE: 409
NTFTEYTMH                                                                    9

SEQ ID NO: 410                  moltype = AA   length = 17
FEATURE                         Location/Qualifiers
REGION                          1..17
                                note = Monoclonal antibody 5D9E10E4 Heavy chain variable
                                  region CDR2
source                          1..17
                                mol_type = protein
                                organism = synthetic construct
SEQUENCE: 410
GFNPNNGVTN YNQKFKG                                                           17

SEQ ID NO: 411                  moltype = AA   length = 13
FEATURE                         Location/Qualifiers
REGION                          1..13
                                note = Monoclonal antibody 5D9E10E4 Heavy chain variable
                                  region CDR3
source                          1..13
                                mol_type = protein
                                organism = synthetic construct
SEQUENCE: 411
RYYHSTYVFY FDS                                                               13

SEQ ID NO: 412                  moltype = DNA   length = 324
FEATURE                         Location/Qualifiers
misc_feature                    1..324
                                note = Monoclonal antibody 5D9E10E4 Light chain variable
                                  region sequence - K-2,6,8,14,15
source                          1..324
                                mol_type = other DNA
                                organism = synthetic construct
SEQUENCE: 412
```

```
gatatccaga tgacacagac tacatcctcc ctgtctgcct ctctgggaga cagagtcacc    60
atcagttgca gtgcaagtca gggcattagc aattatttaa actggtttca gcagaaacca   120
gatggaacta ttaagctcct gatctattac acatcaagtt tacattcagg agtcccatca   180
aggttcagtg gcagtgggtc tgggacagat tattctctca ccatcagtaa tgtggaacct   240
gaagatattg ccacttacta ttgtcagcag tatagtaagc ttccttacac gttcggaggg   300
gggaccaagc tggagataaa acgg                                          324

SEQ ID NO: 413          moltype = AA  length = 108
FEATURE                 Location/Qualifiers
REGION                  1..108
                        note = Monoclonal antibody 5D9E10E4 Translated protein,
                        wherein the underlined sequence is the complementarity
                        determining region (CDR)
source                  1..108
                        mol_type = protein
                        organism = synthetic construct
SEQUENCE: 413
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 414          moltype = AA  length = 11
FEATURE                 Location/Qualifiers
REGION                  1..11
                        note = Monoclonal antibody 5D9E10E4 Light chain variable
                        region CDR 1
source                  1..11
                        mol_type = protein
                        organism = synthetic construct
SEQUENCE: 414
SASQGISNYL N                                                         11

SEQ ID NO: 415          moltype = AA  length = 7
FEATURE                 Location/Qualifiers
REGION                  1..7
                        note = Monoclonal antibody 5D9E10E4 Light chain variable
                        region CDR2
source                  1..7
                        mol_type = protein
                        organism = synthetic construct
SEQUENCE: 415
YTSSLHS                                                               7

SEQ ID NO: 416          moltype = AA  length = 9
FEATURE                 Location/Qualifiers
REGION                  1..9
                        note = Monoclonal antibody 5D9E10E4 Light chain variable
                        region CDR3
source                  1..9
                        mol_type = protein
                        organism = synthetic construct
SEQUENCE: 416
QQYSKLPYT                                                             9

SEQ ID NO: 417          moltype = DNA  length = 363
FEATURE                 Location/Qualifiers
misc_feature            1..363
                        note = Monoclonal antibody 5D9G2C4 - Heavy chain variable
                        region sequence - H-4,9,10,11,13
source                  1..363
                        mol_type = other DNA
                        organism = synthetic construct
SEQUENCE: 417
gtccagctgc aacagtctgg acctgatctg gtgaagcctg ggacttcagt gaagatatcc    60
tgtaagactt ctggaaacac attcactgaa tacaccatgc actgggtgaa gcagagccat   120
ggaaagagcc ttgagtggat tggaggtttt aatcctaaca atggtgttac taactacaac   180
cagaagttca gggcaaggc cacattgact gtagacaagt cctccagcac agcctacatg   240
gagctccgca gcctgacatc tgaggattct gcagtctatt actgtgcaag acgttactac   300
catagtacct acgtgttcta cttttgactcc tggggccaag gcaccactct cacagtctcc   360
tca                                                                 363

SEQ ID NO: 418          moltype = AA  length = 121
FEATURE                 Location/Qualifiers
REGION                  1..121
                        note = Monoclonal antibody 5D9G2C4 Translated protein,
                        wherein the underlined sequence is the complementarity
                        determining region (CDR)
source                  1..121
                        mol_type = protein
                        organism = synthetic construct
```

```
SEQUENCE: 418
VQLQQSGPDL VKPGTSVKIS CKTSGNTFTE YTMHWVKQSH GKSLEWIGGF NPNNGVTNYN    60
QKFKGKATLT VDKSSSTAYM ELRSLTSEDS AVYYCARRYY HSTYVFYFDS WGQGTTLTVS   120
S                                                                  121

SEQ ID NO: 419          moltype = AA   length = 9
FEATURE                 Location/Qualifiers
REGION                  1..9
                        note = Monoclonal antibody 5D9G2C4 Heavy chain variable
                         region CDR1
source                  1..9
                        mol_type = protein
                        organism = synthetic construct
SEQUENCE: 419
NTFTEYTMH                                                             9

SEQ ID NO: 420          moltype = AA   length = 17
FEATURE                 Location/Qualifiers
REGION                  1..17
                        note = Monoclonal antibody 5D9G2C4 Heavy chain variable
                         region CDR2
source                  1..17
                        mol_type = protein
                        organism = synthetic construct
SEQUENCE: 420
GFNPNNGVTN YNQKFKG                                                   17

SEQ ID NO: 421          moltype = AA   length = 13
FEATURE                 Location/Qualifiers
REGION                  1..13
                        note = Monoclonal antibody 5D9G2C4 Heavy chain variable
                         region CDR3
source                  1..13
                        mol_type = protein
                        organism = synthetic construct
SEQUENCE: 421
RYYHSTYVFY FDS                                                       13

SEQ ID NO: 422          moltype = DNA   length = 324
FEATURE                 Location/Qualifiers
misc_feature            1..324
                        note = Monoclonal antibody 5D9G2C4 Light chain variable
                         region sequence - K-4,6,7,8,10
source                  1..324
                        mol_type = other DNA
                        organism = synthetic construct
SEQUENCE: 422
gatatccaga tgacacagac tacatcctcc ctgtctgcct ctctgggaga cagagtcacc    60
atcagttgca gtgcaagtca gggcattagc aattatttaa actggtttca gcagaaacca   120
gatgaaacta ttaagctcct gatctattac acatcaagtt acattcagg agtcccatca    180
aggttcagtg gcagtgggtc tgggacagat tattctctca ccatcagtaa tgtggaacct   240
gaagatattg ccacttacta ttgtcagcag tatagtaagc ttccttacac gttcggaggg   300
gggaccaagc tggagataaa acgg                                          324

SEQ ID NO: 423          moltype = AA   length = 108
FEATURE                 Location/Qualifiers
REGION                  1..108
                        note = Monoclonal antibody 5D9G2C4 Translated protein,
                         wherein the underlined sequence is the complementarity
                         determining region (CDR)
source                  1..108
                        mol_type = protein
                        organism = synthetic construct
SEQUENCE: 423
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 424          moltype = AA   length = 11
FEATURE                 Location/Qualifiers
REGION                  1..11
                        note = Monoclonal antibody 5D9G2C4 Light chain variable
                         region CDR 1
source                  1..11
                        mol_type = protein
                        organism = synthetic construct
SEQUENCE: 424
SASQGISNYL N                                                         11

SEQ ID NO: 425          moltype = AA   length = 7
```

```
FEATURE                 Location/Qualifiers
REGION                  1..7
                        note = Monoclonal antibody 5D9G2C4 Light chain variable
                          region CDR2
source                  1..7
                        mol_type = protein
                        organism = synthetic construct
SEQUENCE: 425
YTSSLHS                                                                    7

SEQ ID NO: 426          moltype = AA  length = 9
FEATURE                 Location/Qualifiers
REGION                  1..9
                        note = Monoclonal antibody 5D9G2C4 Light chain variable
                          region CDR3
source                  1..9
                        mol_type = protein
                        organism = synthetic construct
SEQUENCE: 426
QQYSKLPYT                                                                  9

SEQ ID NO: 427          moltype = DNA  length = 363
FEATURE                 Location/Qualifiers
misc_feature            1..363
                        note = Monoclonal antibody 5F3A5D4 - Heavy chain variable
                          region sequence - H-2,3,4,13,15
source                  1..363
                        mol_type = other DNA
                        organism = synthetic construct
SEQUENCE: 427
gtccagctgc aacagtctgg acctgatctg gtgaagcctg ggacttcagt gaagatatcc    60
tgtaagactt ctggaaacac attcactgaa tacaccatgc actgggtgaa gcagagccat   120
ggaaagagcc ttgagtggat tggaggtttt aatcctaaca atggtgttac taactacaac   180
cagaagttca aggcaaggc cacattgact gtagacaagt cctccagcac agcctacatg   240
gagctccgca gcctgacatc tgaggattct gcagtctatt actgtgcaag acgttactac   300
catagtaccct acgtgttcta ctttgactcc tggggccaag gcaccactct cacagtctcc   360
tca                                                                  363

SEQ ID NO: 428          moltype = AA  length = 121
FEATURE                 Location/Qualifiers
REGION                  1..121
                        note = Monoclonal antibody 5F3A5D4 Translated protein,
                          wherein the underlined sequence is the complementarity
                          determining region (CDR)
source                  1..121
                        mol_type = protein
                        organism = synthetic construct
SEQUENCE: 428
VQLQQSGPDL VKPGTSVKIS CKTSGNTFTE YTMHWVKQSH GKSLEWIGGF NPNNGVTNYN     60
QKFKGKATLT VDKSSSTAYM ELRSLTSEDS AVYYCARRYY HSTYVFYFDS WGQGTTLTVS    120
S                                                                    121

SEQ ID NO: 429          moltype = AA  length = 9
FEATURE                 Location/Qualifiers
REGION                  1..9
                        note = Monoclonal antibody 5F3A5D4 Heavy chain variable
                          region CDR1
source                  1..9
                        mol_type = protein
                        organism = synthetic construct
SEQUENCE: 429
NTFTEYTMH                                                                  9

SEQ ID NO: 430          moltype = AA  length = 17
FEATURE                 Location/Qualifiers
REGION                  1..17
                        note = Monoclonal antibody 5F3A5D4 Heavy chain variable
                          region CDR2
source                  1..17
                        mol_type = protein
                        organism = synthetic construct
SEQUENCE: 430
GFNPNNGVTN YNQKFKG                                                        17

SEQ ID NO: 431          moltype = AA  length = 13
FEATURE                 Location/Qualifiers
REGION                  1..13
                        note = Monoclonal antibody 5F3A5D4 Heavy chain variable
                          region CDR3
```

```
source                    1..13
                          mol_type = protein
                          organism = synthetic construct
SEQUENCE: 431
RYYHSTYVFY FDS                                                       13

SEQ ID NO: 432            moltype = DNA   length = 324
FEATURE                   Location/Qualifiers
misc_feature              1..324
                          note = Monoclonal antibody 5F3A5D4 Light chain variable
                           region sequence - K-1,2,3,4,9
source                    1..324
                          mol_type = other DNA
                          organism = synthetic construct
SEQUENCE: 432
gatatccaga tgacacagac tacatcctcc ctgtctgcct ctctgggaga cagagtcacc    60
atcagttgca gtgcaagtca gggcattagc aattatttaa actggtttca gcagaaacca   120
gatggaacta ttaagctcct gatctattac acatcaagtt tacattcagg agtcccatca   180
aggttcagtg gcagtgggtc tgggacagat tattctctca ccatcagtaa tgtgaacct    240
gaagatattg ccacttacta ttgtcagcag tatagtaagc ttccttacac gttcggaggg   300
gggaccaagc tggagataaa acgg                                          324

SEQ ID NO: 433            moltype = AA   length = 108
FEATURE                   Location/Qualifiers
REGION                    1..108
                          note = Monoclonal antibody 5F3A5D4 Translated protein,
                           wherein the underlined sequence is the complementarity
                           determining region (CDR)
source                    1..108
                          mol_type = protein
                          organism = synthetic construct
SEQUENCE: 433
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR                108

SEQ ID NO: 434            moltype = AA   length = 11
FEATURE                   Location/Qualifiers
REGION                    1..11
                          note = Monoclonal antibody 5F3A5D4 Light chain variable
                           region CDR1
source                    1..11
                          mol_type = protein
                          organism = synthetic construct
SEQUENCE: 434
SASQGISNYL N                                                         11

SEQ ID NO: 435            moltype = AA   length = 7
FEATURE                   Location/Qualifiers
REGION                    1..7
                          note = Monoclonal antibody 5F3A5D4 Light chain variable
                           region CDR2
source                    1..7
                          mol_type = protein
                          organism = synthetic construct
SEQUENCE: 435
YTSSLHS                                                              7

SEQ ID NO: 436            moltype = AA   length = 9
FEATURE                   Location/Qualifiers
REGION                    1..9
                          note = Monoclonal antibody 5F3A5D4 Light chain variable
                           region CDR3
source                    1..9
                          mol_type = protein
                          organism = synthetic construct
SEQUENCE: 436
QQYSKLPYT                                                            9

SEQ ID NO: 437            moltype = DNA   length = 357
FEATURE                   Location/Qualifiers
misc_feature              1..357
                          note = Monoclonal antibody 8F9A5A1 - Heavy chain variable
                           region sequence - H-3,4,6,10,11
source                    1..357
                          mol_type = other DNA
                          organism = synthetic construct
SEQUENCE: 437
atccagttgg tgcagtctgg acctgagctg aagaagcctg gagagacagt caagatctcc    60
tgcaaggctt ctgggtatac cttcacaaac tatggaatga actgggtgaa gcaggctcca   120
```

```
ggaaagggtt taaagtggat gggctggata acacctaca ctggagagcc aacatatgtt    180
gatgacttca agggacggtt tgccttctct ttgaaacct  ctgccaccac tgcctatttg    240
cagatcaaca acctcaaaaa tgaggacacg tctacatatt tctgtgcaag attgagggg    300
atacgaccgg gtcccttggc ttactggggc caagggactc tggtcactgt ctctgca      357

SEQ ID NO: 438           moltype = AA   length = 119
FEATURE                  Location/Qualifiers
REGION                   1..119
                         note = Monoclonal antibody 8F9A5A1 Translated protein,
                           wherein the underlined sequence is the complementarity
                           determining region (CDR)
source                   1..119
                         mol_type = protein
                         organism = synthetic construct
SEQUENCE: 438
IQLVQSGPEL KKPGETVKIS CKASGYTFTN YGMNWVKQAP GKGLKWMGWI NTYTGEPTYV    60
DDFKGRFAFS LETSATTAYL QINNLKNEDT STYFCARLRG IRPGPLAYWG QGTLVTVSA    119

SEQ ID NO: 439           moltype = AA   length = 9
FEATURE                  Location/Qualifiers
REGION                   1..9
                         note = Monoclonal antibody 8F9A5A1 Heavy chain variable
                           region CDR1
source                   1..9
                         mol_type = protein
                         organism = synthetic construct
SEQUENCE: 439
YTFTNYGMN                                                             9

SEQ ID NO: 440           moltype = AA   length = 17
FEATURE                  Location/Qualifiers
REGION                   1..17
                         note = Monoclonal antibody 8F9A5A1 Heavy chain variable
                           region CDR2
source                   1..17
                         mol_type = protein
                         organism = synthetic construct
SEQUENCE: 440
WINTYTGEPT YVDDFKG                                                   17

SEQ ID NO: 441           moltype = AA   length = 11
FEATURE                  Location/Qualifiers
REGION                   1..11
                         note = Monoclonal antibody 8F9A5A1 Heavy chain variable
                           region CDR3
source                   1..11
                         mol_type = protein
                         organism = synthetic construct
SEQUENCE: 441
LRGIRPGPLA Y                                                         11

SEQ ID NO: 442           moltype = DNA   length = 321
FEATURE                  Location/Qualifiers
misc_feature             1..321
                         note = Monoclonal antibody 8F9A5A1 Light chain variable
                           region sequence - K-1,2,3,4,5
source                   1..321
                         mol_type = other DNA
                         organism = synthetic construct
SEQUENCE: 442
gaaattttgc tcacccagtc tccagcaatc atagctgcat ctcctgggga gaaggtcacc    60
atcacctgca gtgccagctc aagtgtaagt tacatgaact ggtaccagca gaaaccagga   120
tcctccccca aaatatggat ttatggtata tccaacctgg cttctggagt tcctgctcgc   180
ttcagtggca gtgggtctgg gacatctttc tctttcacaa tcaacagcat ggaggctgaa   240
gatgttgcca cttattactg tcagcaaagg agtagttacc cacccacgtt cggagggggg   300
accaagctgg aaataaaacg g                                             321

SEQ ID NO: 443           moltype = AA   length = 107
FEATURE                  Location/Qualifiers
REGION                   1..107
                         note = Monoclonal antibody 8F9A5A1 Translated protein,
                           wherein the underlined sequence is the complementarity
                           determining region (CDR)
source                   1..107
                         mol_type = protein
                         organism = synthetic construct
SEQUENCE: 443
EILLTQSPAI IAASPGEKVT ITCSASSSVS YMNWYQQKPG SSPKIWIYGI SNLASGVPAR    60
FSGSGSGTSF SFTINSMEAE DVATYYCQQR SSYPPTFGGG TKLEIKR                 107
```

-continued

```
SEQ ID NO: 444            moltype = AA   length = 10
FEATURE                   Location/Qualifiers
REGION                    1..10
                          note = Monoclonal antibody 8F9A5A1 Light chain variable
                           region CDR 1
source                    1..10
                          mol_type = protein
                          organism = synthetic construct
SEQUENCE: 444
SASSSVSYMN                                                                  10

SEQ ID NO: 445            moltype = AA   length = 7
FEATURE                   Location/Qualifiers
REGION                    1..7
                          note = Monoclonal antibody 8F9A5A1 Light chain variable
                           region CDR2
source                    1..7
                          mol_type = protein
                          organism = synthetic construct
SEQUENCE: 445
GISNLAS                                                                      7

SEQ ID NO: 446            moltype = AA   length = 9
FEATURE                   Location/Qualifiers
REGION                    1..9
                          note = Monoclonal antibody 8F9A5A1 Light chain variable
                           region CDR3
source                    1..9
                          mol_type = protein
                          organism = synthetic construct
SEQUENCE: 446
QQRSSYPPT                                                                    9

SEQ ID NO: 447            moltype = DNA   length = 363
FEATURE                   Location/Qualifiers
misc_feature              1..363
                          note = Monoclonal antibody 8H5H5G4 - Heavy chain variable
                           region sequence - H-1,3,5,6,10
source                    1..363
                          mol_type = other DNA
                          organism = synthetic construct
SEQUENCE: 447
gtccagctgc aacagtctgg acctgatctg gtgaagcctg ggacttcagt gaagatatcc            60
tgtaagactt ctggaaacac attcactgaa tacaccatgc actgggtgaa gcagagccat           120
ggaaagagcc ttgagtggat tggaggtttt aatcctaaca atggtgttac taactacaac           180
cagaagttca agggcaaggc cacattgact gtagacaagt cctccagcac agcctacatg           240
gagctccgca gcctgacatc tgaggattct gcagtctatt actgtgcaag acgttactac           300
catagtaccc tcgtgttcta ctttgactcc tggggccaag gcaccactct cacagtctcc           360
tca                                                                        363

SEQ ID NO: 448            moltype = AA   length = 121
FEATURE                   Location/Qualifiers
REGION                    1..121
                          note = Monoclonal antibody 8H5H5G4 Translated protein,
                           wherein the underlined sequence is the complementarity
                           determining region (CDR)
source                    1..121
                          mol_type = protein
                          organism = synthetic construct
SEQUENCE: 448
VQLQQSGPDL VKPGTSVKIS CKTSGNTFTE YTMHWVKQSH GKSLEWIGGF NPNNGVTNYN            60
QKFKGKATLT VDKSSSTAYM ELRSLTSEDS AVYYCARRYY HSTYVFYFDS WGQGTTLTVS           120
S                                                                          121

SEQ ID NO: 449            moltype = AA   length = 9
FEATURE                   Location/Qualifiers
REGION                    1..9
                          note = Monoclonal antibody 8H5H5G4 Heavy chain variable
                           region CDR1
source                    1..9
                          mol_type = protein
                          organism = synthetic construct
SEQUENCE: 449
NTFTEYTMH                                                                    9

SEQ ID NO: 450            moltype = AA   length = 17
FEATURE                   Location/Qualifiers
REGION                    1..17
```

```
                        note = Monoclonal antibody 8H5H5G4 Heavy chain variable
                           region CDR2
source                  1..17
                        mol_type = protein
                        organism = synthetic construct
SEQUENCE: 450
GFNPNNGVTN YNQKFKG                                                         17

SEQ ID NO: 451          moltype = AA   length = 13
FEATURE                 Location/Qualifiers
REGION                  1..13
                        note = Monoclonal antibody 8H5H5G4 Heavy chain variable
                           region CDR3
source                  1..13
                        mol_type = protein
                        organism = synthetic construct
SEQUENCE: 451
RYYHSTYVFY FDS                                                             13

SEQ ID NO: 452          moltype = DNA   length = 324
FEATURE                 Location/Qualifiers
misc_feature            1..324
                        note = Monoclonal antibody 8H5H5G4 Light chain variable
                           region sequence - K-2,5,8,9,15
source                  1..324
                        mol_type = other DNA
                        organism = synthetic construct
SEQUENCE: 452
gatatccaga tgacacagac tacatcctcc ctgtctgcct ctctgggaga cagagtcacc      60
atcagttgca gtgcaagtca gggcattagc aattatttaa actggtttca gcagaaacca    120
gatggaacta ttaagctcct gatctattac acatcaagtt tacattcagg agtcccatca    180
aggttcagtg gcagtgggtc tgggacagat tattctctca ccatcagtaa tgtggaacct    240
gaagatattg ccacttacta ttgtcagcag tatagtaagc ttccttacac gttcggaggg    300
gggaccaagc tggagataaa acgg                                            324

SEQ ID NO: 453          moltype = AA   length = 108
FEATURE                 Location/Qualifiers
REGION                  1..108
                        note = Monoclonal antibody 8H5H5G4 Translated protein,
                           wherein the underlined sequence is the complementarity
                           determining region (CDR)
source                  1..108
                        mol_type = protein
                        organism = synthetic construct
SEQUENCE: 453
DIQMTQTTSS LSASLGDRVT ISCSASQGIS NYLNWFQQKP DGTIKLLIYY TSSLHSGVPS      60
RFSGSGSGTD YSLTISNVEP EDIATYYCQQ YSKLPYTFGG GTKLEIKR                  108

SEQ ID NO: 454          moltype = AA   length = 11
FEATURE                 Location/Qualifiers
REGION                  1..11
                        note = Monoclonal antibody 8H5H5G4 Light chain variable
                           region CDR 1
source                  1..11
                        mol_type = protein
                        organism = synthetic construct
SEQUENCE: 454
SASQGISNYL N                                                               11

SEQ ID NO: 455          moltype = AA   length = 7
FEATURE                 Location/Qualifiers
REGION                  1..7
                        note = Monoclonal antibody 8H5H5G4 Light chain variable
                           region CDR2
source                  1..7
                        mol_type = protein
                        organism = synthetic construct
SEQUENCE: 455
YTSSLHS                                                                     7

SEQ ID NO: 456          moltype = AA   length = 9
FEATURE                 Location/Qualifiers
REGION                  1..9
                        note = Monoclonal antibody 8H5H5G4 Light chain variable
                           region CDR3
source                  1..9
                        mol_type = protein
                        organism = synthetic construct
SEQUENCE: 456
```

QQYSKLPYT 9

SEQ ID NO: 457    moltype =    length =
SEQUENCE: 457
000

SEQ ID NO: 458    moltype =    length =
SEQUENCE: 458
000

SEQ ID NO: 459    moltype =    length =
SEQUENCE: 459
000

SEQ ID NO: 460    moltype =    length =
SEQUENCE: 460
000

SEQ ID NO: 461    moltype =    length =
SEQUENCE: 461
000

SEQ ID NO: 462    moltype =    length =
SEQUENCE: 462
000

SEQ ID NO: 463    moltype =    length =
SEQUENCE: 463
000

SEQ ID NO: 464    moltype =    length =
SEQUENCE: 464
000

SEQ ID NO: 465    moltype =    length =
SEQUENCE: 465
000

SEQ ID NO: 466    moltype =    length =
SEQUENCE: 466
000

SEQ ID NO: 467    moltype =    length =
SEQUENCE: 467
000

SEQ ID NO: 468    moltype =    length =
SEQUENCE: 468
000

SEQ ID NO: 469    moltype =    length =
SEQUENCE: 469
000

SEQ ID NO: 470    moltype =    length =
SEQUENCE: 470
000

SEQ ID NO: 471    moltype =    length =
SEQUENCE: 471
000

SEQ ID NO: 472    moltype =    length =
SEQUENCE: 472
000

SEQ ID NO: 473    moltype =    length =
SEQUENCE: 473
000

SEQ ID NO: 474    moltype =    length =
SEQUENCE: 474
000

SEQ ID NO: 475    moltype =    length =
SEQUENCE: 475
000

SEQ ID NO: 476    moltype =    length =

| | | |
|---|---|---|
| SEQUENCE: 476 000 | | |
| SEQ ID NO: 477 SEQUENCE: 477 000 | moltype = | length = |
| SEQ ID NO: 478 SEQUENCE: 478 000 | moltype = | length = |
| SEQ ID NO: 479 SEQUENCE: 479 000 | moltype = | length = |
| SEQ ID NO: 480 SEQUENCE: 480 000 | moltype = | length = |
| SEQ ID NO: 481 SEQUENCE: 481 000 | moltype = | length = |
| SEQ ID NO: 482 SEQUENCE: 482 000 | moltype = | length = |
| SEQ ID NO: 483 SEQUENCE: 483 000 | moltype = | length = |
| SEQ ID NO: 484 SEQUENCE: 484 000 | moltype = | length = |
| SEQ ID NO: 485 SEQUENCE: 485 000 | moltype = | length = |
| SEQ ID NO: 486 SEQUENCE: 486 000 | moltype = | length = |
| SEQ ID NO: 487 SEQUENCE: 487 000 | moltype = | length = |
| SEQ ID NO: 488 SEQUENCE: 488 000 | moltype = | length = |
| SEQ ID NO: 489 SEQUENCE: 489 000 | moltype = | length = |
| SEQ ID NO: 490 SEQUENCE: 490 000 | moltype = | length = |
| SEQ ID NO: 491 SEQUENCE: 491 000 | moltype = | length = |
| SEQ ID NO: 492 SEQUENCE: 492 000 | moltype = | length = |
| SEQ ID NO: 493 SEQUENCE: 493 000 | moltype = | length = |
| SEQ ID NO: 494 SEQUENCE: 494 000 | moltype = | length = |
| SEQ ID NO: 495 SEQUENCE: 495 000 | moltype = | length = |

-continued

| | | |
|---|---|---|
| SEQ ID NO: 496<br>SEQUENCE: 496 | moltype = | length = 000 |
| SEQ ID NO: 497<br>SEQUENCE: 497 | moltype = | length = 000 |
| SEQ ID NO: 498<br>SEQUENCE: 498 | moltype = | length = 000 |
| SEQ ID NO: 499<br>SEQUENCE: 499 | moltype = | length = 000 |
| SEQ ID NO: 500<br>SEQUENCE: 500 | moltype = | length = 000 |
| SEQ ID NO: 501<br>SEQUENCE: 501 | moltype = | length = 000 |
| SEQ ID NO: 502<br>SEQUENCE: 502 | moltype = | length = 000 |
| SEQ ID NO: 503<br>SEQUENCE: 503 | moltype = | length = 000 |
| SEQ ID NO: 504<br>SEQUENCE: 504 | moltype = | length = 000 |
| SEQ ID NO: 505<br>SEQUENCE: 505 | moltype = | length = 000 |
| SEQ ID NO: 506<br>SEQUENCE: 506 | moltype = | length = 000 |
| SEQ ID NO: 507<br>SEQUENCE: 507 | moltype = | length = 000 |
| SEQ ID NO: 508<br>SEQUENCE: 508 | moltype = | length = 000 |
| SEQ ID NO: 509<br>SEQUENCE: 509 | moltype = | length = 000 |
| SEQ ID NO: 510<br>SEQUENCE: 510 | moltype = | length = 000 |
| SEQ ID NO: 511<br>SEQUENCE: 511 | moltype = | length = 000 |
| SEQ ID NO: 512<br>SEQUENCE: 512 | moltype = | length = 000 |
| SEQ ID NO: 513<br>SEQUENCE: 513 | moltype = | length = 000 |
| SEQ ID NO: 514<br>SEQUENCE: 514 | moltype = | length = 000 |
| SEQ ID NO: 515<br>SEQUENCE: 515 | moltype = | length = 000 |

SEQ ID NO: 516       moltype =    length =
SEQUENCE: 516
000

SEQ ID NO: 517       moltype =    length =
SEQUENCE: 517
000

SEQ ID NO: 518       moltype =    length =
SEQUENCE: 518
000

SEQ ID NO: 519       moltype =    length =
SEQUENCE: 519
000

SEQ ID NO: 520       moltype =    length =
SEQUENCE: 520
000

SEQ ID NO: 521       moltype =    length =
SEQUENCE: 521
000

SEQ ID NO: 522       moltype =    length =
SEQUENCE: 522
000

SEQ ID NO: 523       moltype =    length =
SEQUENCE: 523
000

SEQ ID NO: 524       moltype =    length =
SEQUENCE: 524
000

SEQ ID NO: 525       moltype =    length =
SEQUENCE: 525
000

SEQ ID NO: 526       moltype =    length =
SEQUENCE: 526
000

SEQ ID NO: 527       moltype =    length =
SEQUENCE: 527
000

SEQ ID NO: 528       moltype =    length =
SEQUENCE: 528
000

SEQ ID NO: 529       moltype =    length =
SEQUENCE: 529
000

SEQ ID NO: 530       moltype =    length =
SEQUENCE: 530
000

SEQ ID NO: 531       moltype =    length =
SEQUENCE: 531
000

SEQ ID NO: 532       moltype =    length =
SEQUENCE: 532
000

SEQ ID NO: 533       moltype =    length =
SEQUENCE: 533
000

SEQ ID NO: 534       moltype =    length =
SEQUENCE: 534
000

SEQ ID NO: 535       moltype =    length =
SEQUENCE: 535

000

SEQ ID NO: 536         moltype =    length =
SEQUENCE: 536
000

SEQ ID NO: 537         moltype =    length =
SEQUENCE: 537
000

SEQ ID NO: 538         moltype =    length =
SEQUENCE: 538
000

SEQ ID NO: 539         moltype =    length =
SEQUENCE: 539
000

SEQ ID NO: 540         moltype =    length =
SEQUENCE: 540
000

SEQ ID NO: 541         moltype =    length =
SEQUENCE: 541
000

SEQ ID NO: 542         moltype =    length =
SEQUENCE: 542
000

SEQ ID NO: 543         moltype =    length =
SEQUENCE: 543
000

SEQ ID NO: 544         moltype =    length =
SEQUENCE: 544
000

SEQ ID NO: 545         moltype =    length =
SEQUENCE: 545
000

SEQ ID NO: 546         moltype =    length =
SEQUENCE: 546
000

SEQ ID NO: 547         moltype =    length =
SEQUENCE: 547
000

SEQ ID NO: 548         moltype =    length =
SEQUENCE: 548
000

SEQ ID NO: 549         moltype =    length =
SEQUENCE: 549
000

SEQ ID NO: 550         moltype =    length =
SEQUENCE: 550
000

SEQ ID NO: 551         moltype =    length =
SEQUENCE: 551
000

SEQ ID NO: 552         moltype =    length =
SEQUENCE: 552
000

SEQ ID NO: 553         moltype =    length =
SEQUENCE: 553
000

SEQ ID NO: 554         moltype =    length =
SEQUENCE: 554
000

SEQ ID NO: 555         moltype =    length =

| | | |
|---|---|---|
| SEQUENCE: 555 000 | | |
| SEQ ID NO: 556 SEQUENCE: 556 000 | moltype = | length = |
| SEQ ID NO: 557 SEQUENCE: 557 000 | moltype = | length = |
| SEQ ID NO: 558 SEQUENCE: 558 000 | moltype = | length = |
| SEQ ID NO: 559 SEQUENCE: 559 000 | moltype = | length = |
| SEQ ID NO: 560 SEQUENCE: 560 000 | moltype = | length = |
| SEQ ID NO: 561 SEQUENCE: 561 000 | moltype = | length = |
| SEQ ID NO: 562 SEQUENCE: 562 000 | moltype = | length = |
| SEQ ID NO: 563 SEQUENCE: 563 000 | moltype = | length = |
| SEQ ID NO: 564 SEQUENCE: 564 000 | moltype = | length = |
| SEQ ID NO: 565 SEQUENCE: 565 000 | moltype = | length = |
| SEQ ID NO: 566 SEQUENCE: 566 000 | moltype = | length = |
| SEQ ID NO: 567 SEQUENCE: 567 000 | moltype = | length = |
| SEQ ID NO: 568 SEQUENCE: 568 000 | moltype = | length = |
| SEQ ID NO: 569 SEQUENCE: 569 000 | moltype = | length = |
| SEQ ID NO: 570 SEQUENCE: 570 000 | moltype = | length = |
| SEQ ID NO: 571 SEQUENCE: 571 000 | moltype = | length = |
| SEQ ID NO: 572 SEQUENCE: 572 000 | moltype = | length = |
| SEQ ID NO: 573 SEQUENCE: 573 000 | moltype = | length = |
| SEQ ID NO: 574 SEQUENCE: 574 000 | moltype = | length = |

-continued

| | | |
|---|---|---|
| SEQ ID NO: 575
SEQUENCE: 575
000 | moltype = | length = |
| SEQ ID NO: 576
SEQUENCE: 576
000 | moltype = | length = |
| SEQ ID NO: 577
SEQUENCE: 577
000 | moltype = | length = |
| SEQ ID NO: 578
SEQUENCE: 578
000 | moltype = | length = |
| SEQ ID NO: 579
SEQUENCE: 579
000 | moltype = | length = |
| SEQ ID NO: 580
SEQUENCE: 580
000 | moltype = | length = |
| SEQ ID NO: 581
SEQUENCE: 581
000 | moltype = | length = |
| SEQ ID NO: 582
SEQUENCE: 582
000 | moltype = | length = |
| SEQ ID NO: 583
SEQUENCE: 583
000 | moltype = | length = |
| SEQ ID NO: 584
SEQUENCE: 584
000 | moltype = | length = |
| SEQ ID NO: 585
SEQUENCE: 585
000 | moltype = | length = |
| SEQ ID NO: 586
SEQUENCE: 586
000 | moltype = | length = |
| SEQ ID NO: 587
SEQUENCE: 587
000 | moltype = | length = |
| SEQ ID NO: 588
SEQUENCE: 588
000 | moltype = | length = |
| SEQ ID NO: 589
SEQUENCE: 589
000 | moltype = | length = |
| SEQ ID NO: 590
SEQUENCE: 590
000 | moltype = | length = |
| SEQ ID NO: 591
SEQUENCE: 591
000 | moltype = | length = |
| SEQ ID NO: 592
SEQUENCE: 592
000 | moltype = | length = |
| SEQ ID NO: 593
SEQUENCE: 593
000 | moltype = | length = |
| SEQ ID NO: 594
SEQUENCE: 594
000 | moltype = | length = |

| SEQ ID NO: 595 | moltype = | length = |
| --- | --- | --- |
| SEQUENCE: 595 | | |
| 000 | | |

| SEQ ID NO: 596 | moltype = | length = |
| --- | --- | --- |
| SEQUENCE: 596 | | |
| 000 | | |

| SEQ ID NO: 597 | moltype = | length = |
| --- | --- | --- |
| SEQUENCE: 597 | | |
| 000 | | |

| SEQ ID NO: 598 | moltype = | length = |
| --- | --- | --- |
| SEQUENCE: 598 | | |
| 000 | | |

| SEQ ID NO: 599 | moltype = | length = |
| --- | --- | --- |
| SEQUENCE: 599 | | |
| 000 | | |

| SEQ ID NO: 600 | moltype = | length = |
| --- | --- | --- |
| SEQUENCE: 600 | | |
| 000 | | |

| SEQ ID NO: 601 | moltype = | length = |
| --- | --- | --- |
| SEQUENCE: 601 | | |
| 000 | | |

| SEQ ID NO: 602 | moltype = | length = |
| --- | --- | --- |
| SEQUENCE: 602 | | |
| 000 | | |

| SEQ ID NO: 603 | moltype = | length = |
| --- | --- | --- |
| SEQUENCE: 603 | | |
| 000 | | |

| SEQ ID NO: 604 | moltype = | length = |
| --- | --- | --- |
| SEQUENCE: 604 | | |
| 000 | | |

| SEQ ID NO: 605 | moltype = | length = |
| --- | --- | --- |
| SEQUENCE: 605 | | |
| 000 | | |

| SEQ ID NO: 606 | moltype = | length = |
| --- | --- | --- |
| SEQUENCE: 606 | | |
| 000 | | |

| SEQ ID NO: 607 | moltype = | length = |
| --- | --- | --- |
| SEQUENCE: 607 | | |
| 000 | | |

| SEQ ID NO: 608 | moltype = | length = |
| --- | --- | --- |
| SEQUENCE: 608 | | |
| 000 | | |

| SEQ ID NO: 609 | moltype = | length = |
| --- | --- | --- |
| SEQUENCE: 609 | | |
| 000 | | |

| SEQ ID NO: 610 | moltype = | length = |
| --- | --- | --- |
| SEQUENCE: 610 | | |
| 000 | | |

| SEQ ID NO: 611 | moltype = | length = |
| --- | --- | --- |
| SEQUENCE: 611 | | |
| 000 | | |

| SEQ ID NO: 612 | moltype = | length = |
| --- | --- | --- |
| SEQUENCE: 612 | | |
| 000 | | |

| SEQ ID NO: 613 | moltype = | length = |
| --- | --- | --- |
| SEQUENCE: 613 | | |
| 000 | | |

| SEQ ID NO: 614 | moltype = | length = |
| --- | --- | --- |
| SEQUENCE: 614 | | |

000

SEQ ID NO: 615        moltype =    length =
SEQUENCE: 615
000

SEQ ID NO: 616        moltype =    length =
SEQUENCE: 616
000

SEQ ID NO: 617        moltype =    length =
SEQUENCE: 617
000

SEQ ID NO: 618        moltype =    length =
SEQUENCE: 618
000

SEQ ID NO: 619        moltype =    length =
SEQUENCE: 619
000

SEQ ID NO: 620        moltype =    length =
SEQUENCE: 620
000

SEQ ID NO: 621        moltype =    length =
SEQUENCE: 621
000

SEQ ID NO: 622        moltype =    length =
SEQUENCE: 622
000

SEQ ID NO: 623        moltype =    length =
SEQUENCE: 623
000

SEQ ID NO: 624        moltype =    length =
SEQUENCE: 624
000

SEQ ID NO: 625        moltype =    length =
SEQUENCE: 625
000

SEQ ID NO: 626        moltype =    length =
SEQUENCE: 626
000

SEQ ID NO: 627        moltype =    length =
SEQUENCE: 627
000

SEQ ID NO: 628        moltype =    length =
SEQUENCE: 628
000

SEQ ID NO: 629        moltype =    length =
SEQUENCE: 629
000

SEQ ID NO: 630        moltype =    length =
SEQUENCE: 630
000

SEQ ID NO: 631        moltype =    length =
SEQUENCE: 631
000

SEQ ID NO: 632        moltype =    length =
SEQUENCE: 632
000

SEQ ID NO: 633        moltype =    length =
SEQUENCE: 633
000

SEQ ID NO: 634        moltype =    length =

| | | |
|---|---|---|
| SEQUENCE: 634 000 | | |
| SEQ ID NO: 635 SEQUENCE: 635 000 | moltype = | length = |
| SEQ ID NO: 636 SEQUENCE: 636 000 | moltype = | length = |
| SEQ ID NO: 637 SEQUENCE: 637 000 | moltype = | length = |
| SEQ ID NO: 638 SEQUENCE: 638 000 | moltype = | length = |
| SEQ ID NO: 639 SEQUENCE: 639 000 | moltype = | length = |
| SEQ ID NO: 640 SEQUENCE: 640 000 | moltype = | length = |
| SEQ ID NO: 641 SEQUENCE: 641 000 | moltype = | length = |
| SEQ ID NO: 642 SEQUENCE: 642 000 | moltype = | length = |
| SEQ ID NO: 643 SEQUENCE: 643 000 | moltype = | length = |
| SEQ ID NO: 644 SEQUENCE: 644 000 | moltype = | length = |
| SEQ ID NO: 645 SEQUENCE: 645 000 | moltype = | length = |
| SEQ ID NO: 646 SEQUENCE: 646 000 | moltype = | length = |
| SEQ ID NO: 647 SEQUENCE: 647 000 | moltype = | length = |
| SEQ ID NO: 648 SEQUENCE: 648 000 | moltype = | length = |
| SEQ ID NO: 649 SEQUENCE: 649 000 | moltype = | length = |
| SEQ ID NO: 650 SEQUENCE: 650 000 | moltype = | length = |
| SEQ ID NO: 651 SEQUENCE: 651 000 | moltype = | length = |
| SEQ ID NO: 652 SEQUENCE: 652 000 | moltype = | length = |
| SEQ ID NO: 653 SEQUENCE: 653 000 | moltype = | length = |

| | | |
|---|---|---|
| SEQ ID NO: 654<br>SEQUENCE: 654<br>000 | moltype = | length = |
| SEQ ID NO: 655<br>SEQUENCE: 655<br>000 | moltype = | length = |
| SEQ ID NO: 656<br>SEQUENCE: 656<br>000 | moltype = | length = |
| SEQ ID NO: 657<br>SEQUENCE: 657<br>000 | moltype = | length = |
| SEQ ID NO: 658<br>SEQUENCE: 658<br>000 | moltype = | length = |
| SEQ ID NO: 659<br>SEQUENCE: 659<br>000 | moltype = | length = |
| SEQ ID NO: 660<br>SEQUENCE: 660<br>000 | moltype = | length = |
| SEQ ID NO: 661<br>SEQUENCE: 661<br>000 | moltype = | length = |
| SEQ ID NO: 662<br>SEQUENCE: 662<br>000 | moltype = | length = |
| SEQ ID NO: 663<br>SEQUENCE: 663<br>000 | moltype = | length = |
| SEQ ID NO: 664<br>SEQUENCE: 664<br>000 | moltype = | length = |
| SEQ ID NO: 665<br>SEQUENCE: 665<br>000 | moltype = | length = |
| SEQ ID NO: 666<br>SEQUENCE: 666<br>000 | moltype = | length = |
| SEQ ID NO: 667<br>SEQUENCE: 667<br>000 | moltype = | length = |
| SEQ ID NO: 668<br>SEQUENCE: 668<br>000 | moltype = | length = |
| SEQ ID NO: 669<br>SEQUENCE: 669<br>000 | moltype = | length = |
| SEQ ID NO: 670<br>SEQUENCE: 670<br>000 | moltype = | length = |
| SEQ ID NO: 671<br>SEQUENCE: 671<br>000 | moltype = | length = |
| SEQ ID NO: 672<br>SEQUENCE: 672<br>000 | moltype = | length = |
| SEQ ID NO: 673<br>SEQUENCE: 673<br>000 | moltype = | length = |

| | | |
|---|---|---|
| SEQ ID NO: 674<br>SEQUENCE: 674<br>000 | moltype = | length = |
| SEQ ID NO: 675<br>SEQUENCE: 675<br>000 | moltype = | length = |
| SEQ ID NO: 676<br>SEQUENCE: 676<br>000 | moltype = | length = |
| SEQ ID NO: 677<br>SEQUENCE: 677<br>000 | moltype = | length = |
| SEQ ID NO: 678<br>SEQUENCE: 678<br>000 | moltype = | length = |
| SEQ ID NO: 679<br>SEQUENCE: 679<br>000 | moltype = | length = |
| SEQ ID NO: 680<br>SEQUENCE: 680<br>000 | moltype = | length = |
| SEQ ID NO: 681<br>SEQUENCE: 681<br>000 | moltype = | length = |
| SEQ ID NO: 682<br>SEQUENCE: 682<br>000 | moltype = | length = |
| SEQ ID NO: 683<br>SEQUENCE: 683<br>000 | moltype = | length = |
| SEQ ID NO: 684<br>SEQUENCE: 684<br>000 | moltype = | length = |
| SEQ ID NO: 685<br>SEQUENCE: 685<br>000 | moltype = | length = |
| SEQ ID NO: 686<br>SEQUENCE: 686<br>000 | moltype = | length = |
| SEQ ID NO: 687<br>SEQUENCE: 687<br>000 | moltype = | length = |
| SEQ ID NO: 688<br>SEQUENCE: 688<br>000 | moltype = | length = |
| SEQ ID NO: 689<br>SEQUENCE: 689<br>000 | moltype = | length = |
| SEQ ID NO: 690<br>SEQUENCE: 690<br>000 | moltype = | length = |
| SEQ ID NO: 691<br>SEQUENCE: 691<br>000 | moltype = | length = |
| SEQ ID NO: 692<br>SEQUENCE: 692<br>000 | moltype = | length = |
| SEQ ID NO: 693<br>SEQUENCE: 693 | moltype = | length = |

-continued

000

SEQ ID NO: 694        moltype =    length =
SEQUENCE: 694
000

SEQ ID NO: 695        moltype =    length =
SEQUENCE: 695
000

SEQ ID NO: 696        moltype =    length =
SEQUENCE: 696
000

SEQ ID NO: 697        moltype =    length =
SEQUENCE: 697
000

SEQ ID NO: 698        moltype =    length =
SEQUENCE: 698
000

SEQ ID NO: 699        moltype =    length =
SEQUENCE: 699
000

SEQ ID NO: 700        moltype =    length =
SEQUENCE: 700
000

SEQ ID NO: 701        moltype =    length =
SEQUENCE: 701
000

SEQ ID NO: 702        moltype =    length =
SEQUENCE: 702
000

SEQ ID NO: 703        moltype =    length =
SEQUENCE: 703
000

SEQ ID NO: 704        moltype =    length =
SEQUENCE: 704
000

SEQ ID NO: 705        moltype =    length =
SEQUENCE: 705
000

SEQ ID NO: 706        moltype =    length =
SEQUENCE: 706
000

SEQ ID NO: 707        moltype =    length =
SEQUENCE: 707
000

SEQ ID NO: 708        moltype =    length =
SEQUENCE: 708
000

SEQ ID NO: 709        moltype =    length =
SEQUENCE: 709
000

SEQ ID NO: 710        moltype =    length =
SEQUENCE: 710
000

SEQ ID NO: 711        moltype =    length =
SEQUENCE: 711
000

SEQ ID NO: 712        moltype =    length =
SEQUENCE: 712
000

SEQ ID NO: 713        moltype =    length =

-continued

| | | |
|---|---|---|
| SEQUENCE: 713 000 | | |
| SEQ ID NO: 714 SEQUENCE: 714 000 | moltype = | length = |
| SEQ ID NO: 715 SEQUENCE: 715 000 | moltype = | length = |
| SEQ ID NO: 716 SEQUENCE: 716 000 | moltype = | length = |
| SEQ ID NO: 717 SEQUENCE: 717 000 | moltype = | length = |
| SEQ ID NO: 718 SEQUENCE: 718 000 | moltype = | length = |
| SEQ ID NO: 719 SEQUENCE: 719 000 | moltype = | length = |
| SEQ ID NO: 720 SEQUENCE: 720 000 | moltype = | length = |
| SEQ ID NO: 721 SEQUENCE: 721 000 | moltype = | length = |
| SEQ ID NO: 722 SEQUENCE: 722 000 | moltype = | length = |
| SEQ ID NO: 723 SEQUENCE: 723 000 | moltype = | length = |
| SEQ ID NO: 724 SEQUENCE: 724 000 | moltype = | length = |
| SEQ ID NO: 725 SEQUENCE: 725 000 | moltype = | length = |
| SEQ ID NO: 726 SEQUENCE: 726 000 | moltype = | length = |
| SEQ ID NO: 727 SEQUENCE: 727 000 | moltype = | length = |
| SEQ ID NO: 728 SEQUENCE: 728 000 | moltype = | length = |
| SEQ ID NO: 729 SEQUENCE: 729 000 | moltype = | length = |
| SEQ ID NO: 730 SEQUENCE: 730 000 | moltype = | length = |
| SEQ ID NO: 731 SEQUENCE: 731 000 | moltype = | length = |
| SEQ ID NO: 732 SEQUENCE: 732 000 | moltype = | length = |

-continued

SEQ ID NO: 733    moltype =    length =
SEQUENCE: 733
000

SEQ ID NO: 734    moltype =    length =
SEQUENCE: 734
000

SEQ ID NO: 735    moltype =    length =
SEQUENCE: 735
000

SEQ ID NO: 736    moltype =    length =
SEQUENCE: 736
000

SEQ ID NO: 737    moltype =    length =
SEQUENCE: 737
000

SEQ ID NO: 738    moltype =    length =
SEQUENCE: 738
000

SEQ ID NO: 739    moltype =    length =
SEQUENCE: 739
000

SEQ ID NO: 740    moltype =    length =
SEQUENCE: 740
000

SEQ ID NO: 741    moltype =    length =
SEQUENCE: 741
000

SEQ ID NO: 742    moltype =    length =
SEQUENCE: 742
000

SEQ ID NO: 743    moltype =    length =
SEQUENCE: 743
000

SEQ ID NO: 744    moltype =    length =
SEQUENCE: 744
000

SEQ ID NO: 745    moltype =    length =
SEQUENCE: 745
000

SEQ ID NO: 746    moltype =    length =
SEQUENCE: 746
000

SEQ ID NO: 747    moltype =    length =
SEQUENCE: 747
000

SEQ ID NO: 748    moltype =    length =
SEQUENCE: 748
000

SEQ ID NO: 749    moltype =    length =
SEQUENCE: 749
000

SEQ ID NO: 750    moltype =    length =
SEQUENCE: 750
000

SEQ ID NO: 751    moltype =    length =
SEQUENCE: 751
000

SEQ ID NO: 752    moltype =    length =
SEQUENCE: 752
000

```
SEQ ID NO: 753        moltype =   length =
SEQUENCE: 753
000

SEQ ID NO: 754        moltype =   length =
SEQUENCE: 754
000

SEQ ID NO: 755        moltype =   length =
SEQUENCE: 755
000

SEQ ID NO: 756        moltype =   length =
SEQUENCE: 756
000

SEQ ID NO: 757        moltype =   length =
SEQUENCE: 757
000

SEQ ID NO: 758        moltype =   length =
SEQUENCE: 758
000

SEQ ID NO: 759        moltype =   length =
SEQUENCE: 759
000

SEQ ID NO: 760        moltype =   length =
SEQUENCE: 760
000

SEQ ID NO: 761        moltype =   length =
SEQUENCE: 761
000

SEQ ID NO: 762        moltype =   length =
SEQUENCE: 762
000

SEQ ID NO: 763        moltype =   length =
SEQUENCE: 763
000

SEQ ID NO: 764        moltype =   length =
SEQUENCE: 764
000

SEQ ID NO: 765        moltype =   length =
SEQUENCE: 765
000

SEQ ID NO: 766        moltype =   length =
SEQUENCE: 766
000

SEQ ID NO: 767        moltype =   length =
SEQUENCE: 767
000

SEQ ID NO: 768        moltype =   length =
SEQUENCE: 768
000

SEQ ID NO: 769        moltype =   length =
SEQUENCE: 769
000

SEQ ID NO: 770        moltype =   length =
SEQUENCE: 770
000

SEQ ID NO: 771        moltype =   length =
SEQUENCE: 771
000

SEQ ID NO: 772        moltype =   length =
SEQUENCE: 772
```

000

SEQ ID NO: 773        moltype =     length =
SEQUENCE: 773
000

SEQ ID NO: 774        moltype =     length =
SEQUENCE: 774
000

SEQ ID NO: 775        moltype =     length =
SEQUENCE: 775
000

SEQ ID NO: 776        moltype =     length =
SEQUENCE: 776
000

SEQ ID NO: 777        moltype =     length =
SEQUENCE: 777
000

SEQ ID NO: 778        moltype =     length =
SEQUENCE: 778
000

SEQ ID NO: 779        moltype =     length =
SEQUENCE: 779
000

SEQ ID NO: 780        moltype =     length =
SEQUENCE: 780
000

SEQ ID NO: 781        moltype =     length =
SEQUENCE: 781
000

SEQ ID NO: 782        moltype =     length =
SEQUENCE: 782
000

SEQ ID NO: 783        moltype =     length =
SEQUENCE: 783
000

SEQ ID NO: 784        moltype =     length =
SEQUENCE: 784
000

SEQ ID NO: 785        moltype =     length =
SEQUENCE: 785
000

SEQ ID NO: 786        moltype =     length =
SEQUENCE: 786
000

SEQ ID NO: 787        moltype =     length =
SEQUENCE: 787
000

SEQ ID NO: 788        moltype =     length =
SEQUENCE: 788
000

SEQ ID NO: 789        moltype =     length =
SEQUENCE: 789
000

SEQ ID NO: 790        moltype =     length =
SEQUENCE: 790
000

SEQ ID NO: 791        moltype =     length =
SEQUENCE: 791
000

SEQ ID NO: 792        moltype =     length =

```
SEQUENCE: 792
000

SEQ ID NO: 793          moltype =     length =
SEQUENCE: 793
000

SEQ ID NO: 794          moltype =     length =
SEQUENCE: 794
000

SEQ ID NO: 795          moltype =     length =
SEQUENCE: 795
000

SEQ ID NO: 796          moltype =     length =
SEQUENCE: 796
000

SEQ ID NO: 797          moltype =     length =
SEQUENCE: 797
000

SEQ ID NO: 798          moltype =     length =
SEQUENCE: 798
000

SEQ ID NO: 799          moltype =     length =
SEQUENCE: 799
000

SEQ ID NO: 800          moltype =     length =
SEQUENCE: 800
000

SEQ ID NO: 801          moltype =     length =
SEQUENCE: 801
000

SEQ ID NO: 802          moltype =     length =
SEQUENCE: 802
000

SEQ ID NO: 803          moltype =     length =
SEQUENCE: 803
000

SEQ ID NO: 804          moltype =     length =
SEQUENCE: 804
000

SEQ ID NO: 805          moltype =     length =
SEQUENCE: 805
000

SEQ ID NO: 806          moltype =     length =
SEQUENCE: 806
000

SEQ ID NO: 807          moltype =     length =
SEQUENCE: 807
000

SEQ ID NO: 808          moltype =     length =
SEQUENCE: 808
000

SEQ ID NO: 809          moltype =     length =
SEQUENCE: 809
000

SEQ ID NO: 810          moltype =     length =
SEQUENCE: 810
000

SEQ ID NO: 811          moltype =     length =
SEQUENCE: 811
000
```

| | | |
|---|---|---|
| SEQ ID NO: 812 SEQUENCE: 812 | moltype = 000 | length = |
| SEQ ID NO: 813 SEQUENCE: 813 | moltype = 000 | length = |
| SEQ ID NO: 814 SEQUENCE: 814 | moltype = 000 | length = |
| SEQ ID NO: 815 SEQUENCE: 815 | moltype = 000 | length = |
| SEQ ID NO: 816 SEQUENCE: 816 | moltype = 000 | length = |
| SEQ ID NO: 817 SEQUENCE: 817 | moltype = 000 | length = |
| SEQ ID NO: 818 SEQUENCE: 818 | moltype = 000 | length = |
| SEQ ID NO: 819 SEQUENCE: 819 | moltype = 000 | length = |
| SEQ ID NO: 820 SEQUENCE: 820 | moltype = 000 | length = |
| SEQ ID NO: 821 SEQUENCE: 821 | moltype = 000 | length = |
| SEQ ID NO: 822 SEQUENCE: 822 | moltype = 000 | length = |
| SEQ ID NO: 823 SEQUENCE: 823 | moltype = 000 | length = |
| SEQ ID NO: 824 SEQUENCE: 824 | moltype = 000 | length = |
| SEQ ID NO: 825 SEQUENCE: 825 | moltype = 000 | length = |
| SEQ ID NO: 826 SEQUENCE: 826 | moltype = 000 | length = |
| SEQ ID NO: 827 SEQUENCE: 827 | moltype = 000 | length = |
| SEQ ID NO: 828 SEQUENCE: 828 | moltype = 000 | length = |
| SEQ ID NO: 829 SEQUENCE: 829 | moltype = 000 | length = |
| SEQ ID NO: 830 SEQUENCE: 830 | moltype = 000 | length = |
| SEQ ID NO: 831 SEQUENCE: 831 | moltype = 000 | length = |

| | | |
|---|---|---|
| SEQ ID NO: 832 SEQUENCE: 832 000 | moltype = | length = |
| SEQ ID NO: 833 SEQUENCE: 833 000 | moltype = | length = |
| SEQ ID NO: 834 SEQUENCE: 834 000 | moltype = | length = |
| SEQ ID NO: 835 SEQUENCE: 835 000 | moltype = | length = |
| SEQ ID NO: 836 SEQUENCE: 836 000 | moltype = | length = |
| SEQ ID NO: 837 SEQUENCE: 837 000 | moltype = | length = |
| SEQ ID NO: 838 SEQUENCE: 838 000 | moltype = | length = |
| SEQ ID NO: 839 SEQUENCE: 839 000 | moltype = | length = |
| SEQ ID NO: 840 SEQUENCE: 840 000 | moltype = | length = |
| SEQ ID NO: 841 SEQUENCE: 841 000 | moltype = | length = |
| SEQ ID NO: 842 SEQUENCE: 842 000 | moltype = | length = |
| SEQ ID NO: 843 SEQUENCE: 843 000 | moltype = | length = |
| SEQ ID NO: 844 SEQUENCE: 844 000 | moltype = | length = |
| SEQ ID NO: 845 SEQUENCE: 845 000 | moltype = | length = |
| SEQ ID NO: 846 SEQUENCE: 846 000 | moltype = | length = |
| SEQ ID NO: 847 SEQUENCE: 847 000 | moltype = | length = |
| SEQ ID NO: 848 SEQUENCE: 848 000 | moltype = | length = |
| SEQ ID NO: 849 SEQUENCE: 849 000 | moltype = | length = |
| SEQ ID NO: 850 SEQUENCE: 850 000 | moltype = | length = |
| SEQ ID NO: 851 SEQUENCE: 851 | moltype = | length = |

000

SEQ ID NO: 852          moltype =     length =
SEQUENCE: 852
000

SEQ ID NO: 853          moltype =     length =
SEQUENCE: 853
000

SEQ ID NO: 854          moltype =     length =
SEQUENCE: 854
000

SEQ ID NO: 855          moltype =     length =
SEQUENCE: 855
000

SEQ ID NO: 856          moltype =     length =
SEQUENCE: 856
000

SEQ ID NO: 857          moltype =     length =
SEQUENCE: 857
000

SEQ ID NO: 858          moltype =     length =
SEQUENCE: 858
000

SEQ ID NO: 859          moltype =     length =
SEQUENCE: 859
000

SEQ ID NO: 860          moltype =     length =
SEQUENCE: 860
000

SEQ ID NO: 861          moltype =     length =
SEQUENCE: 861
000

SEQ ID NO: 862          moltype =     length =
SEQUENCE: 862
000

SEQ ID NO: 863          moltype =     length =
SEQUENCE: 863
000

SEQ ID NO: 864          moltype =     length =
SEQUENCE: 864
000

SEQ ID NO: 865          moltype =     length =
SEQUENCE: 865
000

SEQ ID NO: 866          moltype =     length =
SEQUENCE: 866
000

SEQ ID NO: 867          moltype =     length =
SEQUENCE: 867
000

SEQ ID NO: 868          moltype =     length =
SEQUENCE: 868
000

SEQ ID NO: 869          moltype =     length =
SEQUENCE: 869
000

SEQ ID NO: 870          moltype =     length =
SEQUENCE: 870
000

SEQ ID NO: 871          moltype =     length =

| | | |
|---|---|---|
| SEQUENCE: 871 000 | | |
| SEQ ID NO: 872 SEQUENCE: 872 000 | moltype = | length = |
| SEQ ID NO: 873 SEQUENCE: 873 000 | moltype = | length = |
| SEQ ID NO: 874 SEQUENCE: 874 000 | moltype = | length = |
| SEQ ID NO: 875 SEQUENCE: 875 000 | moltype = | length = |
| SEQ ID NO: 876 SEQUENCE: 876 000 | moltype = | length = |
| SEQ ID NO: 877 SEQUENCE: 877 000 | moltype = | length = |
| SEQ ID NO: 878 SEQUENCE: 878 000 | moltype = | length = |
| SEQ ID NO: 879 SEQUENCE: 879 000 | moltype = | length = |
| SEQ ID NO: 880 SEQUENCE: 880 000 | moltype = | length = |
| SEQ ID NO: 881 SEQUENCE: 881 000 | moltype = | length = |
| SEQ ID NO: 882 SEQUENCE: 882 000 | moltype = | length = |
| SEQ ID NO: 883 SEQUENCE: 883 000 | moltype = | length = |
| SEQ ID NO: 884 SEQUENCE: 884 000 | moltype = | length = |
| SEQ ID NO: 885 SEQUENCE: 885 000 | moltype = | length = |
| SEQ ID NO: 886 SEQUENCE: 886 000 | moltype = | length = |
| SEQ ID NO: 887 SEQUENCE: 887 000 | moltype = | length = |
| SEQ ID NO: 888 SEQUENCE: 888 000 | moltype = | length = |
| SEQ ID NO: 889 SEQUENCE: 889 000 | moltype = | length = |
| SEQ ID NO: 890 SEQUENCE: 890 000 | moltype = | length = |

-continued

| | | |
|---|---|---|
| SEQ ID NO: 891 SEQUENCE: 891 | moltype = | length = 000 |
| SEQ ID NO: 892 SEQUENCE: 892 | moltype = | length = 000 |
| SEQ ID NO: 893 SEQUENCE: 893 | moltype = | length = 000 |
| SEQ ID NO: 894 SEQUENCE: 894 | moltype = | length = 000 |
| SEQ ID NO: 895 SEQUENCE: 895 | moltype = | length = 000 |
| SEQ ID NO: 896 SEQUENCE: 896 | moltype = | length = 000 |
| SEQ ID NO: 897 SEQUENCE: 897 | moltype = | length = 000 |
| SEQ ID NO: 898 SEQUENCE: 898 | moltype = | length = 000 |
| SEQ ID NO: 899 SEQUENCE: 899 | moltype = | length = 000 |
| SEQ ID NO: 900 SEQUENCE: 900 | moltype = | length = 000 |
| SEQ ID NO: 901 SEQUENCE: 901 | moltype = | length = 000 |
| SEQ ID NO: 902 SEQUENCE: 902 | moltype = | length = 000 |
| SEQ ID NO: 903 SEQUENCE: 903 | moltype = | length = 000 |
| SEQ ID NO: 904 SEQUENCE: 904 | moltype = | length = 000 |
| SEQ ID NO: 905 SEQUENCE: 905 | moltype = | length = 000 |
| SEQ ID NO: 906 SEQUENCE: 906 | moltype = | length = 000 |
| SEQ ID NO: 907 SEQUENCE: 907 | moltype = | length = 000 |
| SEQ ID NO: 908 SEQUENCE: 908 | moltype = | length = 000 |
| SEQ ID NO: 909 SEQUENCE: 909 | moltype = | length = 000 |
| SEQ ID NO: 910 SEQUENCE: 910 | moltype = | length = 000 |

| | | |
|---|---|---|
| SEQ ID NO: 911<br>SEQUENCE: 911<br>000 | moltype = | length = |
| SEQ ID NO: 912<br>SEQUENCE: 912<br>000 | moltype = | length = |
| SEQ ID NO: 913<br>SEQUENCE: 913<br>000 | moltype = | length = |
| SEQ ID NO: 914<br>SEQUENCE: 914<br>000 | moltype = | length = |
| SEQ ID NO: 915<br>SEQUENCE: 915<br>000 | moltype = | length = |
| SEQ ID NO: 916<br>SEQUENCE: 916<br>000 | moltype = | length = |
| SEQ ID NO: 917<br>SEQUENCE: 917<br>000 | moltype = | length = |
| SEQ ID NO: 918<br>SEQUENCE: 918<br>000 | moltype = | length = |
| SEQ ID NO: 919<br>SEQUENCE: 919<br>000 | moltype = | length = |
| SEQ ID NO: 920<br>SEQUENCE: 920<br>000 | moltype = | length = |
| SEQ ID NO: 921<br>SEQUENCE: 921<br>000 | moltype = | length = |
| SEQ ID NO: 922<br>SEQUENCE: 922<br>000 | moltype = | length = |
| SEQ ID NO: 923<br>SEQUENCE: 923<br>000 | moltype = | length = |
| SEQ ID NO: 924<br>SEQUENCE: 924<br>000 | moltype = | length = |
| SEQ ID NO: 925<br>SEQUENCE: 925<br>000 | moltype = | length = |
| SEQ ID NO: 926<br>SEQUENCE: 926<br>000 | moltype = | length = |
| SEQ ID NO: 927<br>SEQUENCE: 927<br>000 | moltype = | length = |
| SEQ ID NO: 928<br>SEQUENCE: 928<br>000 | moltype = | length = |
| SEQ ID NO: 929<br>SEQUENCE: 929<br>000 | moltype = | length = |
| SEQ ID NO: 930<br>SEQUENCE: 930 | moltype = | length = |

000

SEQ ID NO: 931  moltype =  length =
SEQUENCE: 931
000

SEQ ID NO: 932  moltype =  length =
SEQUENCE: 932
000

SEQ ID NO: 933  moltype =  length =
SEQUENCE: 933
000

SEQ ID NO: 934  moltype =  length =
SEQUENCE: 934
000

SEQ ID NO: 935  moltype =  length =
SEQUENCE: 935
000

SEQ ID NO: 936  moltype =  length =
SEQUENCE: 936
000

SEQ ID NO: 937  moltype =  length =
SEQUENCE: 937
000

SEQ ID NO: 938  moltype =  length =
SEQUENCE: 938
000

SEQ ID NO: 939  moltype =  length =
SEQUENCE: 939
000

SEQ ID NO: 940  moltype =  length =
SEQUENCE: 940
000

SEQ ID NO: 941  moltype =  length =
SEQUENCE: 941
000

SEQ ID NO: 942  moltype =  length =
SEQUENCE: 942
000

SEQ ID NO: 943  moltype =  length =
SEQUENCE: 943
000

SEQ ID NO: 944  moltype =  length =
SEQUENCE: 944
000

SEQ ID NO: 945  moltype =  length =
SEQUENCE: 945
000

SEQ ID NO: 946  moltype =  length =
SEQUENCE: 946
000

SEQ ID NO: 947  moltype =  length =
SEQUENCE: 947
000

SEQ ID NO: 948  moltype =  length =
SEQUENCE: 948
000

SEQ ID NO: 949  moltype =  length =
SEQUENCE: 949
000

SEQ ID NO: 950  moltype =  length =

```
SEQUENCE: 950
000

SEQ ID NO: 951        moltype =   length =
SEQUENCE: 951
000

SEQ ID NO: 952        moltype =   length =
SEQUENCE: 952
000

SEQ ID NO: 953        moltype =   length =
SEQUENCE: 953
000

SEQ ID NO: 954        moltype =   length =
SEQUENCE: 954
000

SEQ ID NO: 955        moltype =   length =
SEQUENCE: 955
000

SEQ ID NO: 956        moltype =   length =
SEQUENCE: 956
000

SEQ ID NO: 957        moltype =   length =
SEQUENCE: 957
000

SEQ ID NO: 958        moltype =   length =
SEQUENCE: 958
000

SEQ ID NO: 959        moltype =   length =
SEQUENCE: 959
000

SEQ ID NO: 960        moltype =   length =
SEQUENCE: 960
000

SEQ ID NO: 961        moltype =   length =
SEQUENCE: 961
000

SEQ ID NO: 962        moltype =   length =
SEQUENCE: 962
000

SEQ ID NO: 963        moltype =   length =
SEQUENCE: 963
000

SEQ ID NO: 964        moltype =   length =
SEQUENCE: 964
000

SEQ ID NO: 965        moltype =   length =
SEQUENCE: 965
000

SEQ ID NO: 966        moltype =   length =
SEQUENCE: 966
000

SEQ ID NO: 967        moltype =   length =
SEQUENCE: 967
000

SEQ ID NO: 968        moltype =   length =
SEQUENCE: 968
000

SEQ ID NO: 969        moltype =   length =
SEQUENCE: 969
000
```

| | | |
|---|---|---|
| SEQ ID NO: 970<br>SEQUENCE: 970<br>000 | moltype = | length = |
| SEQ ID NO: 971<br>SEQUENCE: 971<br>000 | moltype = | length = |
| SEQ ID NO: 972<br>SEQUENCE: 972<br>000 | moltype = | length = |
| SEQ ID NO: 973<br>SEQUENCE: 973<br>000 | moltype = | length = |
| SEQ ID NO: 974<br>SEQUENCE: 974<br>000 | moltype = | length = |
| SEQ ID NO: 975<br>SEQUENCE: 975<br>000 | moltype = | length = |
| SEQ ID NO: 976<br>SEQUENCE: 976<br>000 | moltype = | length = |
| SEQ ID NO: 977<br>SEQUENCE: 977<br>000 | moltype = | length = |
| SEQ ID NO: 978<br>SEQUENCE: 978<br>000 | moltype = | length = |
| SEQ ID NO: 979<br>SEQUENCE: 979<br>000 | moltype = | length = |
| SEQ ID NO: 980<br>SEQUENCE: 980<br>000 | moltype = | length = |
| SEQ ID NO: 981<br>SEQUENCE: 981<br>000 | moltype = | length = |
| SEQ ID NO: 982<br>SEQUENCE: 982<br>000 | moltype = | length = |
| SEQ ID NO: 983<br>SEQUENCE: 983<br>000 | moltype = | length = |
| SEQ ID NO: 984<br>SEQUENCE: 984<br>000 | moltype = | length = |
| SEQ ID NO: 985<br>SEQUENCE: 985<br>000 | moltype = | length = |
| SEQ ID NO: 986<br>SEQUENCE: 986<br>000 | moltype = | length = |
| SEQ ID NO: 987<br>SEQUENCE: 987<br>000 | moltype = | length = |
| SEQ ID NO: 988<br>SEQUENCE: 988<br>000 | moltype = | length = |
| SEQ ID NO: 989<br>SEQUENCE: 989<br>000 | moltype = | length = |

-continued

```
SEQ ID NO: 990          moltype =    length =
SEQUENCE: 990
000

SEQ ID NO: 991          moltype =    length =
SEQUENCE: 991
000

SEQ ID NO: 992          moltype =    length =
SEQUENCE: 992
000

SEQ ID NO: 993          moltype =    length =
SEQUENCE: 993
000

SEQ ID NO: 994          moltype =    length =
SEQUENCE: 994
000

SEQ ID NO: 995          moltype =    length =
SEQUENCE: 995
000

SEQ ID NO: 996          moltype =    length =
SEQUENCE: 996
000

SEQ ID NO: 997          moltype =    length =
SEQUENCE: 997
000

SEQ ID NO: 998          moltype =    length =
SEQUENCE: 998
000

SEQ ID NO: 999          moltype =    length =
SEQUENCE: 999
000

SEQ ID NO: 1000         moltype =    length =
SEQUENCE: 1000
000

SEQ ID NO: 1001         moltype = AA  length = 121
FEATURE                 Location/Qualifiers
REGION                  1..121
                        note = Anti-NME7 B3 peptide monoclonal antibodies - 8F9A4P3
                         Heavy chain variable region sequence mouse
source                  1..121
                        mol_type = protein
                        organism = synthetic construct
SEQUENCE: 1001
VQLQQSGPEL VKPGASVKIS CKTSGNTFTE YTMHWVKQSH GKSLEWIGGF NPNNGVTNYN    60
QKFKGKATLT VDKSSSTAYM ELRSLTSEDS AVYYCARRYY HSLYVFYFDY WGQGTTLTVS   120
S                                                                  121

SEQ ID NO: 1002         moltype = AA  length = 98
FEATURE                 Location/Qualifiers
REGION                  1..98
                        note = IGHV1-24*01 V-REGION sequence human (closest match
                         hu antibody sequence)
source                  1..98
                        mol_type = protein
                        organism = synthetic construct
SEQUENCE: 1002
QVQLVQSGAE VKKPGASVKV SCKVSGYTLT ELSMHWVRQA PGKGLEWMGG FDPEDGETIY    60
AQKFQGRVTM TEDTSTDTAY MELSSLRSED TAVYYCAT                            98

SEQ ID NO: 1003         moltype = AA  length = 15
FEATURE                 Location/Qualifiers
REGION                  1..15
                        note = IGHJ4*01 J-REGION sequence human (closest match hu
                         antibody sequence)
source                  1..15
                        mol_type = protein
                        organism = synthetic construct
SEQUENCE: 1003
```

```
YFDYWGQGTL VTVSS                                                              15

SEQ ID NO: 1004         moltype = AA  length = 122
FEATURE                 Location/Qualifiers
REGION                  1..122
                        note = humanized 8F9A4P3 Heavy chain variable region
                         sequence
source                  1..122
                        mol_type = protein
                        organism = synthetic construct
SEQUENCE: 1004
QVQLVQSGAE VKKPGASVKV SCKVSGNTFT EYTMHWVRQA PGKGLEWMGG FNPNNGVTNY    60
NQKFKGRVTM TEDTSTDTAY MELSSLRSED TAVYYCARRY YHSLYVFYFD YWGQGTLVTV   120
SS                                                                 122

SEQ ID NO: 1005         moltype = AA  length = 122
FEATURE                 Location/Qualifiers
REGION                  1..122
                        note = humanized 8F9A4P3 Heavy chain variable region
                         sequence (codon optimized)
source                  1..122
                        mol_type = protein
                        organism = synthetic construct
SEQUENCE: 1005
QVQLVQSGAE VKKPGASVKV SCKVSGNTFT EYTMHWVRQA PGKGLEWMGG FNPNNGVTNY    60
NQKFKGRVTM TEDTSTDTAY MELSSLRSED TAVYYCARRY YHSLYVFYFD YWGQGTLVTV   120
SS                                                                 122

SEQ ID NO: 1006         moltype = AA  length = 122
FEATURE                 Location/Qualifiers
REGION                  1..122
                        note = Modified humanized 8F9A4P3 Heavy chain variable
                         region sequence
source                  1..122
                        mol_type = protein
                        organism = synthetic construct
SEQUENCE: 1006
QVQLVQSGAE VKKPGASVKV SCKVSGNTFT EYTMHWVRQA PGKGLEWIGG FNPNNGVTNY    60
NQKFKGKVTL TVDTSSSTAY MELSSLRSED TAVYYCARRY YHSLYVFYFD YWGQGTLVTV   120
SS                                                                 122

SEQ ID NO: 1007         moltype = AA  length = 122
FEATURE                 Location/Qualifiers
REGION                  1..122
                        note = Modified humanized 8F9A4P3 Heavy chain variable
                         region sequence (codon optimized)
source                  1..122
                        mol_type = protein
                        organism = synthetic construct
SEQUENCE: 1007
QVQLVQSGAE VKKPGASVKV SCKVSGNTFT EYTMHWVRQA PGKGLEWIGG FNPNNGVTNY    60
NQKFKGKVTL TVDTSSSTAY MELSSLRSED TAVYYCARRY YHSLYVFYFD YWGQGTLVTV   120
SS                                                                 122

SEQ ID NO: 1008         moltype = AA  length = 108
FEATURE                 Location/Qualifiers
REGION                  1..108
                        note = 8F9A4P3 Light chain variable region sequence mouse
source                  1..108
                        mol_type = protein
                        organism = synthetic construct
SEQUENCE: 1008
ETTVTQSPAS LSMAIGEKVT IRCITSTDID DDMNWYQQKP GEPPKLLISE GNTLRPGVPS    60
RFSSSGYGTD FVFTIENMLS EDVADYYCLQ SDNLPLTFGS GTKLEIKR                108

SEQ ID NO: 1009         moltype = AA  length = 88
FEATURE                 Location/Qualifiers
REGION                  1..88
                        note = IGKV5-2*01 V-REGION sequence human (closest match hu
                         antibody sequence)
source                  1..88
                        mol_type = protein
                        organism = synthetic construct
SEQUENCE: 1009
ETTLTQSPAF MSATPGDKVN ISCKASQDID DDMNWYQQKP GEAAIFIIQE ATTLVPGIPP    60
RFSGSGYGTD FTLTINNIES EDAAYYFC                                      88

SEQ ID NO: 1010         moltype = AA  length = 12
FEATURE                 Location/Qualifiers
```

```
REGION                    1..12
                          note = IGKJ4*02 J-REGION sequence human (closest match hu
                           antibody sequence)
source                    1..12
                          mol_type = protein
                          organism = synthetic construct
SEQUENCE: 1010
LTFGGGTKVE IK                                                            12

SEQ ID NO: 1011           moltype = AA  length = 108
FEATURE                   Location/Qualifiers
REGION                    1..108
                          note = humanized 8F9A4P3 Light chain variable region
                           sequence
source                    1..108
                          mol_type = protein
                          organism = synthetic construct
SEQUENCE: 1011
ETTLTQSPAF MSATPGDKVN ISCITSTDID DDMNWYQQKP GEAAIFIIQE GNTLRPGIPP          60
RFSGSGYGTD FTLTINNIES EDAAYYFCLQ SDNLPLTFGG GTKVEIKR                     108

SEQ ID NO: 1012           moltype = AA  length = 108
FEATURE                   Location/Qualifiers
REGION                    1..108
                          note = humanized 8F9A4P3 Light chain variable region
                           sequence (codon optimized)
source                    1..108
                          mol_type = protein
                          organism = synthetic construct
SEQUENCE: 1012
ETTLTQSPAF MSATPGDKVN ISCITSTDID DDMNWYQQKP GEAAIFIIQE GNTLRPGIPP          60
RFSGSGYGTD FTLTINNIES EDAAYYFCLQ SDNLPLTFGG GTKVEIKR                     108

SEQ ID NO: 1013           moltype = AA  length = 108
FEATURE                   Location/Qualifiers
REGION                    1..108
                          note = Modified humanized 8F9A4P3 Light chain variable
                           region sequence
source                    1..108
                          mol_type = protein
                          organism = synthetic construct
SEQUENCE: 1013
ETTVTQSPAF MSATPGDKVT ISCITSTDID DDMNWYQQKP GEAAILLISE GNTLRPGIPP          60
RFSSSGYGTD FTLTINNIES EDAAYYFCLQ SDNLPLTFGG GTKVEIKR                     108

SEQ ID NO: 1014           moltype = AA  length = 108
FEATURE                   Location/Qualifiers
REGION                    1..108
                          note = Modified humanized 8F9A4P3 Light chain variable
                           region sequence (codon optimized)
source                    1..108
                          mol_type = protein
                          organism = synthetic construct
SEQUENCE: 1014
ETTVTQSPAF MSATPGDKVT ISCITSTDID DDMNWYQQKP GEAAILLISE GNTLRPGIPP          60
RFSSSGYGTD FTLTINNIES EDAAYYFCLQ SDNLPLTFGG GTKVEIKR                     108

SEQ ID NO: 1015           moltype = AA  length = 245
FEATURE                   Location/Qualifiers
REGION                    1..245
                          note = Modified humanized 8F9A4P3 sequence (codon
                           optimized) - humanized heavy and light chains joined via a
                           flexible linker
source                    1..245
                          mol_type = protein
                          organism = synthetic construct
SEQUENCE: 1015
QVQLVQSGAE VKKPGASVKV SCKVSGNTFT EYTMHWVRQA PGKGLEWIGG FNPNNGVTNY          60
NQKFKGKVTL TVDTSSSTAY MELSSLRSED TAVYYCARRY YHSLYVFYFD YWGQGTLVTV         120
SSGGGGSGGG GSGGGGSETT VTQSPAFMSA TPGDKVTISC ITSTDIDDDM NWYQQKPGEA         180
AILLISEGNT LRPGIPPRFS SSGYGTDFTL TINNIESEDA AYYFCLQSDN LPLTFGGGTK         240
VEIKR                                                                   245

SEQ ID NO: 1016           moltype = AA  length = 119
FEATURE                   Location/Qualifiers
REGION                    1..119
                          note = 8F9A5A1 Heavy chain variable region sequence
source                    1..119
                          mol_type = protein
```

```
                              organism  =  synthetic construct
SEQUENCE: 1016
IQLVQSGPEL KKPGETVKIS CKASGYTFTN YGMNWVKQAP GKGLKWMGWI NTYTGEPTYV   60
DDFKGRFAFS LETSATTAYL QINNLKNEDT STYFCARLRG IRPGPLAYWG QGTLVTVSA   119

SEQ ID NO: 1017          moltype = AA   length = 98
FEATURE                  Location/Qualifiers
REGION                   1..98
                         note = IGHV7-81*01 V-REGION sequence
source                   1..98
                         mol_type = protein
                         organism = synthetic construct
SEQUENCE: 1017
QVQLVQSGHE VKQPGASVKV SCKASGYSFT TYGMNWVPQA PGQGLEWMGW FNTYTGNPTY   60
AQGFTGRFVF SMDTSASTAY LQISSLKAED MAMYYCAR                           98

SEQ ID NO: 1018          moltype = AA   length = 15
FEATURE                  Location/Qualifiers
REGION                   1..15
                         note = IGHJ4*03 J-REGION sequence
source                   1..15
                         mol_type = protein
                         organism = synthetic construct
SEQUENCE: 1018
YFDYWGQGTL VTVSS                                                    15

SEQ ID NO: 1019          moltype = AA   length = 120
FEATURE                  Location/Qualifiers
REGION                   1..120
                         note = humanized 8F9A5A1 Heavy chain variable region
                           sequence
source                   1..120
                         mol_type = protein
                         organism = synthetic construct
SEQUENCE: 1019
QVQLVQSGHE VKQPGASVKV SCKASGYTFT NYGMNWVPQA PGQGLEWMGW INTYTGEPTY   60
VDDFKGRFVF SMDTSASTAY LQISSLKAED MAMYYCARLR GIRPGPLAYW GQGTLVTVSS  120

SEQ ID NO: 1020          moltype = AA   length = 120
FEATURE                  Location/Qualifiers
REGION                   1..120
                         note = humanized 8F9A5A1 Heavy chain variable region
                           sequence (codon optimized)
source                   1..120
                         mol_type = protein
                         organism = synthetic construct
SEQUENCE: 1020
QVQLVQSGHE VKQPGASVKV SCKASGYTFT NYGMNWVPQA PGQGLEWMGW INTYTGEPTY   60
VDDFKGRFVF SMDTSASTAY LQISSLKAED MAMYYCARLR GIRPGPLAYW GQGTLVTVSS  120

SEQ ID NO: 1021          moltype = AA   length = 120
FEATURE                  Location/Qualifiers
REGION                   1..120
                         note = Modified humanized 8F9A5A1 Heavy chain variable
                           region sequence
source                   1..120
                         mol_type = protein
                         organism = synthetic construct
SEQUENCE: 1021
QIQLVQSGPE VKQPGASVKV SCKASGYTFT NYGMNWVKQA PGQGLEWMGW INTYTGEPTY   60
VDDFKGRFAF SMDTSASTAY LQISSLKAED TATYYCARLR GIRPGPLAYW GQGTLVTVSS  120

SEQ ID NO: 1022          moltype = AA   length = 120
FEATURE                  Location/Qualifiers
REGION                   1..120
                         note = Modified humanized 8F9A5A1 Heavy chain variable
                           region sequence (codon optimized)
source                   1..120
                         mol_type = protein
                         organism = synthetic construct
SEQUENCE: 1022
QIQLVQSGPE VKQPGASVKV SCKASGYTFT NYGMNWVKQA PGQGLEWMGW INTYTGEPTY   60
VDDFKGRFAF SMDTSASTAY LQISSLKAED TATYYCARLR GIRPGPLAYW GQGTLVTVSS  120

SEQ ID NO: 1023          moltype = AA   length = 107
FEATURE                  Location/Qualifiers
REGION                   1..107
                         note = 8F9A5A1 Light chain variable region sequence
source                   1..107
```

```
                              mol_type = protein
                              organism = synthetic construct
SEQUENCE: 1023
EILLTQSPAI IAASPGEKVT ITCSASSSVS YMNWYQQKPG SSPKIWIYGI SNLASGVPAR      60
FSGSGSGTSF SFTINSMEAE DVATYYCQQR SSYPPTFGGG TKLEIKR                  107

SEQ ID NO: 1024            moltype = AA  length = 93
FEATURE                    Location/Qualifiers
REGION                     1..93
                           note = IGKV3D-15*02 V-REGION sequence
source                     1..93
                           mol_type = protein
                           organism = synthetic construct
SEQUENCE: 1024
EIVMMQSPAT LSVSPGERAT LSCRASQSVS SNLAWYQQKP GQAPRLLIYG ASTRATGIPA      60
RFSGSGSGTE FTLTISSLQS EDFAVYYCQQ YNN                                  93

SEQ ID NO: 1025            moltype = AA  length = 12
FEATURE                    Location/Qualifiers
REGION                     1..12
                           note = IGKJ4*02 J-REGION sequence
source                     1..12
                           mol_type = protein
                           organism = synthetic construct
SEQUENCE: 1025
LTFGGGTKVE IK                                                         12

SEQ ID NO: 1026            moltype = AA  length = 107
FEATURE                    Location/Qualifiers
REGION                     1..107
                           note = humanized 8F9A5A1 Light chain variable region
                             sequence
source                     1..107
                           mol_type = protein
                           organism = synthetic construct
SEQUENCE: 1026
EIVMMQSPAT LSVSPGERAT LSCSASSSVS YMNWYQQKPG QAPRLLIYGI SNLASGIPAR      60
FSGSGSGTEF TLTISSLQSE DFAVYYCQQR SSYPPTFGGG TKVEIKR                  107

SEQ ID NO: 1027            moltype = AA  length = 107
FEATURE                    Location/Qualifiers
REGION                     1..107
                           note = humanized 8F9A5A1 Light chain variable region
                             sequence (codon optimized)
source                     1..107
                           mol_type = protein
                           organism = synthetic construct
SEQUENCE: 1027
EIVMMQSPAT LSVSPGERAT LSCSASSSVS YMNWYQQKPG QAPRLLIYGI SNLASGIPAR      60
FSGSGSGTEF TLTISSLQSE DFAVYYCQQR SSYPPTFGGG TKVEIKR                  107

SEQ ID NO: 1028            moltype = AA  length = 107
FEATURE                    Location/Qualifiers
REGION                     1..107
                           note = Modified humanized 8F9A5A1 Light chain variable
                             region sequence
source                     1..107
                           mol_type = protein
                           organism = synthetic construct
SEQUENCE: 1028
EIVLTQSPAT LSVSPGERAT LSCSASSSVS YMNWYQQKPG QAPRLWIYGI SNLASGIPAR      60
FSGSGSGTSF SLTISSLQSE DFAVYYCQQR SSYPPTFGGG TKVEIKR                  107

SEQ ID NO: 1029            moltype = AA  length = 107
FEATURE                    Location/Qualifiers
REGION                     1..107
                           note = Modified humanized 8F9A5A1 Light chain variable
                             region sequence (codon optimized)
source                     1..107
                           mol_type = protein
                           organism = synthetic construct
SEQUENCE: 1029
EIVLTQSPAT LSVSPGERAT LSCSASSSVS YMNWYQQKPG QAPRLWIYGI SNLASGIPAR      60
FSGSGSGTSF SLTISSLQSE DFAVYYCQQR SSYPPTFGGG TKVEIKR                  107

SEQ ID NO: 1030            moltype = AA  length = 242
FEATURE                    Location/Qualifiers
REGION                     1..242
                           note = Modified humanized 8F9A5A1 scFV sequence (codon
```

```
                        optimized)
source                  1..242
                        mol_type = protein
                        organism = synthetic construct
SEQUENCE: 1030
QIQLVQSGPE VKQPGASVKV SCKASGYTFT NYGMNWVKQA PGQGLEWMGW INTYTGEPTY     60
VDDFKGRFAF SMDTSASTAY LQISSLKAED TATYYCARLR GIRPGPLAYW GQGTLVTVSS    120
GGGGSGGGGS GGGGSEIVLT QSPATLSVSP GERATLSCSA SSSVSYMNWY QQKPGQAPRL    180
WIYGISNLAS GIPARFSGSG SGTSFSLTIS SLQSEDFAVY YCQQRSSYPP TFGGGTKVEI    240
KR                                                                  242

SEQ ID NO: 1031         moltype = AA  length = 121
FEATURE                 Location/Qualifiers
REGION                  1..121
                        note = 8H5H5G4 Heavy chain variable region sequence
source                  1..121
                        mol_type = protein
                        organism = synthetic construct
SEQUENCE: 1031
VQLQQSGPDL VKPGTSVKIS CKTSGNTFTE YTMHWVKQSH GKSLEWIGGF NPNNGVTNYN     60
QKFKGKATLT VDKSSSTAYM ELRSLTSEDS AVYYCARRYY HSTYVFYFDS WGQGTTLTVS    120
S                                                                   121

SEQ ID NO: 1032         moltype = AA  length = 98
FEATURE                 Location/Qualifiers
REGION                  1..98
                        note = IGHV1-24*01 V-REGION sequence
source                  1..98
                        mol_type = protein
                        organism = synthetic construct
SEQUENCE: 1032
QVQLVQSGAE VKKPGASVKV SCKVSGYTLT ELSMHWVRQA PGKGLEWMGG FDPEDGETIY     60
AQKFQGRVTM TEDTSTDTAY MELSSLRSED TAVYYCAT                             98

SEQ ID NO: 1033         moltype = AA  length = 15
FEATURE                 Location/Qualifiers
REGION                  1..15
                        note = IGHJ4*03 J-REGION sequence
source                  1..15
                        mol_type = protein
                        organism = synthetic construct
SEQUENCE: 1033
YFDYWGQGTL VTVSS                                                     15

SEQ ID NO: 1034         moltype = AA  length = 122
FEATURE                 Location/Qualifiers
REGION                  1..122
                        note = Humanized 8H5H5G4 Heavy chain variable region
                         sequence
source                  1..122
                        mol_type = protein
                        organism = synthetic construct
SEQUENCE: 1034
QVQLVQSGAE VKKPGASVKV SCKVSGNTFT EYTMHWVRQA PGKGLEWMGG FNPNNGVTNY     60
NQKFKGRVTM TEDTSTDTAY MELSSLRSED TAVYYCARRY YHSTYVFYFD SWGQGTLVTV    120
SS                                                                  122

SEQ ID NO: 1035         moltype = AA  length = 122
FEATURE                 Location/Qualifiers
REGION                  1..122
                        note = Humanized 8H5H5G4 Heavy chain variable region
                         sequence (codon optimized)
source                  1..122
                        mol_type = protein
                        organism = synthetic construct
SEQUENCE: 1035
QVQLVQSGAE VKKPGASVKV SCKVSGNTFT EYTMHWVRQA PGKGLEWMGG FNPNNGVTNY     60
NQKFKGRVTM TEDTSTDTAY MELSSLRSED TAVYYCARRY YHSTYVFYFD SWGQGTLVTV    120
SS                                                                  122

SEQ ID NO: 1036         moltype = AA  length = 122
FEATURE                 Location/Qualifiers
REGION                  1..122
                        note = Modified Humanized 8H5H5G4 Heavy chain variable
                         region sequence
source                  1..122
                        mol_type = protein
                        organism = synthetic construct
SEQUENCE: 1036
```

```
QVQLVQSGAE VKKPGASVKV SCKVSGNTFT EYTMHWVRQA PGKGLEWIGG FNPNNGVTNY    60
NQKFKGKVTL TVDTSSSTAY MELSSLRSED TAVYYCARRY YHSTYVFYFD SWGQGTLVTV   120
SS                                                                 122

SEQ ID NO: 1037         moltype = AA  length = 122
FEATURE                 Location/Qualifiers
REGION                  1..122
                        note = Modified Humanized 8H5H5G4 Heavy chain variable
                         region sequence (codon optimized)
source                  1..122
                        mol_type = protein
                        organism = synthetic construct
SEQUENCE: 1037
QVQLVQSGAE VKKPGASVKV SCKVSGNTFT EYTMHWVRQA PGKGLEWIGG FNPNNGVTNY    60
NQKFKGKVTL TVDTSSSTAY MELSSLRSED TAVYYCARRY YHSTYVFYFD SWGQGTLVTV   120
SS                                                                 122

SEQ ID NO: 1038         moltype = AA  length = 108
FEATURE                 Location/Qualifiers
REGION                  1..108
                        note = 8H5H5G4 Light chain variable region sequence
source                  1..108
                        mol_type = protein
                        organism = synthetic construct
SEQUENCE: 1038
DIQMTQTTSS LSASLGDRVT ISCSASQGIS NYLNWFQQKP DGTIKLLIYY TSSLHSGVPS    60
RFSGSGSGTD YSLTISNVEP EDIATYYCQQ YSKLPYTFGG GTKLEIKR               108

SEQ ID NO: 1039         moltype = AA  length = 95
FEATURE                 Location/Qualifiers
REGION                  1..95
                        note = IGKV1-27*01 V-REGION sequence
source                  1..95
                        mol_type = protein
                        organism = synthetic construct
SEQUENCE: 1039
DIQMTQSPSS LSASVGDRVT ITCRASQGIS NYLAWYQQKP GKVPKLLIYA ASTLQSGVPS    60
RFSGSGSGTD FTLTISSLQP EDVATYYCQK YNSAP                              95

SEQ ID NO: 1040         moltype = AA  length = 12
FEATURE                 Location/Qualifiers
REGION                  1..12
                        note = IGKJ4*02 J-REGION sequence
source                  1..12
                        mol_type = protein
                        organism = synthetic construct
SEQUENCE: 1040
LTFGGGTKVE IK                                                       12

SEQ ID NO: 1041         moltype = AA  length = 108
FEATURE                 Location/Qualifiers
REGION                  1..108
                        note = humanized 8H5H5G4 Light chain variable region
                         sequence
source                  1..108
                        mol_type = protein
                        organism = synthetic construct
SEQUENCE: 1041
DIQMTQSPSS LSASVGDRVT ITCSASQGIS NYLNWYQQKP GKVPKLLIYY TSSLHSGVPS    60
RFSGSGSGTD FTLTISSLQP EDVATYYCQQ YSKLPYTFGG GTKVEIKR               108

SEQ ID NO: 1042         moltype = AA  length = 108
FEATURE                 Location/Qualifiers
REGION                  1..108
                        note = humanized 8H5H5G4 Light chain variable region
                         sequence (codon optimized)
source                  1..108
                        mol_type = protein
                        organism = synthetic construct
SEQUENCE: 1042
DIQMTQSPSS LSASVGDRVT ITCSASQGIS NYLNWYQQKP GKVPKLLIYY TSSLHSGVPS    60
RFSGSGSGTD FTLTISSLQP EDVATYYCQQ YSKLPYTFGG GTKVEIKR               108

SEQ ID NO: 1043         moltype = AA  length = 108
FEATURE                 Location/Qualifiers
REGION                  1..108
                        note = Modified humanized 8H5H5G4 Light chain variable
                         region sequence
source                  1..108
```

```
                        mol_type = protein
                        organism = synthetic construct
SEQUENCE: 1043
DIQMTQSPSS LSASVGDRVT ITCSASQGIS NYLNWYQQKP GKVPKLLIYY TSSLHSGVPS   60
RFSGSGSGTD YTLTISSLQP EDVATYYCQQ YSKLPYTFGG GTKVEIKR               108

SEQ ID NO: 1044         moltype = AA  length = 108
FEATURE                 Location/Qualifiers
REGION                  1..108
                        note = Modified humanized 8H5H5G4 Light chain variable
                         region sequence (codon optimized)
source                  1..108
                        mol_type = protein
                        organism = synthetic construct
SEQUENCE: 1044
DIQMTQSPSS LSASVGDRVT ITCSASQGIS NYLNWYQQKP GKVPKLLIYY TSSLHSGVPS   60
RFSGSGSGTD YTLTISSLQP EDVATYYCQQ YSKLPYTFGG GTKVEIKR               108

SEQ ID NO: 1045         moltype = AA  length = 245
FEATURE                 Location/Qualifiers
REGION                  1..245
                        note = Modified humanized 8H5H5G4 scFV sequence (codon
                         optimized)
source                  1..245
                        mol_type = protein
                        organism = synthetic construct
SEQUENCE: 1045
QVQLVQSGAE VKKPGASVKV SCKVSGNTFT EYTMHWVRQA PGKGLEWIGG FNPNNGVTNY   60
NQKFKGKVTL TVDTSSSTAY MELSSLRSED TAVYYCARRY YHSTYVFYFD SWGQGTLVTV  120
SSGGGGSGGG GSGGGGSDIQ MTQSPSSLSA SVGDRVTITC SASQGISNYL NWYQQKPGKV  180
PKLLIYYTSS LHSGVPSRFS GSGSGTDYTL TISSLQPEDV ATYYCQQYSK LPYTFGGGTK  240
VEIKR                                                              245

SEQ ID NO: 1046         moltype = AA  length = 330
FEATURE                 Location/Qualifiers
REGION                  1..330
                        note = Human IgG1 heavy chain constant region sequence:
                         (for making full antibody - pair with either kappa or
                         lambda constant region; 2 plasmids, express together)
source                  1..330
                        mol_type = protein
                        organism = synthetic construct
SEQUENCE: 1046
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 1047         moltype = AA  length = 326
FEATURE                 Location/Qualifiers
REGION                  1..326
                        note = Human IgG2 heavy chain constant region sequence:
                         (for making full antibody - pair with either kappa or
                         lambda constant region; 2 plasmids, express together)
source                  1..326
                        mol_type = protein
                        organism = synthetic construct
SEQUENCE: 1047
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 1048         moltype = AA  length = 107
FEATURE                 Location/Qualifiers
REGION                  1..107
                        note = Human Kappa light chain constant region sequence
source                  1..107
                        mol_type = protein
                        organism = synthetic construct
SEQUENCE: 1048
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 1049         moltype = AA  length = 106
```

```
FEATURE                 Location/Qualifiers
REGION                  1..106
                        note = Human Lambda light chain constant region sequence
source                  1..106
                        mol_type = protein
                        organism = synthetic construct
SEQUENCE: 1049
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 1050         moltype = AA  length = 232
FEATURE                 Location/Qualifiers
REGION                  1..232
                        note = Human IgG1 Fc region sequence: (to be fused to scFv
                         for homo-dimerizes)
source                  1..232
                        mol_type = protein
                        organism = synthetic construct
SEQUENCE: 1050
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 1051         moltype = AA  length = 228
FEATURE                 Location/Qualifiers
REGION                  1..228
                        note = Human IgG2 Fc region sequence
source                  1..228
                        mol_type = protein
                        organism = synthetic construct
SEQUENCE: 1051
ERKCCVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP APIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGK                228

SEQ ID NO: 1052         moltype =    length =
SEQUENCE: 1052
000

SEQ ID NO: 1053         moltype =    length =
SEQUENCE: 1053
000

SEQ ID NO: 1054         moltype =    length =
SEQUENCE: 1054
000

SEQ ID NO: 1055         moltype =    length =
SEQUENCE: 1055
000

SEQ ID NO: 1056         moltype =    length =
SEQUENCE: 1056
000

SEQ ID NO: 1057         moltype =    length =
SEQUENCE: 1057
000

SEQ ID NO: 1058         moltype =    length =
SEQUENCE: 1058
000

SEQ ID NO: 1059         moltype =    length =
SEQUENCE: 1059
000

SEQ ID NO: 1060         moltype =    length =
SEQUENCE: 1060
000

SEQ ID NO: 1061         moltype =    length =
SEQUENCE: 1061
000

SEQ ID NO: 1062         moltype =    length =
SEQUENCE: 1062
```

| | | |
|---|---|---|
| 000 | | |
| SEQ ID NO: 1063<br>SEQUENCE: 1063<br>000 | moltype = | length = |
| SEQ ID NO: 1064<br>SEQUENCE: 1064<br>000 | moltype = | length = |
| SEQ ID NO: 1065<br>SEQUENCE: 1065<br>000 | moltype = | length = |
| SEQ ID NO: 1066<br>SEQUENCE: 1066<br>000 | moltype = | length = |
| SEQ ID NO: 1067<br>SEQUENCE: 1067<br>000 | moltype = | length = |
| SEQ ID NO: 1068<br>SEQUENCE: 1068<br>000 | moltype = | length = |
| SEQ ID NO: 1069<br>SEQUENCE: 1069<br>000 | moltype = | length = |
| SEQ ID NO: 1070<br>SEQUENCE: 1070<br>000 | moltype = | length = |
| SEQ ID NO: 1071<br>SEQUENCE: 1071<br>000 | moltype = | length = |
| SEQ ID NO: 1072<br>SEQUENCE: 1072<br>000 | moltype = | length = |
| SEQ ID NO: 1073<br>SEQUENCE: 1073<br>000 | moltype = | length = |
| SEQ ID NO: 1074<br>SEQUENCE: 1074<br>000 | moltype = | length = |
| SEQ ID NO: 1075<br>SEQUENCE: 1075<br>000 | moltype = | length = |
| SEQ ID NO: 1076<br>SEQUENCE: 1076<br>000 | moltype = | length = |
| SEQ ID NO: 1077<br>SEQUENCE: 1077<br>000 | moltype = | length = |
| SEQ ID NO: 1078<br>SEQUENCE: 1078<br>000 | moltype = | length = |
| SEQ ID NO: 1079<br>SEQUENCE: 1079<br>000 | moltype = | length = |
| SEQ ID NO: 1080<br>SEQUENCE: 1080<br>000 | moltype = | length = |
| SEQ ID NO: 1081<br>SEQUENCE: 1081<br>000 | moltype = | length = |
| SEQ ID NO: 1082 | moltype = | length = |

```
SEQUENCE: 1082
000

SEQ ID NO: 1083          moltype =   length =
SEQUENCE: 1083
000

SEQ ID NO: 1084          moltype =   length =
SEQUENCE: 1084
000

SEQ ID NO: 1085          moltype =   length =
SEQUENCE: 1085
000

SEQ ID NO: 1086          moltype =   length =
SEQUENCE: 1086
000

SEQ ID NO: 1087          moltype =   length =
SEQUENCE: 1087
000

SEQ ID NO: 1088          moltype =   length =
SEQUENCE: 1088
000

SEQ ID NO: 1089          moltype =   length =
SEQUENCE: 1089
000

SEQ ID NO: 1090          moltype =   length =
SEQUENCE: 1090
000

SEQ ID NO: 1091          moltype =   length =
SEQUENCE: 1091
000

SEQ ID NO: 1092          moltype =   length =
SEQUENCE: 1092
000

SEQ ID NO: 1093          moltype =   length =
SEQUENCE: 1093
000

SEQ ID NO: 1094          moltype =   length =
SEQUENCE: 1094
000

SEQ ID NO: 1095          moltype =   length =
SEQUENCE: 1095
000

SEQ ID NO: 1096          moltype =   length =
SEQUENCE: 1096
000

SEQ ID NO: 1097          moltype =   length =
SEQUENCE: 1097
000

SEQ ID NO: 1098          moltype =   length =
SEQUENCE: 1098
000

SEQ ID NO: 1099          moltype =   length =
SEQUENCE: 1099
000

SEQ ID NO: 1100          moltype =   length =
SEQUENCE: 1100
000

SEQ ID NO: 1101          moltype = DNA  length = 366
FEATURE                  Location/Qualifiers
misc_feature             1..366
                         note = Humanized 8F9A4A3 H-1.46 heavy chain variable domain
```

```
                        sequence
source                  1..366
                        mol_type = other DNA
                        organism = synthetic construct
SEQUENCE: 1101
caagtgcagc tggtgcagag cggcgccgag gtgaagaaac ctggcgccag cgtgaaagtg  60
tcctgcaagg ccagcggcaa tacattcacc gagtacacaa tgcactgggt cagacaggcc  120
cccgccagg gcctggaatg gatcggcgga tttaacccca caacggcgt gacaaactac  180
aaccagaagt tcaagggcaa ggtgaccatc acaagagca ccagcagcac caccgtgtac  240
atggaactgt cttctctgcg gagcgaggat accgccgtgt actattgtgc cagacggtac  300
taccacagcc tgtacgtgtt ctacttcgac tactgggac agggcaccct ggttaccgtg  360
tcctct                                                            366

SEQ ID NO: 1102         moltype = AA  length = 122
FEATURE                 Location/Qualifiers
REGION                  1..122
                        note = Humanized 8F9A4A3 H-1.46 heavy chain variable domain
                        sequence
source                  1..122
                        mol_type = protein
                        organism = synthetic construct
SEQUENCE: 1102
QVQLVQSGAE VKKPGASVKV SCKASGNTFT EYTMHWVRQA PGQGLEWIGG FNPNNGVTNY  60
NQKFKGKVTI TRDTSSSTVY MELSSLRSED TAVYYCARRY YHSLYVFYFD YWGQGTLVTV  120
SS                                                                122

SEQ ID NO: 1103         moltype = DNA  length = 321
FEATURE                 Location/Qualifiers
misc_feature            1..321
                        note = Humanized 8F9A4A3 L-1.6 light chain variable domain
                        sequence
source                  1..321
                        mol_type = other DNA
                        organism = synthetic construct
SEQUENCE: 1103
gatatccaga tgacacagag ccctagctcc ctgagcgcca gcgtgggcga ccgggtcacc  60
attacatgca gcgcttctca gggcatctcc aactacctga actggtacca gcagaaaccc  120
ggcaaggccc ctaagctgct gatcttctac accagctctc tgcacagcgg cgtgccatct  180
agattcagcg gatctggcag cggcaccgac tacaccctga ccatcagctc cctccagcct  240
gaggacttcg ccacctacta ctgtcagcaa tacagcaagc tgccttatac ctttggcggc  300
ggaacaaagg tggaaatcaa g                                           321

SEQ ID NO: 1104         moltype = AA  length = 107
FEATURE                 Location/Qualifiers
REGION                  1..107
                        note = Humanized 8F9A4A3 L-1.6 light chain variable domain
                        sequence
source                  1..107
                        mol_type = protein
                        organism = synthetic construct
SEQUENCE: 1104
DIQMTQSPSS LSASVGDRVT ITCSASQGIS NYLNWYQQKP GKAPKLLIFY TSSLHSGVPS  60
RFSGSGSGTD YTLTISSLQP EDFATYYCQQ YSKLPYTFGG GTKVEIK              107

SEQ ID NO: 1105         moltype = DNA  length = 366
FEATURE                 Location/Qualifiers
misc_feature            1..366
                        note = Humanized 8F9A4A3 H-4.4 heavy chain variable domain
                        sequence
source                  1..366
                        mol_type = other DNA
                        organism = synthetic construct
SEQUENCE: 1105
caagtgcagc tgcaggagag cggacctggc ctggttaagc ctggaggcac cctgtctctg  60
acatgtgctg tgtctggcaa tacctttacc gagtacacca tgcactgggt gcggcagcct  120
ccaggcaagg gcctggaatg gatcggcggc ttcaacccca caacggcgt gacaaattac  180
aaccagaaat tcaagggaaa agtgaccatc accgtggata gtccaagaa cacccttcagc  240
ctcaagctga gcagcgtgac agccgccgac accgccgtgt actactgcgc cagaagatac  300
tatcacagcc tgtacgtgtt ctacttcgac tactggggcc agggcacact ggtcaccgtg  360
tccagc                                                            366

SEQ ID NO: 1106         moltype = AA  length = 122
FEATURE                 Location/Qualifiers
REGION                  1..122
                        note = Humanized 8F9A4A3 H-4.4 heavy chain variable domain
                        sequence
source                  1..122
                        mol_type = protein
                        organism = synthetic construct
```

```
SEQUENCE: 1106
QVQLQESGPG LVKPGGTLSL TCAVSGNTFT EYTMHWVRQP PGKGLEWIGG FNPNNGVTNY    60
NQKFKGKVTI TVDKSKNTFS LKLSSVTAAD TAVYYCARRY YHSLYVFYFD YWGQGTLVTV   120
SS                                                                 122

SEQ ID NO: 1107          moltype = DNA  length = 321
FEATURE                  Location/Qualifiers
misc_feature             1..321
                         note = Humanized 8F9A4A3 L-4.1 light chain variable domain
                           sequence
source                   1..321
                         mol_type = other DNA
                         organism = synthetic construct
SEQUENCE: 1107
gatatcgtga tgacccagag cccagacagc ctggcagtga gtctgggtga gcgtgctaca    60
atcaactgca gcgccagcca gggcatctcc aactacctga attggtatca gcagaaacct   120
ggccaggctc ctaagctgct gatcttctac accagcagcc tgcacagcgg cgtgccagat   180
agattcagcg gcagcggatc tggcaccgac tacactgacc ccatttcttc tctccaggcc   240
gaggacgtgg ccgtctacta ctgtcagcaa tacagcaagc tgccttacac ctttggcgga   300
ggcacaaagg tggaaatcaa g                                             321

SEQ ID NO: 1108          moltype = AA  length = 107
FEATURE                  Location/Qualifiers
REGION                   1..107
                         note = Humanized 8F9A4A3 L-4.1 light chain variable domain
                           sequence
source                   1..107
                         mol_type = protein
                         organism = synthetic construct
SEQUENCE: 1108
DIVMTQSPDS LAVSLGERAT INCSASQGIS NYLNWYQQKP GQAPKLLIFY TSSLHSGVPD    60
RFSGSGSGTD YTLTISSLQA EDVAVYYCQQ YSKLPYTFGG GTKVEIK                 107

SEQ ID NO: 1109          moltype = AA  length = 107
FEATURE                  Location/Qualifiers
REGION                   1..107
                         note = 8F9A4A3L
source                   1..107
                         mol_type = protein
                         organism = synthetic construct
SEQUENCE: 1109
DIQMTQTTSS LSASLGDRVT LSCSASQGIS NYLNWYQQKP DGTVELLIFY TSSLHSGVPS    60
RFSGSGSGTD YSLTISNLEP EDIATYYCQQ YSKLPYTFGG GTKLEIK                 107

SEQ ID NO: 1110          moltype = AA  length = 187
FEATURE                  Location/Qualifiers
REGION                   1..187
                         note = NME4
source                   1..187
                         mol_type = protein
                         organism = synthetic construct
SEQUENCE: 1110
MGGLFWRSAL RGLRCGPRAP GPSLLVRHGS GGPSWTRERT LVAVKPDGVQ RRLVGDVIQR    60
FERRGFTLVG MKMLQAPESV LAEHYQDLRR KPFYPALIRY MSSGPVVAMV WEGYNVVRAS   120
RAMIGHTDSA EAAPGTIRGD FSVHISRNVI HASDSVEGAQ REIQLWFQSS ELVSWADGGQ   180
HSSIHPA                                                             187

SEQ ID NO: 1111          moltype = AA  length = 254
FEATURE                  Location/Qualifiers
REGION                   1..254
                         note = NME5
source                   1..254
                         mol_type = protein
                         organism = synthetic construct
SEQUENCE: 1111
MEISMPPPQI YVEKTLAIIK PDIVDKEEEI QDIILRSGFT IVQRRKLRLS PEQCSNFYVE    60
KYGKMFFPNL TAYMSSGPLV AMILARHKAI SYWLELLGPN NSLVAKETHP DSLRAIYGTD   120
DLRNALHGSN DFAAAEREIR FMFPEVIVEP IPIGQAAKDY LNLHIMPTLL EGLTELCKQK   180
PADPLFWYMC CRREHWTLRS ILLVCMSGIR MSLPHCADYC SFVEGFEIWL ADWLLKNNPN   240
KPKLCHHPIV EEPY                                                     254

SEQ ID NO: 1112          moltype = AA  length = 588
FEATURE                  Location/Qualifiers
REGION                   1..588
                         note = NME8
source                   1..588
                         mol_type = protein
                         organism = synthetic construct
SEQUENCE: 1112
```

```
MASKKREVQL QTVINNQSLW DEMLQNKGLT VIDVYQAWCG PCRAMQPLFR KLKNELNEDE    60
ILHFAVAEAD NIVTLQPFRD KCEPVFLFSV NGKIIEKIQG ANAPLVNKKV INLIDEERKI   120
AAGEMARPQY PEIPLVDSDS EVSEESPCES VQELYSIAII KPDAVISKKV LEIKRKITKA   180
GFIIEAEHKT VLTEEQVVNF YSRIADQCDF EEFVSFMTSG LSYILVVSQG SKHNPPSEET   240
EPQTDTEPNE RSEDQPEVEA QVTPGMMKNK QDSLQEYLER QHLAQLCDIE EDAANVAKFM   300
DAFFPDFKKM KSMKLEKTLA LLRPNLFHER KDDVLRIIKD EDFKILEQRQ VVLSEKEAQA   360
LCKEYENEDY FNKLIENMTS GPSLALVLLR DNGLQYWKQL LGPRTVEEAI EYFPESLCAQ   420
FAMDSLPVNQ LYGSDSLETA EREIQHFFPL QSTLGLIKPH ATSEQREQIL KIVKEAGFDL   480
TQVKKMFLTP EQIEKIYPKV TGKDFYKDLL EMLSVGPSMV MILTKWNAVA EWRRLMGPTD   540
PEEAKLLSPD SIRAQFGISK LKNIVHGASN AYEAKEVVNR LFEDPEEN                588

SEQ ID NO: 1113          moltype = DNA   length = 78
FEATURE                  Location/Qualifiers
misc_feature             1..78
                         note = Mouse 8F9A4A3 heavy chain variable domain framework 1
source                   1..78
                         mol_type = other DNA
                         organism = synthetic construct
SEQUENCE: 1113
gaggtccagc tgcaacagtc tggacctgaa ctggtgaagc ctggggcttc agtgaagata    60
tcctgcaaga cttctgga                                                  78

SEQ ID NO: 1114          moltype = AA    length = 26
FEATURE                  Location/Qualifiers
REGION                   1..26
                         note = Mouse 8F9A4A3 heavy chain variable domain framework 1
source                   1..26
                         mol_type = protein
                         organism = synthetic construct
SEQUENCE: 1114
EVQLQQSGPE LVKPGASVKI SCKTSG                                         26

SEQ ID NO: 1115          moltype = DNA   length = 27
FEATURE                  Location/Qualifiers
misc_feature             1..27
                         note = Heavy chain variable region CDR1
source                   1..27
                         mol_type = other DNA
                         organism = synthetic construct
SEQUENCE: 1115
aacacattca ctgaatacac catgcac                                        27

SEQ ID NO: 1116          moltype = DNA   length = 42
FEATURE                  Location/Qualifiers
misc_feature             1..42
                         note = Mouse 8F9A4A3 heavy chain variable domain framework 2
source                   1..42
                         mol_type = other DNA
                         organism = synthetic construct
SEQUENCE: 1116
tgggtgaagc agagccatgg aaagagcctt gagtggattg ga                       42

SEQ ID NO: 1117          moltype = AA    length = 14
FEATURE                  Location/Qualifiers
REGION                   1..14
                         note = Mouse 8F9A4A3 heavy chain variable domain framework 2
source                   1..14
                         mol_type = protein
                         organism = synthetic construct
SEQUENCE: 1117
WVKQSHGKSL EWIG                                                      14

SEQ ID NO: 1118          moltype = DNA   length = 51
FEATURE                  Location/Qualifiers
misc_feature             1..51
                         note = Mouse 8F9A4A3 Heavy chain variable region CDR2
source                   1..51
                         mol_type = other DNA
                         organism = synthetic construct
SEQUENCE: 1118
ggttttaatc ctaacaatgg tgttactaac tacaaccaga agttcaaggg c              51

SEQ ID NO: 1119          moltype = DNA   length = 96
FEATURE                  Location/Qualifiers
misc_feature             1..96
                         note = Mouse 4A3 heavy chain variable domain framework 3
source                   1..96
                         mol_type = other DNA
                         organism = synthetic construct
```

```
SEQUENCE: 1119
aaggccacat tgactgtaga caagtcctcc agcacagcct acatggagct ccgcagcctg    60
acatctgagg attctgcagt ctattactgt gcaaga                             96

SEQ ID NO: 1120          moltype = AA  length = 32
FEATURE                  Location/Qualifiers
REGION                   1..32
                         note = Mouse 4A3 heavy chain variable domain framework 3
source                   1..32
                         mol_type = protein
                         organism = synthetic construct
SEQUENCE: 1120
KATLTVDKSS STAYMELRSL TSEDSAVYYC AR                                  32

SEQ ID NO: 1121          moltype = DNA  length = 39
FEATURE                  Location/Qualifiers
misc_feature             1..39
                         note = Mouse 8F9A4A3 Heavy chain variable region CDR3
source                   1..39
                         mol_type = other DNA
                         organism = synthetic construct
SEQUENCE: 1121
cggtactacc atagtctcta cgtgttttac tttgactac                           39

SEQ ID NO: 1122          moltype = DNA  length = 69
FEATURE                  Location/Qualifiers
misc_feature             1..69
                         note = Mouse 8F9A4A3 light chain variable domain framework 1
source                   1..69
                         mol_type = other DNA
                         organism = synthetic construct
SEQUENCE: 1122
gatatccaga tgacacagac tacatcctcc ctgtctgcct ctctgggaga cagagtcacc    60
ctcagttgc                                                           69

SEQ ID NO: 1123          moltype = AA  length = 23
FEATURE                  Location/Qualifiers
REGION                   1..23
                         note = Mouse 8F9A4A3 light chain variable domain framework 1
source                   1..23
                         mol_type = protein
                         organism = synthetic construct
SEQUENCE: 1123
DIQMTQTTSS LSASLGDRVT LSC                                            23

SEQ ID NO: 1124          moltype = DNA  length = 33
FEATURE                  Location/Qualifiers
misc_feature             1..33
                         note = Mouse 8F9A4A3 Light chain variable region CDR 1
source                   1..33
                         mol_type = other DNA
                         organism = synthetic construct
SEQUENCE: 1124
agtgcaagtc agggcattag caattattta aac                                 33

SEQ ID NO: 1125          moltype = DNA  length = 45
FEATURE                  Location/Qualifiers
misc_feature             1..45
                         note = Mouse 4A3 light chain variable domain framework 2
source                   1..45
                         mol_type = other DNA
                         organism = synthetic construct
SEQUENCE: 1125
tggtatcagc agaaaccaga tggaactgtt gaactcctga tcttt                    45

SEQ ID NO: 1126          moltype = AA  length = 15
FEATURE                  Location/Qualifiers
REGION                   1..15
                         note = Mouse 4A3 light chain variable domain framework 2
source                   1..15
                         mol_type = protein
                         organism = synthetic construct
SEQUENCE: 1126
WYQQKPDGTV ELLIF                                                     15

SEQ ID NO: 1127          moltype = DNA  length = 21
FEATURE                  Location/Qualifiers
misc_feature             1..21
                         note = Mouse 8F9A4A3 Light chain variable region CDR2
```

```
source                   1..21
                         mol_type = other DNA
                         organism = synthetic construct
SEQUENCE: 1127
tacacatcaa gtttacactc a                                              21

SEQ ID NO: 1128          moltype = DNA  length = 96
FEATURE                  Location/Qualifiers
misc_feature             1..96
                         note = Mouse 8F9A4A3 light chain variable domain framework 3
source                   1..96
                         mol_type = other DNA
                         organism = synthetic construct
SEQUENCE: 1128
ggagtcccat caaggttcag tggcagtggg tctgggacag attattctct caccatcagc    60
aacctggaac ctgaagatat tgccacttac tattgt                              96

SEQ ID NO: 1129          moltype = AA  length = 32
FEATURE                  Location/Qualifiers
REGION                   1..32
                         note = Mouse 8F9A4A3 light chain variable domain framework 3
source                   1..32
                         mol_type = protein
                         organism = synthetic construct
SEQUENCE: 1129
GVPSRFSGSG SGTDYSLTIS NLEPEDIATY YC                                  32

SEQ ID NO: 1130          moltype = DNA  length = 27
FEATURE                  Location/Qualifiers
misc_feature             1..27
                         note = Mouse 8F9A4A3 Light chain variable region CDR3
source                   1..27
                         mol_type = other DNA
                         organism = synthetic construct
SEQUENCE: 1130
cagcagtata gtaagcttcc ttacacg                                        27

SEQ ID NO: 1131          moltype = DNA  length = 366
FEATURE                  Location/Qualifiers
misc_feature             1..366
                         note = Humanized 8F9A4A3 H-ori heavy chain variable domain
                         sequence
source                   1..366
                         mol_type = other DNA
                         organism = synthetic construct
SEQUENCE: 1131
caggttcagc tggttcagtc tggtgcagaa gtgaagaaac ctggcgcctc tgtgaaggtg    60
tcctgcaagg tgtccggaaa taccttcacc gagtacacca tgcactgggt ccgacaggcc   120
cctggcaaag gacttgaatg gatgggcggc ttcaacccca caacggcgt gaccaactac   180
aaccagaaat tcaagggccg cgtgaccatg accgaggaca aagcacaga caccgcctac   240
atgaactga gcagcctgag aagcgaggac accgccgtgt actactgcgc cagaaggtac   300
taccacagcc tgtacgtgtt ctacttcgac tactgggcc agggcaccct ggtcacagtt   360
tcttct                                                              366

SEQ ID NO: 1132          moltype = DNA  length = 366
FEATURE                  Location/Qualifiers
misc_feature             1..366
                         note = Humanized 8F9A4A3 H-3.15 heavy chain variable domain
                         sequence
source                   1..366
                         mol_type = other DNA
                         organism = synthetic construct
SEQUENCE: 1132
gaggtgcagc tggtggaaag cggcggcggc ctggttaagc ctggcggatc tctgagactg    60
agctgtgccg cttctggcaa taccttcacc gagtacacca tgcactgggt gcggcaggcc   120
cctggaaaag gcctggaatg gatcggcgga tttaacccca caacggcgt gacaaattac   180
aaccagaaat tcaagggcaa ggtcaccatc acaagagata gagcaagaa caccctgtac   240
ctgcaaatga acagcctgaa gtccgaggac accgccgtgt actactgcgc cagacggtac   300
taccacagcc tctatgtgtt ctacttcgac tactgggcc agggcacact ggtcaccgtg   360
tccagc                                                              366

SEQ ID NO: 1133          moltype = AA  length = 122
FEATURE                  Location/Qualifiers
REGION                   1..122
                         note = Humanized 8F9A4A3 H-3.15 heavy chain variable domain
                         sequence
source                   1..122
                         mol_type = protein
                         organism = synthetic construct
```

```
SEQUENCE: 1133
EVQLVESGGG LVKPGGSLRL SCAASGNTFT EYTMHWVRQA PGKGLEWIGG FNPNNGVTNY    60
NQKFKGKFTI TRDKSKNTLY LQMNSLKSED TAVYYCARRY YHSLYVFYFD YWGQGTLVTV   120
SS                                                                 122

SEQ ID NO: 1134         moltype = DNA   length = 321
FEATURE                 Location/Qualifiers
misc_feature            1..321
                        note = Humanized 8F9A4A3 L-3.15 light chain variable domain
                          sequence
source                  1..321
                        mol_type = other DNA
                        organism = synthetic construct
SEQUENCE: 1134
gagatcgtga tgacccagag cccagctaca cttagtgtga gtccaggtga acgggctacc    60
ctgtcctgca gcgccagcca gggcatcagc aactacctga actggtacca gcagaaacct   120
ggccaggccc ctagactgct gatcttctac accagcagcc tgcacagcgg catccccgcc   180
agattcagcg gcagcggctc tggaaacaga cacaccctga caatctctag cctgcagtct   240
gaagattttg ccgtctacta ctgtcagcaa tacagcaagc tgccttatac cttcggcggc   300
ggaaccaagg tggaaattaa g                                             321

SEQ ID NO: 1135         moltype = AA    length = 107
FEATURE                 Location/Qualifiers
REGION                  1..107
                        note = Humanized 8F9A4A3 L-3.15 light chain variable domain
                          sequence
source                  1..107
                        mol_type = protein
                        organism = synthetic construct
SEQUENCE: 1135
EIVMTQSPAT LSVSPGERAT LSCSASQGIS NYLNWYQQKP GQAPRLLIFY TSSLHSGIPA    60
RFSGSGSGTD YTLTISSLQS EDFAVYYCQQ YSKLPYTFGG GTKVEIK                 107

SEQ ID NO: 1136         moltype = DNA   length = 321
FEATURE                 Location/Qualifiers
misc_feature            1..321
                        note = Mouse 8F9A4A3 Light chain variable region sequence
source                  1..321
                        mol_type = other DNA
                        organism = synthetic construct
SEQUENCE: 1136
gatatccaga tgacacagac tacatcctcc ctgtctgcct ctctgggaga cagagtcacc    60
ctcagttgca gtgcaagtca gggcattagc aattatttaa actggtatca gcagaaacca   120
gatggaactg ttgaactcct gatcttttac acatcaagtt tacactcagg agtcccatca   180
aggttcagtg gcagtgggtc tgggacagat tattctctca ccatcagcaa cctggaacct   240
gaagatattg ccacttacta ttgtcagcag tatagtaagc ttccttacac gttcggaggg   300
gggaccaagc tggaaataaa a                                             321

SEQ ID NO: 1137         moltype = AA    length = 152
FEATURE                 Location/Qualifiers
source                  1..152
                        mol_type = protein
                        organism = Homo sapiens
SEQUENCE: 1137
MANCERTFIA IKPDGVQRGL VGEIIKRFEQ KGFRLVGLKF MQASEDLLKE HYVDLKDRPF    60
FAGLVKYMHS GPVVAMVWEG LNVVKTGRVM LGETNPADSK PGTIRGDFCI QVGRNIIHGS   120
DSVESAEKEI GLWFHPEELV DYTSCAQNWI YE                                 152

SEQ ID NO: 1138         moltype = DNA   length = 366
FEATURE                 Location/Qualifiers
misc_feature            1..366
                        note = Monoclonal antibody 8F9A4A3 "4A3"
source                  1..366
                        mol_type = other DNA
                        organism = synthetic construct
SEQUENCE: 1138
gaggtccagc tgcaacagtc tggacctgaa ctggtgaagc ctggggcttc agtgaagata    60
tcctgcaaga cttctggaaa cacattcact gaatacacca tgcactgggt gaagcagagc   120
catggaaaga gccttgagtg gattggaggt tttaatccta caaatggtgt tactaactac   180
aaccagaagt tcaagggcaa ggccacattg actgtagaca gtcctccag cacagcctac   240
atggagctcc gcagcctgac atctgaggat tctgcagtct attactgtgc aagacggtac   300
taccatagtc tctacgtgtt ttactttgac tactggggcc aaggcaccac tctcacagtc   360
tcctca                                                              366

SEQ ID NO: 1139         moltype = AA    length = 122
FEATURE                 Location/Qualifiers
REGION                  1..122
                        note = Monoclonal antibody 8F9A4A3 "4A3"
source                  1..122
```

```
                        mol_type = protein
                        organism = synthetic construct
SEQUENCE: 1139
EVQLQQSGPE LVKPGASVKI SCKTSGNTFT EYTMHWVKQS HGKSLEWIGG FNPNNGVTNY      60
NQKFKGKATL TVDKSSSTAY MELRSLTSED SAVYYCARRY YHSLYVFYFD YWGQGTTLTV     120
SS                                                                    122

SEQ ID NO: 1140         moltype = AA  length = 131
FEATURE                 Location/Qualifiers
source                  1..131
                        mol_type = protein
                        organism = Homo sapiens
SEQUENCE: 1140
EKTLALIKPD AISKAGEIIE IINKAGFTIT KLKMMMLSRK EALDFHVDHQ SRPFFNELIQ      60
FITTGPIIAM EILRDDAICE WKRLLGPANS GVARTDASES IRALFGTDGI RNAAHGPDSF     120
ASAAREMELF F                                                          131

SEQ ID NO: 1141         moltype = AA  length = 376
FEATURE                 Location/Qualifiers
source                  1..376
                        mol_type = protein
                        organism = Homo sapiens
SEQUENCE: 1141
MNHSERFVFI AEWYDPNASL LRRYELLFYP GDGSVEMHDV KNHRTFLKRT KYDNLHLEDL      60
FIGNKVNVFS RQLVLIDYGD QYTARQLGSR KEKTLALIKP DAISKAGEII EIINKAGFTI     120
TKLKMMMLSR KEALDFHVDH QSRPFFNELI QFITTGPIIA MEILRDDAIC EWKRLLGPAN     180
SGVARTDASE SIRALFGTDG IRNAAHGPDS FASAAREMEL FFPSSGGCGP ANTAKFTNCT     240
CCIVKPHAVS EGLLGKILMA IRDAGFEISA MQMFNMDRVN VEEFYEVYKG VVTEYHDMVT     300
EMYSGPCVAM EIQQNNATKT FREFCGPADP EIARHLRPGT LRAIFGKTKI QNAVHCTDLP     360
EDGLLEVQYF FKILDN                                                     376

SEQ ID NO: 1142         moltype = AA  length = 30
FEATURE                 Location/Qualifiers
REGION                  1..30
                        note = B3 region of NME7
source                  1..30
                        mol_type = protein
                        organism = synthetic construct
SEQUENCE: 1142
AIFGKTKIQN AVHCTDLPED GLLEVQYFFC                                       30

SEQ ID NO: 1143         moltype = AA  length = 139
FEATURE                 Location/Qualifiers
source                  1..139
                        mol_type = protein
                        organism = Homo sapiens
SEQUENCE: 1143
NCTCCIVKPH AVSEGLLGKI LMAIRDAGFE ISAMQMFNMD RVNVEEFYEV YKGVVTEYHD      60
MVTEMYSGPC VAMEIQQNNA TKTFREFCGP ADPEIARHLR PGTLRAIFGK TKIQNAVHCT     120
DLPEDGLLEV QYFFKILDN                                                  139

SEQ ID NO: 1144         moltype = AA  length = 11
FEATURE                 Location/Qualifiers
REGION                  1..11
                        note = Light Chain CDR1 region
source                  1..11
                        mol_type = protein
                        organism = synthetic construct
SEQUENCE: 1144
ITSTDIDDDM N                                                           11

SEQ ID NO: 1145         moltype = AA  length = 7
FEATURE                 Location/Qualifiers
REGION                  1..7
                        note = Light Chain CDR2 region
source                  1..7
                        mol_type = protein
                        organism = synthetic construct
SEQUENCE: 1145
EGNTLRP                                                                 7

SEQ ID NO: 1146         moltype = AA  length = 9
FEATURE                 Location/Qualifiers
REGION                  1..9
                        note = Light Chain CDR3 region
source                  1..9
                        mol_type = protein
                        organism = synthetic construct
SEQUENCE: 1146
```

-continued

```
LQSDNLPLT                                                             9

SEQ ID NO: 1147         moltype = AA  length = 23
FEATURE                 Location/Qualifiers
REGION                  1..23
                        note = Mouse 5F3A5D4-2 light chain variable domain
                          framework 1
source                  1..23
                        mol_type = protein
                        organism = synthetic construct
SEQUENCE: 1147
DIQMTQTTSS LSASLGDRVT ISC                                             23

SEQ ID NO: 1148         moltype = DNA  length = 45
FEATURE                 Location/Qualifiers
misc_feature            1..45
                        note = Mouse 5F3A5D4-2 light chain variable domain
                          framework 2
source                  1..45
                        mol_type = other DNA
                        organism = synthetic construct
SEQUENCE: 1148
tggtttcagc agaaaccaga tggaactatt aagctcctga tctat              45

SEQ ID NO: 1149         moltype = AA  length = 15
FEATURE                 Location/Qualifiers
REGION                  1..15
                        note = Mouse 5F3A5D4-2 light chain variable domain
                          framework 2
source                  1..15
                        mol_type = protein
                        organism = synthetic construct
SEQUENCE: 1149
WFQQKPDGTI KLLIY                                                      15

SEQ ID NO: 1150         moltype = DNA  length = 21
FEATURE                 Location/Qualifiers
misc_feature            1..21
                        note = Mouse 5F3A5D4-2 light chain variable domain
                          Complementarity -determining region 2
source                  1..21
                        mol_type = other DNA
                        organism = synthetic construct
SEQUENCE: 1150
tacacatcaa gtttacattc a                                               21

SEQ ID NO: 1151         moltype = DNA  length = 96
FEATURE                 Location/Qualifiers
misc_feature            1..96
                        note = Mouse 5F3A5D4-2 light chain variable domain
                          framework 3
source                  1..96
                        mol_type = other DNA
                        organism = synthetic construct
SEQUENCE: 1151
ggagtcccat caaggttcag tggcagtggg tctgggacag attattctct caccatcagt     60
aatgtggaac ctgaagatat tgccacttac tattgt                               96

SEQ ID NO: 1152         moltype = AA  length = 32
FEATURE                 Location/Qualifiers
REGION                  1..32
                        note = Mouse 5F3A5D4-2 light chain variable domain
                          framework 3
source                  1..32
                        mol_type = protein
                        organism = synthetic construct
SEQUENCE: 1152
GVPSRFSGSG SGTDYSLTIS NVEPEDIATY YC                                   32

SEQ ID NO: 1153         moltype = DNA  length = 30
FEATURE                 Location/Qualifiers
misc_feature            1..30
                        note = Mouse 5F3A5D4-2 light chain variable domain
                          framework 4
source                  1..30
                        mol_type = other DNA
                        organism = synthetic construct
SEQUENCE: 1153
ttcggagggg ggaccaagct ggagataaaa                                      30
```

```
SEQ ID NO: 1154         moltype = AA   length = 10
FEATURE                 Location/Qualifiers
REGION                  1..10
                        note = Mouse 5F3A5D4-2 light chain variable domain
                          framework 4
source                  1..10
                        mol_type = protein
                        organism = synthetic construct
SEQUENCE: 1154
FGGGTKLEIK                                                                10

SEQ ID NO: 1155         moltype = DNA   length = 366
FEATURE                 Location/Qualifiers
misc_feature            1..366
                        note = Mouse 5F3A5D4-V2 heavy chain variable domain sequence
source                  1..366
                        mol_type = other DNA
                        organism = synthetic construct
SEQUENCE: 1155
gaggtccagc tgcaacagtc tggacctgat ctggtgaagc ctgggacttc agtgaagata      60
tcctgtaaga cttctggaaa cacattcact gaatacatca tgcactgggt gaagcagagc     120
catggaaaga gccttgagtg gattggaggt tttaatccta caatggtgt tactaactac      180
aaccagaagt tcaagggcaa ggccacattg actagaca gtcctccag cacagcctac        240
atggagctcc gcagcctgac atctgaggat tctgcagtct attactgtgc aagacgttac    300
taccatagta cctacgtgtt ctactttgac cctggggcc aaggcaccac tctcacagtc     360
tcctca                                                                366

SEQ ID NO: 1156         moltype = DNA   length = 69
FEATURE                 Location/Qualifiers
misc_feature            1..69
                        note = Mouse 5F3A5D4-3 light chain variable domain
                          framework 1
source                  1..69
                        mol_type = other DNA
                        organism = synthetic construct
SEQUENCE: 1156
gatatccaga tgacacagac tacatcctcc ctgtctgcct ctctgggaga cagagtcacc      60
ctcagttgc                                                              69

SEQ ID NO: 1157         moltype = DNA   length = 30
FEATURE                 Location/Qualifiers
misc_feature            1..30
                        note = Mouse 5F3A5D4-3 light chain variable domain
                          framework 4
source                  1..30
                        mol_type = other DNA
                        organism = synthetic construct
SEQUENCE: 1157
ttcggagggg ggaccaagct ggaaataaaa                                       30

SEQ ID NO: 1158         moltype = DNA   length = 366
FEATURE                 Location/Qualifiers
misc_feature            1..366
                        note = Humanized 5F3A5D4-V2 H-1.27 heavy chain variable
                          domain sequence
source                  1..366
                        mol_type = other DNA
                        organism = synthetic construct
SEQUENCE: 1158
caagtgcagc tggtccagag cggcgccgag gtgaaaaagc ctggcgccag cgtgaaggtg      60
tcctgcaagg tgtctggcaa taccttcacc gagtacacca tgcactgggt gcggcaggcc     120
cctgaaaag gcctggaatg gatcggcgga tttaaccca caacggcgt gaccaactac        180
aaccagaagt tcaagggcaa ggttacactg accgtgaca ccagcctcct taccgcctac      240
atggaactga gcagcctgag aagcgaggat acagccgtgt actattgtgc agaagatac      300
taccacagca cctacgtgtt ctacttcgac agctggggcc agggcacact ggtgacagtg    360
tccagc                                                                366

SEQ ID NO: 1159         moltype = DNA   length = 366
FEATURE                 Location/Qualifiers
misc_feature            1..366
                        note = Humanized 5F3A5D4-V2 H-1.46 heavy chain variable
                          domain sequence
source                  1..366
                        mol_type = other DNA
                        organism = synthetic construct
SEQUENCE: 1159
caagtgcagc tggtgcagag cggagccgag gtgaaaaagc ccggcgcttc tgtgaaggtg      60
tcttgtaaag ccagcggcaa caccttcacc gagtacacca tgcactgggt gcggcaggcc     120
```

```
cctggccagg gcctggaatg gatcggcggc tttaatccta caacggcgt gacaaactac    180
aaccagaagt tcaagggcaa ggttacaatc accagagata ccagcagctc taccgtgtac    240
atggaactga gcagcctgag aagcgaggac accgccgtgt attactgcgc cagacggtac    300
taccacagca cctacgtgtt ctacttcgac agctggggcc agggaacact ggtcacagtg    360
tcctcc                                                              366

SEQ ID NO: 1160          moltype = AA    length = 122
FEATURE                  Location/Qualifiers
REGION                   1..122
                         note = Humanized 5F3A5D4-V2 H-1.46 heavy chain variable
                           domain sequence
source                   1..122
                         mol_type = protein
                         organism = synthetic construct
SEQUENCE: 1160
QVQLVQSGAE VKKPGASVKV SCKASGNTFT EYTMHWVRQA PGQGLEWIGG FNPNNGVTNY    60
NQKFKGKVTI TRDTSSSTVY MELSSLRSED TAVYYCARRY YHSTYVFYFD SWGQGTLVTV   120
SS                                                                 122

SEQ ID NO: 1161          moltype = DNA    length = 366
FEATURE                  Location/Qualifiers
misc_feature             1..366
                         note = Humanized 5F3A5D4-V2 H-3.15 heavy chain variable
                           domain sequence
source                   1..366
                         mol_type = other DNA
                         organism = synthetic construct
SEQUENCE: 1161
gaggtgcagc tggtggaaag cggaggaggc ctggttaagc ctggaggcag cctgagactg    60
agctgtgccg cttctggcaa taccttcacc gagtacacca tgcactgggt gcggcaggcc   120
cctggcaaag gcctggaatg gatcggcggc ttcaaccca acaacggcgt gacaaattac    180
aaccagaaat tcaagggcaa gtttacaatc accagagata gtctaagaa cacactctat    240
ctgcaaatga acagcctgaa gtccgaggac accgccgtgt actactgcgc cagacggtac   300
taccacagca catacgtgtt ctacttcgac agctggggcc agggcaccct ggtcaccgtg   360
tccagc                                                             366

SEQ ID NO: 1162          moltype = AA    length = 122
FEATURE                  Location/Qualifiers
REGION                   1..122
                         note = Humanized 5F3A5D4-V2 H-3.15 heavy chain variable
                           domain sequence
source                   1..122
                         mol_type = protein
                         organism = synthetic construct
SEQUENCE: 1162
EVQLVESGGG LVKPGGSLRL SCAASGNTFT EYTMHWVRQA PGKGLEWIGG FNPNNGVTNY    60
NQKFKGKFTI TRDSKNTLY LQMNSLKSED TAVYYCARRY YHSTYVFYFD SWGQGTLVTV   120
SS                                                                 122

SEQ ID NO: 1163          moltype = DNA    length = 366
FEATURE                  Location/Qualifiers
misc_feature             1..366
                         note = Humanized 5F3A5D4-V2 H-4.4 heavy chain variable
                           domain sequence
source                   1..366
                         mol_type = other DNA
                         organism = synthetic construct
SEQUENCE: 1163
caagtgcagc tgcaggagag cggacctggc ctggtcaagc ctggcggcac cctgagcctc    60
acctgtgctg tttctggcaa taccttcacc gagtacacca tgcactgggt gcggcagcct   120
ccaggcaaag gcctggaatg gatcggcgga tttaacccca acaacggcgt gacaaattac   180
aaccagaaat tcaagggcaa ggtgaccatc acagtggata gtccaagaa cacccttcagc   240
ctgaagctgt ctagcgtgac agccgccgac accgccgtgt actactgcgc cagaagatac   300
tatcacagca cctacgtgtt ctacttcgac agctggggac agggcacact ggtgacagtg   360
tccagc                                                             366

SEQ ID NO: 1164          moltype = AA    length = 122
FEATURE                  Location/Qualifiers
REGION                   1..122
                         note = Humanized 5F3A5D4-V2 H-4.4 heavy chain variable
                           domain sequence
source                   1..122
                         mol_type = protein
                         organism = synthetic construct
SEQUENCE: 1164
QVQLQESGPG LVKPGGTLSL TCAVSGNTFT EYTMHWVRQP PGKGLEWIGG FNPNNGVTNY    60
NQKFKGKVTI TVDKSKNTFS LKLSSVTAAD TAVYYCARRY YHSTYVFYFD SWGQGTLVTV   120
SS                                                                 122
```

| SEQ ID NO: 1165 | moltype = DNA length = 321 |
| --- | --- |
| FEATURE | Location/Qualifiers |
| misc_feature | 1..321 |
| | note = Humanized 5F3A5D4-2 L-1.6 light chain variable |
| | domain sequence |
| source | 1..321 |
| | mol_type = other DNA |
| | organism = synthetic construct |

SEQUENCE: 1165
```
gatatccaga tgacacagag ccctagctcc ctgagcgcca gcgtgggcga ccgggtcacc   60
attacatgca gcgcttctca gggcatctcc aactacctga actggtttca gcagaaaccc  120
ggcaaggccc ctaagctgct gatctattac accagctctc tgcacagcgg cgtgccatct  180
agattcagcg gatctggcag cggcaccgac tacaccctga ccatcagctc cctccagcct  240
gaggacttcg ccacctacta ctgtcagcaa tacagcaagc tgccttatac ctttggcggc  300
ggaacaaagg tggaaatcaa g                                            321
```

| SEQ ID NO: 1166 | moltype = AA length = 107 |
| --- | --- |
| FEATURE | Location/Qualifiers |
| REGION | 1..107 |
| | note = Humanized 5F3A5D4-2 L-1.6 light chain variable |
| | domain sequence |
| source | 1..107 |
| | mol_type = protein |
| | organism = synthetic construct |

SEQUENCE: 1166
```
DIQMTQSPSS LSASVGDRVT ITCSASQGIS NYLNWFQQKP GKAPKLLIYY TSSLHSGVPS   60
RFSGSGSGTD YTLTISSLQP EDFATYYCQQ YSKLPYTFGG GTKVEIK                107
```

| SEQ ID NO: 1167 | moltype = DNA length = 321 |
| --- | --- |
| FEATURE | Location/Qualifiers |
| misc_feature | 1..321 |
| | note = Humanized 5F3A5D4-2 L-3.15 light chain variable |
| | domain sequence |
| source | 1..321 |
| | mol_type = other DNA |
| | organism = synthetic construct |

SEQUENCE: 1167
```
gagatcgtga tgacccagag cccagctaca cttagtgtga gtccaggtga acgggctacc   60
ctgtcctgca gcgccagcca gggcatcagc aactacctga actggtttca gcagaaacct  120
ggccaggccc ctagactgct gatctattac accagcagcc tgcacagcgg catccccgcc  180
agattcagcg gcagcggctc tggaacagac tacaccctga caatctctag cctgcagtct  240
gaagattttg ccgtctacta ctgtcagcaa tacagcaagc tgccttatac cttcggcggc  300
ggaaccaagg tggaaattaa g                                            321
```

| SEQ ID NO: 1168 | moltype = AA length = 107 |
| --- | --- |
| FEATURE | Location/Qualifiers |
| REGION | 1..107 |
| | note = Humanized 5F3A5D4-2 L-3.15 light chain variable |
| | domain sequence |
| source | 1..107 |
| | mol_type = protein |
| | organism = synthetic construct |

SEQUENCE: 1168
```
EIVMTQSPAT LSVSPGERAT LSCSASQGIS NYLNWFQQKP GQAPRLLIYY TSSLHSGIPA   60
RFSGSGSGTD YTLTISSLQS EDFAVYYCQQ YSKLPYTFGG GTKVEIK                107
```

| SEQ ID NO: 1169 | moltype = DNA length = 321 |
| --- | --- |
| FEATURE | Location/Qualifiers |
| misc_feature | 1..321 |
| | note = Humanized 5F3A5D4-2 L-4.1 light chain variable |
| | domain sequence |
| source | 1..321 |
| | mol_type = other DNA |
| | organism = synthetic construct |

SEQUENCE: 1169
```
gatatcgtga tgacccagag cccagacagc ctggcagtga gtctgggtga gcgtgctaca   60
atcaactgca gcgccagcca gggcatctcc aactacctga ttggtttca gcagaaacct  120
ggccaggctc ctaagctgct gatctattac accagcagcc tgcacagcgg cgtgccagat  180
agattcagcg gcagcggatc tggcaccgac tacacactga ccatttcttc tctccaggcc  240
gaggacgtgg ccgtctacta ctgtcagcaa tacagcaagc tgccttacac ctttggcgga  300
ggcacaaagg tggaaatcaa g                                            321
```

| SEQ ID NO: 1170 | moltype = AA length = 107 |
| --- | --- |
| FEATURE | Location/Qualifiers |
| REGION | 1..107 |
| | note = Humanized 5F3A5D4-2 L-4.1 light chain variable |
| | domain sequence |
| source | 1..107 |
| | mol_type = protein |

|  |  |  |
|---|---|---|
| | organism = synthetic construct | |
| SEQUENCE: 1170 | | |
| DIVMTQSPDS LAVSLGERAT INCSASQGIS NYLNWFQQKP GQAPKLLIYY TSSLHSGVPD | | 60 |
| RFSGSGSGTD YTLTISSLQA EDVAVYYCQQ YSKLPYTFGG GTKVEIK | | 107 |
| | | |
| SEQ ID NO: 1171 | moltype = DNA   length = 69 | |
| FEATURE | Location/Qualifiers | |
| misc_feature | 1..69 | |
| | note = Mouse 5F3A5D4-2 light chain variable domain | |
| | framework 1 | |
| source | 1..69 | |
| | mol_type = other DNA | |
| | organism = synthetic construct | |
| SEQUENCE: 1171 | | |
| gatatccaga tgacacagac tacatcctcc ctgtctgcct ctctgggaga cagagtcacc | | 60 |
| atcagttgc | | 69 |
| | | |
| SEQ ID NO: 1172 | moltype = AA   length = 122 | |
| FEATURE | Location/Qualifiers | |
| REGION | 1..122 | |
| | note = Mouse 5F3A5D4-V2 heavy chain variable domain sequence | |
| source | 1..122 | |
| | mol_type = protein | |
| | organism = synthetic construct | |
| SEQUENCE: 1172 | | |
| EVQLQQSGPD LVKPGTSVKI SCKTSGNTFT EYTMHWVKQS HGKSLEWIGG FNPNNGVTNY | | 60 |
| NQKFKGKATL TVDKSSSTAY MELRSLTSED SAVYYCARRY YHSTYVFYFD SWGQGTTLTV | | 120 |
| SS | | 122 |
| | | |
| SEQ ID NO: 1173 | moltype = DNA   length = 78 | |
| FEATURE | Location/Qualifiers | |
| misc_feature | 1..78 | |
| | note = Mouse 5F3A5D4-V2 heavy chain variable domain | |
| | framework 1 | |
| source | 1..78 | |
| | mol_type = other DNA | |
| | organism = synthetic construct | |
| SEQUENCE: 1173 | | |
| gaggtccagc tgcaacagtc tggacctgat ctggtgaagc ctgggacttc agtgaagata | | 60 |
| tcctgtaaga cttctgga | | 78 |
| | | |
| SEQ ID NO: 1174 | moltype = AA   length = 26 | |
| FEATURE | Location/Qualifiers | |
| REGION | 1..26 | |
| | note = Mouse 5F3A5D4-V2 heavy chain variable domain | |
| | framework 1 | |
| source | 1..26 | |
| | mol_type = protein | |
| | organism = synthetic construct | |
| SEQUENCE: 1174 | | |
| EVQLQQSGPD LVKPGTSVKI SCKTSG | | 26 |
| | | |
| SEQ ID NO: 1175 | moltype = AA   length = 32 | |
| FEATURE | Location/Qualifiers | |
| REGION | 1..32 | |
| | note = Mouse 5F3A5D4-V2 heavy chain variable domain | |
| | framework 3 | |
| source | 1..32 | |
| | mol_type = protein | |
| | organism = synthetic construct | |
| SEQUENCE: 1175 | | |
| KATLTVDKSS STAYMELRSL TSEDSAVYYC AR | | 32 |
| | | |
| SEQ ID NO: 1176 | moltype = DNA   length = 39 | |
| FEATURE | Location/Qualifiers | |
| misc_feature | 1..39 | |
| | note = Mouse 5F3A5D4-V2 heavy chain variable domain | |
| | Complementarity -determining region 3 | |
| source | 1..39 | |
| | mol_type = other DNA | |
| | organism = synthetic construct | |
| SEQUENCE: 1176 | | |
| cgttactacc atagtaccta cgtgttctac tttgactcc | | 39 |
| | | |
| SEQ ID NO: 1177 | moltype = DNA   length = 33 | |
| FEATURE | Location/Qualifiers | |
| misc_feature | 1..33 | |
| | note = Mouse 5F3A5D4-V2 heavy chain variable domain | |
| | framework 4 | |

```
source                      1..33
                            mol_type = other DNA
                            organism = synthetic construct
SEQUENCE: 1177
tggggccaag gcaccactct cacagtctcc tca                                    33

SEQ ID NO: 1178             moltype = AA  length = 11
FEATURE                     Location/Qualifiers
REGION                      1..11
                            note = Mouse 5F3A5D4-V2 heavy chain variable domain
                             framework 4
source                      1..11
                            mol_type = protein
                            organism = synthetic construct
SEQUENCE: 1178
WGQGTTLTVS S                                                            11

SEQ ID NO: 1179             moltype = DNA  length = 321
FEATURE                     Location/Qualifiers
misc_feature                1..321
                            note = Mouse 5F3A5D4-2 light chain variable domain sequence
source                      1..321
                            mol_type = other DNA
                            organism = synthetic construct
SEQUENCE: 1179
gatatccaga tgacacagac tacatcctcc ctgtctgcct ctctgggaga cagagtcacc        60
atcagttgca gtgcaagtca gggcattagc aattatttaa actggtttca gcagaaacca       120
gatggaacta ttaagctcct gatctattac acatcaagtt tacattcagg agtcccatca       180
aggttcagtg gcagtgggtc tgggacagat tattctctca ccatcagtaa tgtggaacct       240
gaagatattg ccacttacta ttgtcagcag tatagtaagc ttccttacac gttcggaggg       300
gggaccaagc tggagataaa a                                                 321

SEQ ID NO: 1180             moltype = AA  length = 107
FEATURE                     Location/Qualifiers
REGION                      1..107
                            note = Mouse 5F3A5D4-2 light chain variable domain sequence
source                      1..107
                            mol_type = protein
                            organism = synthetic construct
SEQUENCE: 1180
DIQMTQTTSS LSASLGDRVT ISCSASQGIS NYLNWFQQKP DGTIKLLIYY TSSLHSGVPS        60
RFSGSGSGTD YSLTISNVEP EDIATYYCQQ YSKLPYTFGG GTKLEIK                     107

SEQ ID NO: 1181             moltype = AA  length = 122
FEATURE                     Location/Qualifiers
REGION                      1..122
                            note = Humanized 5F3A5D4-V2 H-1.27 heavy chain variable
                             domain sequence
source                      1..122
                            mol_type = protein
                            organism = synthetic construct
SEQUENCE: 1181
QVQLVQSGAE VKKPGASVKV SCKVSGNTFT EYTMHWVRQA PGKGLEWIGG FNPNNGVTNY        60
NQKFKGKVTL TVDTSSSTAY MELSSLRSED TAVYYCARRY YHSTYVFYFD SWGQGTLVTV       120
SS                                                                     122

SEQ ID NO: 1182             moltype = DNA  length = 321
FEATURE                     Location/Qualifiers
misc_feature                1..321
                            note = Humanized 5F3A5D4-3 L-1.6 light chain variable
                             domain sequence
source                      1..321
                            mol_type = other DNA
                            organism = synthetic construct
SEQUENCE: 1182
gatatccaga tgacacagag ccctagctcc ctgagcgcca gcgtgggcga ccgggtcacc        60
attacatgca gcgcttctca gggcatctcc aactacctga actggtacca gcagaaaccc       120
ggcaaggccc ctaagctgct gatcttctac accagctctc tgcacagcgg cgtgccatct       180
agattcagcg gatctggcag cggcaccgac tacaccctga ccatcagctc cctccagcct       240
gaggacttcg ccacctacta ctgtcagcaa tacagcaagc tgccttatac ctttggcggc       300
ggaacaaagg tggaaatcaa g                                                 321

SEQ ID NO: 1183             moltype = AA  length = 107
FEATURE                     Location/Qualifiers
REGION                      1..107
                            note = Humanized 5F3A5D4-3 L-1.6 light chain variable
                             domain sequence
source                      1..107
                            mol_type = protein
```

```
                        organism = synthetic construct
SEQUENCE: 1183
DIQMTQSPSS LSASVGDRVT ITCSASQGIS NYLNWYQQKP GKAPKLLIFY TSSLHSGVPS    60
RFSGSGSGTD YTLTISSLQP EDFATYYCQQ YSKLPYTFGG GTKVEIK                 107

SEQ ID NO: 1184         moltype = DNA   length = 321
FEATURE                 Location/Qualifiers
misc_feature            1..321
                        note = Humanized 5F3A5D4-3 L-4.1 light chain variable
                         domain sequence
source                  1..321
                        mol_type = other DNA
                        organism = synthetic construct
SEQUENCE: 1184
gatatcgtga tgacccagag cccagacagc ctggcagtga gtctgggtga gcgtgctaca    60
atcaactgca gcgccagcca gggcatctcc aactacctga attggtatca gcagaaacct   120
ggccaggctc ctaagctgct gatcttctac accagcagcc tgcacagcgg cgtgccagat   180
agattcagcg gcagcggatc tggcaccgac tacacactga ccatttcttc tctccaggcc   240
gaggacgtgg ccgtctacta ctgtcagcaa tacagcaagc tgccttacac ctttggcgga   300
ggcacaaagg tggaaatcaa g                                             321

SEQ ID NO: 1185         moltype = AA   length = 107
FEATURE                 Location/Qualifiers
REGION                  1..107
                        note = Humanized 5F3A5D4-3 L-4.1 light chain variable
                         domain sequence
source                  1..107
                        mol_type = protein
                        organism = synthetic construct
SEQUENCE: 1185
DIVMTQSPDS LAVSLGERAT INCSASQGIS NYLNWYQQKP GQAPKLLIFY TSSLHSGVPD    60
RFSGSGSGTD YTLTISSLQA EDVAVYYCQQ YSKLPYTFGG GTKVEIK                 107

SEQ ID NO: 1186         moltype = AA   length = 107
FEATURE                 Location/Qualifiers
REGION                  1..107
                        note = Mouse 5F3A5D4-3 light chain variable domain sequence
source                  1..107
                        mol_type = protein
                        organism = synthetic construct
SEQUENCE: 1186
DIQMTQTTSS LSASLGDRVT LSCSASQGIS NYLNWYQQKP DGTVELLIFY TSSLHSGVPS    60
RFSGSGSGTD YSLTISNLEP EDIATYYCQQ YSKLPYTFGG GTKLEIK                 107

SEQ ID NO: 1187         moltype = DNA   length = 27
FEATURE                 Location/Qualifiers
misc_feature            1..27
                        note = Mouse 5F3A5D4-V2 heavy chain variable domain
                         Complementarity-determining region 1
source                  1..27
                        mol_type = other DNA
                        organism = synthetic construct
SEQUENCE: 1187
aacacattca ctgaatacac catgcac                                        27

SEQ ID NO: 1188         moltype = DNA   length = 42
FEATURE                 Location/Qualifiers
misc_feature            1..42
                        note = Mouse 5F3A5D4-V2 heavy chain variable domain
                         framework 2
source                  1..42
                        mol_type = other DNA
                        organism = synthetic construct
SEQUENCE: 1188
tgggtgaagc agagccatgg aaagagcctt gagtggattg ga                       42

SEQ ID NO: 1189         moltype = AA   length = 14
FEATURE                 Location/Qualifiers
REGION                  1..14
                        note = Mouse 5F3A5D4-V2 heavy chain variable domain
                         framework 2
source                  1..14
                        mol_type = protein
                        organism = synthetic construct
SEQUENCE: 1189
WVKQSHGKSL EWIG                                                      14

SEQ ID NO: 1190         moltype = DNA   length = 51
FEATURE                 Location/Qualifiers
```

```
misc_feature            1..51
                        note = Mouse 5F3A5D4-V2 heavy chain variable domain
                         Complementarity -determining region 2
source                  1..51
                        mol_type = other DNA
                        organism = synthetic construct
SEQUENCE: 1190
ggttttaatc ctaacaatgg tgttactaac tacaaccaga agttcaaggg c          51

SEQ ID NO: 1191         moltype = DNA   length = 96
FEATURE                 Location/Qualifiers
misc_feature            1..96
                        note = Mouse 5F3A5D4-V2 heavy chain variable domain
                         framework 3
source                  1..96
                        mol_type = other DNA
                        organism = synthetic construct
SEQUENCE: 1191
aaggccacat tgactgtaga caagtcctcc agcacagcct acatggagct ccgcagcctg 60
acatctgagg attctgcagt ctattactgt gcaaga                          96

SEQ ID NO: 1192         moltype = AA    length = 23
FEATURE                 Location/Qualifiers
REGION                  1..23
                        note = Mouse 5F3A5D4-3 light chain variable domain
                         framework 1
source                  1..23
                        mol_type = protein
                        organism = synthetic construct
SEQUENCE: 1192
DIQMTQTTSS LSASLGDRVT LSC                                        23

SEQ ID NO: 1193         moltype = DNA   length = 33
FEATURE                 Location/Qualifiers
misc_feature            1..33
                        note = Mouse 5F3A5D4-2 light chain variable domain
                         Complementarity -determining region 1
source                  1..33
                        mol_type = other DNA
                        organism = synthetic construct
SEQUENCE: 1193
agtgcaagtc agggcattag caattattta aac                             33

SEQ ID NO: 1194         moltype = DNA   length = 33
FEATURE                 Location/Qualifiers
misc_feature            1..33
                        note = Mouse 5F3A5D4-3 light chain variable domain
                         Complementarity -determining region 1
source                  1..33
                        mol_type = other DNA
                        organism = synthetic construct
SEQUENCE: 1194
agtgcaagtc agggcattag caattattta aac                             33

SEQ ID NO: 1195         moltype = DNA   length = 45
FEATURE                 Location/Qualifiers
misc_feature            1..45
                        note = Mouse 5F3A5D4-3 light chain variable domain
                         framework 2
source                  1..45
                        mol_type = other DNA
                        organism = synthetic construct
SEQUENCE: 1195
tggtatcagc agaaaccaga tggaactgtt gaactcctga tcttt                45

SEQ ID NO: 1196         moltype = AA    length = 15
FEATURE                 Location/Qualifiers
REGION                  1..15
                        note = Mouse 5F3A5D4-3 light chain variable domain
                         framework 2
source                  1..15
                        mol_type = protein
                        organism = synthetic construct
SEQUENCE: 1196
WYQQKPDGTV ELLIF                                                 15

SEQ ID NO: 1197         moltype = DNA   length = 21
FEATURE                 Location/Qualifiers
misc_feature            1..21
```

```
                        note = Mouse 5F3A5D4-3 light chain variable domain
                           Complementarity -determining region 2
source                  1..21
                        mol_type = other DNA
                        organism = synthetic construct
SEQUENCE: 1197
tacacatcaa gtttacactc a                                                    21

SEQ ID NO: 1198         moltype = DNA   length = 96
FEATURE                 Location/Qualifiers
misc_feature            1..96
                        note = Mouse 5F3A5D4-3 light chain variable domain
                           framework 3
source                  1..96
                        mol_type = other DNA
                        organism = synthetic construct
SEQUENCE: 1198
ggagtcccat caaggttcag tggcagtggg tctgggacag attattctct caccatcagc          60
aacctggaac ctgaagatat tgccacttac tattgt                                    96

SEQ ID NO: 1199         moltype = AA   length = 32
FEATURE                 Location/Qualifiers
REGION                  1..32
                        note = Mouse 5F3A5D4-3 light chain variable domain
                           framework 3
source                  1..32
                        mol_type = protein
                        organism = synthetic construct
SEQUENCE: 1199
GVPSRFSGSG SGTDYSLTIS NLEPEDIATY YC                                        32

SEQ ID NO: 1200         moltype = DNA   length = 27
FEATURE                 Location/Qualifiers
misc_feature            1..27
                        note = Mouse 5F3A5D4-2 light chain variable domain
                           Complementarity -determining region 3
source                  1..27
                        mol_type = other DNA
                        organism = synthetic construct
SEQUENCE: 1200
cagcagtata gtaagcttcc ttacacg                                              27

SEQ ID NO: 1201         moltype = DNA   length = 27
FEATURE                 Location/Qualifiers
misc_feature            1..27
                        note = Mouse 5F3A5D4-3 light chain variable domain
                           Complementarity -determining region 3
source                  1..27
                        mol_type = other DNA
                        organism = synthetic construct
SEQUENCE: 1201
cagcagtata gtaagcttcc ttacacg                                              27

SEQ ID NO: 1202         moltype = DNA   length = 321
FEATURE                 Location/Qualifiers
misc_feature            1..321
                        note = Humanized 5F3A5D4-3 L-3.15 light chain variable
                           domain sequence
source                  1..321
                        mol_type = other DNA
                        organism = synthetic construct
SEQUENCE: 1202
gagatcgtga tgacccagag cccagctaca cttagtgtga gtccaggtga acgggctacc          60
ctgtcctgca gcgccagcca gggcatcagc aactacctga actggtacca gcagaaacct         120
ggccaggccc ctagactgct gatcttctac accagcagcc tgcacagcgg catccccgcc         180
agattcagcg gcagcggctc tggaacagac tacaccctga caatctctag cctgcagtct         240
gaagattttg ccgtctacta ctgtcagcaa tacagcaagc tgccttatac cttcggcggc         300
ggaaccaagg tggaaattaa g                                                   321

SEQ ID NO: 1203         moltype = AA   length = 107
FEATURE                 Location/Qualifiers
REGION                  1..107
                        note = Humanized 5F3A5D4-3 L-3.15 light chain variable
                           domain sequence
source                  1..107
                        mol_type = protein
                        organism = synthetic construct
SEQUENCE: 1203
EIVMTQSPAT LSVSPGERAT LSCSASQGIS NYLNWYQQKP GQAPRLLIFY TSSLHSGIPA          60
```

```
RFSGSGSGTD YTLTISSLQS EDFAVYYCQQ YSKLPYTFGG GTKVEIK                    107

SEQ ID NO: 1204           moltype = DNA   length = 321
FEATURE                   Location/Qualifiers
misc_feature              1..321
                          note = Mouse 5F3A5D4-3 light chain variable domain sequence
source                    1..321
                          mol_type = other DNA
                          organism = synthetic construct
SEQUENCE: 1204
gatatccaga tgacacagac tacatcctcc ctgtctgcct ctctgggaga cagagtcacc      60
ctcagttgca gtgcaagtca gggcattagc aattatttaa actggtatca gcagaaacca    120
gatggaactg ttgaactcct gatcttttac acatcaagtt acactcaggg agtcccatca    180
aggttcagtg gcagtgggtc tgggacagat tattctctca ccatcagcaa cctggaacct    240
gaagatattg ccacttacta ttgtcagcag tatagtaagc ttccttacac gttcggaggg    300
gggaccaagc tggaaataaa a                                              321

SEQ ID NO: 1205           moltype = AA   length = 121
FEATURE                   Location/Qualifiers
REGION                    1..121
                          note = 8F9A4A3H
source                    1..121
                          mol_type = protein
                          organism = synthetic construct
SEQUENCE: 1205
VQLQQSGPEL VKPGASVKIS CKTSGNTFTE YTMHWVKQSH GKSLEWIGGF NPNNGVTNYN      60
QKFKGKATLT VDKSSSTAYM ELRSLTSEDS AVYYCARRYY HSLYVFYFDY WGQGTTLTVS    120
S                                                                    121

SEQ ID NO: 1206           moltype = AA   length = 122
FEATURE                   Location/Qualifiers
REGION                    1..122
                          note = Humanized 8F9A4A3 H-ori heavy chain variable domain
                            sequence
source                    1..122
                          mol_type = protein
                          organism = synthetic construct
SEQUENCE: 1206
QVQLVQSGAE VKKPGASVKV SCKVSGNTFT EYTMHWVRQA PGKGLEWMGG FNPNNGVTNY      60
NQKFKGRVTM TEDTSTDTAY MELSSLRSED TAVYYCARRY YHSLYVFYFD YWGQGTLVTV    120
SS                                                                   122

SEQ ID NO: 1207           moltype = AA   length = 10
FEATURE                   Location/Qualifiers
REGION                    1..10
                          note = Mouse 5F3A5D4-3 light chain variable domain
                            framework 4 (FR4) sequence
source                    1..10
                          mol_type = protein
                          organism = synthetic construct
SEQUENCE: 1207
FGGGTKLEIK                                                             10

SEQ ID NO: 1208           moltype = AA   length = 11
FEATURE                   Location/Qualifiers
REGION                    1..11
                          note = Mouse 5F3A5D4-2 light chain variable domain
                            Complementarity -determining region 1 (CDR1) sequence
source                    1..11
                          mol_type = protein
                          organism = synthetic construct
SEQUENCE: 1208
SASQGISNYL N                                                           11

SEQ ID NO: 1209           moltype = AA   length = 11
FEATURE                   Location/Qualifiers
REGION                    1..11
                          note = Mouse 5F3A5D4-3 light chain variable domain
                            Complementarity -determining region 1 (CDR1) sequence
source                    1..11
                          mol_type = protein
                          organism = synthetic construct
SEQUENCE: 1209
SASQGISNYL N                                                           11

SEQ ID NO: 1210           moltype = AA   length = 7
FEATURE                   Location/Qualifiers
REGION                    1..7
                          note = Mouse 5F3A5D4-2 light chain variable domain
```

```
                    Complementarity -determining region 2 (CDR2) sequence
source              1..7
                    mol_type = protein
                    organism = synthetic construct
SEQUENCE: 1210
YTSSLHS                                                                    7

SEQ ID NO: 1211     moltype = AA  length = 7
FEATURE             Location/Qualifiers
REGION              1..7
                    note = Mouse 5F3A5D4-3 light chain variable domain
                     Complementarity -determining region 2 (CDR2) sequence
source              1..7
                    mol_type = protein
                    organism = synthetic construct
SEQUENCE: 1211
YTSSLHS                                                                    7

SEQ ID NO: 1212     moltype = AA  length = 9
FEATURE             Location/Qualifiers
REGION              1..9
                    note = Mouse 5F3A5D4-2 light chain variable domain
                     Complementarity -determining region 3 (CDR3) sequence
source              1..9
                    mol_type = protein
                    organism = synthetic construct
SEQUENCE: 1212
QQYSKLPYT                                                                  9

SEQ ID NO: 1213     moltype = AA  length = 9
FEATURE             Location/Qualifiers
REGION              1..9
                    note = Mouse 5F3A5D4-3 light chain variable domain
                     Complementarity -determining region 3 (CDR3) sequence
source              1..9
                    mol_type = protein
                    organism = synthetic construct
SEQUENCE: 1213
QQYSKLPYT                                                                  9
```

The invention claimed is:

1. A nucleic acid encoding a monoclonal antibody, a bispecific antibody, a bispecific T-cell engager, a Fab, or a single chain variable fragment antibody (scFv) comprising:
   (a) a heavy chain variable region (HCV) comprising the sequence of any one of SEQ ID NOs: 1160, 1162, 1164, and 1181; and
   a light chain variable region (LCV) comprising complementarity determining regions (CDRs) comprising a light chain CDR1 (LC-CDR1) comprising the sequence of SEQ ID NO: 434, an LC-CDR2 comprising the sequence of SEQ ID NO: 435, and an LC-CDR3 comprising the sequence of SEQ ID NO: 436; or
   (b) an HCV comprising CDRs comprising a heavy chain CDR1 (HC-CDR1) comprising the sequence of SEQ ID NO: 429, an HC-CDR2 comprising the sequence of SEQ ID NO: 430, and an HC-CDR3 comprising the sequence of SEQ ID NO: 431; and
   an LCV comprising the sequence of any one of SEQ ID NOs: 1166, 1168, 1170, 1183, 1203, and 1185;
   wherein the monoclonal antibody, the bispecific antibody, the bispecific T-cell engager, the Fab, or the scFv binds to NME7.

2. The nucleic acid of claim 1, wherein the HCV comprises the sequence of any one of SEQ ID NOs: 1160, 1162, 1164, and 1181; and the LCV comprises the sequence of any one of SEQ ID NOs: 1166, 1168, 1170, 1183, 1203, and 1185.

3. The nucleic acid of claim 1, wherein the HCV comprises the sequence of SEQ ID NO: 1164, and the LCV comprises the sequence of any one of SEQ ID NOs: 1166, 1168, 1170, 1183, 1203, and 1185.

4. The nucleic acid of claim 1, wherein the HCV comprises the sequence of any one of SEQ ID NOs: 1160, 1162, 1164, and 1181; and the LCV comprises the sequence of SEQ ID NO: 1185.

5. The nucleic acid of claim 1, wherein the nucleic acid encodes the monoclonal antibody.

6. The nucleic acid of claim 1, wherein the nucleic acid encodes the bispecific antibody.

7. The nucleic acid of claim 1, wherein the nucleic acid encodes the bispecific T-cell engager.

8. The nucleic acid of claim 1, wherein the nucleic acid encodes the scFv.

9. A cell comprising the nucleic acid of claim 1.

* * * * *